US008067379B2

(12) United States Patent
Bennett et al.

(10) Patent No.: US 8,067,379 B2
(45) Date of Patent: Nov. 29, 2011

(54) SULFUR COMPOUNDS AS INHIBITORS OF HEPATITIS C VIRUS NS3 SERINE PROTEASE

(75) Inventors: Frank Bennett, Cranford, NJ (US);
Raymond G. Lovey, Miami, FL (US);
Yuhua Huang, Westfield, NJ (US);
Siska Hendrata, Kenilworth, NJ (US);
Anil K. Saksena, Upper Montclair, NJ (US); Stephane L. Bogen, Somerset, NJ (US); Yi-Tsung Liu, Morris Township, NJ (US); F. George Njoroge, Warren, NJ (US); Srikanth Venkatraman, Woodbridge, NJ (US); Kevin X. Chen, Edison, NJ (US); Mousumi Sannigrahi, Summit, NJ (US); Ashok Arasappan, Bridgewater, NJ (US); Viyyoor M. Girijavallabhan, Parsippany, NJ (US);
Francisco Velazquez, Clinton, NJ (US);
Latha G. Nair, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 1931 days.

(21) Appl. No.: 11/064,673

(22) Filed: Feb. 24, 2005

(65) Prior Publication Data

US 2007/0042968 A1 Feb. 22, 2007

Related U.S. Application Data

(60) Provisional application No. 60/548,670, filed on Feb. 27, 2004.

(51) Int. Cl.
*A61K 38/06* (2006.01)
(52) U.S. Cl. ...................... 514/21.9; 530/331
(58) Field of Classification Search ............... 514/21.9; 530/331
See application file for complete search history.

(56) References Cited

U.S. PATENT DOCUMENTS

| 5,712,145 | A | 1/1998 | Houghton et al. |
|---|---|---|---|
| 6,608,027 | B1 | 8/2003 | Tsantrizos et al. |
| 6,911,428 | B2 | 6/2005 | Zhu et al. |
| 7,012,066 | B2 | 3/2006 | Saksena et al. |
| 7,244,721 | B2 | 7/2007 | Saksena et al. |
| 7,816,326 | B2 | 10/2010 | Velazquez et al. |
| 2003/0216325 | A1 | 11/2003 | Saksena et al. |
| 2007/0197448 | A1 | 8/2007 | Velazquez et al. |

FOREIGN PATENT DOCUMENTS

| WO | 98-14181 A1 | 4/1998 |
|---|---|---|
| WO | 98-17679 A1 | 4/1998 |
| WO | 98-22496 A2 | 5/1998 |
| WO | 99-07734 A2 | 2/1999 |
| WO | 00-09543 A2 | 2/2000 |
| WO | 00-09558 A1 | 2/2000 |
| WO | WO 00/09543 | 2/2000 |
| WO | 01-74768 A2 | 10/2001 |
| WO | 01-77113 A2 | 10/2001 |
| WO | 01-81325 A2 | 11/2001 |
| WO | 02-08187 A1 | 1/2002 |
| WO | 02-08244 A2 | 1/2002 |
| WO | 02-08251 A2 | 1/2002 |
| WO | 02-08256 A2 | 1/2002 |
| WO | WO 02/08244 | 1/2002 |
| WO | WO 02/18369 | 3/2002 |
| WO | 02-48172 A2 | 6/2002 |
| WO | WO 03/062265 | 7/2003 |
| WO | 2005-087731 A | 9/2005 |
| WO | 2006-130628 A | 12/2006 |

OTHER PUBLICATIONS

Newman et al., DDT vol. 8, Oct. 2003, p. 898-90.*
Chawla et al., CRIPS vol. 5, No. 1, Jan.-Mar. 2004, p. 9-12.*
Saksena et al., caplus an 2002:90062.*
International Search Report for PCT/US2005/005795—6 Pages.
Berenguer et al., "Hepatitis B and C Viruses: Molecular Identification and Targeted Antiviral Therapies", Proceedings of the Association of American Physicians, 110(2):98-112 (1998).
Dimasi et al., "Characterization of Engineered Hepatitis C Virus NS3 Protease Inhibitors Affinity Selected from Human Pancreatic Secretory Trypsin Inhibitor and Minibody Repertoires", Journal of Virology, 71(10):7461-7469 (1997).
Elzouki et al., "Serine Protease Inhibitors in Patients with Chronic Viral Hepatitis", Journal of Hepatology, 27:42-48 (1997).
Failla et al., "Redesigning the Substrate Specificity of the Hepatitis C Virus NS3 Protease", Folding & Design, 1(1):35-42 (1996).
Han et al., "alpha-Ketoamides, alpha-Ketoesters and alpha-Diketones as HCV NS3 Protease Inhibitors", Bioorganic & Medicinal Chemistry Letters, 10:711-713 (2000).
Hoofnagle et al., "The Treatment of Chronic Viral Hepatitis", The New England Journal of Medicine, 336(5):347-356 (1997).
Ingallinella et al., "Potent Peptide Inhibitors of Human Hepatitis C Virus NS3 Protease are Obtained by Optimizing the Cleavage Products", Biochemistry, 37:8906-8914 (1998).
Kolykhalov et al., "Specifically of the Hepatitis C Virus NS3 Serine Protease: Effects of Substitutions at the 3/4A, 4A/4B, 4B/5A, and 5A/5B Cleavage Sites on Polyprotein Processing", Journal of Virology, 68(11):7525-7533 (1994).
Komoda et al., "Substrate Requirements of Hepatitis C Virus Serine Proteinase for Intermolecular Polypeptides Cleavage in *Escherichia coli*", Journal of Virology, 68(11):7351-7357 (1994).
Landro et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 36:9340-9348 (1997).
Pizzi et al., "Molecular Model of the Specificity Pocket of the Hepatitis C VIrus Protease: Implications for Substrate Recognition", Proceedings of the National Academy Sciences of the USA, 91:888-892 (1994).

(Continued)

*Primary Examiner* — Sun Jae Loewe
(74) *Attorney, Agent, or Firm* — Julie M. Lake; Sheldon O. Heber

(57) ABSTRACT

The present invention discloses novel compounds which have HCV protease inhibitory activity as well as methods for preparing such compounds. In another embodiment, the invention discloses pharmaceutical compositions comprising such compounds as well as methods of using them to treat disorders associated with the HCV protease.

43 Claims, No Drawings

OTHER PUBLICATIONS

Llinas-Brunet et al., "Peptide-Based Inhibitors of the Hepatitis C Virus Serine Protease", Bioorganic & Medicinal Chemmistry Letters 8:1713-1718 (1998).

Marchetti et al., "Synthesis of Two Novel Cyclic Biphenyl Ether Analogs of an Inhibitor of HCV NS3 Protease", Synlett S1:1000-1002 (1999).

Martin et al., "Design of Selective Eglin Inhibitors of HCV NS3 Proteinase", Biochemistry, 37:11459-11468 (1998).

Martin, et al., "Affinity Selection of a Carmelized VH Domain Antibody Inhibitor of Hepatitis C virus NS3 Protease", Protein Engineering, 10(5):607-614 (1997).

BioWorld Today, 9(217):1-5 (1998).

International Search Report for PCT Application No. PCT/US01/22678 dated Jun. 7, 2002.

International Search Report for PCT Application No. PCT/US2008/004549 dated Mar. 25, 2009.

* cited by examiner

SULFUR COMPOUNDS AS INHIBITORS OF HEPATITIS C VIRUS NS3 SERINE PROTEASE

FIELD OF THE INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention additionally discloses novel compounds as inhibitors of the HCV NS3/NS4a serine protease. This application claims priority from U.S. provisional application Ser. No. 60/548,670 filed Feb. 27, 2004.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH) (see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

Recently, an HCV protease necessary for polypeptide processing and viral replication has been identified, cloned and expressed. (See, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy. The inventive compounds can inhibit such protease. They also can modulate the processing of hepatitis C virus (HCV) polypeptide.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) Proc. Natl. Acad. Sci (USA) 91:888-892, Failla et al. (1996) Folding & Design 1:35-42. The NS3/NS4a cleavage site is also more tolerant of mutagenesis than the other sites. See, e.g., Kollykhalov et al. (1994) J. Virol. 68:7525-7533. It has also been found that acidic residues in the region upstream of the cleavage site are required for efficient cleavage. See, e.g., Komoda et al. (1994) J. Virol. 68:7351-7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) Biochem. 36:9340-9348, Ingallinella et al. (1998) Biochem. 37:8906-8914, Llinás-Brunet et al. (1998) Bioorg. Med. Chem. Lett. 8:1713-1718), inhibitors based on the 70-amino acid polypeptide eglin c (Martin et al. (1998) Biochem. 37:11459-11468, inhibitors affinity selected from human pancreatic secretory trypsin inhibitor (hPSTI-C3) and minibody repertoires (MBip) (Dimasi et al. (1997) J. Virol. 71:7461-7469), cV$_H$E2 (a "camelized" variable domain antibody fragment) (Martin et al. (1997) Protein Eng. 10:607-614), and α1-antichymotrypsin (ACT) (Elzouki et al.) (1997) J. Hepat. 27:42-28). A ribozyme designed to selectively destroy hepatitis C virus RNA has recently been disclosed (see, BioWorld Today 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

Reference is made to WO 00/59929 (U.S. Pat. No. 6,608,027, Assignee: Boehringer Ingelheim (Canada) Ltd.; Published Oct. 12, 2000) which discloses peptide derivatives of the formula:

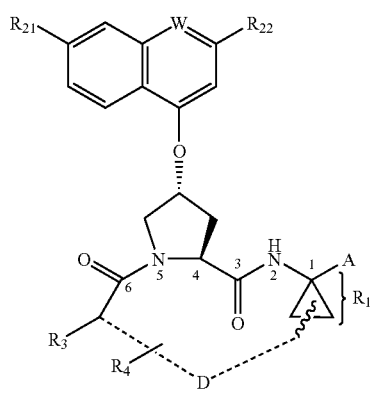

Reference is made to A. Marchetti et al, *Synlett*, S1, 1000-1002 (1999) describing the synthesis of bicylic analogs of an inhibitor of HCV NS3 protease. A compound disclosed therein has the formula:

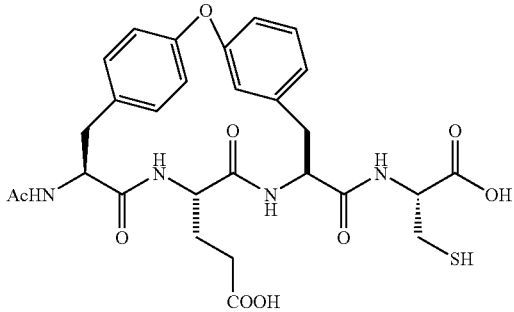

Reference is also made to W. Han et al, *Bioorganic & Medicinal Chem. Lett*, (2000) 10, 711-713, which describes the preparation of certain α-ketoamides, α-ketoesters and α-diketones containing allyl and ethyl functionalities.

Reference is also made to WO 00/09558 (Assignee: Boehringer Ingelheim Limited; Published Feb. 24, 2000) which discloses peptide derivatives of the formula:

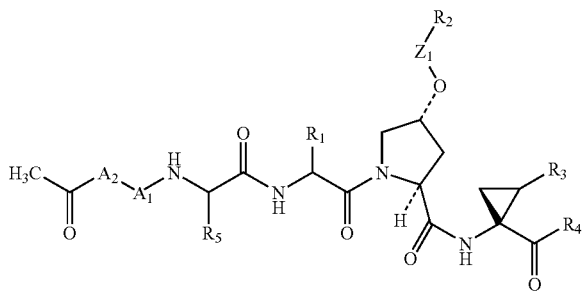

where the various elements are defined therein. An illustrative compound of that series is:

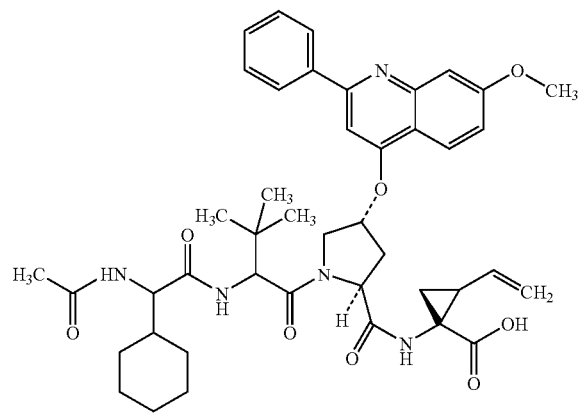

Reference is also made to WO 00/09543 (Assignee: Boehringer Ingelheim Limited; Published Feb. 24, 2000) which discloses peptide derivatives of the formula:

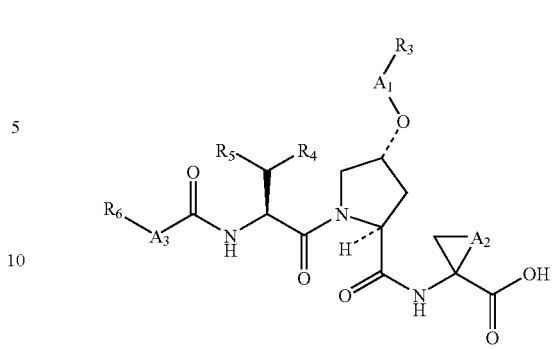

where the various elements are defined therein. An illustrative compound of that series is:

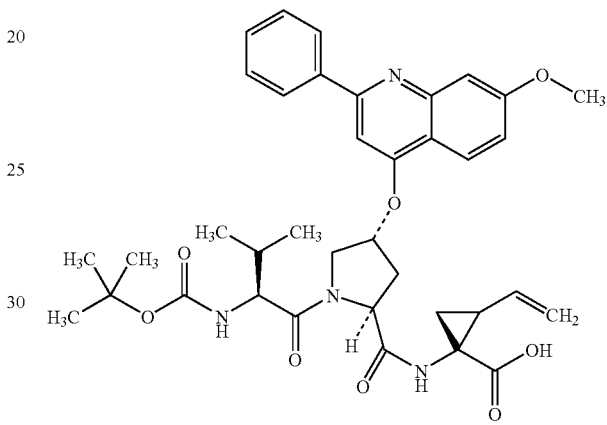

Reference is also made to U.S. Pat. No. 6,608,027 (Boehringer Ingelheim, Canada) which discloses NS3 protease inhibitors of the type:

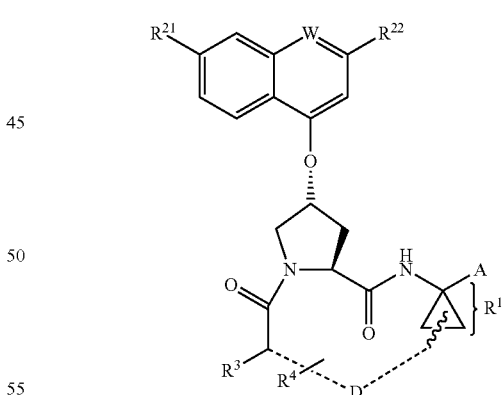

wherein the various moieties are defined therein.

Current therapies for hepatitis C include interferon-α (INF$_\alpha$) and combination therapy with ribavirin and interferon. See, e.g., Beremguer et al., (1998) *Proc. Assoc. Am. Physicians* 110(2):98-112. These therapies suffer from a low sustained response rate and frequent side effects. See, e.g., Hoofnagle et al. (1997) *N. Engl. J. Med.* 336:347. Currently, no vaccine is available for HCV infection.

Reference is further made to WO 01/74768 (Assignee: Vertex Pharmaceuticals Inc) published Oct. 11, 2001, which discloses certain compounds of the following general formula (R is defined therein) as NS3-serine protease inhibitors of Hepatitis C virus:

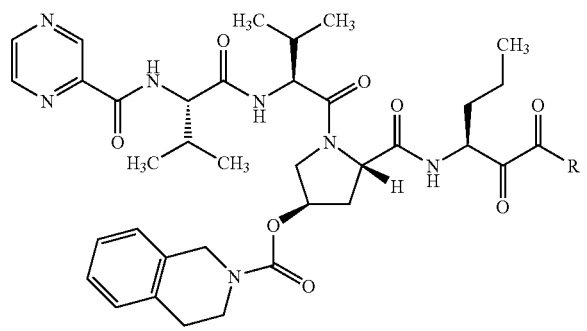

A specific compound disclosed in the afore-mentioned WO 01/74768 has the following formula:

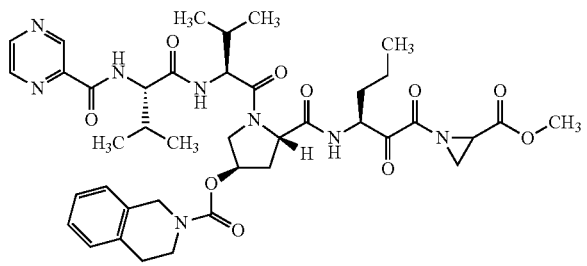

PCT Publications WO 01/77113; WO 01/081325; WO 02/08198; WO 02/08256; WO 02/08187; WO 02/08244; WO 02/48172; WO 02/08251; and pending U.S. patent application Ser. No. 10/052,386, filed Jan. 18, 2002, disclose various types of peptides and/or other compounds as NS-3 serine protease inhibitors of hepatitis C virus. The disclosures of those applications are incorporated herein by reference thereto.

There is a need for new treatments and therapies for HCV infection. There is a need for compounds useful in the treatment or prevention or amelioration of one or more symptoms of hepatitis C.

There is a need for methods of treatment or prevention or amelioration of one or more symptoms of hepatitis C.

There is a need for methods for modulating the activity of serine proteases, particularly the HCV NS3/NS4a serine protease, using the compounds provided herein.

There is a need for methods of modulating the processing of the HCV polypeptide using the compounds provided herein.

SUMMARY OF THE INVENTION

In its many embodiments, the present invention provides a novel class of inhibitors of the HCV protease, pharmaceutical compositions containing one or more of the compounds, methods of preparing pharmaceutical formulations comprising one or more such compounds, and methods of treatment or prevention of HCV or amelioration of one or more of the symptoms of hepatitis C using one or more such compounds or one or more such formulations. Also provided are methods of modulating the interaction of an HCV polypeptide with HCV protease. Among the compounds provided herein, compounds that inhibit HCV NS3/NS4a serine protease activity are preferred. The present invention discloses compounds, as well as pharmaceutically acceptable salts, solvates or esters of said compounds, said compounds having the general structure shown in structural Formula I:

Formula I

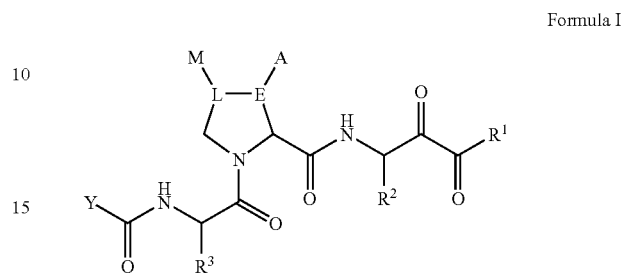

wherein:

$R^1$ is H, $OR^8$, $NR^9R^{10}$, or $CHR^9R^{10}$, wherein $R^8$, $R^9$ and $R^{10}$ can be the same or different, each being independently selected from the group consisting of H, alkyl-, alkenyl-, alkynyl-, aryl-, heteroalkyl-, heteroaryl-, cycloalkyl-, heterocyclyl-, arylalkyl-, and heteroarylalkyl;

A and M can be the same or different, each being independently selected from R, OR, NHR, NRR', SR, $SO_2R$, and halo; or A and M are connected to each other such that the moiety:

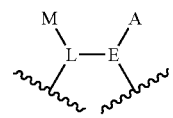

shown above in Formula I forms either a three, four, six, seven or eight-membered cycloalkyl, a four to eight-membered heterocyclyl, a six to ten-membered aryl, or a five to ten-membered heteroaryl;

E is C(H) or C(R);

L is C(H), C(R), $CH_2C(R)$, or $C(R)CH_2$;

R, R', $R^2$, and $R^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that NRR' forms a four to eight-membered heterocyclyl;

and Y is selected from the following moieties:

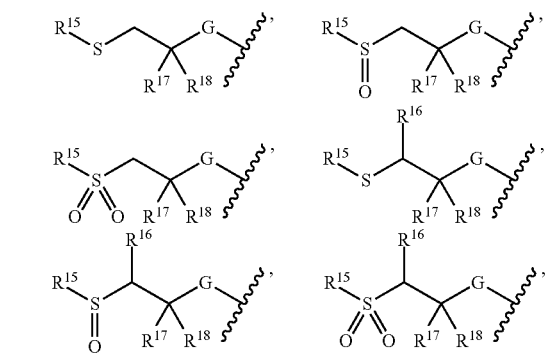

-continued

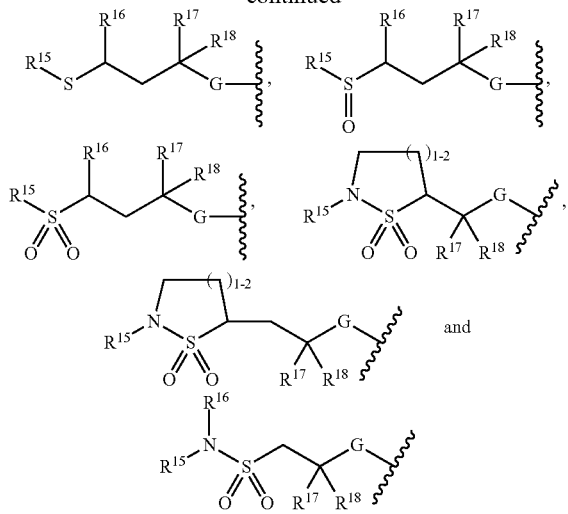

wherein G is NH or O; and $R^{15}$, $R^{16}$, $R^{17}$ and $R^{18}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or_alternately, (i) $R^{15}$ and $R^{16}$ are connected to each other to form a four to eight-membered cyclic structure, and (ii) likewise, independently $R^{17}$ and $R^{18}$ are connected to each other to form a three to eight-membered cycloalkyl or heterocyclyl; wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkylsulfonamido, arylsulfonamido, alkyl, aryl, heteroaryl, keto, carboxy, carbalkoxy, carboxamido, alkoxycarbonylamino, alkoxycarbonyloxy, alkylureido, arylureido, halo, cyano, and nitro.

The above-noted statement "A and M are connected to each other such that the moiety:

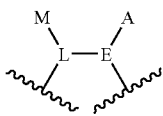

shown above in Formula I forms either a three, four, six, seven or eight-membered cycloalkyl, a four to eight-membered heterocyclyl, a six to ten-membered aryl, or a five to ten-membered heteroaryl" can be illustrated in a non-limiting manner as follows. Thus, for example, in the case where A and M are connected such that the moiety:

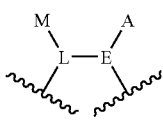

shown above in Formula I forms a six-membered cycloalkyl (cyclohexyl), Formula I can be depicted as:

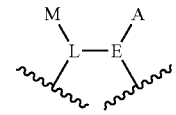

One with ordinary skill in the art will appreciate that similar depictions for Formula I can be arrived at when A and M shown above in the moiety:

$$\underset{L-E}{\overset{M\phantom{-}A}{\diagdown\phantom{-}\diagup}}$$

(M-L-E-A taken together) are connected to form a three, four, seven or eight-membered cycloalkyl, a four to eight-membered heterocyclyl, a six to ten-membered aryl, or a five to ten-membered heteroaryl.

The statement "alternately, (i) $R^{15}$ and $R^{16}$ are connected to each other to form a four to eight-membered cyclic structure, and (ii) likewise, independently $R^{17}$ and $R^{18}$ are connected to form a three to eight-membered cycloalkyl or heterocyclyl" means the following possibilities: (i) $R^{15}$ and $R^{16}$ are connected to form a cyclic structure while $R^{17}$ and $R^{18}$ are not; (ii) $R^{17}$ and $R^{18}$ are connected to form a cyclic structure while $R^{15}$ and $R^{16}$ are not; and (iii) $R^{15}$ and $R^{16}$ are connected to form a cyclic structure, and $R^{17}$ and $R^{18}$ are also connected to form a cyclic structure. These possibilities can occur independent of one another.

In the above noted definitions of R, R', $R^2$ and $R^3$, preferred alkyl is made of one to ten carbon atoms, preferred alkenyl or alkynyl is made of two to ten carbon atoms, preferred cycloalkyl is made of three to eight carbon atoms, and preferred heteroalkyl, heteroaryl or heterocycloalkyl has one to six oxygen, nitrogen, sulfur, or phosphorus atoms.

The compounds represented by Formula I, by themselves or in combination with one or more other suitable agents disclosed herein, can be useful for treating diseases such as, for example, HCV, HIV, (AIDS, Acquired Immune Deficiency Syndrome), and related disorders, as well as for modulating the activity of hepatitis C virus (HCV) protease, preventing HCV, or ameliorating one or more symptoms of hepatitis C. Such modulation, treatment, prevention or amelioration can be done with the inventive compounds as well as with pharmaceutical compositions or formulations comprising such compounds. Without being limited to theory, it is believed that the HCV protease may be the NS3 or NS4a protease. The inventive compounds can inhibit such protease. They can also modulate the processing of hepatitis C virus (HCV) polypeptide.

DETAILED DESCRIPTION

In an embodiment, the present invention discloses compounds which are represented by structural Formula I or a pharmaceutically acceptable salt or solvate or ester thereof, wherein the various moieties are as defined above.

In another embodiment, $R^1$ is $NR^9R^{10}$, and $R^9$ is H, $R^{10}$ is H, or $R^{14}$ wherein $R^{14}$ is H, alkyl, aryl, heteroalkyl, heteroaryl, cycloalkyl, alkyl-aryl, alkyl-heteroaryl, aryl-alkyl, alkenyl, alkynyl or heteroaryl-alkyl.

In another embodiment, $R^{14}$ is selected from the group consisting of:

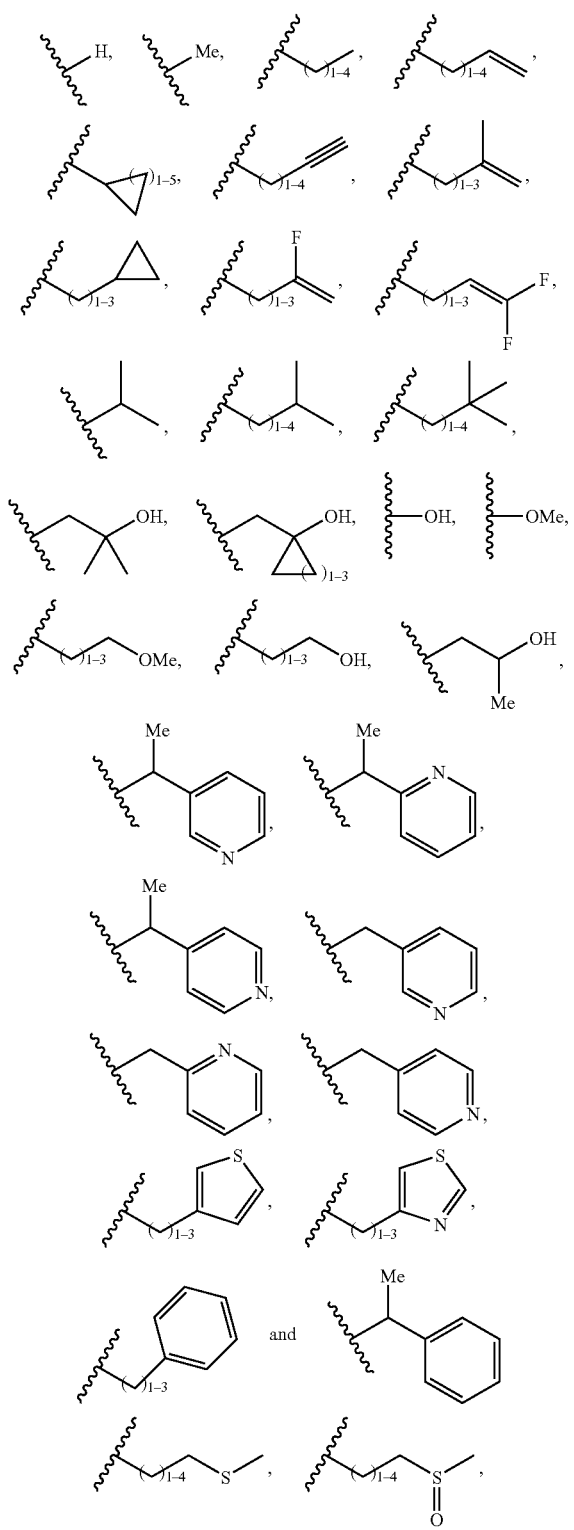

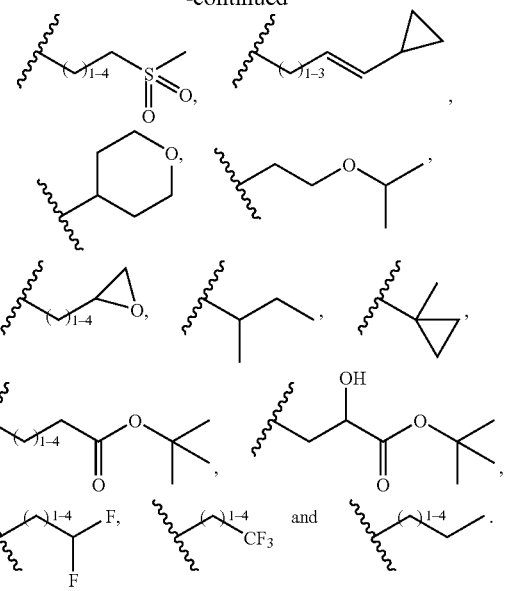

In another embodiment, $R^2$ is selected from the group consisting of the following moieties:

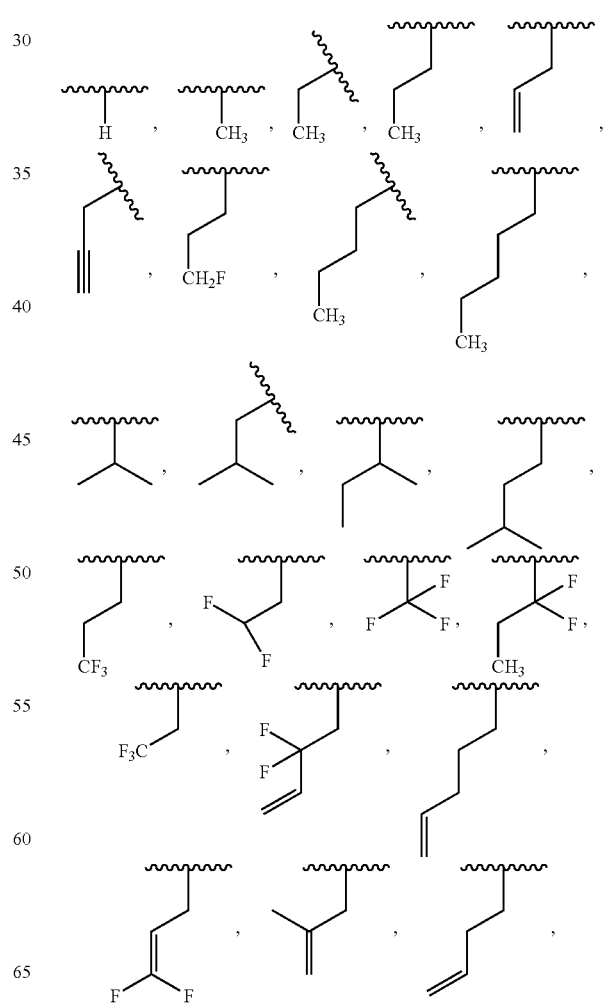

-continued
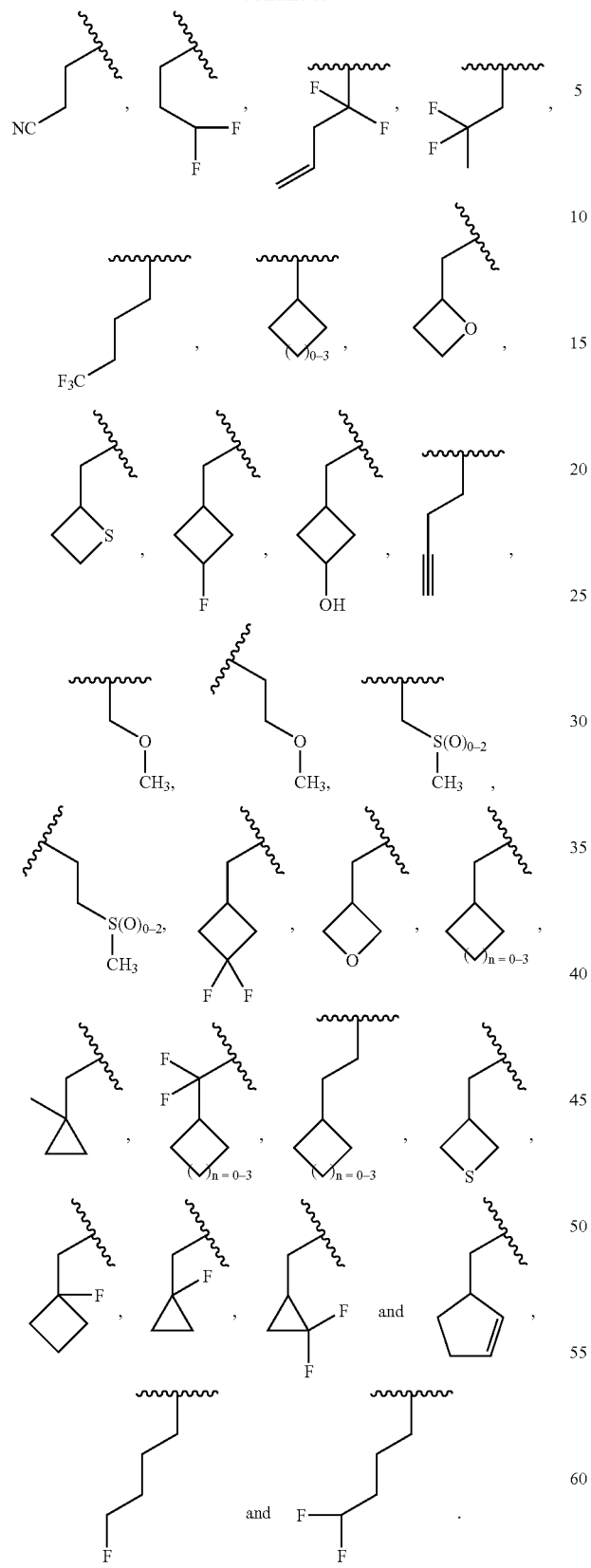
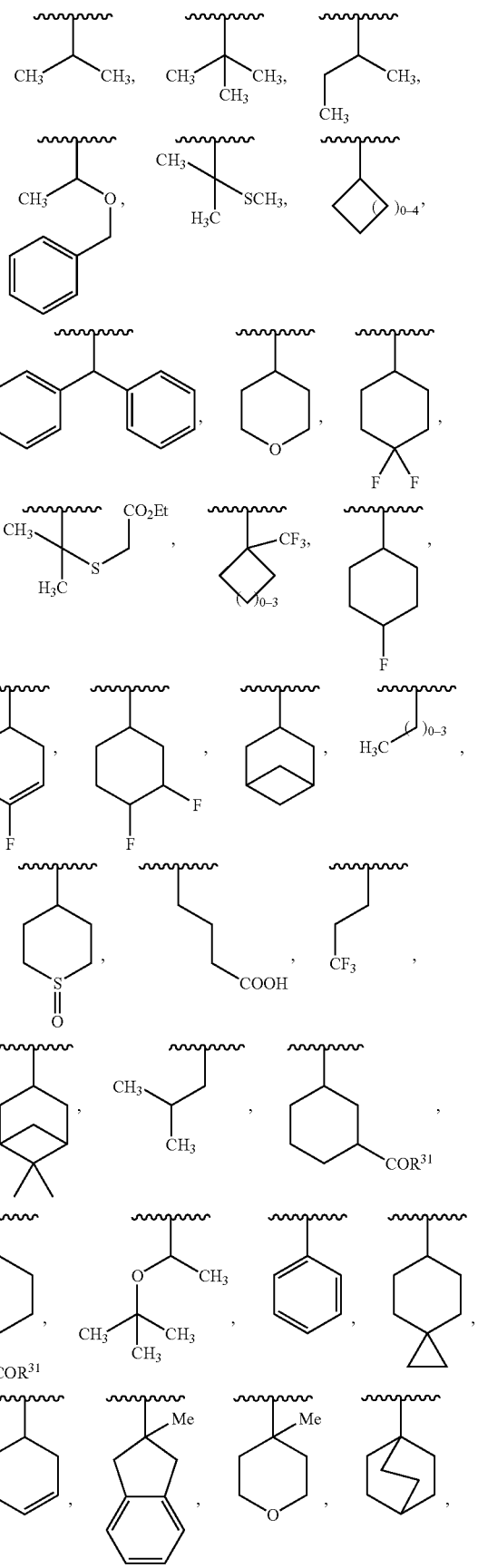
In another embodiment, $R^3$ is selected from the group consisting of:

-continued
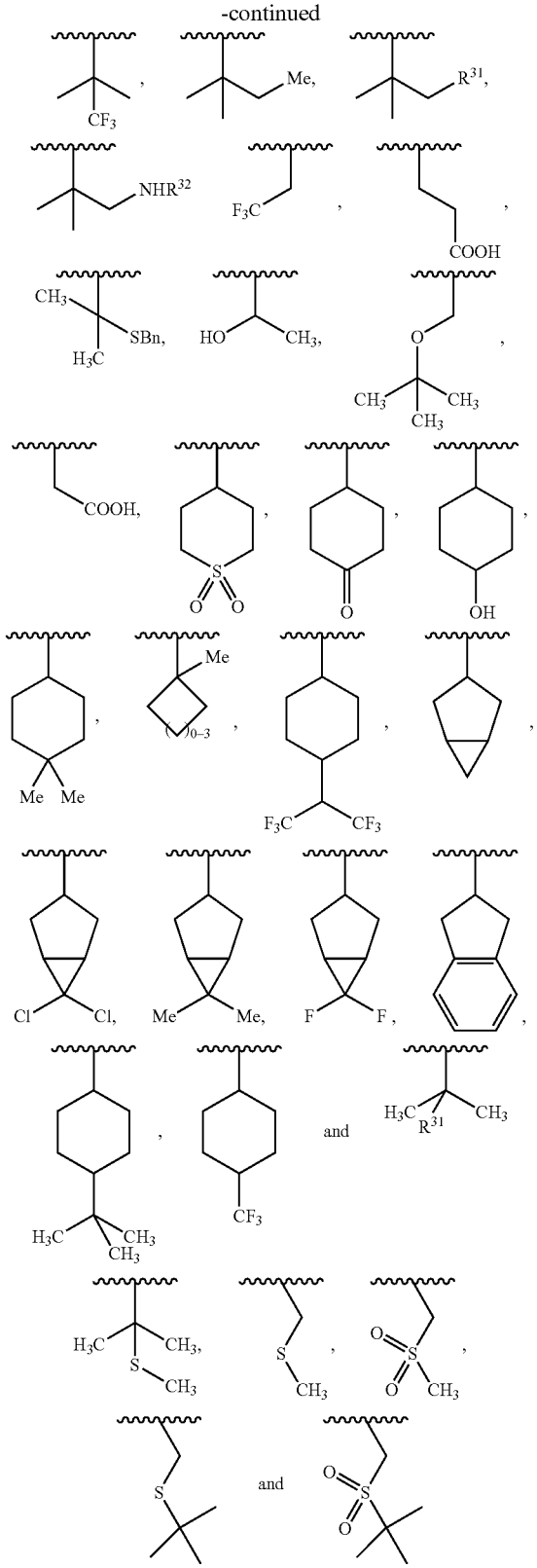
wherein $R^{31}$ is OH or O-alkyl; and
$R^{32}$ is H, C(O)CH$_3$, C(O)OtBu or C(O)N(H)tBu. In an additional embodiment, $R^3$ is selected from the group consisting of the following moieties:
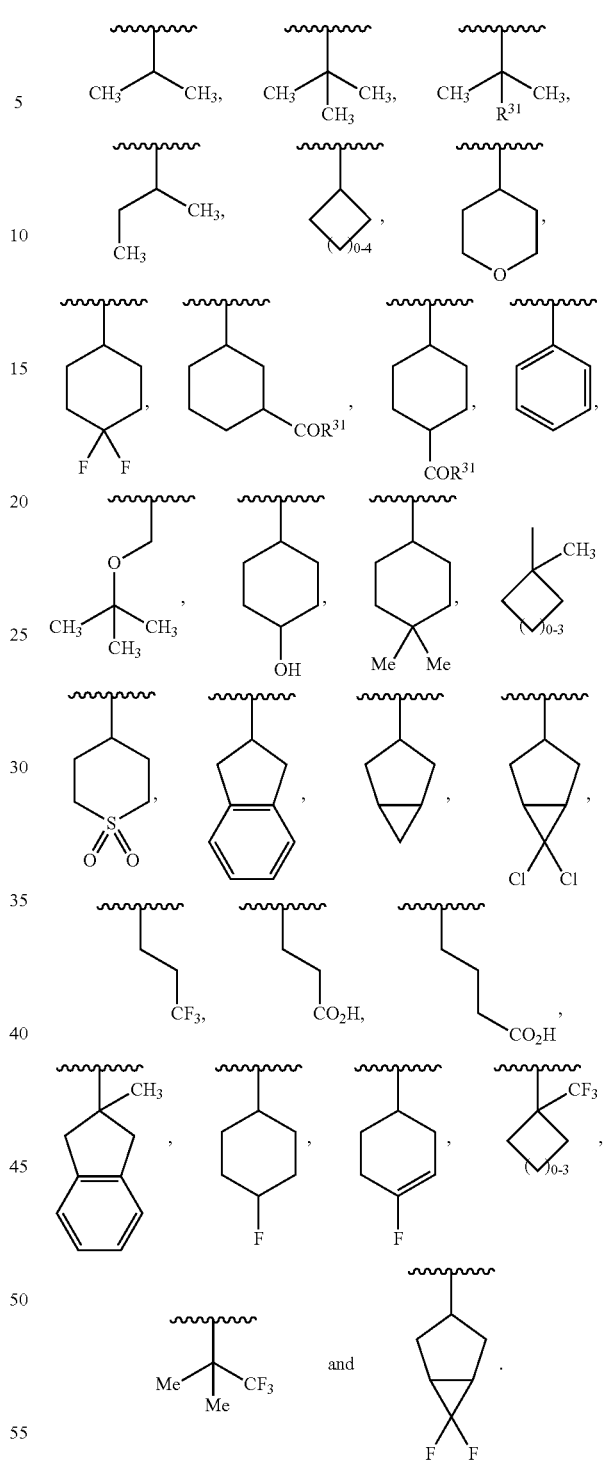
In another embodiment, Y is selected from the following moieties:
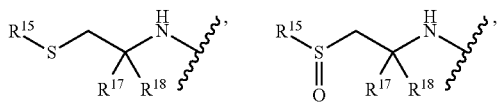

-continued

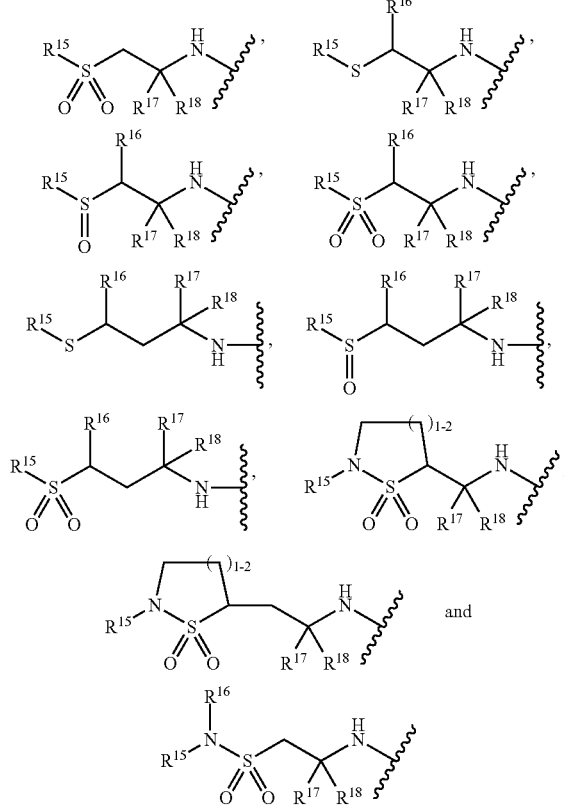

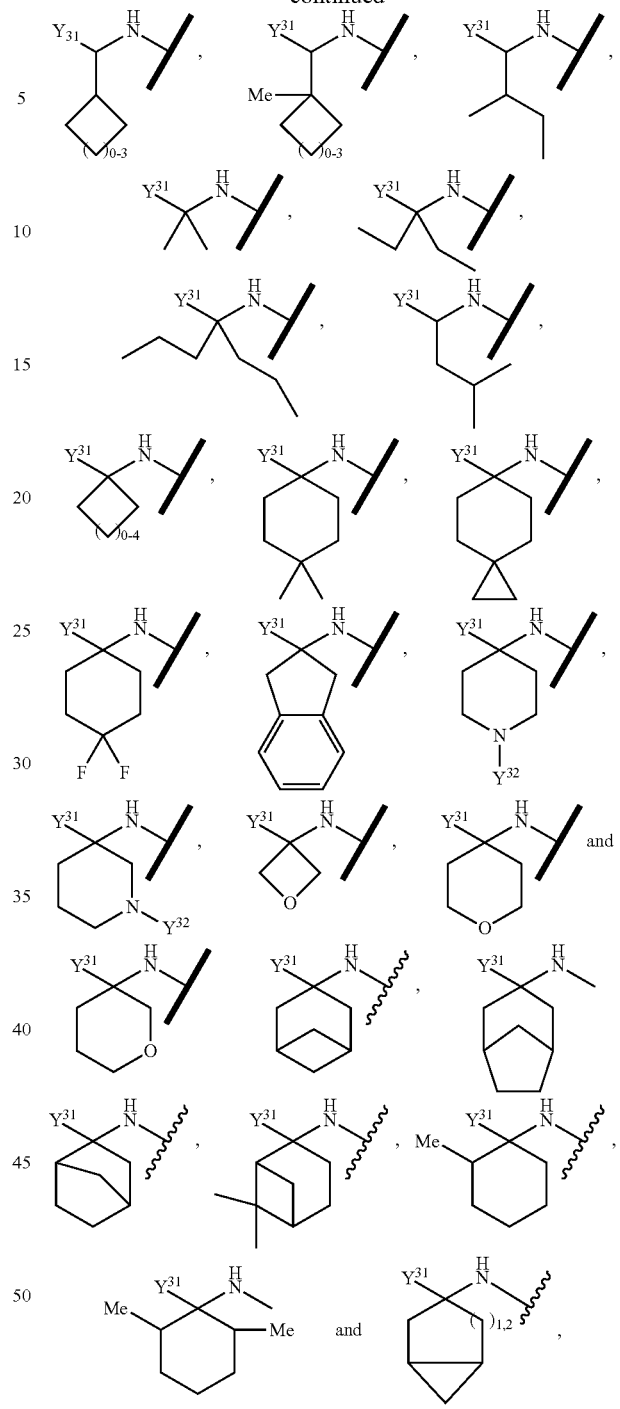

wherein $R^{15}$, $R^{16}$, $R^{17}$ and $R^{18}$ can be the same or different, each being independently selected from the group consisting of H, alkyl, heteroalkyl, alkenyl, heteroalkenyl, alkynyl, heteroalkynyl, cycloalkyl, heterocyclyl, aryl, and heteroaryl, or alternately, $R^{15}$ and $R^{16}$ are connected to each other to form a four to eight-membered cycloalkyl or heterocyclic structure, and/or $R^{17}$ and $R^{18}$ are connected to each other to form a three to eight-membered cycloalkyl or heterocyclyl, wherein each of said aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkylsulfonamido, arylsulfonamido, carboxy, carbalkoxy, carboxamido, alkoxycarbonylamino, alkoxycarbonyloxy, alkylureido, arylureido, halo, cyano, and nitro.

In an additional embodiment, Y is selected from the group consisting of:

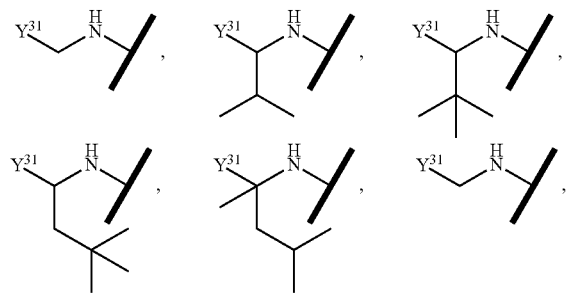

wherein $Y^{31}$ selected from the group consisting of:

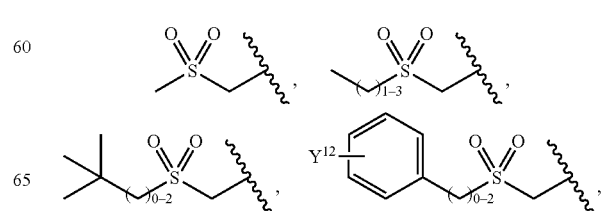

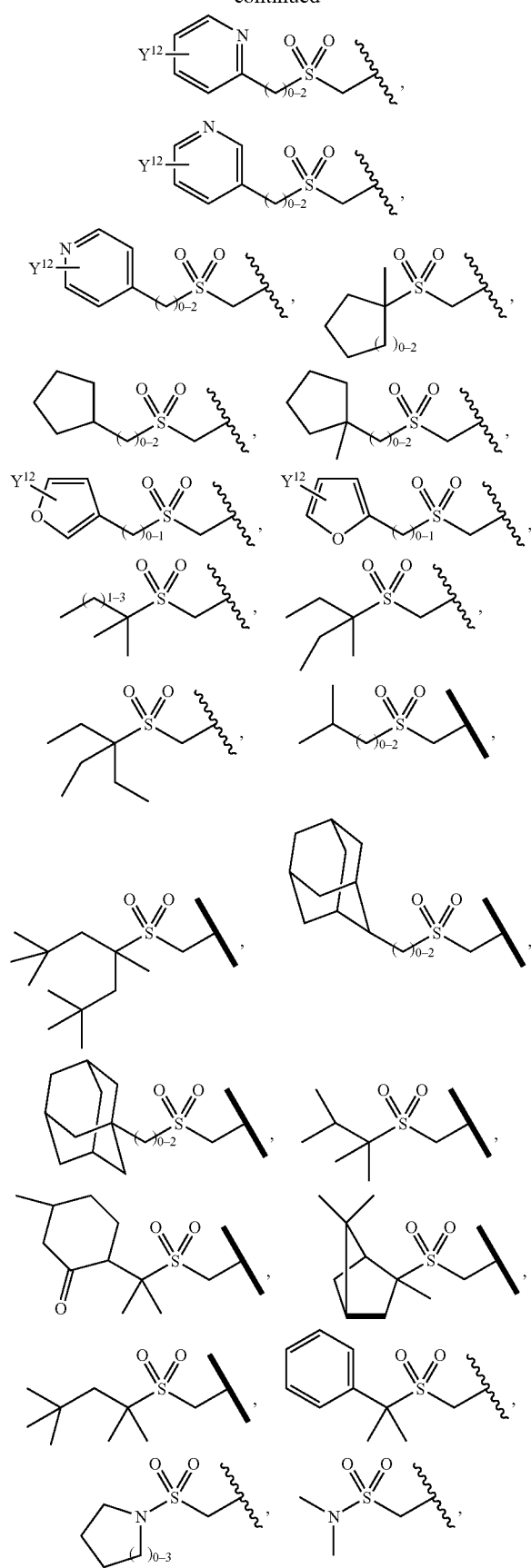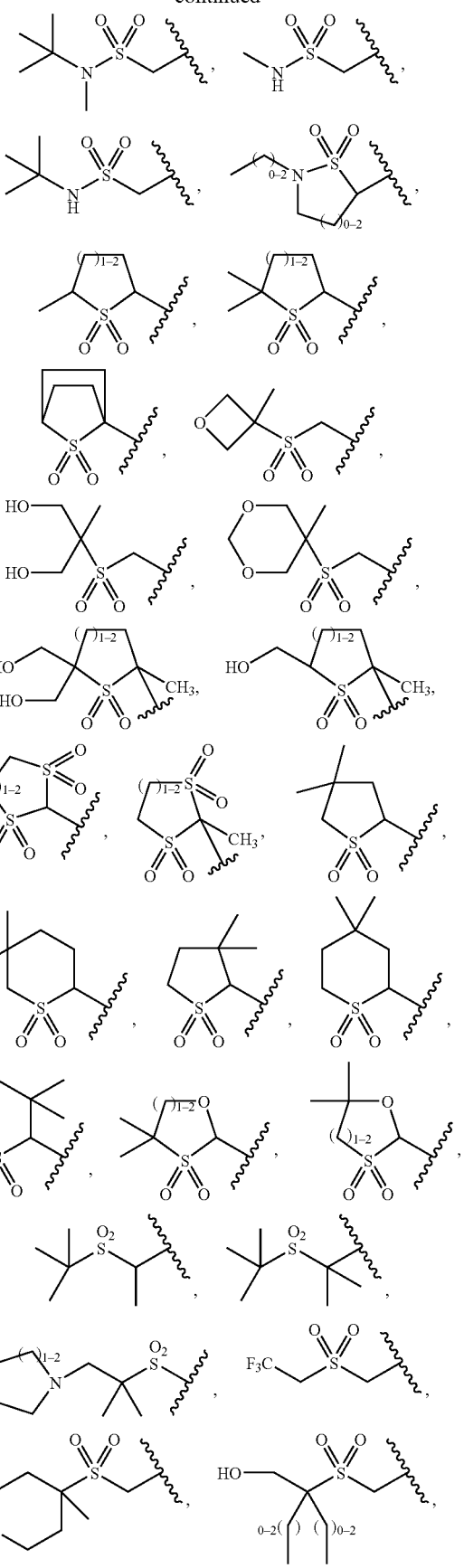

-continued
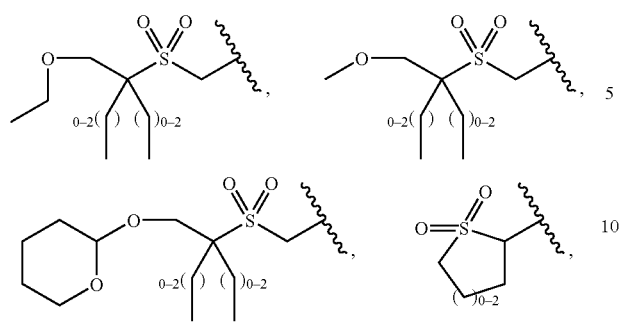
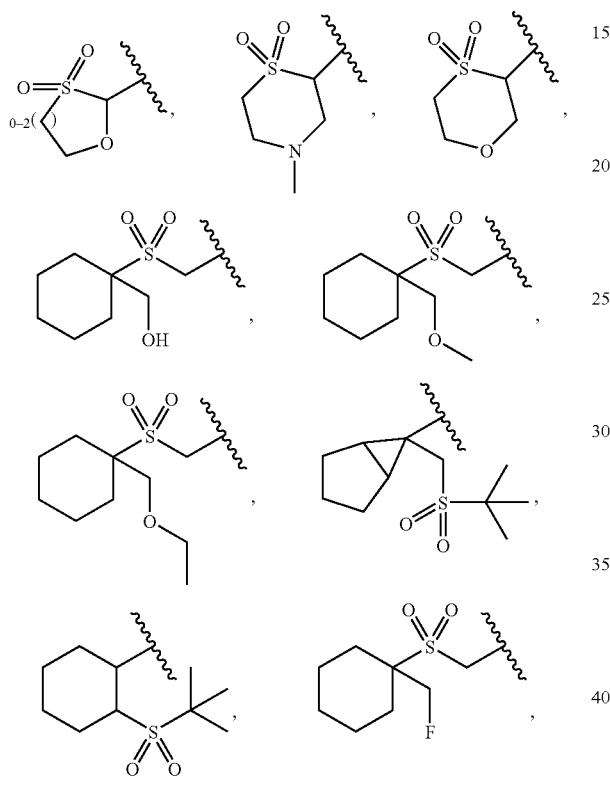
$Y^{32}$ selected from the group consisting of:
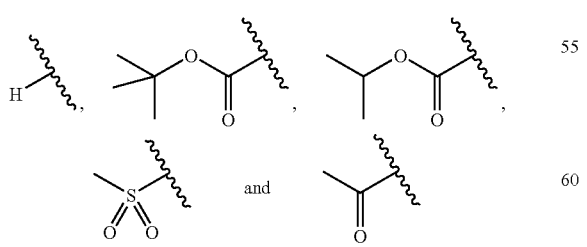
and $Y^{12}$ is selected from the group consisting of H, CO$_2$H, CO$_2$Me, OMe, F, Cl, Br, NH$_2$, N(H)S(O$_2$)CH$_3$, N(H)C(O)CH$_3$, NO$_2$, S(O$_2$)NH$_2$, CF$_3$, Me, OH, OCF$_3$, and C(O)NH$_2$.
In another embodiment, the moiety:
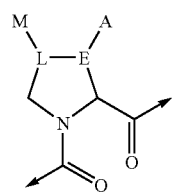
is selected from the following structures:
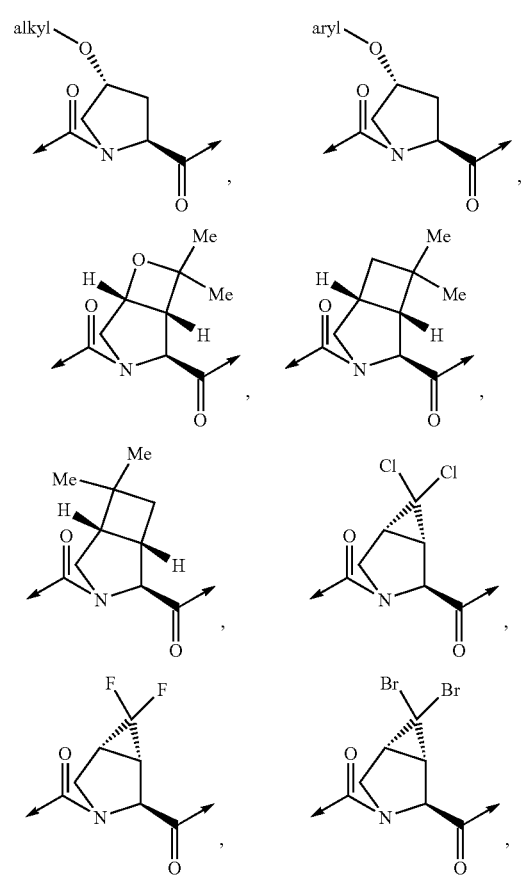
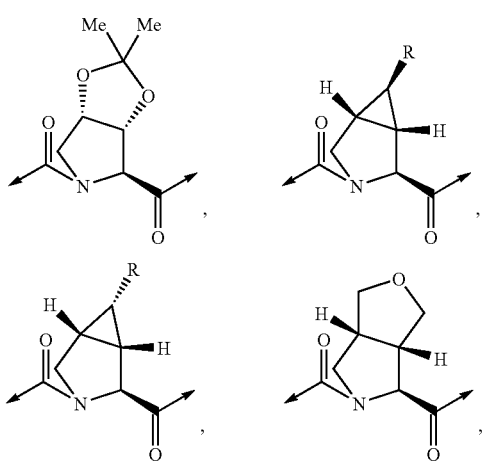

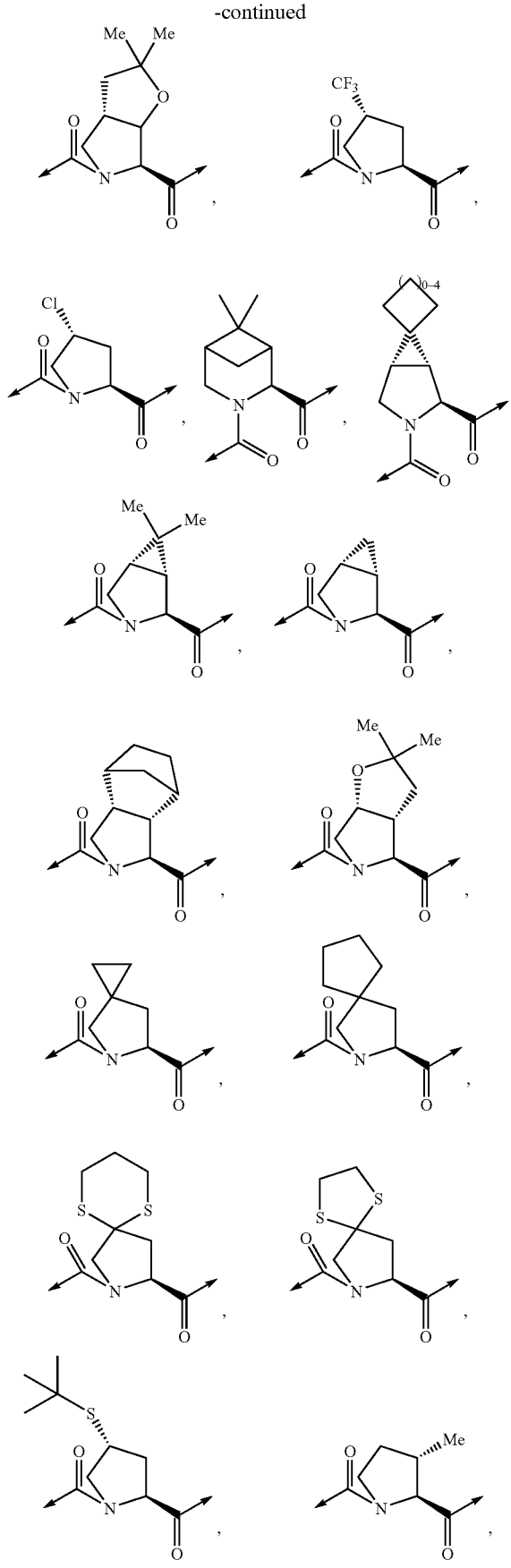
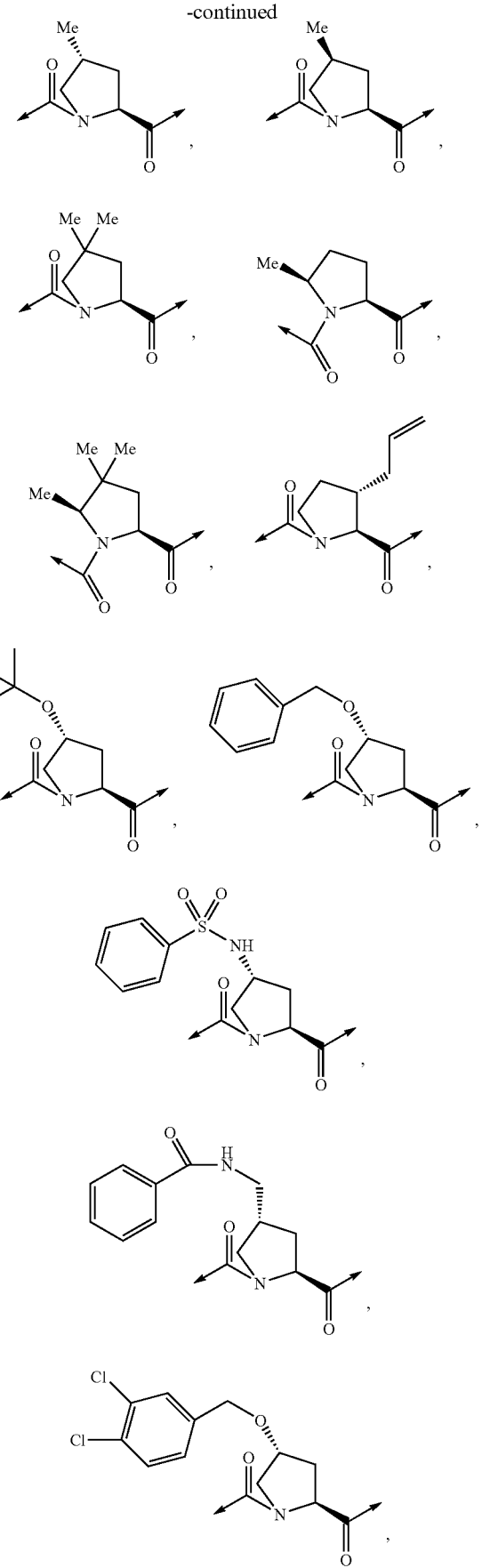

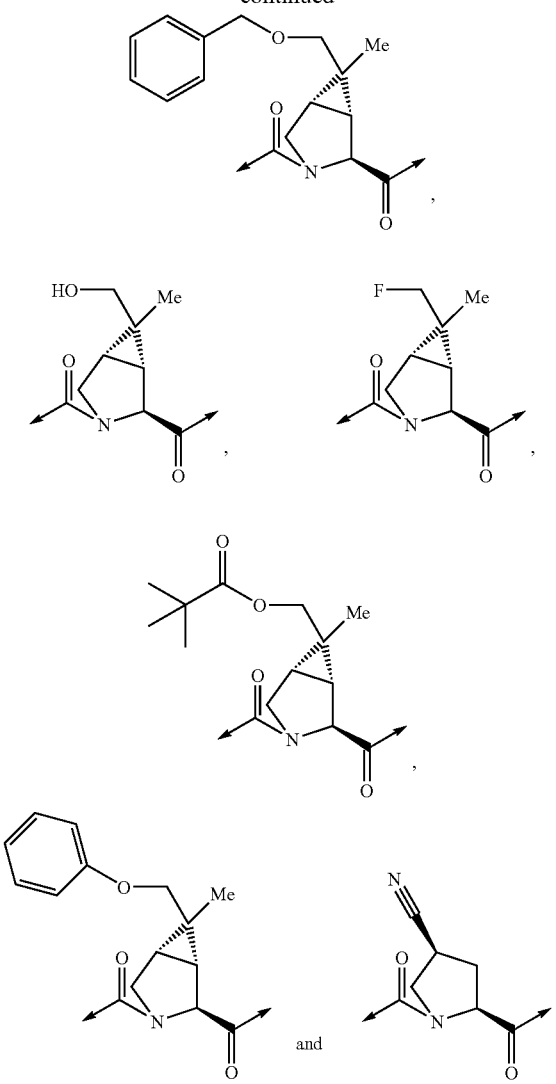
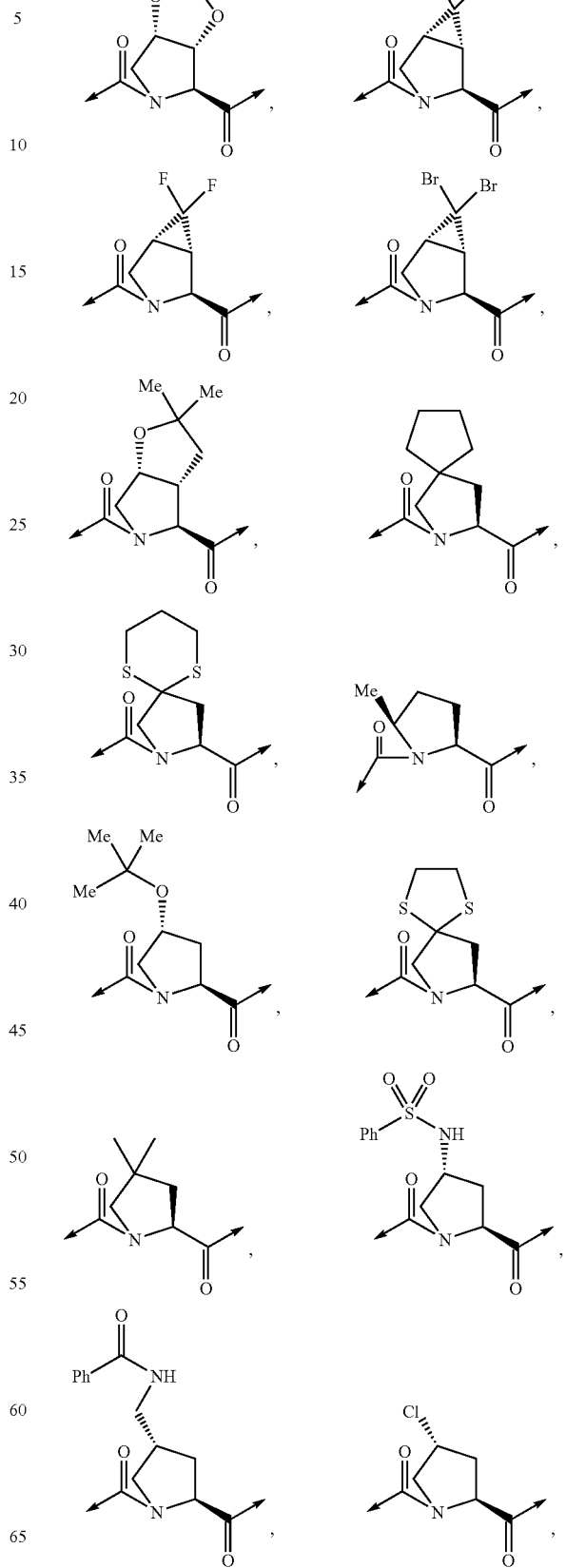
In an additional embodiment, the moiety:
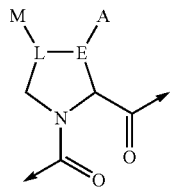
is selected from the following structures:
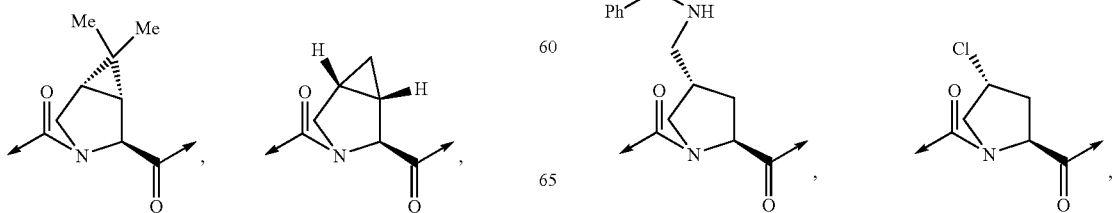

-continued
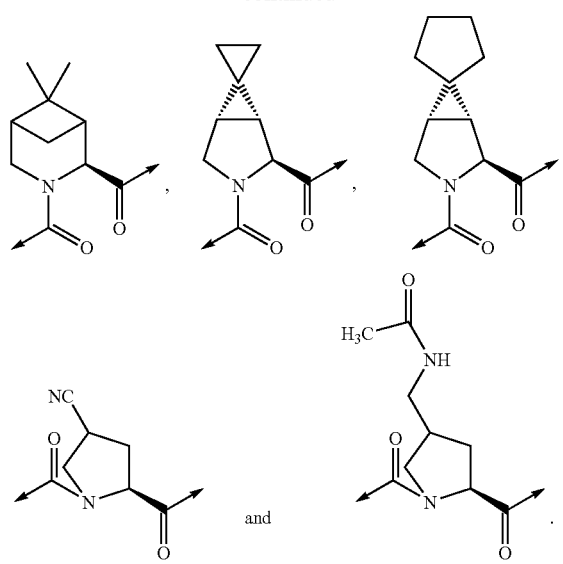
In an additional embodiment, the moiety:
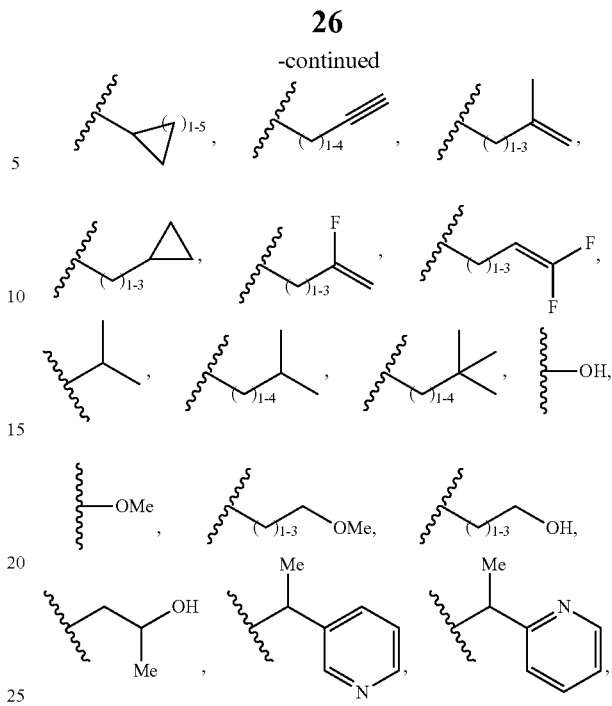
is selected from the following structures:
In a still additional embodiment, $R^1$ is $NHR^{14}$, where $R^{14}$ is selected from the group consisting of:
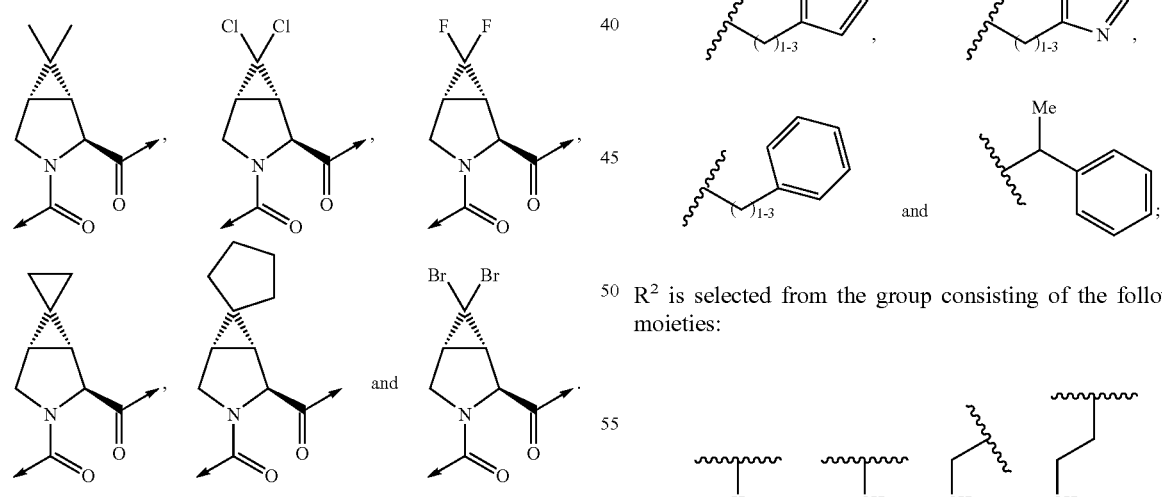
$R^2$ is selected from the group consisting of the following moieties:
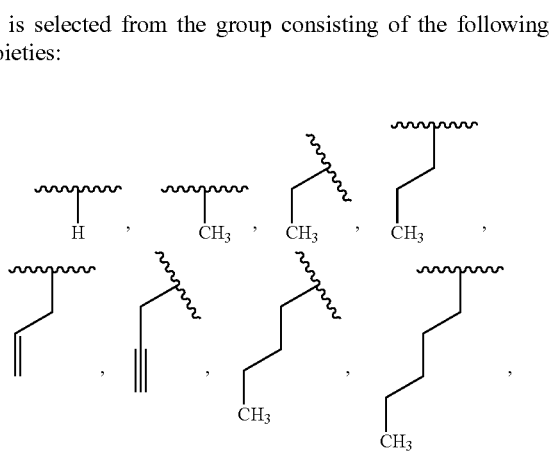

-continued
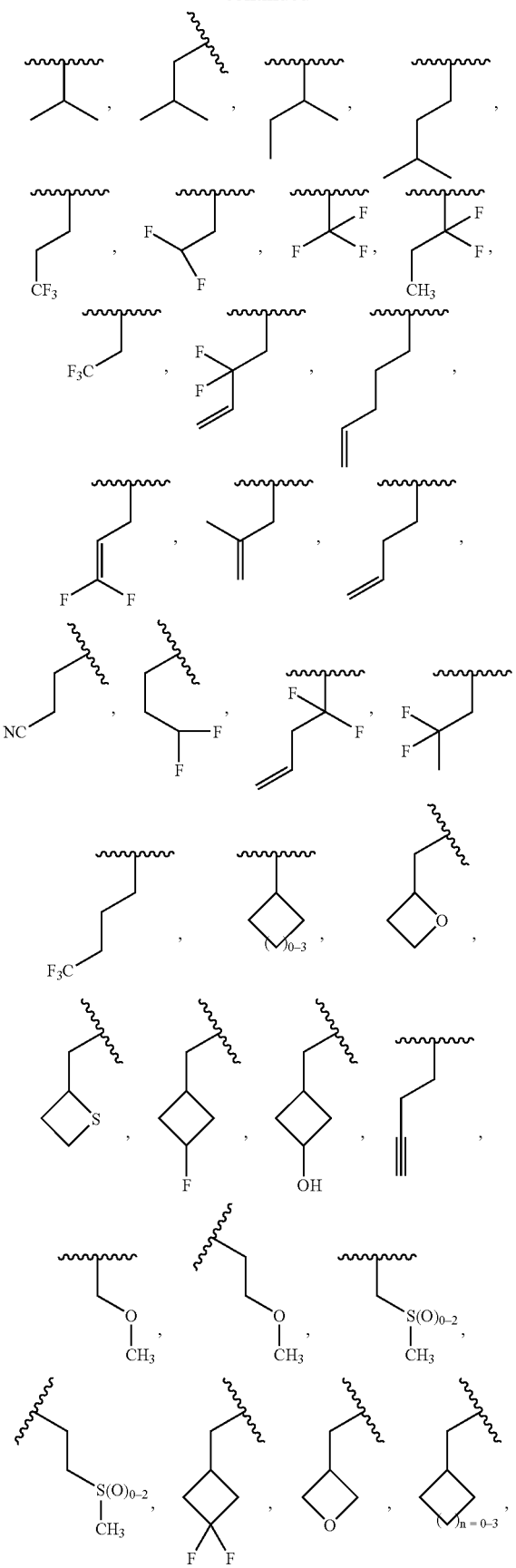
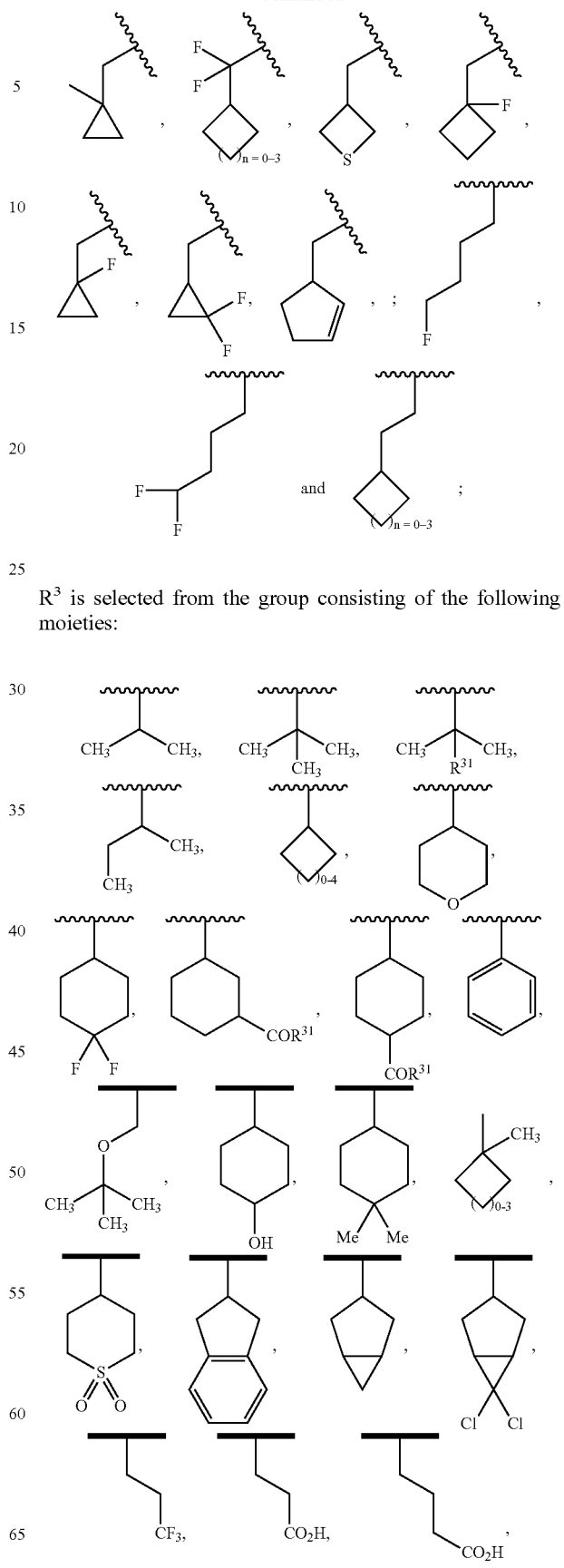
$R^3$ is selected from the group consisting of the following moieties:

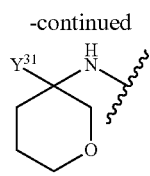
-continued
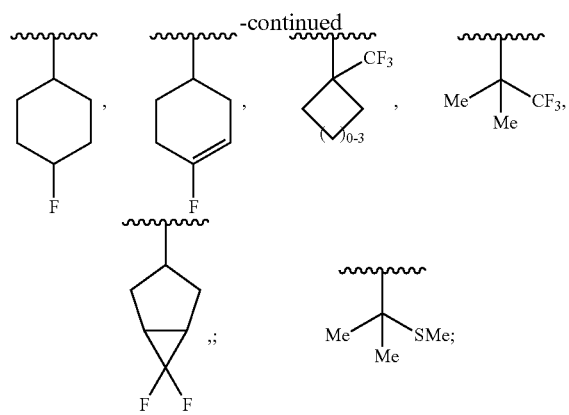
Y is selected from the group consisting of:
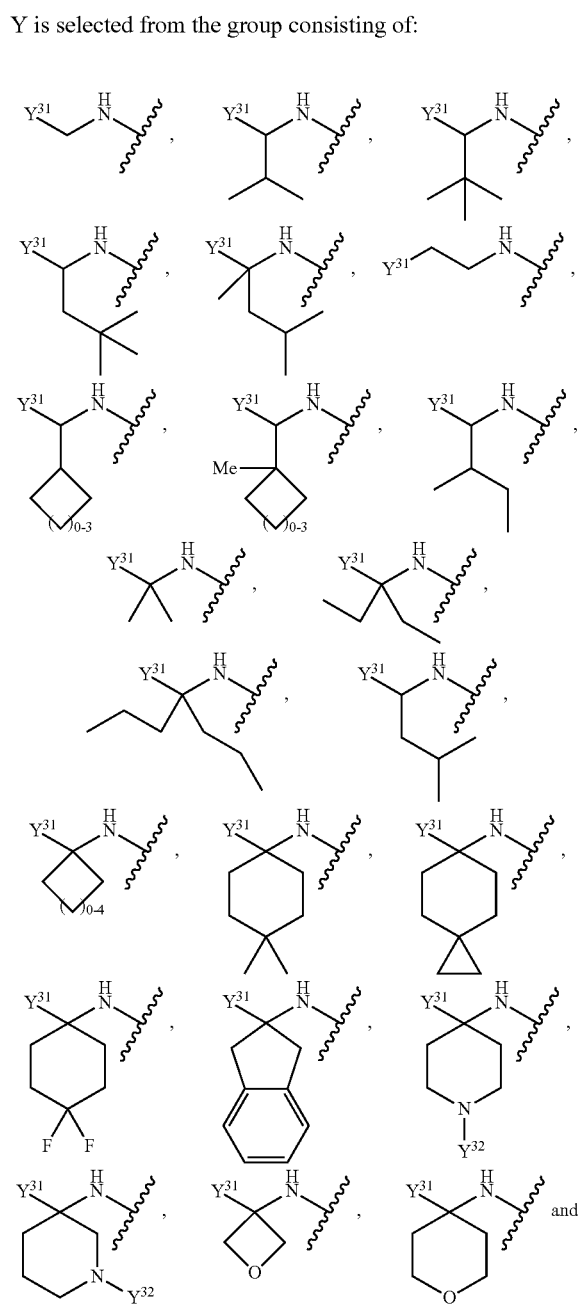
-continued
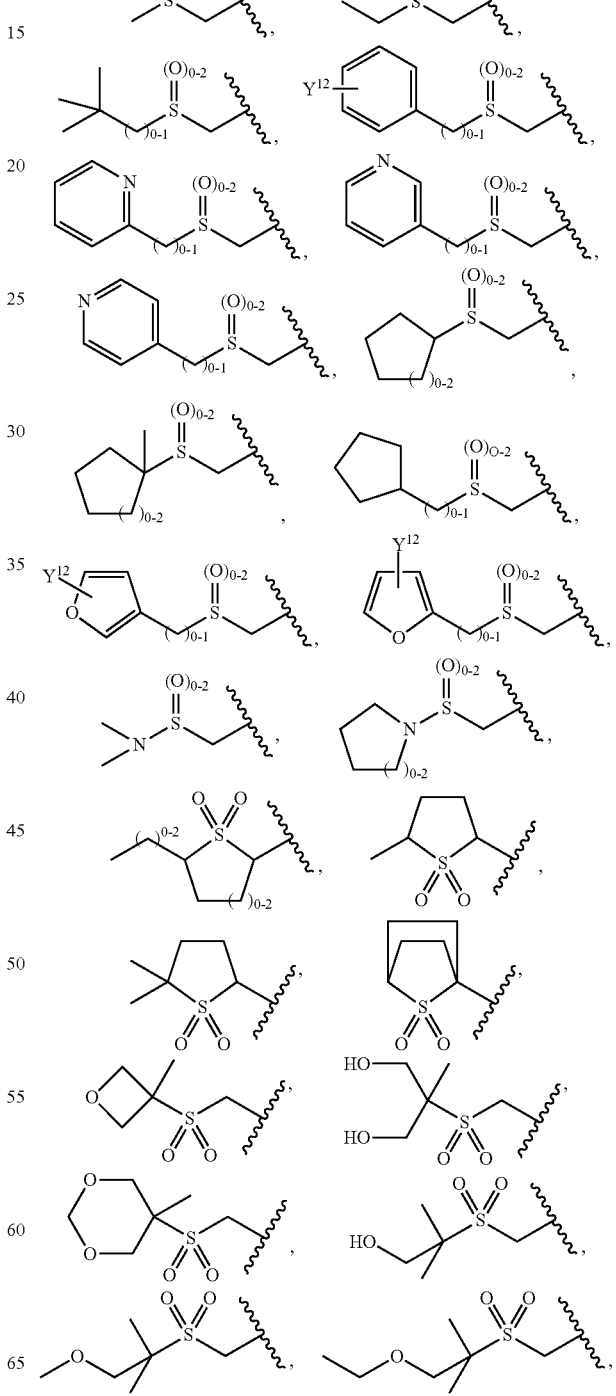
wherein $Y^{31}$ is selected from the group consisting of:

-continued

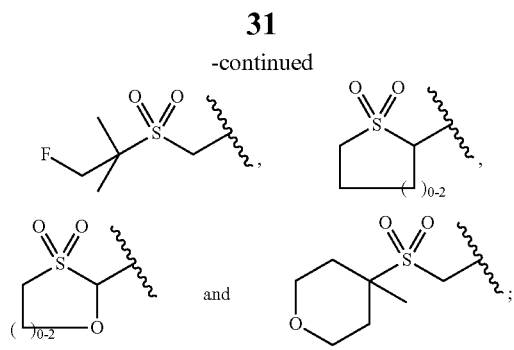

$Y^{32}$ is selected from the group consisting of:

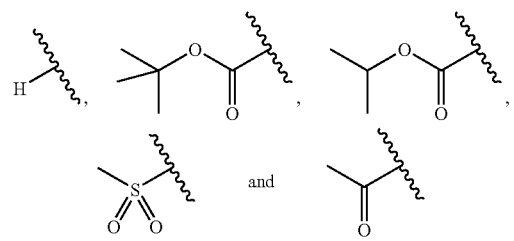

and $Y^{12}$ is selected from the group consisting of H, $CO_2H$, $CO_2Me$, OMe, F, Cl, Br, $NH_2$, $N(H)S(O_2)CH_3$, $N(H)C(O)CH_3$, $NO_2$, $S(O_2)NH_2$, $CF_3$, Me, OH, $OCF_3$, and $C(O)NH_2$; and the moiety:

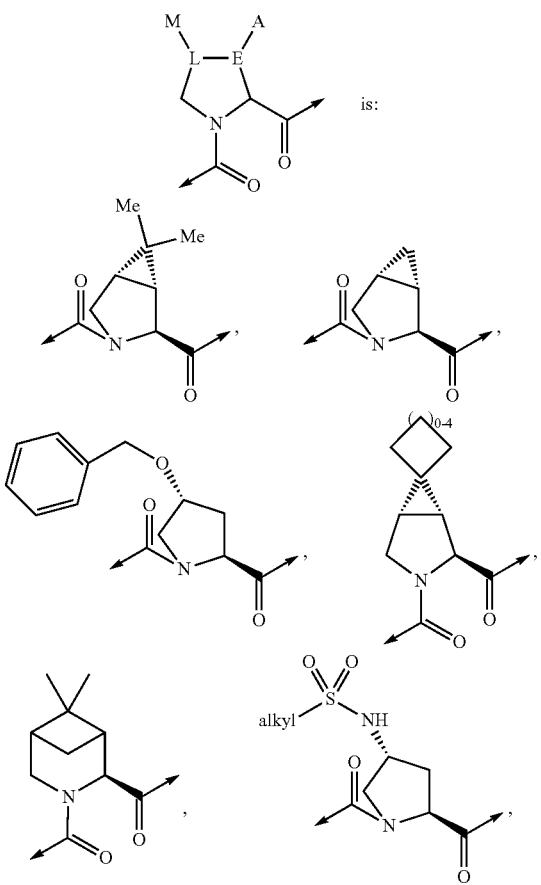

-continued

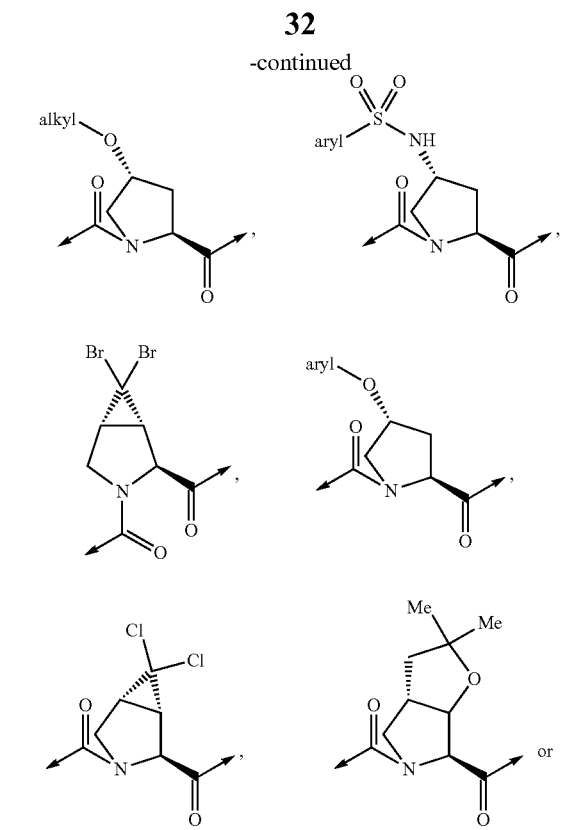

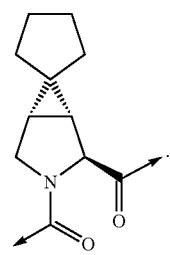

or

Yet another embodiment of the invention discloses compounds in Table 1 below, as well as shown later in Table 1, Table 3, Table 3A, Table 4, Table 4A and Table 5:

TABLE 1

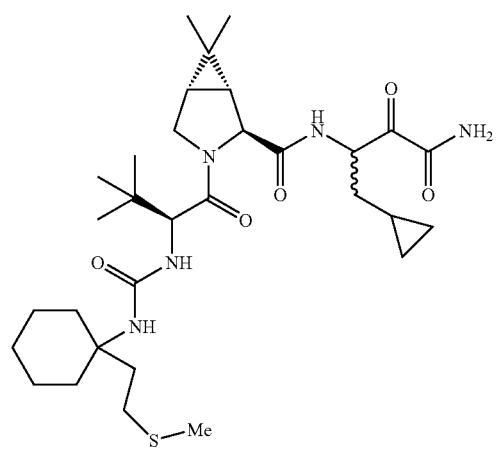

TABLE 1-continued
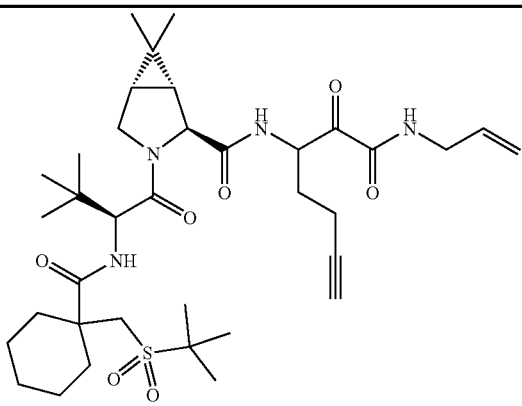
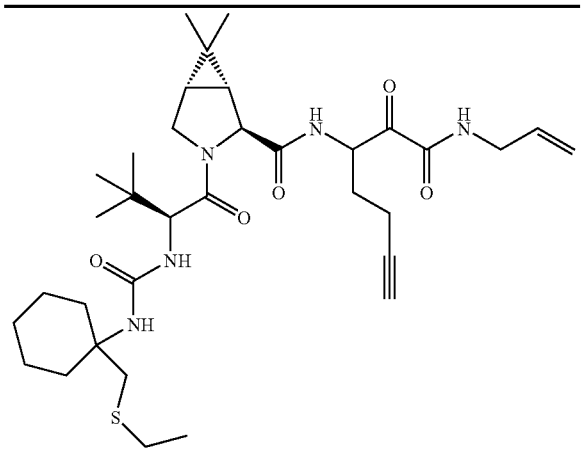
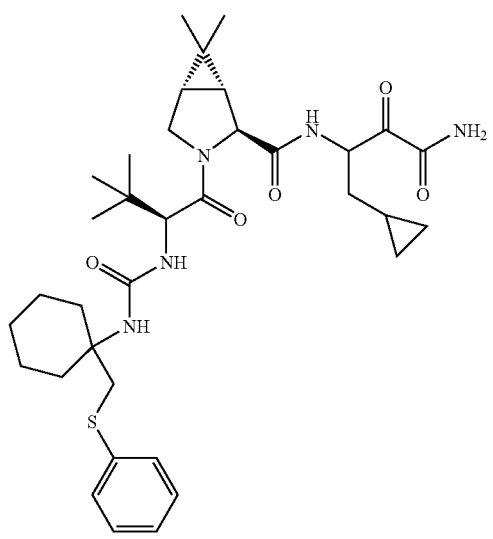
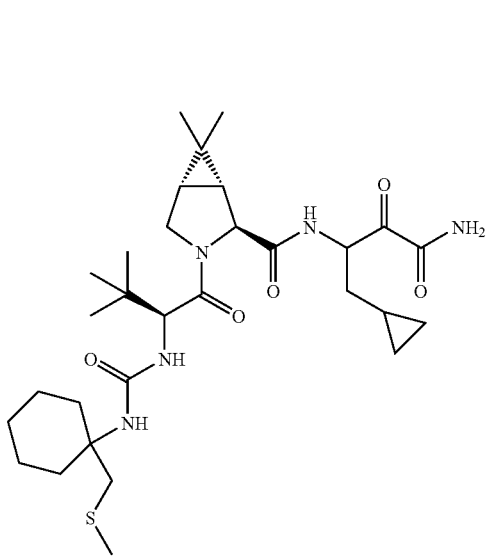
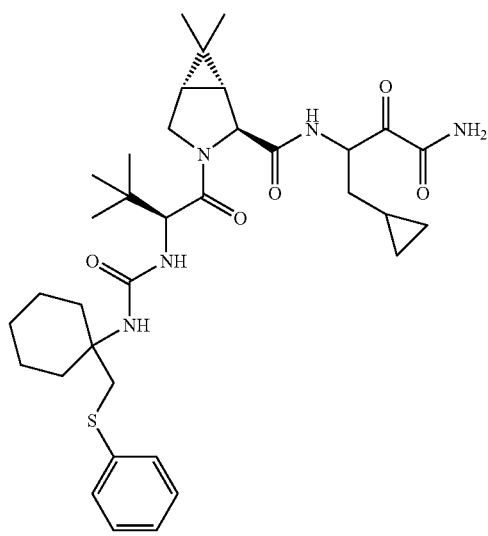

TABLE 1-continued
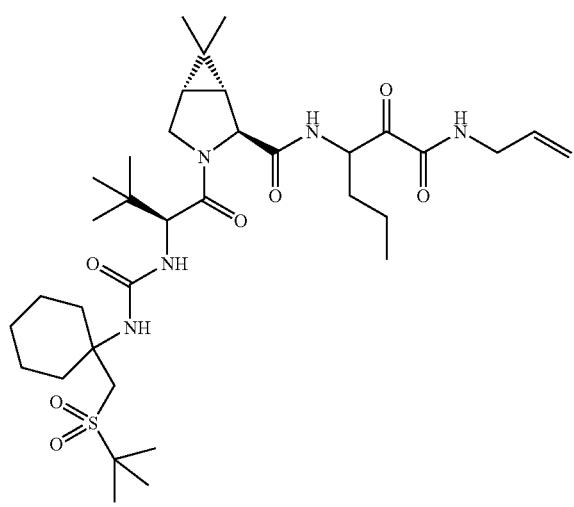
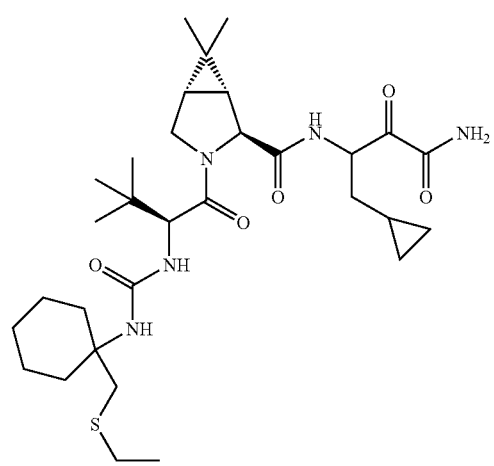
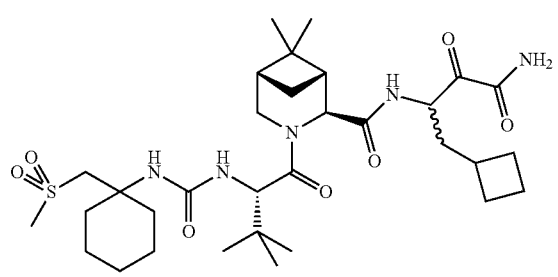
TABLE 1-continued
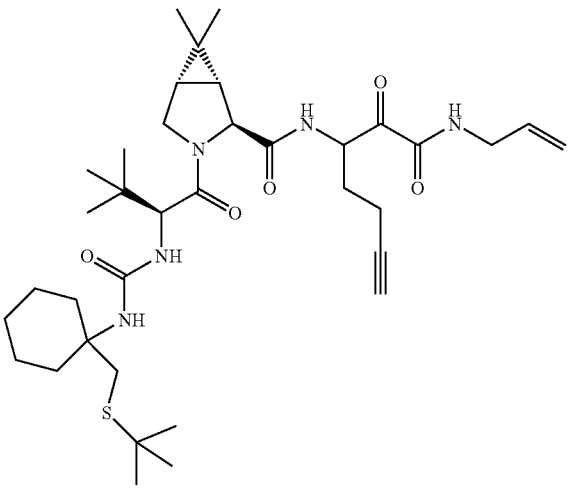
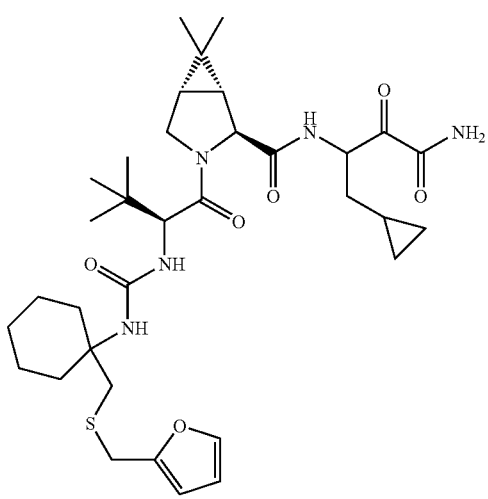

TABLE 1-continued
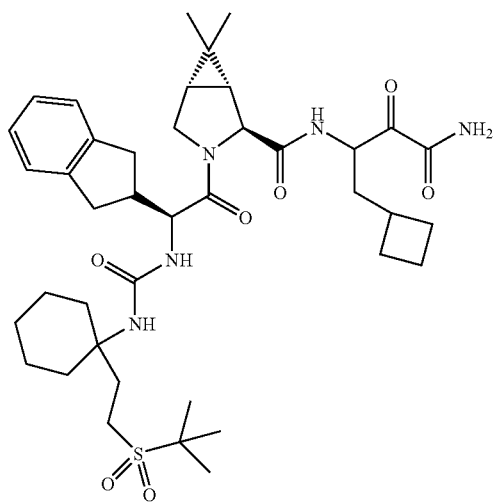
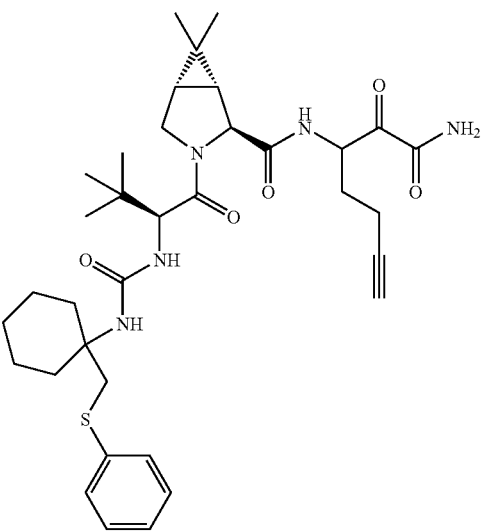
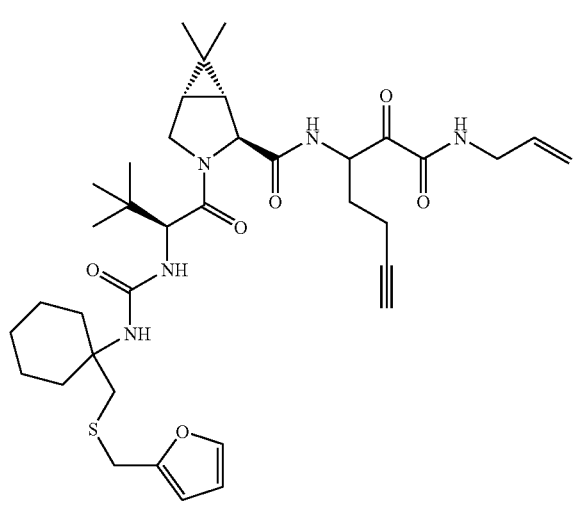
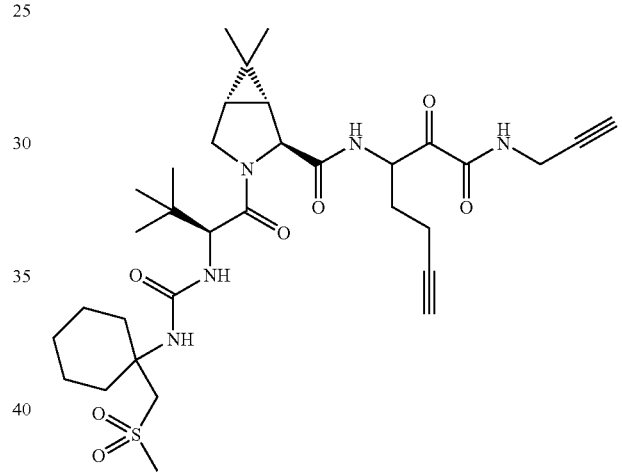
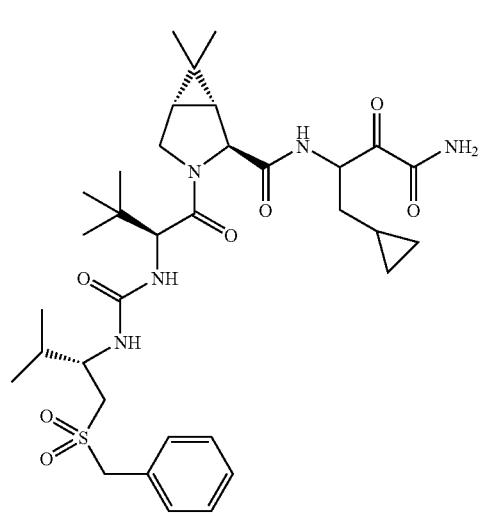

TABLE 1-continued
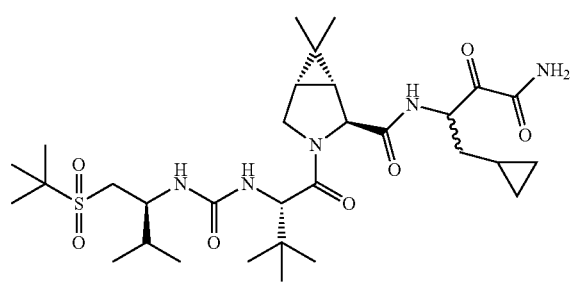

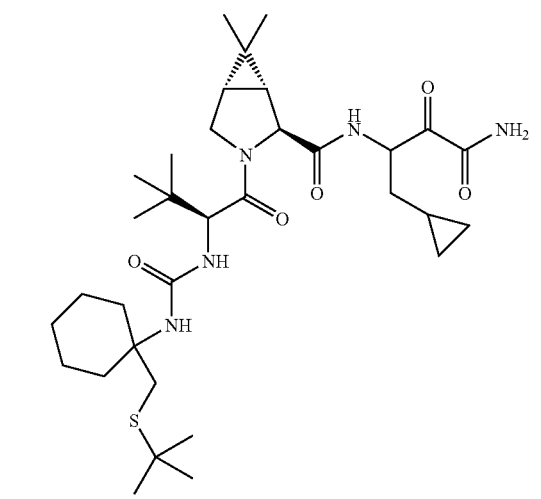
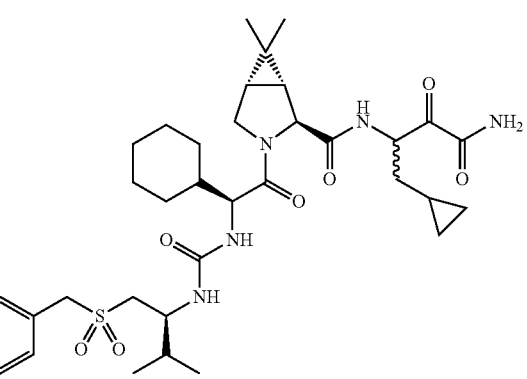
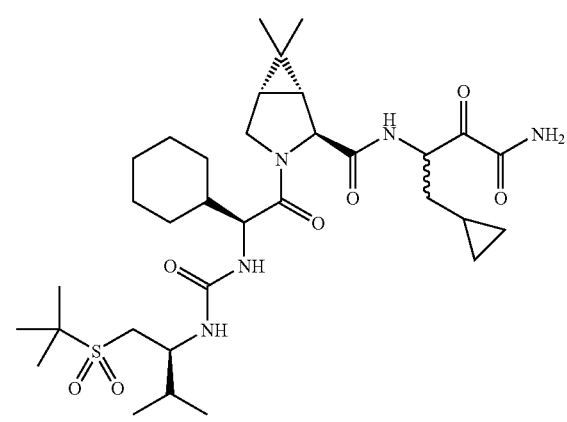
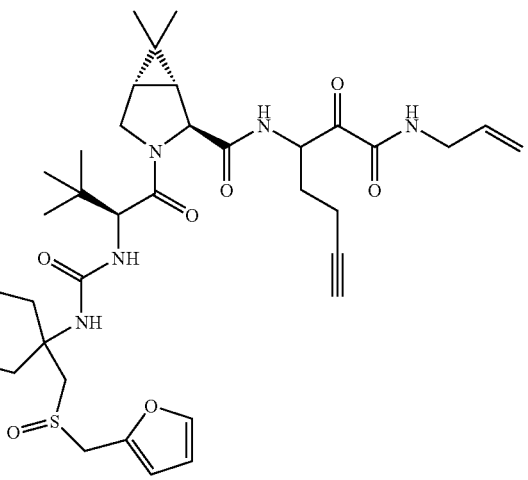

TABLE 1-continued
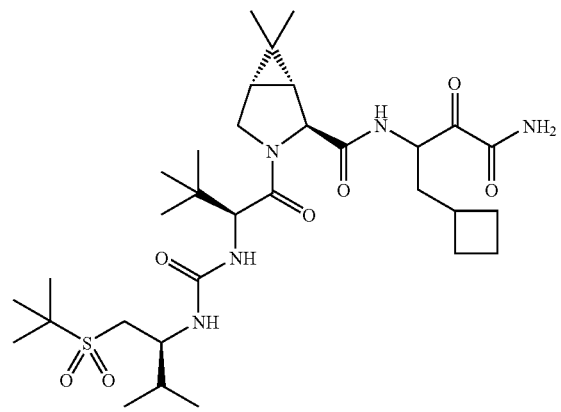
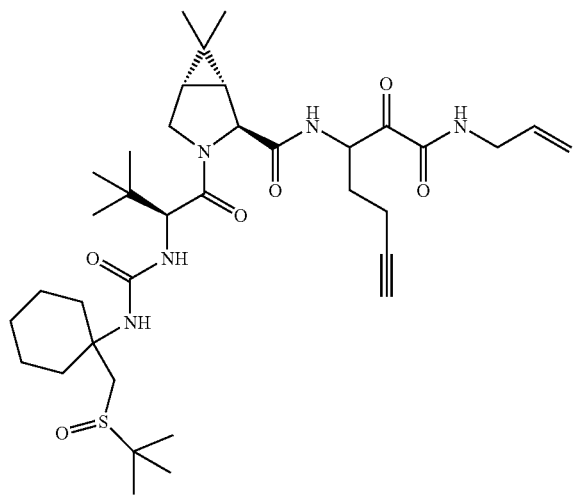
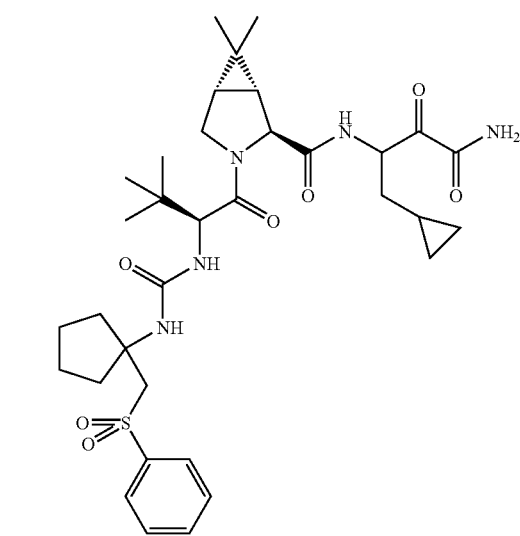
TABLE 1-continued
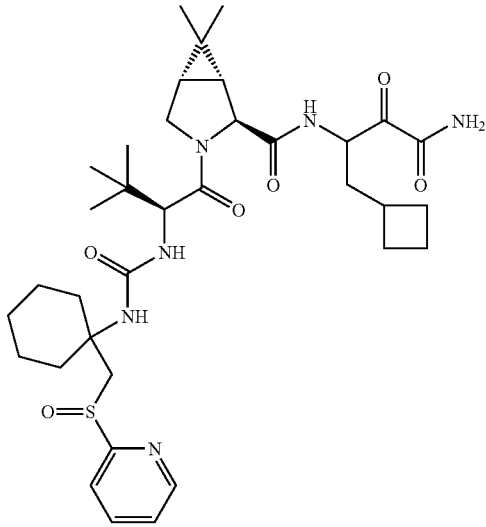
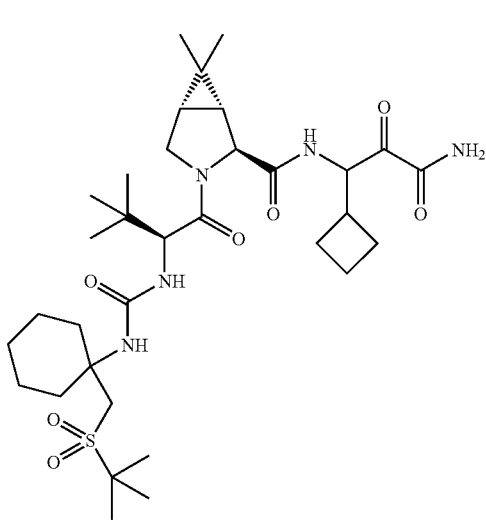
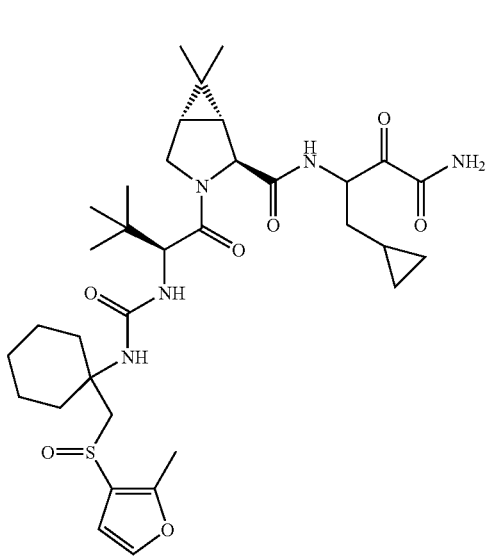

TABLE 1-continued
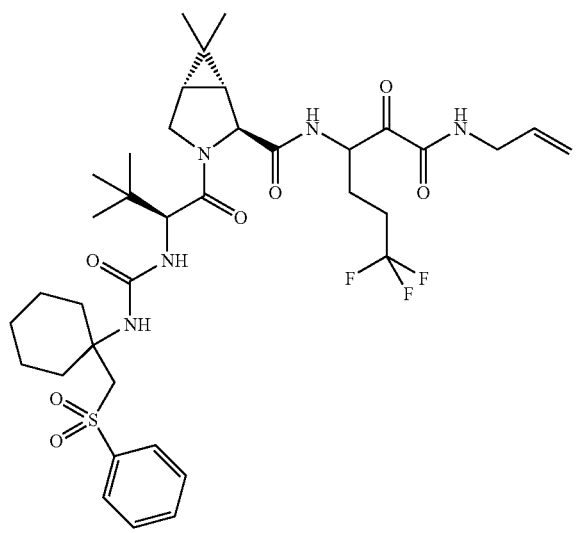
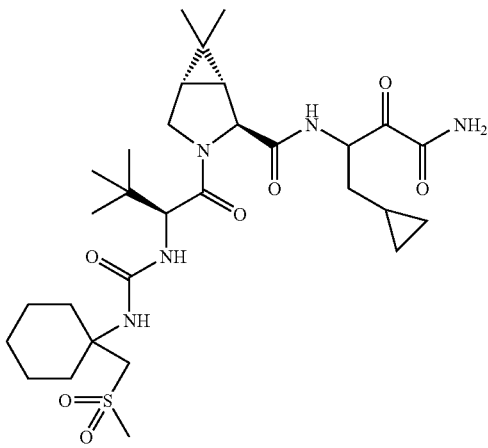
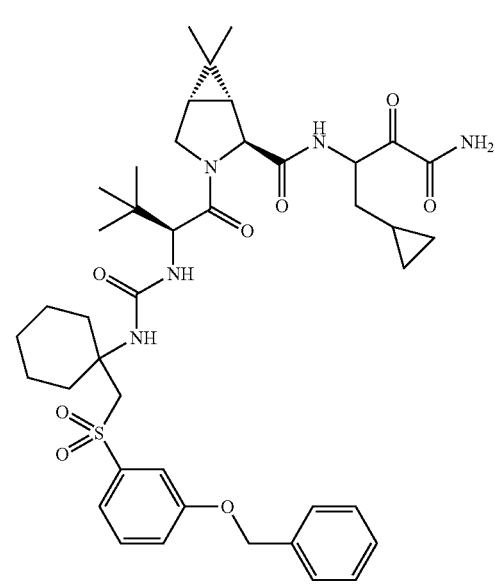
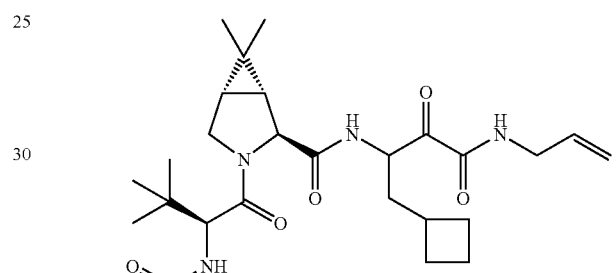
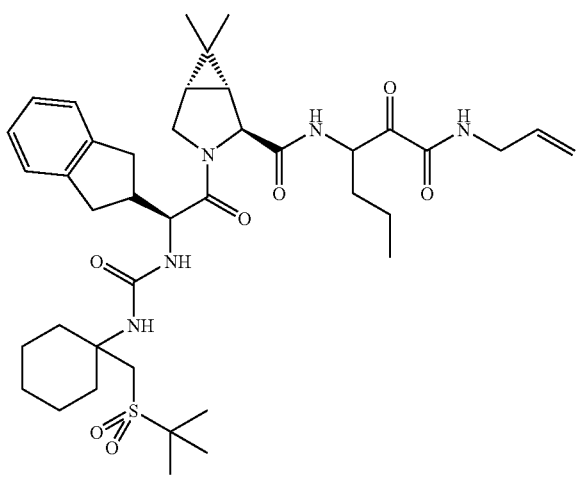
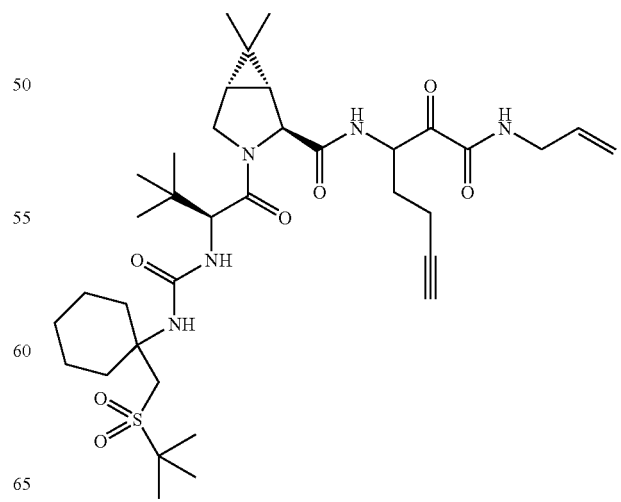

TABLE 1-continued
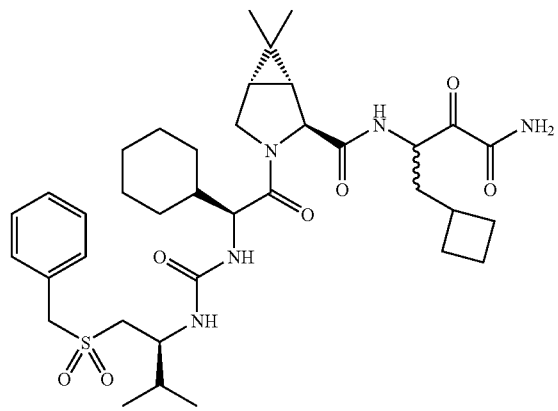
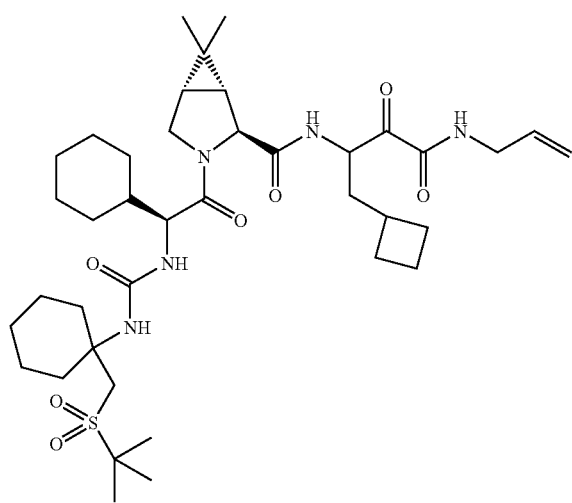
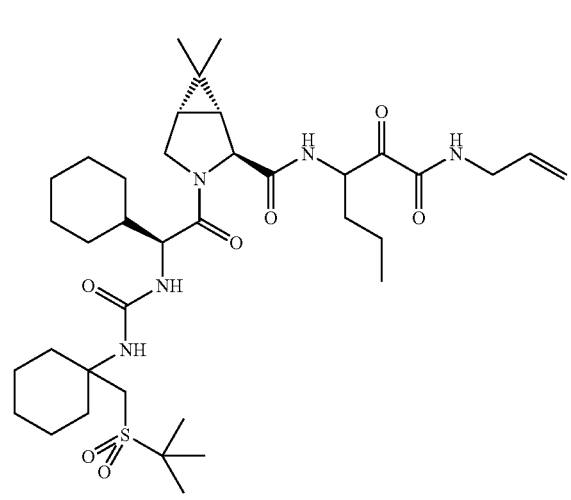
TABLE 1-continued

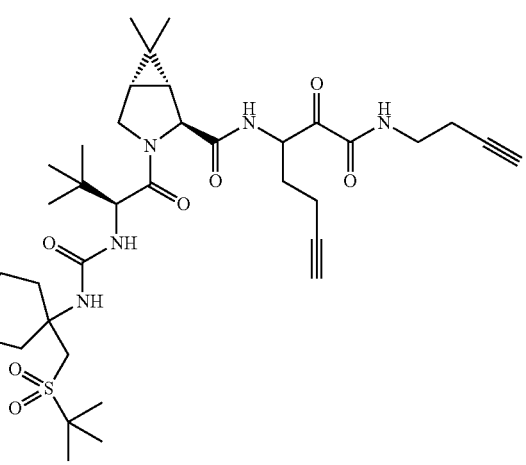
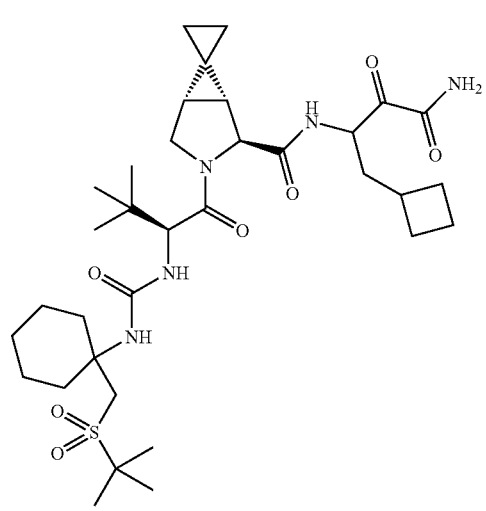

TABLE 1-continued
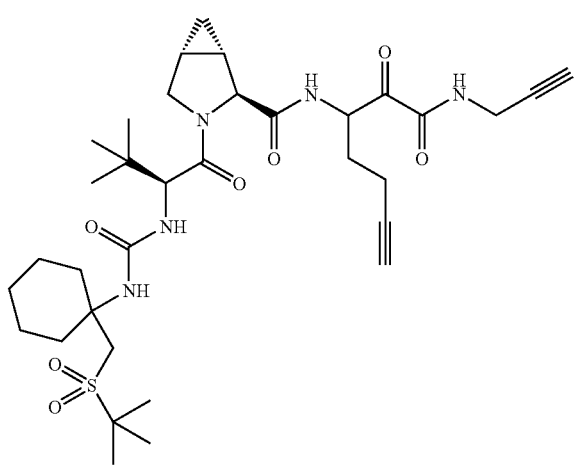
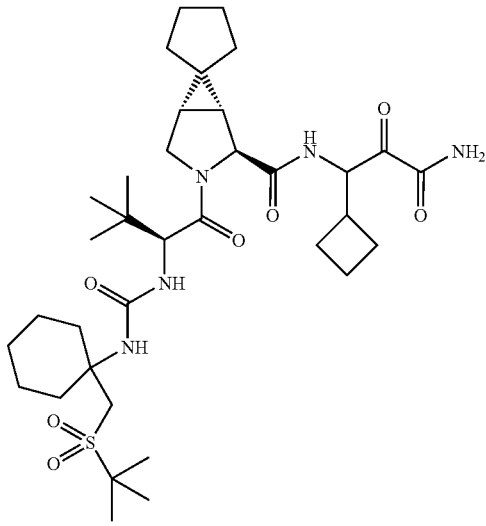
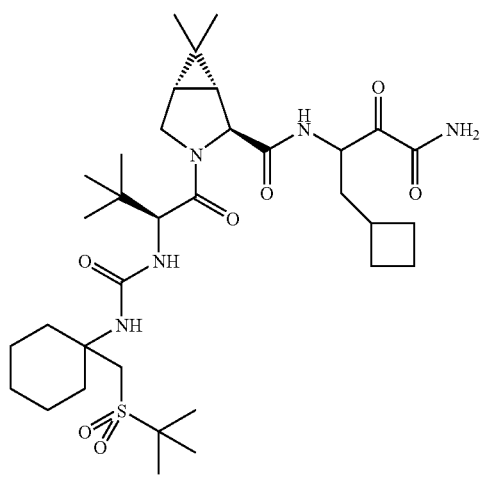
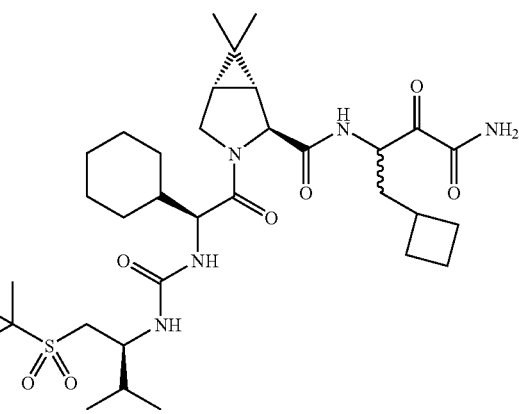
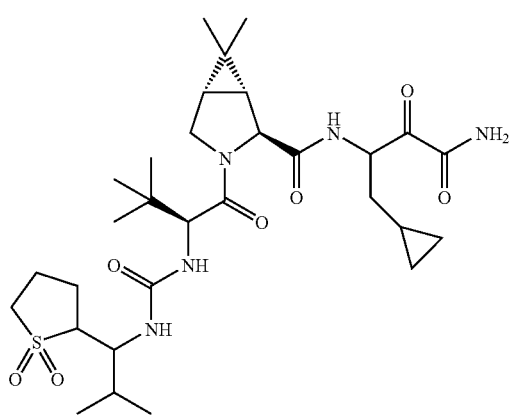
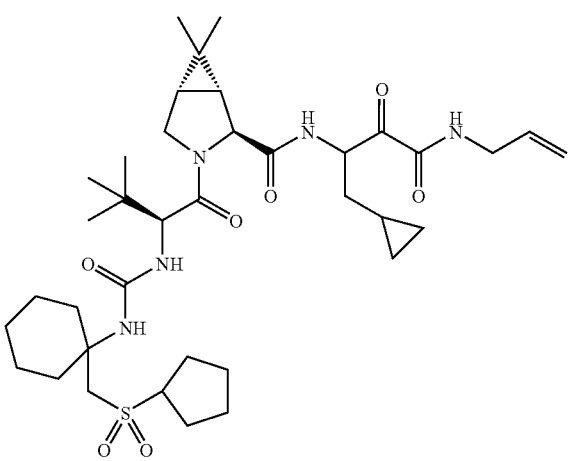

TABLE 1-continued
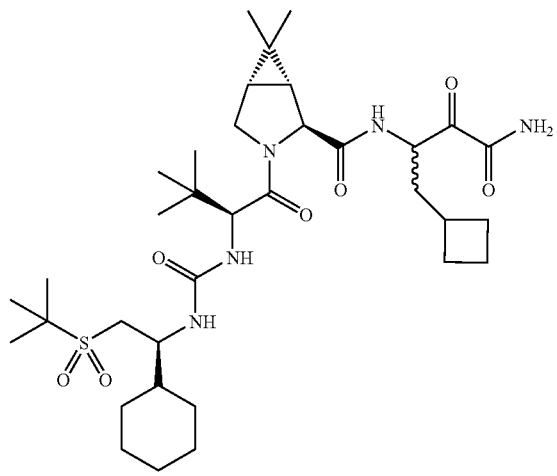
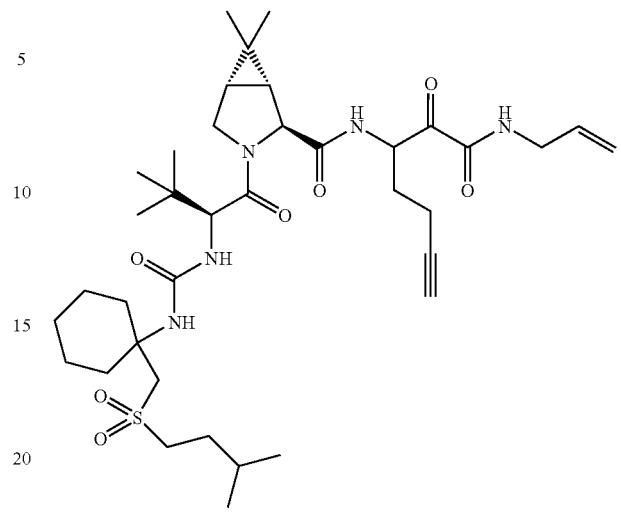
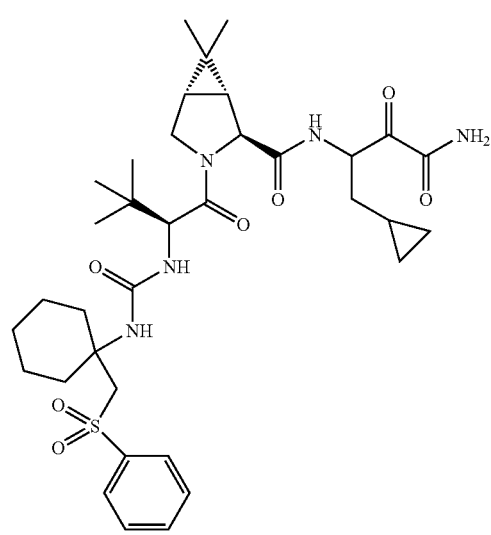
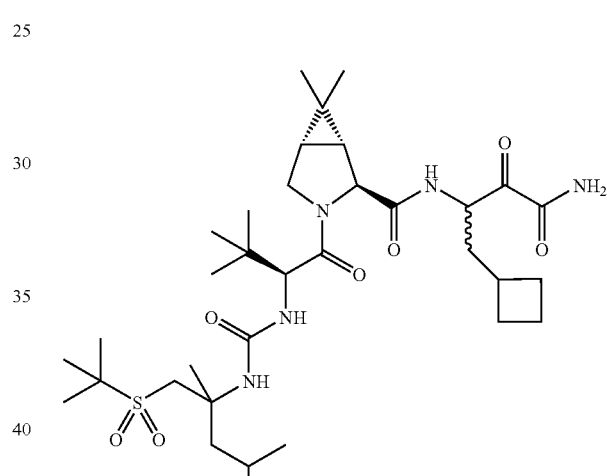
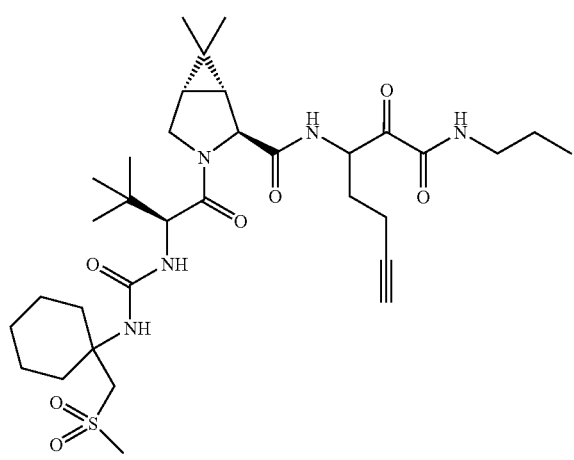
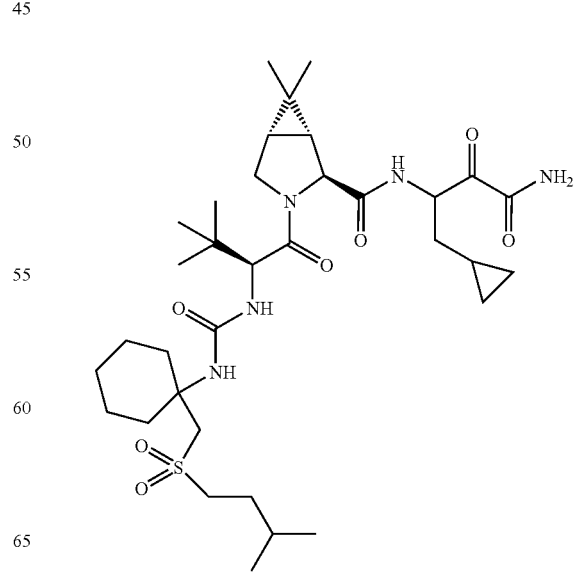

TABLE 1-continued
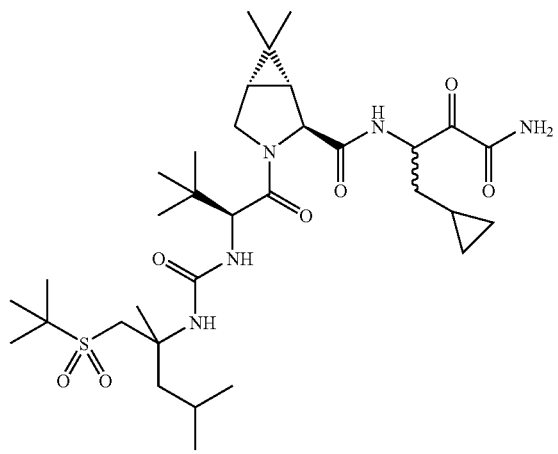
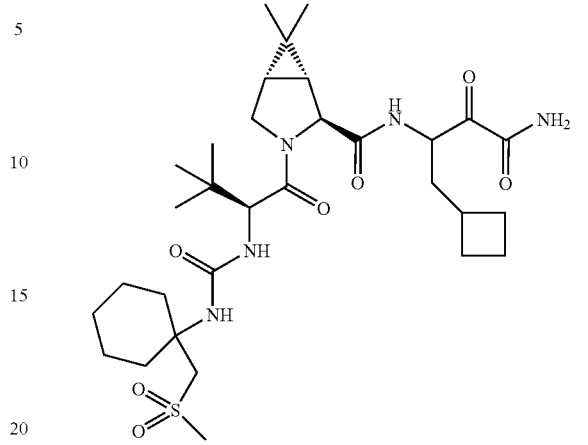
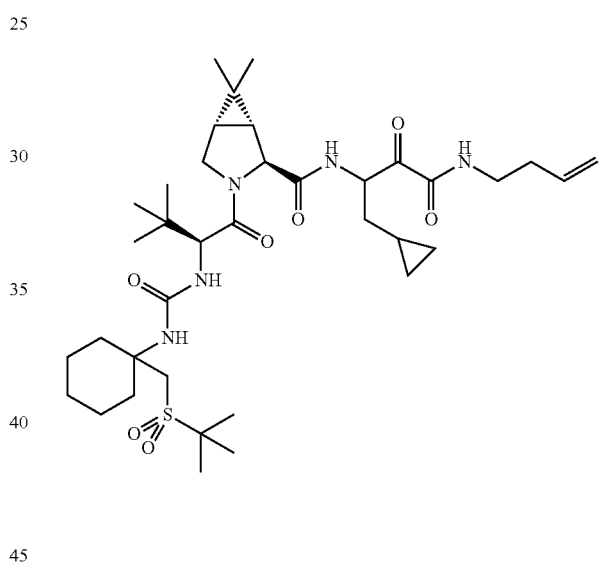
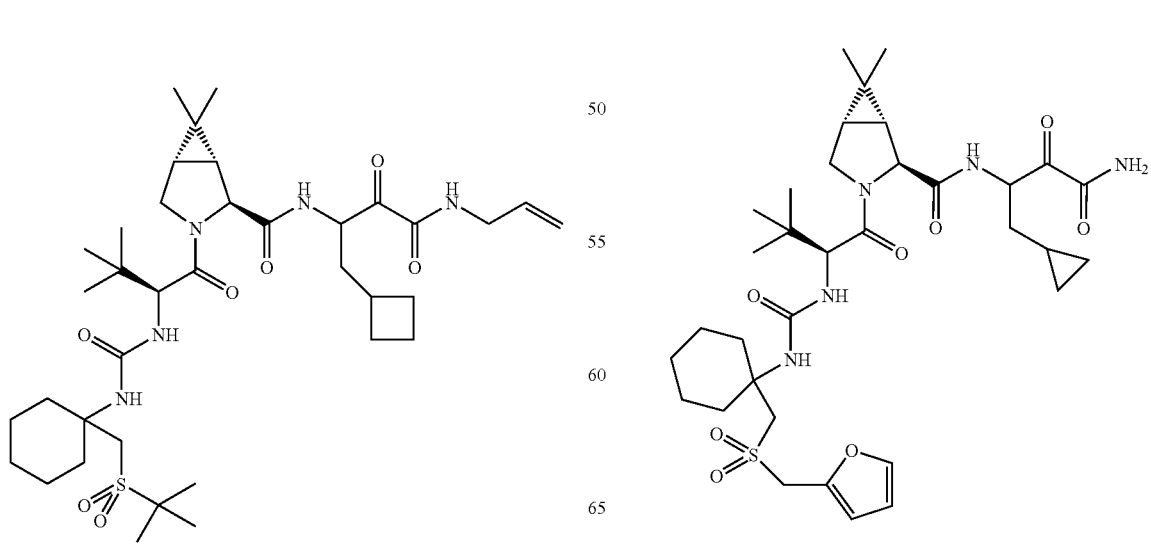

TABLE 1-continued
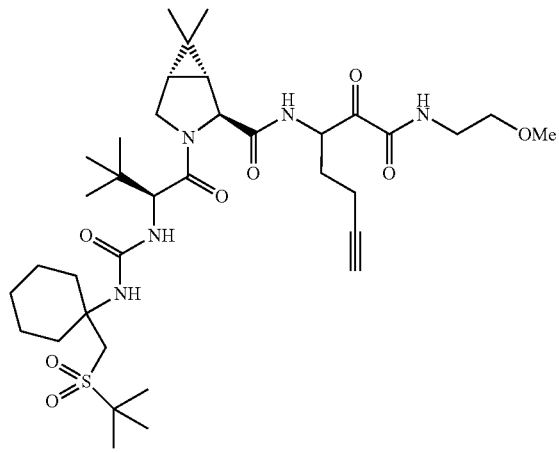
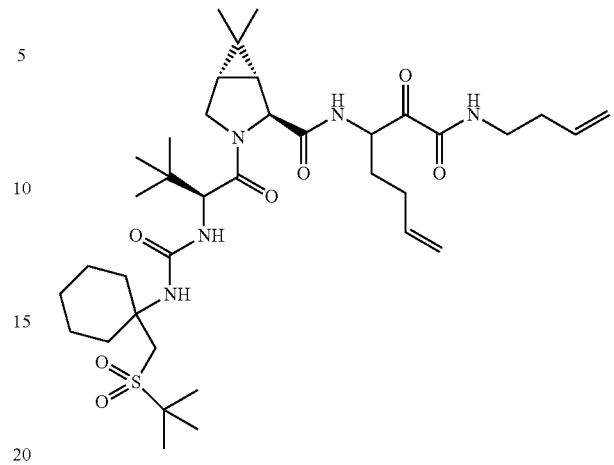
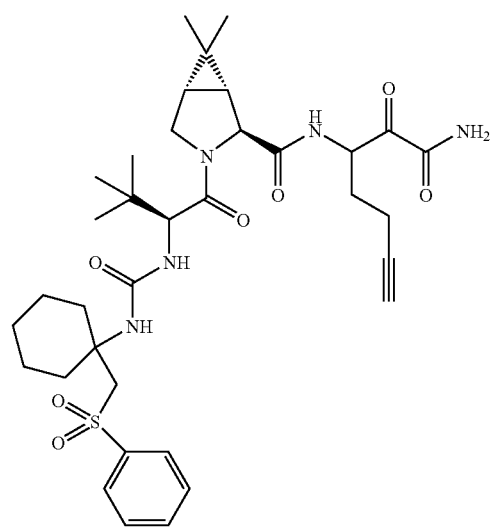
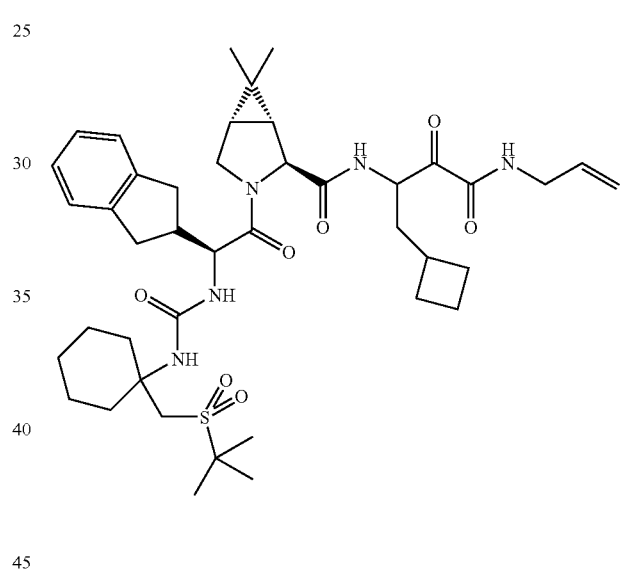
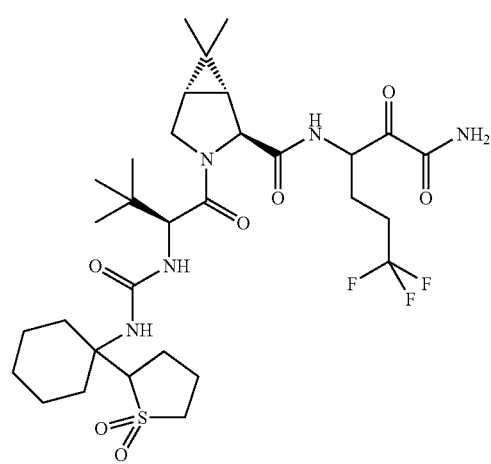
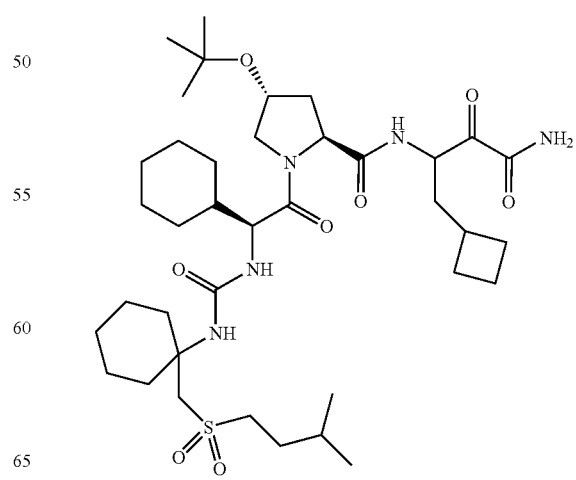

TABLE 1-continued
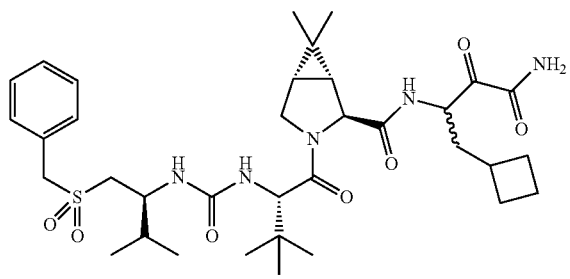
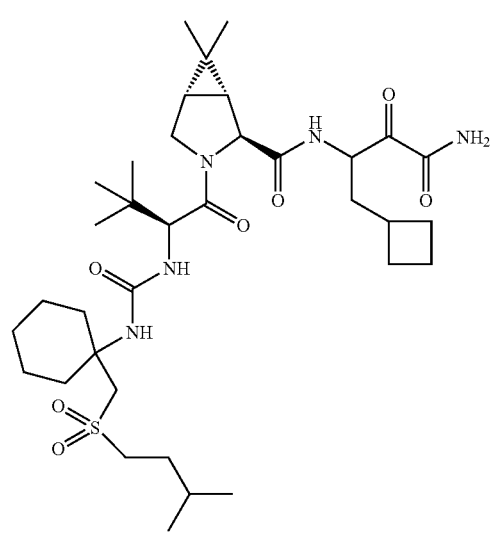
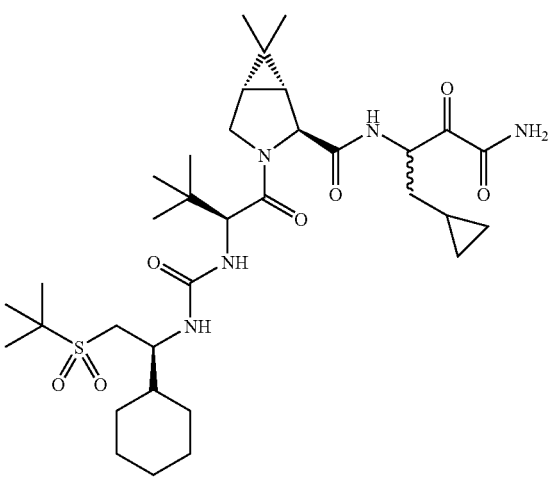
TABLE 1-continued
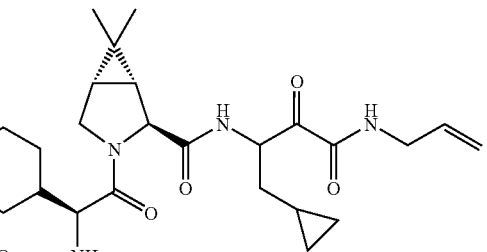
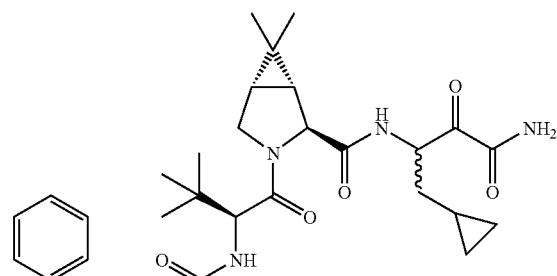
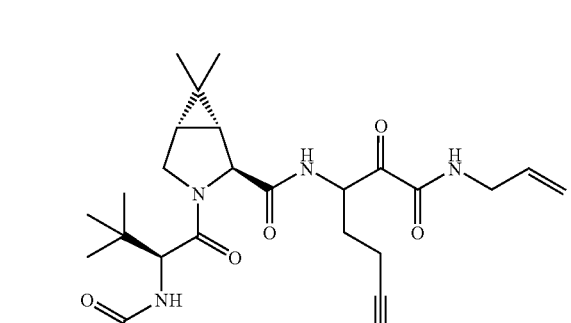

TABLE 1-continued
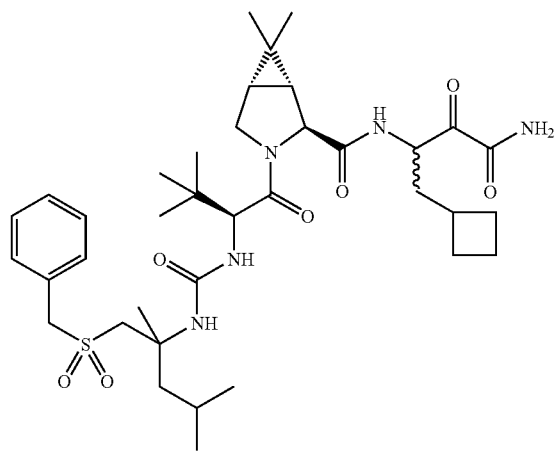
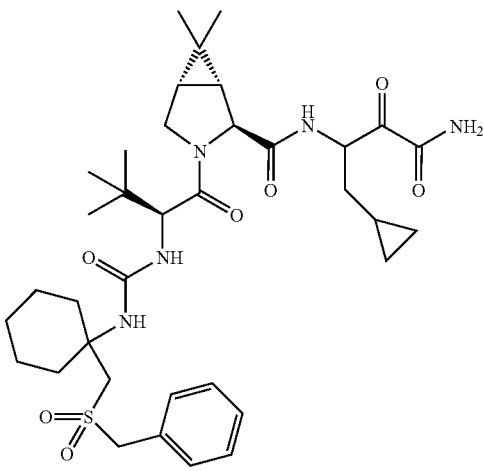
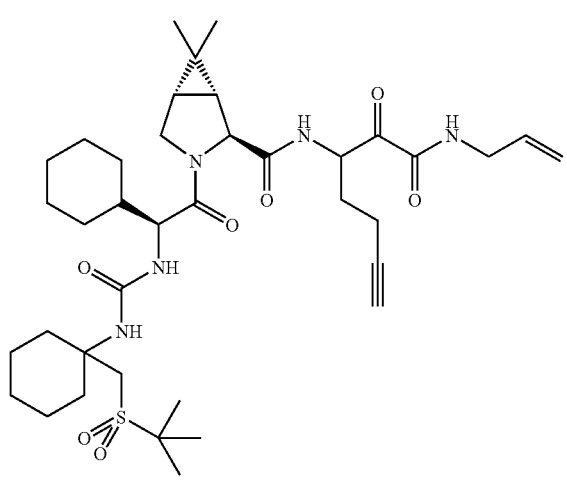
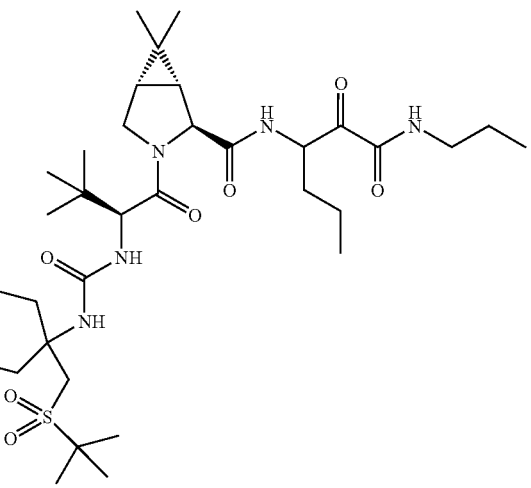
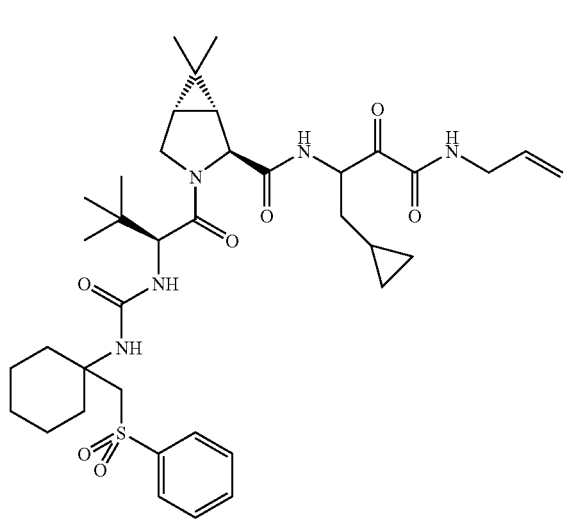
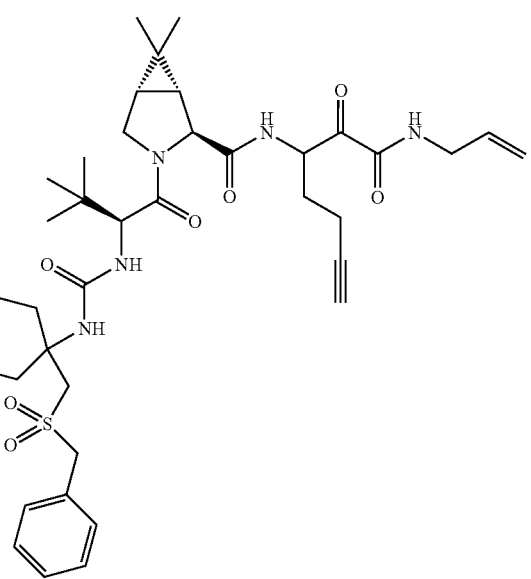

TABLE 1-continued
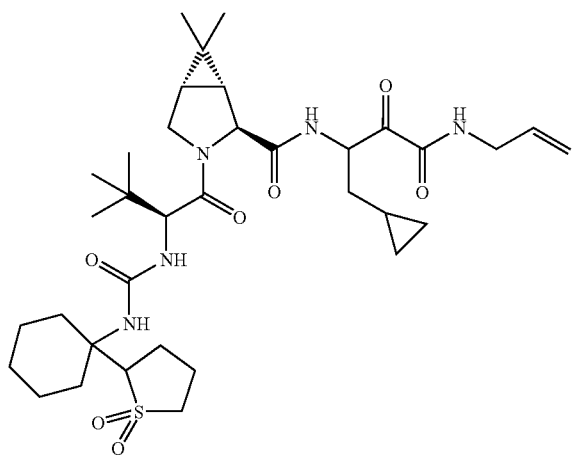
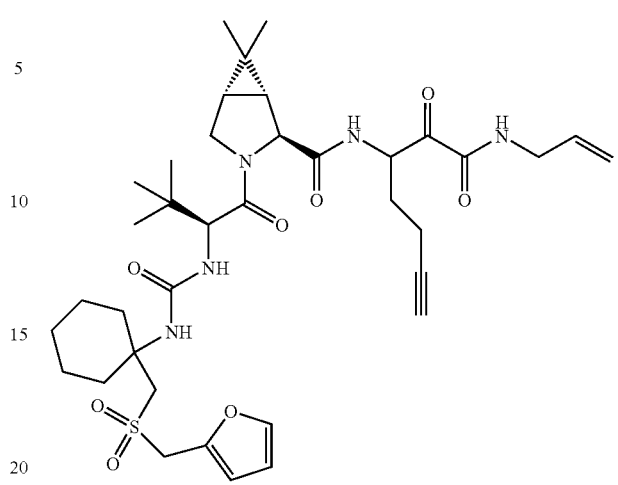
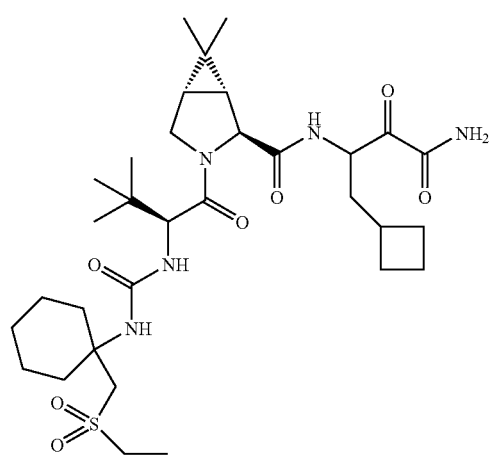
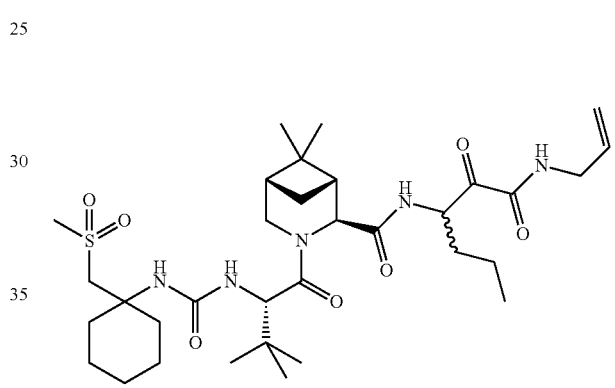
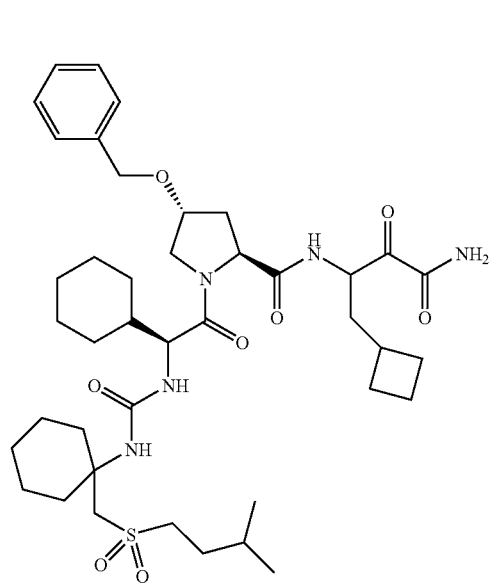
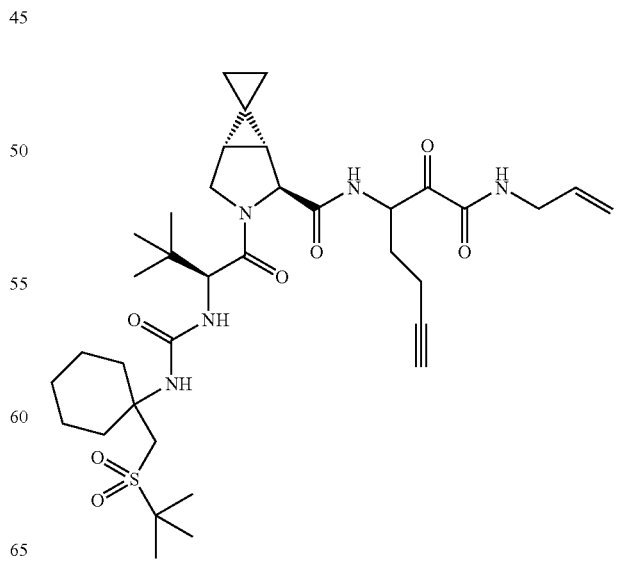

TABLE 1-continued
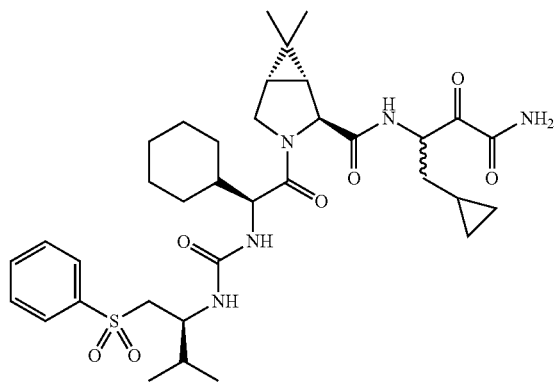
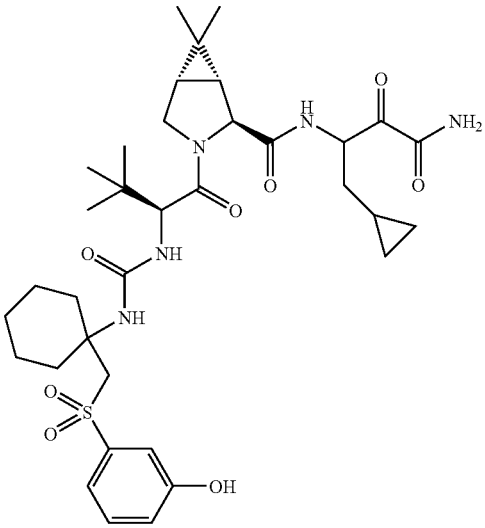
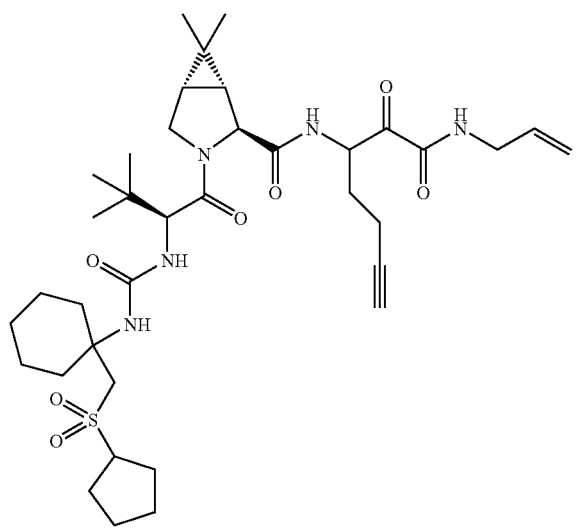
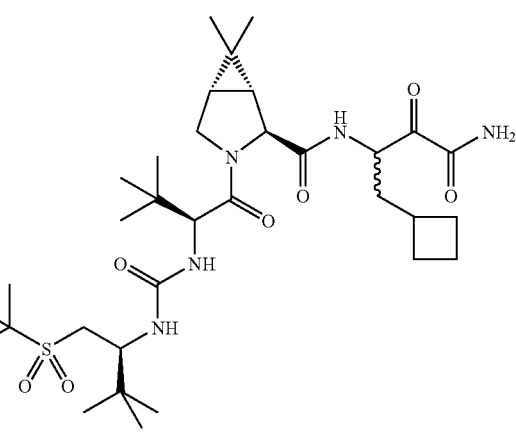
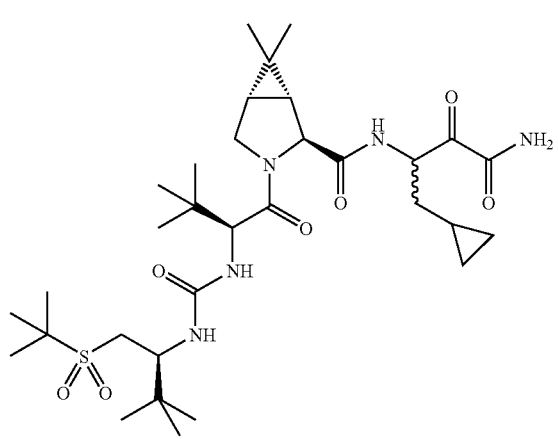
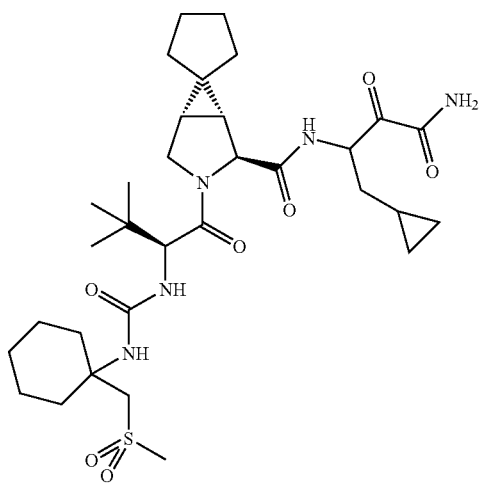

TABLE 1-continued
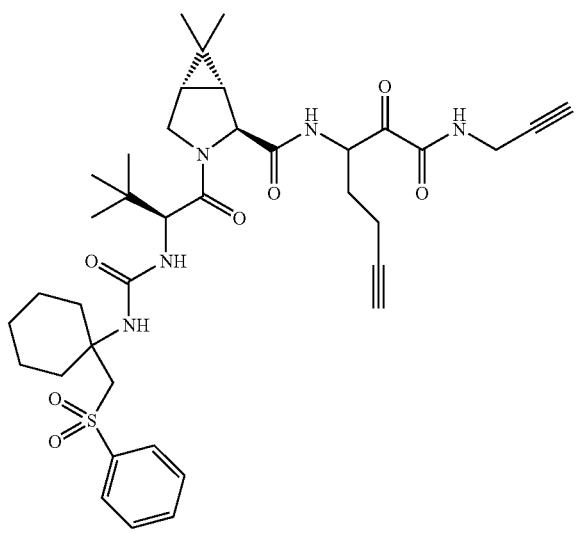
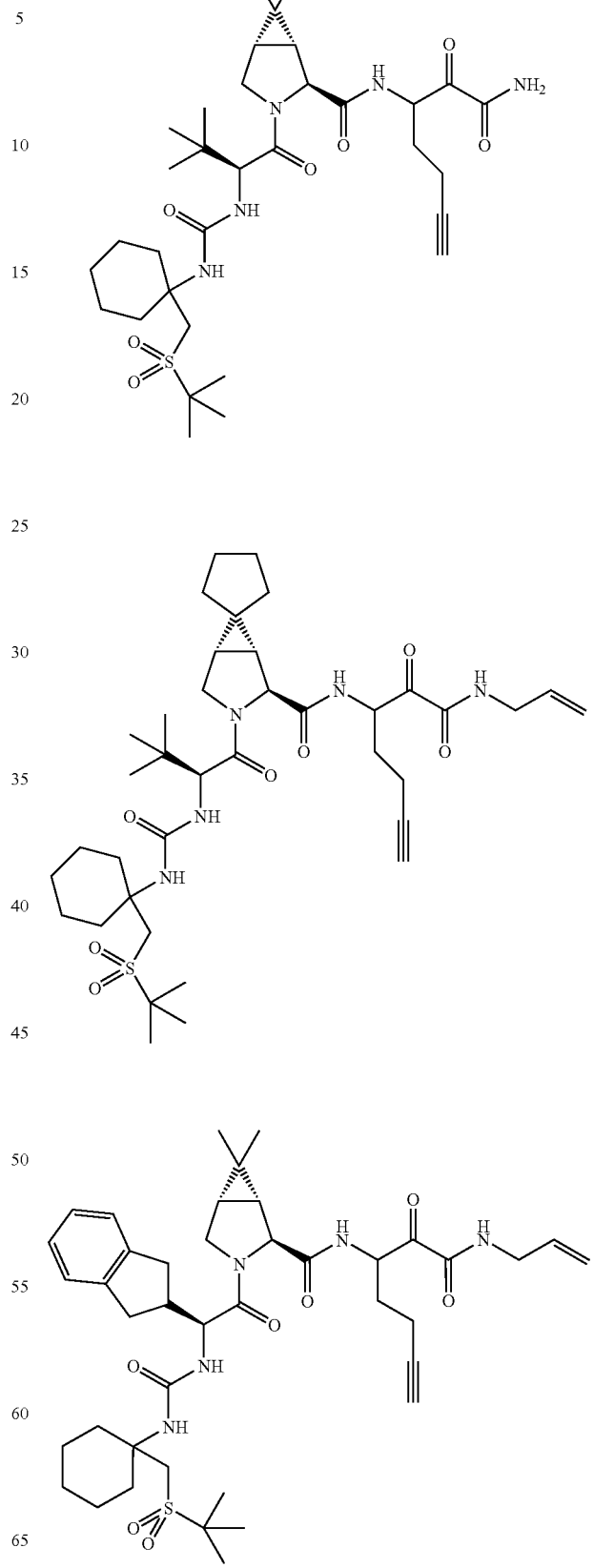

TABLE 1-continued
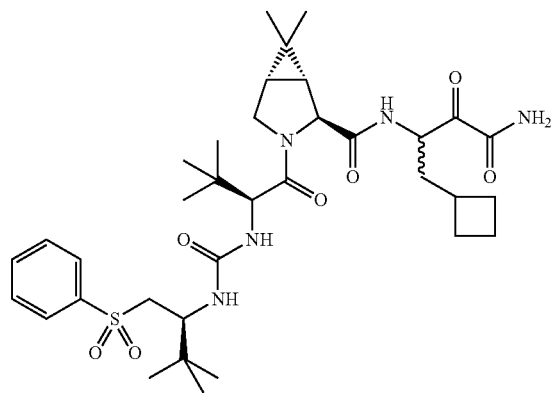
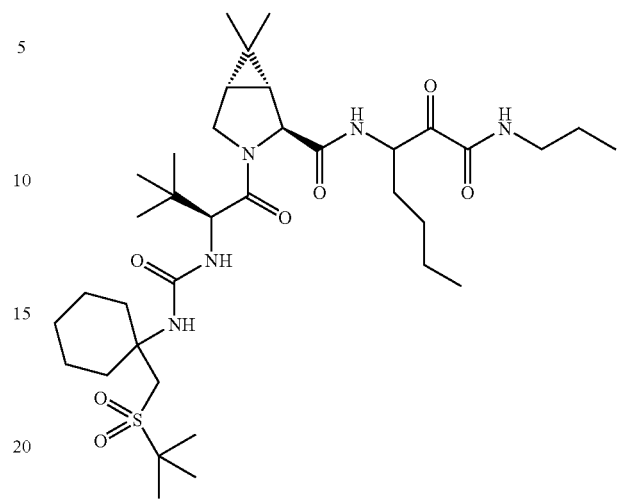
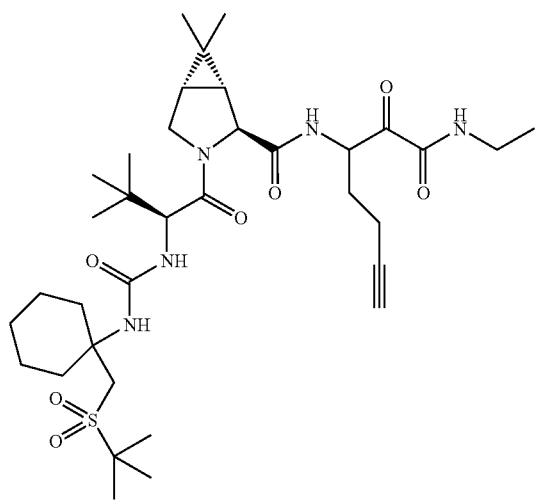
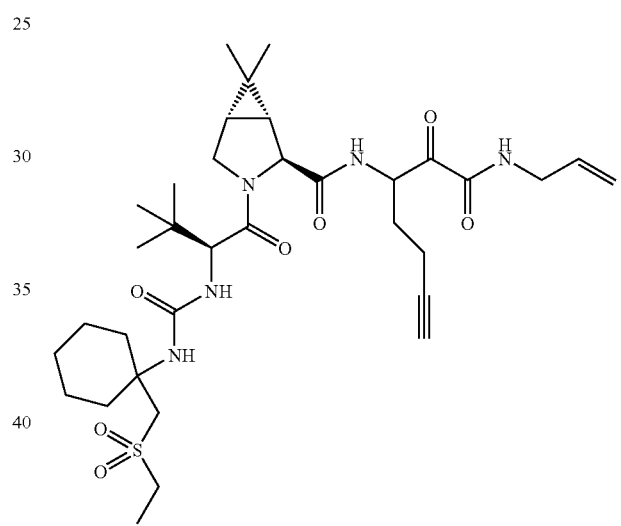
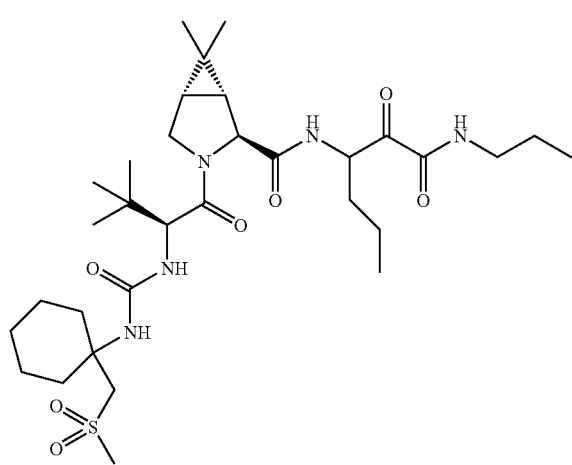
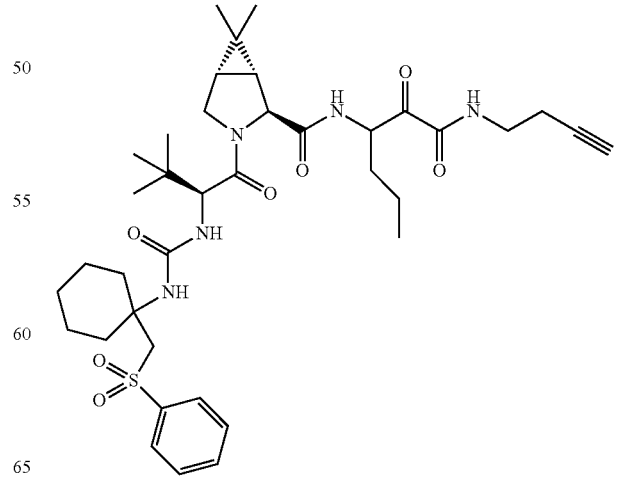

TABLE 1-continued
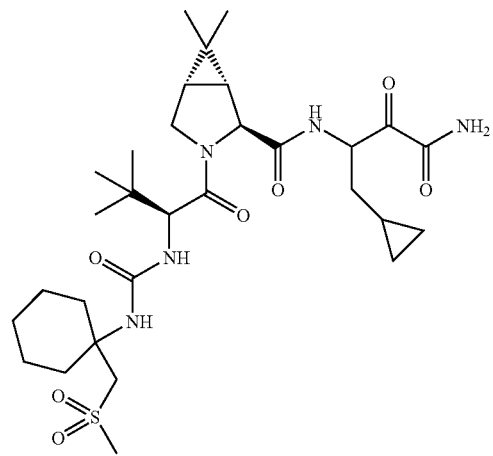
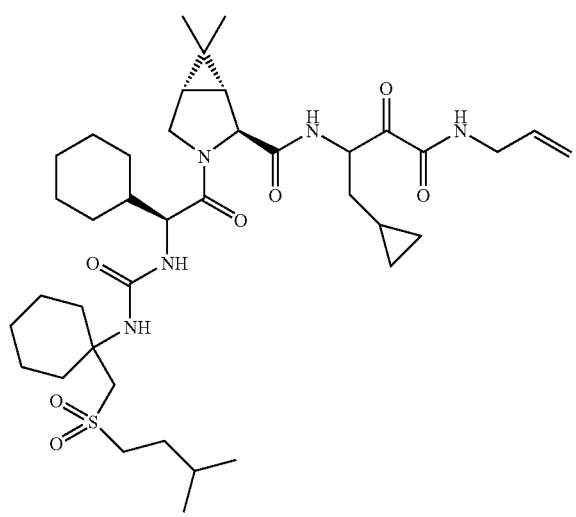
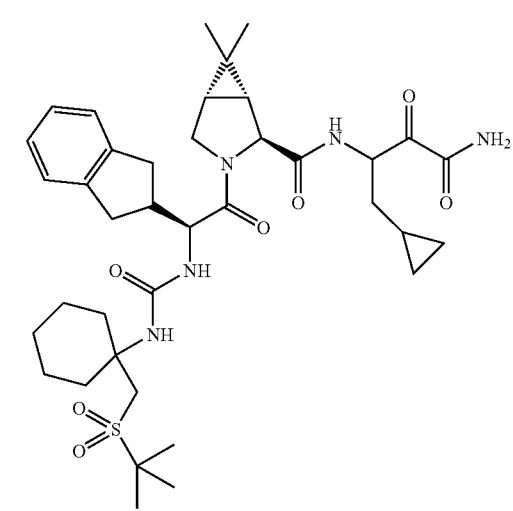
TABLE 1-continued
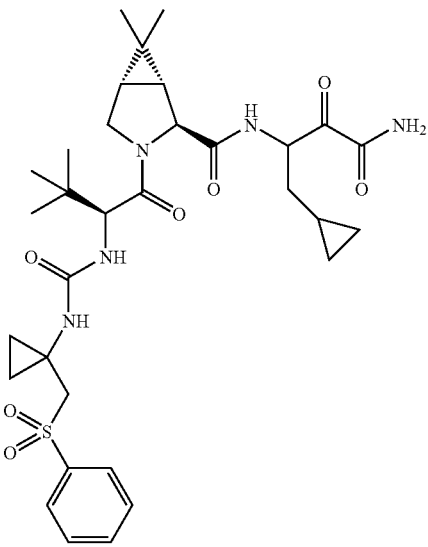
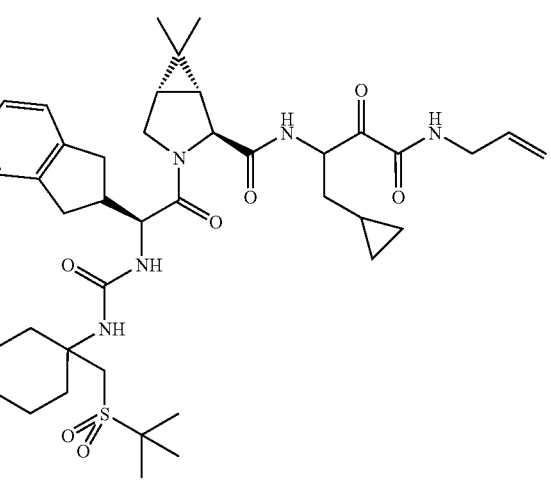
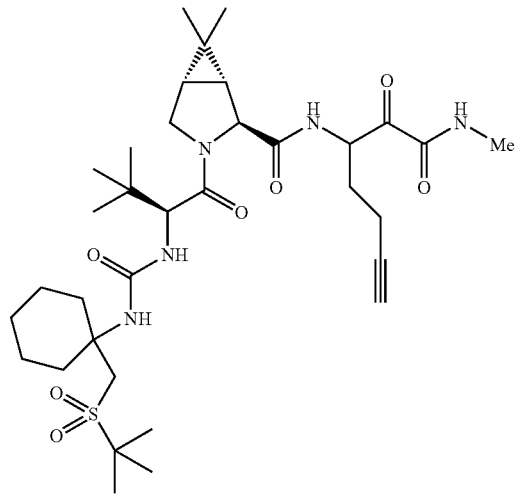

TABLE 1-continued
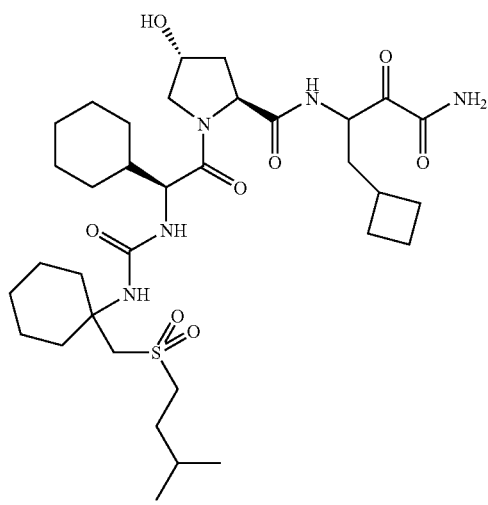
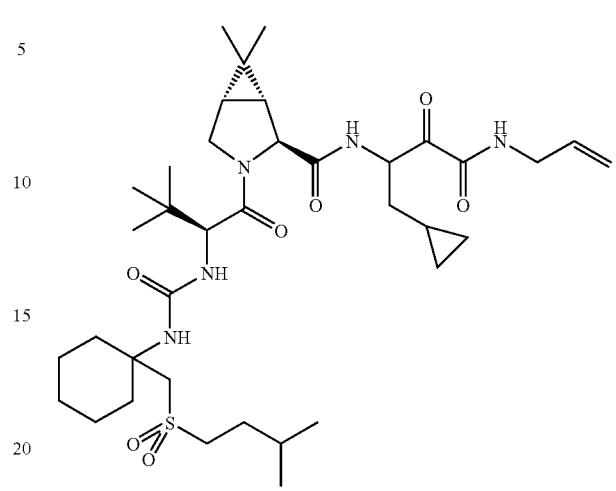
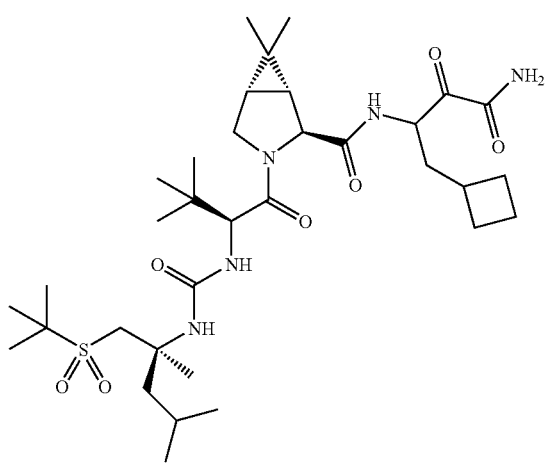
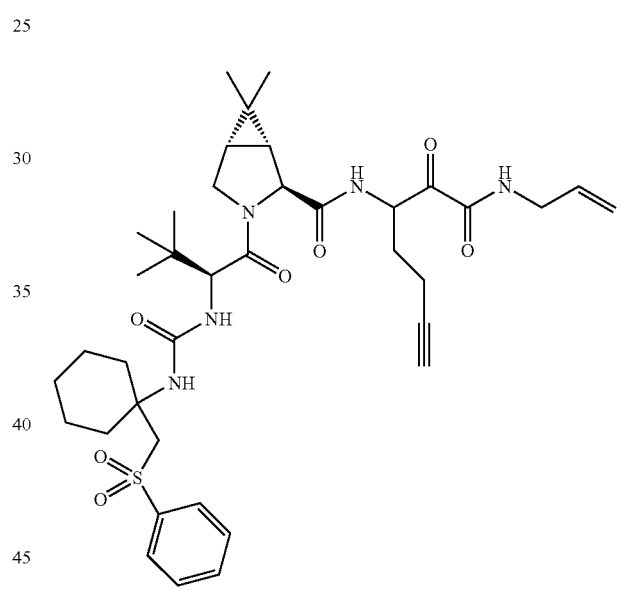
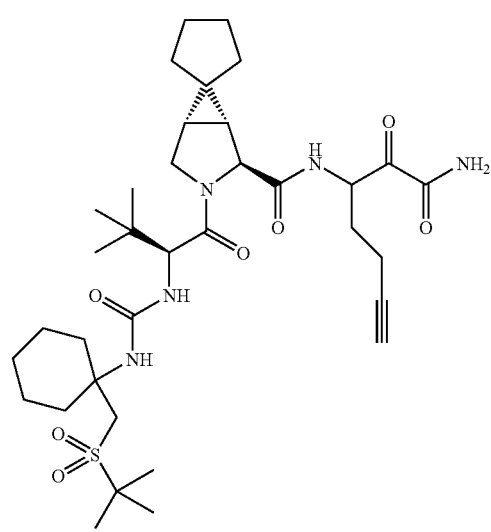
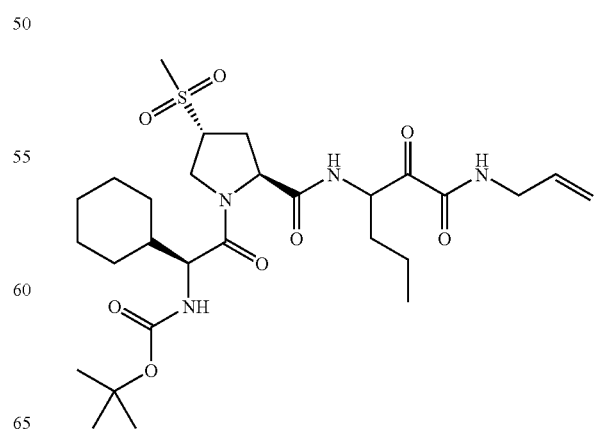

TABLE 1-continued
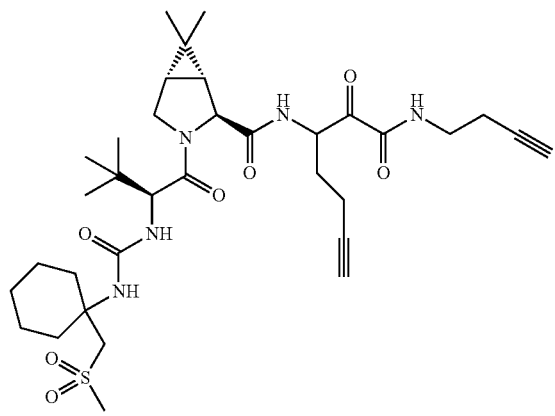
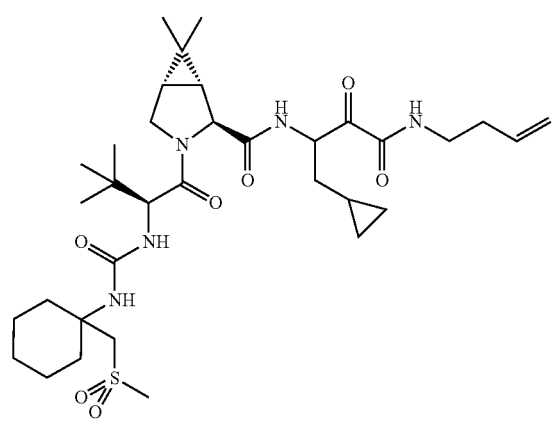
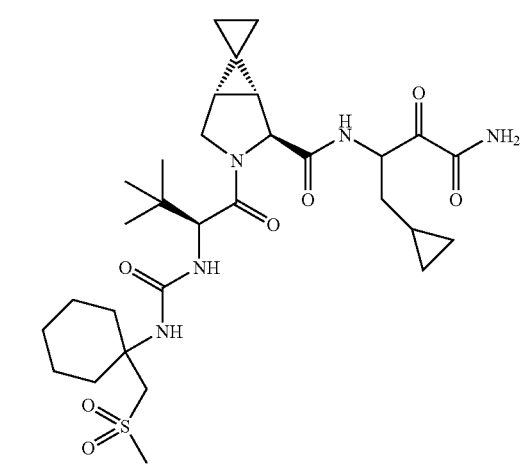
TABLE 1-continued
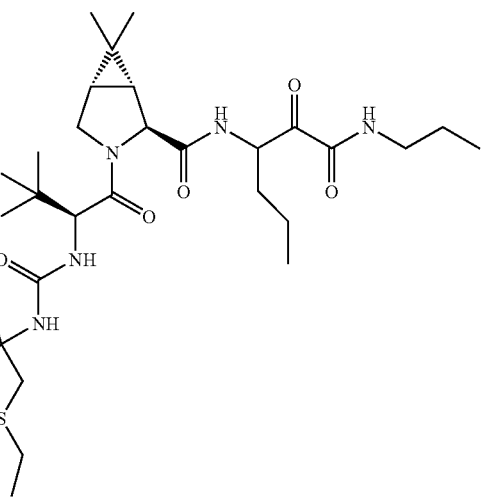
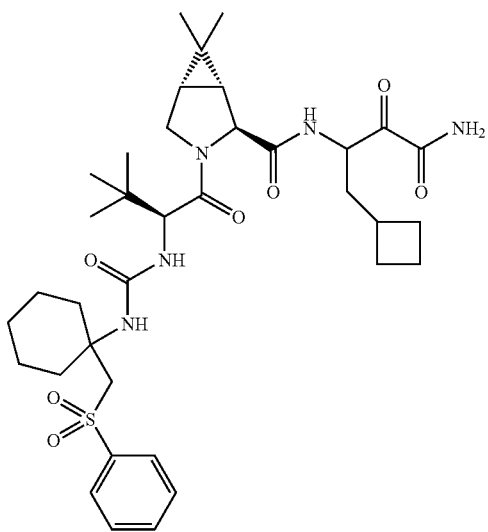

TABLE 1-continued
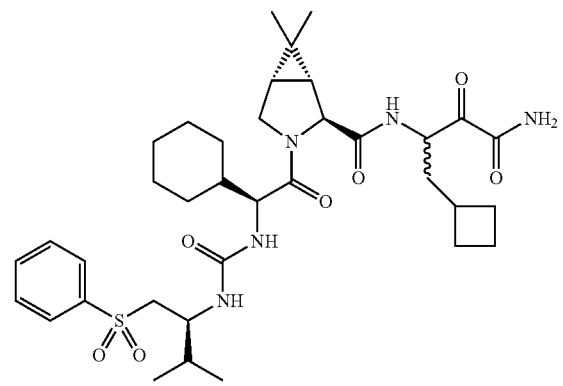
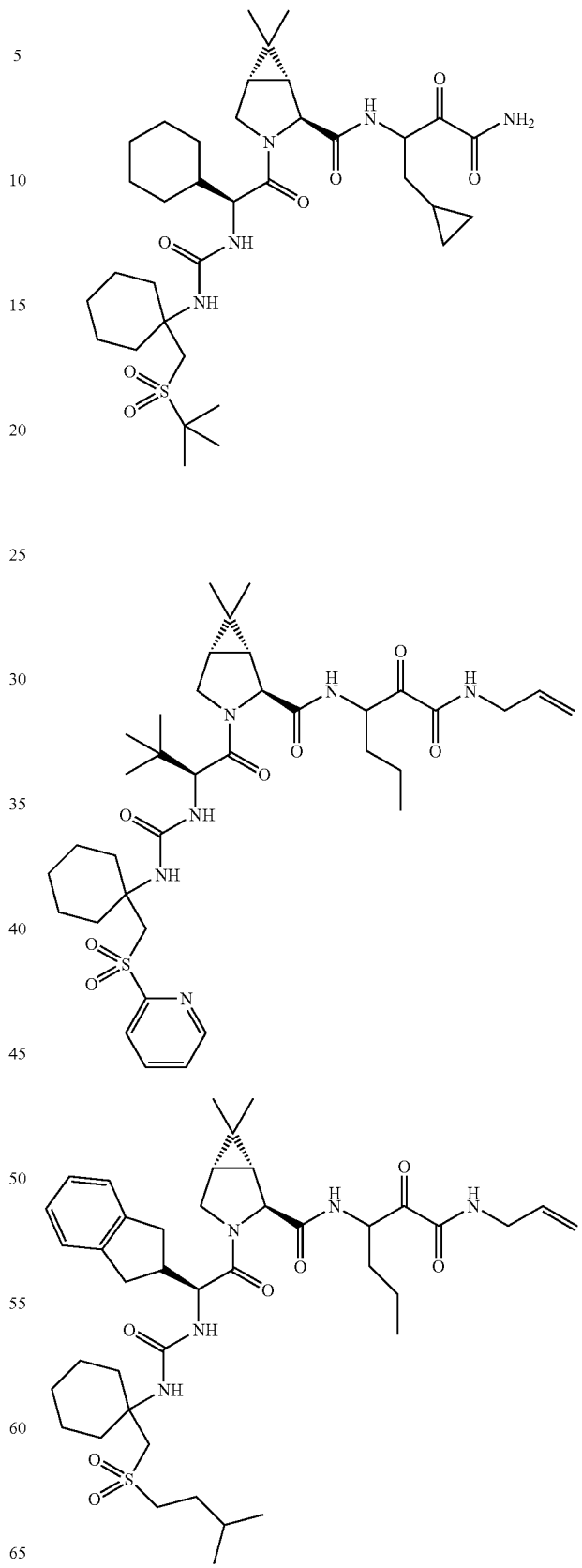

TABLE 1-continued
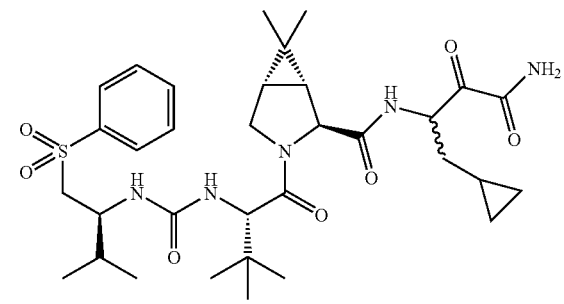
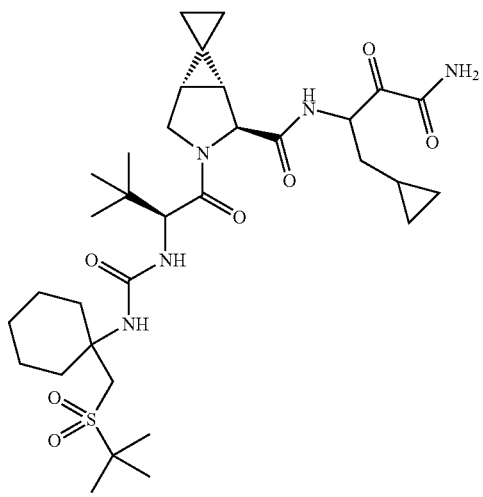
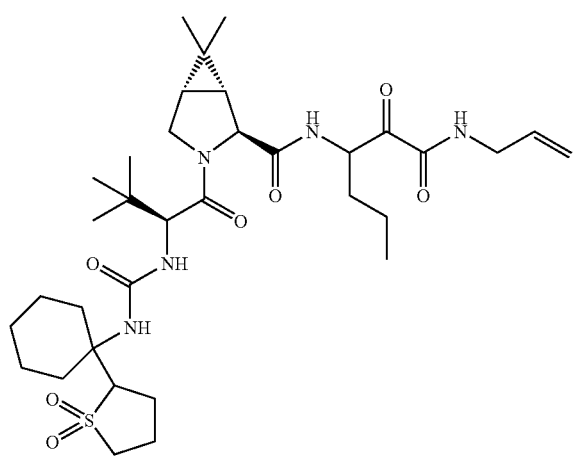
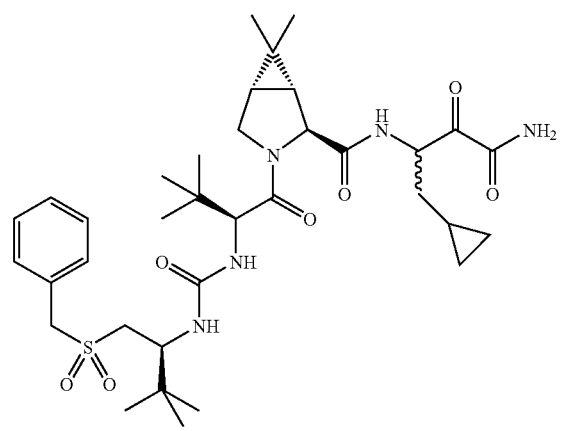
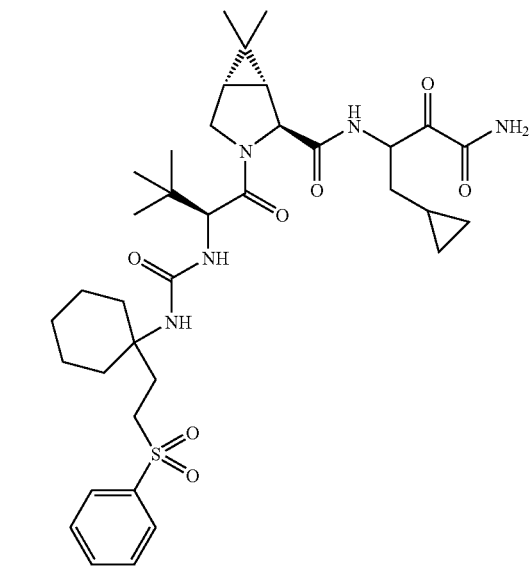
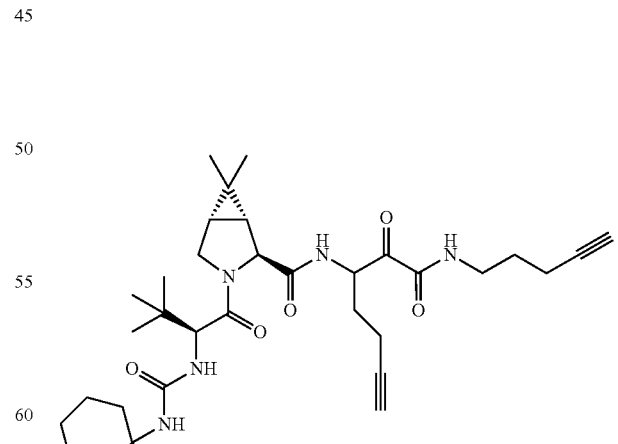

TABLE 1-continued
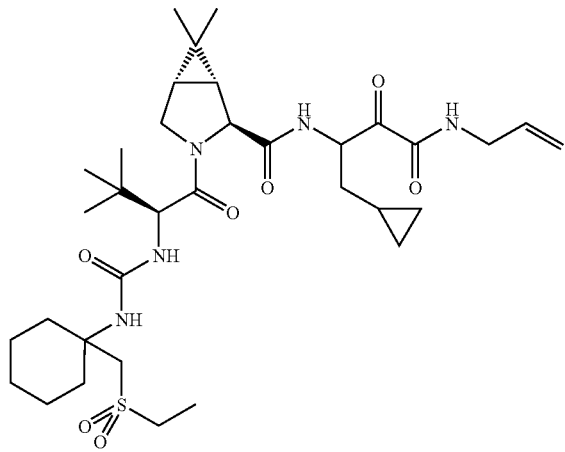
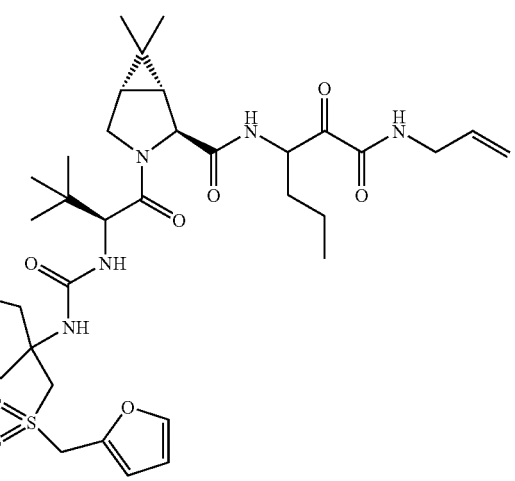
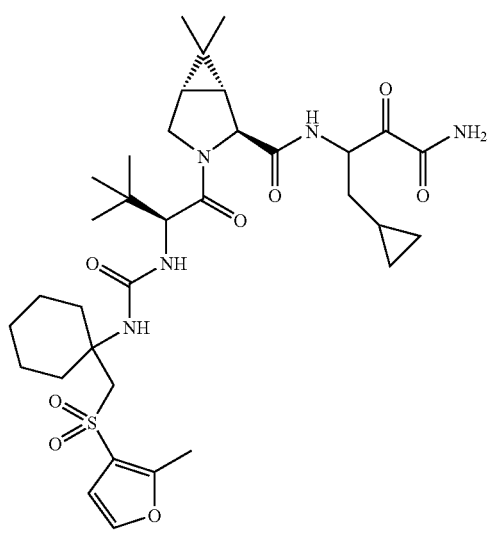
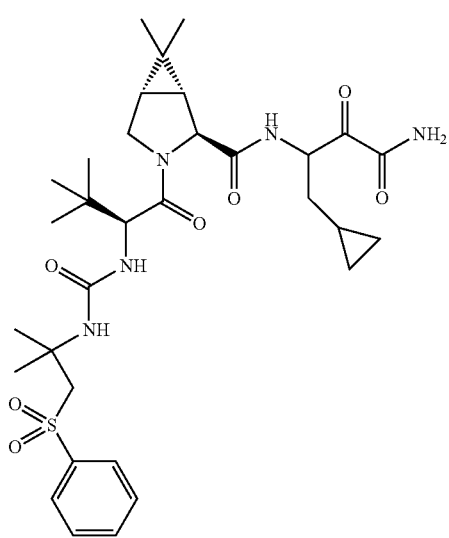
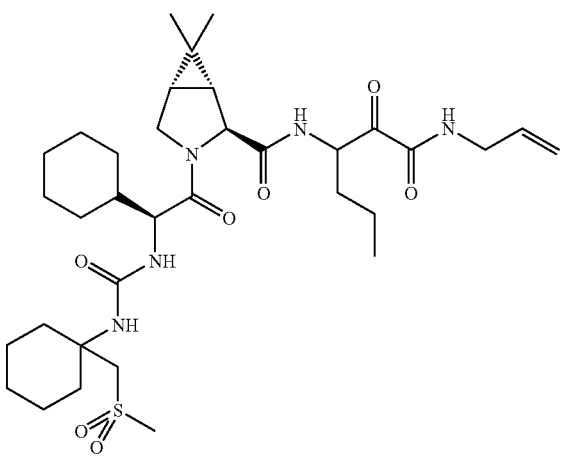

TABLE 1-continued
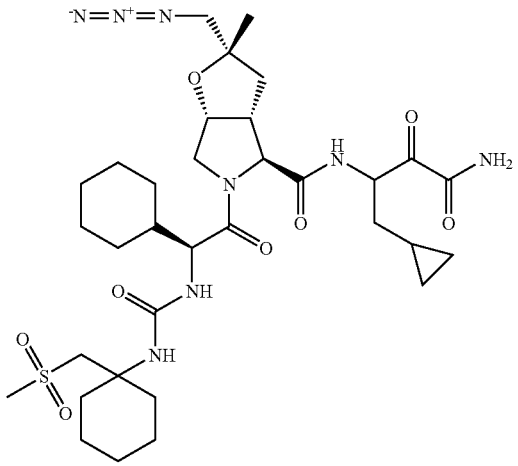
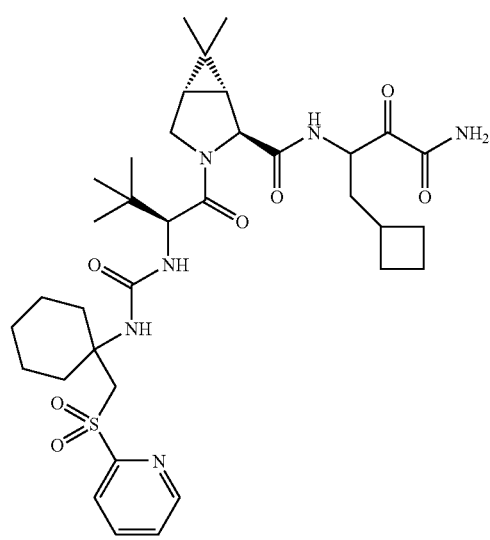
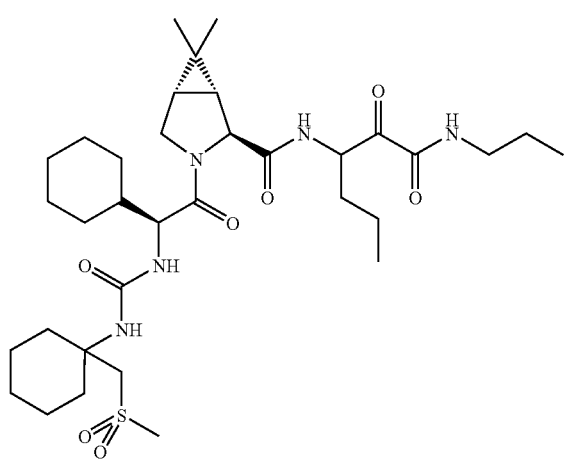
TABLE 1-continued
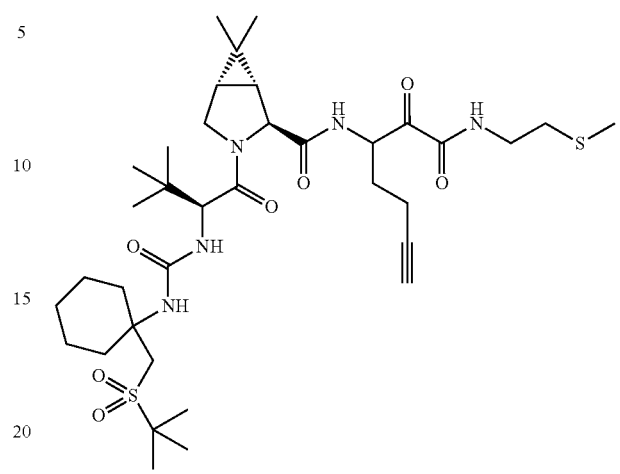
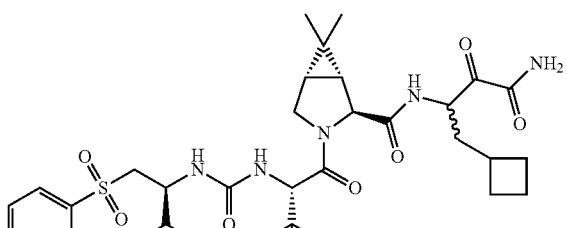
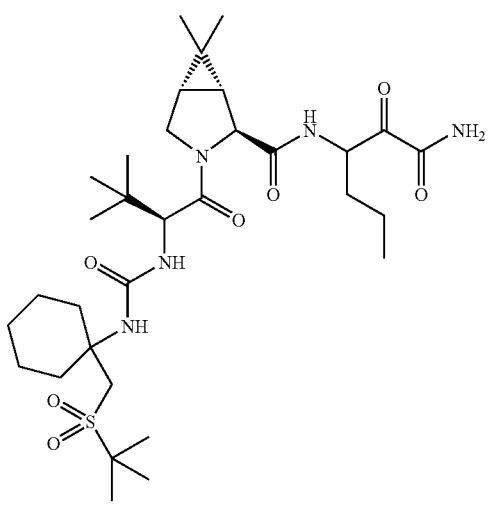

TABLE 1-continued
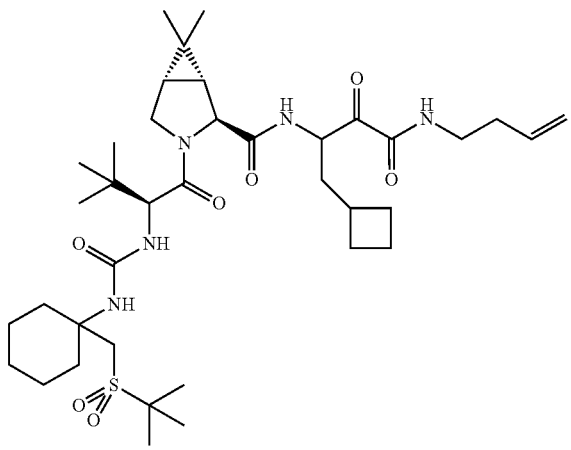
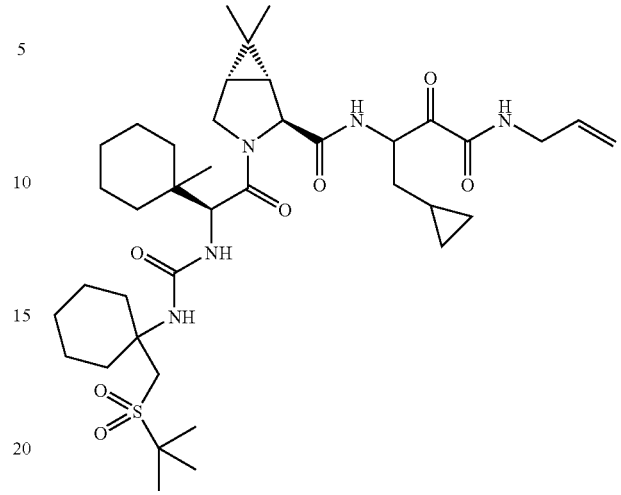
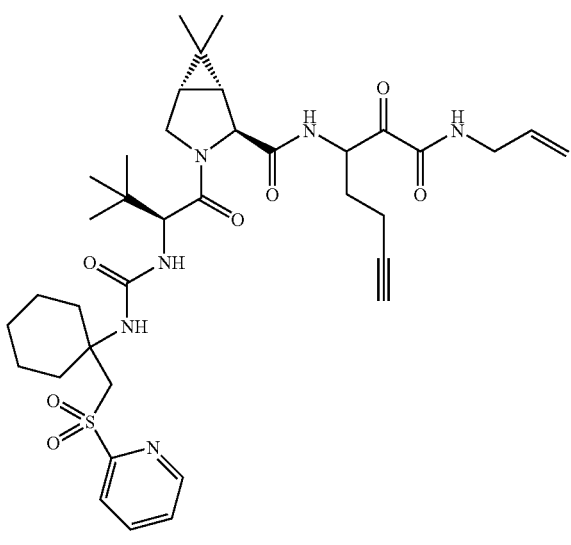
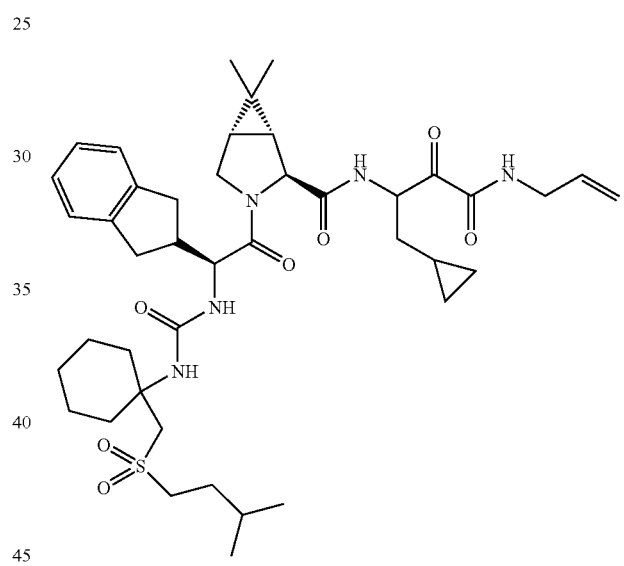
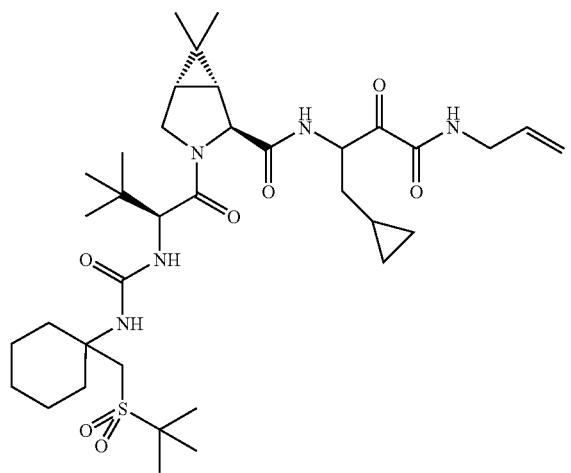
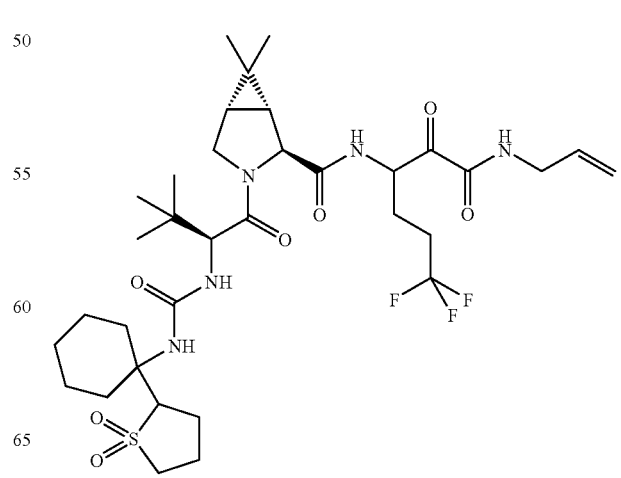

TABLE 1-continued
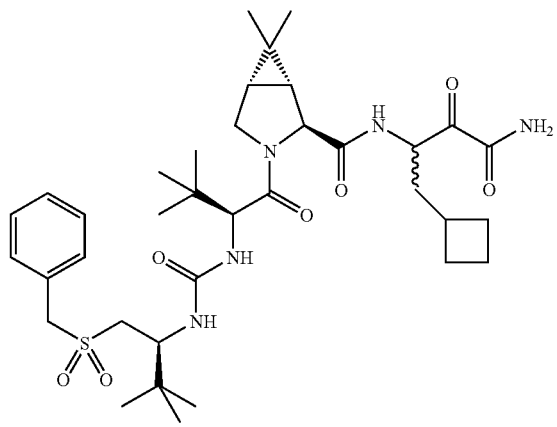
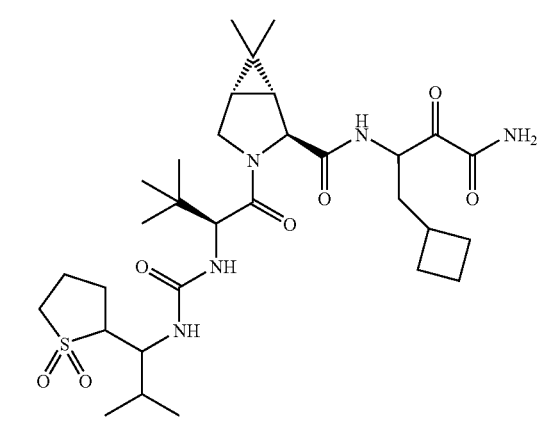
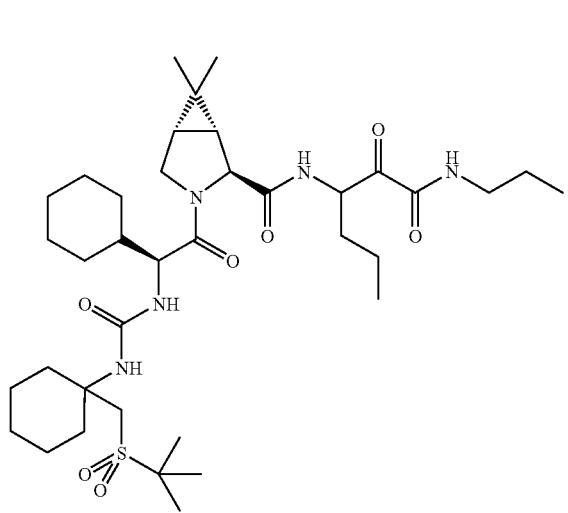
TABLE 1-continued
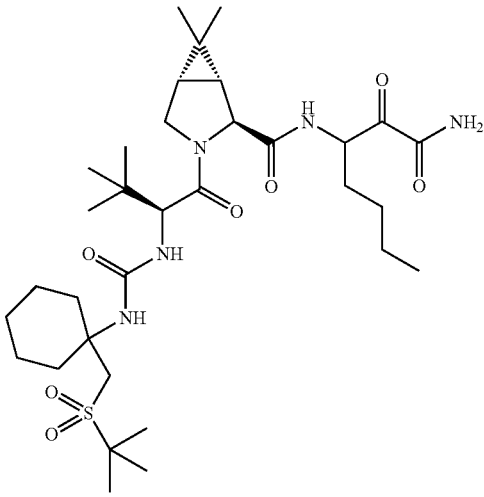
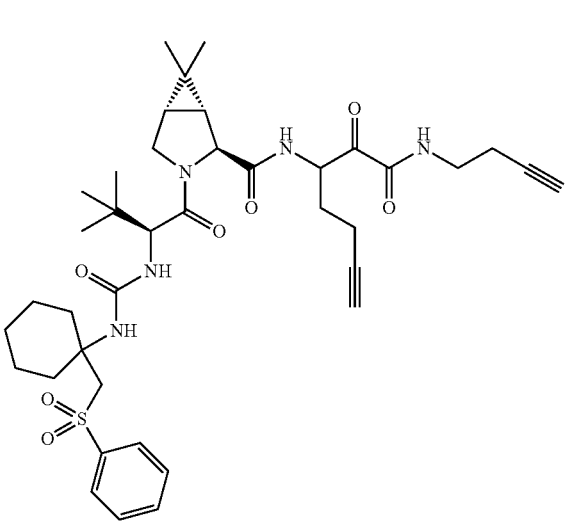

TABLE 1-continued
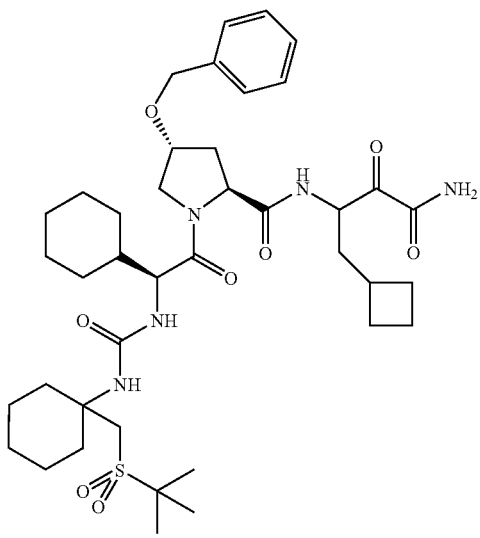
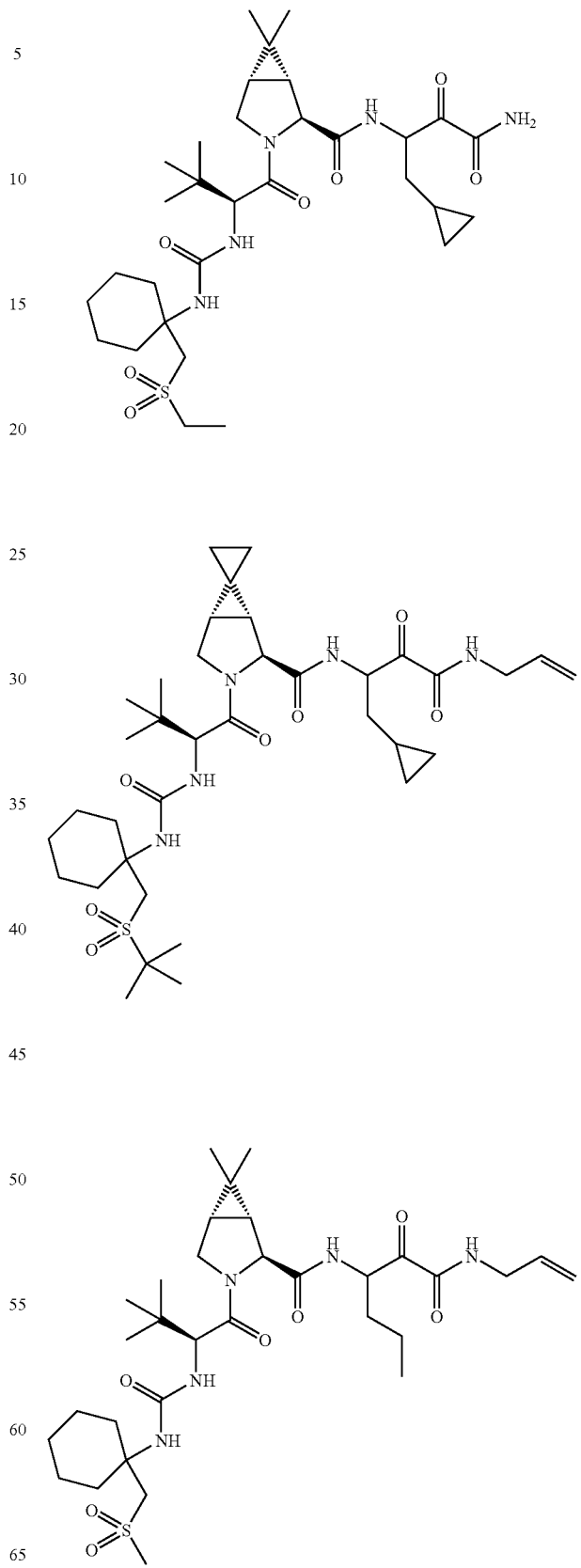

TABLE 1-continued
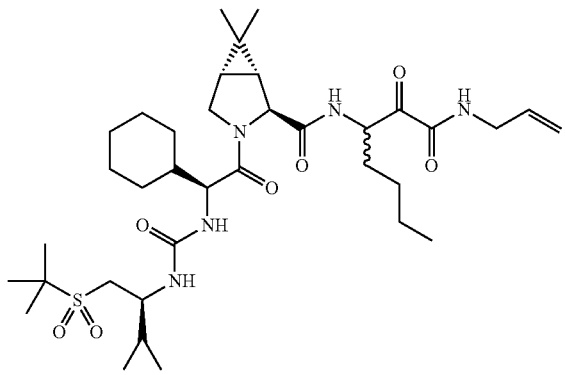
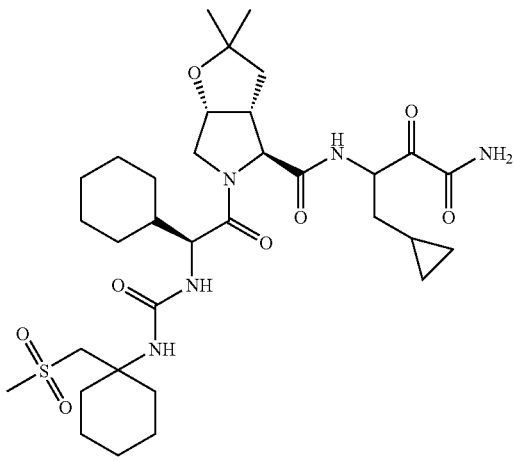
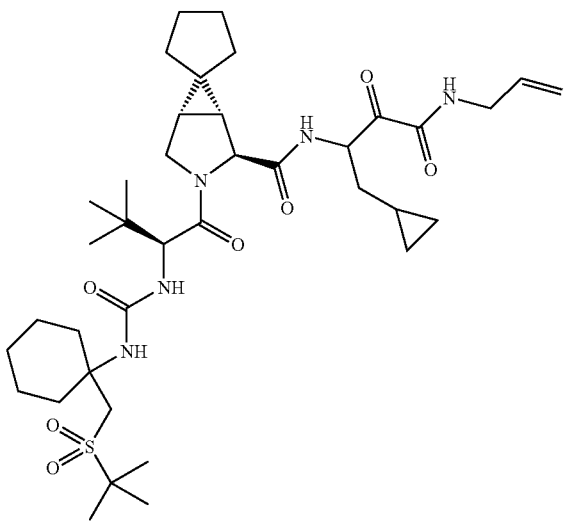
TABLE 1-continued
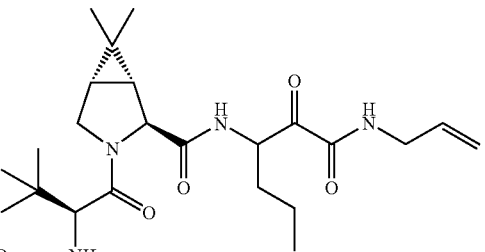
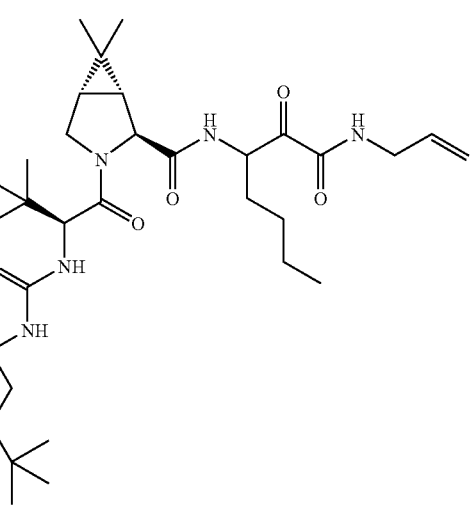
In an additional embodiment, this invention discloses the following compounds in Table 2:
TABLE 2
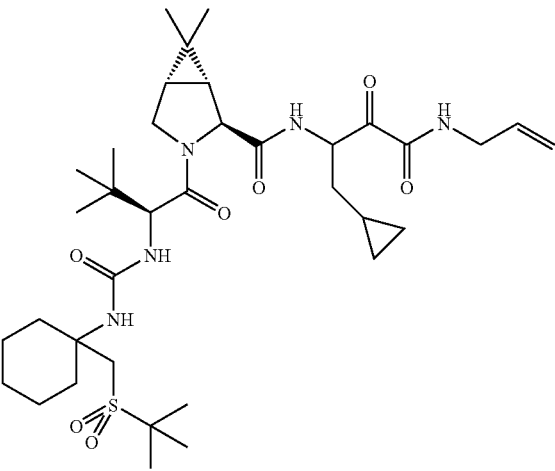

TABLE 2-continued
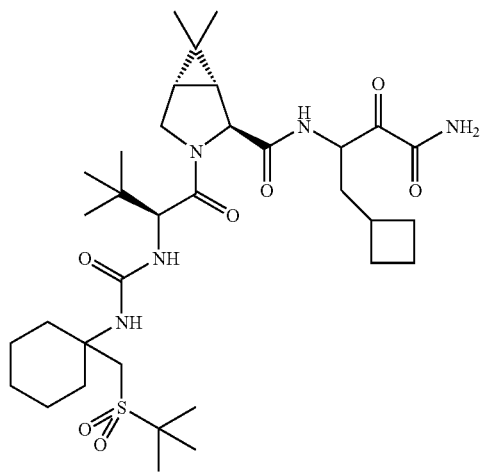
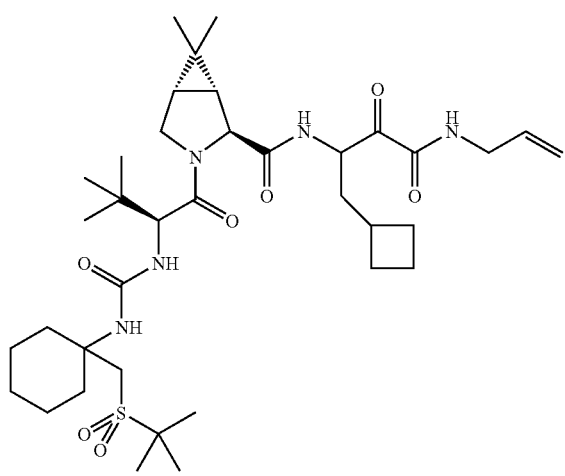
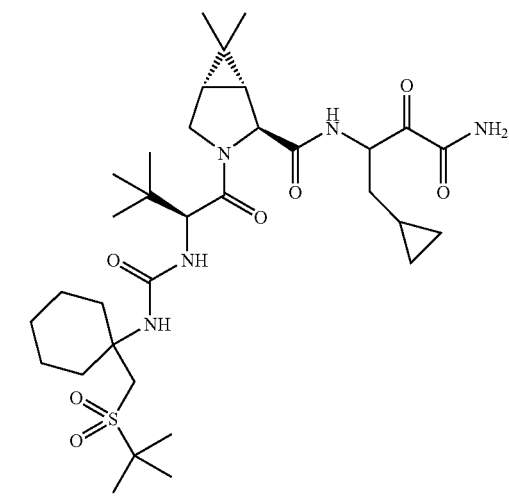
TABLE 2-continued
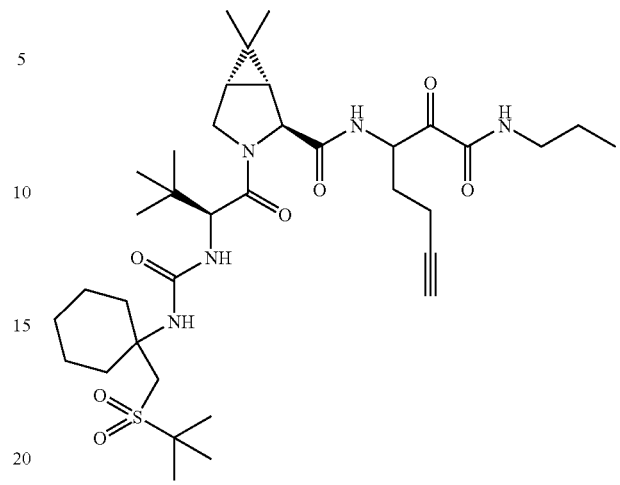
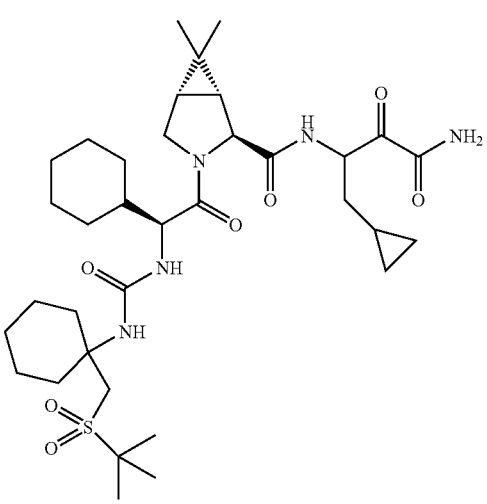
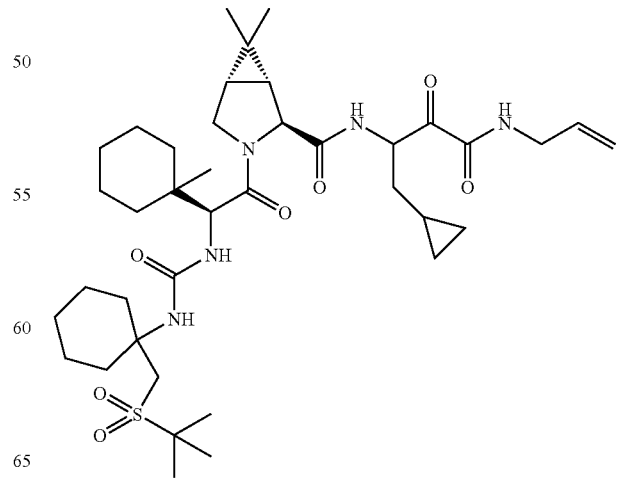

TABLE 2-continued
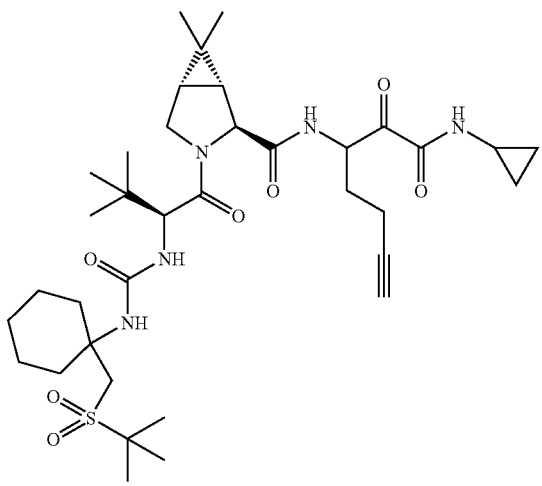
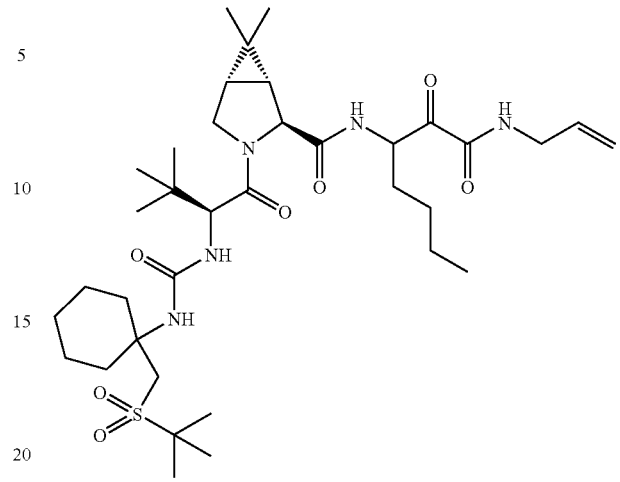
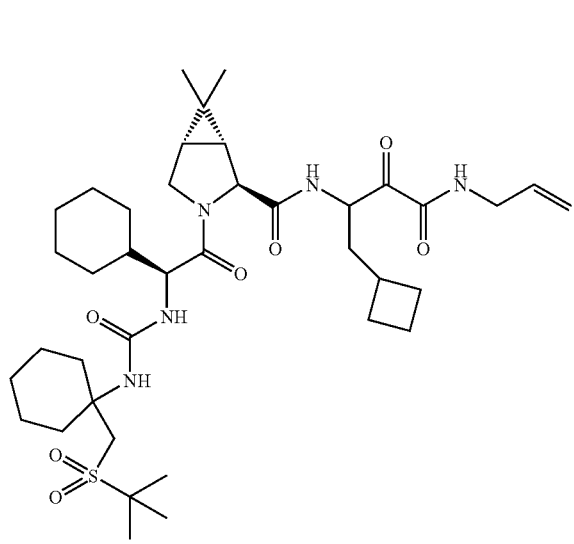
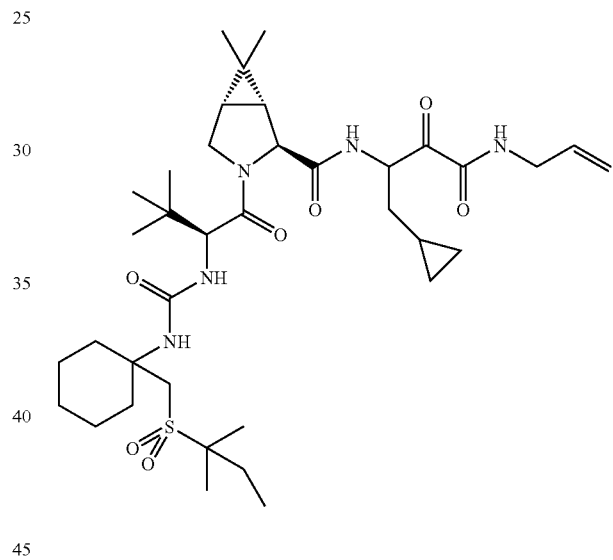
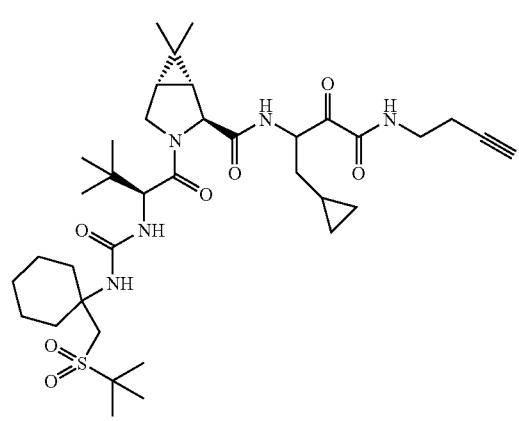

TABLE 2-continued

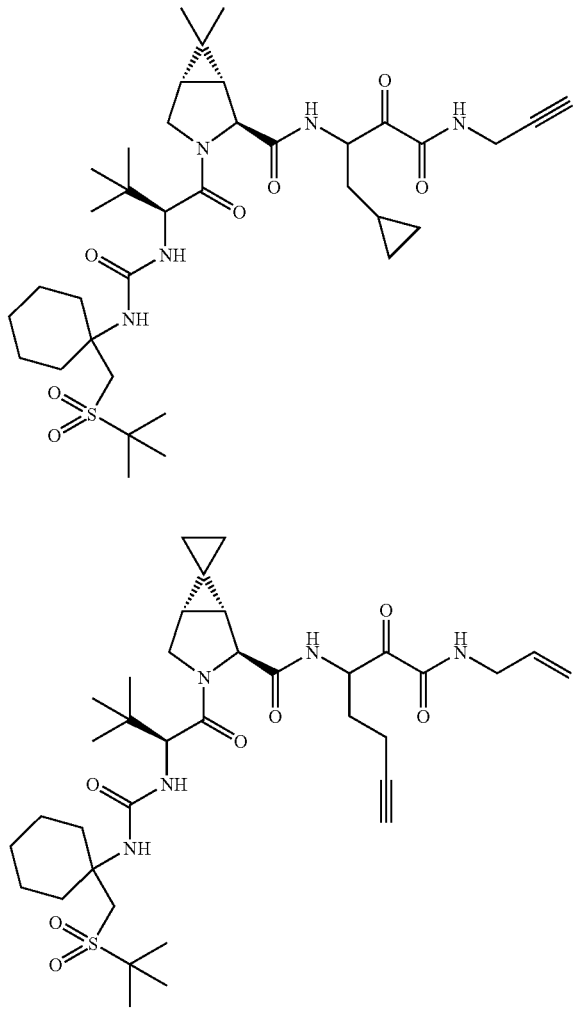

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" or "halo" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

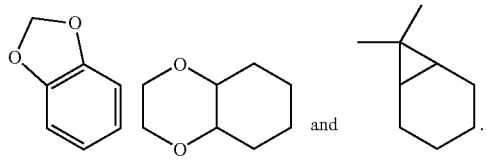

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

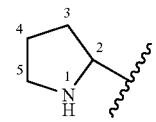

there is no —OH attached directly to carbons marked 2 and 5.

It should also be noted that tautomeric forms such as, for example, the moieties:

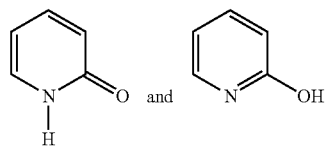

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "one or more" or "at least one", when indicating the number of substituents, compounds, combination agents and the like, refers to at least one, and up to the maximum number of chemically and physically permissible, substituents, compounds, combination agents and the like, that are present or added, depending on the context. Such techniques and knowledge are well known within the skills of the concerned artisan.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have the hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts, Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prod rug of enantiomers, stereoisomers, rotamers, tautomers, positional isomers, racemates or prodrugs of the inventive compounds.

Polymorphic forms of the compounds of Formula I, and of the salts, solvates, esters and prodrugs of the compounds of Formula I, are intended to be included in the present invention.

It is to be understood that the utility of the compounds of Formula I for the therapeutic applications discussed herein is applicable to each compound by itself or to the combination or combinations of one or more compounds of Formula I as illustrated, for example, in the next immediate paragraph. The same understanding also applies to pharmaceutical composition(s) comprising such compound or compounds and method(s) of treatment involving such compound or compounds.

The compounds according to the invention can have pharmacological properties; in particular, the compounds of Formula I can be inhibitors of HCV protease, each compound by itself or one or more compounds of Formula I can be combined with one or more compounds selected from within Formula I: The compound(s) can be useful for treating diseases such as, for example, HCV, HIV, (AIDS, Acquired Immune Deficiency Syndrome), and related disorders, as well as for modulating the activity of hepatitis C virus (HCV) protease, preventing HCV, or ameliorating one or more symptoms of hepatitis C.

The compounds of Formula I may be used for the manufacture of a medicament to treat disorders associated with the HCV protease, for example, the method comprising bringing into intimate contact a compound of Formula I a pharmaceutically acceptable carrier.

In another embodiment, this invention provides pharmaceutical compositions comprising the inventive compound or compounds as an active ingredient. The pharmaceutical compositions generally additionally comprise at least one pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

The compounds of the invention may also be administered orally, intravenously, intranasally or subcutaneously.

The compounds of the invention may also comprise preparations which are in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the inventive compounds or pharmaceutical compositions disclosed above for treatment of diseases such as, for example, hepatitis C and the like. The method comprises administering a therapeutically effective amount of the inventive compound or pharmaceutical composition to a patient having such a disease or diseases and in need of such a treatment.

In yet another embodiment, the compounds of the invention may be used for the treatment of HCV in humans in monotherapy mode or in a combination therapy (e.g., dual combination, triple combination etc.) mode such as, for example, in combination with antiviral and/or immunomodulatory agents. Examples of such antiviral and/or immunomodulatory agents include Ribavirin (from Schering-Plough Corporation, Madison, N.J.) and Levovirin™ (from ICN Pharmaceuticals, Costa Mesa, Calif.), VP 50406™ (from Viropharma, Incorporated, Exton, Pa.), ISIS 14803™ (from ISIS Pharmaceuticals, Carlsbad, Calif.), Heptazyme™ (from Ribozyme Pharmaceuticals, Boulder, Colo.), VX 497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

As stated earlier, the invention includes tautomers, rotamers, enantiomers and other stereoisomers of the inventive compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Illustrative procedures are outlined in the following reaction schemes. The illustrations should not be construed to limit the scope of the invention which is defined in the appended claims. Alternative mechanistic pathways and analogous structures will be apparent to those skilled in the art.

It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

For the procedures described below, the following abbreviations are used:
THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et2O: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
DMF-DMA: N,N-Dimethylformamide-dimethylacetal
iBoc: isobutoxycarbonyl
iPr: isopropyl
$^t$Bu or Bu$^t$: tert-Butyl
Boc: tert-Butyloxycarbonyl Cbz: Benzyloxycarbonyl
Cp: Cylcopentyldienyl
Ts: p-toluenesulfonyl
Me: Methyl
HATU: O-(7-azabenzotriazol-1-yl)-1,1,3,3-tetramethyluronium hexafluorophosphate
DMAP: 4-N,N-Dimethylaminopyridine
BOP: Benzotriazol-1-yl-oxy-tris(dimethylamino)hexafluorophosphate
PCC: Pyridiniumchlorochromate
KHMDS: Potassium Hexamethyldisilazide or Potassium bis(trimethylsilylamide)
NaHMDS: Sodium Hexamethyldisilazide or Sodium bis(trimethylsilylamide)
LiHMDS: Lithium Hexamethyldisilazide or Lithium bis(trimethylsilylamide)
10% Pd/C: 10% Palladium on carbon (by weight).
TG: Thioglycerol General Schemes for Preparation of Target Compounds Compounds of the present invention were synthesized using the general schemes (Methods A-E) described below.

Method A

Deprotection of the N—Boc functionality of 1.01 under acidic conditions provided the hydrochloride salt 1.02 which was subsequently coupled with N—Boc-tert-leucine under peptide coupling methodology to afford 1.03. N—Boc deprotection followed by treatment with appropriate isocyanate gave the urea 1.05. Hydrolysis of the methyl ester provided the acid 1.06. Peptide coupling of the acid 1.06 with the appropriate $P_1$-$P'$ primary amide moiety afforded the hydroxylamide 1.07. Oxidation (Moffatt oxidation or related process—see, T. T. Tidwell, *Synthesis,* 1990, 857), or Dess-Martin Periodinane—*J. Org. Chem.,* (1983) 48, 4155) resulted in the target compound 1.08.

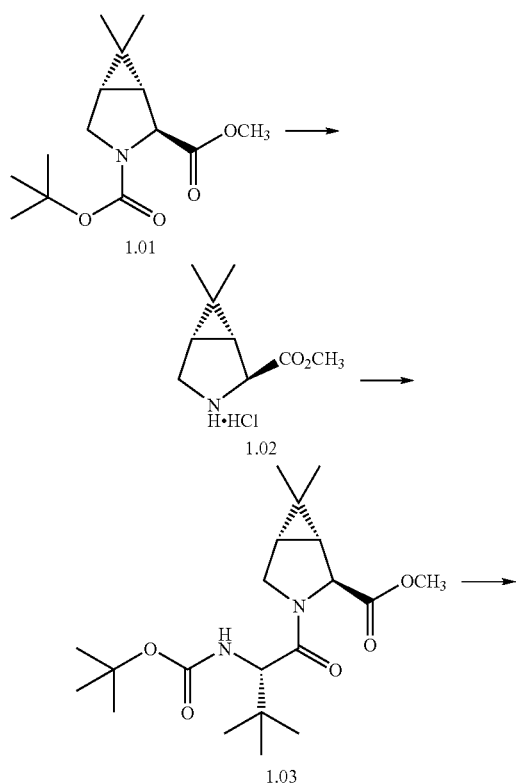

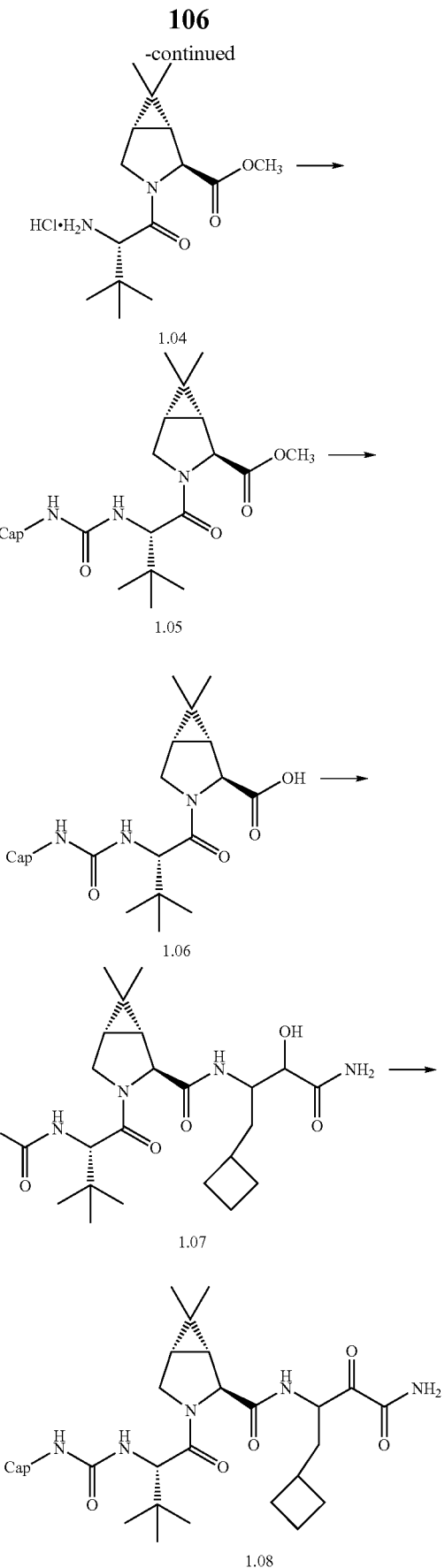

Method B

Peptide coupling of the acid 1.06 with the appropriate P$_1$-P' secondary amide moiety afforded the hydroxylamide 1.09. Oxidation (Moffatt or Dess-Martin's) resulted in the target compound 1.10.

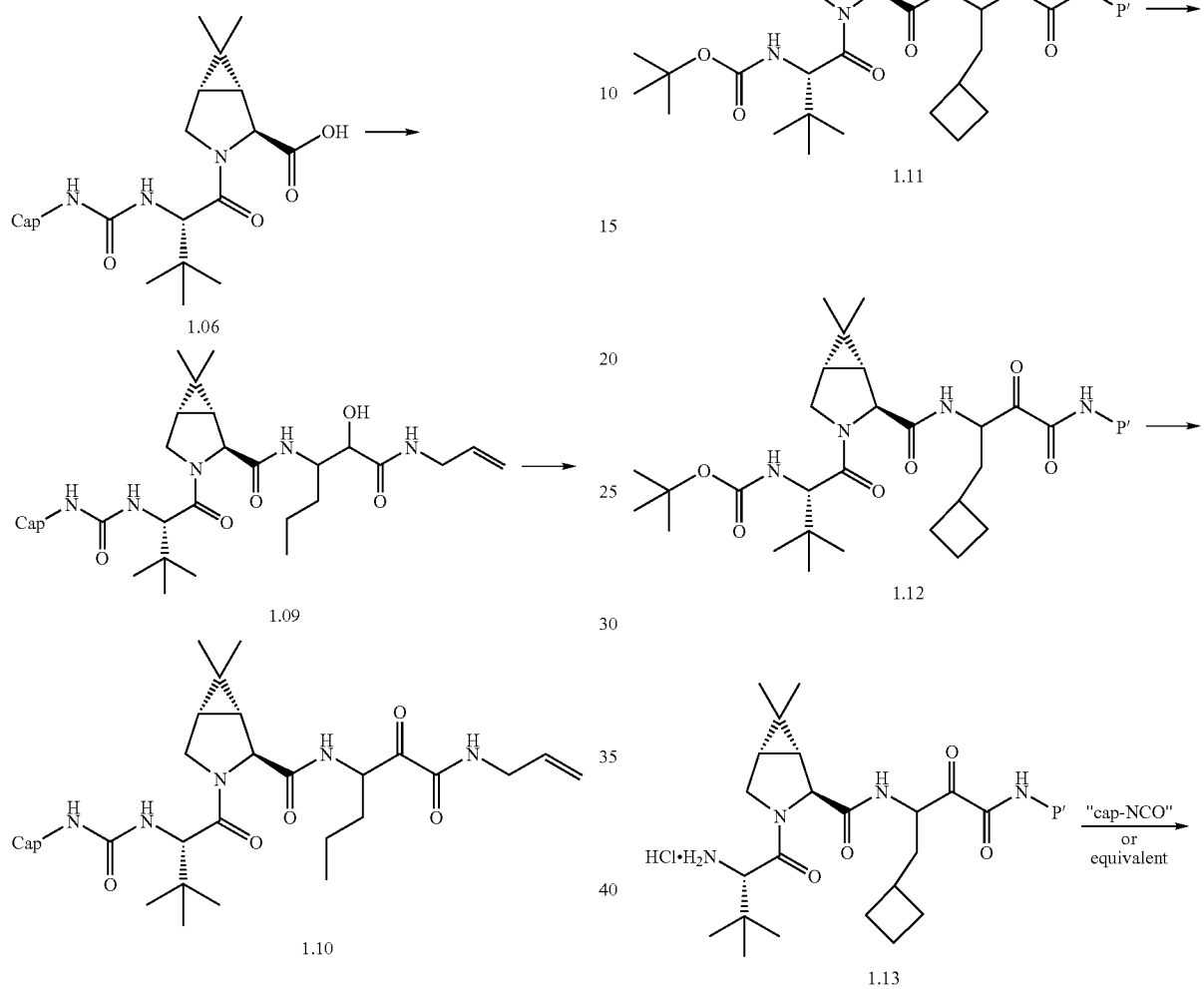

Method C

In another variation, peptide coupling of the N—Boc-P2-P$_3$-acid 1.17 with the appropriate P$_1$-P' amide moiety afforded the hydroxylamide 1.11. Oxidation (Moffatt or Dess-Martin Periodinane) resulted in the keto amide 1.12. Deprotection of the N—Boc functionality gave the hydrochloride salt 1.13. Treatment with a suitable isocyanate (or isocyanate equivalent) resulted in the target compound 1.14.

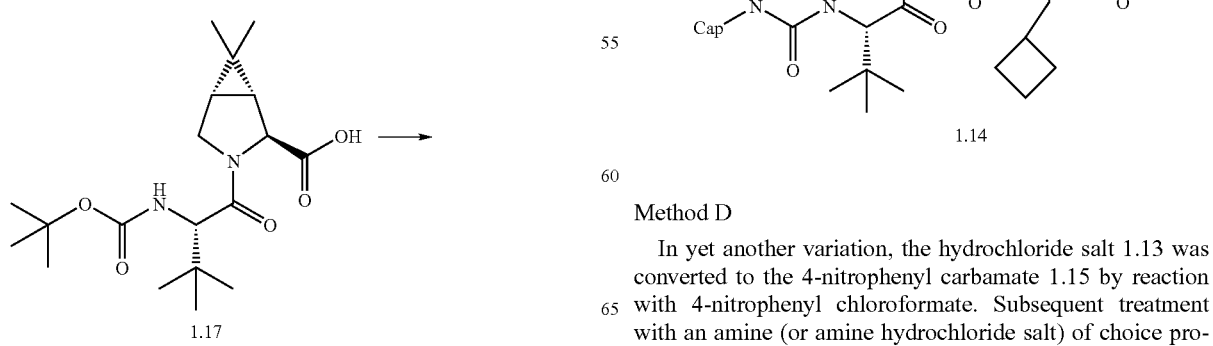

Method D

In yet another variation, the hydrochloride salt 1.13 was converted to the 4-nitrophenyl carbamate 1.15 by reaction with 4-nitrophenyl chloroformate. Subsequent treatment with an amine (or amine hydrochloride salt) of choice provided the target compound 1.14.

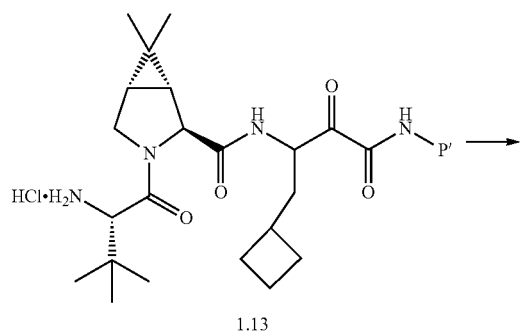

1.13

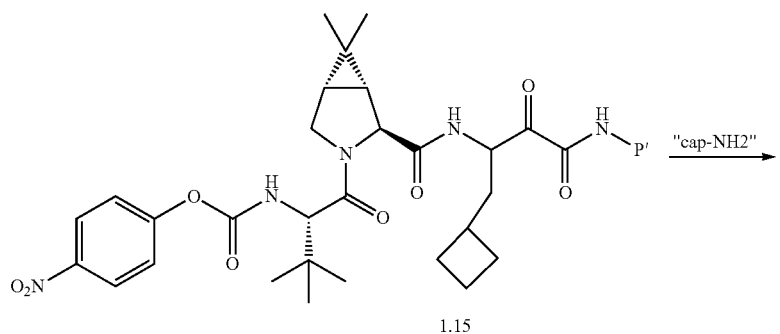

1.15

"cap-NH2"

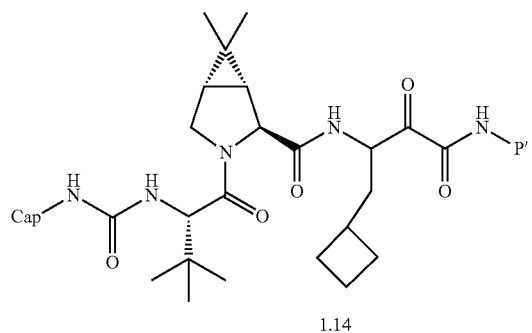

1.14

Method E

In yet another variation, the dipeptide hydrochloride salt 1.03 was converted to the 4-nitrophenyl carbamate as described above. Treatment with an amine (or amine hydrochloride salt) of choice provided the urea derivative 1.05. Hydrolysis and further elaboration as described in Methods A/B provided the target compounds 1.14.

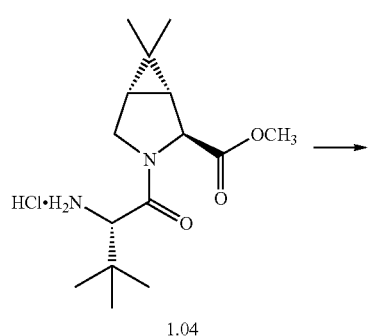

1.04

-continued

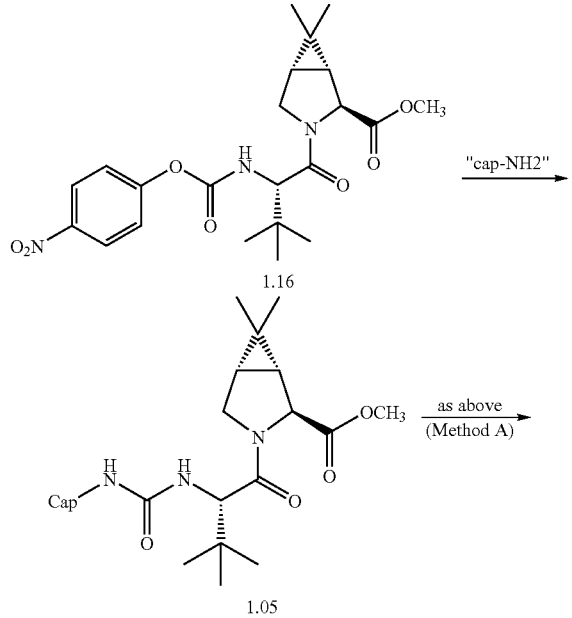

1.16

"cap-NH2"

1.05 as above (Method A)

111

-continued

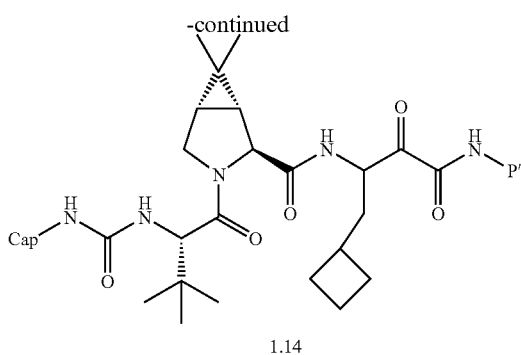

1.14

Preparation of P1-P' Moieties
Preparation of Intermediates 10.11 and 10.12

Step 1.

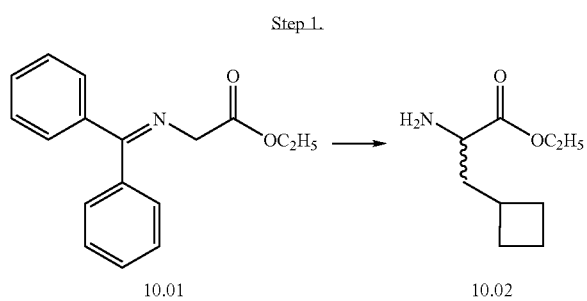

10.01          10.02

A stirred solution of ketimine 10.01 (50 g, 187.1 mmol) under N₂ in dry THF (400 mL) was cooled to –78° C. and treated with 1 M solution of K-ᵗBuO (220 mL, 1.15 equiv.) in THF. The reaction mixture was warmed to 0° C. and stirred for 1 h and treated with bromomethyl cyclobutane (28 mL, 249 mmol). The reaction mixture was stirred at room temperature for 48 h and concentrated in vacuo. The residue was dissolved in Et₂O (300 mL) and treated with aq. HCl (2 M, 300 mL) The resulting solution was stirred at room temperature for 5 h and extracted with Et₂O (1 L). The aqueous layer was made basic to pH ~12-14 with NaOH (50% aq.) and extracted with CH₂Cl₂ (3×300 mL). The combined organic layers were dried (MgSO₄), filtered, and concentrated to give the pure amine (10.02, 18 g) as a colorless oil.

Step 2.

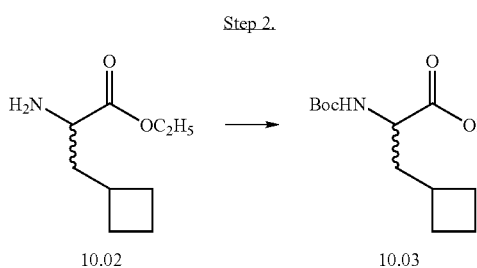

10.02          10.03

A solution of the amine 10.02 (18 g, 105.2 mmol) at 0° C. in CH₂Cl₂ (350 mL) was treated with di-tert-butyldicarbonate (23 g, 105.4 mmol) and stirred at rt. for 12 h. After the completion of the reaction (TLC), the reaction mixture was concentrated in vacuo and the residue was dissolved in THF/H₂O (200 ml, 1:1) and treated with LiOH.H₂O (6.5 g, 158.5 mmol) and stirred at room temperature for 3 h. The reaction mixture was concentrated and the basic aqueous layer was

112 extracted with Et₂O. The aqueous layer was acidified with conc. HCl to pH~1-2 and extracted with CH₂Cl₂. The combined organic layers were dried (MgSO₄), filtered, and concentrated in vacuo to yield 10.03 as a colorless viscous oil which was used for the next step without any further purification.

Step 3.

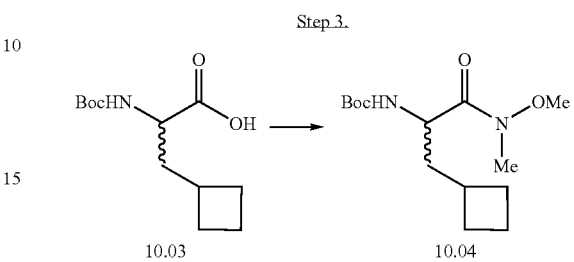

10.03          10.04

A solution of the acid 10.03 (15.0 g, 62 mmol) in CH₂Cl₂ (250 mL) was treated with BOP reagent (41.1 g, 93 mmol), N-methyl morpholine (27 mL), N,O-dimethyl hydroxylamine hydrochloride (9.07 g, 93 mmol) and stirred overnight at rt. The reaction mixture was diluted with 1 N aq. HCl (250 mL), and the layers were separated and the aqueous layer was extracted with CH₂Cl₂ (3×300 ml). The combined organic layers were dried (MgSO₄), filtered and concentrated in vacuo and purified by chromatography (SiO₂, EtOAc/Hex 2:3) to yield the amide 10.04 (15.0 g) as a colorless solid.

Step 4.

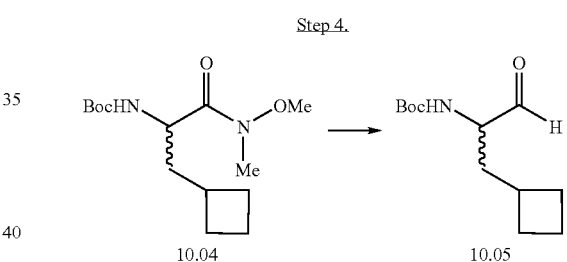

10.04          10.05

A solution of the amide 10.04 (15 g, 52.1 mmol) in dry THF (200 mL) was treated dropwise with a solution of LiAlH₄ (1M, 93 mL, 93 mmol) at 0° C. The reaction mixture was stirred at room temperature for 1 h and carefully quenched at 0° C. with a solution of KHSO₄ (10% aq.) and stirred for 0.5 h. The reaction mixture was diluted with aq. HCl (1 M, 150 mL) and extracted with CH₂Cl₂ (3×200 mL), The combined organic layers were washed with aq. HCl (1 M), saturated NaHCO₃, brine, and dried (MgSO₄). The mixture was filtered and concentrated in vacuo to yield 10.05 as a viscous colorless oil (14 g).

Step 5:

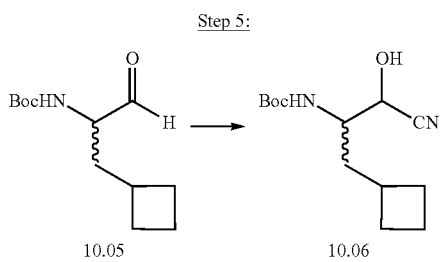

10.05          10.06

A solution of the aldehyde 10.05 (14 g, 61.6 mmol) in CH₂Cl₂ (50 mL), was treated with Et₃N (10.73 mL, 74.4 mmol), and acetone cyanohydrin (10.86 g, 127.57 mmol) and stirred at room temperature for 24 hrs. The reaction mixture was concentrated in vacuo and diluted with aq. HCl (1 M, 200 mL) and extracted into CH₂Cl₂ (3×200 mL). The combined organic layer were washed with H₂O, brine, dried (MgSO₄), filtered, concentrated in vacuo and purified by chromatography (SiO₂, EtOAc/Hex 1:4) to yield 10.06 (10.3 g) as a colorless liquid Step 6.

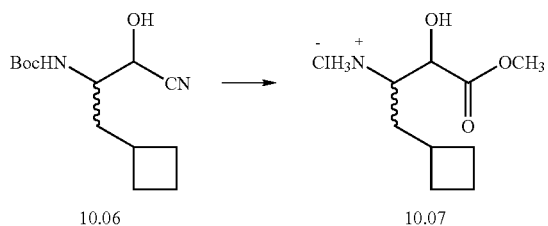

Methanol saturated with HCl*, prepared by bubbling HCl gas through CH₃OH (700 ml) at 0° C., was treated with the cyanohydrin 10.06 and heated to reflux for 24 h. The reaction was concentrated in vacuo to yield 10.07, which was used in the next step without purification.
* Alternatively 6M HCl prepared by addition of AcCl to dry methanol can also be used.

Step 7.

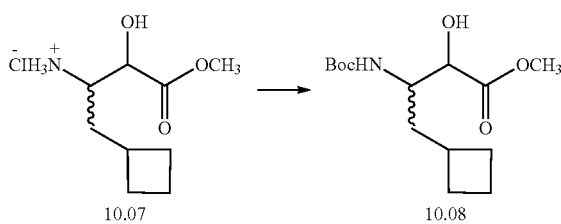

A solution of the amine hydrochloride 10.07 in CH₂Cl₂ (200 mL) was treated with Et₃N (45.0 mL, 315 mmol) and Boc₂O (45.7 g, 209 mmol) at −78° C. The reaction mixture was then stirred at room temperature overnight and diluted with HCl (2 M, 200 mL) and extracted into CH₂Cl₂. The combined organic layers were dried (MgSO₄) filtered, concentrated in vacuo and purified by chromatography (EtOAc/Hex 1:4) to yield hydroxy ester 10.08.

Step 8.

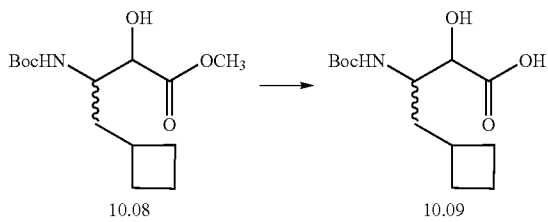

A solution of methyl ester 10.08 (3 g, 10.5 mmol) in THF/H₂O (1:1) was treated with LiOH.H₂O (645 mg, 15.75 mmol) and stirred at rt. for 2 h. The reaction mixture was acidified with aq HCl (1 M, 15 mL) and concentrated in vacuo. The residue was dried in vacuum to afford 10.09 in quantitative yield.

Step 9.

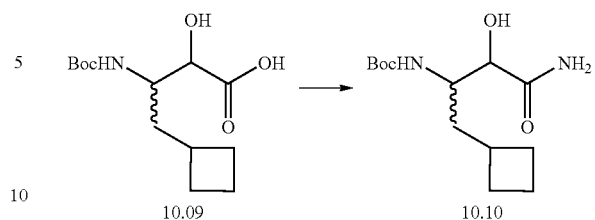

A solution of the acid 10.09 (from above) in CH₂Cl₂ (50 mL) and DMF (25 mL) was treated with NH₄Cl (2.94 g, 55.5 mmol), EDCl (3.15 g, 16.5 mmol), HOOBt (2.69 g, 16.5 mmol), and NMM (4.4 g, 44 mmol). The reaction mixture was stirred at room temperature for 3 d. The solvents were removed under vacuo and the residue was diluted with aq. HCl (250 mL) and extracted with CH₂Cl₂. The combined organic layers were washed with aq. saturated NaHCO₃, dried (MgSO₄) filtered concentrated in vacuo to obtain 10.10, which was used as it was in the following steps. (Alternatively 10.10 can also be obtained directly by the reaction of 10.06 (4.5 g, 17.7 mmol) with aq. H₂O₂ (10 mL), LiOH.H₂O (820 mg, 20.8 mmol) at 0° C. in 50 mL of CH₃OH for 0.5 h.).

Step 10.

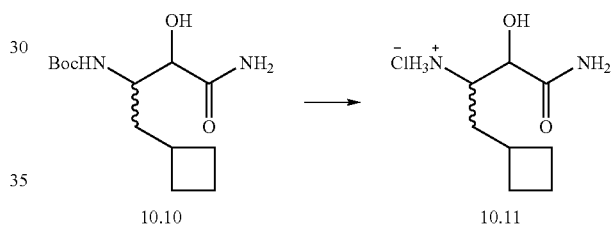

A solution of 10.10 obtained in the previous step was dissolved in 4 N HCl in dioxane and stirred at rt. for 2 h. The reaction mixture was concentrated in vacuo to give the intermediate 10.11 as a solid, which was used without further purification.

Step 11.

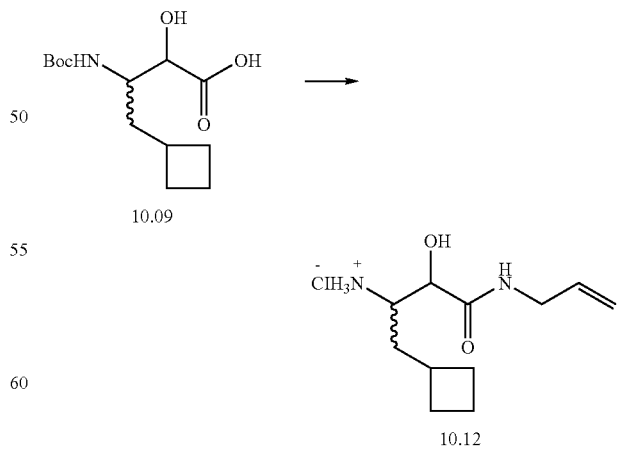

The required intermediate 10.12 was obtained from compound 10.09 using essentially the procedures described above in Steps 9, 10 with appropriate reagents.

Preparation of Intermediate 11.01

Step 1

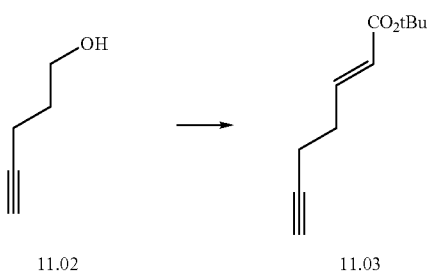

To a solution of 4-pentyn-1-ol, 11.02 (4.15 g; Aldrich) was added Dess-Martin Periodinane (30.25 g; Aldrich) and the resulting mixture was stirred for 45 min. before the addition of (tert-Butoxycarbonylmethylene)triphenylphosphorane (26.75 g; Aldrich). The resulting dark reaction was stirred overnight, diluted with EtOAc), washed with aq. sodium sulfite. sat. aq. NaHCO3, water, brine and dried. The volatiles were removed under reduced pressure and the residue was purified by silica gel column chromatography using 1% EtOAc in hexanes as eluent to give the desired compound, 11.03 (3.92 g). Some impure fractions were also obtained but set aside at this time.

Step 2

Using the alkene 11.03 (1.9 g) in n-propanol (20 ml; Aldrich)), benzyl carbamate (4.95 g; Aldrich) in n-propanol (40 ml), NaOH (1.29 g) in water (79 ml), tert-butyl hypochlorite (3.7 ml), (DHQ)2PHAL (0.423 g; Aldrich)) in n-propanol (37.5 ml), and potassium osmate:dehydrate (0.1544 g; Aldrich) and the procedure set forth in *Angew. Chem. Int. Ed. Engl* (1998), 35, (23/24), pp. 2813-7. gave a crude product which was purified by silica gel column chromatography using EtOAc:Hexanes (1:5) to give the desired amino alcohol 11.04 (1.37 g, 37%) as a white solid.

Step 3

To the ester 11.04 (0.700 g) was added 4M HCl in dioxane (20 ml; Aldrich) and the resulting mixture was allowed to stand at room temperature overnight. The volatiles were removed under reduced pressure to give the acid 11.05 (0.621 g) as a white solid.

Step 4

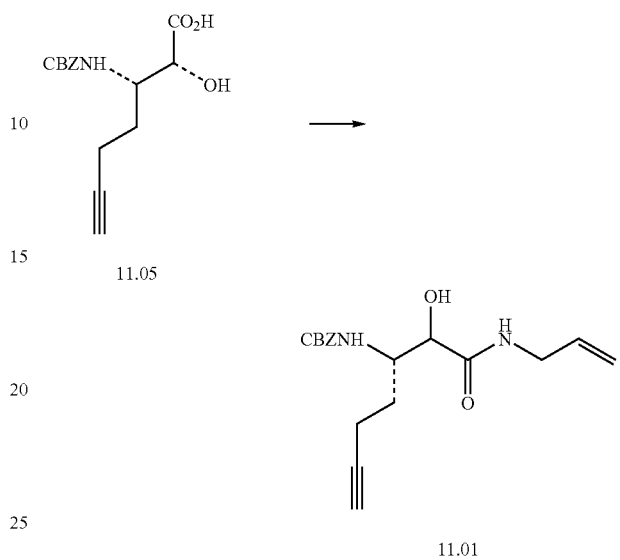

BOP reagent (3.65 g; Sigma) followed by triethylamine (3.45 ml) were added to a dichloromethane (20 ml) solution of the carboxylic acid 11.05 (2.00 g) and allyl amine (0.616 ml) at room temperature and the resulting mixture was stirred overnight. The reaction mixture was partitioned between EtOAc and 10% aq. HCl. The organic phase was separated, washed with sat. aq. sodium bicarbonate, water, dried (magnesium sulfate). The crude reaction product was purified by silica gel column chromatography using (EtOAc:Hexanes; 70:30) as eluent to provide the desired amide 11.01 (1.73 g) as a viscous yellow oil.

Preparation of Intermediates 12.03 and 12.04

Step 1

Compound 12.01 was converted to the required material 12.02 using essentially the procedures described for Intermediate 10.11, Steps 3-8.

Step 2

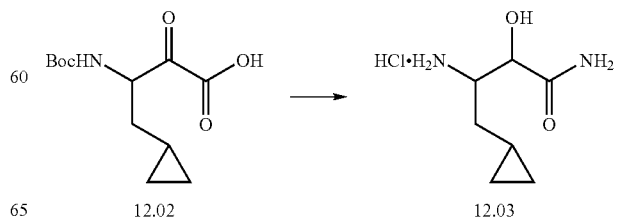

Compound 12.02 was converted to the required intermediate 12.03 using essentially the procedures described for Intermediate 10.11, Steps 9, 10.

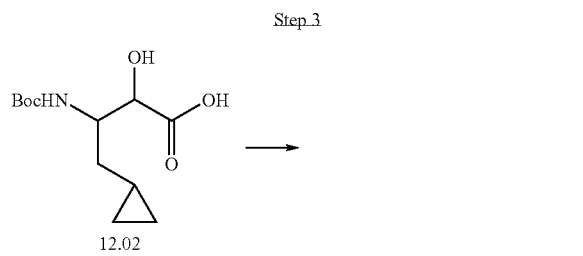

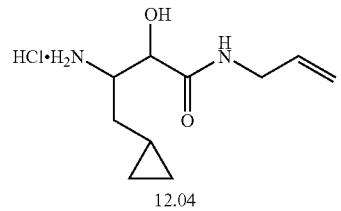

Compound 12.02 was converted to the required intermediate 12.03 using essentially the procedures described for Intermediate 10.12, Step 11.

Preparation of Intermediate 13.01

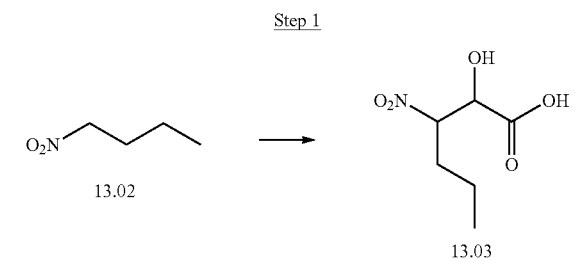

To a stirred solution of 1-nitrobutane, 13.02 (16.5 g, 0.16 mol) and glyoxylic acid in H$_2$O (28.1 g, 0.305 mol) and MeOH (122 mL) at 0° C.-5° C., was added dropwise triethylamine (93 mL, 0.667 mol) over 2 hrs. The solution was warmed to room temperature, stirred overnight and concentrated to dryness to give an oil. The oil was then dissolved in H$_2$O and acidified to pH =1 with 10% HCl, followed by extraction with EtOAc. The combined organic solution was washed with brine, dried over Na$_2$SO$_4$, filtered and concentrated to dryness to give the product 13.03 (28.1 g, 99% yield).

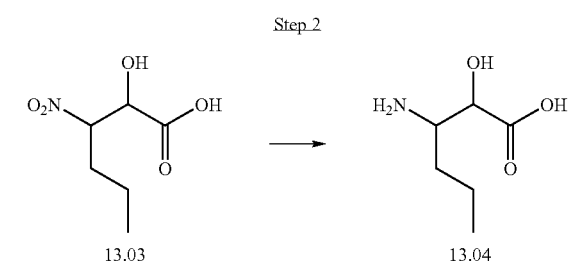

To a stirred solution of compound 13.03 (240 g, 1.35 mol) in acetic acid (1.25 L) was added 10% Pd/C (37 g). The resulting solution was hydrogenated at 59 psi for 3 hrs and then at 60 psi overnight. The acetic acid was then evaporated and azeotroped 3 times with toluene, then triturated with MeOH and ether. The solution was then filtered and azeotroped twice with toluene to afford 13.04 as an off white solid (131 g, 0.891 mol, 66%).

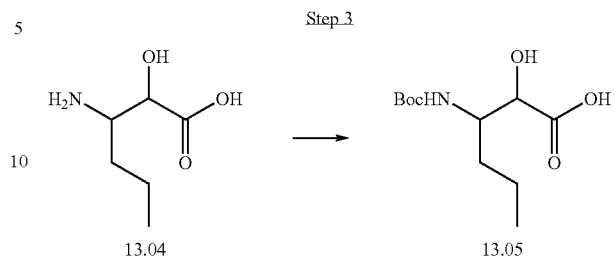

To a stirred solution of the amino acid 13.04 (2.0 g, 13.6 mmol) in dioxane (10 mL) and H$_2$O (5 mL) at 0° C., was added 1N NaOH solution (4.3 mL, 14.0 mmol). The resulting solution was stirred for 10 minutes, followed by addition of di-t-butyldicarbonate (0.110 g, 14.0 mmol) and stirred at 0° C. for 15 minutes. The solution was then warmed to room temperature, stirred for 45 minutes and kept at refrigerator overnight and concentrated to dryness to give a crude material. To the solution of this crude material in EtOAc (100 mL) and ice, was added KHSO$_4$ (3.36 g) and H$_2$O (32 mL) and stirred for 4-6 minutes. The organic layer was then separated and the aqueous layer was extracted twice with EtOAc and the combined organic layer was washed with water, brine, dried over Na$_2$SO$_4$, filtered and concentrated to dryness to give the product 13.05 as a clear gum (3.0 g, 89% yield).

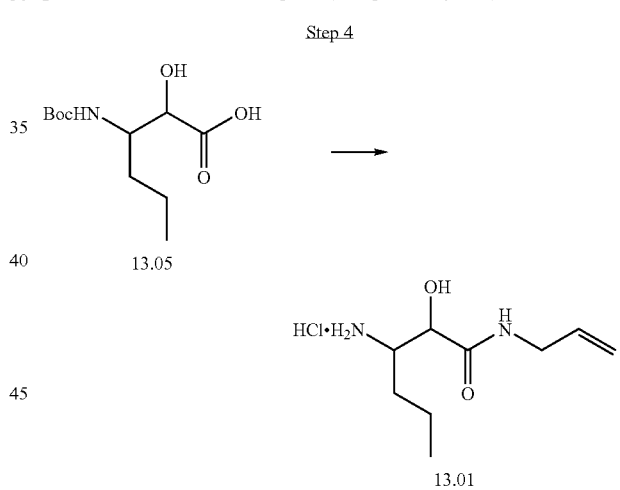

Compound 13.05 was converted to the required intermediate 13.01 using essentially the procedures described for Intermediate 10.12, Step 11.

Preparation of Intermediate 14.01

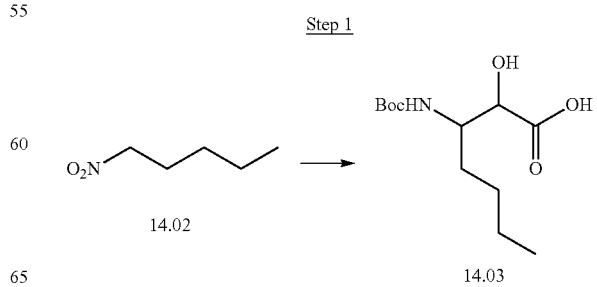

Compound 14.02 was converted to the required material 14.03 using essentially the procedures described for Intermediate 13.01, Steps 1-3.

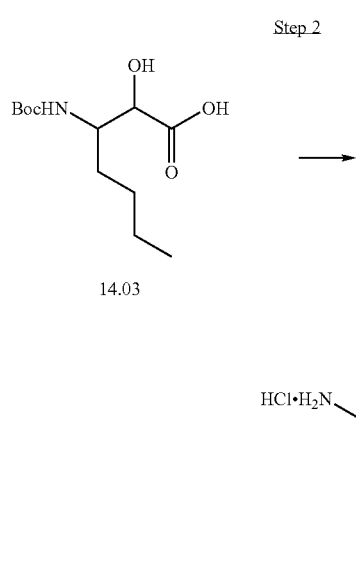

14.03

14.01

Compound 14.03 was converted to the required intermediate 14.01 using essentially the procedures described for Intermediate 10.12, Step 11. Preparation of Intermediate 15.01

Step 1

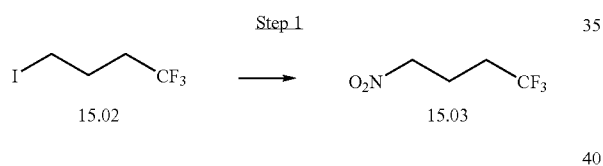

15.02    15.03

To a suspension of silver nitrite (9 g, 58.5 mmol) in diethyl ether (25 mL) at 0° C. was added a solution of 4-iodo-1,1,1-trifluorobutane, 15.02 (10 g, 42.0 mmol) in diethyl ether (25 mL) slowly through an addition funnel (approx. 15 min). The resulting mixture was vigorously stirred at 0° C. and warmed to rt. After 50 h, the solid material was filtered off through a celite pad. The resulting diethyl ether solution was concentrated in vacuo to give 15.03 as colorless oil, which was used without further purification.

Step 2

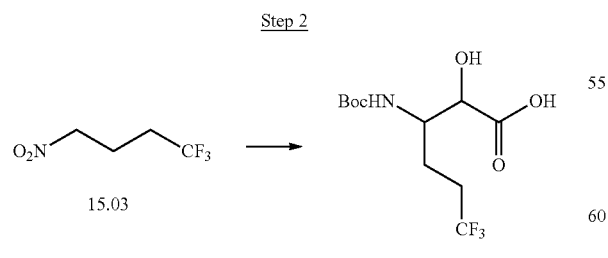

15.03    15.04

Compound 15.03 was converted to the required material 15.04 using essentially the procedures described for Intermediate 13.01, Steps 1-3.

Step 3

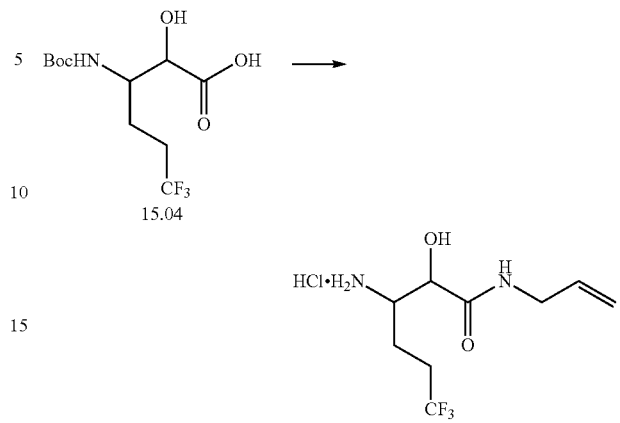

15.04

15.01

Compound 15.04 was converted to the required intermediate 15.01 using essentially the procedures described for Intermediate 10.12, Step 11.

Preparation of Intermediate 16.01

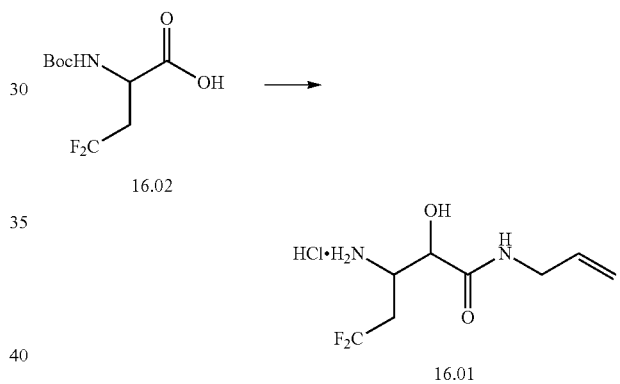

16.02

16.01

The acid 16.02 (Winkler, D.; Burger, K., *Synthesis*, 1996, 1419) is processed as described above (preparation of Intermediate 10.12) to give the expected intermediate 16.01

Preparation of P2/P3-P2 Moieties

Preparation of Intermediate 20.01

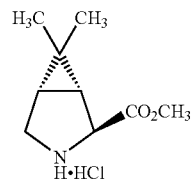

The amino ester 20.01 was prepared following the method of R. Zhang and J. S. Madalengoitia (*J. Org. Chem.* 1999, 64, 330), with the exception that the Boc group was cleaved by the reaction of the Boc-protected amino acid with methanolic HCl.

(Note: In a variation of the reported synthesis, the sulfonium ylide was replaced with the corresponding phosphonium ylide).

Preparation of Intermediate 20.04

Step 1

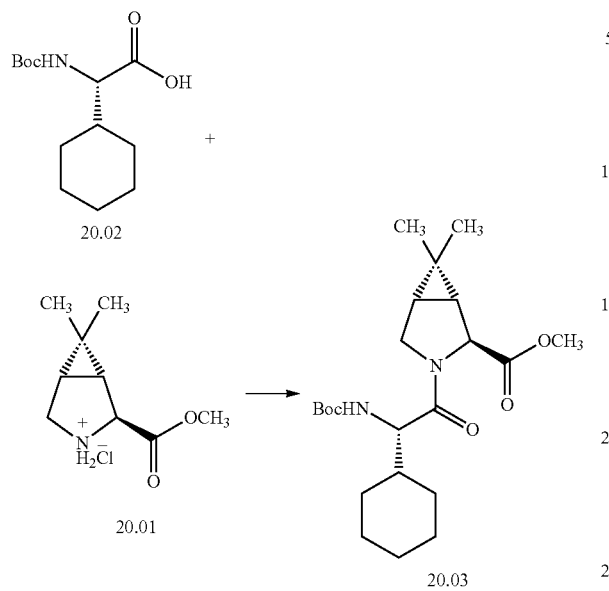

A solution of commercial amino acid Boc-Chg-OH, 20.02 (Senn chemicals, 6.64 g, 24.1 mmol) and amine hydrochloride 20.01 (4.5 g, 22 mmol) in $CH_2Cl_2$ (100 mL) at 0° C. was treated with BOP reagent and stirred at rt. for 15 h. The reaction mixture was concentrated in vacuo, then it was diluted with aq. 1 M HCl and extracted into EtOAc (3×200 mL). The combined organic layers were washed with saturated $NaHCO_3$ (200 mL), dried ($MgSO_4$), filtered and concentrated in vacuo, and chromatographed ($SiO_2$, EtOAc/Hex 3:7) to obtain 20.03 (6.0 g) as a colorless solid.

Step 2

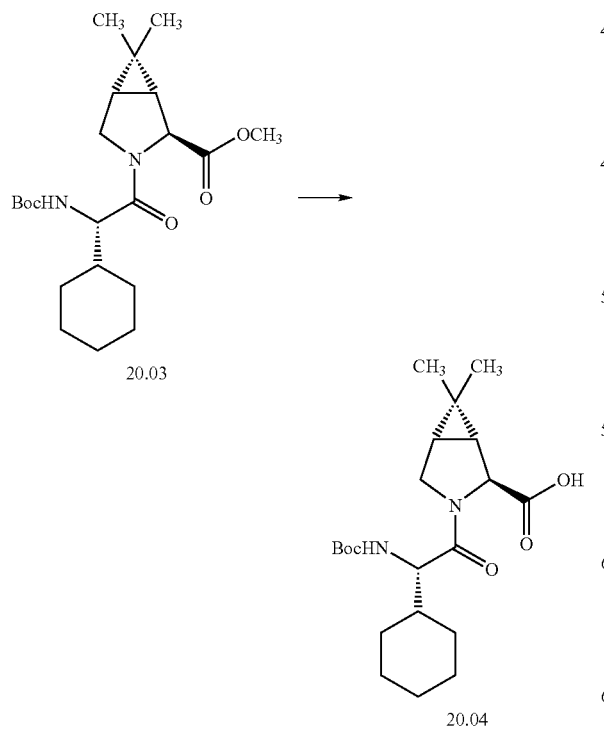

A solution of methyl ester 20.03 (4.0 g, 9.79 mmol) in $THF/H_2O$ (1:1) was treated with $LiOH.H_2O$ (401 mg, 9.79 mmol) and stirred at rt. for 3 h. The reaction mixture was acidified with aq. HCl and concentrated in vacuo to obtain the required intermediate, free acid 20.04.

Preparation of Intermediate 20.07

Step 1

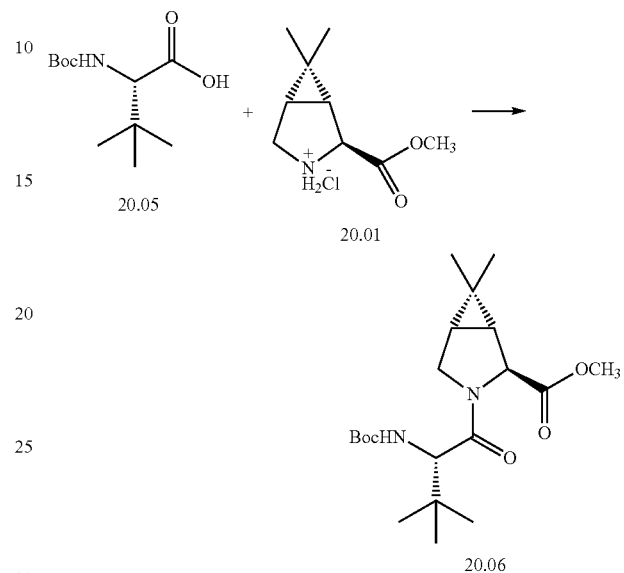

A solution of Boc-tert-Leu 20.05 (Fluka, 5.0 g 21.6 mmol) in dry $CH_2Cl_2$/DMF (50 mL, 1:1) was cooled to 0° C. and treated with the amine salt 20.01 (5.3 g, 25.7 mmol), NMM (6.5 g, 64.8 mmol) and BOP reagent (11.6 g, 25.7 mmol). The reaction was stirred at rt. for 24 h, diluted with aq. HCl (1 M) and extracted with $CH_2Cl_2$. The combined organic layers were washed with HCl (aq, 1 M), saturated $NaHCO_3$, brine, dried ($MgSO_4$), filtered and concentrated in vacuo and purified by chromatography (SiO2, Acetone/Hexane 1:5) to yield 20.06 as a colorless solid.

Step 2

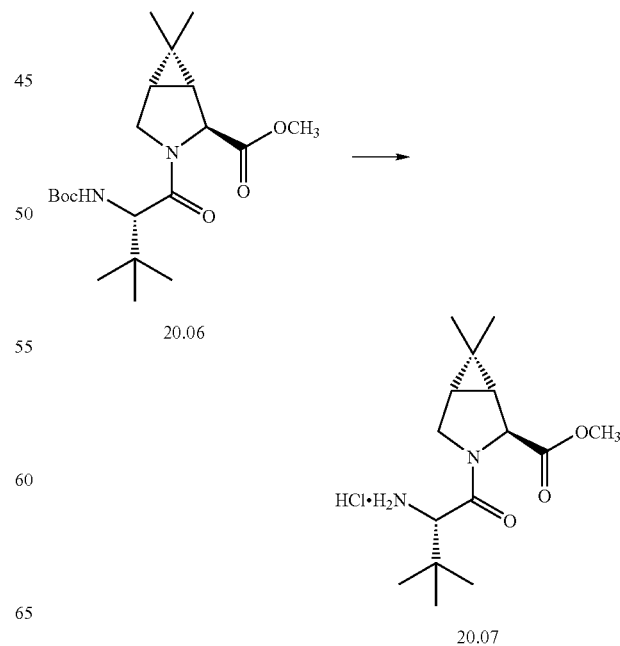

A solution of methyl ester 20.06 (4.0 g, 10.46 mmol) was dissolved in 4M HCl in dioxane and stirred at rt. for 3 h. The reaction mixture was concentrated in vacuo to obtain the amine hydrochloride salt, 20.07 which was used without purification.

Preparation of Intermediate 20.10

Step 1

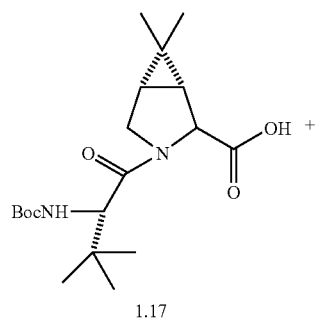

1.17

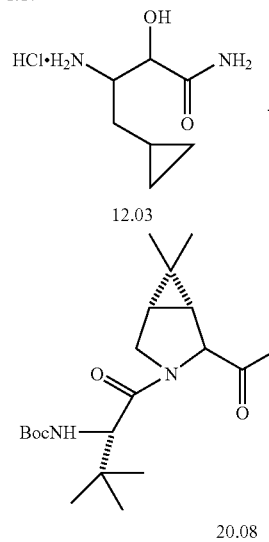

To a −20° C. solution 1.17 (10.4 g, 28 mmol) in DCM (300 mL) was added HATU (1.05 equiv, 29.4 mmol, 11.2 g), amine salt, Intermediate 12.03 (1.0 equiv, 28 mmol, 5.48 g). After 10 min at −20° C., DIPEA (3.6 equiv, 100 mmol, 17.4 mL) was added. Reaction was stirred at this temp for 16 hr. After 16 hr, the reaction was diluted with EtOAc and washed successively with NaHCO$_3$, citric acid (10% w/w) and brine. Organic layer was dried over MgSO$_4$, filtered and concentrated in vacuo to yield 14 g of the required intermediate 20.08.

Step 2

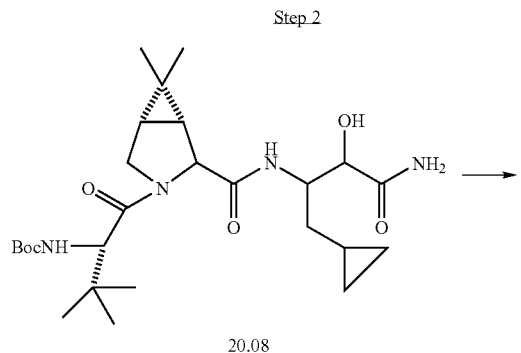

20.08

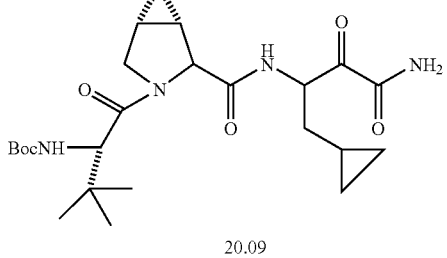

20.09

The hydroxyamide 20.08 was oxidized to the required ketoamide 20.09 in a manner described for Example 198 (Step 8). LC-MS=507 (M+H)$^+$.

Step 3

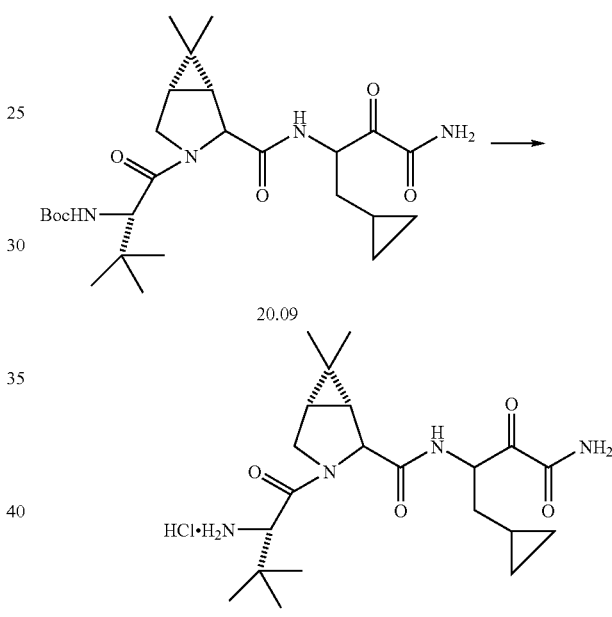

Deprotection of the t-Boc functionality of 20.09 to give the required material 20.10 was carried out as described for the transformation of 20.06 to 20.07.

Preparation of Intermediate 21.01:

Step 1:

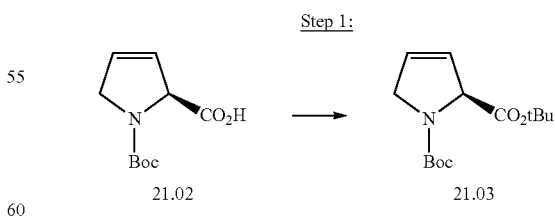

To a stirred solution of N—Boc-3,4-dehydroproline 21.02 (5.0 g, 23.5 mmol), di-tert-butyl dicarbonate (7.5 g, 34.4 mmol), and 4-N,N-dimethylaminopyridine (0.40 g, 3.33 mmol) in acetonitrile (100 mL) at room temperature was added triethylamine (5.0 mL, 35.6 mmol). The resulting solution was stirred at this temperature for 18 h before it was concentrated in vacuo. The dark brown residue was purified by flash column chromatography eluting with 10-25% EtOAc/hexane to give the product 21.03 as a pale yellow oil (5.29 g, 84%).

Step 2:

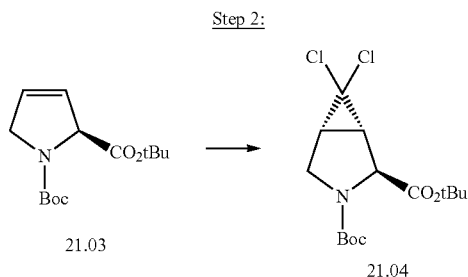

To a stirred solution of the dehydroproline derivative 21.03 (10.1 g, 37.4 mmol), benzyltriethylammonium chloride (1.60 g, 7.02 mmol) in chloroform (120 mL) at room temperature was added 50% aqueous sodium hydroxide (120 g). After vigorously stirred at this temperature for 24 h, the dark mixture was diluted with $CH_2Cl_2$ (200 mL) and diethyl ether (600 mL). After the layers were separated, the aqueous solution was extracted with $CH_2Cl_2/Et_2O$ (1:2, 3×600 mL). The organic solution was dried ($MgSO_4$) and concentrated. The residue was purified by flash column chromatography using 5-20% EtOAc/hexane to afford 9.34 g (71%) of 21.04 as an off-white solid.

Step 3:

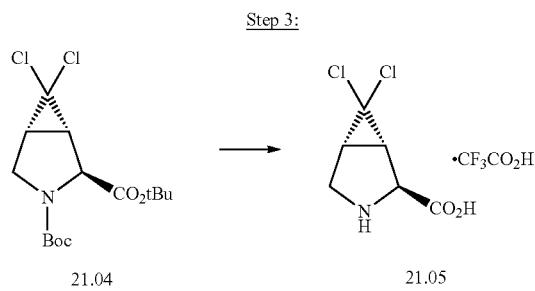

The solution of 21.04 (9.34 g, 26.5 mmol) in $CH_2Cl_2$ (25 mL) and $CF_3CO_2H$ (50 mL) was stirred at room temperature for 4.5 h before it was concentrated in vacuo to give a brown residue, 21.05 which was used in Step 4 without further purification.

Step 4

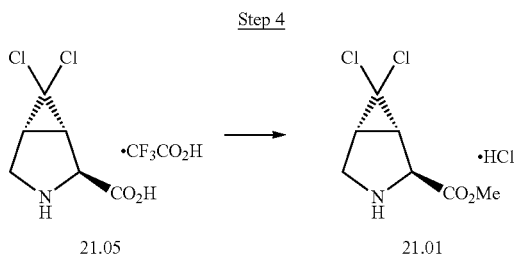

Concentrated hydrochloric acid (4.5 mL) was added to a solution of the residue 21.05 from Step 3 in methanol (70 mL) and the resulting mixture was warmed to 65° C. in an oil bath. After 18 h, the mixture was concentrated in vacuo to give a brown oil 21.01, which was used further without purification.

Preparation of Intermediate 22.01

Step 1

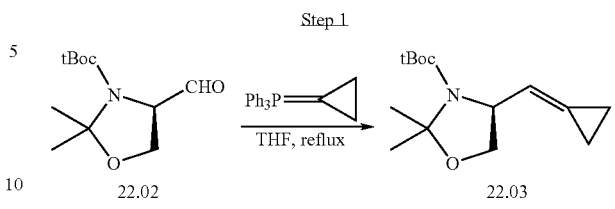

Potassium bis(trimethylsilyl)amide (158 ml of a 0.5M solution in toluene; 79 mmol) was added to a stirred suspension of cyclopropyltriphenylphosphonium bromide (33.12 g; 86.4 mmol) in anhydrous tetrahydrofuran (130 ml) and the resulting orange mixture was stirred under an atmosphere of nitrogen at room temperature for a period of 1 h., before the addition of the aldehyde 22.02 (9.68 g; 42.2 mmol) in THF (8 ml). The reaction was then refluxed under an atmosphere of nitrogen for a period of 2 h. After cooling, methanol, diethyl ether and Rochelles salt were added. The organic phase was separated, washed with brine, dried and concentrated under reduced pressure. The crude reaction product was purified by silica gel column chromatography using EtOAc-hexane (1:99) to EtOAc-hexane (5:95) to provide the alkene 22.03 (8.47 g) as a yellow oil.

Step 2

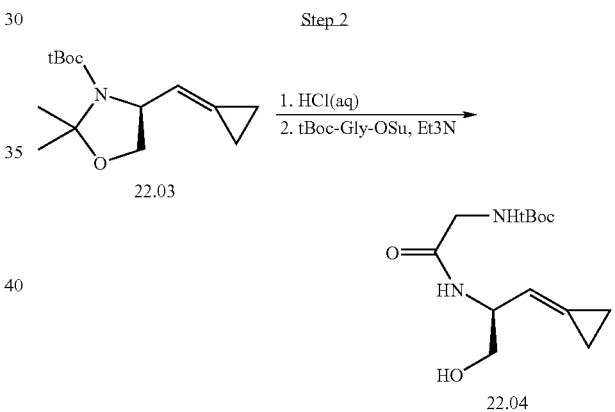

A solution of 1M HCl in MeOH/MeOAc was prepared by adding 14.2 ml of acetyl chloride dropwise into cold methanol and diluting the resulting solution to 200 ml at room temperature.

The carbamate 22.03 (9.49 g; 37.5 mmol) was dissolved in methanol (12 ml) and added to 1M HCl in MeOH/MeOAc (150 ml) while cooled in an ice bath. The resulting mixture was maintained at this temperature for 1 h., then the ice bath was removed and stirring continued overnight at room temperature. The volatiles were removed under reduced pressure to yield a yellow oil which was used in the next step without purification.

The yellow oil was dissolved in a mixture of THF (30 ml) and MeOH (20 ml) and treated with triethylamine (15 ml; 108 mmol) until the solution was pH=9-10. After placing in an ice bath, the mixture was treated with N—Boc-Gly-OSu (11.22 g; 41 mmol). The ice bath was withdrawn and the reaction stirred at room temp. for 1 h. The volatiles were removed under reduced pressure and the residue was purified by silica gel column chromatography using methanol (1-3%) in dichloromethane providing the desired amide 22.04 (9.09 g).

Step 3

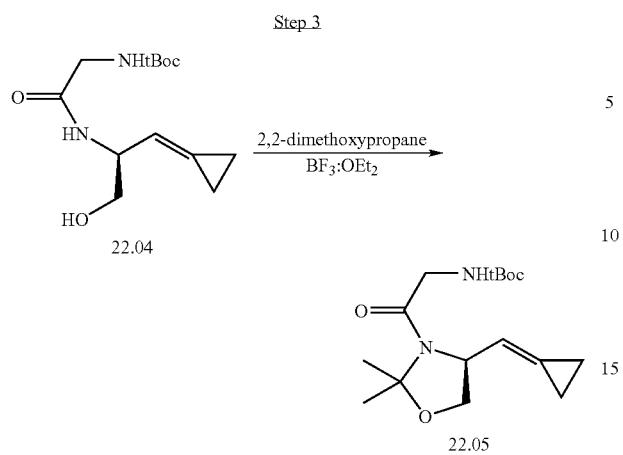

The alcohol 22.04 (9.09 g; 33.6 mmol) was dissolved in acetone (118.5 ml) and treated with 2,2-dimethoxypropane (37.4 ml; 304 mmol) and BF$_3$:Et$_2$O (0.32 ml; 2.6 mmol) and the resulting mixture was stirred at room temperature for a period of 5.5 h The reaction solution was treated with a few drops of triethylamine and the volatiles were removed under reduced pressure. The residue was purified by silica gel column chromatography using 5-25% EtOAc in hexanes to provide the N,O-acetal 22.05 (8.85 g).

Step 4

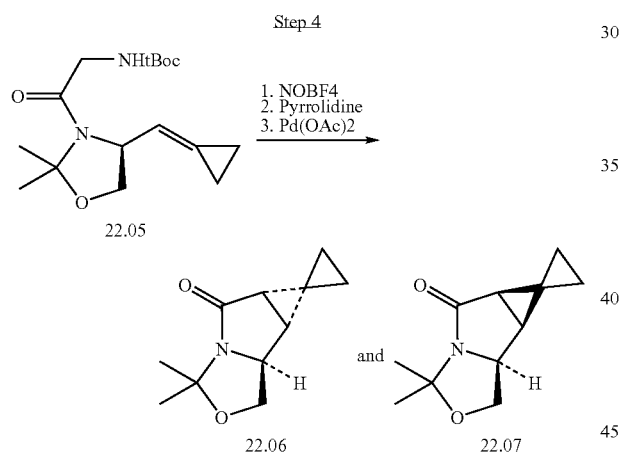

The carbamate 22.05 (8.81 g; 28.4 mmol) was dissolved in acetonitrile (45 ml) and the solution was cooled to −40° C. under an atmosphere of nitrogen. Pyridine (6.9 ml; 85.3 mmol) followed by nitrosium tetrafluoroborate (6.63 g; 56.8 mmol) were added and the resulting reaction mixture maintained below 0° C. until TLC indicated that no starting material remained (approx. 2.25 h.). Pyrrolidine (20 ml; 240 mmol) was added and the cooling bath was withdrawn and stirring was continued at room temperature for 1 h. and then the volatiles were removed under reduced pressure. The residue was quickly passed through a pad of silica gel to provide a yellow oil.

The yellow oil was dissolved in anhydrous benzene (220 ml) and palladium acetate (0.317 g; 1.41 mmol) was added before heating the resulting mixture to reflux, under an atmosphere of nitrogen for a period of 1.5 h. After cooling, the volatiles were removed under reduced pressure and the dark residue was purified by silica gel column chromatography using EtOAc-hexane (1:4) to provide the 1) the trans-pyrrolidinone 22.06 (1.94 g) followed by ii) the cis-pyrrolidinone 22.07 (1.97 g).

Step 5

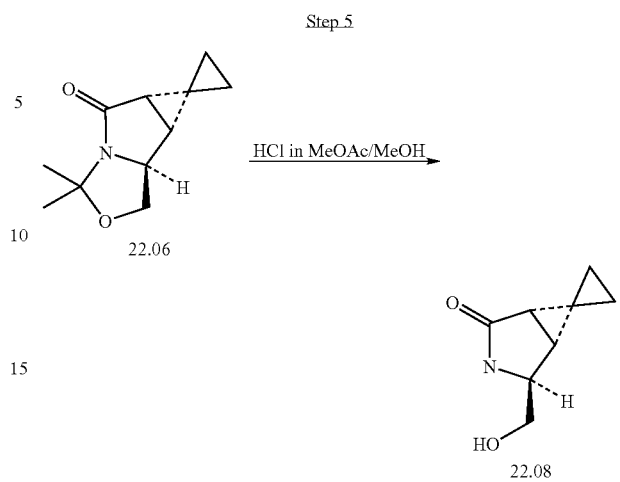

Freshly prepared 1M HCl in MeOAc/MeOH (10 ml; as described above) was added to the N,O-acetal 22.06 and stirred at room temperature for 1 h. The solvent was removed under reduced pressure and the residue was purified by silica gel column chromatography using 0-4% MeOH in dichloromethane as eluent to provide the desired alcohol 22.08 (1.42 g), a yellow oil.

Step 6

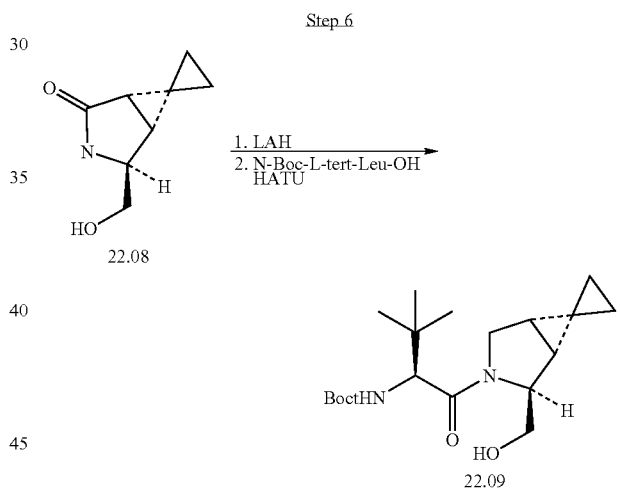

To a solution of the lactam 22.08 (1.29 g; 8.44 mmol) in anhydrous tetrahydrofuran (55 ml) was added lithium aluminum hydride (2.40 g; 63.2 mmol) and the resulting mixture was refluxed for 8 h. After cooling, water, followed by 15% aq. NaOH were added and the resulting mixture was filtered through celite and the solid was washed thoroughly with THF and MeOH. The solvent was removed under reduced pressure and the residue redissolved in dichloromethane, dried and concentrated under reduced pressure to provide the pyrrolidine, used without purification.

Hunigs base (4.5 ml; 25.8 mmol) was added to a mixture of N—Boc-L-tert-Leu-OH (1.76 g; 7.6 mmol), The crude pyrrolidine and HATU (2.89 g; 7.6 mmol) in anhydrous dichloromethane (50 ml) at −60° C., under an atmosphere of nitrogen. The resulting reaction was allowed to come to room temperature slowly, overnight. EtOAc was added and the yellow solution was washed with dil. aq. HCl, sat. aq. sodium bicarbonate, water, brine. The organic layer was dried and concentrated under reduced pressure. The residue was purified by silica gel column chromatography using EtOAc:hexanes (1:3) to give the desired amide 22.09 (2.00 g).

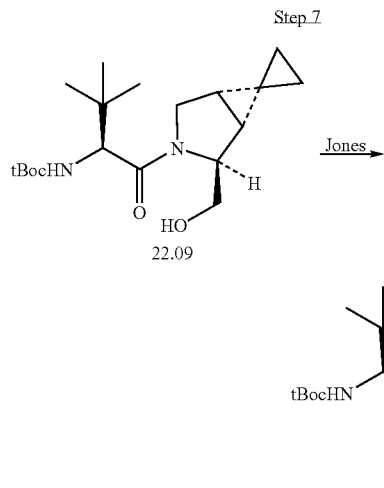

The alcohol 22.09 (2.00 g; 5.67 mmol) was dissolved in acetone (116 ml) and cooled in an ice bath for 10 min. This solution was then added to a cooled Jones reagent (14.2 ml; approx 2 mmol/ml) and the resulting mixture was stirred at 5° C. for 0.5 h and the cooling bath was removed. The reaction was stirred for a further 2 h. at room temp., before adding to sodium sulfate (28.54 g), celite (15 g) in EtOAc (100 ml). Isopropanol (15 ml) was added after 1 min and then stirred for a further 10 min. and filtered. The filtrate was concentrated under reduced pressure, providing a brown oil which was dissolved in EtOAc. This solution was washed with water, 3% aq. citric acid, brine, dried and concentrated to provide the desired carboxylic acid 22.01 (1.64 g) as a white solid.

Preparation of Intermediate 23.01

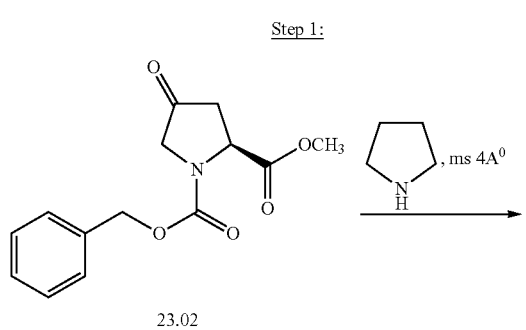

To the mixture of ester 23.02 (6.0 g) and molecular sieve (5.2 g) in anhydrous methylene chloride (35 mL) was added pyrrolidine (5.7 mL, 66.36 mmoL). The resulting brown slurry was stirred at room temperature under $N_2$ for 24 h, filtered and washed with anhydrous $CH_3CN$. The combined filtrate was concentrated to yield the desired product, 23.03.

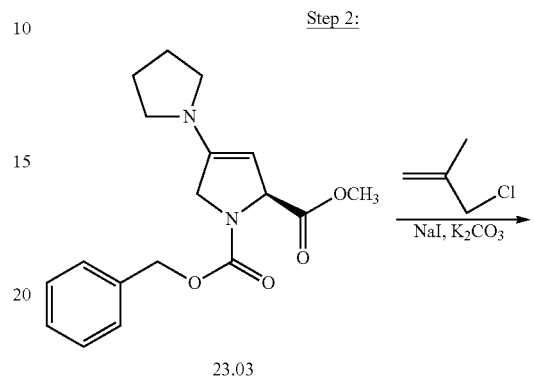

To a solution of the product 23.03 from proceeding step in $CH_3CN$ (35 mL) was added anhydrous $K_2CO_3$, methallyl chloride (2.77 g, 30.5 mmoL), NaI (1.07 g, 6.7 mmoL). The resulting slurry was stirred at ambient temperature under $N_2$ for 24 h. 50 mL of ice-cold water was added followed by 2N $KHSO_4$ solution until pH was 1. EtOAc (100 mL) was added and the mixture was stirred for 0.75 h. Combined organic layer was collected and washed with brine, dried over $MgSO_4$, and evaporated to yield the desired product, 23.04.

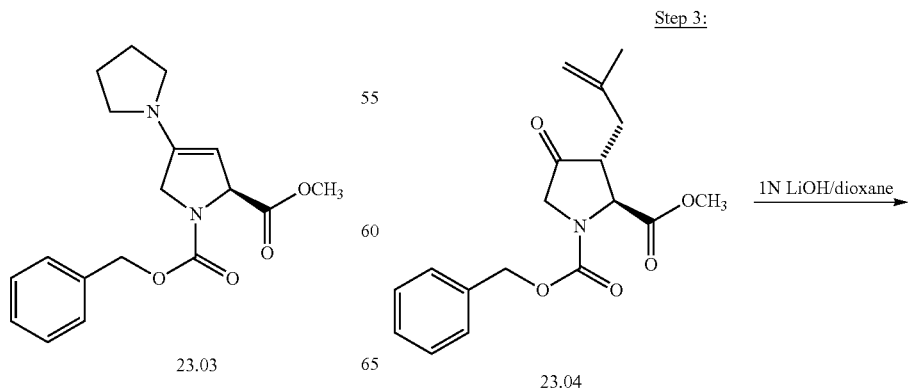

-continued

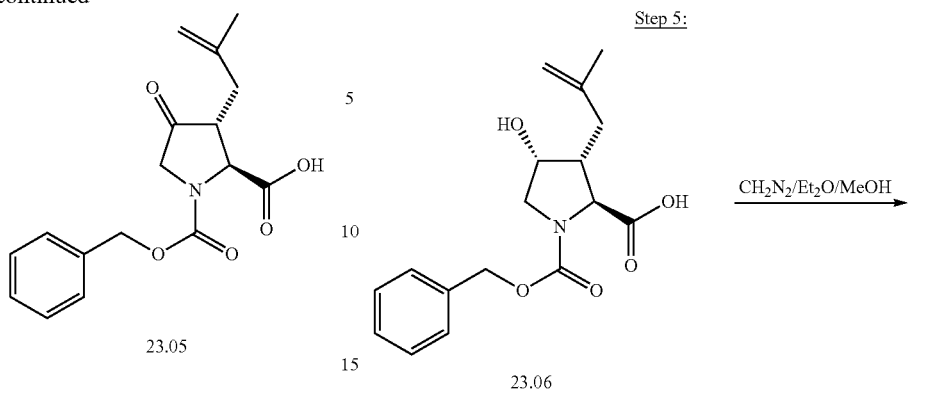

23.05

The product 23.04 from the preceding step (2.7 g, 8.16 mmoL) was dissolved in dioxane (20 mL) and treated with freshly prepared 1N LiOH (9 mL). The reaction mixture was stirred at ambient temperature under $N_2$ for 20 h. The reaction mixture was taken in EtOAc and washed with $H_2O$. The combined aqueous phase was cooled to 0° C. and acidified to pH 1.65 using 1N HCl. The turbid mixture was extracted with EtOAc (2×100 mL). Combined organic layer was washed with brine, dried over $MgSO_4$, and concentrated to give the desired acid, 23.05 (3.40 g).

Step 4:

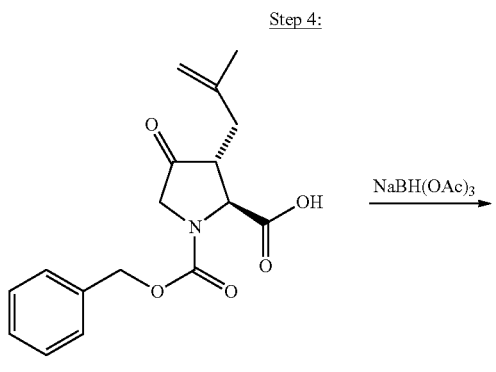

23.05

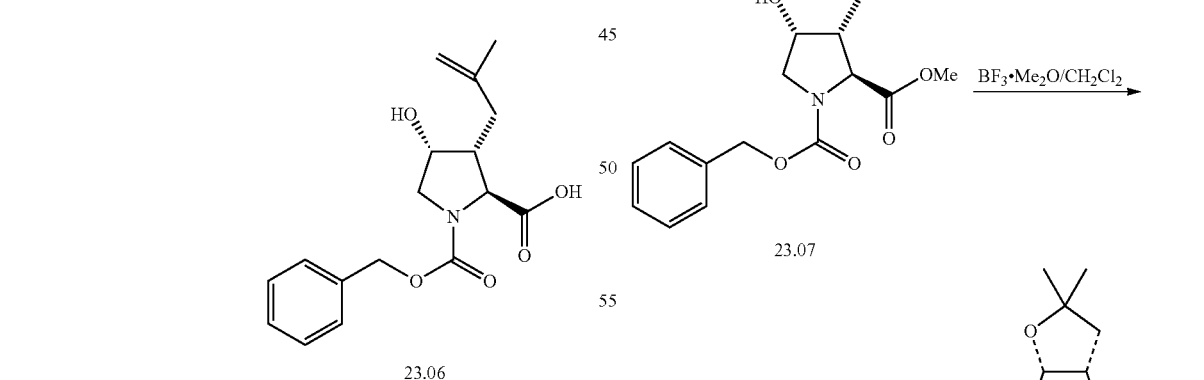

23.06

To a suspension of $NaBH(OAc)_3$ (3.93 g, 18.5 mmoL) in $CH_2Cl_2$ (55 mL) was added a solution of product 23.05 from preceding step in anhydrous $CH_2Cl_2$ (20 mL) and acetic acid (2 mL). The slurry was stirred at ambient temperature for 20 h. Ice cold water (100 mL) was added to the slurry and stirred for ½ hr. Organic layer was separated, filtered, dried and evaporated to yield the desired product, 23.06.

Step 5:

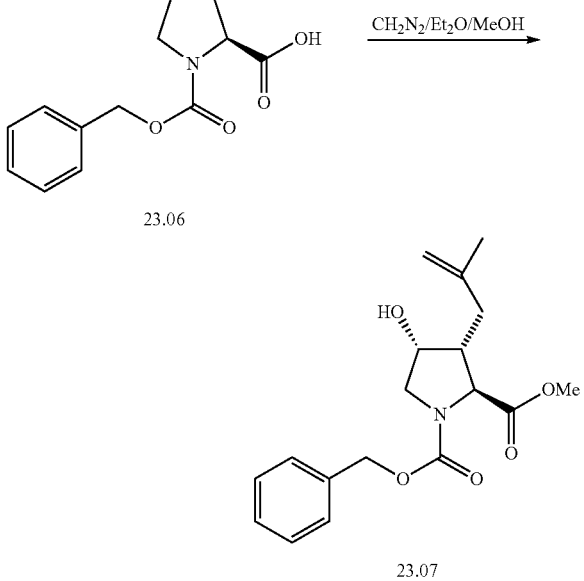

23.07

To a solution of the product 23.06 from preceding step (1.9 g) in MeOH (40 mL) was treated with excess of $CH_2N_2/Et_2O$ solution and stirred for overnight. The reaction mixture was concentrated to dryness to yield a crude residue. The residue was chromatographed on silica gel, eluting with a gradient of EtOAc/hexane to afford 1.07 g of the pure desired product, 23.07.

Step 6:

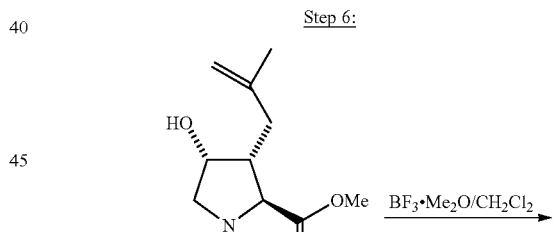

23.07

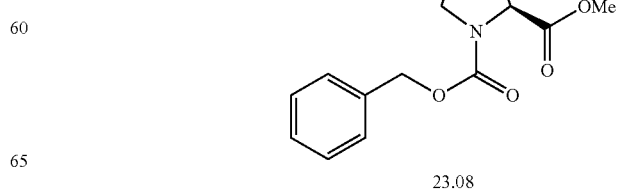

23.08

To a solution of product 23.07 from preceding step (1.36 g) in anhydrous CH$_2$Cl$_2$ (40 mL) was treated with BF$_3$·Me$_2$O (0.7 mL). The reaction mixture was stirred at ambient temperature for 20 h and quenched with sat. NaHCO$_3$ (30 mL) ad stirred for ½ hr. Organic layer was separated and combined organic layer was washed with brine, dried over MgSO$_4$, concentrated to give crude residue. The residue was chromatographed on silica gel eluting with a gradient of EtOAc/hexane to afford 0.88 g of the desired compound, 23.08.

Step 7:

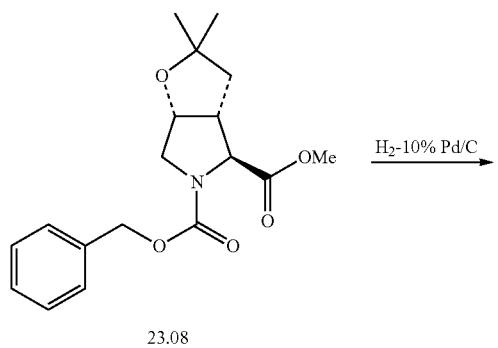

23.08

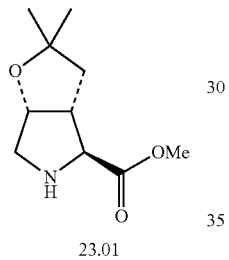

23.01

To a solution of the product 23.08 (0.92 g) from preceding step in MeOH (30 mL) was added 10% Pd/C (0.16 g) at room temperature and hydrogenated at ambient temperature under 1 atm. Pressure. The reaction mixture was stirred for 4 h and concentrated to dryness to yield the desired compound, 23.01.

Preparation of P3 Moieties

Preparation of Intermediate 50.01

Step 1

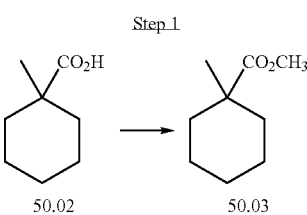

50.02          50.03

To a solution of 50.02 (15 g) in MeOH (150 mL) was added conc HCl (3-4 mL) and the mixture was refluxed for 16 h. The reaction mixture was cooled to room temperature and concentrated. The residue was taken in diethyl ether (250 mL) and washed with cold saturated sodium bicarbonate solution, and brine. The organic layer was dried (Na$_2$SO$_4$) and concentrated to afford the methyl ester 50.03 (12.98 g) which was carried forward without further purification.

Step 2

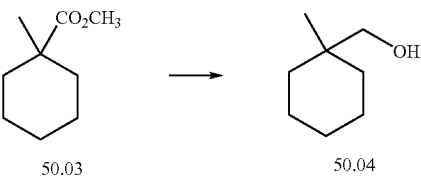

50.03          50.04

The methyl ester 50.03 from above was dissolved in methylene chloride (100 mL) and cooled to −78° C., under nitrogen atmosphere. DIBAL (1.0 M solution in methylene chloride, 200 mL) was added dropwise over 2 h period. The reaction mixture was warmed to room temperature over 16 h. The reaction mixture was cooled to 0° C. and MeOH (5-8 mL) was added dropwise. A solution of aqueous 10% sodium potassium tartarate (200 mL) was slowly added with stirring. Diluted with methylene chloride (100 mL) and separated the organic layer (along with some white precipitate). The organic layer was washed with 1 N HCl (250 mL), brine (200 mL), dried (Na$_2$SO$_4$) and concentrated to provide the alcohol 50.04 (11.00 g) as a clear oil.

Step 3

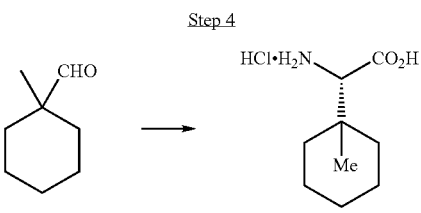

50.05          50.05

The alcohol 50.04 from above was dissolved in methylene chloride (400 mL) and cooled to 0° C. under nitrogen atmosphere. PCC (22.2 g) was added in portions and the reaction mixture was slowly warmed to room temperature over 16 h. The reaction mixture was diluted with diethyl ether (500 mL) and filtered through a pad of celite. The filtrate was concentrated and the residue was taken in diethyl ether (500 mL). This was passed through a pad of silica gel and the filtrate was concentrated to provide the aldehyde 50.05 which was carried forward without further purification.

Step 4

[Structure: CHO on cyclohexane with methyl] → [Structure: HCl·H$_2$N-CH(CO$_2$H)- with cyclohexane and Me]

50.05          50.01

The aldehyde 50.05 from above was converted to the desired material 50.01 using essentially the method of Chakraborty et. al (Tetrahedron, 1995, 51(33), 9179-90).

PREPARATION OF SPECIFIC EXAMPLES

Example 108

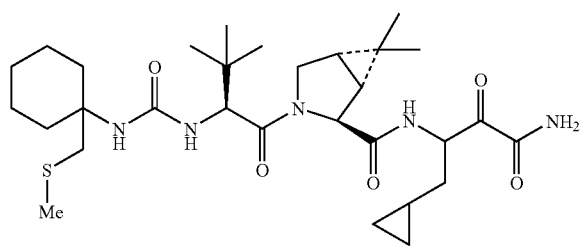

Steps 1 and 2:

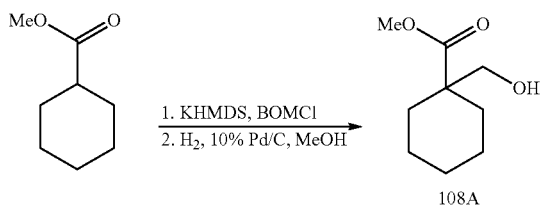

Step 1:
KHMDS (200 ml of a 0.5M solution in toluene) was added, dropwise to a stirred solution of Methyl cyclohexanecarboxylate (11.1 g; 78 mmol) in anhydrous THF (200 ml), at −78 C under an atmosphere of nitrogen. When the addition was complete the reaction was maintained at this temperature for a further 0.5 h. before the addition of Benzyl Chloromethyl Ether (18.6 ml; 134 mmol). The reaction was allowed to warm to room temperature overnight and water (100 ml) was added. Aqueous work-up provided a residue which was purified by silica gel column chromatography using EtOAc; hexanes (1:10) as eluent to give the desired, impure, intermediate ether (14.98 g) as a colorless oil.

Step 2:
A black suspension of 10% Pd/C (0.5 g) and the aforementioned crude ether (4.1 g) in MeOH (80 ml) was exposed to an atmosphere of nitrogen (balloon) at room temp., overnight. The reaction was filtered through a pad of celite and the solid was washed thoroughly with methanol. The combined filtrate was concentrated under reduced pressure and the crude product was purified by silica gel column chromatography using EtOAc; hexanes (1:5) to give the primary alcohol (108A; 0.62 g), a colorless oil.

Step 3:

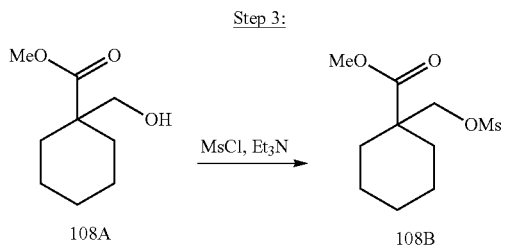

Methanesulfonyl Chloride (0.31 ml) followed by triethylamine (0.75 ml) were added to a stirred solution of the primary alcohol (108A; 0.62 g) at 0 C, under an atmosphere of nitrogen. The resulting mixture was stirred at this temperature for 0.5 h. The reaction mixture was extracted into EtOAc and washed with aqueous 1M HCl, sat. aq. NaHCO3, water, dried (MgSO4) and concentrated. The residue (mesylate 108B; 0.74 g), was obtained as a yellow oil, which was used in subsequent steps without purification.

Step 4:

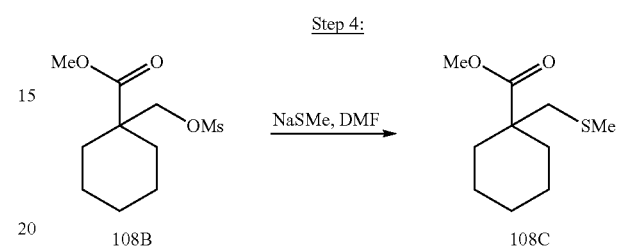

Sodium Methanethiolate (0.236 g; 2 eq.) was added to a DMF (2 ml) solution of the mesylate (108B; 0.42 g) and the mixture was heated to 100 C for 1 h. Aqueous work-up and purification of the crude reaction product by silica gel column chromatography using EtOAc; hexanes (1:20) gave the sulfide (108C, 0.089 g).

Steps 5 and 6:

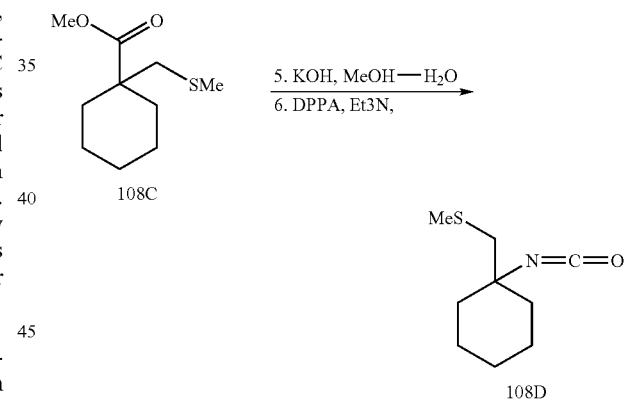

Step 5:
Potassium hydroxide (0.25 g) was dissolved in a mixture of water (1 ml) and ethanol (5 ml) and added to the methyl ester (108C, 0.089 g) and the resulting mixture was heated to reflux, under an atmosphere of nitrogen over a week-end (approx. 72 h.). After cooling, the reaction was partitioned between EtOAc and dilute aq. HCl. The organic phase was separated, washed with brine, dried and concentrated to yield the crude intermediate carboxylic acid, used without purification.

Step 6:
Triethylamine (61 ul) followed by DPPA (95 ul) were added to a toluene solution of the carboxylic acid from the previous step and the reaction was heated to 100 C overnight. After cooling, the reaction mixture was partitioned between EtOAc and sat. aq. sodium bicarbonate. The organic phase was separated, dried and concentrated to yield the isocyanate (108D; 50 mgs), used without purification.

Steps 7 and 8:

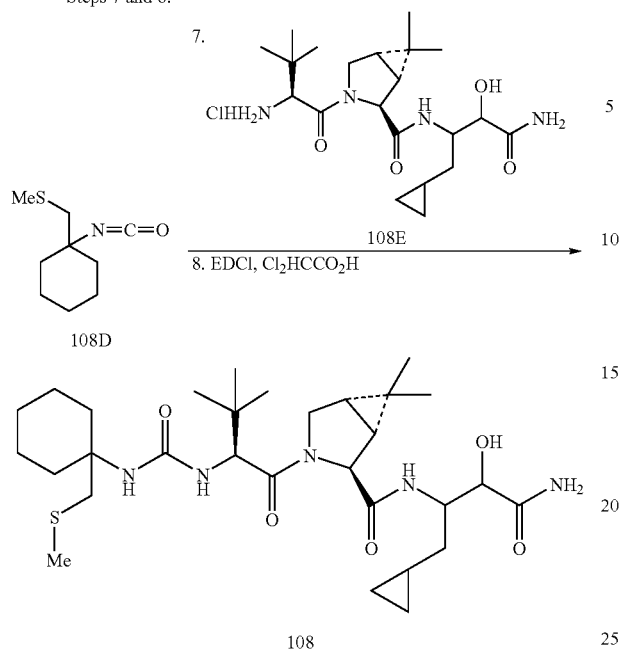

Step 7:

The isocyanate (108D; 50 mg) in dichloromethane (1 ml) was added to a mixture of the hydrochloride salt (108E; prepared from 20.08 in a manner described for the transformation of 20.06 to 20.07; 100 mg) and triethylamine (111 ul) in dichloromethane (2 ml) and the resulting mixture was stirred at room temperature for 4 hours. The reaction mixture was partitioned between EtOAc and 10% aq. HCl. The organic phase was separated, washed with sat. aq. sodium bicarbonate, water, dried (magnesium sulfate) and concentrated to yield a residue which was used in step 8 without purification.

Step 8:

The residue in the aforementioned step was dissolved in a mixture of toluene (3 ml) and dimethylsulfoxide (3 ml) and EDCl (647 mg) followed by dichloroacetic acid (140 ul) were added and the resulting reaction mixture was stirred at room temperature for a period of 4 h. The reaction mixture was partitioned between EtOAc and 5% aq. sodium sulfite. The organic phase was separated, washed with 10% aq. HCl, sat. aq. sodium bicarbonate, water, dried (magnesium sulfate) and concentrated to yield a residue which was purified by silica gel column chromatography using acetone: hexanes (40:60) as eluent to provide the desired keto-amide (108; 11.5 mgs). MS: MH+, 592.1.

Example 185

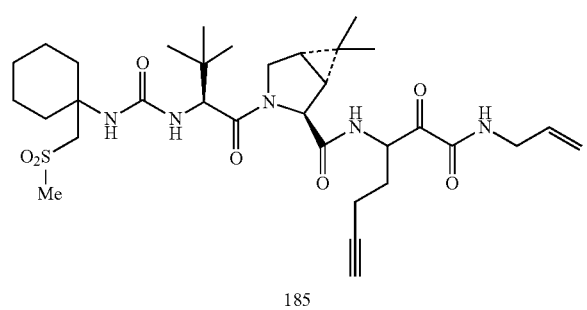

-continued
Step 1:

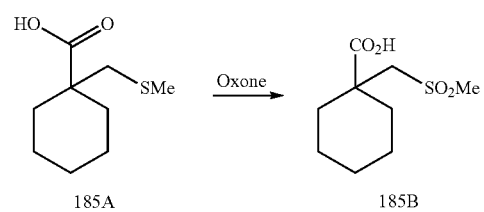

Oxone (5.68 g) was dissolved in water (5 ml) and added to the carboxylic acid 185A (1.25 g) in methanol (5 ml) while cooled in an ice bath. The reaction mixture was allowed to warm to room temp., overnight. The volatiles were removed under reduced pressure and the residue was partitioned between methylene chloride and water. The aqueous phase was separated and extracted with methylene chloride (×2). The combined organic phases were dried and concentrated to yield the sulfone (185B; 1.10 g) as a white solid, used in subsequent procedures without purification.

Steps 2 and 3:

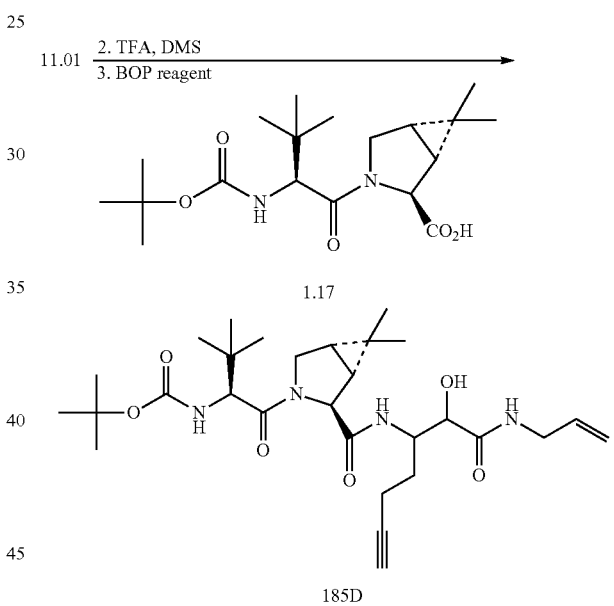

Step 2:

The benzyl carbamate (11.01; 0.16 g) was dissolved in TFA (7 ml) and dimethyl sulfide (1.78 ml) was added and the resulting mixture was allowed to stand at room temperature for a period of 3 h., before removing the volatiles under reduced pressure. This gave a residue which was used in step 3 below.

Step 3:

Triethylamine (111 ul) was added to a mixture of the residue from step 2, the carboxylic acid (1.17; 0.180 g) and BOP reagent (0.236 g) in dichloromethane (5 ml) and the reaction mixture was stirred at room temperature overnight. The reaction was partitioned between ethyl acetate and aq. 10% HCl. The organic phase was separated, washed with sat. aq. sodium bicarbonate, water, dried (magnesium sulfate) and the volatiles removed under reduced pressure. The residue was purified by silica gel column chromatography using EtOAc: Hexanes (70:30) as eluent to give the desired hydroxy-amide (185D; 0.165 g) as a white solid.

Step 4:

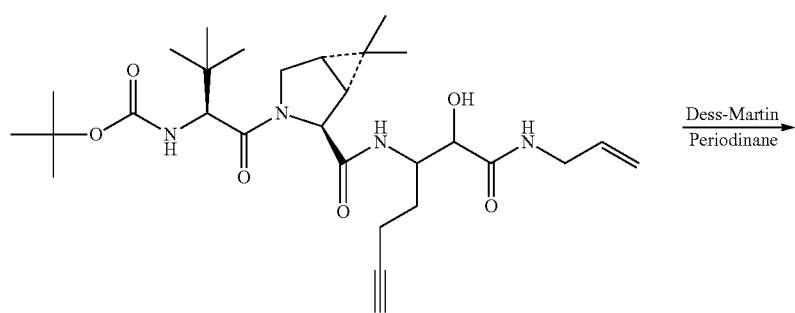

185D

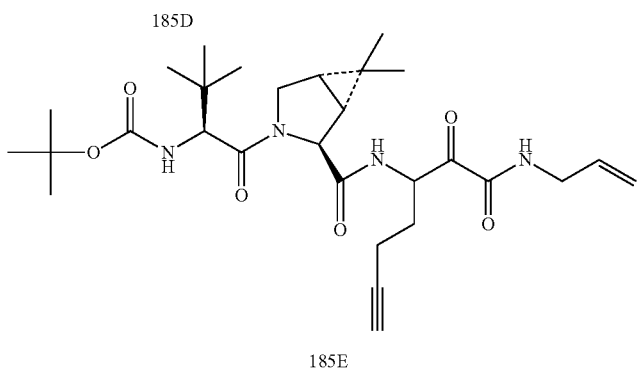

185E

The periodinane (0.236 g) was added to a stirred solution of the alcohol (185D; 0.152 g) in dichloromethane (5 ml) and the resulting white suspension was stirred for a period of 2 h. before being added to a mixture of EtOAc and 5% aq. sodium sulfite. The organic phase was separated washed with sat. aq. sodium bicarbonate, water, dried and the volatiles removed under reduced pressure. The residue was purified by silica gel column chromatography using EtOAc: Hexanes (40:60) as eluent to give the desired keto-amide (185E; 0.147 g) as a white solid. MS: MH+, 545.5.

Step 5:

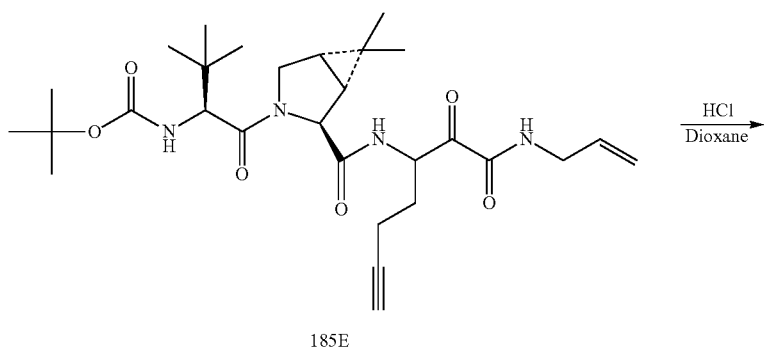

185E

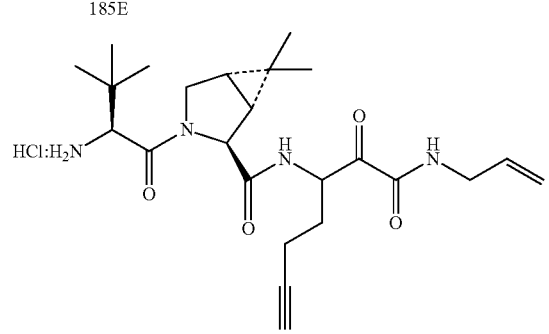

185F

A solution of HCl in dioxane (4M; 5 ml; Aldrich) was added to the carbamate (185E; 0.14 g) and allowed to stand at room temperature for a period of 3 h. The volatiles were removed under reduced pressure to provide the hydrochloride salt (185F; 0.126 g: contains a small quantity of dioxane).

Steps 6 and 7:

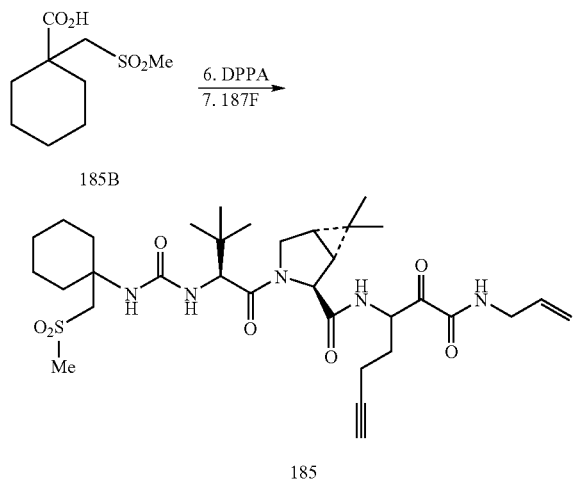

185

Step 6:

DPPA (19 ul) was added to a mixture of the carboxylic acid (185B; 20 mgs) and triethylamine (13 ul) in toluene (1 ml) and the resulting reaction mixture was heated to reflux for a period of 1 h. After cooling, the reaction was partitioned between EtOAc and sat. aq. sodium bicarbonate. The organic phase was separated, dried and the volatiles removed under reduced pressure. Gave the crude intermediate isocyanate which was used in step 7, below without purification.

Step 7:

The product from step 6 was dissolved in dichloromethane (1 mL) and added to a mixture of the hydrochloride salt (185F; 20 mgs) and triethylamine (60 ul) in dichloromethane (1 ml) and the resulting mixture was stirred at room temperature for a period of 1 h. The reaction was partitioned between EtOAc and 10% aq. HCl. The organic phase was separated, washed with sat. aq. sodium bicarbonate, water, dried and the volatiles were removed under reduced pressure. The resulting residue was purified by silica gel plate chromatography using EtOAc: Hexanes (1:1) as eluent to provide the keto-amide (185; 16.3 mgs) as a white solid. MS: MH+, 662.5.

Preparation of Compounds of Formulas 132 and 210 Directly from a Compound of Formula I22

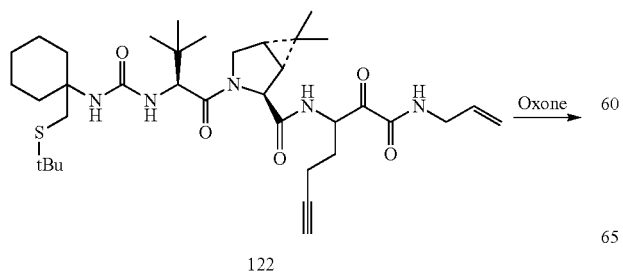

122

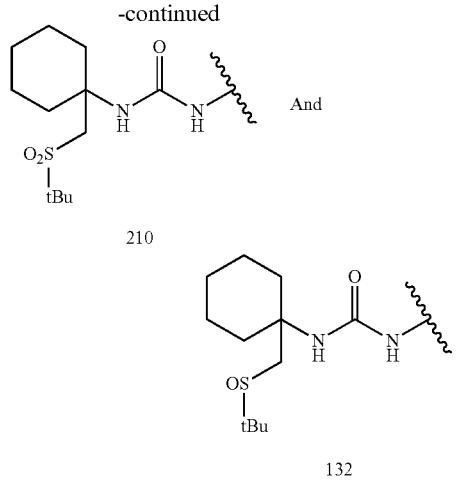

210

132

Using the sulfide 122 (prepared in a similar manner as 108 using methyl ester 210A rather than 108C; 20 mg), oxone (27 mg; 1.5 eq.), water (1 ml), methanol (1 ml) and the procedure set forth previously (185A to 185B) gave a crude reaction product which was purified by silica gel plate chromatography using EtOAc as eluent. Gave the sulfone (210; MH+=704.4; 5.6 mg) as a white solid followed by a mixture of sulfoxides (132; MH+=688.5; 6.3 mg), also a white solid.

Preparation of Compound 113

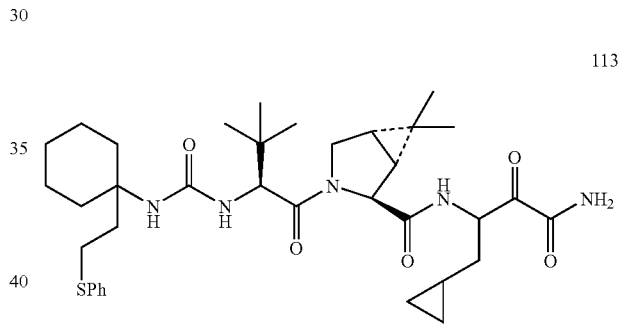

113

Steps 1 and 2:

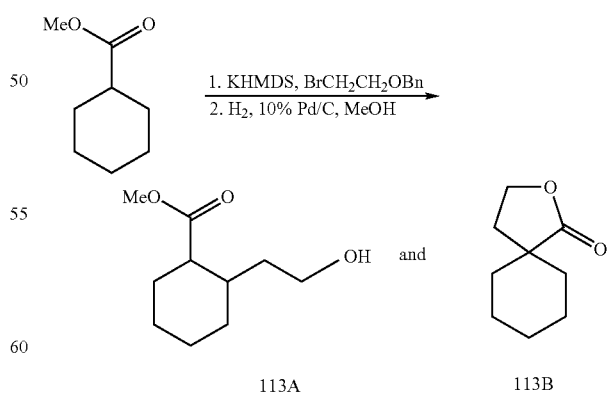

113A  113B

Step 1:

Using Methyl cyclohexanecarboxylate (5.55 g), KHMDS (100 ml of a 0.5M solution in toluene), anhydrous THF (100 ml) and benzyl 2-bromoethyl ether (10.09 g) and the procedure set forth previously (Example 108, Step 1), the desired intermediate benzyl ether (6.83 g) was obtained after silica gel column chromatography (EtOAc:Hexanes: 15:85).

Step 2:
Using the aforementioned benzyl ether (5.00 g), 10% Pd/C (1.00 g), methanol (20 ml) and the procedure set forth previously (Example 108; Step 2) the lactone (113B; 0.87 g), followed by the alcohol (113A; 2.01 g) were obtained following column chromatography on silica gel (EtOAc; Hexanes; 1:10).

Step 3:

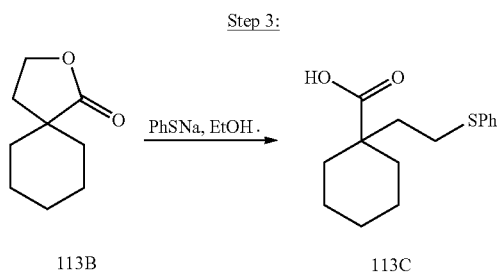

Step 3:
Sodium thiophenoxide (0.68 g) was added to a solution of the lactone (113B; 0.84 g) in ethanol (15 ml) and the resulting mixture was heated to reflux, under an atmosphere of nitrogen overnight. After cooling, aqueous work-up and purification of the crude reaction product by silica gel column chromatography (EtOAc-Hexanes; 30:70) gave the carboxylic acid (113C; 0.32 g), as a yellow solid.
Using previously described chemistry for the conversion of 108C to 108, 113C was converted to 113 in a similar manner. MS, MH+, 668.3.

Preparation of Compound 116:

Steps 1 and 2

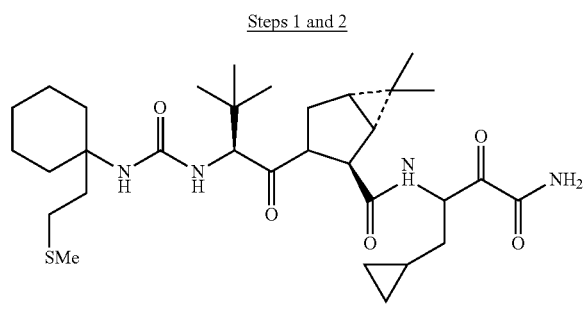

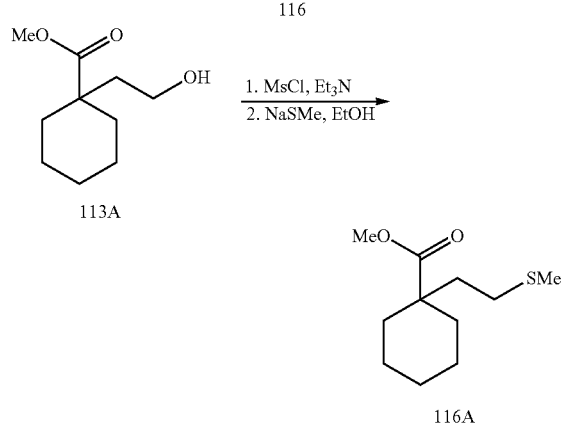

Step 1:
Using the alcohol (113A; 1.00 g), methane sulfonylchloride (1.12 g), triethylamine (0.82 g), methylene chloride (10 ml) and the procedure set forth previously (108A to 108B), the desired, intermediate mesylate was obtained and was used in the next step, without purification.

Step 2:
Using the aforementioned mesylate, sodium methanethiolate (0.75 g), ethanol (10 ml) and the procedure set forth previously (108B to 108C) at room temperature, the desired sulfide (116A; 0.78 g) was obtained after silica gel column chromatography (EtOAc-Hexanes; 1:10). Using the procedures set forth previously (108C to 108D) and (108D to 108), intermediate 116A was transformed into 116. MS; MH+, 606.1.

Preparation of Compound 198

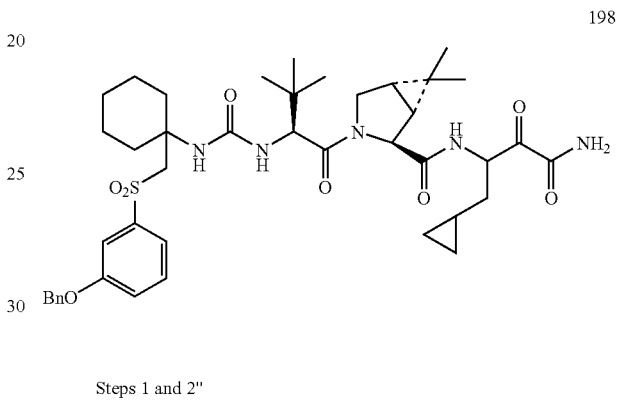

Steps 1 and 2''

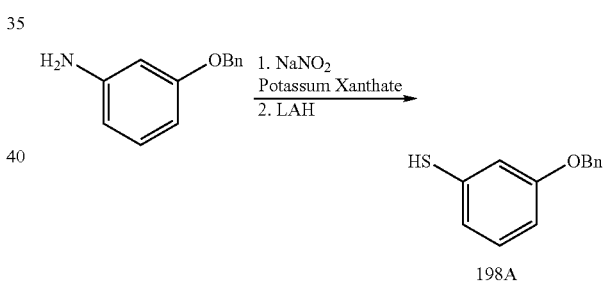

Steps 1 and 2:
Step 1:
3-Benzyloxyaniline (5.00 g; Aldrich) was dissolved in a mixture of conc. HCl (10 ml) and ice (10.00 g) was added. Sodium nitrite (1.85 g) in water (10 ml) was added while cooled in an ice bath. When the addition was complete, Potassium O-Ethylxanthate was added and stirred at this temperature until the evolution of nitrogen gas ceased, then heated at 40-45 C for a period of 1.5 h. After cooling, aqueous work-up and purification by silica gel column chromatography (2-5% EtOAc in hexanes) to give the intermediate xanthate (3.60 g).

Step 2:
Lithium Aluminum Hydride (6.4 ml of a 1M solution in THF) was added dropwise to a stirred solution of the aforementioned xanthate (1.49 g) in THF (10 ml) and stirred at R.T. for a period of 0.5 h. The reaction was quenched with excess acetone and partitioned between EtOAc and aq. 1M HCl. The organic phase was separated, dried and concentrated. The crude reaction product was purified by silica gel column chromatography (1-2% EtOAc in hexanes) to give the thiophenol (198A; 0.84 g), a white solid.

145

Step 3:

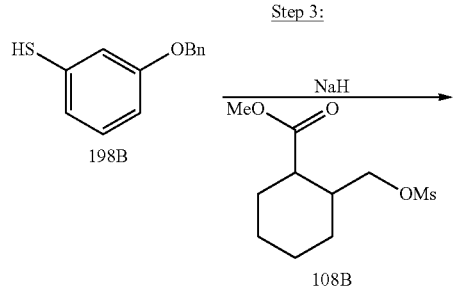

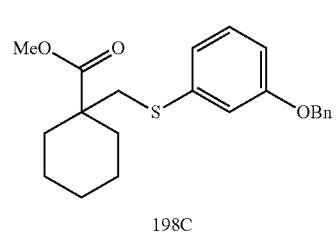

The mercaptan (198B; 0.72 g) was added to a suspension of NaH (0.08 g of a 60% dispersion in mineral oil) in anhydrous DMF, while cooled in an ice bath under an atmosphere of nitrogen. The resulting mixture was stirred for 1 h. and the mesylate (108B; 0.417 g) was added and the reaction was allowed to warm to R.T., overnight. Aqueous work-up and purification of the crude reaction product by silica gel column chromatography (3% EtOAc in hexanes) gave the sulfide (198C, 0.313 g).

Steps 4-6:

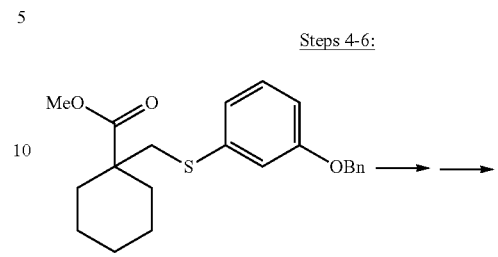

Using the sulfide (198C) generated in the previous step, the isocyanate (198D) is produced using procedures set forth in (108C to 108D) and 185A to 185D). The isocyanate (198D) is used in subsequent procedures without purification.

Step 7:

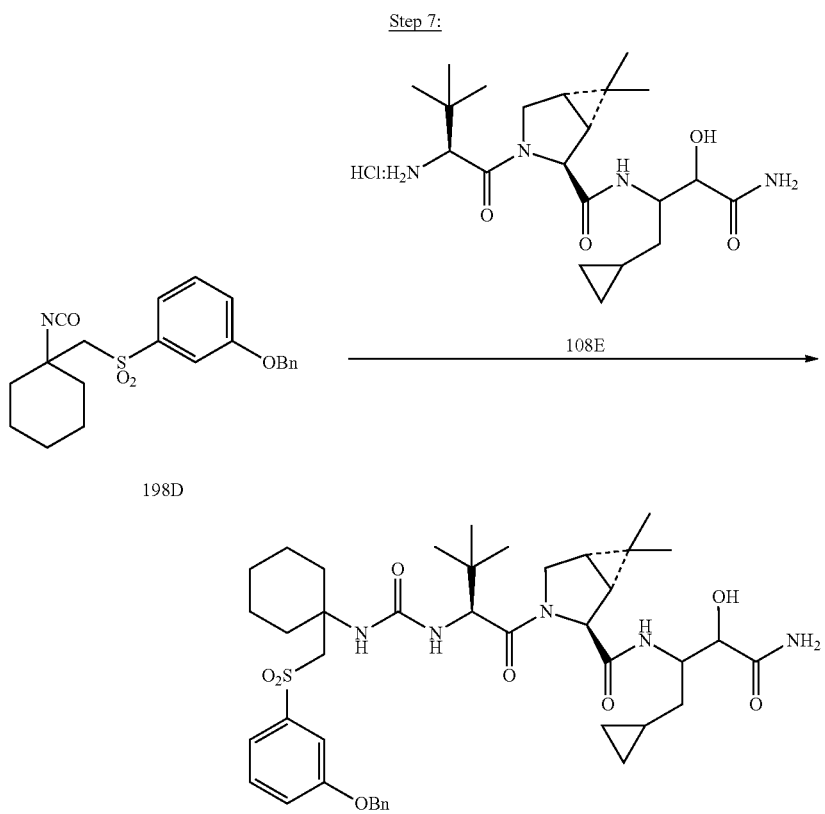

The isocyanate (198D; 0.139 g) in a minimal amount of dichloromethane (approx. 1 ml) was added to a mixture of the hydrochloride salt (108E; 0.080 g) and triethylamine (0.126 ml) and the resulting mixture was stirred at room temperature for a period of 4 hours. The reaction mixture was partitioned between EtOAc and 10% aq. HCl. The organic phase was separated, washed with sat. aq. sodium bicarbonate, water, dried and concentrated. The crude reaction product (198E) was used crude in the next step.

Step 8:

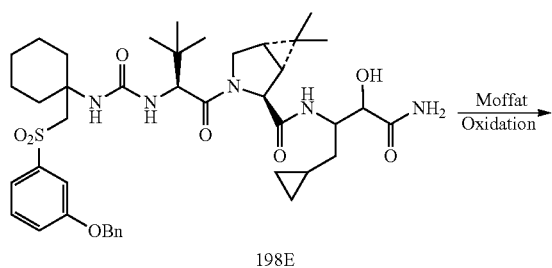

198E

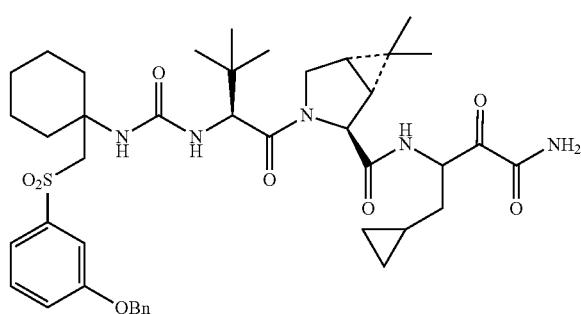

198

The crude product from the previous step (198E) was dissolved in DMSO (3 ml) and toluene (3 ml) and EDCl (0.346 g) followed by dichloroacetic acid (0.074 ml) was added and the resulting mixture was stirred at room temperature for a period of 4 hours. The reaction was partitioned between EtOAc and 5% aq. sodium sulfite. The organic phase was separated, washed with sat. aq. sodium bicarbonate, water, dried and concentrated. The crude reaction product was purified by silica gel column chromatography using acetone: hexane (30:70) as eluent to give the keto-amide (198; MH+=792.2; 55 mgs).

Preparation of the Phenol 199 from Benzyl Ether 198:

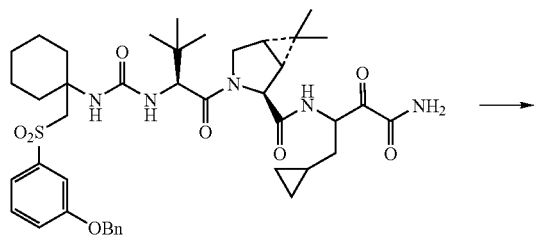

198

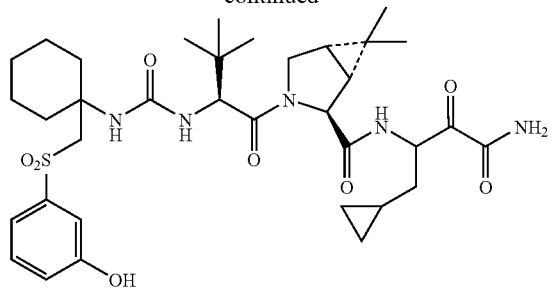

199

10% Pd—C (25 mg) followed by formic acid (0.125 ml) were added to a solution of the benzyl ether (198; 50 mg) in ethanol (4 ml) and the resulting black suspension was refluxed for a period of 1 hour. After cooling, the reaction was filtered through a pad of celite and the solid was washed with methanol. The combined filtrate was concentrated under reduced pressure to give the desired phenol (199; MH+=702.2; 23 mg).

Alternative Preparation of Compound of Formula 210:

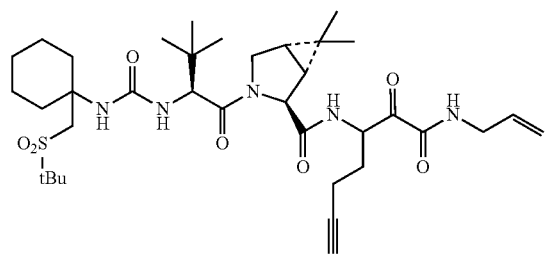

120

Step 1:

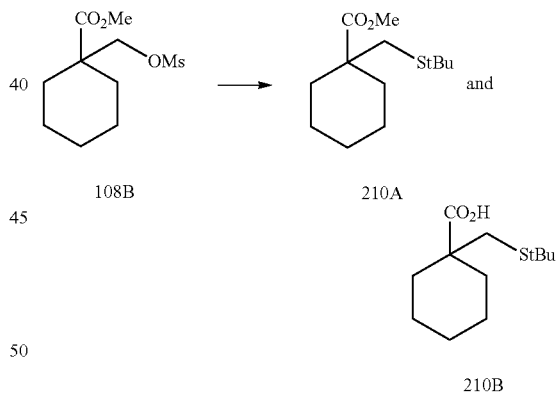

Dimethylformamide (20 ml; anhydrous; Aldrich) was added to sodium hydride (0.56 g; Aldrich) and tert-butyl mercaptan was added to the suspension while cooled in an ice bath under an atmosphere of nitrogen. Once the addition was complete the mesylate (108B; prepared as above from 2.00 g of alcohol; 108A) was added and the resulting mixture was stirred overnight at room temperature. The reaction was partitioned between EtOAc and water and the organic phase was separated, dried (MgSO4). column chromatography on silica gel using EtOAc-Hexanes (2:98) to provide the methyl ester-sulfide (210A; 1.75 g).

EtOAc was added to the aqueous phase and 10% aq. HCl was added until the water layer pH=1. The organic layer was separated, washed with water, dried and concentrated under reduced pressure to give the sulfide-carboxylic acid (210B; 0.747 g) as a white solid.

Step 2:

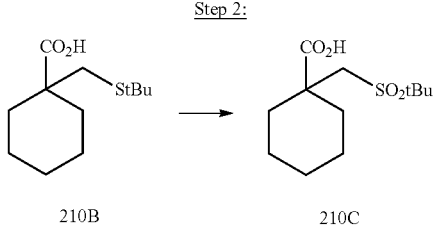

To the sulfide (210B; 2.287 g) in methanol (75 ml) was added a solution of oxone (18.00 g; Aldrich) and the resulting white suspension was stirred overnight at room temperature. The volatiles were removed under reduced pressure and the white solid partitioned between EtOAc and water. The organic phase was separated, dried and concentrated to provide the sulfone (210C, 2.52 g; contains some solvent).

Step 3:

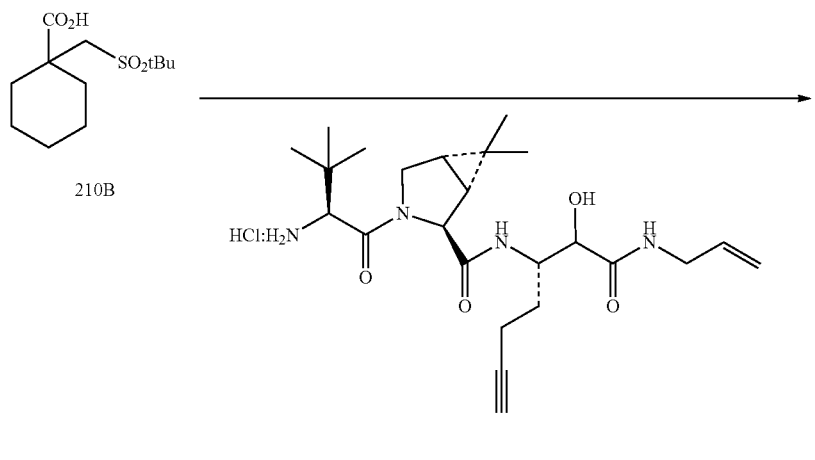

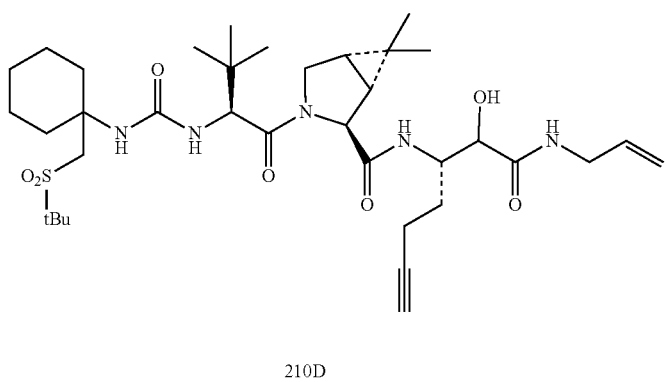

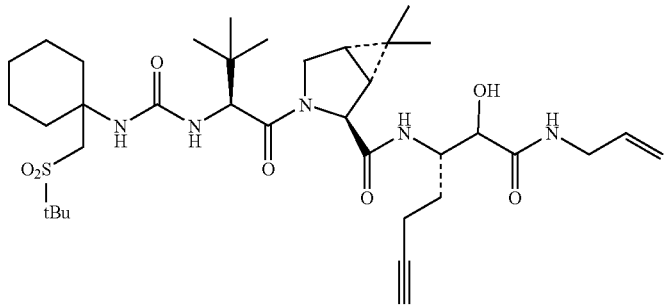

Triethylamine (0.173 ml), followed by DPPA (0.268 ml) were added to a solution of the carboxylic acid (210E; 0.325 g) in toluene (3 ml) and the resulting mixture was heated to 110 C (oil bath) for a period of 1 hour. After cooling the reaction mixture was partitioned between EtOAc and sat. aq. sodium bicarbonate. The organic phase was separated, dried and concentrated. The residue was dissolved in dichloromethane (1 ml) and added to a mixture of the hydrochloride salt (185F; 0.300 g) and triethylamine (0.044 ml) in dichloromethane (3 ml) and the resulting reaction mixture was stirred at room temperature overnight. The reaction was partitioned between EtOAc and 10% aq. HCl, The organic phase was separated, washed with saturated aq. sodium bicarbonate, water, dried and concentrated to yield a crude product which was used in the next step without purification.

Step 4:

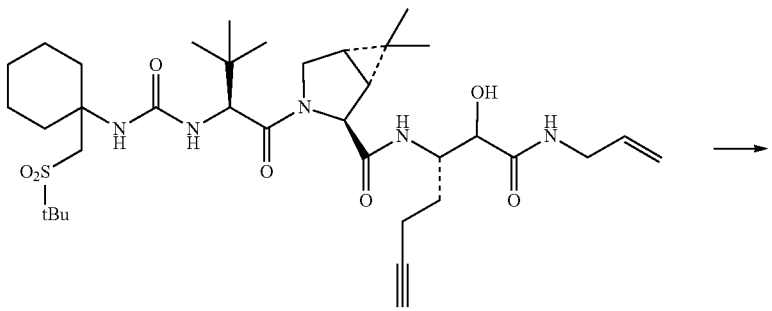

210D

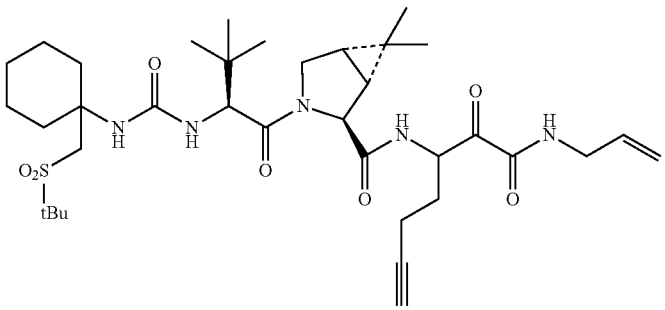

210

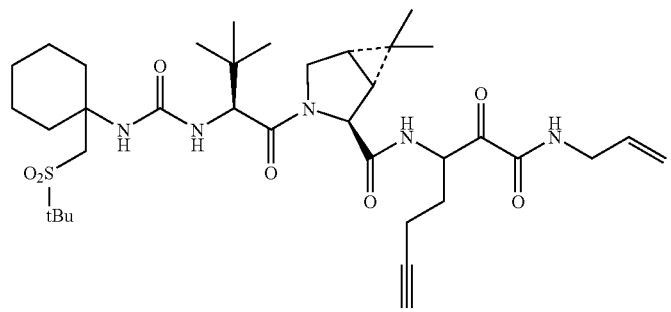

210

The residue from the previous step (210D) was dissolved in dichloromethane (5 ml) and Dess-Martin periodinane (0.527 g) was added and the reaction mixture was stirred at room temperature for 3 hours. The reaction was partitioned between EtOAc and 5% aq. sodium sulfite. The organic phase was separated, washed with sat. aq. sodium bicarbonate, water, dried and the volatiles removed under reduced pressure. The residue was purified by silica gel column chromatography using EtOAc-Hexanes (70:30) as eluent to give the desired keto-amide (210; 0.310 g).

Preparation of Compound of Formula 284:

Step 3:

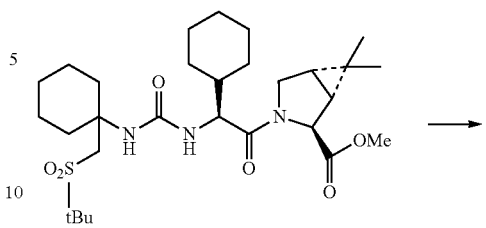

284B

284

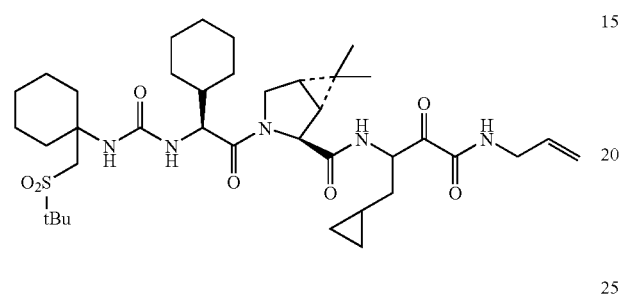

Steps 1 and 2:

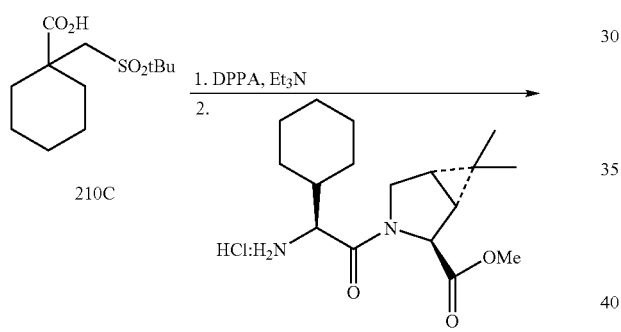

284C

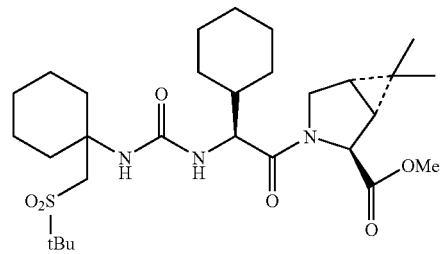

284A

284C

The methyl Ester (284B) was dissolved in a mixture of dioxane (90 ml) and water (30 ml) and lithium hydroxide: monohydrate (0.402 g; 2 eq) was added and the reaction was allowed to stir at room temperature for 3 hours. The reaction mixture was partitioned between EtOAc and 10% aq. HCl. The organic phase was separated, dried and concentrated to yield the carboxylic acid (284C, 2.65 g).

284B

Step 1:

Using the carboxylic acid (210C, 2.52 g), DPPA (2.07 ml), triethylamine (1.34 ml) in toluene (10 ml) and the procedure set above the crude isocyanate was formed.

Step 2:

The intermediate isocyanate was dissolved in dichloromethane (2 ml) and added to a mixture of the hydrochloride salt 284A (prepared from 20.04 using the transformation described for 20.06 to 20.07; 1.66 g) and triethylamine (3.4 ml) and the mixture stirred at room temperature overnight. Aqueous work-up and purification of the residue on silica gel using EtOAc-Hexanes (3:97) gave the desired urea (284B).

Step 4:

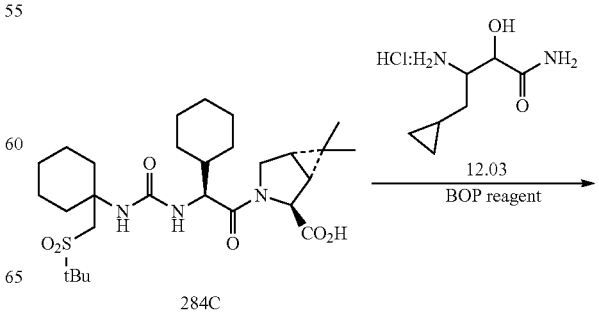

284C

-continued

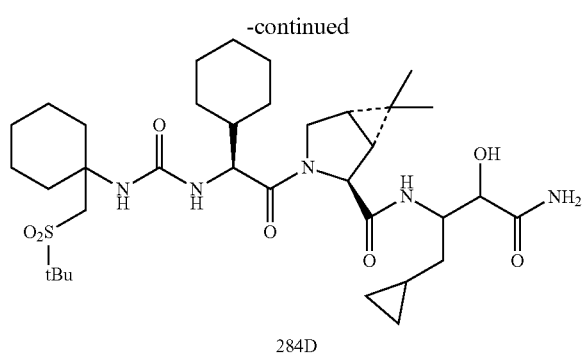

284D

BOP reagent (2.54 g) followed by triethylamine (2.4 ml) were added to a solution of the carboxylic acid (284C, 2.65 g) and the hydrochloride salt (12.03; 0.933 g) in dichloromethane (20 ml) and stirred at room temperature overnight. The reaction was partitioned between EtOAc and 10% aq. HCl. The organic phase was separated, washed with sat. aq. sodium bicarbonate, water, dried and concentrated. The residue was purified by silica gel column chromatography using 2-10% MeOH in dichloromethane as eluent to give the desired amide (284D; 2.92 g).

Step 5:

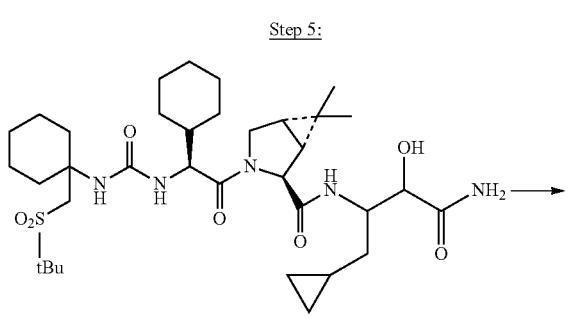

284D

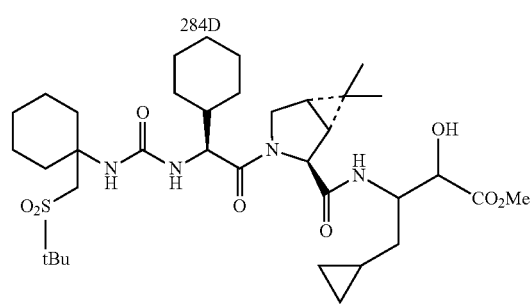

284E

To a solution of the carboxamide (284D; 2.92 g) in methanol (30 ml) was added DMF-DMA (1.12 ml) and the resulting mixture was stirred at room temperature for 3 hours and then refluxed for 1.5 hours until T.L.C. indicated that no starting material was left. After cooling, the reaction was partitioned between diethyl ether and 1N aq. HCl. The organic phase was separated, dried and concentrated. Silica gel column chromatography of the residue gave the methyl ester (284E), which was treated as shown in Step 6, below.

Step 6:

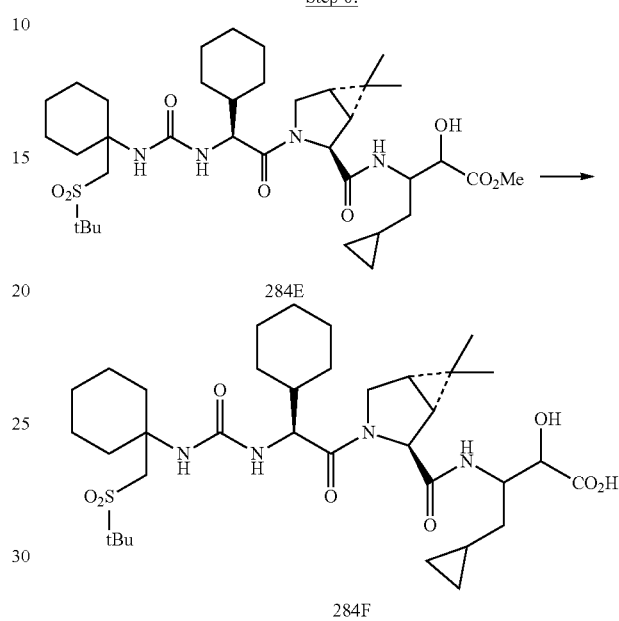

284E

284F

The methyl ester (284E) was dissolved in a mixture of dioxane (30 ml) and water (10 ml) and lithium hydroxide: monohydrate (0.354 g) was added and the resulting mixture was stirred for 3 hours. The reaction was partitioned between EtOAc and 10% aq. HCl. The organic phase was separated, dried and concentrated to provide the carboxylic acid (284F; 2.80 g).

Steps 7 and 8:

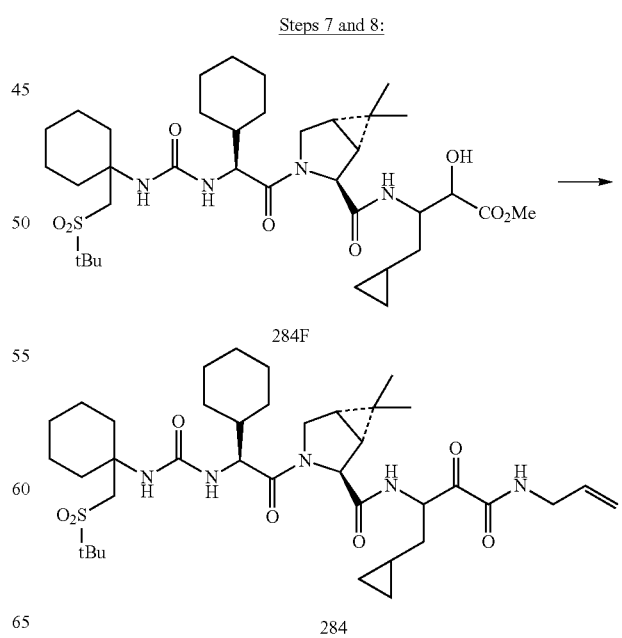

284F

284

Step 7:

Allyl amine (0.045 ml), BOP reagent (0.266 g) and triethylamine (0.25 ml) were added to a mixture of a solution of the hydroxy-acid (284F; 0.348 g) in dichloromethane (5 ml) and the resulting mixture was stirred at room temperature overnight. The reaction was partitioned between EtOAc and 10% aq. HCl. The organic phase was separated, washed with sat. aq. sodium bicarbonate, water, dried and concentrated to provide a residue, used without purification in Step 8, below.

Step 8:

The residue was dissolved in dichloromethane (5 ml) and Dess-Martin periodinane (0.424 g) was added and the reaction mixture was stirred at room temperature for 3 hours. The reaction was partitioned between EtOAc and 5% aq. sodium sulfite. The organic phase was separated, washed with sat. aq, sodium bicarbonate, water, dried and concentrated. The crude reaction product was purified by silica gel column chromatography to yield the desired keto-amide (284; 0.296 g). MH+, 732.2.

Preparative Example 331

Preparation of Intermediates of Formulas 331D and 331E for the Compound of Formula 331

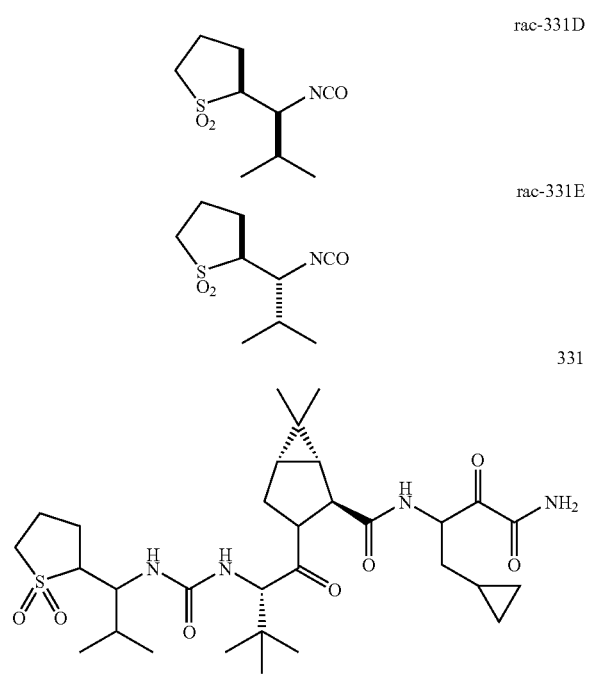

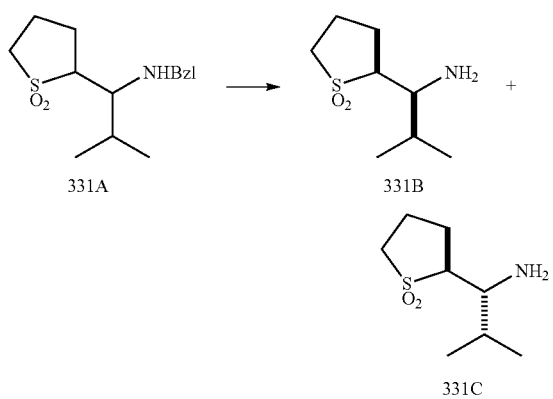

N-benzyl-4-methylbutanimine (prepared as described: *Synthesis*, 1985, 679) and tetrahydrothiophene 1,1-dioxide were reacted in the manner described in Example 336, except at −78° C., to afford compound 331A, which was hydrogenolyzed in the manner described in Example 336, except at a pressure of 1 atm. The crude product was chromatographed on silica gel, eluting with a gradient of EtOAc to 1:1 acetone-EtOAc to obtain first one racemic diastereomer: H$^1$-NMR (CDCl$_3$) δ 3.2 (m, 1H), 3.1-2.9 (m, 3H), 2.3-2.1 (m, 2H), 2.1-1.9 (m, 1H), 1.9-1.7 (m, 2H), 1.02 (d, 3H), 0.85 (d, 3H).

Further elution afforded the other racemic diastereomer: H$^1$-NMR (CDCl$_3$) δ 3.2 (m, 1H), 3.2-2.9 (m, 4H), 2.3-2.1 (m, 3H), 2.1-2.0 (m, 1H), 1.78 (sex., 1H), 0.96 (m, 6H).

Step 2. Preparation of Compounds of Formulas 331D and 331E.

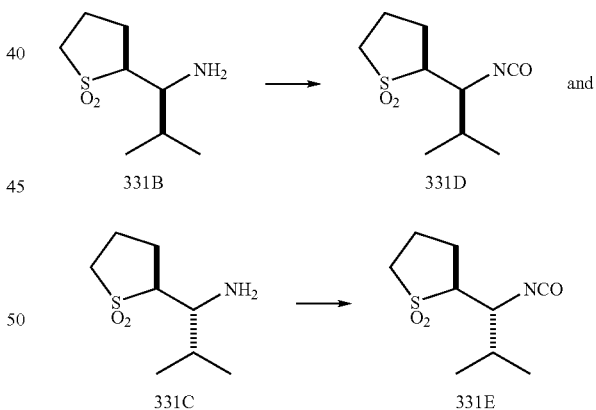

Compounds 331B and 331C were separately reacted with phosgene in the manner described in Example 336 to afford two diastereomeric isocyanates:

Step 1. Preparation of Compounds of Formulas 331B and 331C:

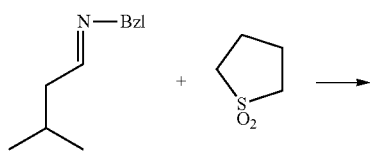

the one, from the higher R$_f$ amine: H$^1$-NMR (CDCl$_3$)) δ 3.79 (dd, J$_1$=9.9 Hz, J$_2$=3.0 Hz, 1H), 3.25 (m, 1H), 3.1-3.0 (m, 2H), 2.25 (m, 2H), 2.2-2.0 (m, 1H), 2.0-1.7 (m, 2H), 1.09 (d, J=6.9 Hz, 3H), 0.93 (d, J=6.9 Hz, 3H).

the other, from the lower R$_f$ amine: H$^1$-NMR (CDCl$_3$)) δ 3.92 (dd, J$_1$=6.6 Hz, J$_2$=4.8 Hz, 1H), 3.3-2.9 (m, 3H), 2.4 (m, 1H), 2.3 (m, 1H), 2.2-2.0 (m, 3H), 1.03 (t, Δv=6.3, 6H).

Preparative Example 336

Preparation of Compound of Formula 336

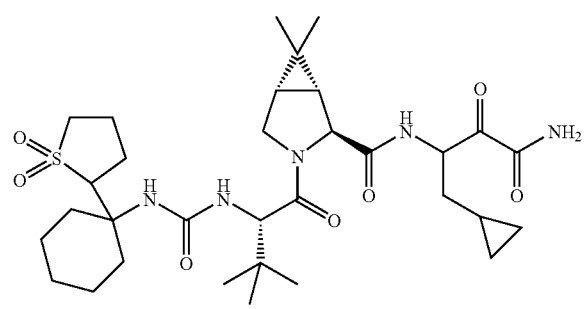

336

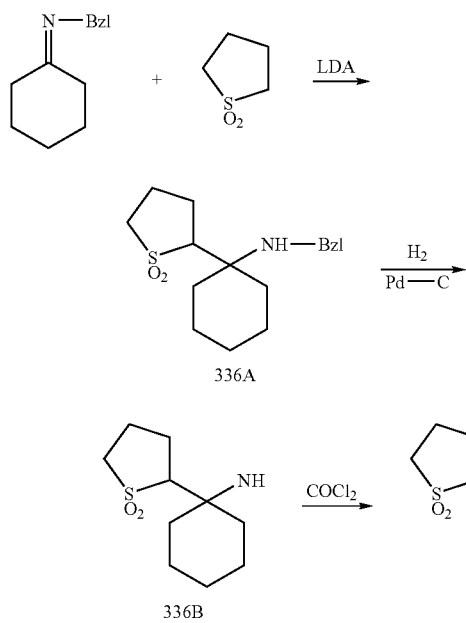

SCHEME 336-1

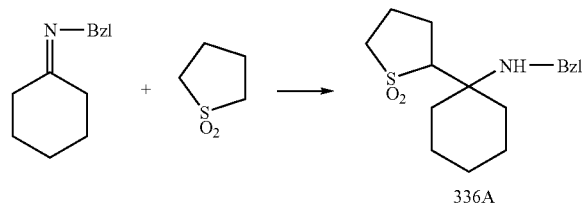

Step 1. Preparation of Compound of Formula 336A.

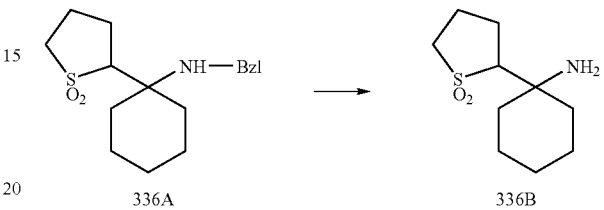

A solution of 20 mL of 2N LDA in hexane-THF was added to 60 mL THF and the solution was cooled to −30° C. Then 4.80 g of tetrahydrothiophene 1,1-dioxide (Aldrich Chemical Co.) was added slowly between −30° C. and −10° C., and the stirred at −10° C. for an additional 10 min. At −10° C., 7.5 g of N-benzylcyclohexylimine (prepared as described: *Synthesis,* 1998, 1609.) was added at once. After 0.5 h at ambient temperature the mixture was quenched with saturated aqueous NaHCO$_3$, and extracted with CH$_2$Cl$_2$. The extracts are dried over anhydrous Mg$_2$SO$_4$, filtered, and the filtrate evaporated. The residue was chromatographed on silica gel, eluting with EtOAc-hexane (3:7) to afford 1.3 g of compound 336A:

H$^1$-NMR (CDCl$_3$): δ 7.5-7.2 (m, 5H), 3.76 (ABq, Δν=230 Hz, J=12, 2H), 3.41 (m, 1H), 3.13 (m, 1H), 2.94 (m, 1H), 2.4-1.3 (m, 14H).

Step 2. Preparation of Compound of Formula 336B.

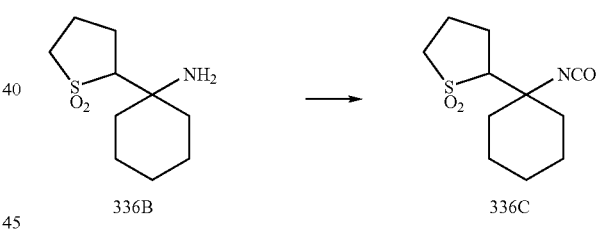

A solution of 1.3 g of compound 336A, 30 mL EtOH, 1.2 mL of 4n HCl/dioxane solution, and 0.35 g of 10% Pd—C was hydrogenated at 3 atm for 1.5 h. The mixture was filtered, and the filtrate evaporated. The residue was treated with 2 n NaOH and extracted with CH$_2$Cl$_2$, the extract was dried and evaporated to leave 0.51 g of compound 336B, which solidified on standing:

H$^1$-NMR (CDCl$_3$δ 3.2-2.9 (m, 3H), 2.4-1.8 (m, 6H), 1.7-1.2 (m, 8H).

Step 3. Preparation of Compound of Formula 336C

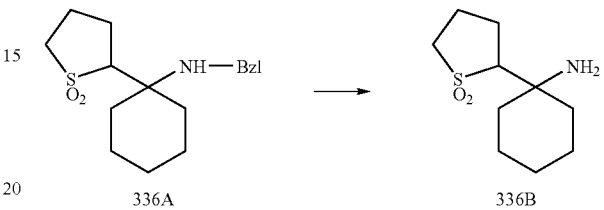

To a solution of 0.75 g phosgene in 30 mL toluene at 0° C. was slowly a solution of 0.5 g of compound 336B and 0.80 mL diisopropylethylamine in 10 mL CH$_2$Cl$_2$. The mixture was stirred at room temperature for 5 h, concentrated to 15 mL, filtered, then diluted with fresh toluene to 18 mL to produce a 0.12 M solution of compound 336C, which was used for subsequent reactions.

Step 4. Preparation of Compound of Formula 336

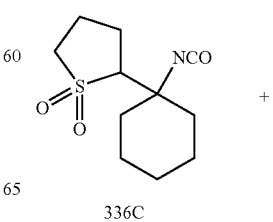

336C

+

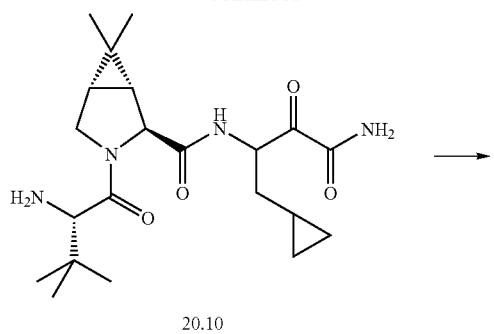

20.10

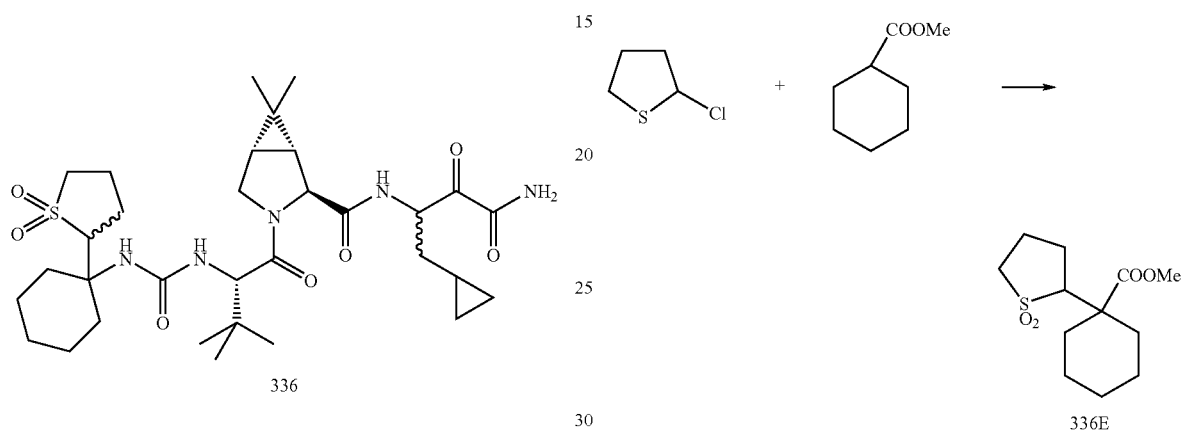

336

Compound 336C was reacted with compound 20.10 in the manner described in preparative example 108 to produce compound 336 as a mixture of diastereomers H$^1$-NMR (DMSO-d$_6$) δ 8.40(m), 8.33 (m), 8.00 (d), 7.75 (s), 6.25 (m), 6.10 (s), 6.01 (s), 4.18 (m), 3.92(m), 3.83 (m), 3.78 (m), 3.13 (m), 2.90 (m) 2.47 (m), 2.1-0.8 (m; Me$_A$: 1.01; Me$_B$: 0.82; Bu$^t$: 0.91), 0.40 (m), 0.19 (m).

Example 336C

Alternate Synthesis of Compound 336C

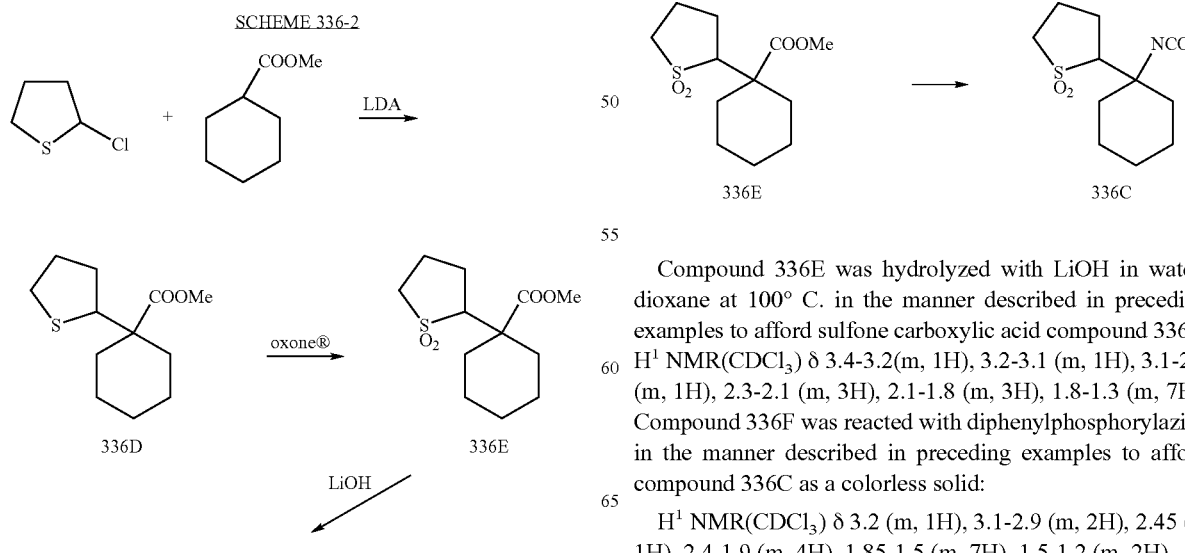

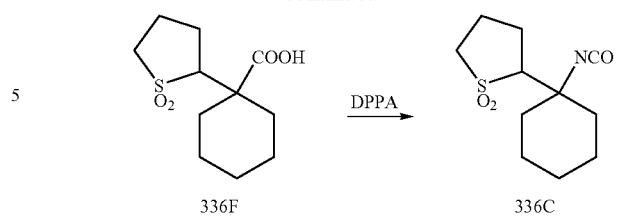

Step 1. Preparation of Compound of Formula 336E.

2-Chlorotetrahydrothiophene (prepared as described: *Chem. Pharm. Bull.*, 1986, 34(9), 3644) was reacted with α-lithiocyclohexanecarboxylic acid in the manner described in preceding examples to afford sulfide ester compound 336D in 39% yield. Compound 336D was oxidized with oxone® in the manner described in preceding examples to afford sulfone ester compound 336E: H$^1$ NMR(CDCl$_3$) δ 3.73 (s, 3H) 3.3-3.0 (m, 2H), 3.0-2.9 (m, 1H), 2.6-2.4 (m, 1H), 2.4-1.3 (m, 13H).

Step 2. Preparation of Compound of Formula 336C.

Compound 336E was hydrolyzed with LiOH in water-dioxane at 100° C. in the manner described in preceding examples to afford sulfone carboxylic acid compound 336F: H$^1$ NMR(CDCl$_3$) δ 3.4-3.2(m, 1H), 3.2-3.1 (m, 1H), 3.1-2.9 (m, 1H), 2.3-2.1 (m, 3H), 2.1-1.8 (m, 3H), 1.8-1.3 (m, 7H). Compound 336F was reacted with diphenylphosphorylazide in the manner described in preceding examples to afford compound 336C as a colorless solid:

H$^1$ NMR(CDCl$_3$) δ 3.2 (m, 1H), 3.1-2.9 (m, 2H), 2.45 (d, 1H), 2.4-1.9 (m, 4H), 1.85-1.5 (m, 7H), 1.5-1.2 (m, 2H).

Synthesis of Compound 349:

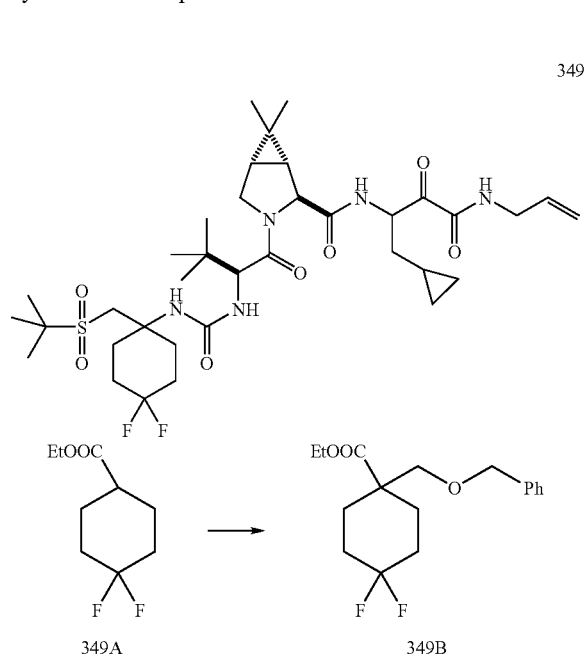

To a solution of the ethyl ester (349A; 10 g; 0.052 mol.) in diethyl ether (50 ml) at −78° C. (bath temp.) was added KHMDS (0.5 M in toluene; 156.087 ml; 1.5 equiv.). The resulting solution was stirred for 30 minutes, then benzyl chloromethyl ether (11.89 ml; density 1.13; 1.65 equiv.) was added. The reaction mixture was stirred at −78° C. to R.T. for 24 h. Reaction was stopped by addition of saturated aq. NH$_4$Cl. It was then diluted with ethyl acetate and the combined organic phase was washed with brine, dried over Na$_2$SO$_4$ and evaporated to dryness in vacuo to provide a light brown oil (24.2 g). It was chromatographed over silica gel (300 g). The column was eluted with 1%-4% ethyl acetate in n-hexane providing in some of the fractions pure 349B (6.54 g).

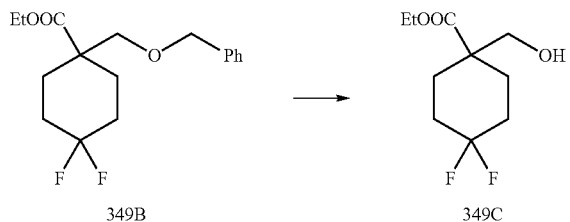

A solution of the benzyl ether (239B; 2.8316 g; 0.0091 mol.) in CHCl$_3$ (49.5 ml) was treated with methane sulfonic acid (22.65 ml) and the reaction mixture stirred at room temperature for ~70 minutes. Ice was added to the reaction mixture and it was diluted with ethyl acetate. The organic phase was washed with saturated NaHCO$_3$, dried over Na$_2$SO$_4$ and evaporated to dryness in vacuo to provide yellowish oil (2.86 g). It was chromatographed over SiO$_2$ (65 g). The column was eluted with 15%-25% ethyl acetate in n-hexane providing in some of the fractions pure 349C (1.5913 g).

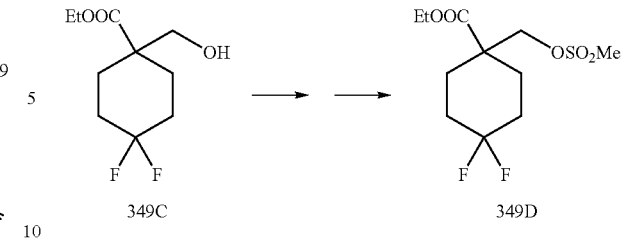

A stirred solution of the alcohol (349C, 1.14 g; 0.0051 mol.) in methylene chloride (6.4 ml) was cooled in ice bath and treated with Et$_3$N (0.7857 ml; density 0.726; 1.1 equiv.) and methanesulfonyl chloride (0.4168 ml; density 1.48; 1.05 equiv.). After ~2 hrs the reaction mixture was diluted with methylene chloride and it was washed with 6N HCl followed by saturated NaHCO$_3$. The organic phase was dried over Na$_2$SO$_4$ and evaporated to dryness in vacuo to provide the mesylate 349D (1.5447 g) as a light yellow oil.


A stirred suspension of NaH (0.4114 g; 60% dispersion in mineral oil; 2 equiv.) in dry DMF was treated with tert.-butyl thiol (1.16 ml; density 0.8; 2 equiv.) with ice bath cooling. The reaction mixture was stirred for 30 minutes after which the mesylate (349D; 1.5447 g; 1 equiv.) was added in dry DMF (8+2 ml). Ice bath was removed and the reaction mixture was stirred at room temperature overnight. The reaction mixture was acidified with 6N HCl and extracted with ethyl acetate. The ethyl acetate extract was dried over Na$_2$SO$_4$ and evaporated to dryness in vacuo to provide crude 349D (2.87 g) which was chromatographed over SiO$_2$ (60 g). The column was eluted with 3% ethyl acetate providing in some of the fractions pure 349E (1.38 g) as a colorless oil.

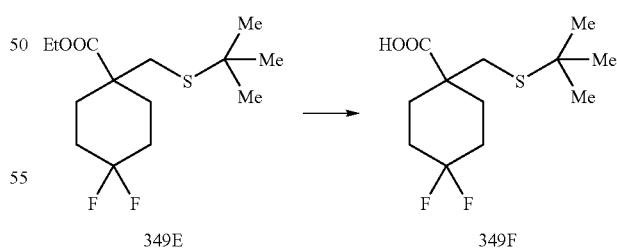

A solution of the ethyl ester (349E; 1.38 g; 0.00468 mol.) in ethanol (16 ml) and water (4.13 ml) was treated with KOH pellets (2.63 g; 10 equiv.). The resulting solution was refluxed for 7 h and then allowed to cool to room temperature overnight. Ethanol was evaporated in vacuo and the residue partitioned between CH$_2$Cl$_2$/water, acidified with 6N HCl to pH 1. The organic phase was separated and the aqueous phase extracted three times with CH$_2$Cl$_2$. The combined organic phase was dried over Na$_2$SO$_4$ and evaporated to dryness in vacuo to provide 349F (1.19 g) as a off white solid, m.p. 93-95° C.

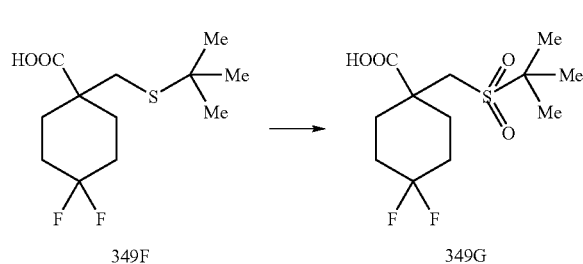

The oxone (8.24 g; 3 equiv.) dissolved in water (31 ml) was added to a stirred solution of the sulfide (349F; 1.19 g; 1 equiv.) in methanol (31 ml) at 0° C. (bath temp). The reaction was stirred at 0° C. to R.T. over the weekend. Solvents were evaporated in-vacuo and the residue partitioned between CH$_2$Cl$_2$/water. The organic layer was separated and the aqueous layer extracted twice with CH$_2$Cl$_2$. The combined organic phase was dried over Na$_2$SO$_4$ and evaporated to dryness in vacuo to provide 349G (1.29 g) as a crystalline solid, m.p. 212° C.

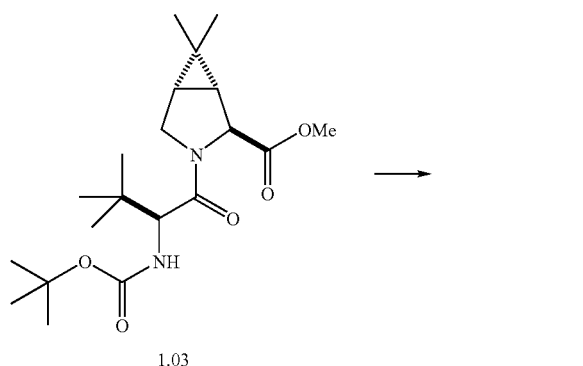

To a cooled (ice bath) solution of the ester (1.03; 4.56 g; 0.0119 mol.) in dioxane (18.23 ml) was added with stirring 1.0 N LiOH (18.23 ml). The reaction mixture was stirred for 2 hrs. TLC indicated some starting material still remaining, so added 2+1 ml 1.0 N LiOH and stirred overnight. Reaction complete by TLC. 6N HCl was added to acidify the reaction mixture to pH 1 and ethyl acetate (150 ml) added. After shaking, the ethyl acetate phase was separated and the aqueous phase extracted with ethyl acetate. The combined ethyl acetate phase was washed once with brine, dried (Na$_2$SO$_4$) and evaporated to dryness in vacuo to provide 1.17 as a amorphous solid (4.7805 g; occluded solvent).

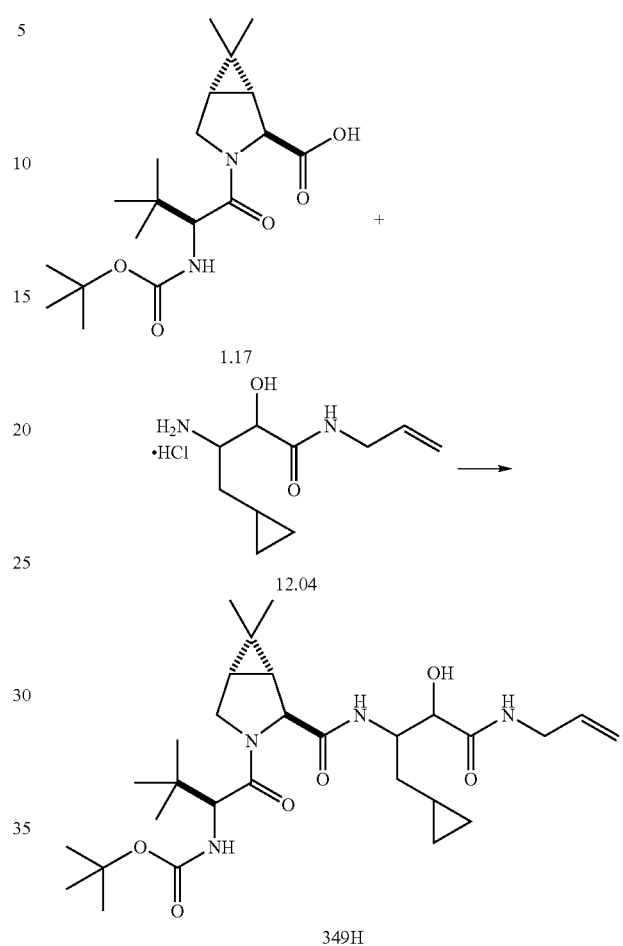

To a −20° C. solution of the acid 1.17 (0.7079 g; 0.00192 mol.) and the amine salt (12.04; 0.5231 g; 1.16 equiv.) in CH$_2$Cl$_2$ (10 ml) was added HATU (0.77 g; 1.05 equiv.) followed by diisopropylethylamine (0.8913 g; 1.2 ml; 3.59 equiv.). The reaction mixture was stirred at −20° C. for ~16 hrs. It was then diluted with EtOAc (~150 ml) and washed successively with satd. NaHCO$_3$, 10% citric acid and dried over Na$_2$SO$_4$. Evaporation of the solvent in vacuo provided a amorphous solid which was chromatographed over SiO$_2$ (42 g). Elution of the column with 50%-60% EtOAc in n-hexane provided in some of the fractions pure 349H (0.7835 g).

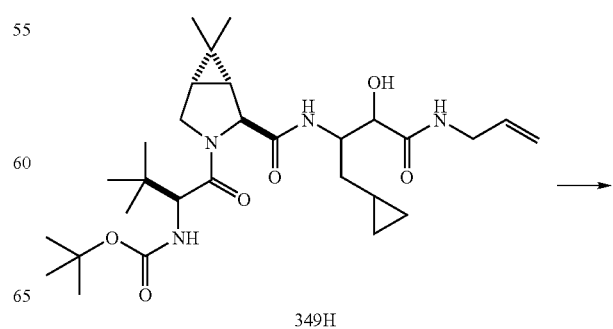

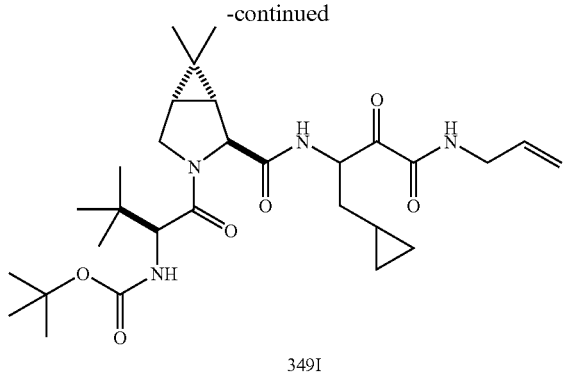

349I

A solution of the hydroxyamide 349H (0.7835 g; 0.00142 mol.) in dry methylene chloride (32 ml) was treated with stirring and cooling (ice bath) with Dess-Martin reagent (1.5134 g; 2.5 equiv.). Ice bath was removed and the reaction mixture was allowed to stir at room temperature for 2.5 hrs. Saturated Na$_2$S$_2$O$_3$ (32 ml) was added to destroy excess oxidant and stirring continued until the cloudy solution turned clear two-phase system. The reaction mixture was then diluted with CH$_2$Cl$_2$ (~100 ml), the organic phase separated and washed once with satd. NaHCO$_3$, water then dried. Evaporation to dryness in vacuo provided 349I (0.7466 g) as an amorphous solid.

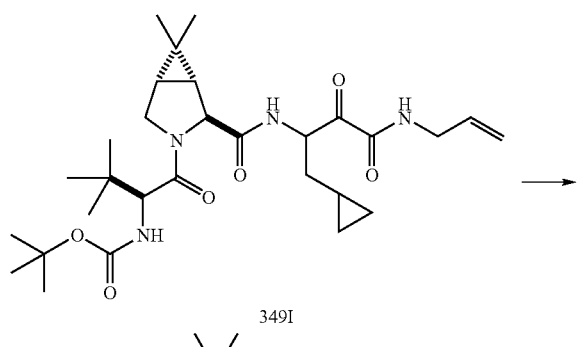

349I

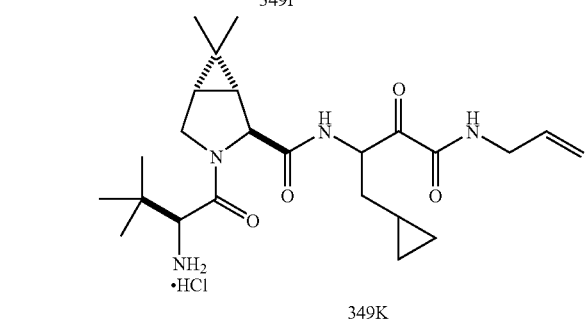

349K

The tert.-butylcarbamate 349I (0.7466 g) was treated with 4M HCl/dioxane (20 ml) and left in a stoppered flask for 45 minutes. Most of the dioxane was evaporated in-vacuo and the residue evaporated with n-hexane twice; the remaining residue was triturated with ether leaving 349K (0.6341 g) as a free flowing solid.

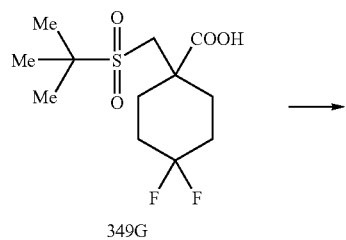

349G

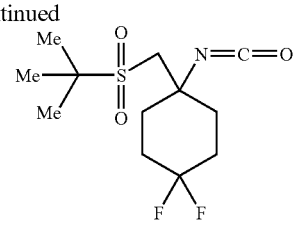

349J

To a toluene solution (7.5 ml) of the acid 349G (0.1 g; 0.0003351 mol.) were added Et$_3$N (0.0467 ml; 46.7 µl; 1 equiv.) followed by diphenylphosphoryl azide (0.072; 72 µl; 1 equiv.). The reaction mixture was refluxed for 1 h. After cooling down, it was treated with ethyl acetate (~50 ml), the organic phase washed with saturated NaHCO$_3$ and concentrated in vacuo to provide 349J (0.1 g).

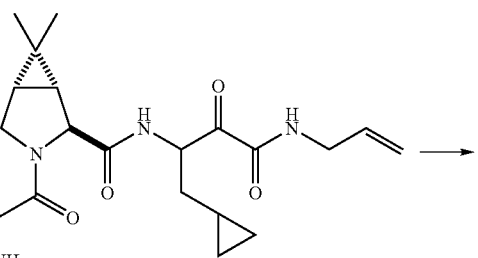

349K

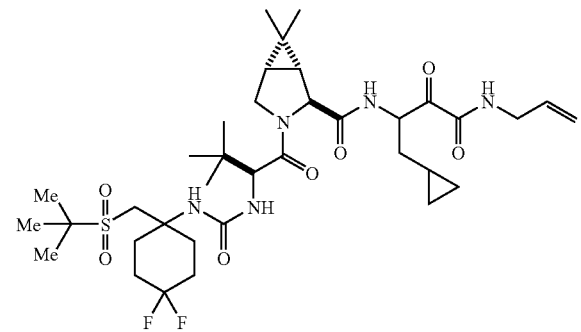

349

To a stirred suspension of the amine hydrochloride 349K (0.1 g; 0.000207 mol.) in methylene chloride (5 ml) was added diisopropylethylamine (0.135 g; 5 equiv.). After 1 minute was added the isocyanate 349J (0.1 g; 0.0003385 mol.). The reaction mixture was stirred at room temperature for 2 hrs. It was then diluted with EtOAc and washed with 1N HCl, satd. NaHCO$_3$, dried over Na$_2$SO$_4$ and finally evaporated to dryness in-vacuo to provide an amorphous solid. It was subjected to preparatory TLC on silica gel plates using 40% acetone in n-hexane as eluent. The uv positive band was extracted with 60% acetone in methylene chloride to provide 349 (0.122 g) as an amorphous solid.

Synthesis of Compound 350:

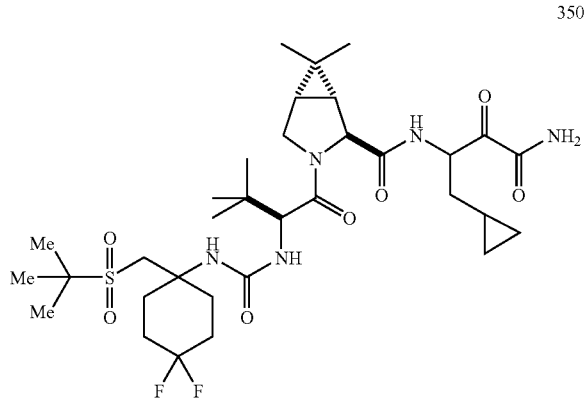

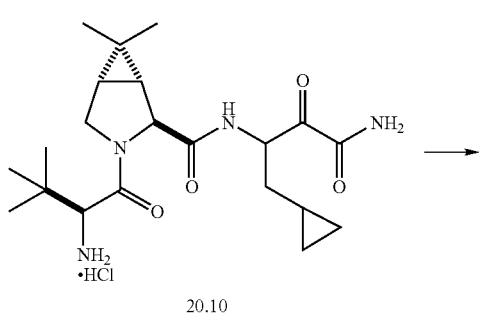

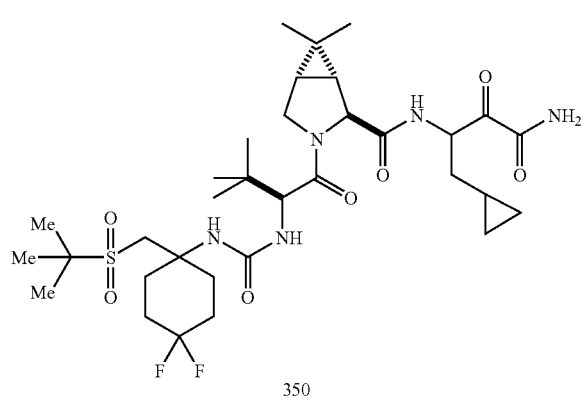

To a stirred suspension of the amine hydrochloride 20.10 (0.0966 g; 0.000223 mol.) in methylene chloride (5 ml) was added diisopropylethylamine (0.144 g; 5 equiv.). After 1 minute was added the isocyanate 349H (0.1 g; 0.0003385 mol.). The reaction mixture was stirred at room temperature for 2 hrs. It was then diluted with EtOAc (~100 ml), then washed with 1N HCl, satd. NaHCO$_3$, dried over Na$_2$SO$_4$ and finally evaporated to dryness in vacuo to provide an amorphous white solid (0.1731 g). It was subjected to preparatory TLC on silica gel using 40% acetone in n-hexane as eluent. The uv positive band was extracted with 60% acetone in methylene chloride to provide 350 (0.0671 g) as an amorphous solid.

Example 145

Preparation of Compound of Formula 145

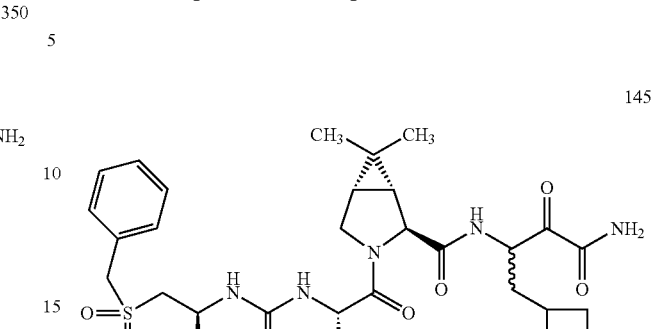

Step 1

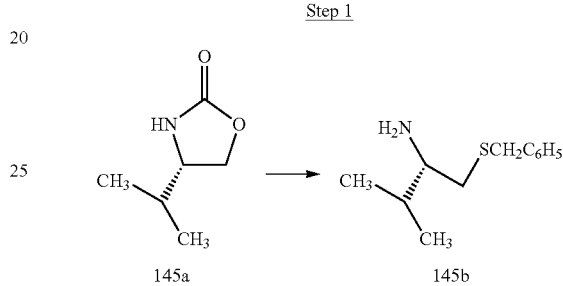

1-Propanol was treated with metallic sodium (361 mg, 15.7 mmol) and stirred at RT for 1 h. After complete dissolution of sodium, benzylthiol (2.74 mL, 23.2 mmol) was added and the reaction mixture was stirred at RT for 0.5 h. (S)-4-isopropyl-oxazolidinone (Aldrich, 1 g, 7.74 mmol) was added and the reaction mixture was heated at reflux for 16 h. The reaction mixture was concentrated in vacuo and the crude mixture was diluted with cold water and extracted with ether (3×150 mL). The combined organic layers were dried, filtered concentrated in vacuo to yield amine 145b. It was converted to the hydrochloride salt with 4 M HCl and dried in high vacuum to yield 145b.HCl (1.9 g).

Step 2

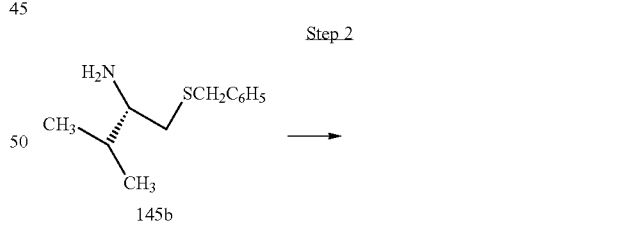

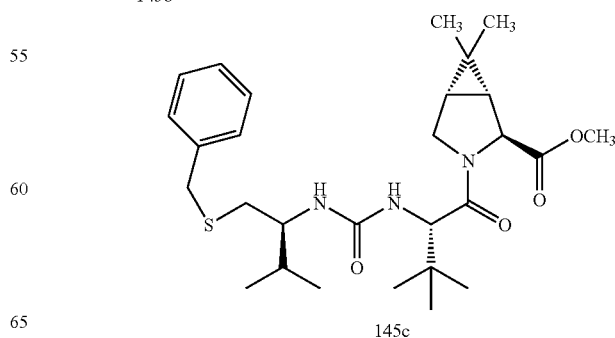

A solution of 145b.HCl (1 g, 4.07 mmol) in CH$_2$Cl$_2$ (50 mL) and satd. NaHCO$_3$ (70 mL) at 0° C. was treated with phosgene (15% in toluene 10 mL) and stirred at 0° C. for 3 h. The reaction mixture was poured into a separatory funnel and the organic layer was separated. The organic layer was washed with cold NaHCO$_3$, brine and dried (MgSO$_4$). It was concentrated and used as it is in next step.

Amine hydrochloride salt (1.04; 865 mg, 2.7 mmol) was dissolved in CH$_2$Cl$_2$/DMF 1:1 and cooled to 0° C. The mixture was treated with (C$_2$H$_5$)$_3$N (682 mg, 6.75 mmol) and isocyanate prepared as above (950 mg, 4.07 mmol) and stirred at RT overnight. The solvent was evaporated and the residue was dissolved in EtOAc. The organic layer was washed with aq. HCl, aq NaHCO3, brine. The reaction mixture was dried, filtered and concentrated in vacuo. The residue was purified by chromatography (SiO$_2$, EtOAc/Hexanes 1:3) to yield 145c (880 mg).

Step 3

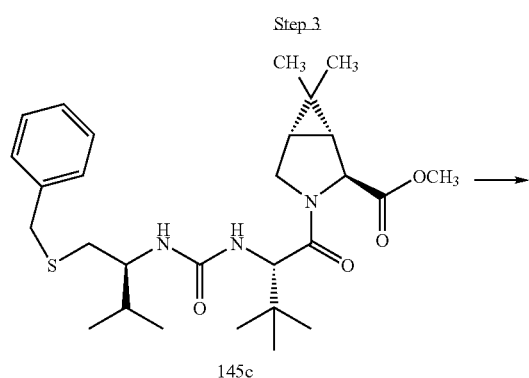

145c

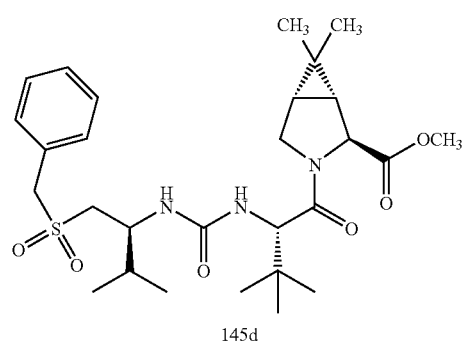

145d

A solution of 145c (500 mg, 0.9 mmol) in 1,2 dichloroethane (10 mL) was treated with MCPBA (70%, 500 mg,) and 0° C. and diluted with ether and aq. solution of Na$_2$S$_2$O$_3$. The organic layer was separated and washed extensively with aq. saturated NaHCO3 and brine. The reaction mixture was dried (MgSO4) filtered concentrated in vacuo and purified by chromatography (SiO$_2$, EtOAc/Hexane 2:3) to yield 145d (530 mg). MS (ESI) 550 [(M+1)$^+$, 100], 381 (95), 353 (20).

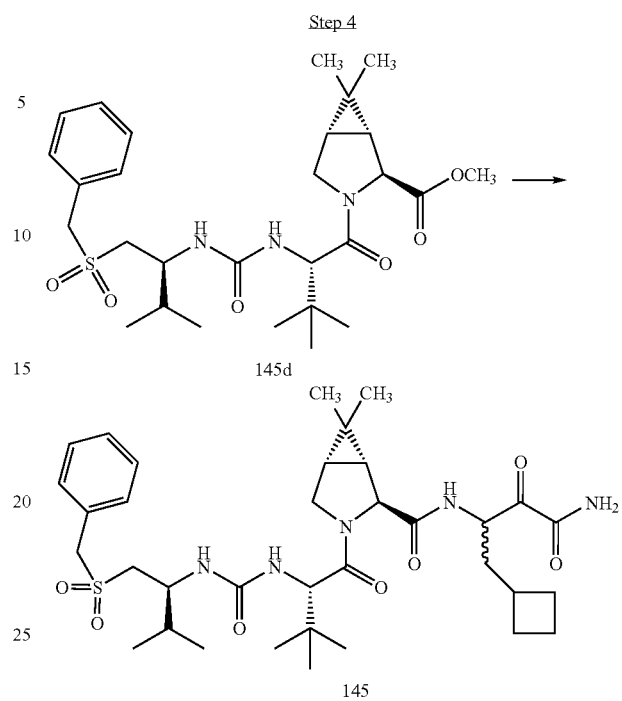

Step 4

145d

145

The conversion of 145d to 145 was identical to the procedure described in the conversion of 284B to 284D and 108D to 108 MS (ESI) 690 [(M+1)$^+$, 100), 381 (30).

Preparation of Intermediate of Formula 347:

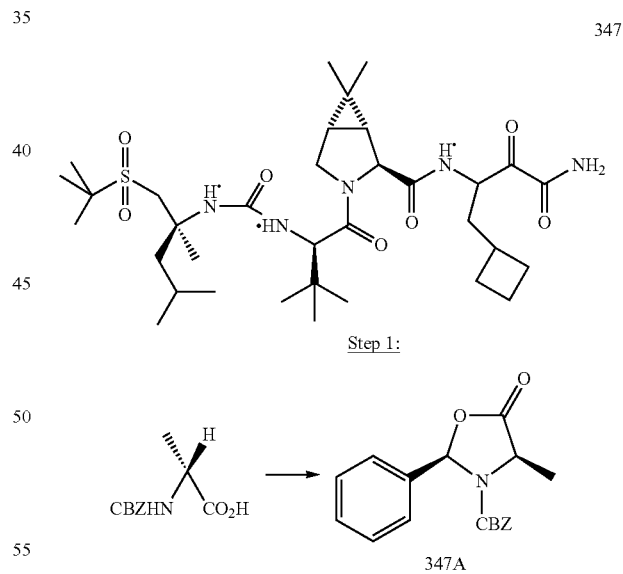

347

Step 1:

347A

Dimethyl benzaldehyde acetal (10.0 mL, 67.2 mmol) was added to a cooled solution of CBZ-D-alanine (15.0 g, 67.2 mmol) in Et$_2$O (180 mL), followed by BF$_3$.Et$_2$O (50.6 mL, 403.2 mmol) over 15 ml. The reaction mixture was stirred at −20° C. for 4 days and quenched by addition of ice cold saturated NaHCO$_3$ (350.0 mL). The organic layer was diluted with Et$_2$O (500 mL), separated, washed with NaHCO$_3$ (5% aqueous solution), brine, dried over MgSO$_4$, filtered and concentrated. The crude was recrystallized using Et$_2$O/hexane to yield 347A (13.6 g, 65%).

Step 2

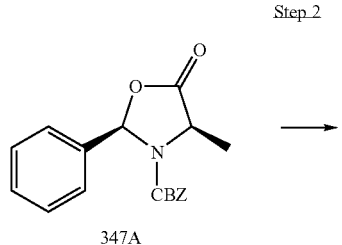

347A

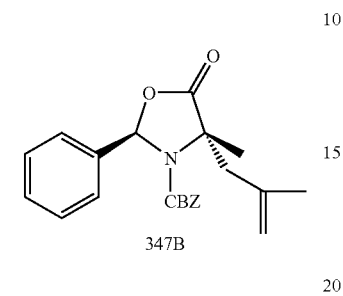

347B

THF (48.0 mL) was added to a flame dried flask and cooled to −35° C. KHDMS (0.5 M solution in PhMe, 42.0 mL, 21 mmol) was added to it, followed by dropwise addition of a mixture of 347A (6.22 g, 20.0 mol) and 3-bromo-2-propene (2.02 mL, 20 mmol) maintaining the internal temperature between −30 and −35° C. The reaction mixture was stirred at −35° C. for 2 h, then allowed to warm up over 2.5 h, quenched by addition of ice cold saturated NaHCO$_3$ (400.0 mL). The organic layer was diluted with Et$_2$O (600 mL), separated, washed with brine, dried over MgSO$_4$, filtered and concentrated. The crude was purified over SiO$_2$ using CH$_2$Cl$_2$ to yield 347B (14.2 g, 90%).

Step 3

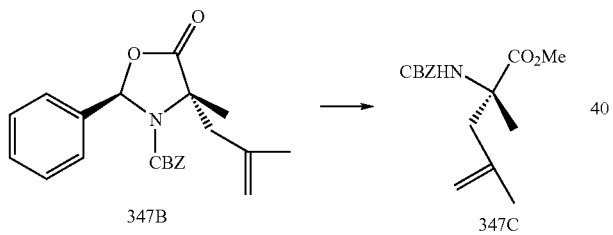

347B 347C

To a solution of 347B (10.7 g, 29.4 mmol) in MeOH (200 mL) was added LiOH (4N, 15 mL) and stirred at RT for 30 min, diluted with H$_2$O (500 mL), extracted with EtOAc (4×400 mL), washed with brine, dried over MgSO$_4$, filtered and concentrated. The crude was purified over SiO$_2$ using CH$_2$Cl$_2$ to yield 347C (8.65 g, 88%).

Step 4

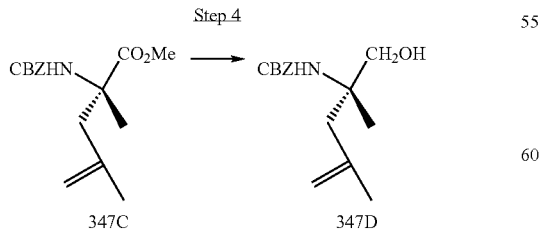

347C 347D

To a ice-cold solution of 347C (8.56 g, 29.4 mmol) in EtOH (100 mL) was added LiBH$_4$ (960 mg, 44.1 mmol) and stirred at RT for 12 h, another portion of LiBH$_4$ (960 mg) was added to it at 5° C. and stirred at RT for 4 h, diluted with H$_2$O (100 mL) and MeOH (100 mL), evaporated to dryness, dissolved in H$_2$O (100 ml), extracted with EtOAc (500 mL), washed with brine, dried over MgSO$_4$, filtered and concentrated. The crude was purified over SiO$_2$ using EtOAc (1-8%) in CH$_2$Cl$_2$ to yield 347D (4.7 g, 60%).

Step 5

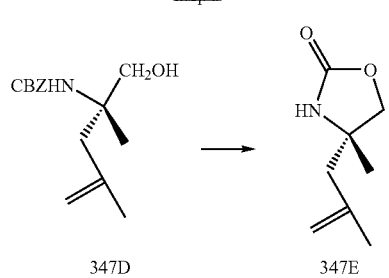

347D 347E t-BuOK (1M in THF, 3.85 mL) was added to a cooled (−5° C.) solution of 347D (4.06 g, 15.4 mmol) in THF (20 mL) and stirred at that temperature for 2 h. The reaction mixture was concentrated, redissolved in EtOAc (250 mL) and NaOH (2N, 50 mL). The organic layer was diluted with EtOAc (600 mL), separated, washed with brine, dried over MgSO$_4$, filtered and concentrated. The crude was purified over SiO$_2$ using 10% CH$_2$Cl$_2$ in EtOAc to yield 347E (1.4 g).

Step 6

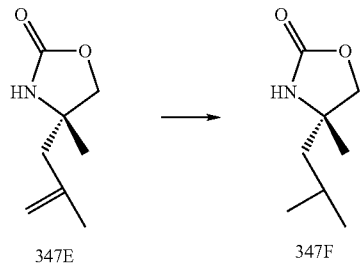

347E 347F 347E (1.37 g, 8.82 mmol) was dissolved in EtOH (25 mL) and Pd—C (10% by weight, 275.0 mg) was added to it. The reaction mixture was stirred under a hydrogen atmosphere for 12 h, filtered, concentrated and purified over SiO$_2$ using 10% CH$_2$Cl$_2$ in EtOAc to yield 347F (1.04 g, 75%).

Step 7

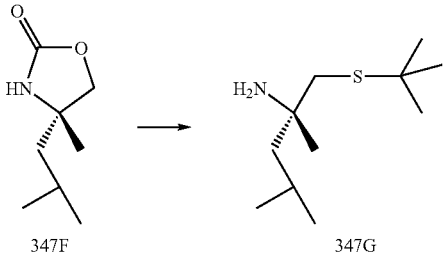

347F 347G 347F (2.58 g, 16.4 mmol) was dissolved in PrOH (40 mL) and NaSBu-t (10.2 g, 82 mmol) was added to it. The reaction mixture was refluxed for 136 h, cooled, evaporated and redissolved in EtOAc, washed with H₂O and the organic layer dried over MgSO₄, filtered and concentrated. The crude was purified over SiO₂ using 30% acetone in CH₂Cl₂ to yield 347G (0.6 g, 19%) and 347F (1.1 g).

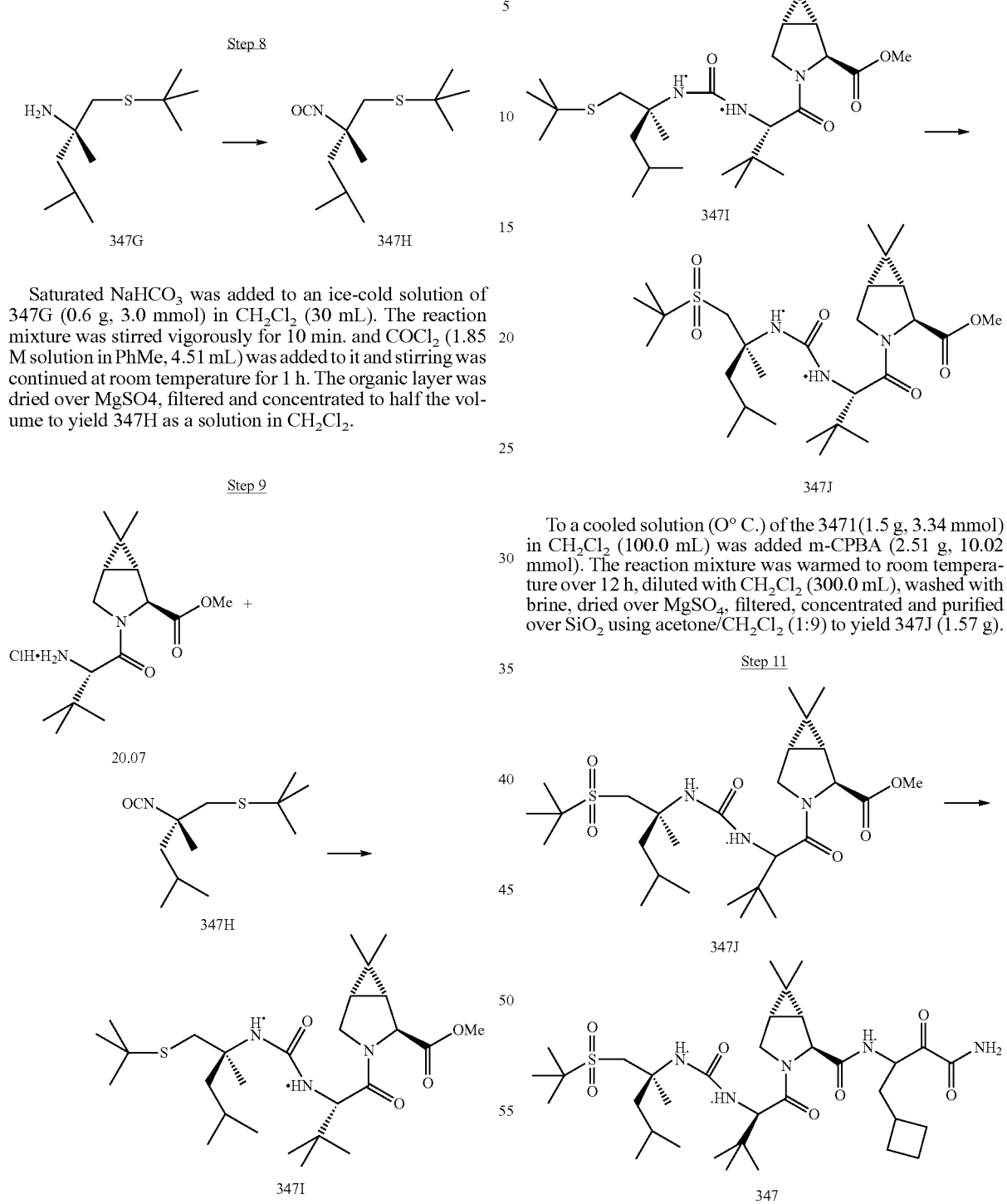

Saturated NaHCO₃ was added to an ice-cold solution of 347G (0.6 g, 3.0 mmol) in CH₂Cl₂ (30 mL). The reaction mixture was stirred vigorously for 10 min. and COCl₂ (1.85 M solution in PhMe, 4.51 mL) was added to it and stirring was continued at room temperature for 1 h. The organic layer was dried over MgSO4, filtered and concentrated to half the volume to yield 347H as a solution in CH₂Cl₂.

To a cooled solution (0° C.) of 347H (685 mg, 3.0 mmol) in DMF (10.0 mL) was added 20.07 (1.05 g, 3.34 mmol), followed by DIPEA (1.45 mL, 8.35 mmol). The reaction mixture was stirred at room temperature for 1.2 h, diluted with ethyl acetate, washed with 3% citric acid, brine, dried over MgSO₄, filtered, concentrated and purified over SiO₂ using acetone/CH₂Cl₂ (1:9) to yield 347I (1.57 g).

To a cooled solution (0° C.) of the 347I (1.5 g, 3.34 mmol) in CH₂Cl₂ (100.0 mL) was added m-CPBA (2.51 g, 10.02 mmol). The reaction mixture was warmed to room temperature over 12 h, diluted with CH₂Cl₂ (300.0 mL), washed with brine, dried over MgSO₄, filtered, concentrated and purified over SiO₂ using acetone/CH₂Cl₂ (1:9) to yield 347J (1.57 g).

The conversion of 347J to 347 was similar in procedure to those described in the conversion of 284B to 284D and 108D to 108 MS(LCMS) calcd. 681.94, found (MH⁺) 683.2.

Table 3 lists some of the inventive compounds and their HCV serine protease inhibitory activity ranges, as determined by the assay described later. The activity is shown as Ki* ranges (nanoMolar), which are: A=<75 nM; B=75-250 nM; and C=>250 nM.

TABLE 3
| | Sulfide Compounds | | |
|---|---|---|---|
| Prep. Ex. | COMPOUND | Select Mass Spectra Data | Ki* range |
| 102 | 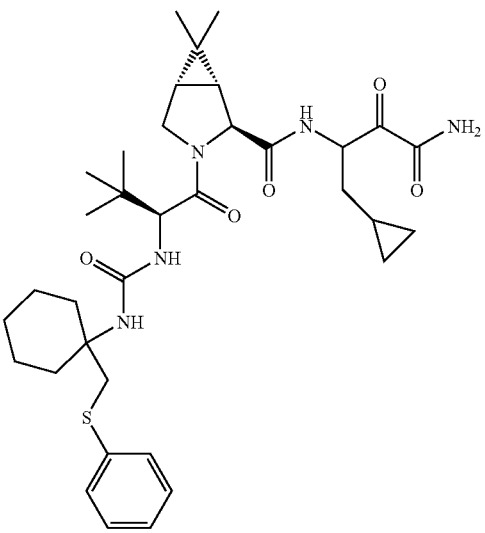 | LCMS; MH+, 654.1 | A |
| 103 | 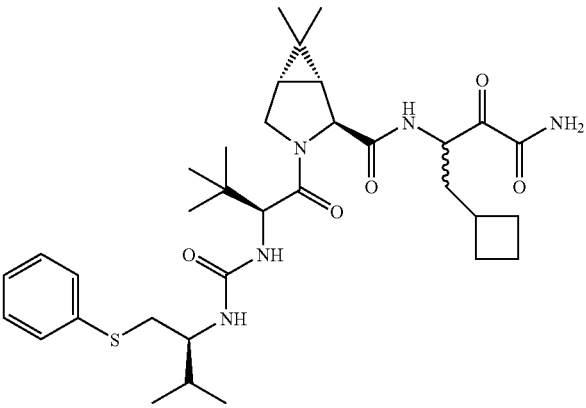 | | B |
| 104 | 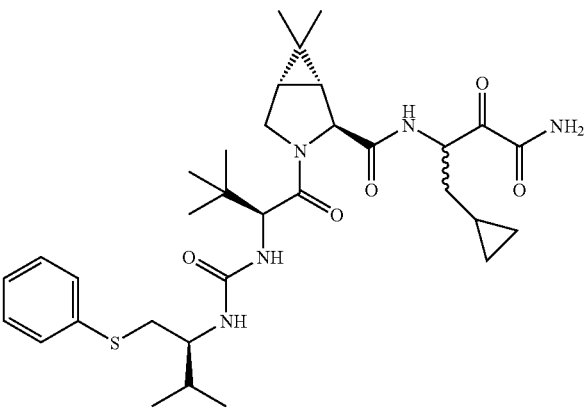 | | A |

TABLE 3-continued

Sulfide Compounds

| Prep. Ex. | COMPOUND | Select Mass Spectra Data | Ki* range |
|---|---|---|---|
| 105 | | | C |
| 106 | | | B |
| 107 | | FABMS, (M + TG)+, 760.5. TG = thioglycerol | A |

TABLE 3-continued
Sulfide Compounds
| Prep. Ex. | COMPOUND | Select Mass Spectra Data | Ki* range |
|---|---|---|---|
| 108 | 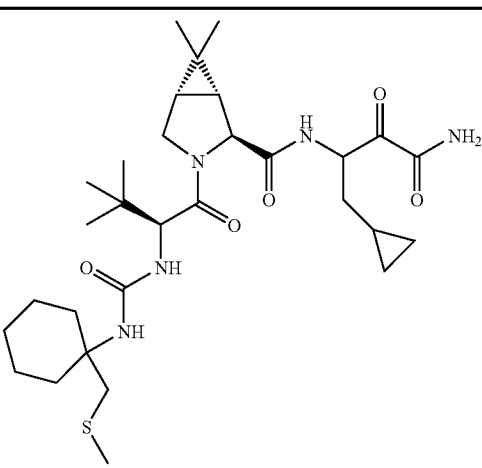 | | A |
| 109 | 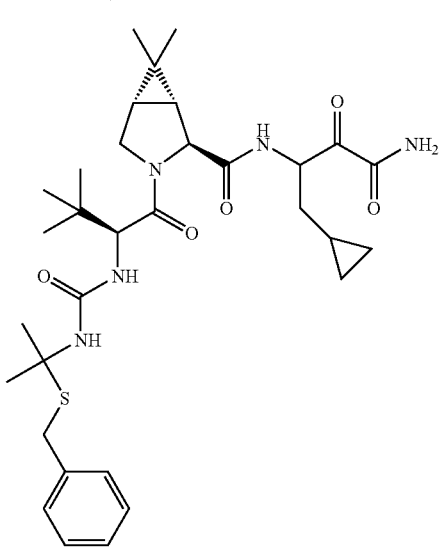 | | A |
| 110 | 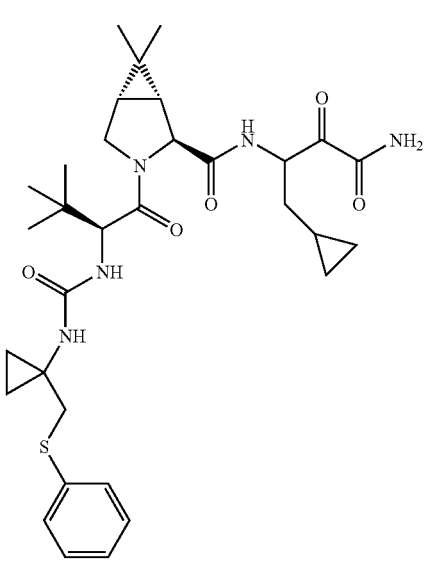 | | A |

TABLE 3-continued
Sulfide Compounds
| Prep. Ex. | COMPOUND | Select Mass Spectra Data | Ki* range |
|---|---|---|---|
| 111 | 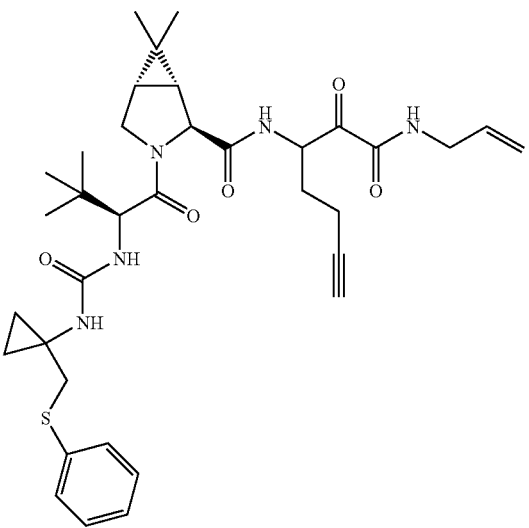 | FABMS: (MH)+, 650.3. | B |
| 112 | 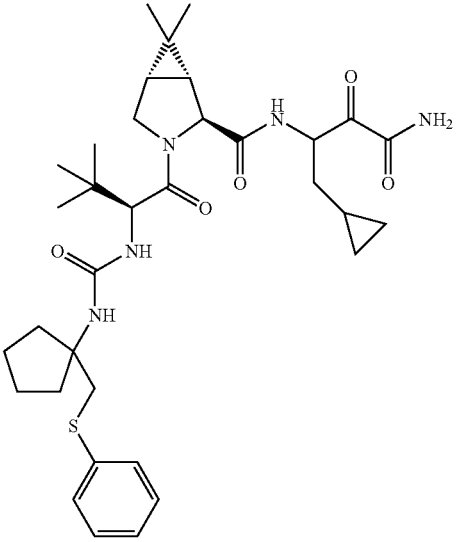 | | A |

TABLE 3-continued
Sulfide Compounds
| Prep. Ex. | COMPOUND | Select Mass Spectra Data | Ki* range |
|---|---|---|---|
| 113 | 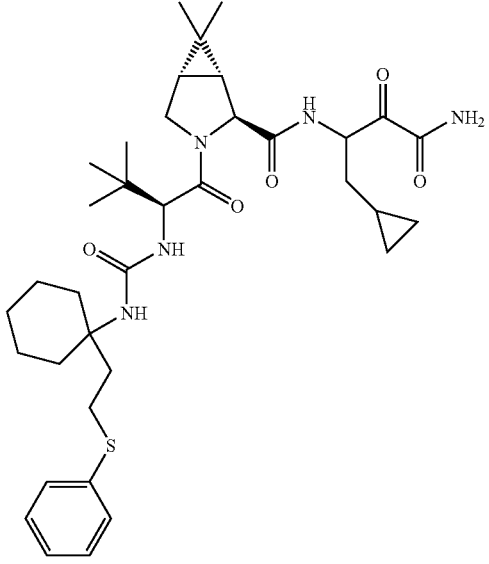 | FABMS: (MH)+, 668.3 | A |
| 114 | 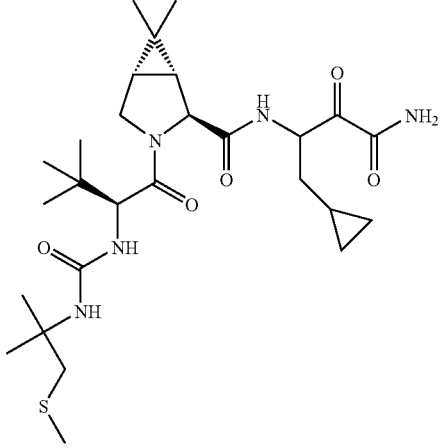 | | A |

TABLE 3-continued
Sulfide Compounds
| Prep. Ex. | COMPOUND | Select Mass Spectra Data | Ki* range |
|---|---|---|---|
| 115 | 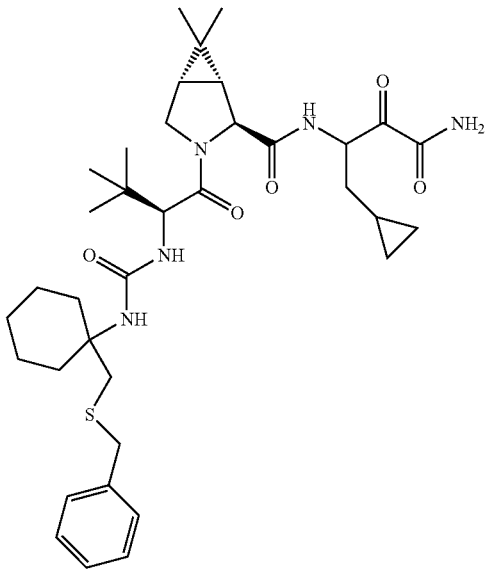 | | A |
| 116 | 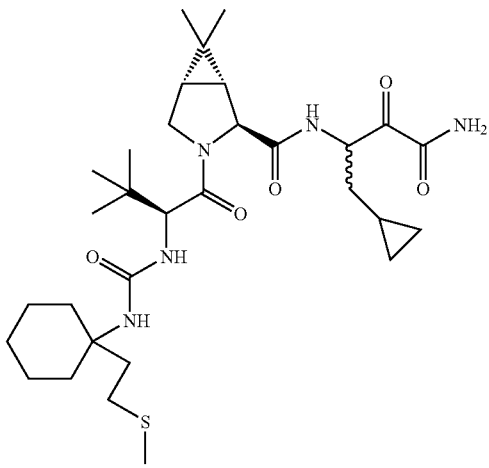 | LCMS; MH+, 606.1. | A |
| 117 | 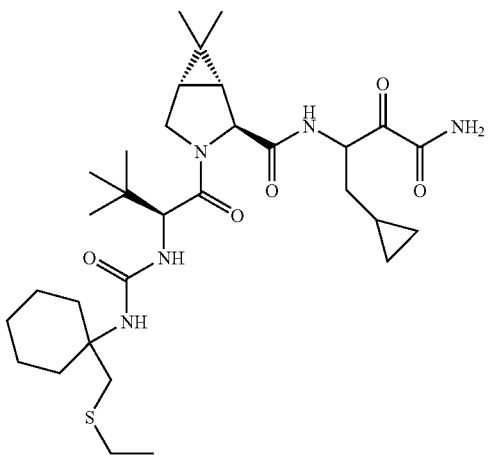 | | A |

TABLE 3-continued
Sulfide Compounds
| Prep. Ex. | COMPOUND | Select Mass Spectra Data | Ki* range |
|---|---|---|---|
| 118 | 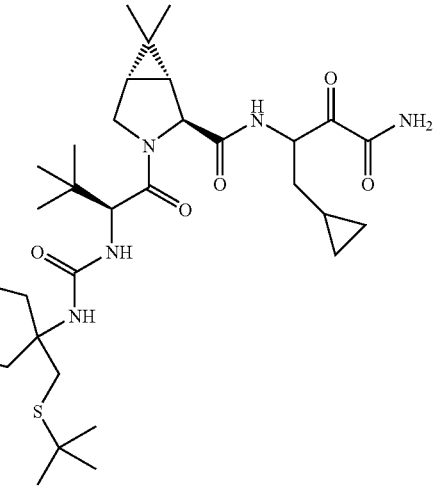 | | A |
| 119 | 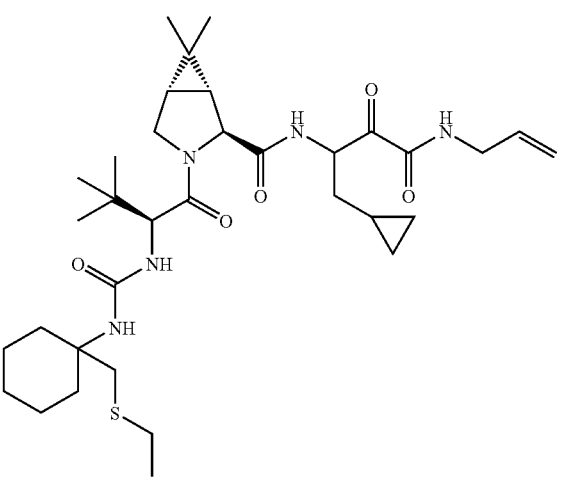 | | B |
| 120 | 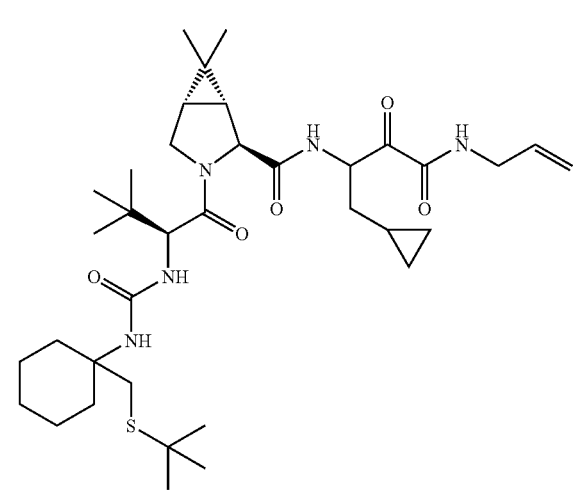 | | C |

TABLE 3-continued
Sulfide Compounds
| Prep. Ex. | COMPOUND | Select Mass Spectra Data | Ki* range |
|---|---|---|---|
| 121 | 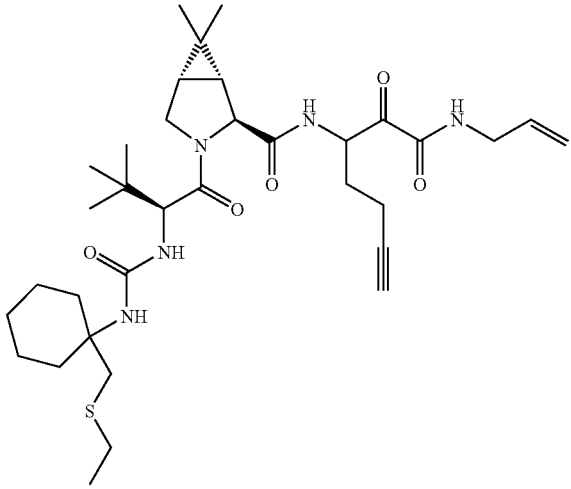 | FABMS; MH+, 644.2 | A |
| 122 | 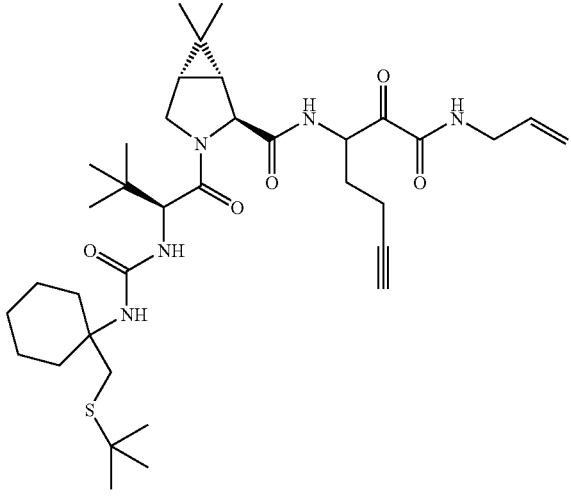 | FAMBS; MH+, 672.5 | A |
| 123 | 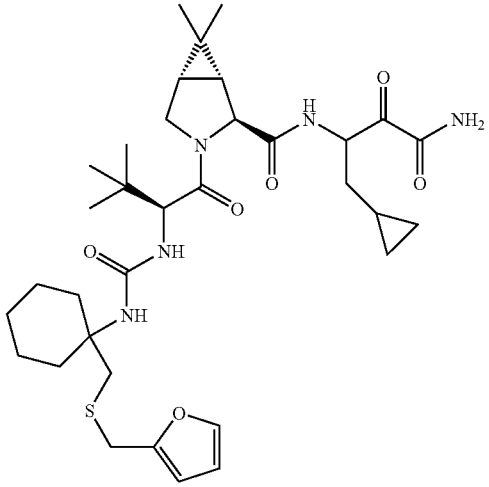 | | A |

TABLE 3-continued
Sulfide Compounds
| Prep. Ex. | COMPOUND | Select Mass Spectra Data | Ki* range |
|---|---|---|---|
| 124 | 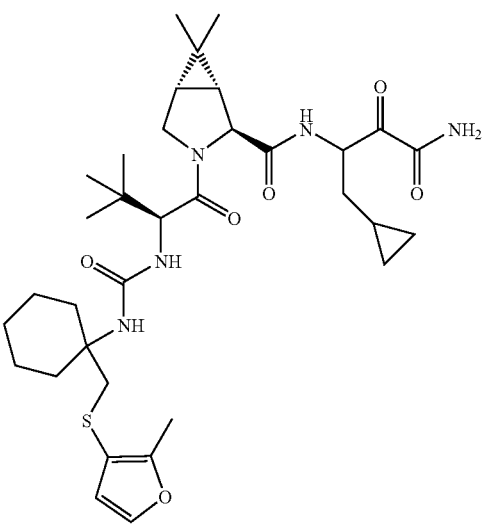 | | B |
| 125 | 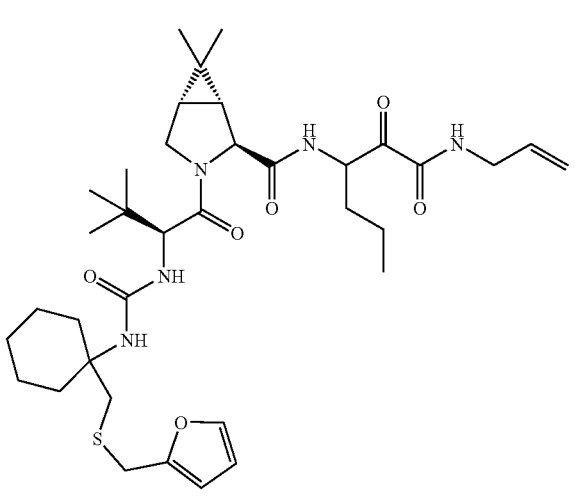 | | B |
| 126 | 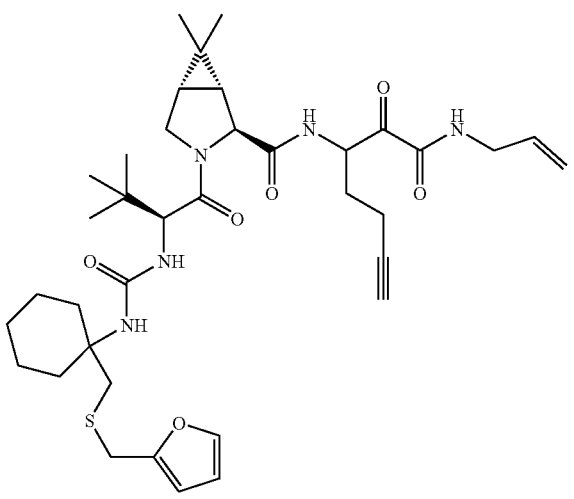 | | A |

TABLE 3-continued
Sulfide Compounds
| Prep. Ex. | COMPOUND | Select Mass Spectra Data | Ki* range |
|---|---|---|---|
| 127 | 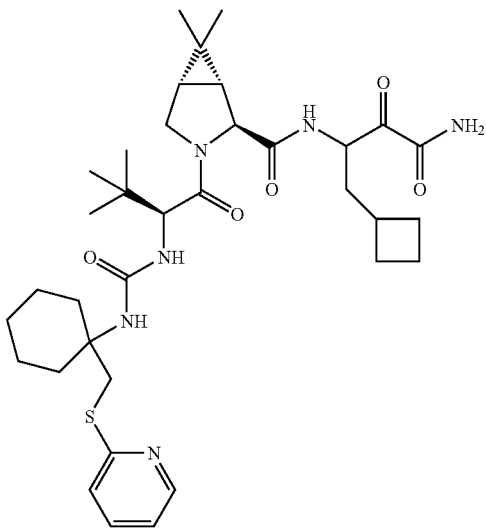 | | A |
| 128 | 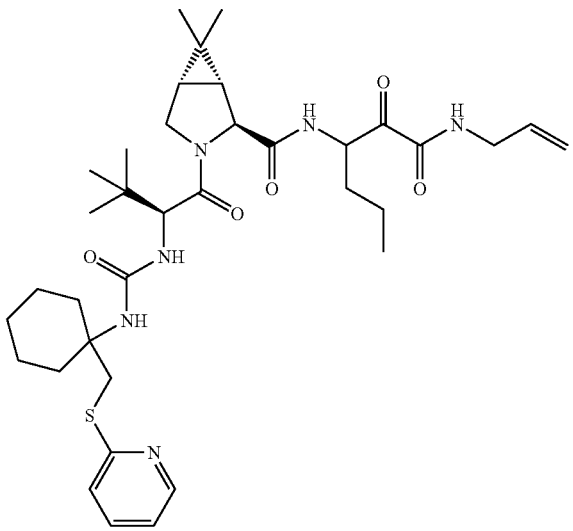 | | B |

US 8,067,379 B2
TABLE 3-continued
Sulfide Compounds
| Prep. Ex. | COMPOUND | Select Mass Spectra Data | Ki* range |
|---|---|---|---|
| 129 | 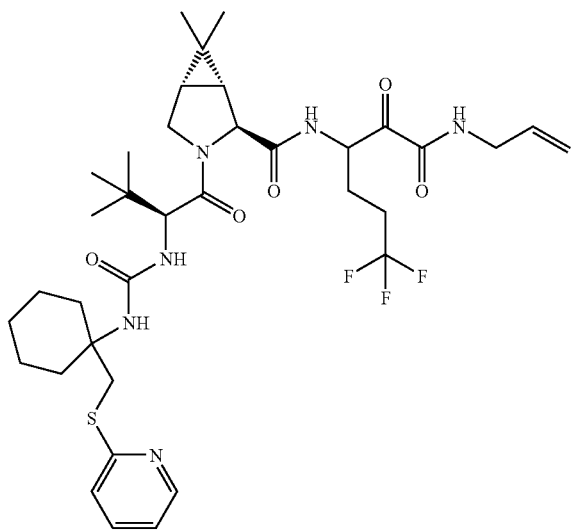 | | C |
| 130 | 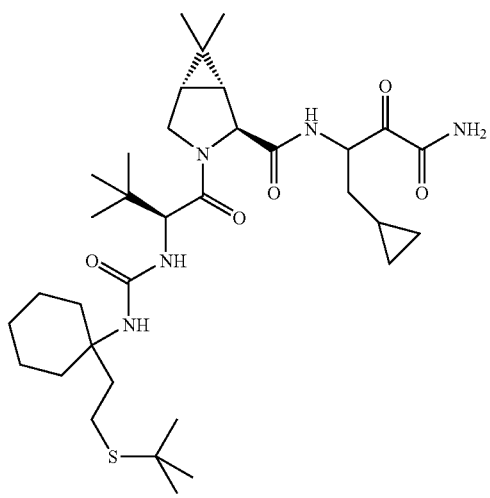 | | B |

TABLE 3-continued

Sulfide Compounds

| Prep. Ex. | COMPOUND | Select Mass Spectra Data | Ki* range |
|---|---|---|---|
| 131 | (structure) | | B |

[Ki* ranges are: A = <75 nM;
B = 75-250 nM; C = >250 nM]

Sulfoxide Compounds

| Prep. Ex. | COMPOUND | Select Mass Spectral Data | Ki* range |
|---|---|---|---|
| 132 | (structure) | FABMS; MH+, 688.5. | A |

-continued

| | Sulfoxide Compounds | | |
|---|---|---|---|
| Prep. Ex. | COMPOUND | Select Mass Spectral Data | Ki* range |
| 133 | | | A |
| 134 | | | A |
| 135 | | | A |

-continued

| | Sulfoxide Compounds | | |
|---|---|---|---|
| Prep. Ex. | COMPOUND | Select Mass Spectral Data | Ki* range |
| 136 | | | A |
| 137 | | | A |
| 138 | | | B |

Sulfoxide Compounds
| Prep. Ex. | COMPOUND | Select Mass Spectral Data | Ki* range |
|---|---|---|---|
| 139 | | | A |
[Ki* ranges are: A = >75 nM;
B = 75-250 nM; C = >250 nM]
Sulfone Compounds
| Prep. Ex. | COMPOUND | Select Mass Spectral Data | Ki* range |
|---|---|---|---|
| 142 | 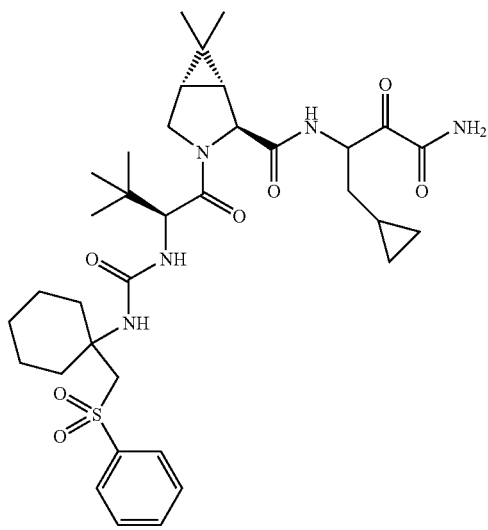 | LCMS: MH+, 686.1. | A |

| | Sulfone Compounds | |
|---|---|---|
| 143 | 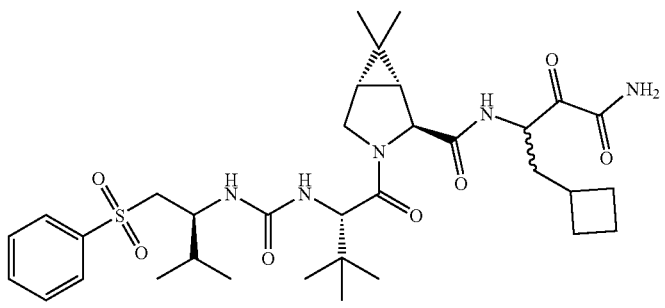 | A |
| 144 | 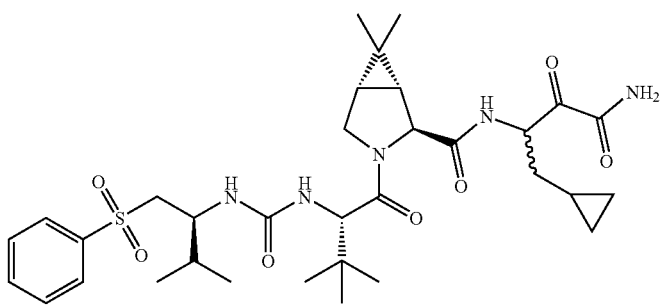 | A |
| 145 | 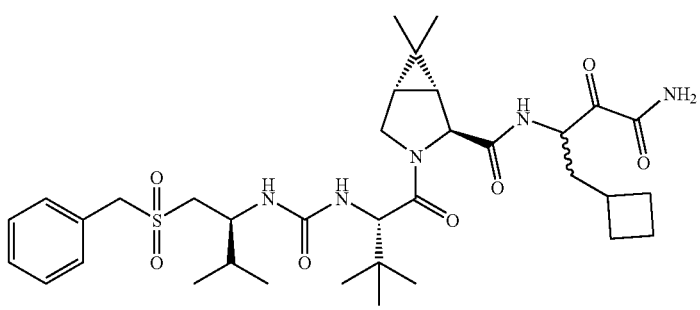 | A |
| 146 | 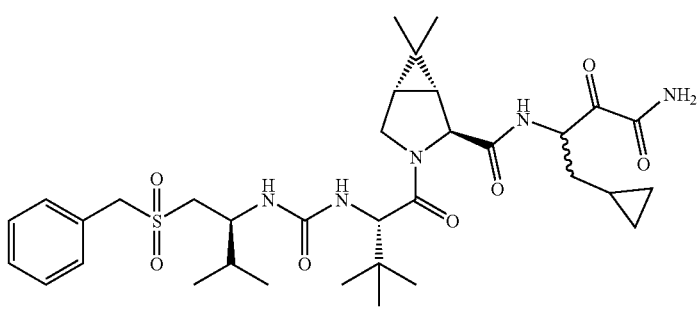 | A |
| 147 | 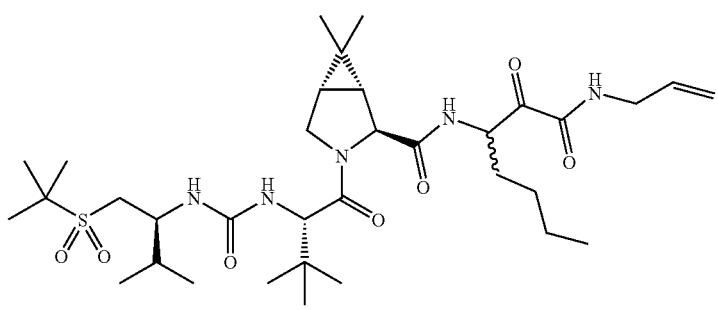 | B |

US 8,067,379 B2
209                                                                                  210
-continued
| Sulfone Compounds |
|---|
148 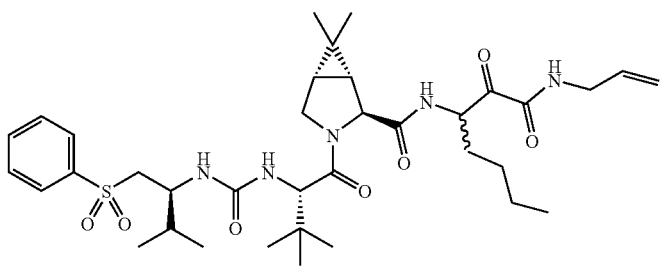 B
149 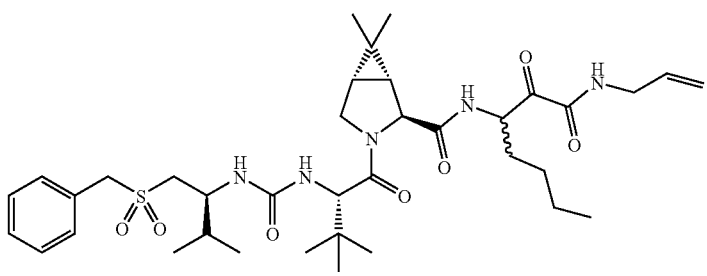 B
150 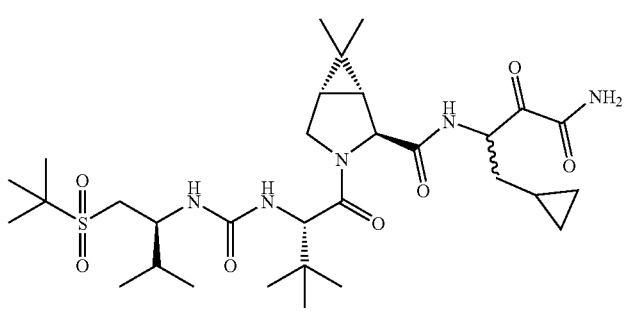 A
151 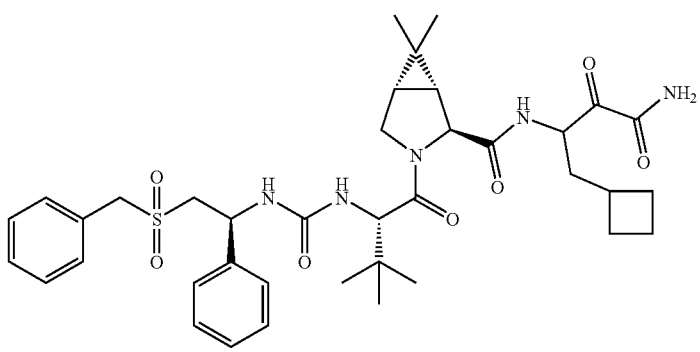 B
152 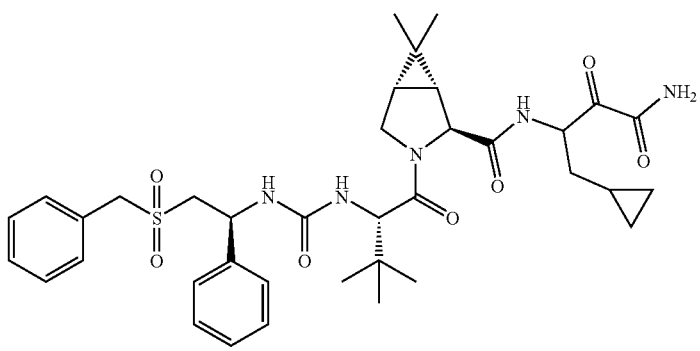 B

Sulfone Compounds
| | | |
|---|---|---|
| 153 | 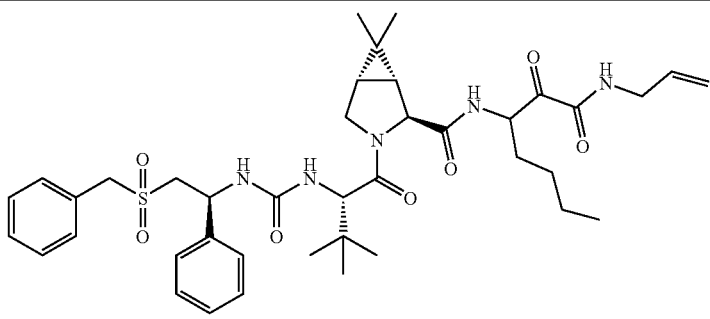 | C |
| 154 | 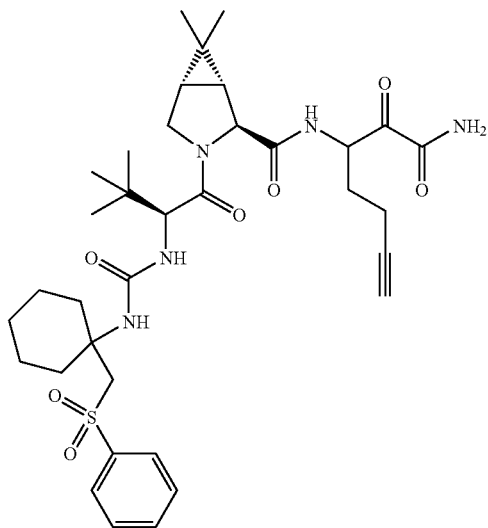 | FABMS; MH+, 684.2.  A |
| 155 | 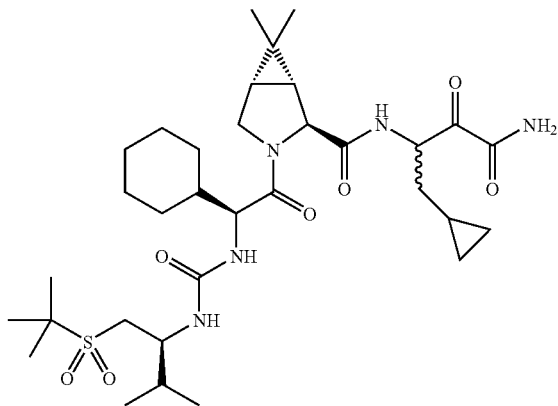 | A |

| Sulfone Compounds | |
|---|---|
| 156 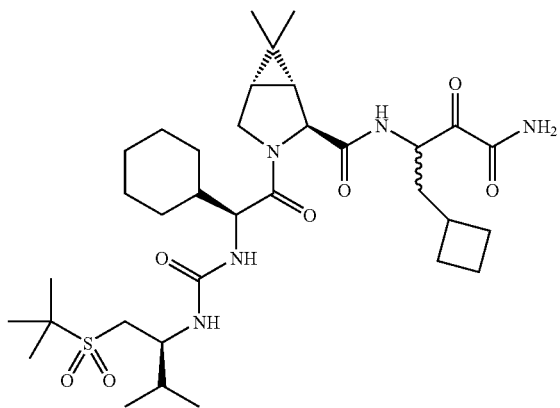 | A |
| 157 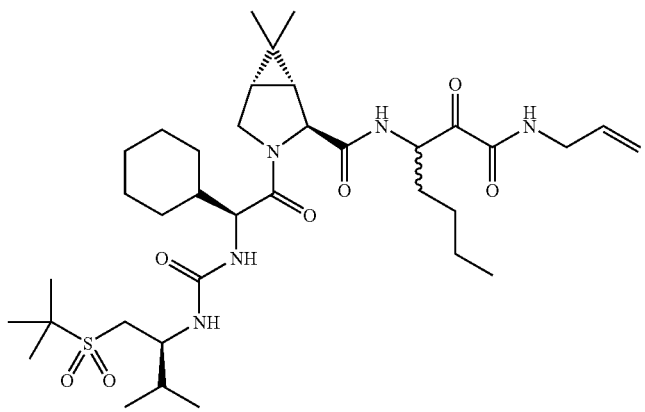 | A |
| 158 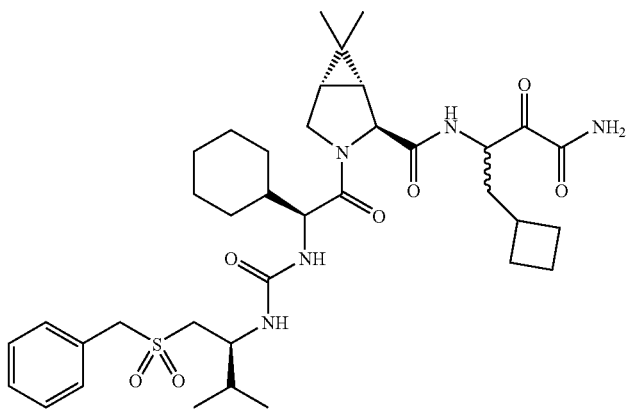 | A |

-continued
Sulfone Compounds
159 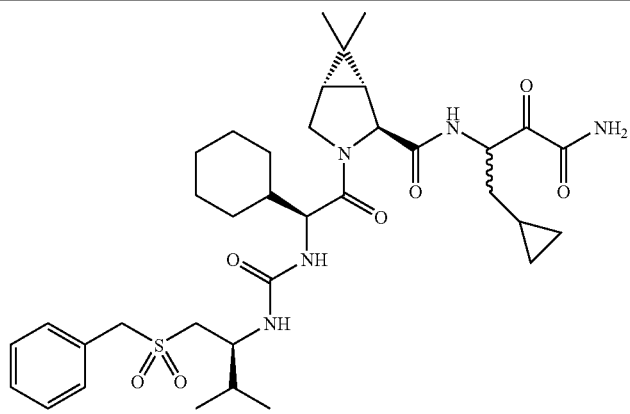 A
160 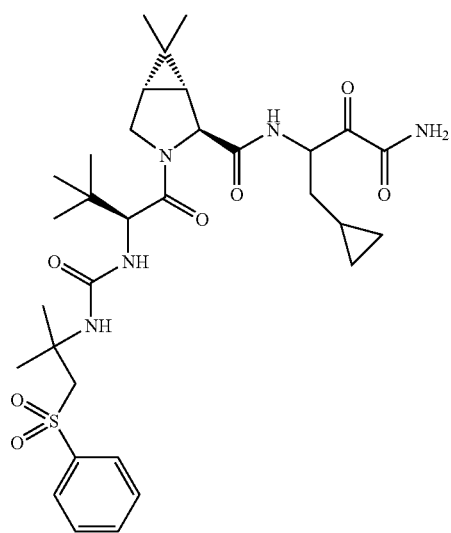 A
161 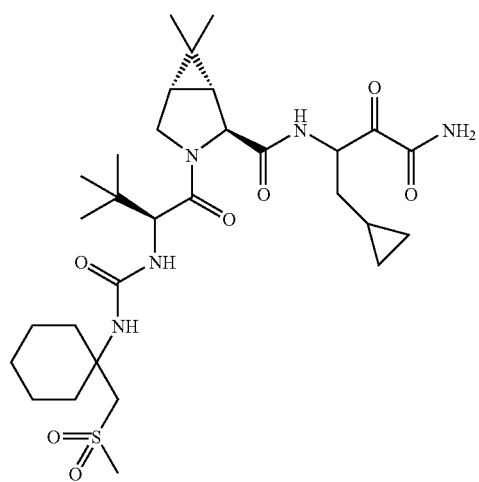 A US 8,067,379 B2
-continued
Sulfone Compounds
162 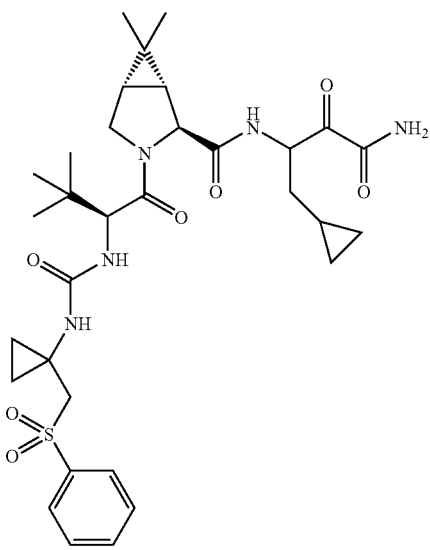 A
163 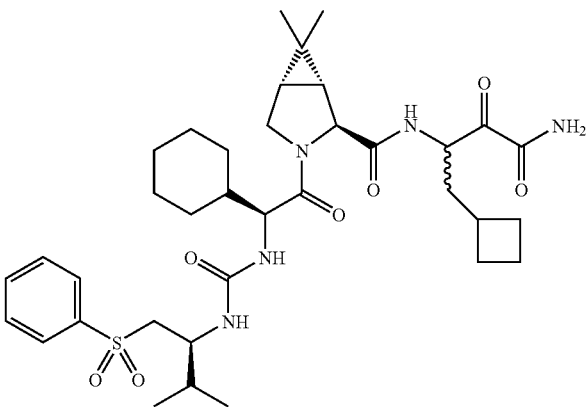 A
164 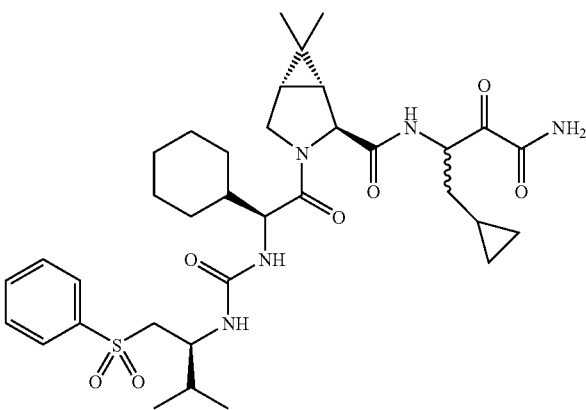 A

Sulfone Compounds
| | | |
|---|---|---|
| 165 | 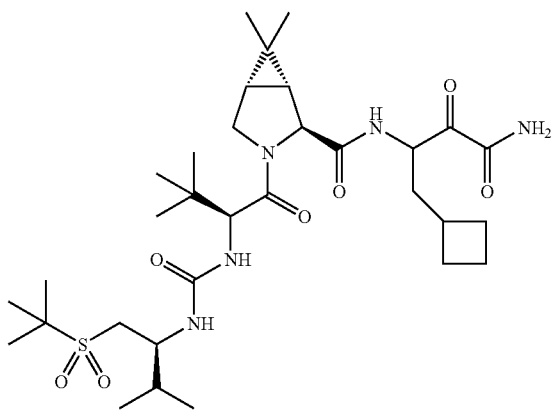 | A |
| 166 | 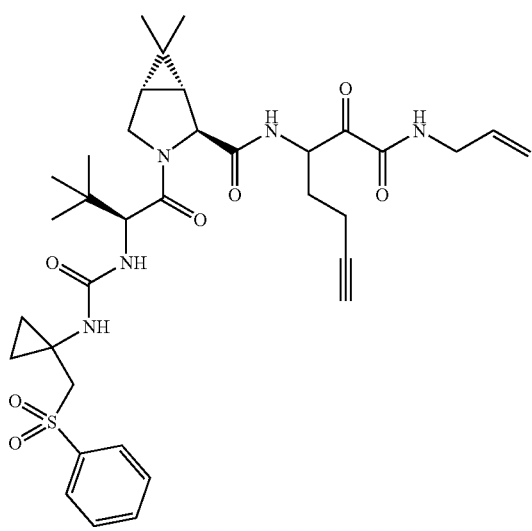 | FAMBS; MH+, 682.3. B |
| 167 | 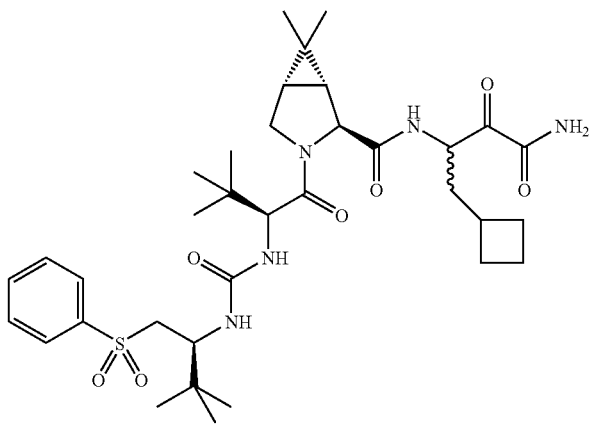 | A |

| Sulfone Compounds | | |
|---|---|---|
| 168 | 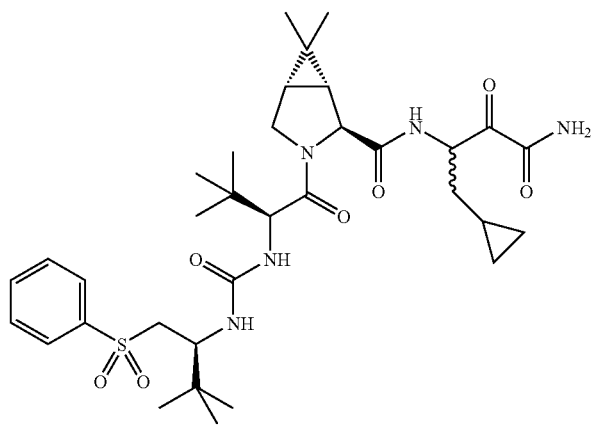 | A |
| 169 | 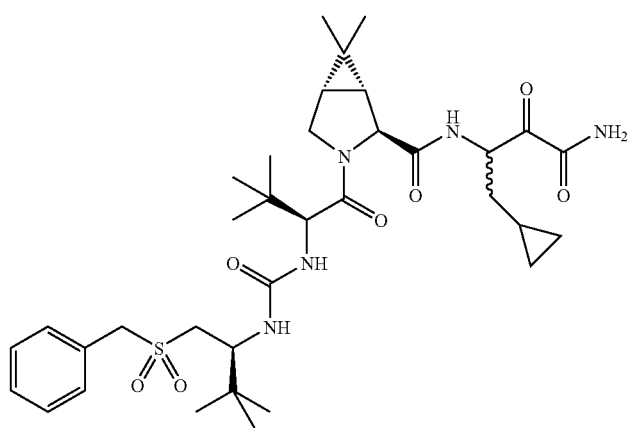 | A |
| 170 | 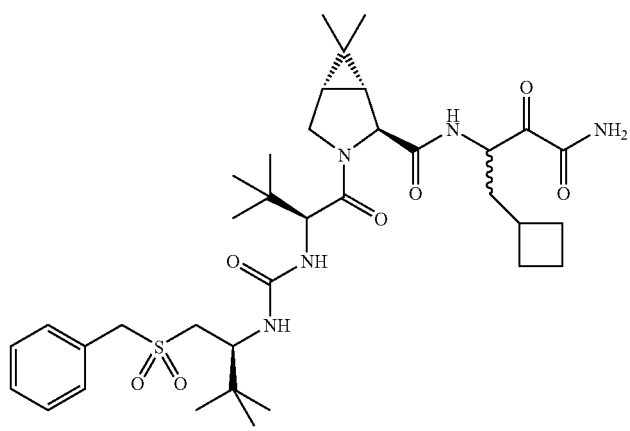 | A |

| | Sulfone Compounds | |
|---|---|---|
| 171 | 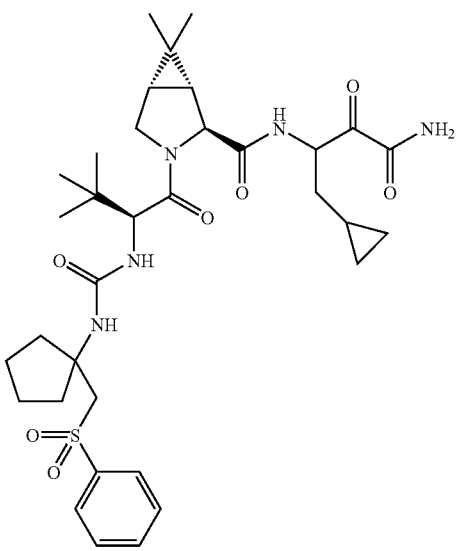 | A |
| 172 |  | LCMS; MH+, 738.2. B |
| 173 | 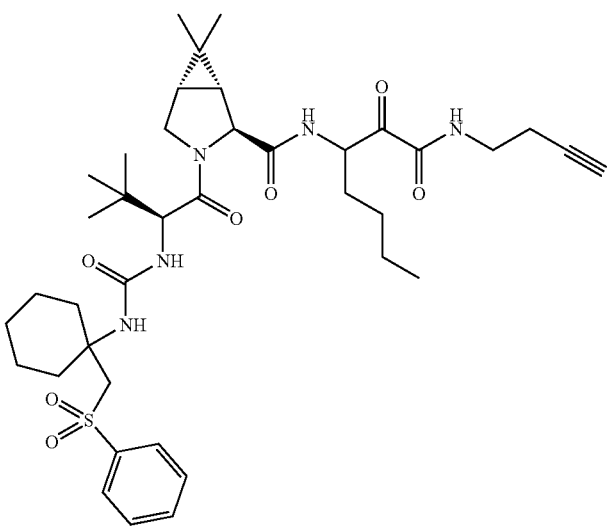 | A |

US 8,067,379 B2
225 226
-continued
Sulfone Compounds
| | | |
|---|---|---|
| 174 | 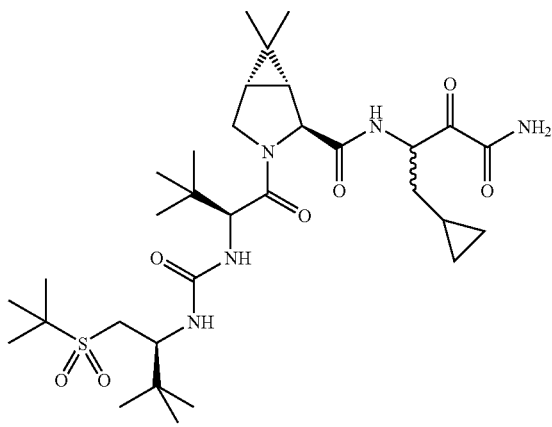 | A |
| 175 | 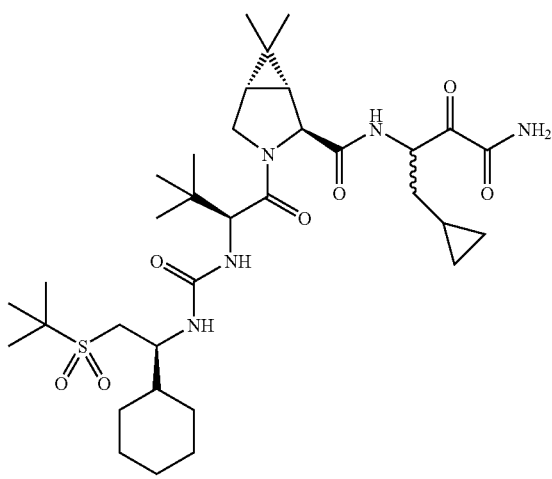 | A |
| 176 | 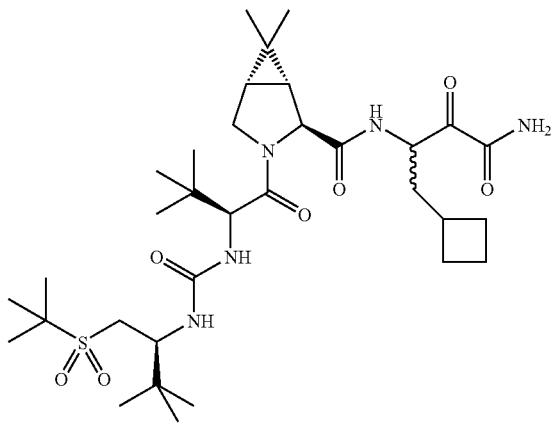 | A |

| | Sulfone Compounds | |
|---|---|---|
| 177 | 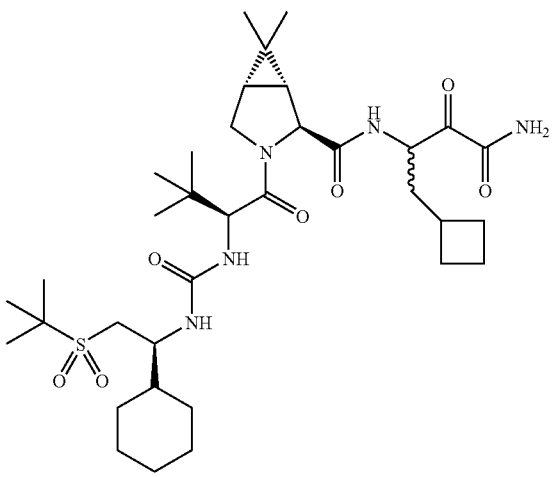 | A |
| 178 | 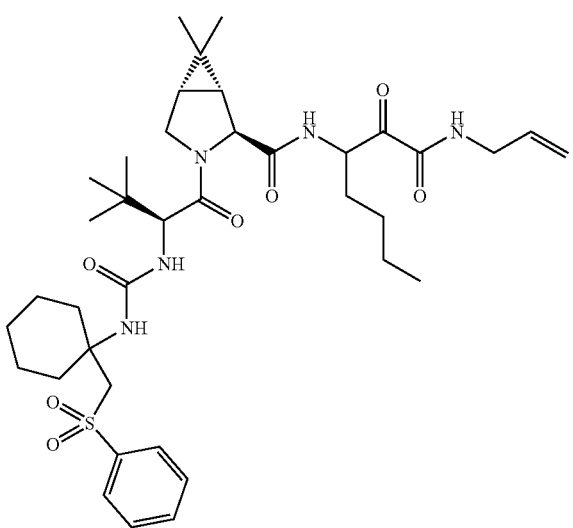 | LCMS; MH+, 714.1. A |
| 179 | 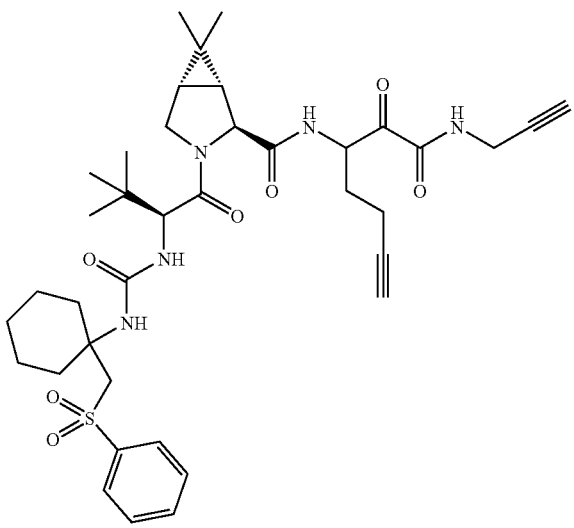 | A |

| | Sulfone Compounds | | |
|---|---|---|---|
| 180 | 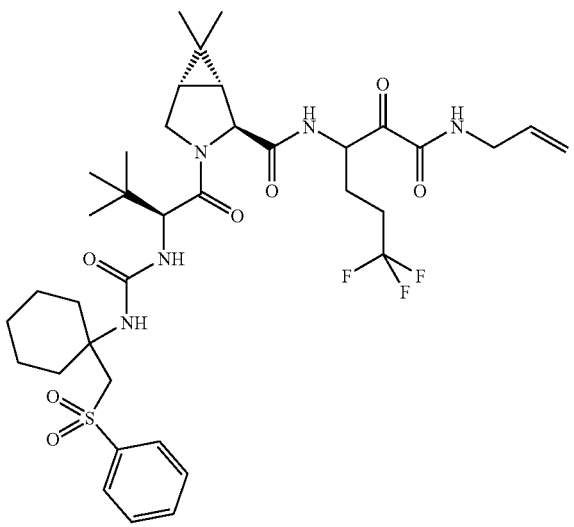 | | A |
| 181 | 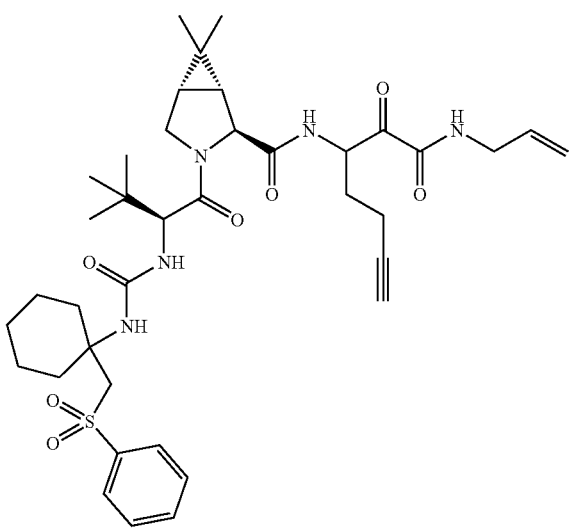 | FABMS; MH+, 724.6. | A |
| 182 | 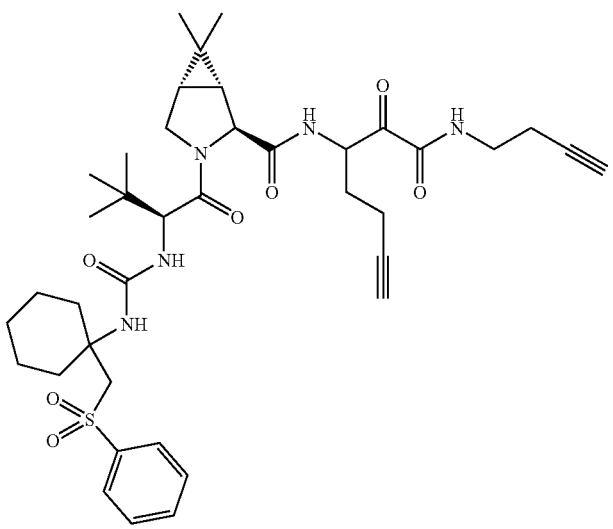 | FAMBS; MH+, 736.5. | A |

231
232
-continued
| Sulfone Compounds | | |
|---|---|---|
| 183 | 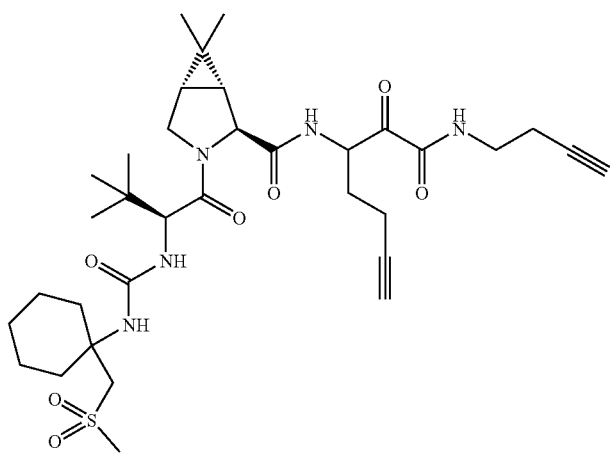 | A |
| 184 | 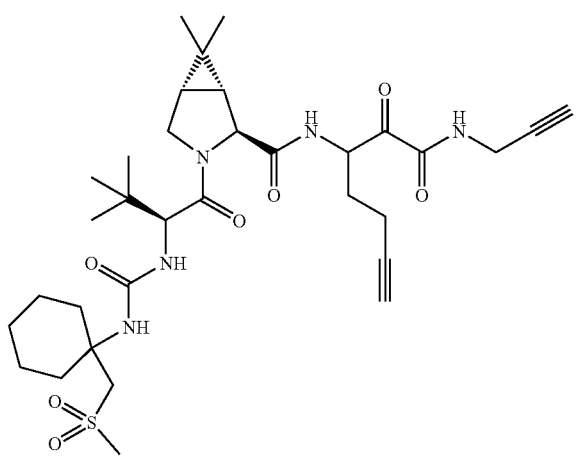 | A |
| 185 | 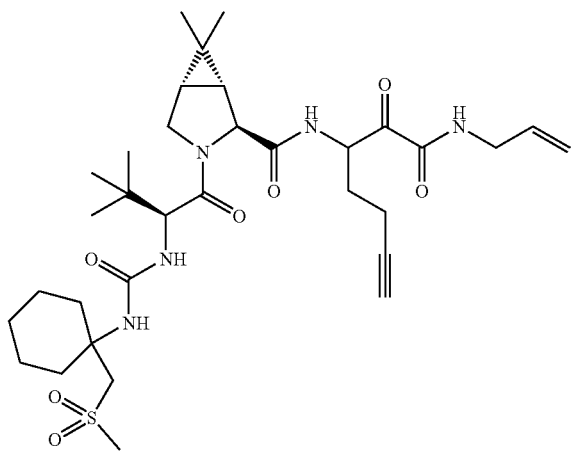 | FAMBS; MH+, 662.5.    A |

| | Sulfone Compounds | | |
|---|---|---|---|
| 186 | 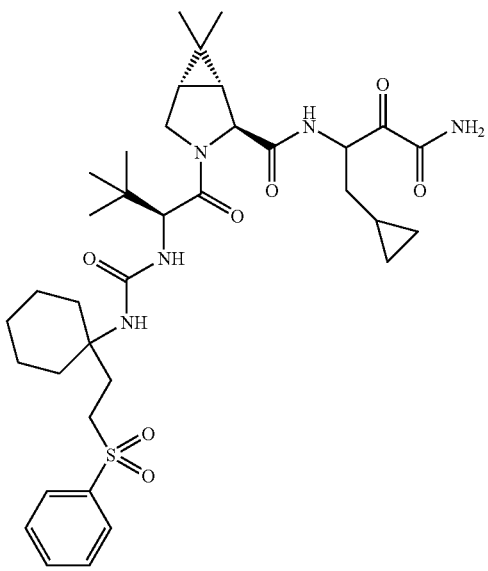 | FAMBS; MH+, 700.3. | A |
| 187 | 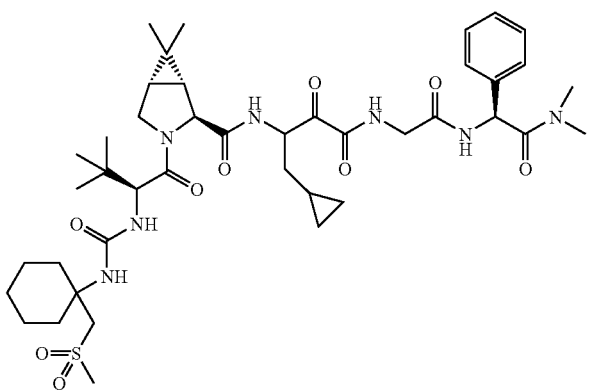 | | A |
| 188 | 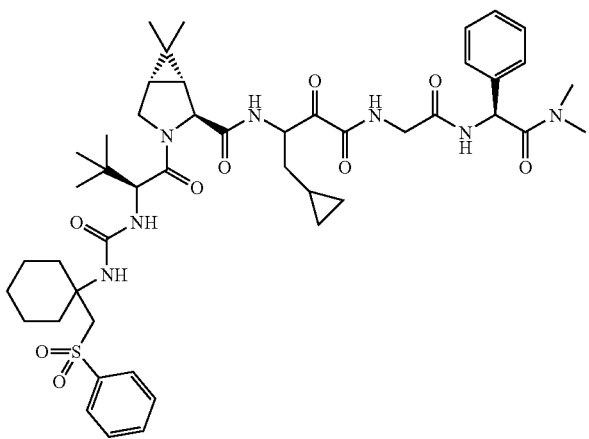 | | A |

Sulfone Compounds
189
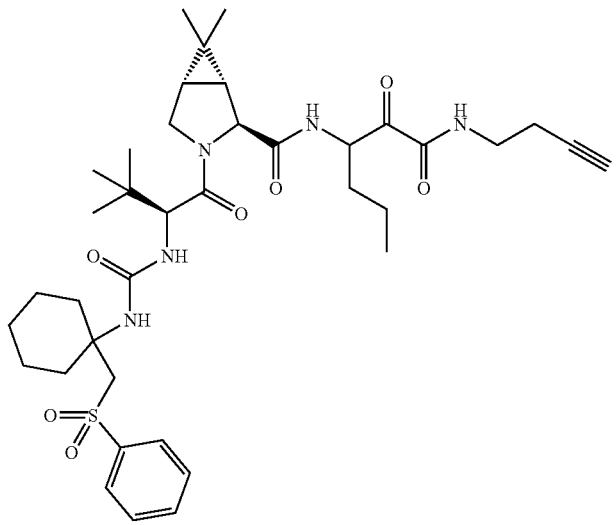
A
190
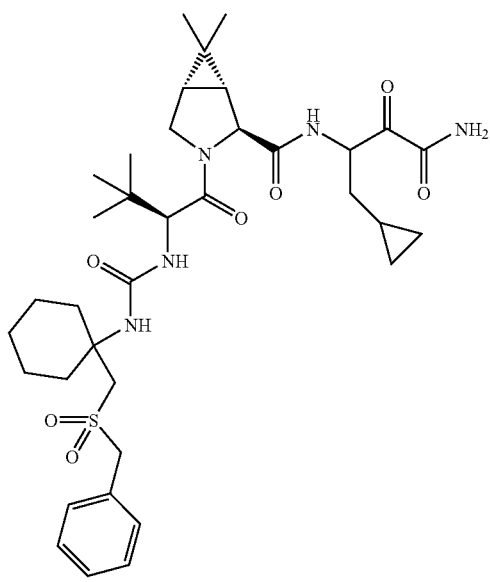
A

US 8,067,379 B2
237                                                                 238
-continued
| | Sulfone Compounds | | |
|---|---|---|---|
| 191 | 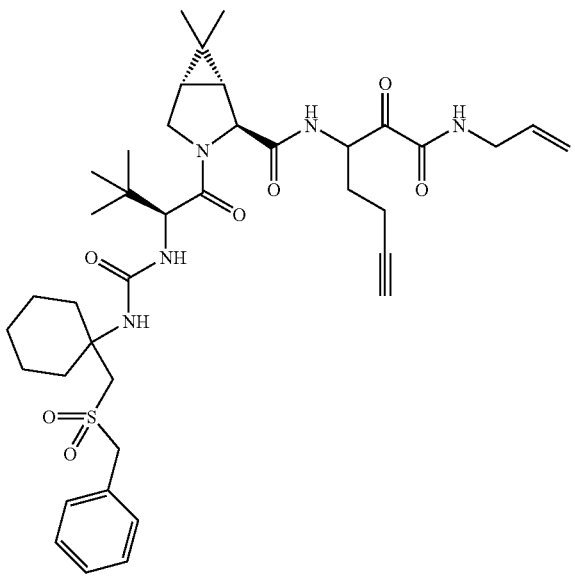 | FAMBS; MH+, 738.4. | A |
| 192 | 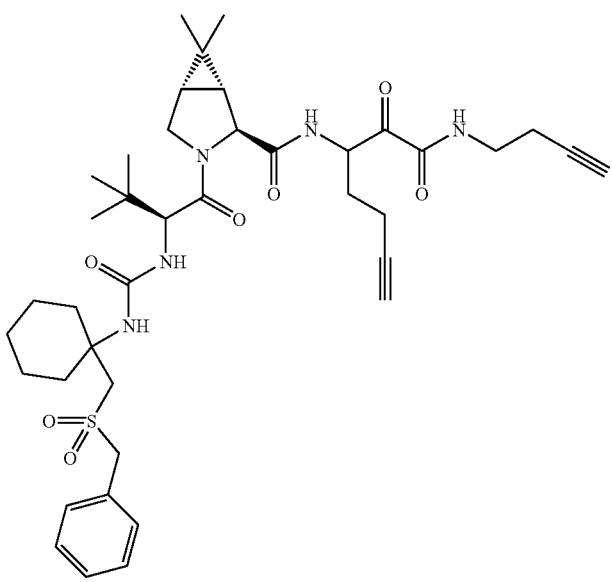 | | A |
| 193 | 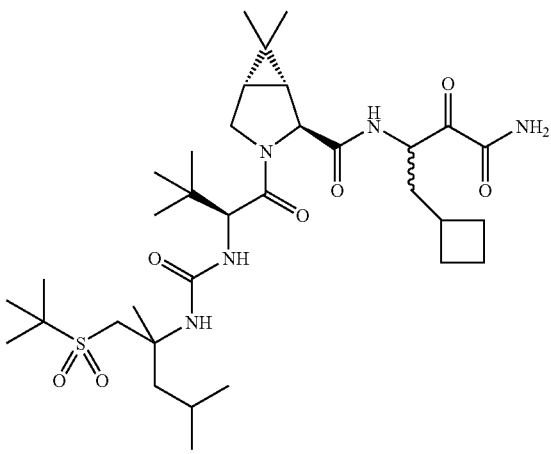 | | A |

| Sulfone Compounds | |
|---|---|
| 194 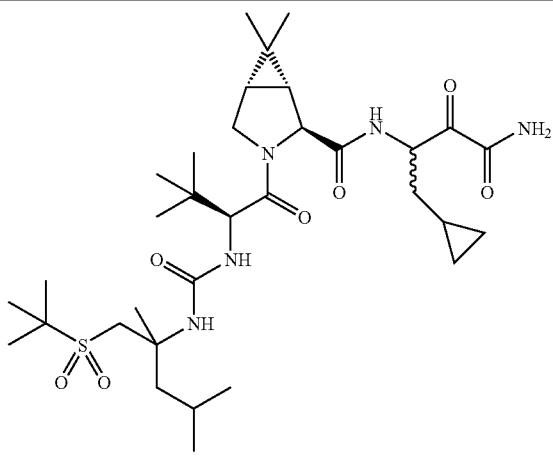 | A |
| 195 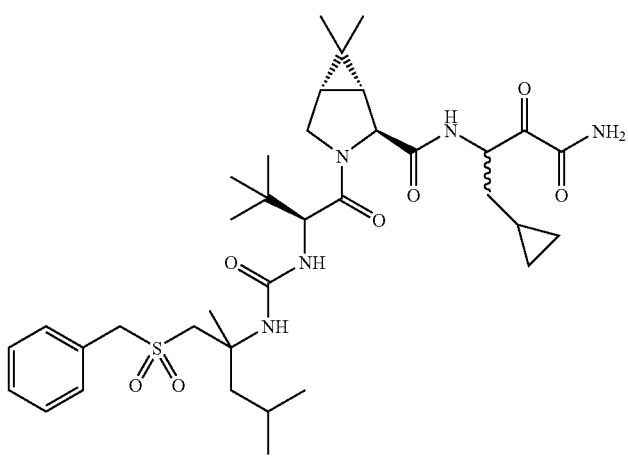 | A |
| 196 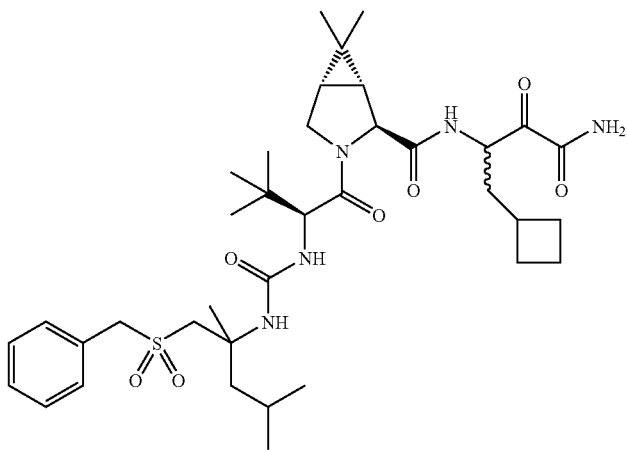 | A |

US 8,067,379 B2
241                                                                                                              242
-continued
| Sulfone Compounds |
| 197 | 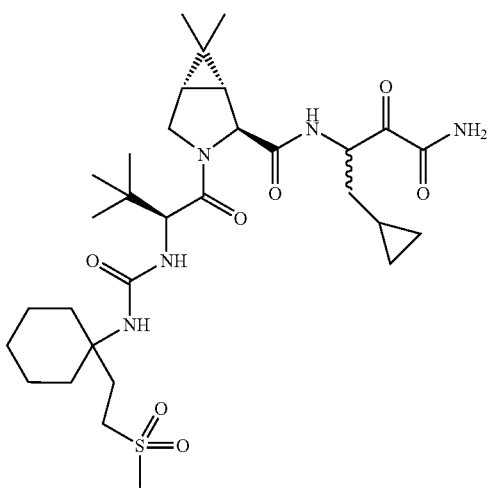 | FAMBS; MH+, 638.3. | A |
| 198 | 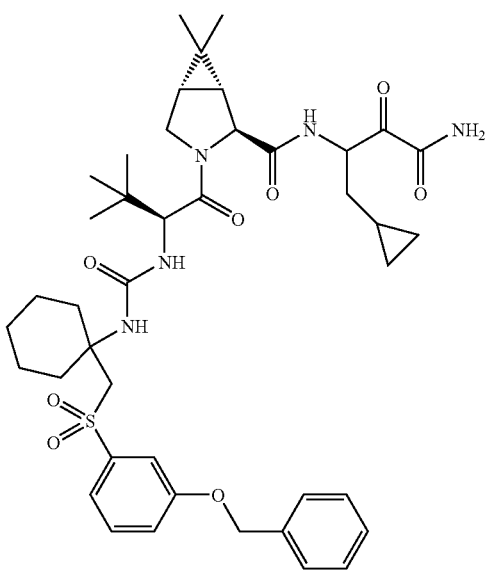 | LCMS; MH+, 792.2. | A |
| 199 | 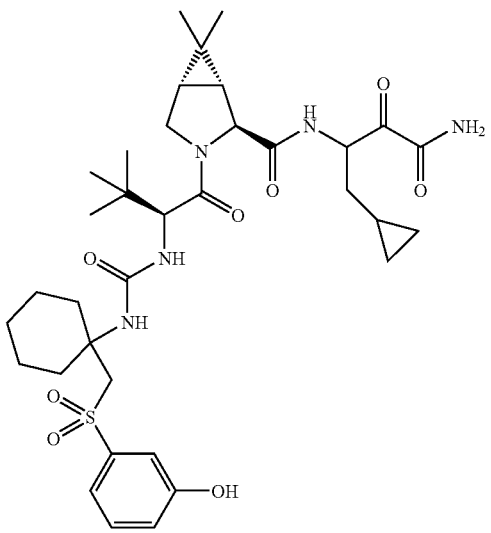 | LCMS: MH+, 702.2. | A |

-continued
Sulfone Compounds
| | | | |
|---|---|---|---|
| 200 | 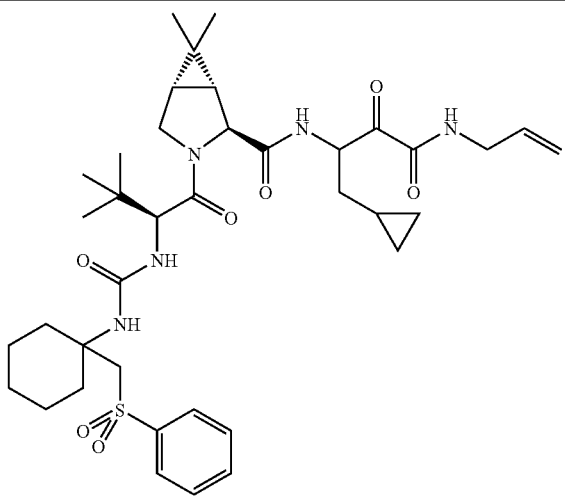 | FAMBS; MH+, 726.5. | A |
| 201 | 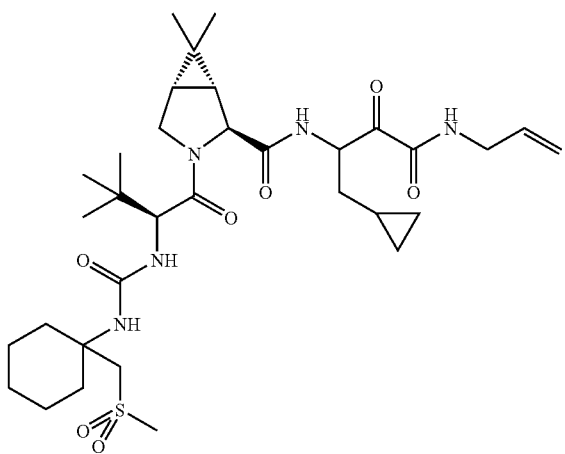 | | A |
| 202 | 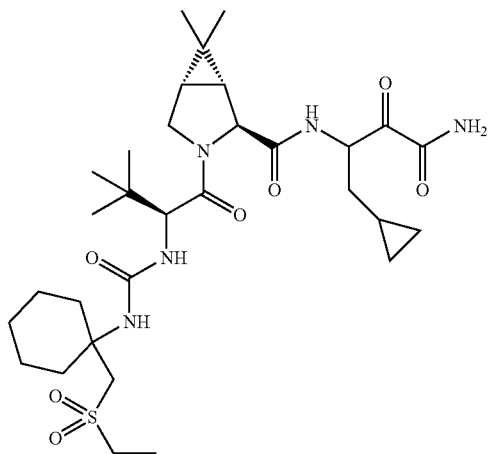 | | A |

Sulfone Compounds
| | | |
|---|---|---|
| 203 | 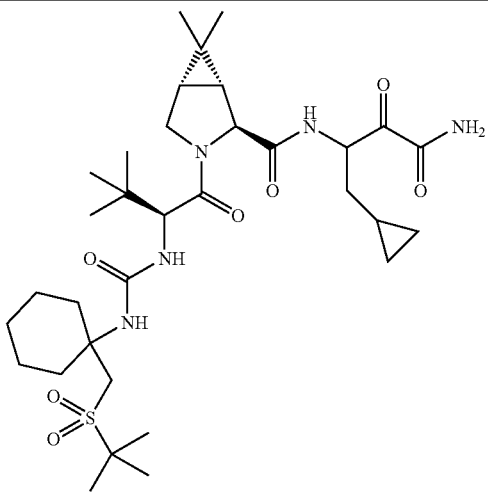 | A |
| 204 | 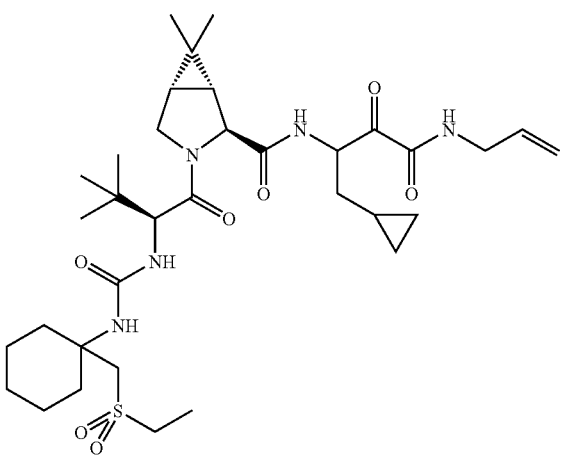 | A |
| 205 | 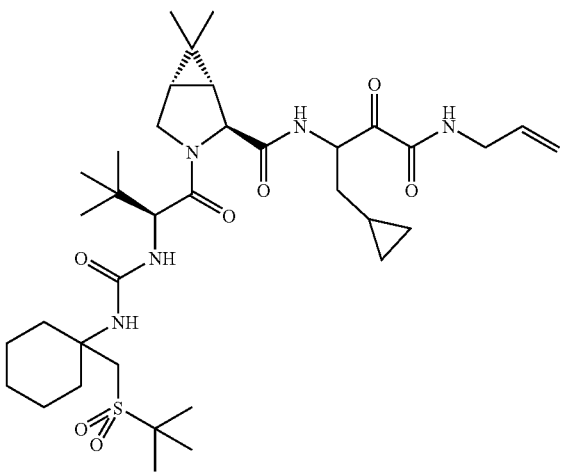 | A |

Sulfone Compounds
| | | | |
|---|---|---|---|
| 206 | 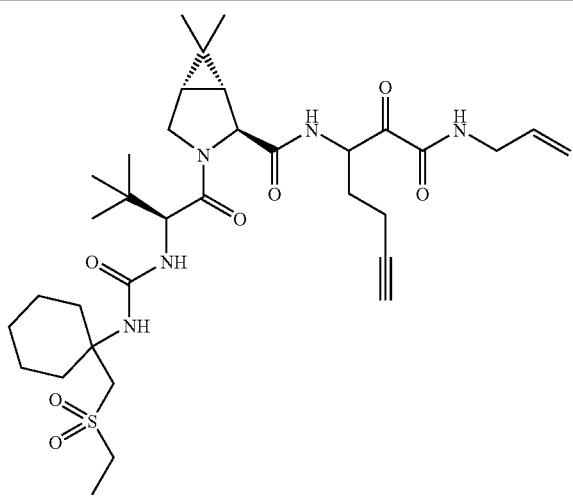 | FAMBS; MH+, 676.7. | A |
| 207 | 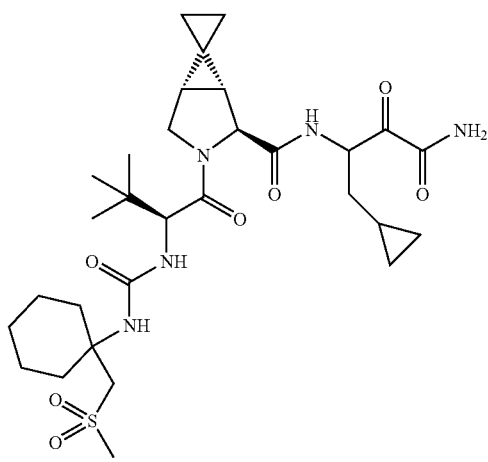 | | A |
| 208 | 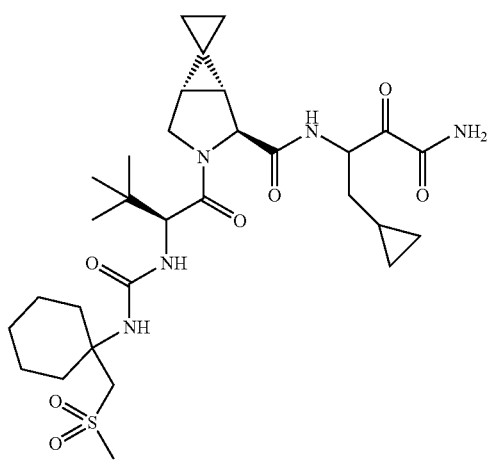 | | A |

| | Sulfone Compounds | | |
|---|---|---|---|
| 209 | 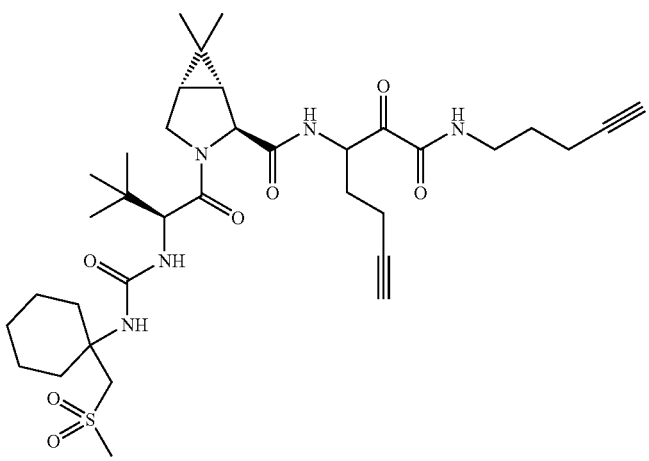 | FAMBS; MH+, 688.3. | A |
| 210 | 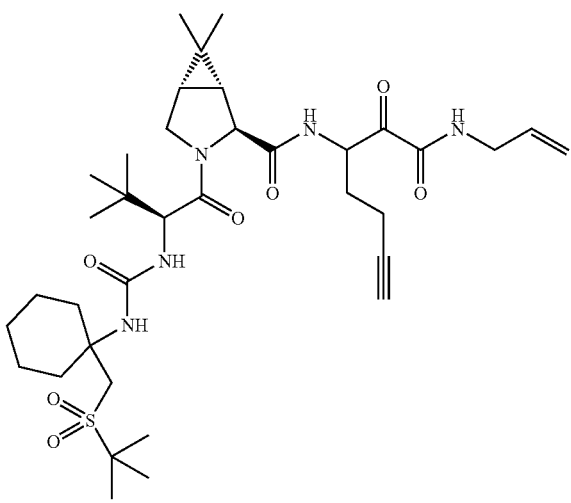 | FAMBS; MH+, 704.4. | A |
| 211 | 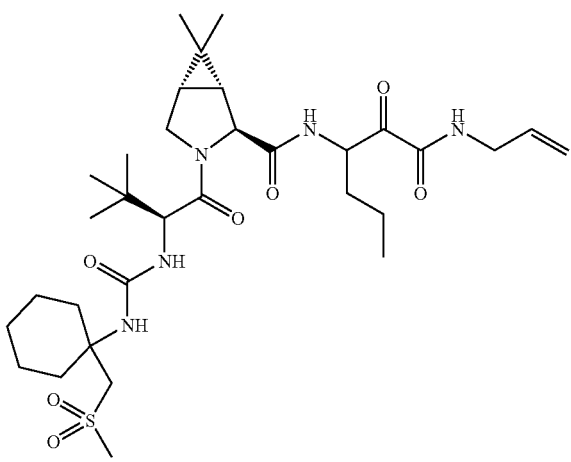 | | A |

Sulfone Compounds
212 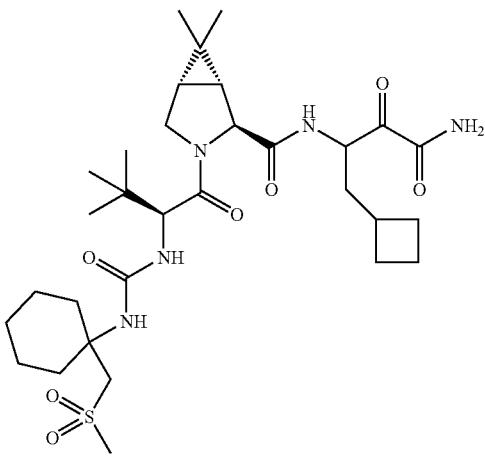 A
213 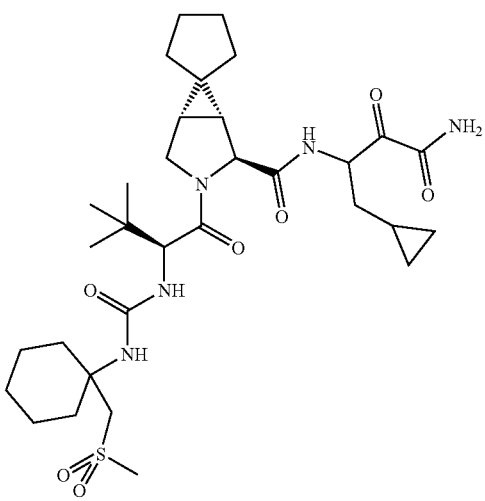 A
214 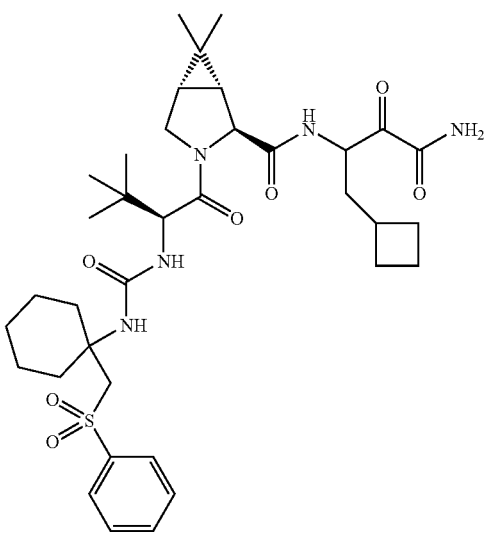 A

| | Sulfone Compounds | | |
|---|---|---|---|
| 215 | 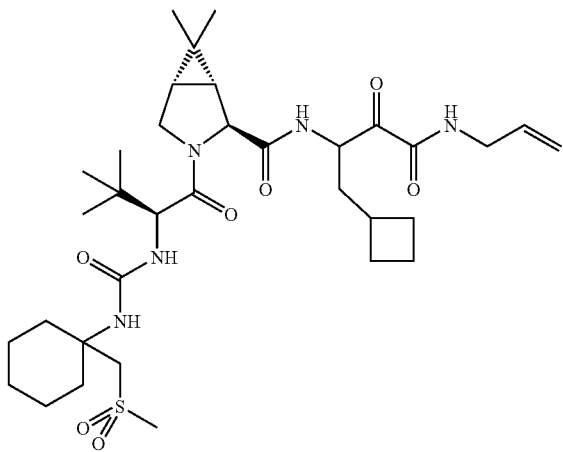 | FAMBS;<br>MH+,<br>678.6. | A |
| 216 | 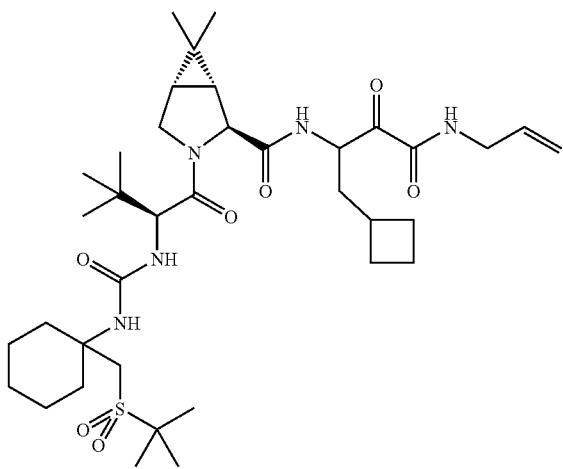 | FAMBS;<br>MH+,<br>720.6. | A |
| 217 | 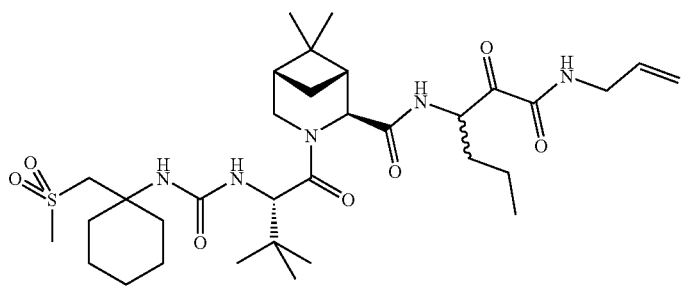 | | A |

| | Sulfone Compounds | | |
|---|---|---|---|
| 218 | 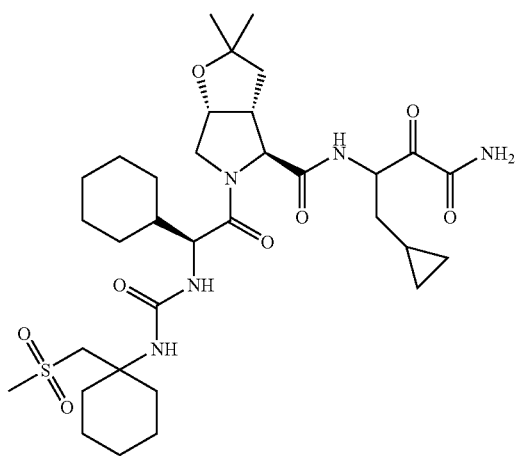 | | A |
| 219 | 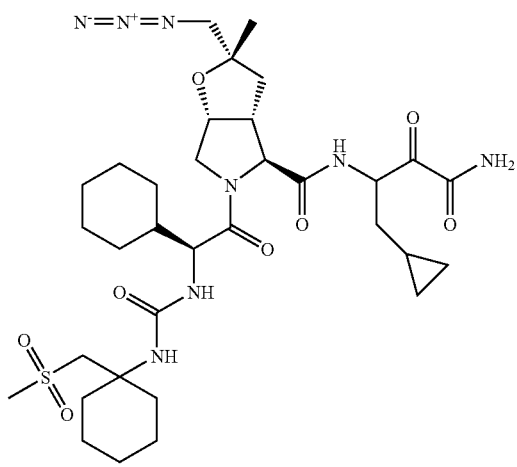 | | A |
| 220 | 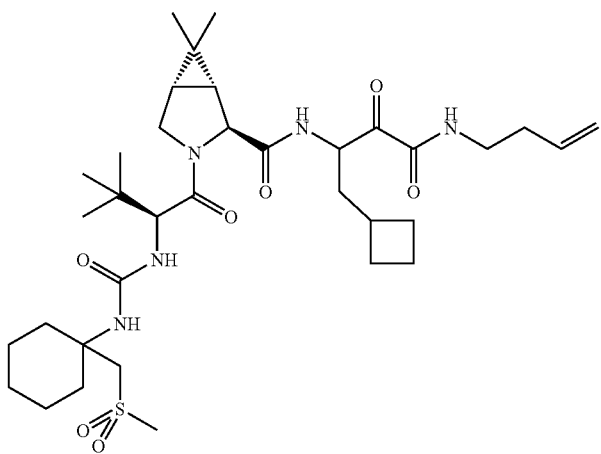 | FAMBS; MH+, 692.5. | A |

US 8,067,379 B2
257                                                                 258
-continued
Sulfone Compounds
221 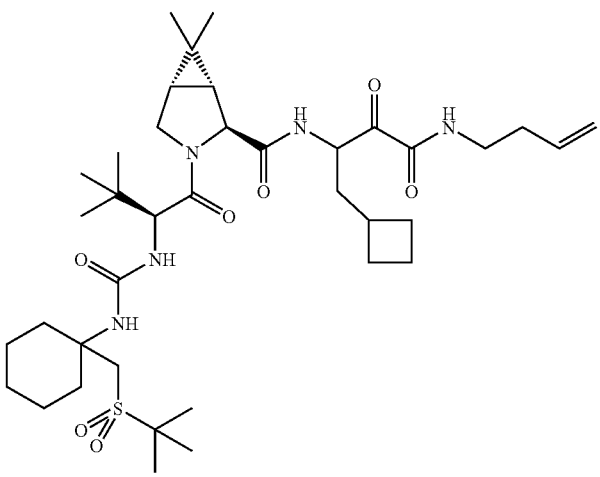 FAMBS; MH+, 734.5.   A
222 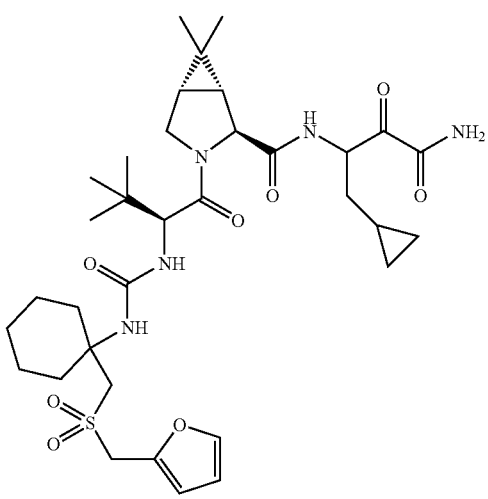   A
223 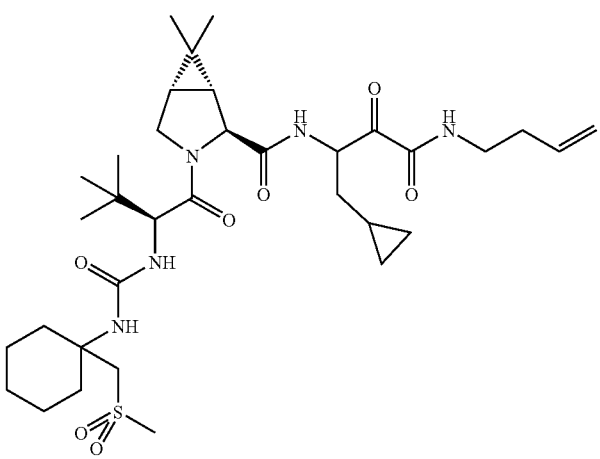 FAMBS; MH+, 678.4.   A US 8,067,379 B2
-continued
Sulfone Compounds
| 224 | 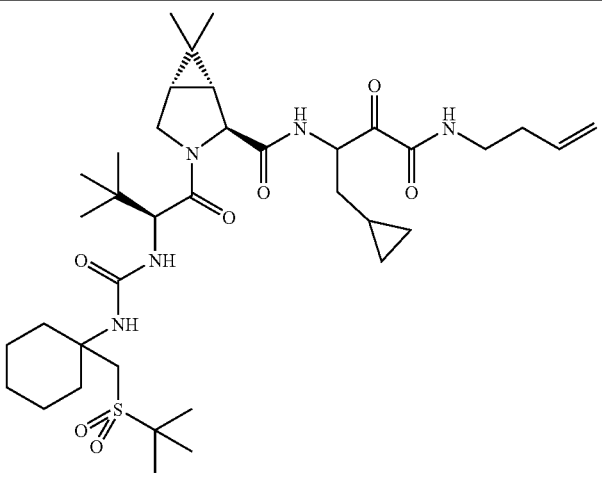 | FAMBS; MH+, 720.8. | A |
| --- | --- | --- | --- |
| 225 | 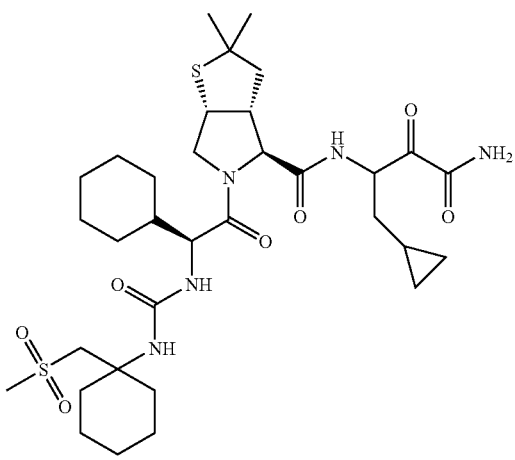 | | B |
| 226 | 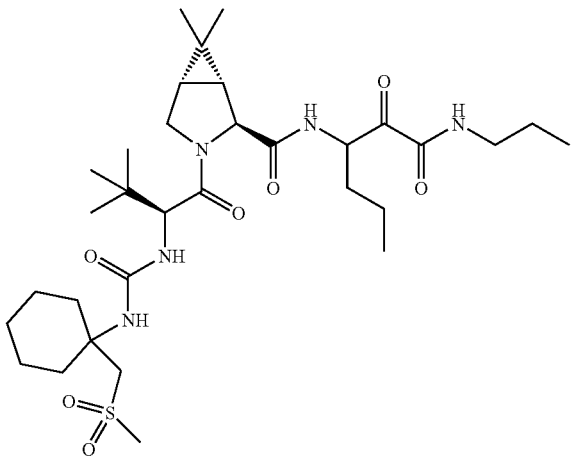 | LCMS; MH+, 654.1. | A |

US 8,067,379 B2
261                                                                    262
-continued
Sulfone Compounds
227                                                                    A
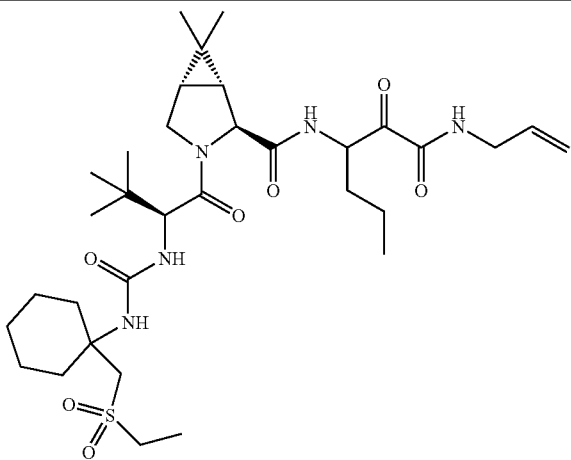
228                                                                    A
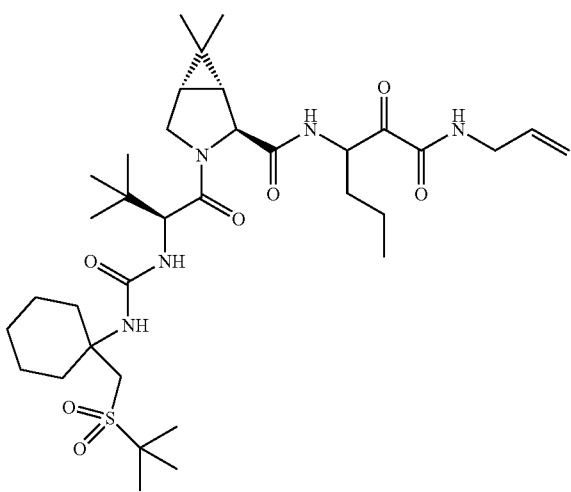
229    FAMBS;    A
       MH+,
       666.5.
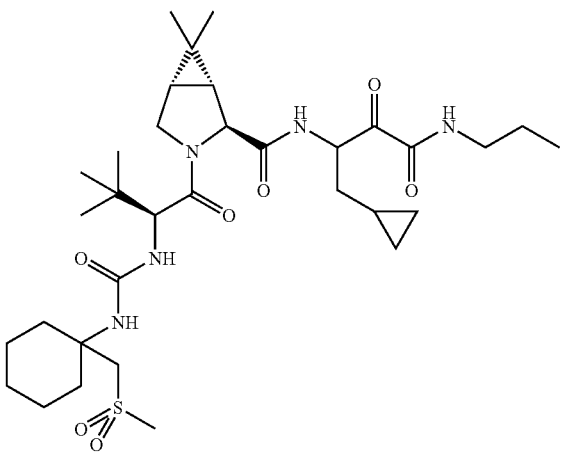

Sulfone Compounds
230 C
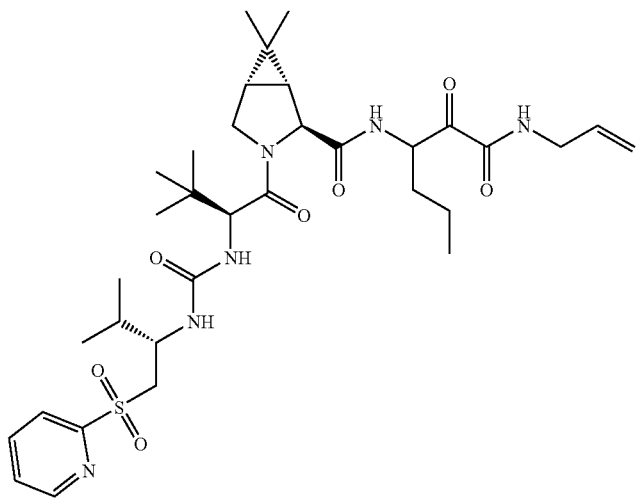
231 A
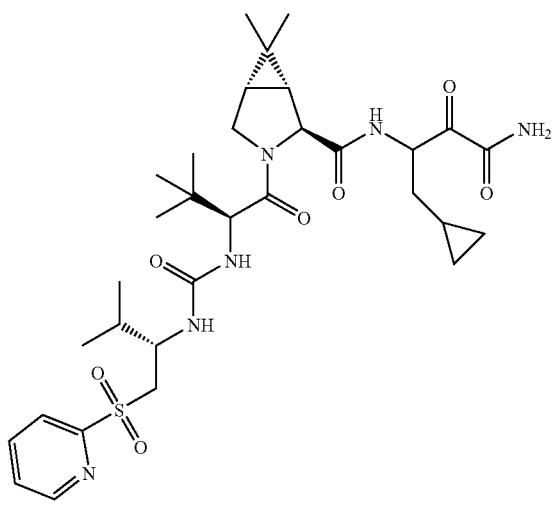
232 A
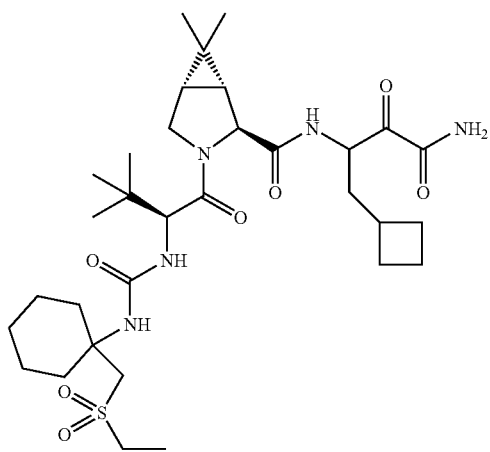

| | Sulfone Compounds | |
|---|---|---|
| 233 | 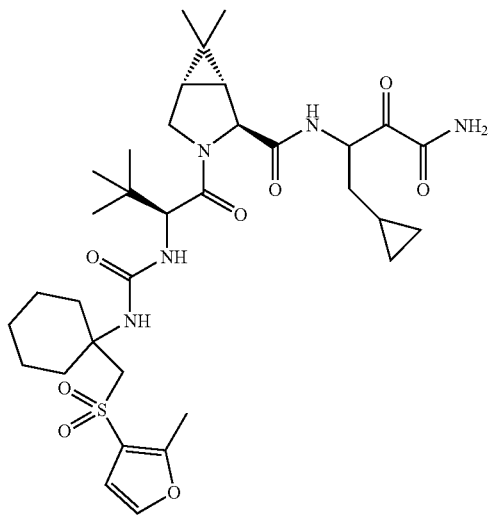 | A |
| 234 | 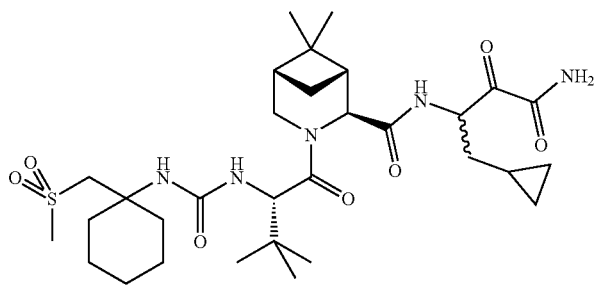 | C |
| 235 | 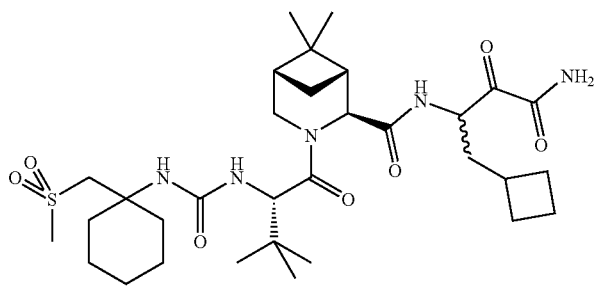 | A |
| 236 | 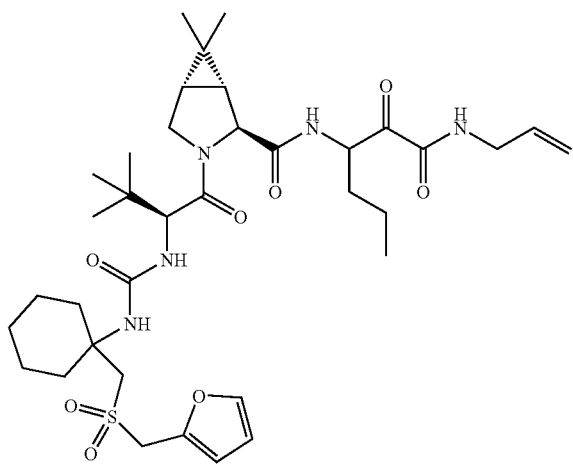 | A |

Sulfone Compounds
237 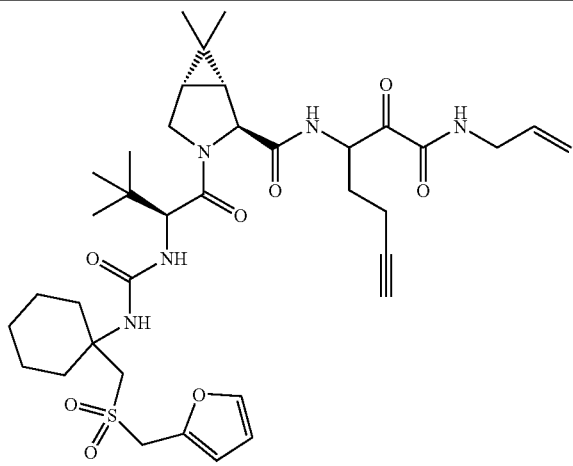 A
238 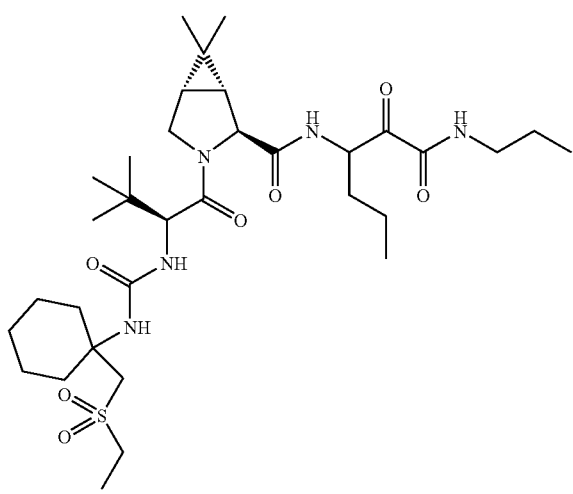 A
239 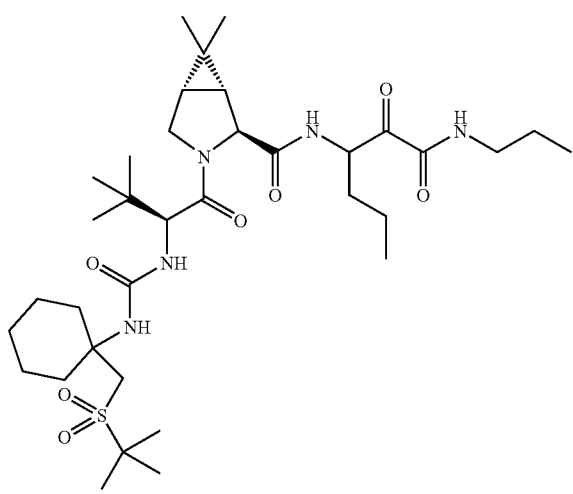 A

| Sulfone Compounds | | |
|---|---|---|
| 240 | 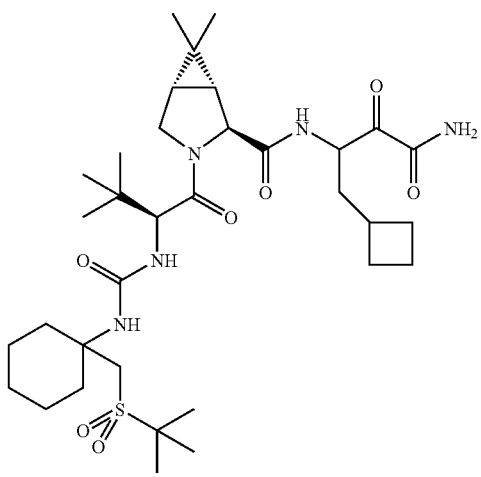 | A |
| 241 | 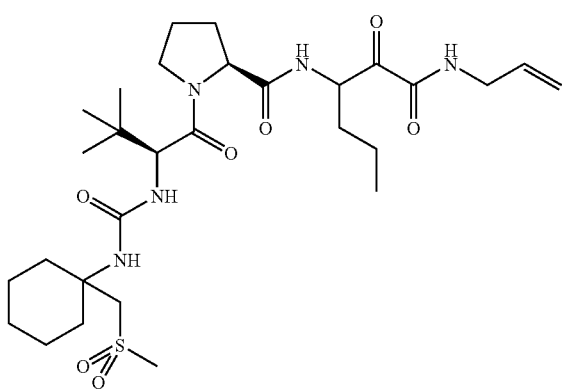 | C |
| 242 | 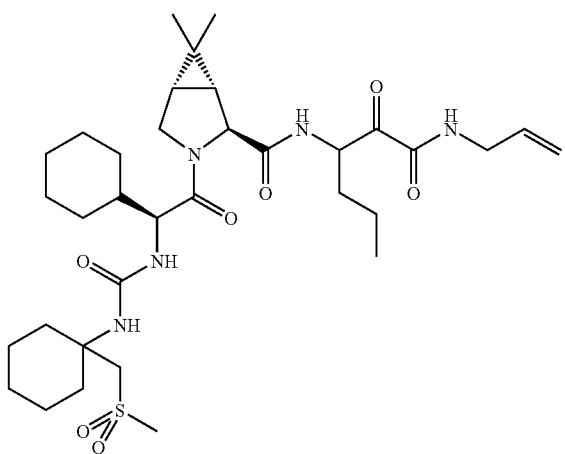 | A |

-continued
Sulfone Compounds
243 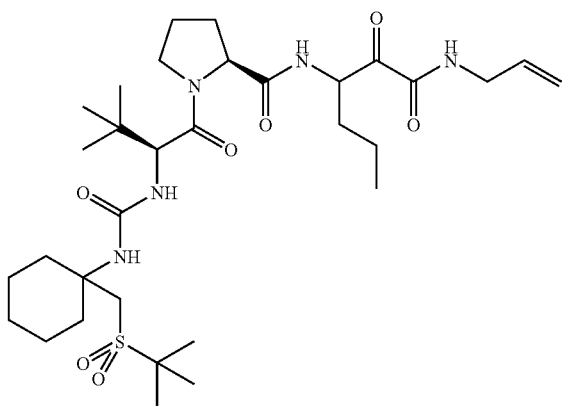 C
244 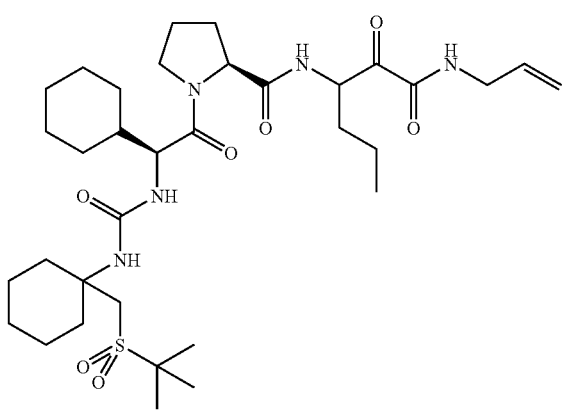 A
245 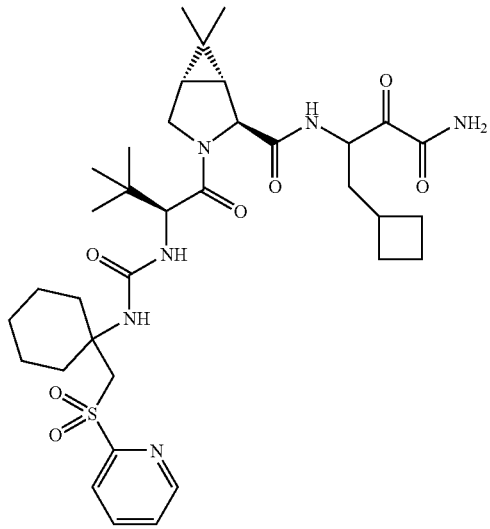 A -continued
Sulfone Compounds
| | | | |
|---|---|---|---|
| 246 | 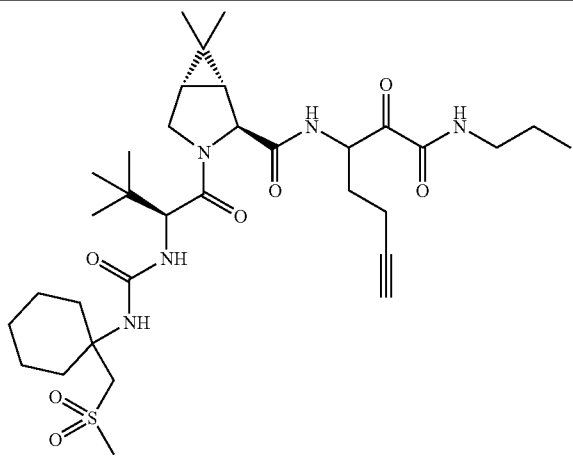 | FAMBS; MH+, 664.2. | A |
| 247 | 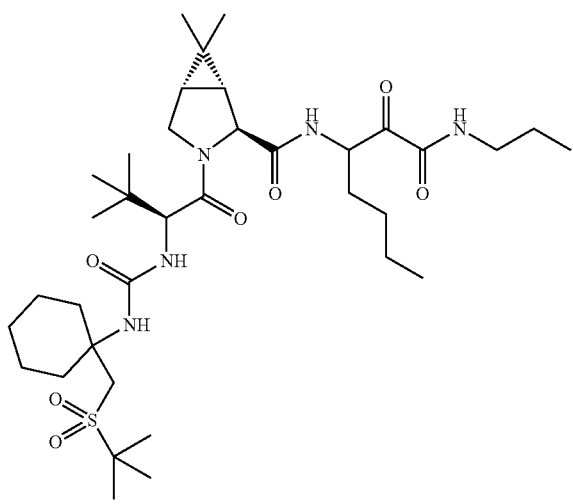 | FAMBS; MH+, 710.3. | A |
| 248 | 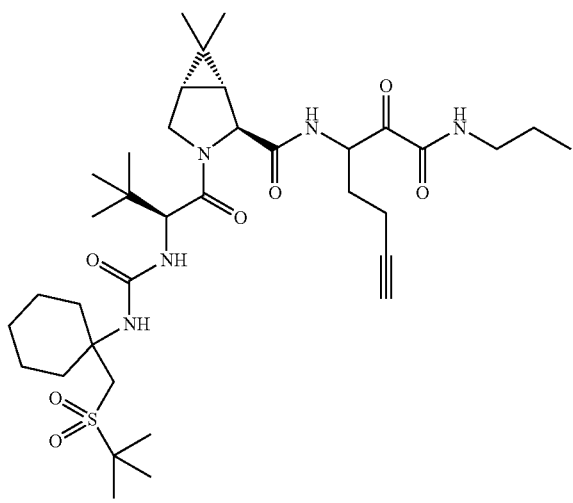 | FAMBS; MH+, 706.5. | A |

-continued
Sulfone Compounds
249 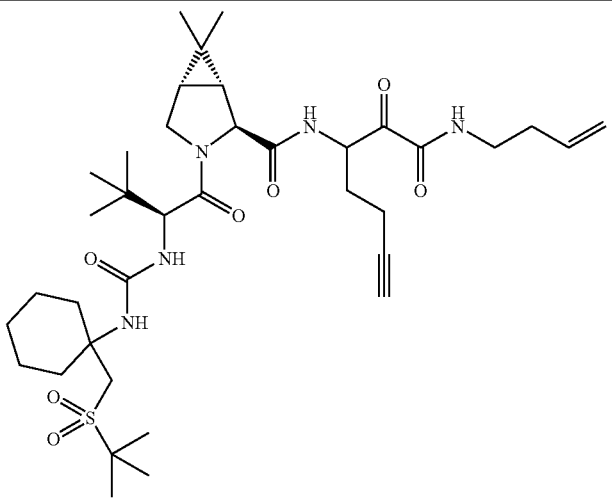 FAMBS; MH+, 718.2. A
250 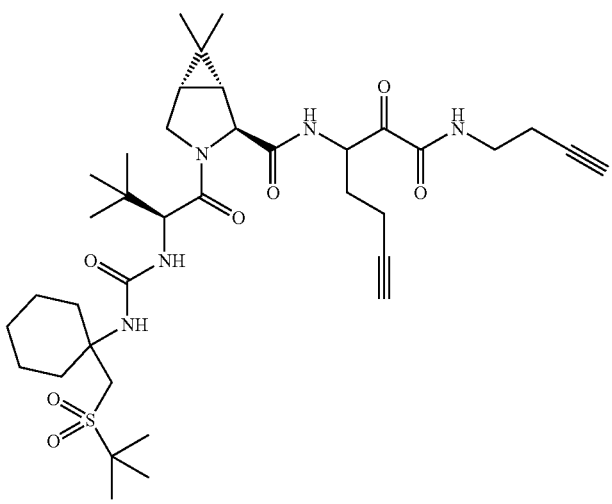 A
251 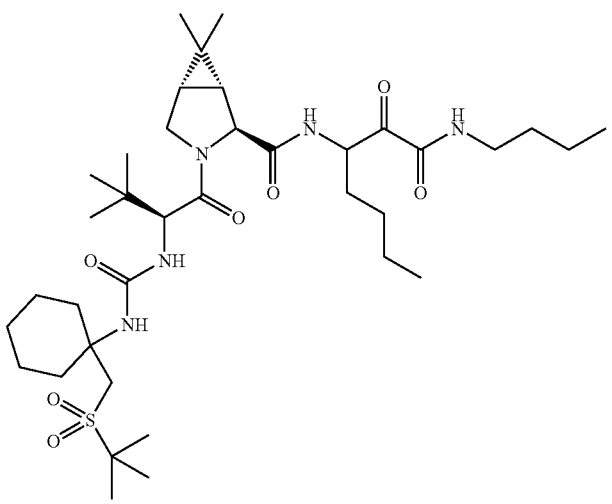 FAMBS; MH+, 724.5. A

Sulfone Compounds
| | | |
|---|---|---|
| 252 | 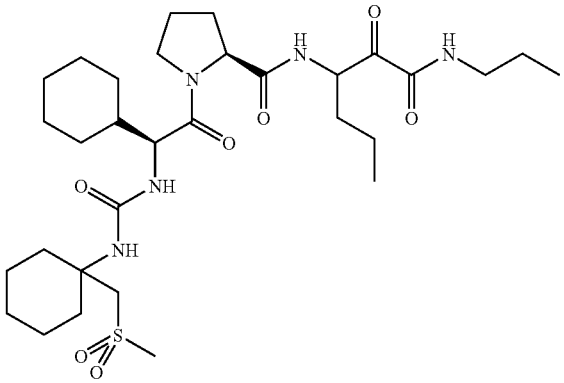 | FAMBS; MH+, 680.4.    A |
| 253 | 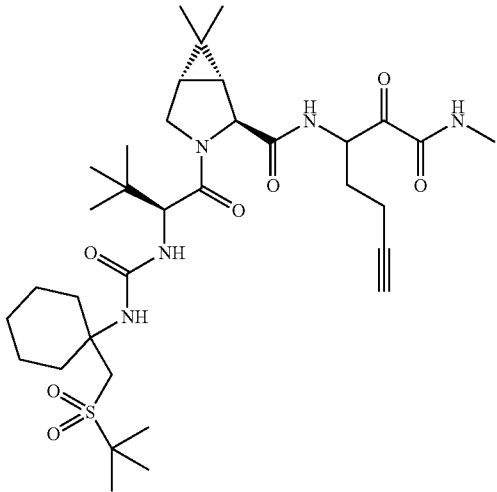 | A |
| 254 | 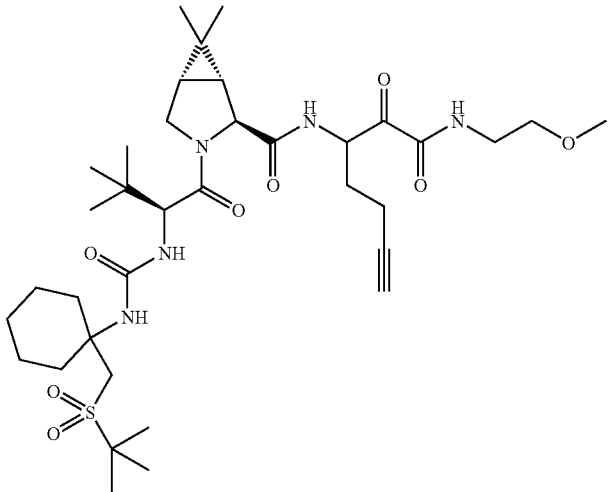 | FAMBS; MH+, 722.1.    A |

Sulfone Compounds
255 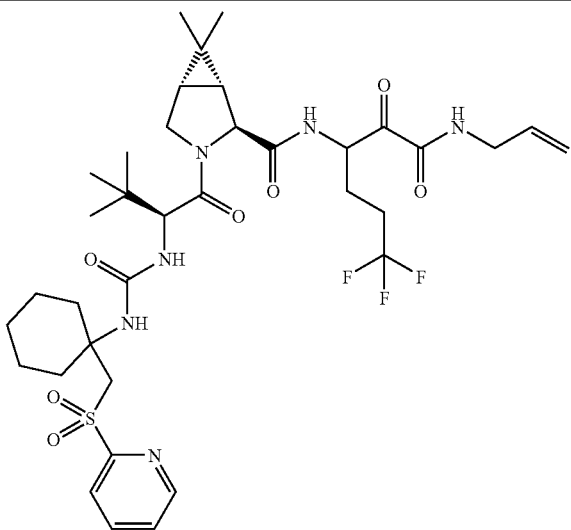 A
256 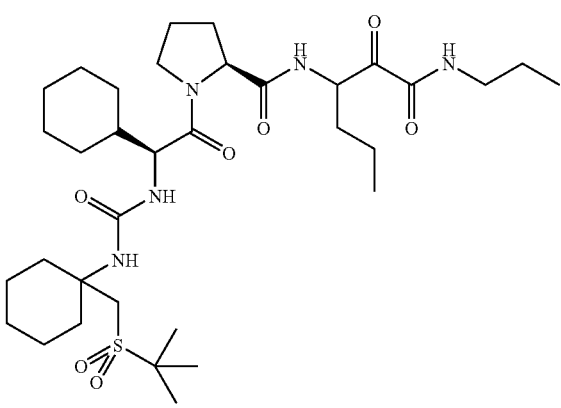 A
257 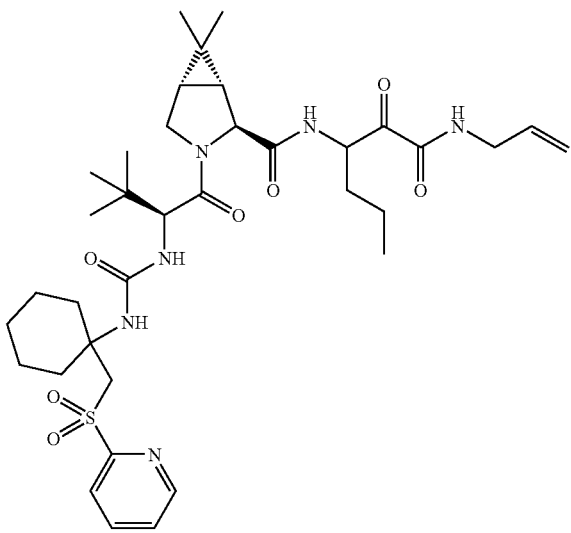 A

-continued
Sulfone Compounds
| | | |
|---|---|---|
| 258 | 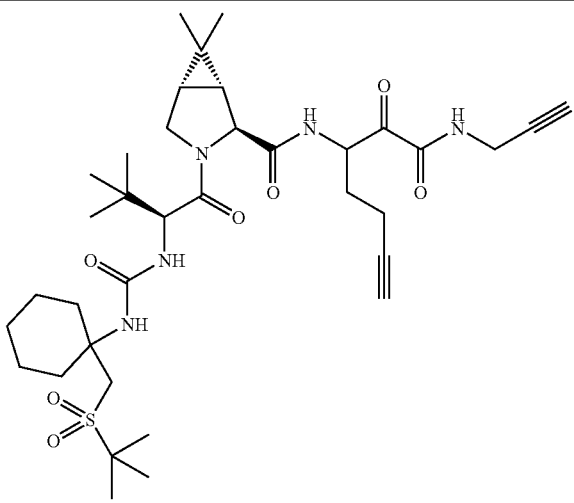 | FAMBS; MH+, 702.3. A |
| 259 | 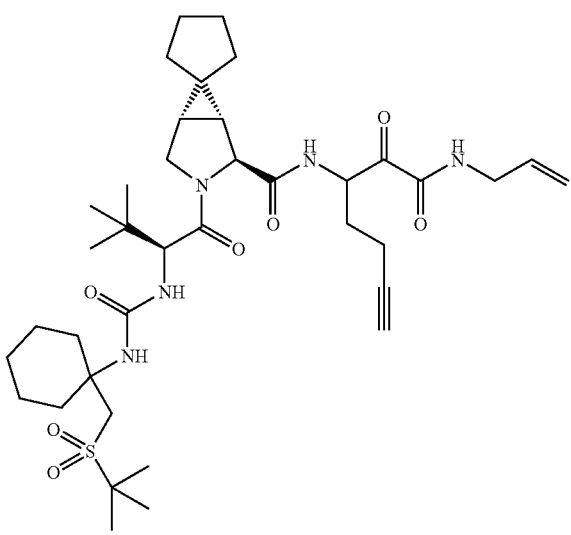 | FAMBS; MH+, 730.5. A |
| 260 | 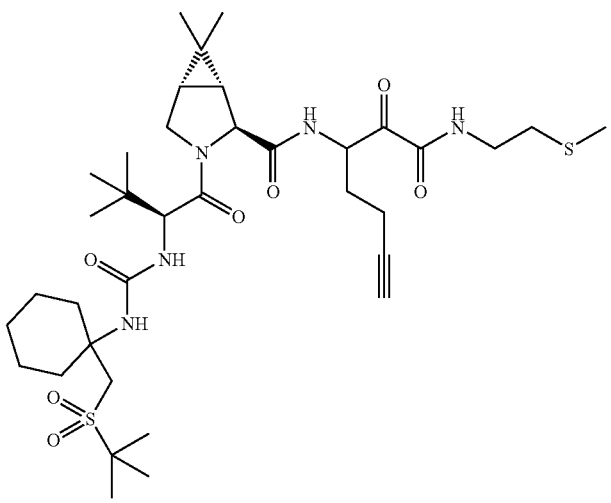 | FAMBS; MH+, 738.4. A |

Sulfone Compounds
| | | |
|---|---|---|
| 261 | 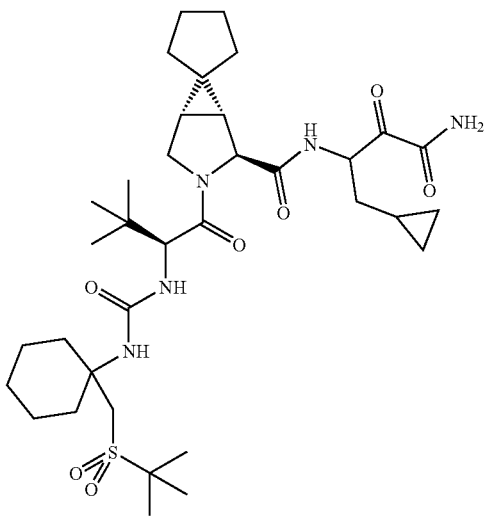 | FAMBS; MH+, 692.5.    A |
| 262 | 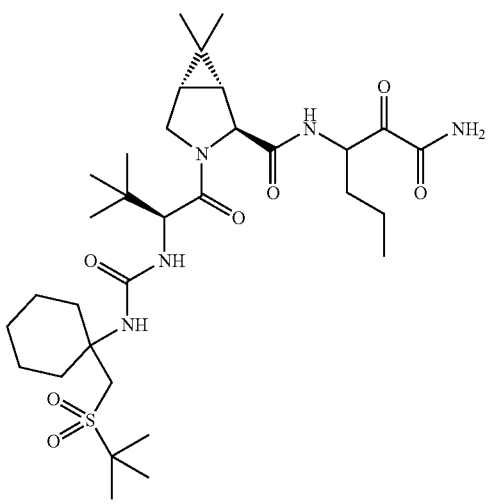 | A |
| 263 | 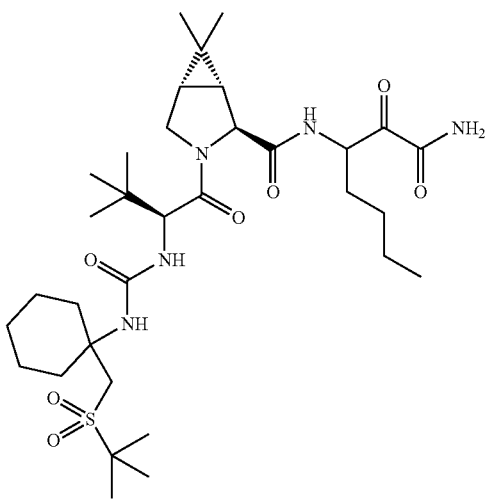 | A |

Sulfone Compounds
| 264 | 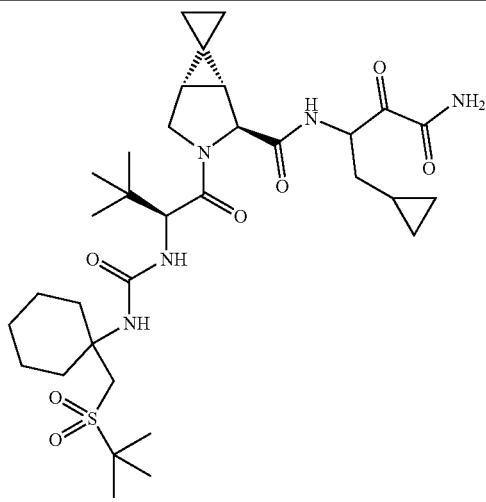 | FAMBS; MH+, 664.4. | A |
| 265 | 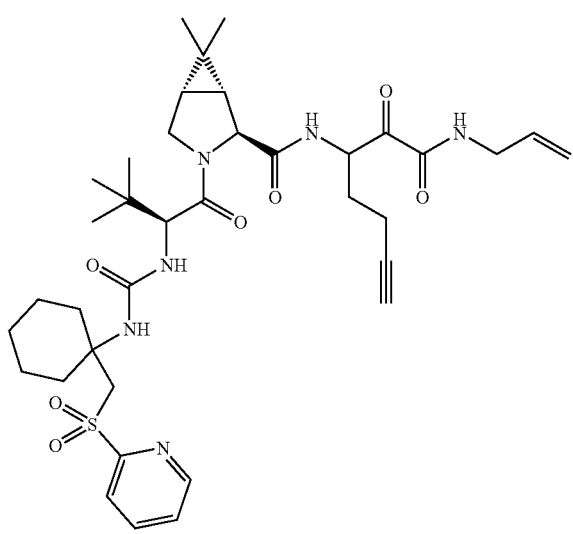 | | A |
| 266 | 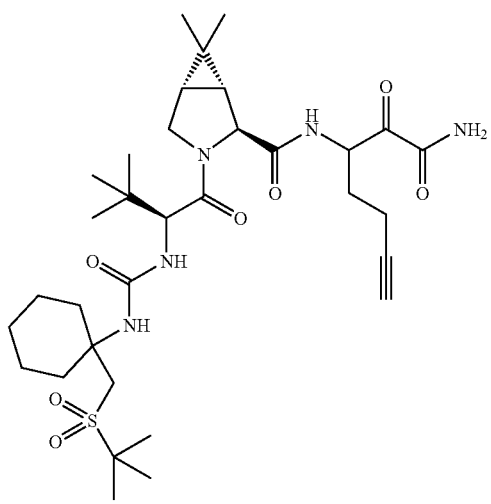 | FAMBS; MH+, 664.2. | A |

| Sulfone Compounds | |
|---|---|
| 267 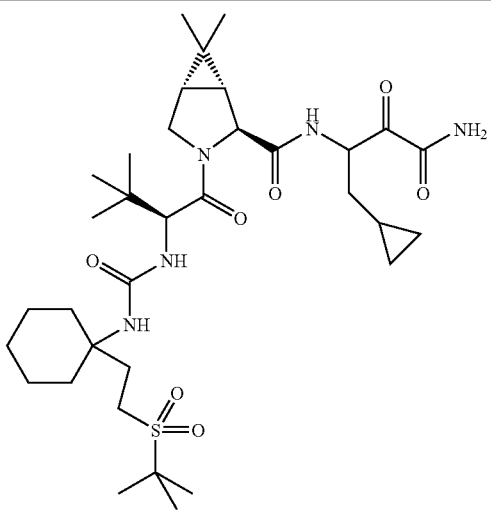 | B |
| 268 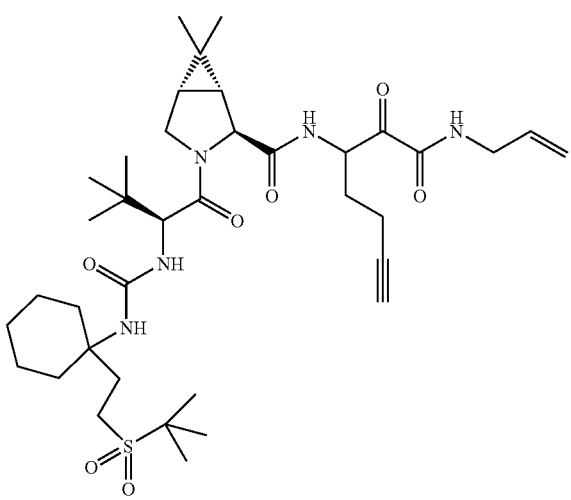 | B |
| 269 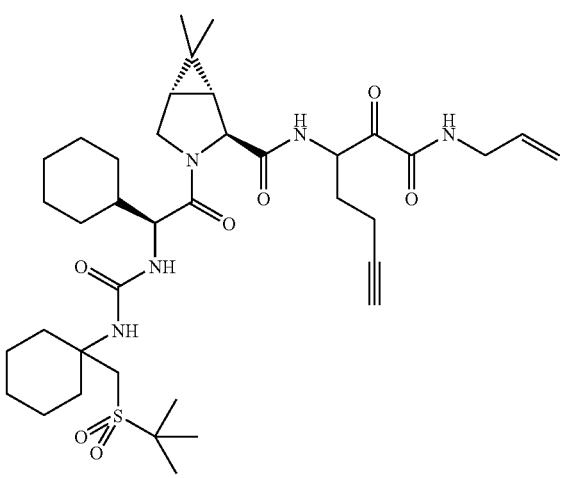 | A |

| | Sulfone Compounds | |
|---|---|---|
| 270 | 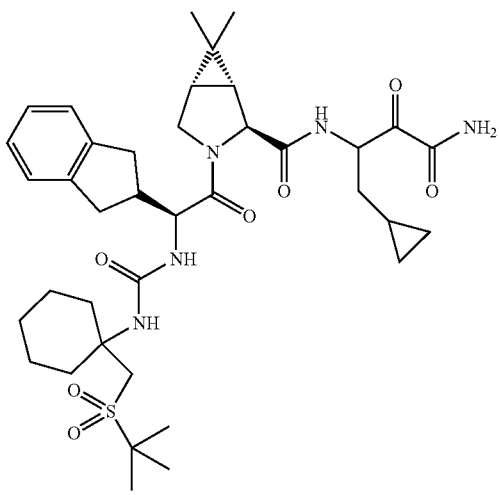 | A |
| 271 | 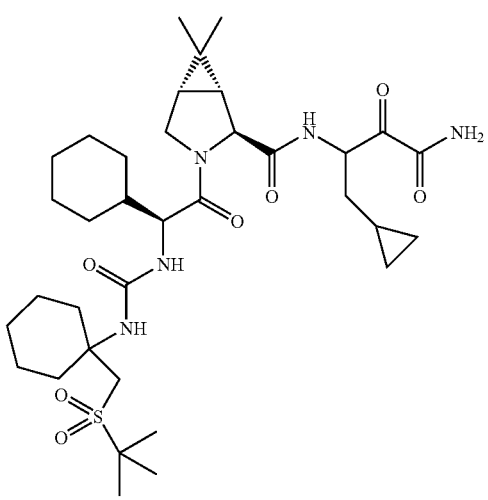 | A |
| 272 | 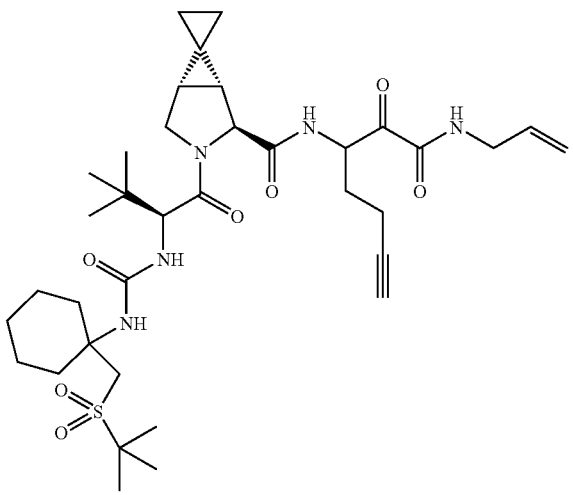 | FAMBS;<br>MH+,<br>702.3. A |

| | Sulfone Compounds | | |
|---|---|---|---|
| 273 | 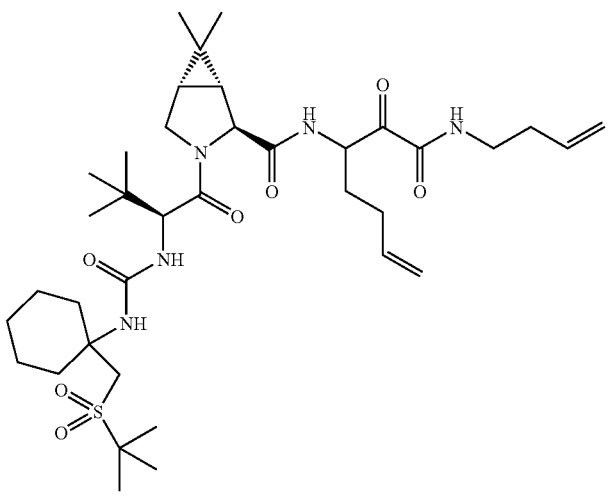 | FAMBS; MH+, 720.5. | A |
| 274 | 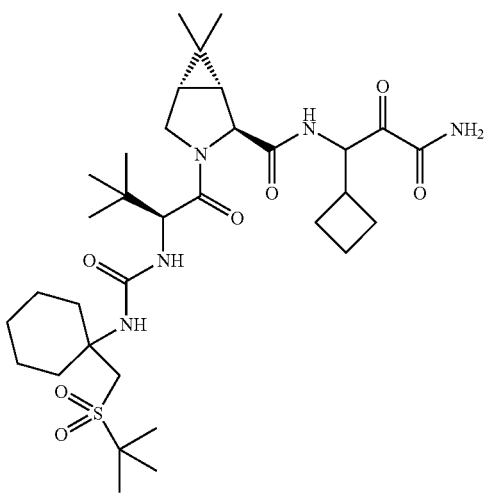 | | A |
| 275 | 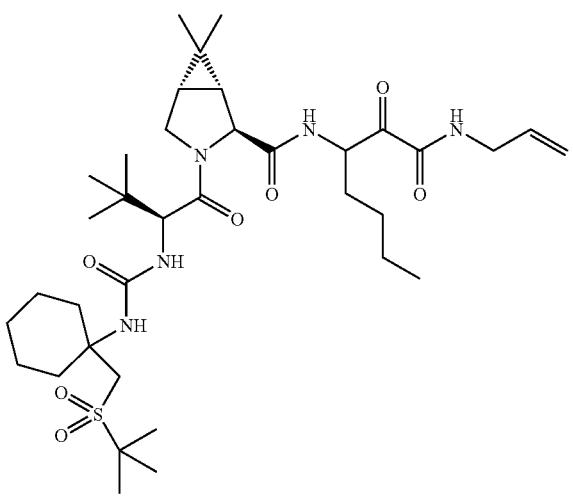 | | A |

| | Sulfone Compounds | | |
|---|---|---|---|
| 276 | 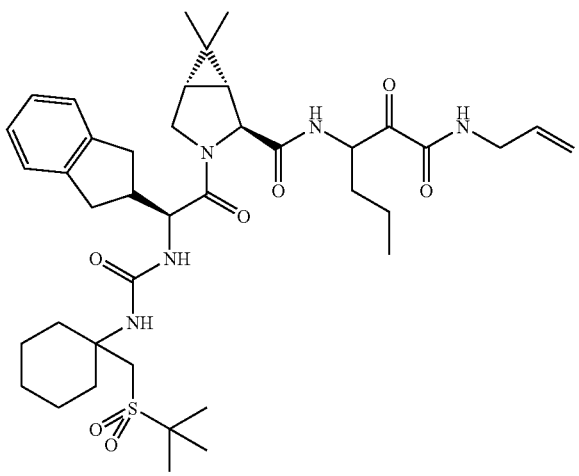 | | A |
| 277 | 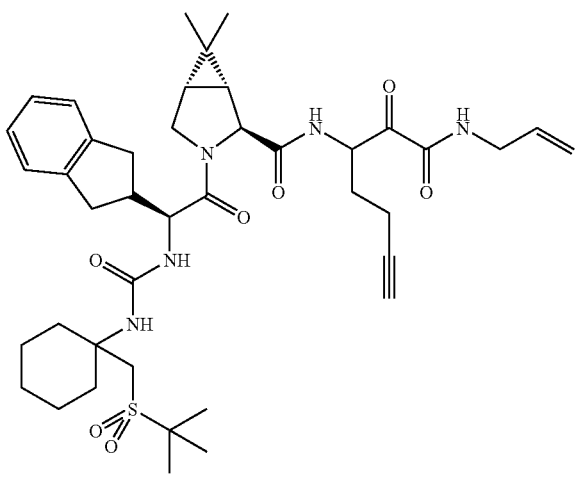 | FAMBS; MH+, 764.8. | A |
| 278 | 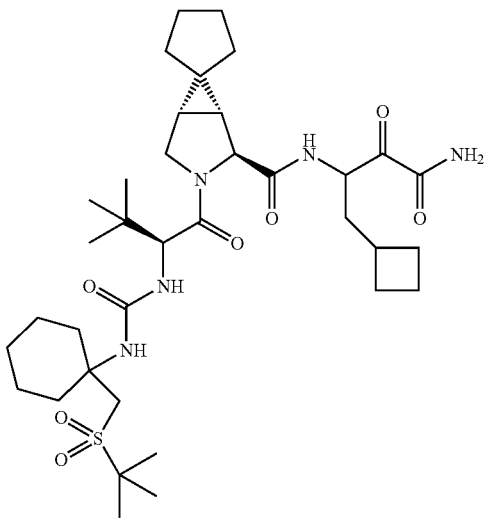 | LCMS; MH+, 706.2. | A |

| | Sulfone Compounds | | |
|---|---|---|---|
| 279 | 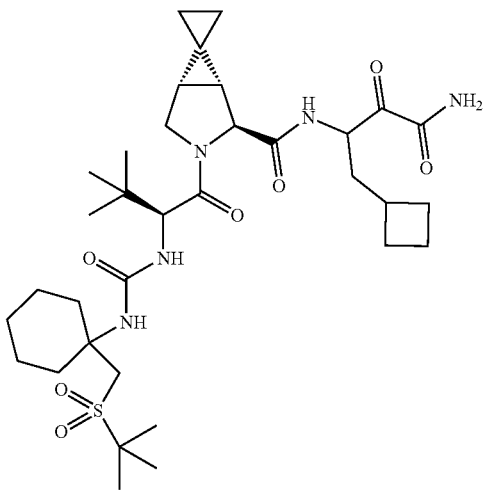 | FAMBS;<br>MH+,<br>678.2. | A |
| 280 | 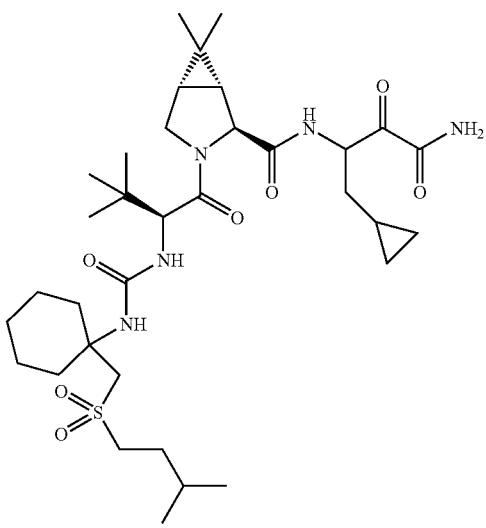 | | A |
| 281 | 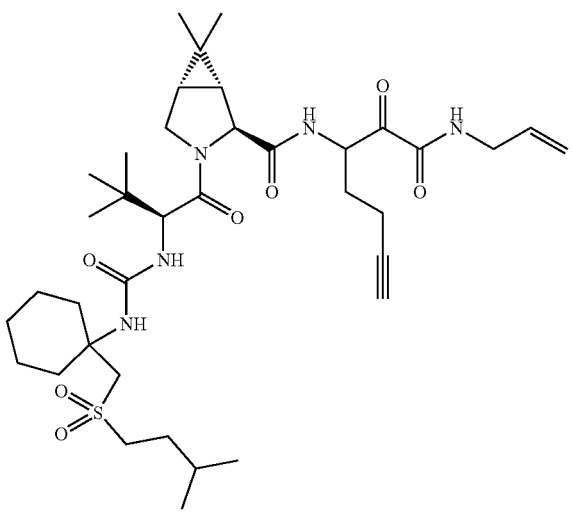 | | A |

Sulfone Compounds
282 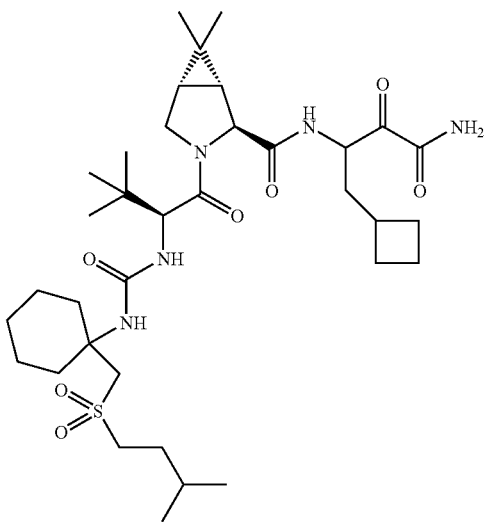 A
283 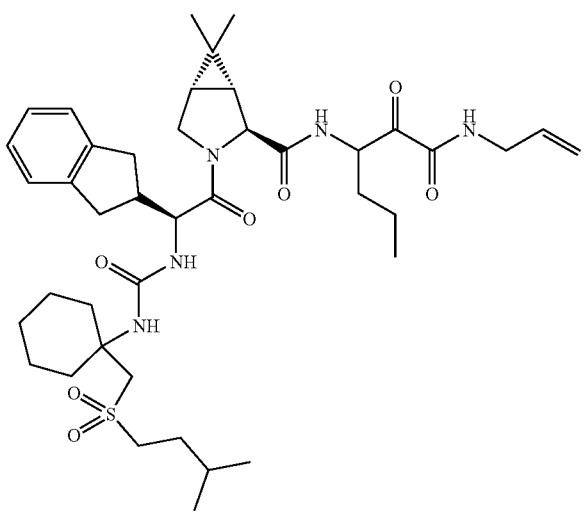 A
284 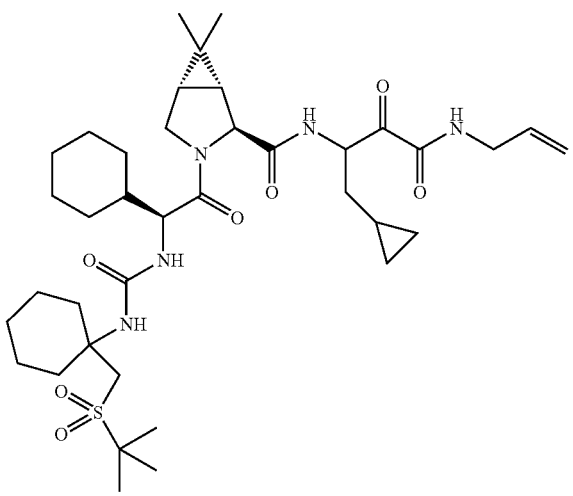 A

-continued
Sulfone Compounds
| | | |
|---|---|---|
| 285 | 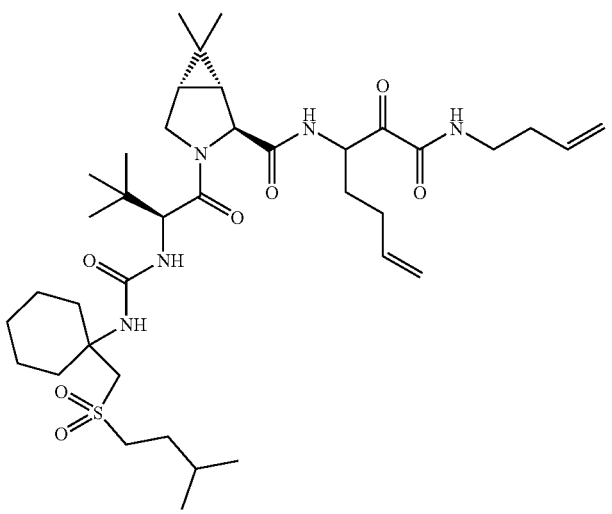 | A |
| 286 | 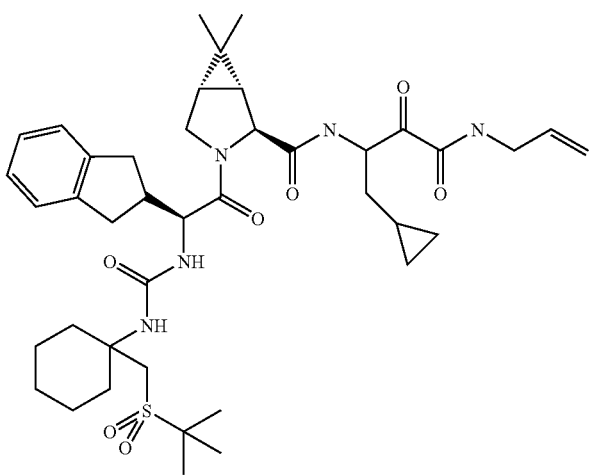 | LCMS; MH+, 766.2. A |
| 287 | 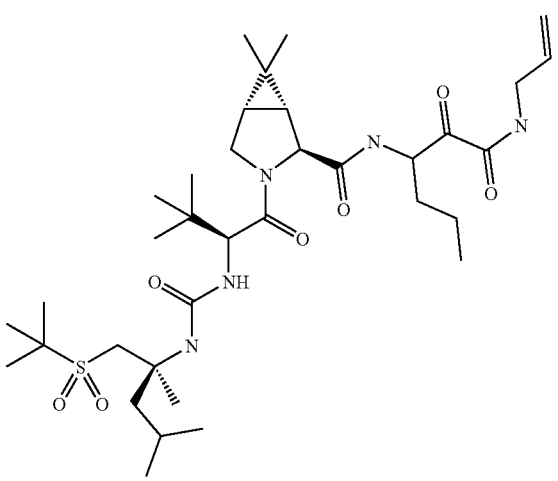 | C |

US 8,067,379 B2
-continued
Sulfone Compounds
288
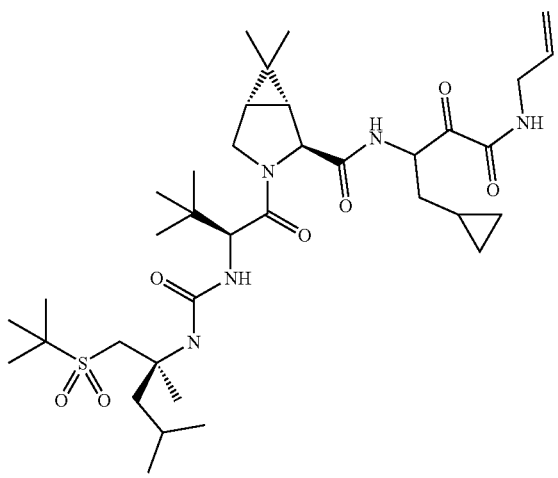
C
289
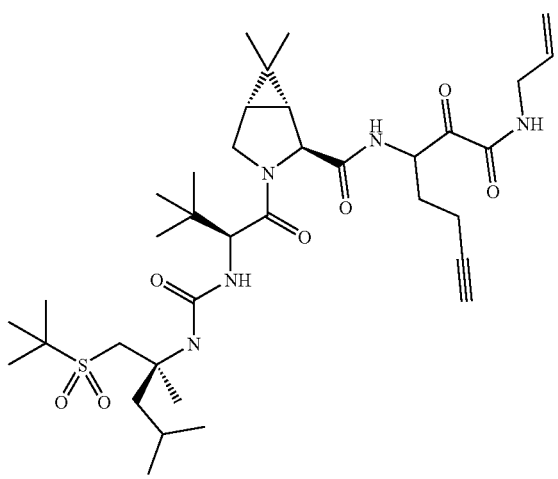
B
290
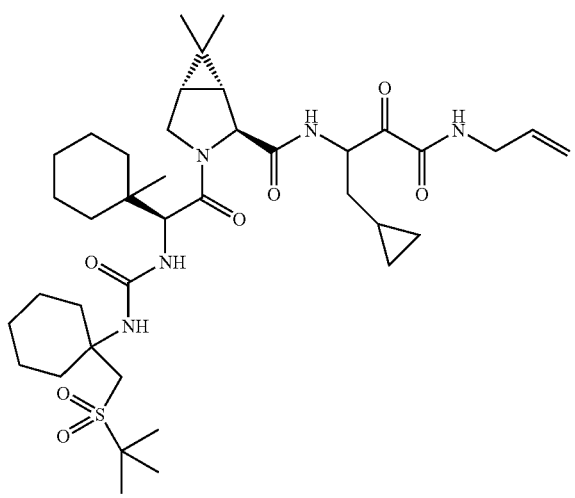
A

| | Sulfone Compounds | |
|---|---|---|
| 291 | 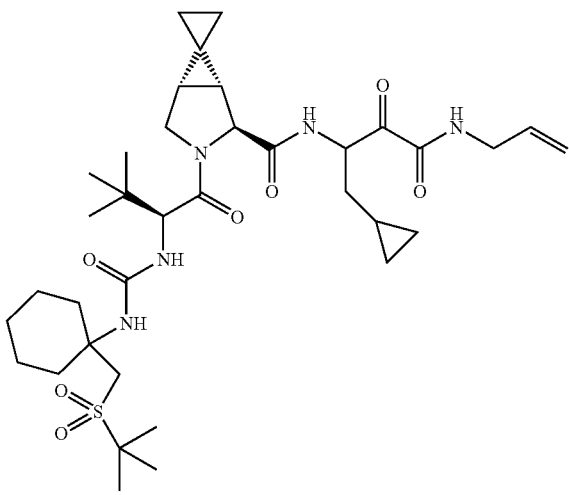 | A |
| 292 | 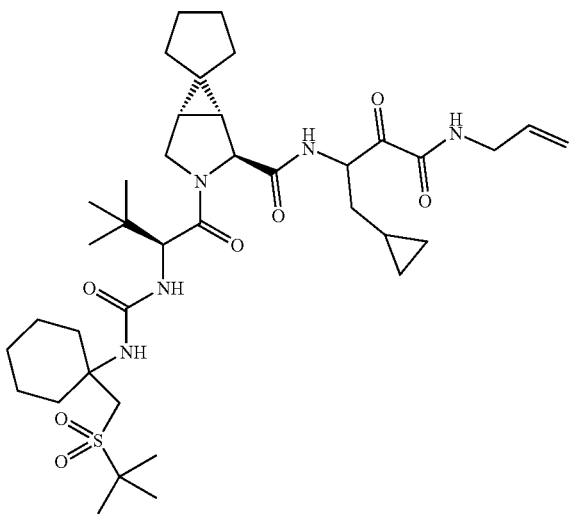 | A |
| 293 | 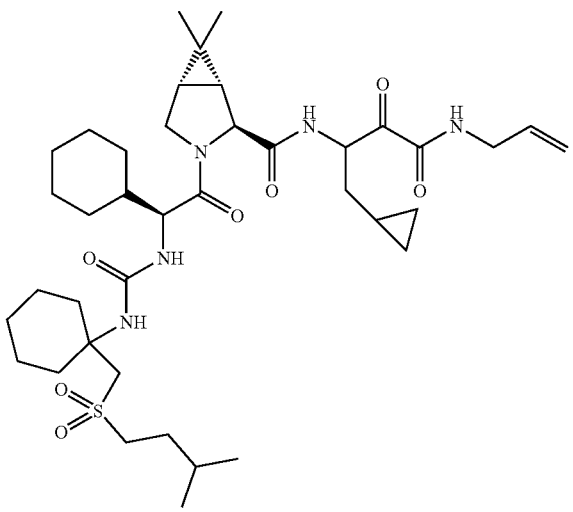 | A |

| | Sulfone Compounds | | |
|---|---|---|---|
| 294 | 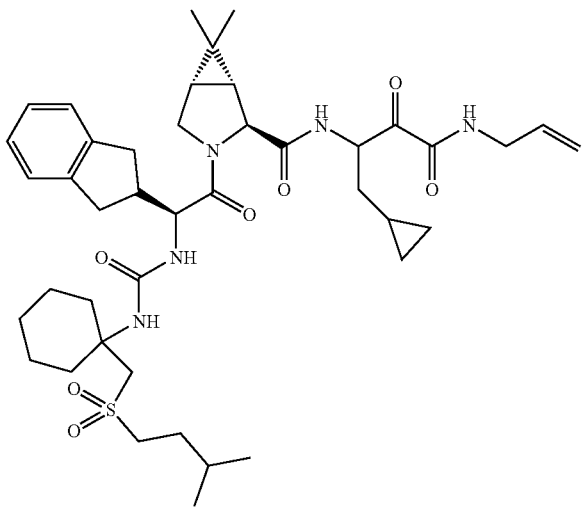 | | A |
| 295 | 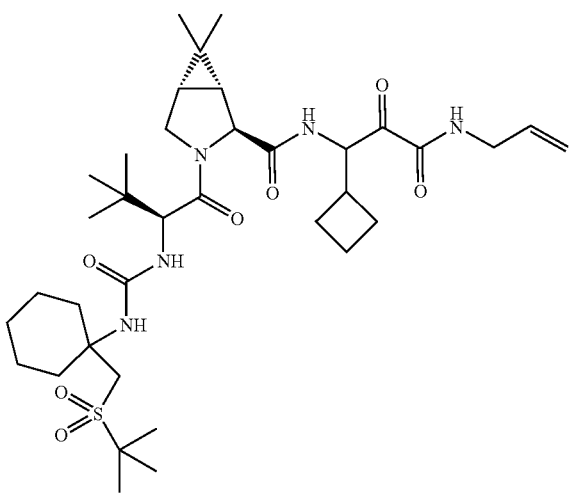 | | B |
| 296 | 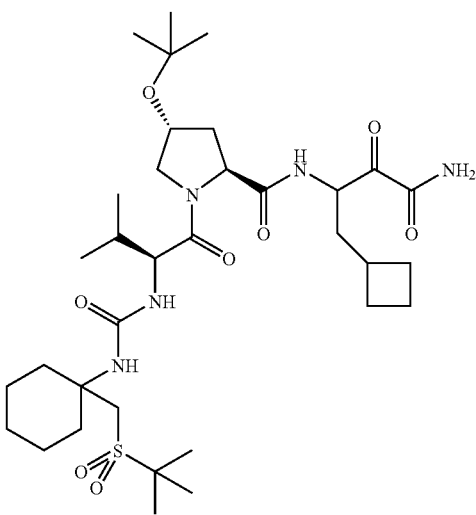 | LCMS; MH+, 712.3. | A |

307 308
-continued
| Sulfone Compounds | | |
|---|---|---|
| 297 | 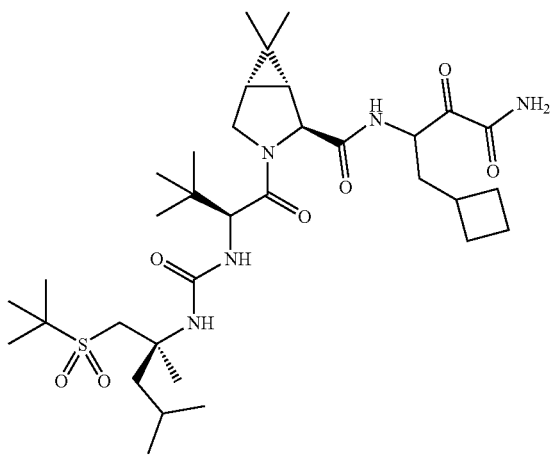 | A |
| 298 | 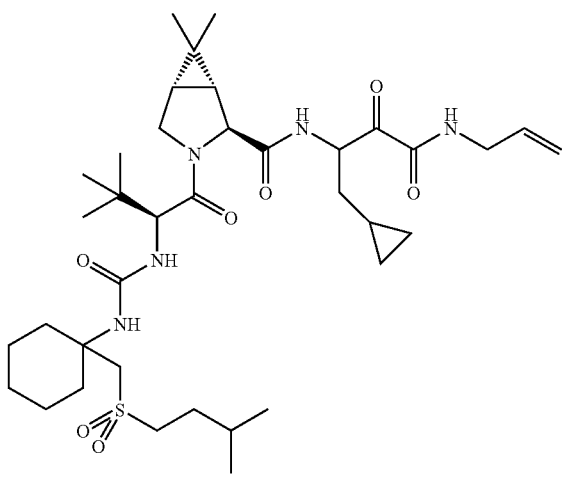 | A |
| 299 | 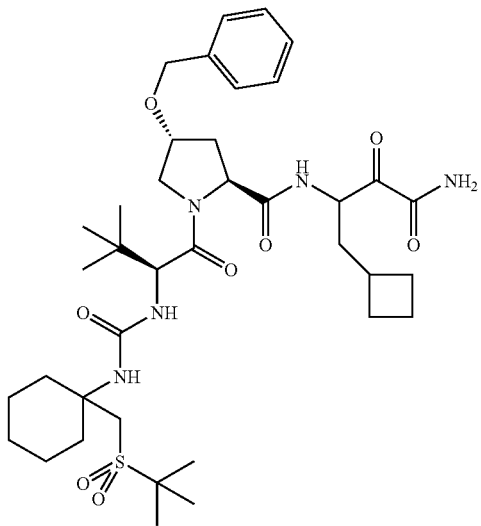 | LCMS; MH+, 746.2. A |

-continued
Sulfone Compounds
| | | |
|---|---|---|
| 300 | 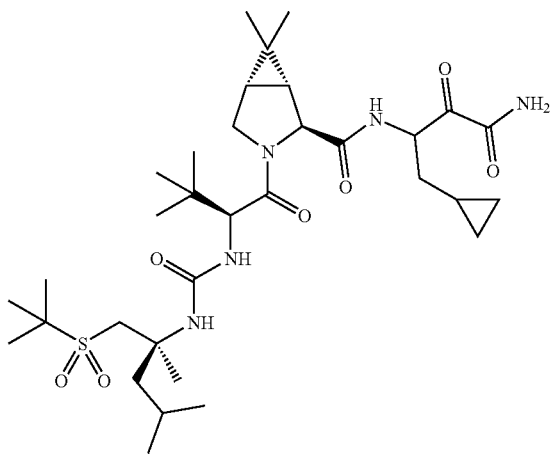 | B |
| 301 | 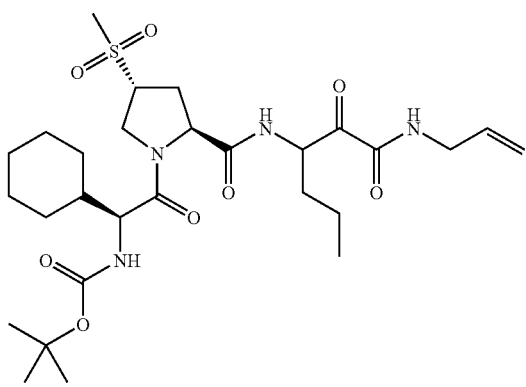 | A |
| 302 | 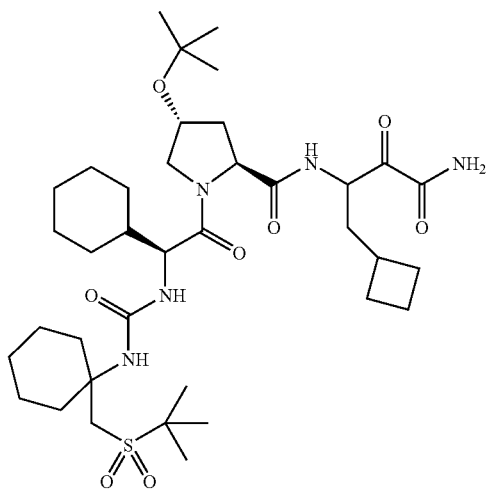 | A |

-continued
Sulfone Compounds
303 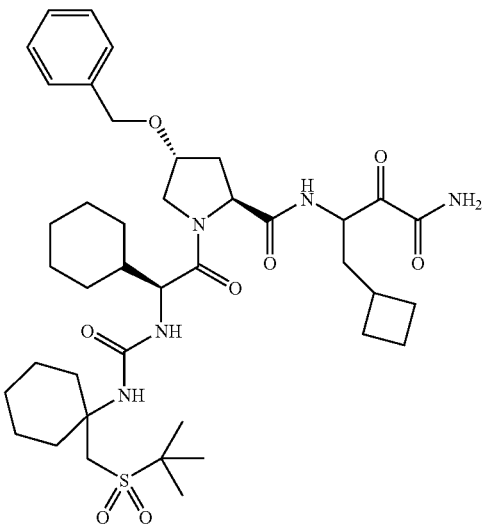 B
304 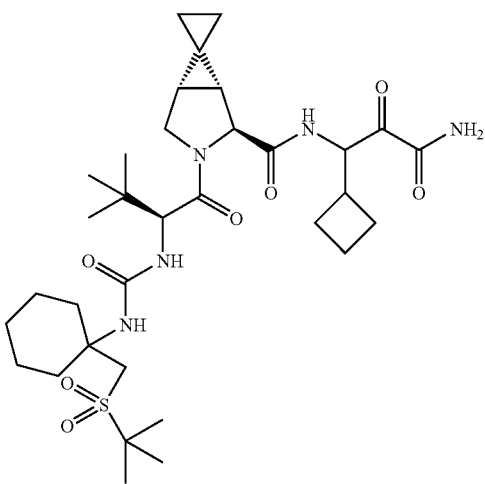 LCMS; MH+, 664.1. C
305 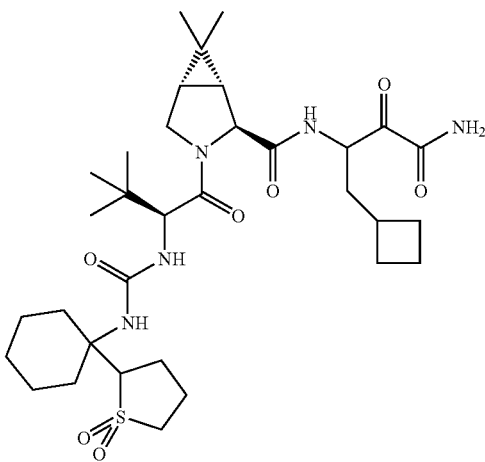 B US 8,067,379 B2
313                                                                314
-continued
Sulfone Compounds
| 306 | 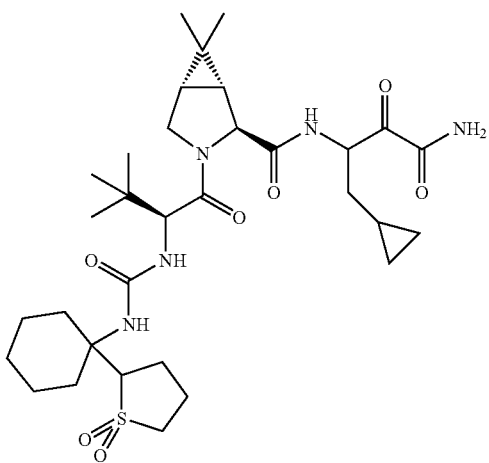 | | A |
| --- | --- | --- | --- |
| 307 | 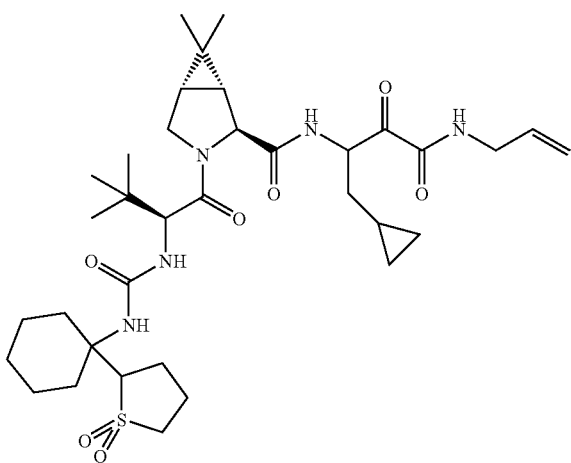 | | A |
| 308 | 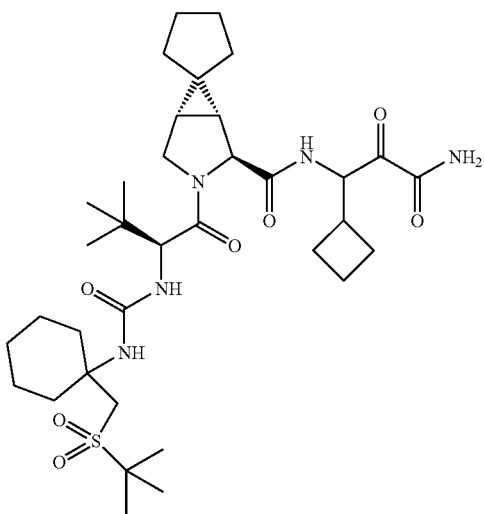 | LCMS; MH+, 692.1. | A |

315                                                              316
-continued
| Sulfone Compounds |
|---|
309 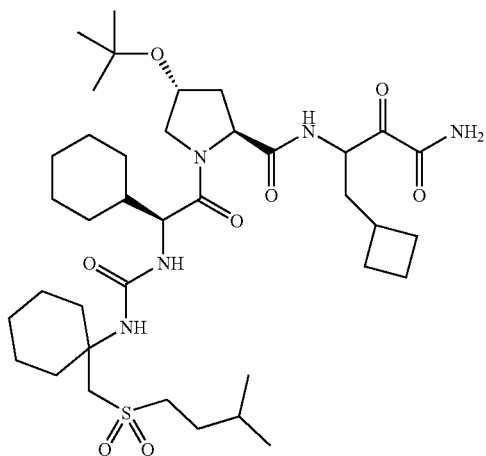 A
310 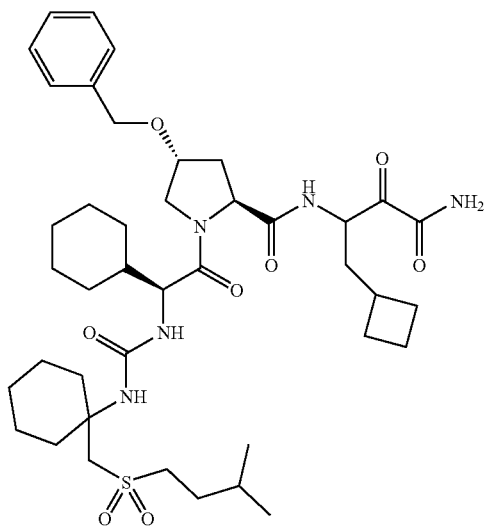 A
311 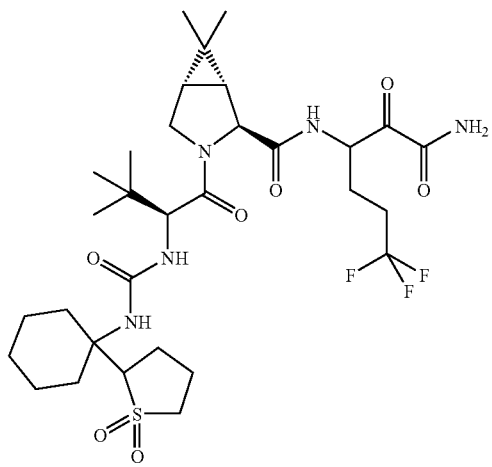 A

Sulfone Compounds
312 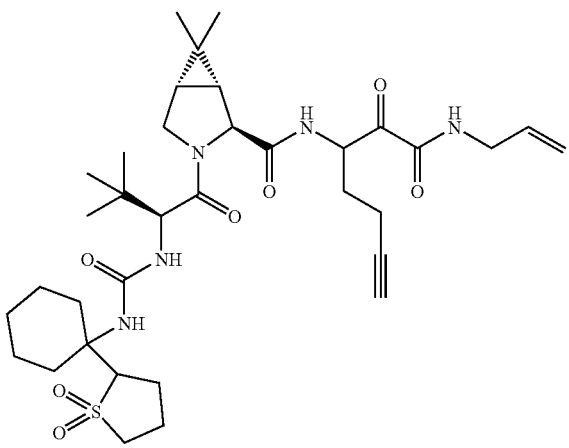 A
313 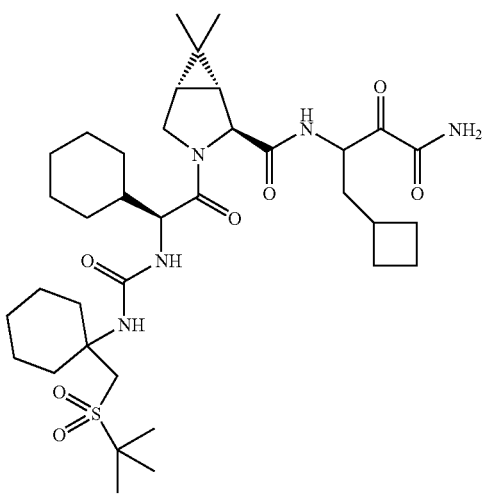 A
314 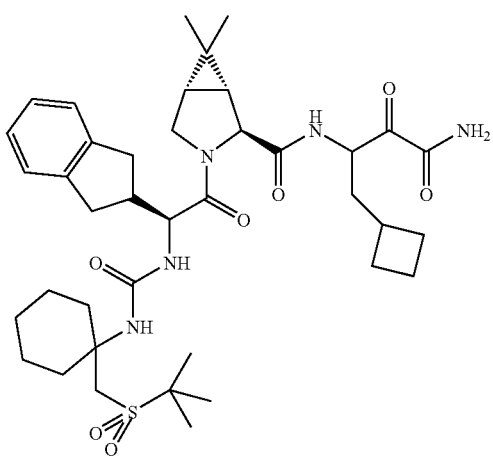 A

| Sulfone Compounds | |
|---|---|
| 315 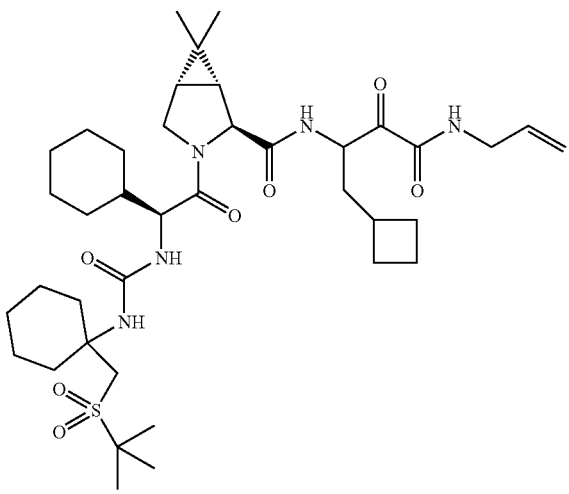 | A |
| 316 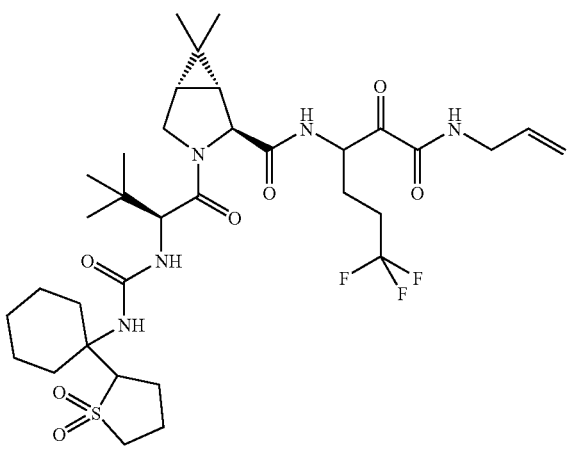 | A |
| 317 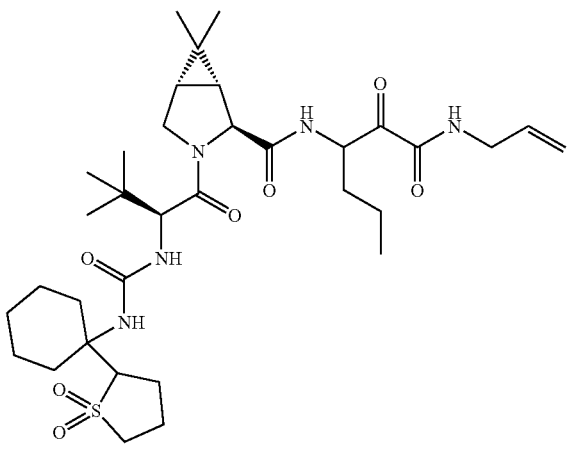 | A |

US 8,067,379 B2
321                                                                 322
-continued
Sulfone Compounds
318 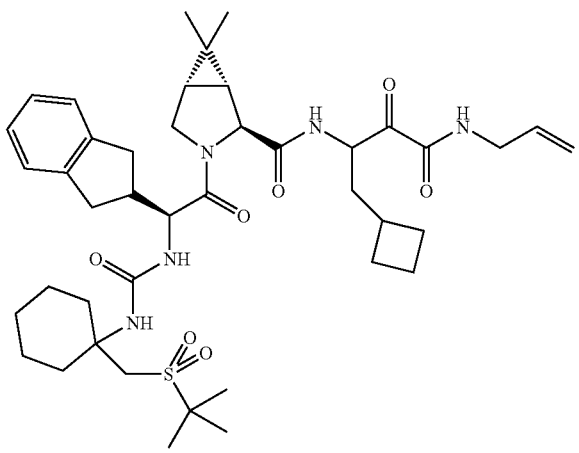 A
319 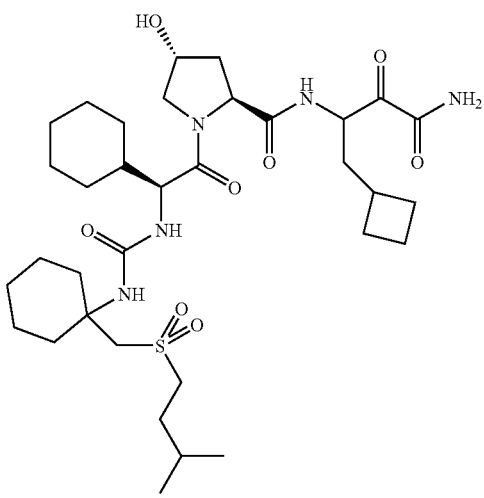 A
320 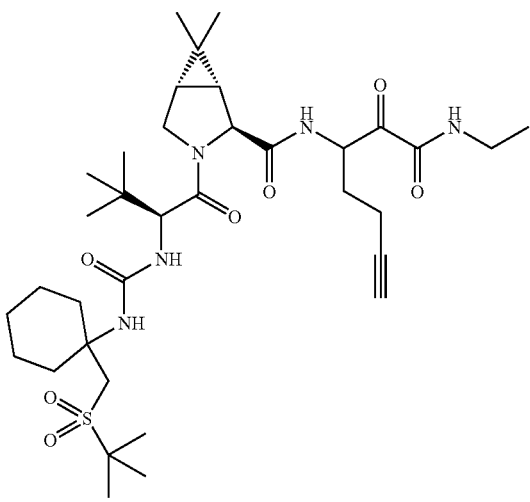 692.3 LCMS; MH+, 692.2.  A US 8,067,379 B2
323                                                                 324
-continued
Sulfone Compounds
| 321 | 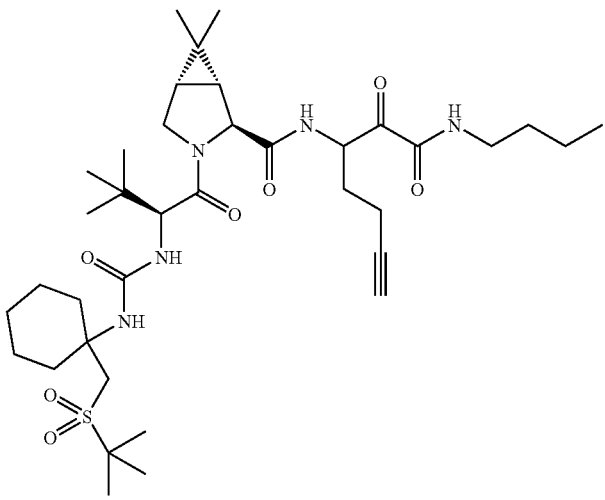 | LCMS; MH+, 720.2. | B |
| --- | --- | --- | --- |
| 322 | 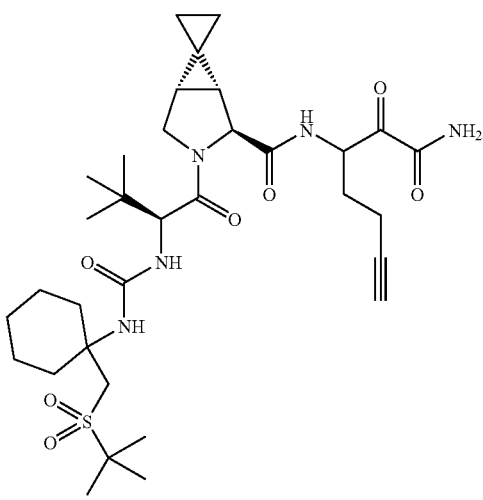 | | B |
| 323 | 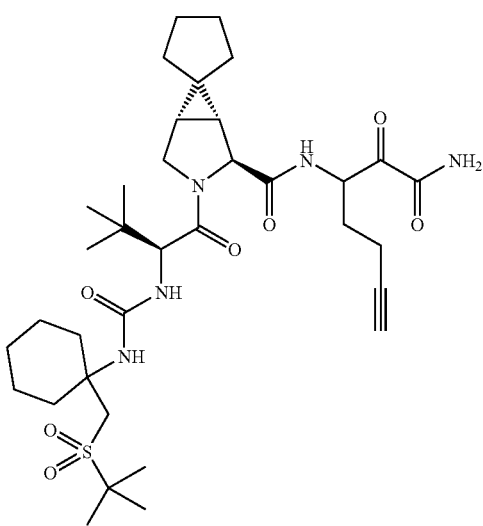 | | A |

-continued
Sulfone Compounds
324 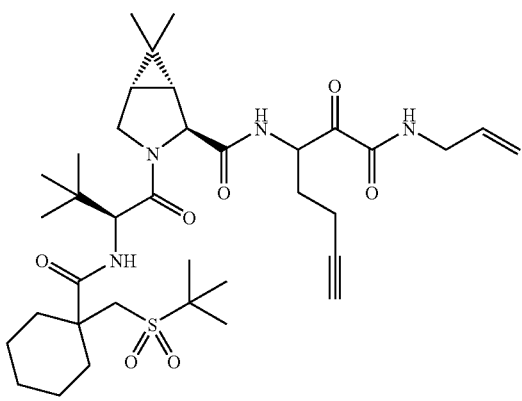 A
325 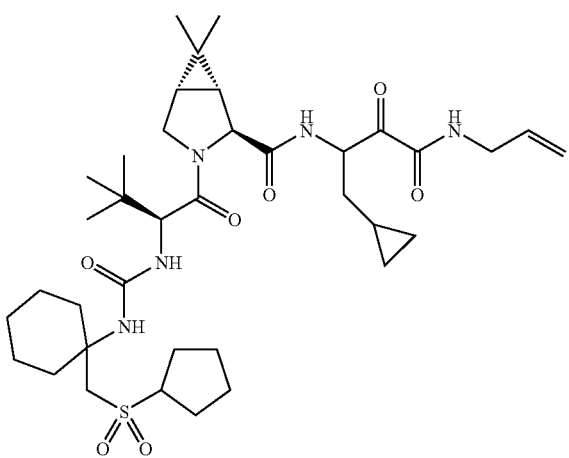 A
326 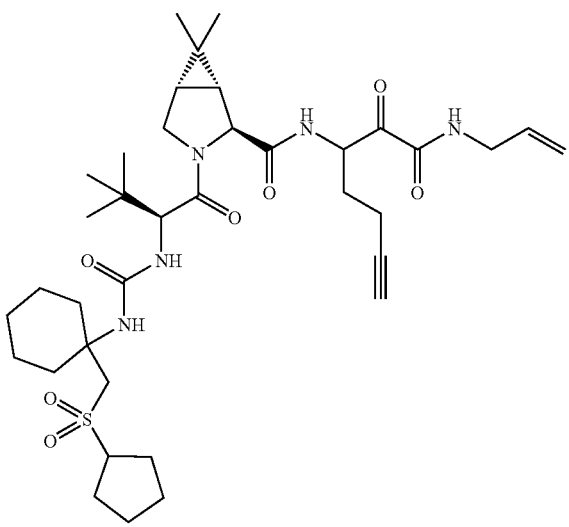 A

| Sulfone Compounds | | |
|---|---|---|
| 327 | 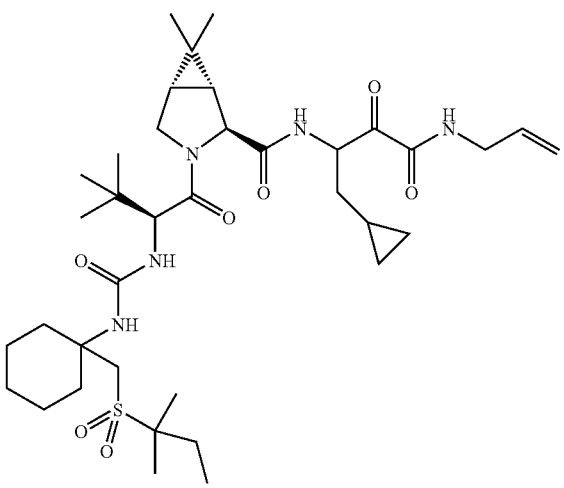 | LCMS; MH+, 720.2.  C |
| 328 | 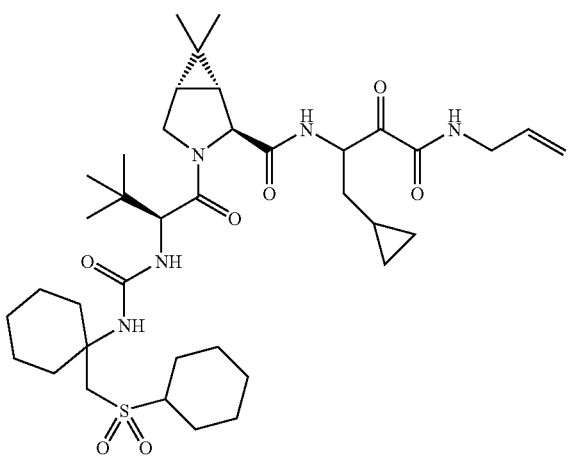 | NA |
| 329 | 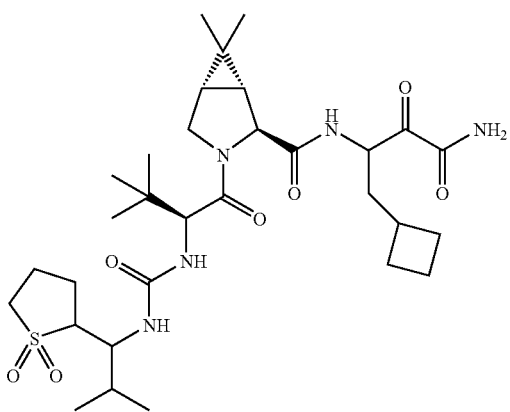 | A |

| | Sulfone Compounds | |
|---|---|---|
| 330 | 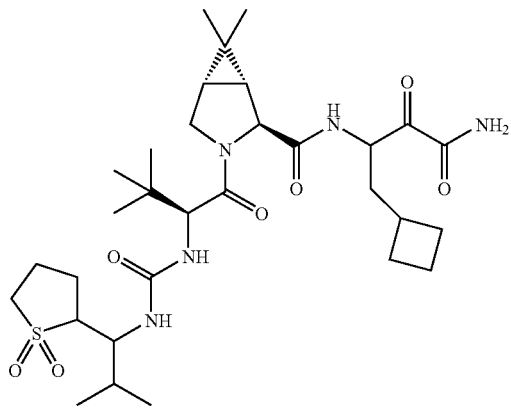 | C |
| 331 | 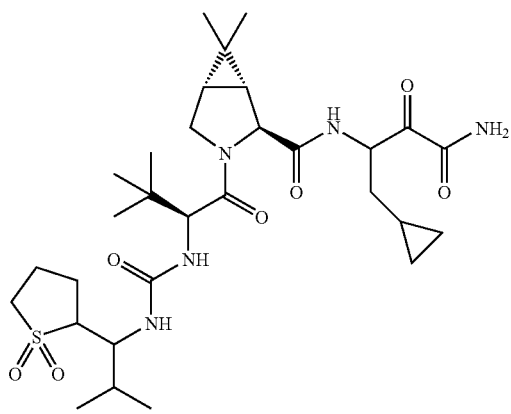 | A |
| 332 | 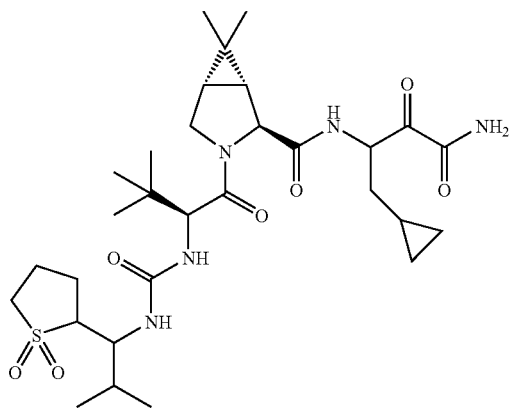 | C |

| Sulfone Compounds | |
|---|---|
| 333 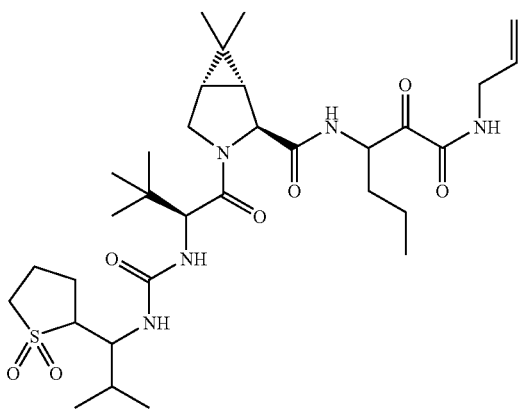 | C |
| 334 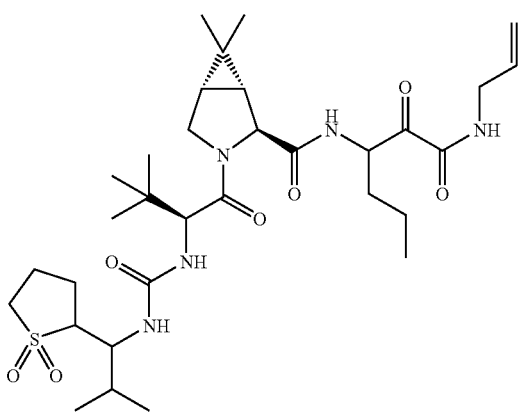 | A |
| 335 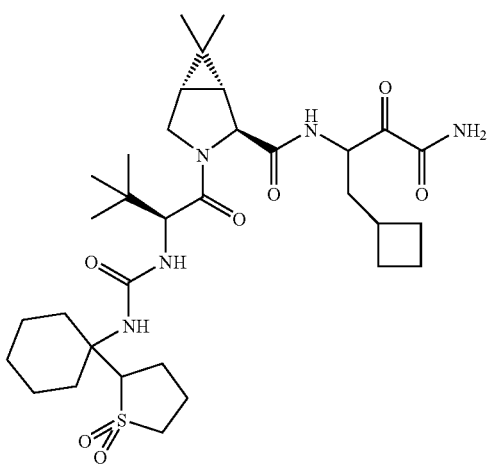 | A |

| | Sulfone Compounds | |
|---|---|---|
| 336 | 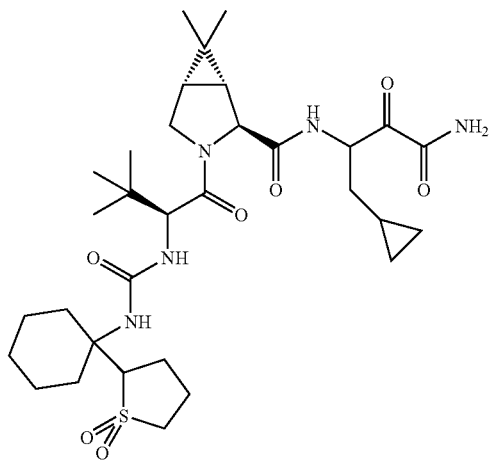 | A |
| 337 | 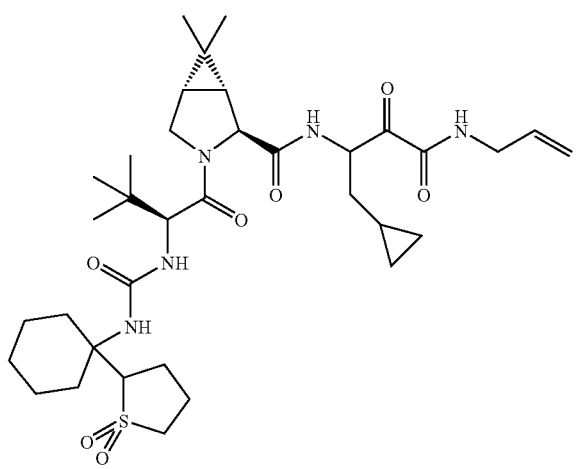 | A |
| 338 | 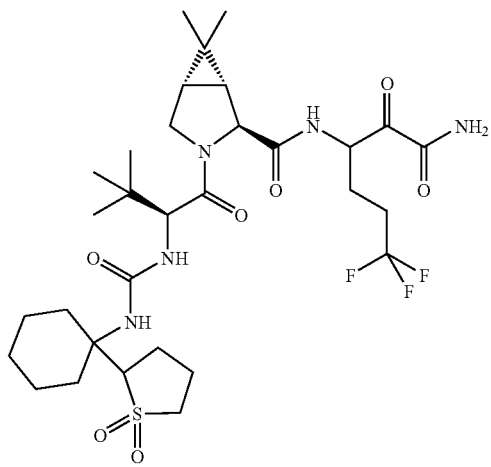 | A |

| Sulfone Compounds | |
|---|---|
| 339 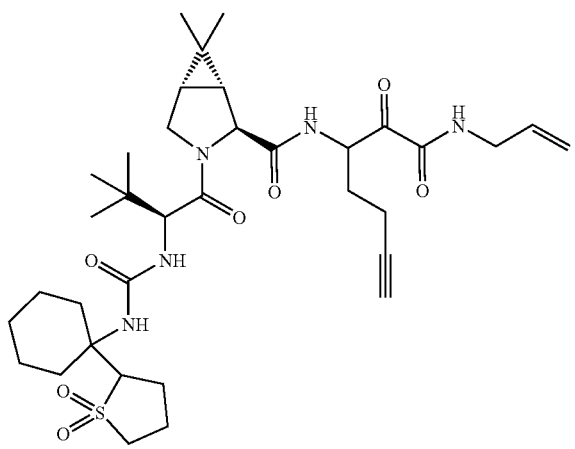 | A |
| 340 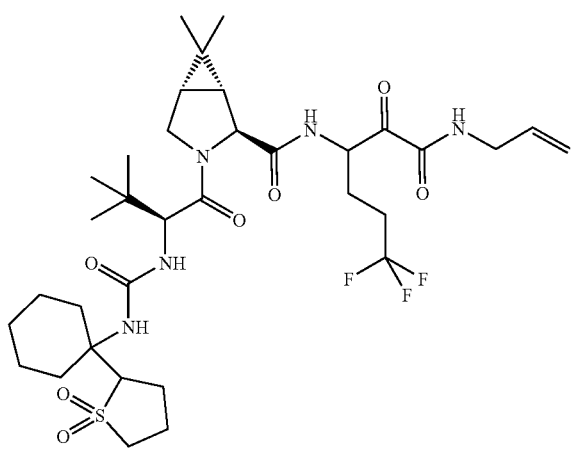 | A |
| 341 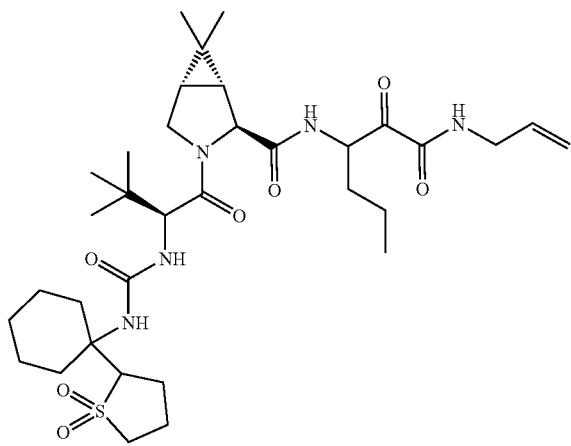 | A |

| Sulfone Compounds | |
|---|---|
| 342 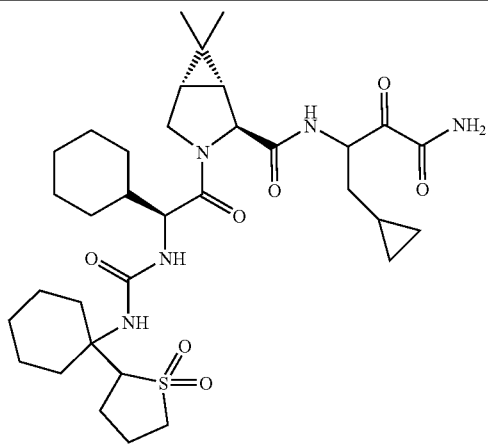 | A |
| 343 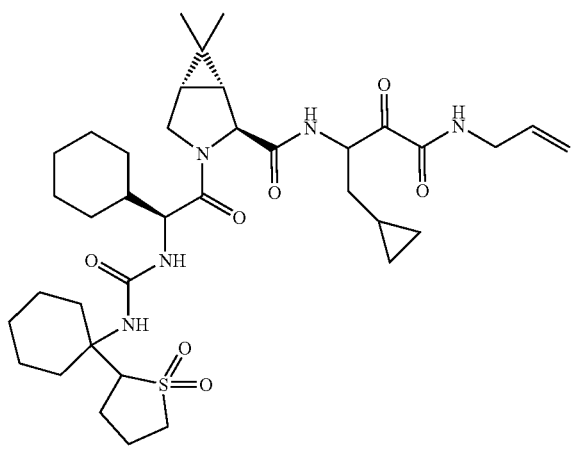 | A |
| 344 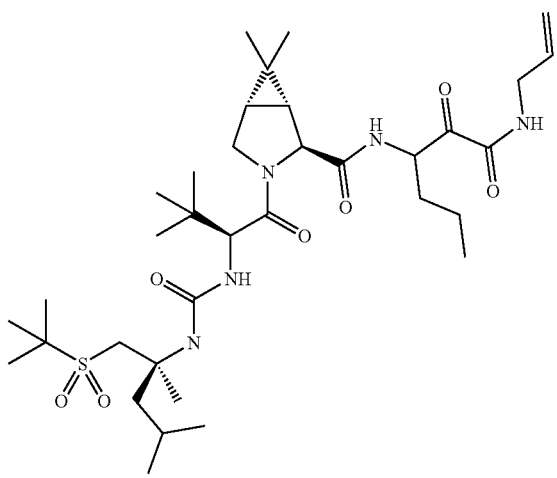 | C |

| Sulfone Compounds | |
|---|---|
| 345 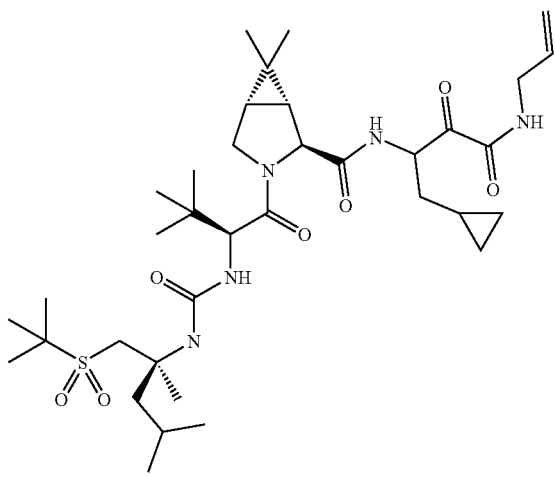 | C |
| 346 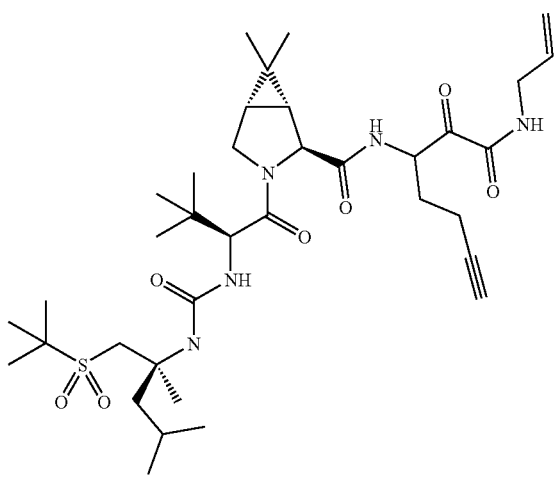 | B |
| 347 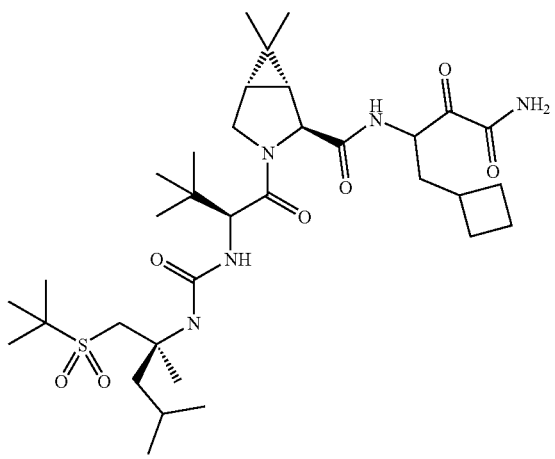 | B |

Sulfone Compounds
348 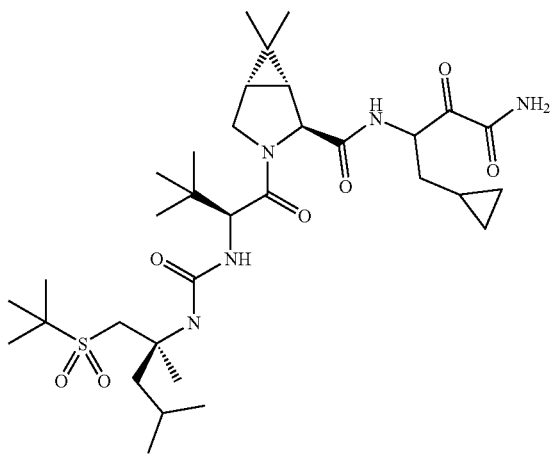 B
349 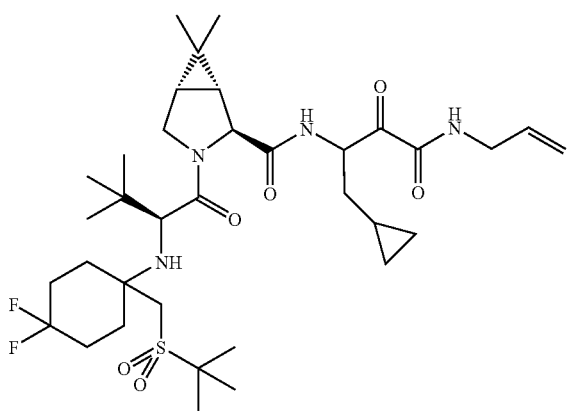 A
350 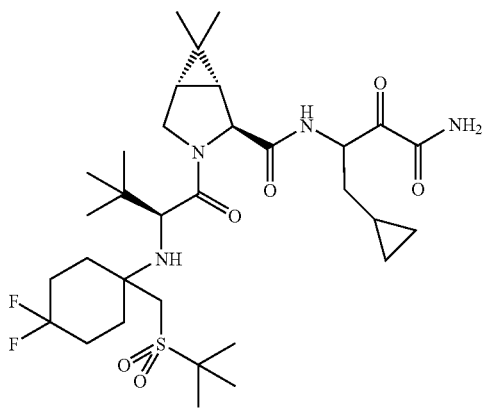 A

Sulfone Compounds
| | | | |
|---|---|---|---|
| 351 | 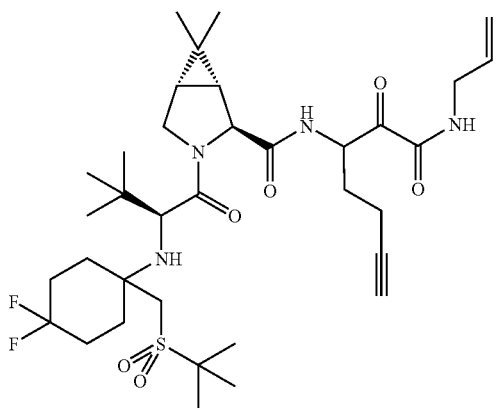 | A | |
| | 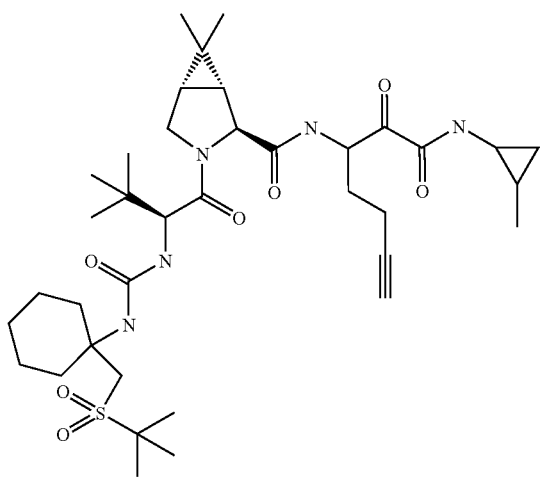 | 18 | 717.9761 |
| | 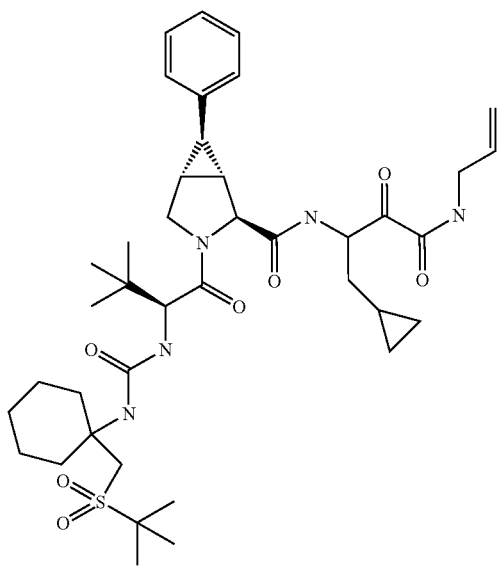 | C | 754.0095 |

-continued
| Sulfone Compounds | | |
|---|---|---|
| 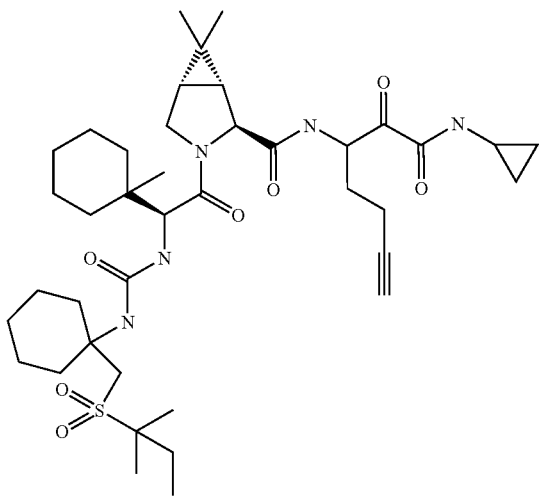 | 7 | 758.0414 |
| 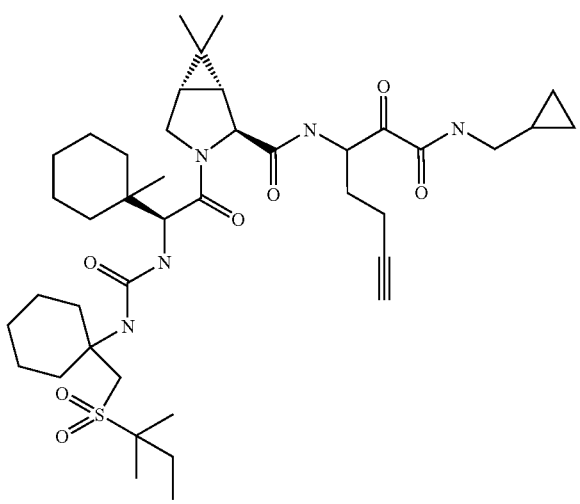 | 10 | 772.0685 |
| 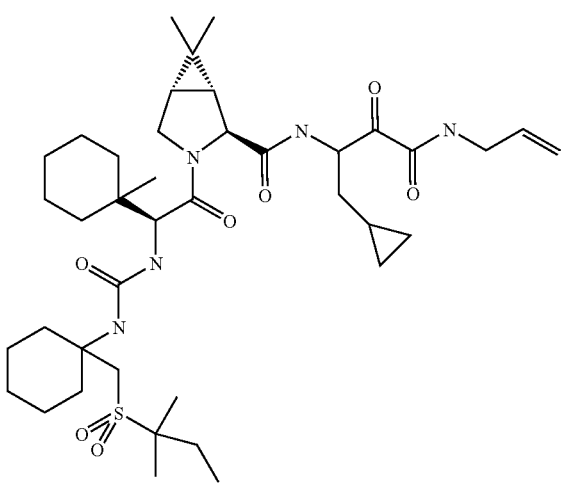 | 14 | 760.0574 |

Sulfone Compounds
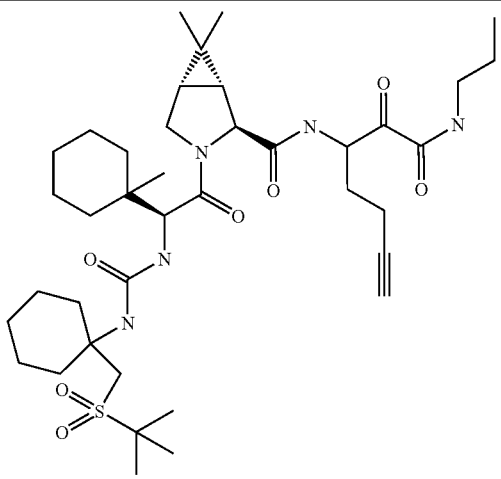
4  746.0303
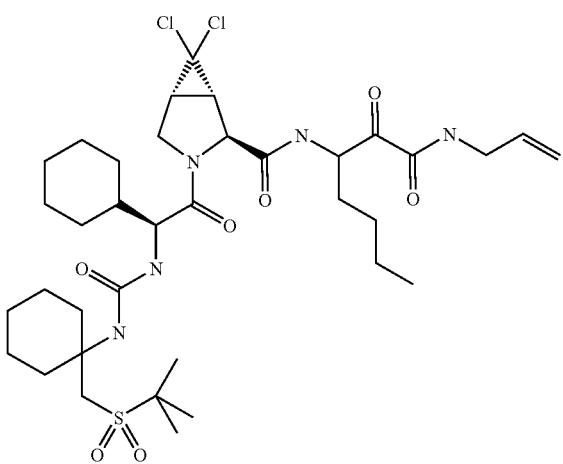
5  774.855
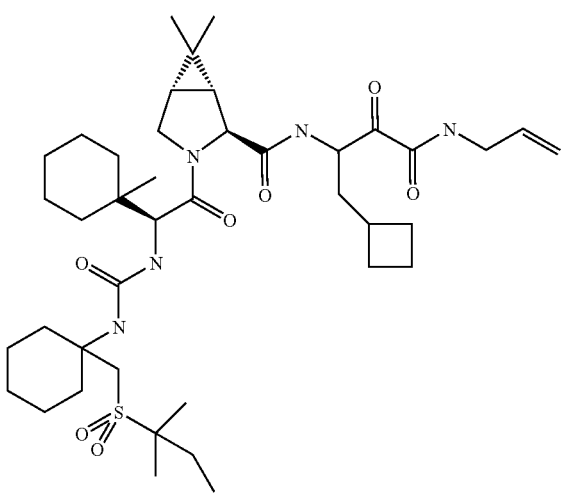
37  774.0844

-continued
Sulfone Compounds
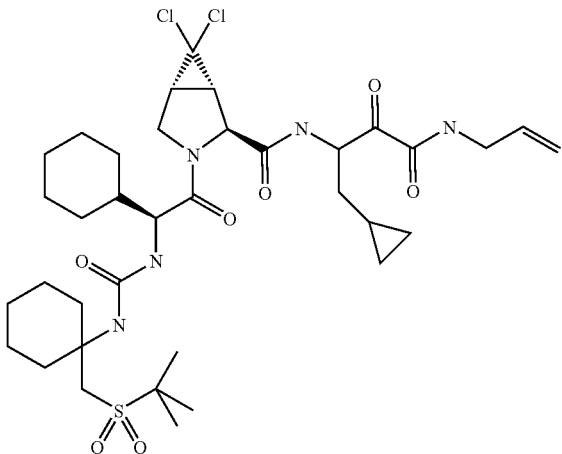
18    772.8391
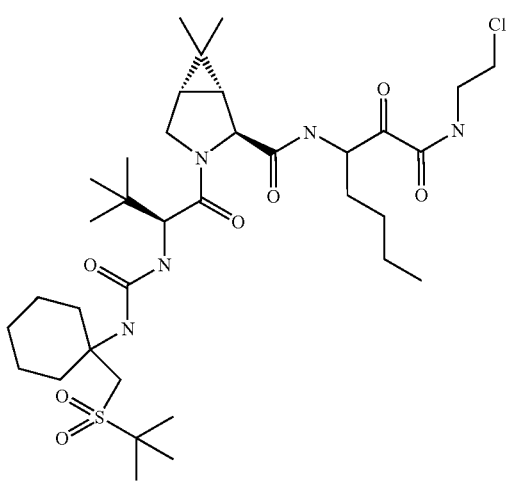
27    730.4148
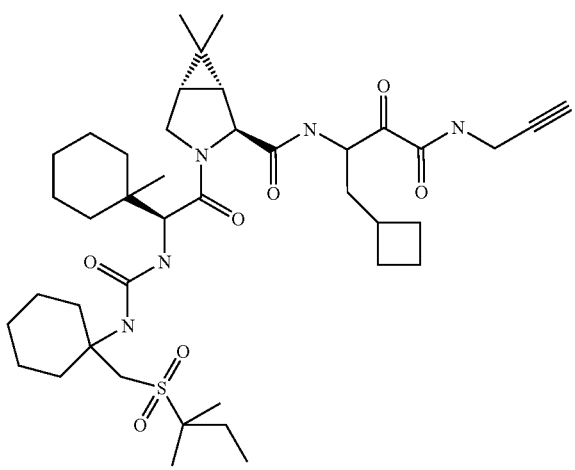
34    772.0685

-continued
Sulfone Compounds
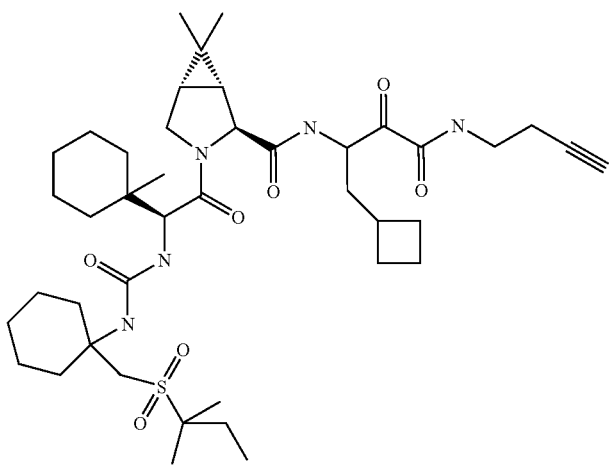
| | |
|---|---|
| 48 | 786.0956 |
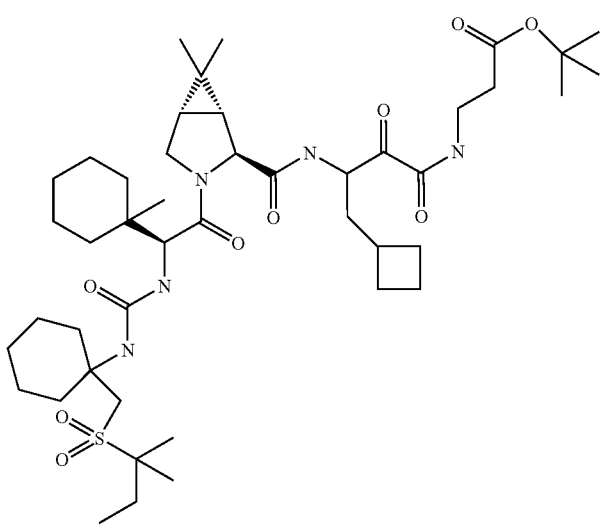
| | |
|---|---|
| 52 | 862.1916 |
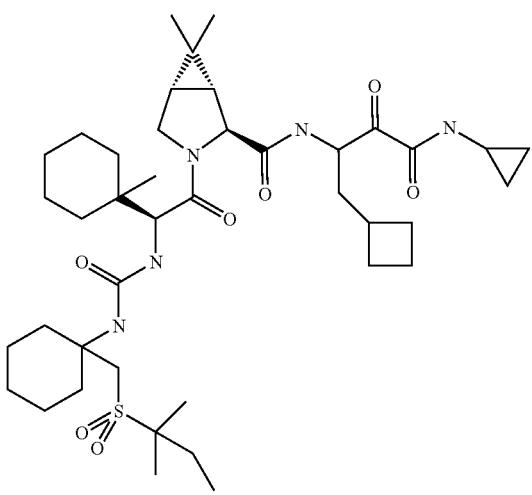
| | |
|---|---|
| 54 | 774.0844 |

-continued
Sulfone Compounds
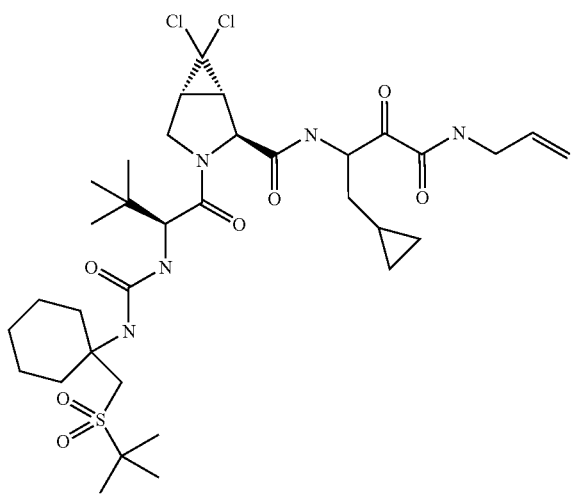
9    746.8008
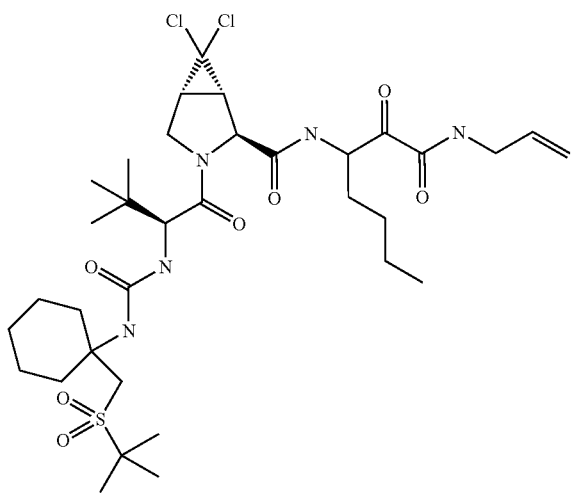
8    748.8168
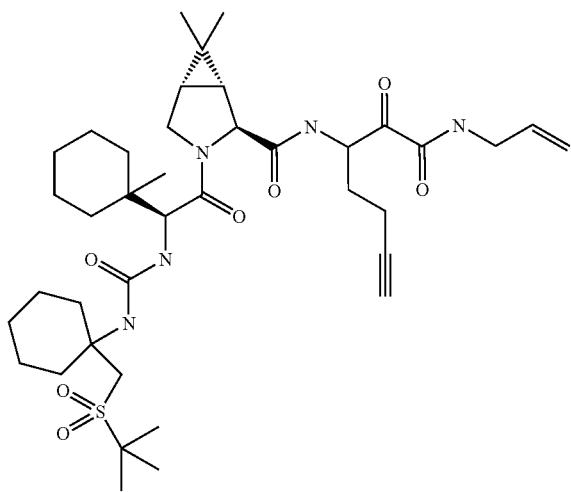
5    744.0143

| Sulfone Compounds | | |
|---|---|---|
| 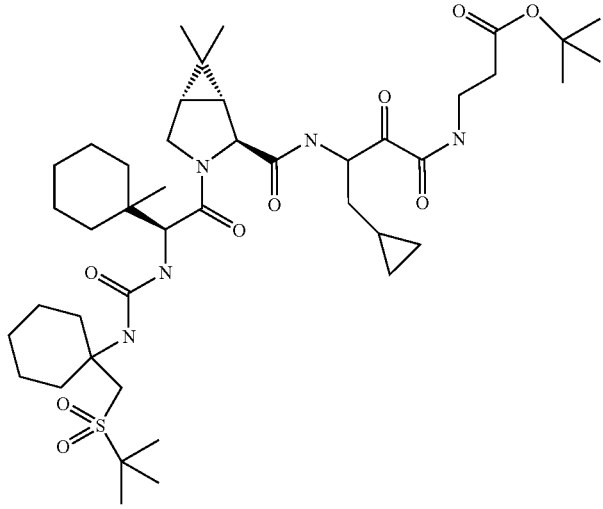 | 17 | 834.1374 |
| 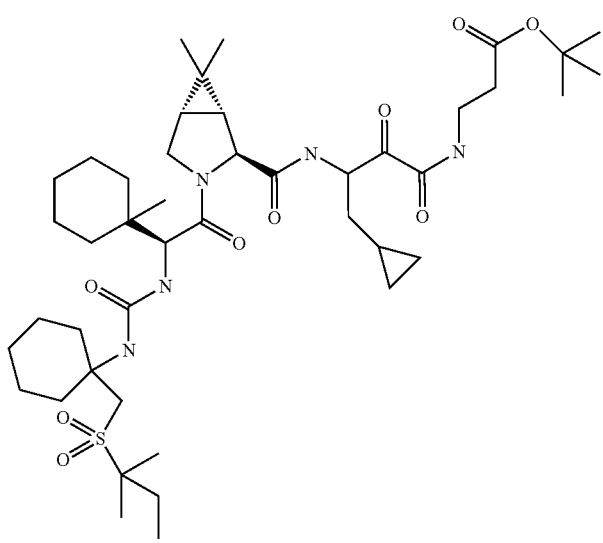 | 19 | 848.1645 |
| 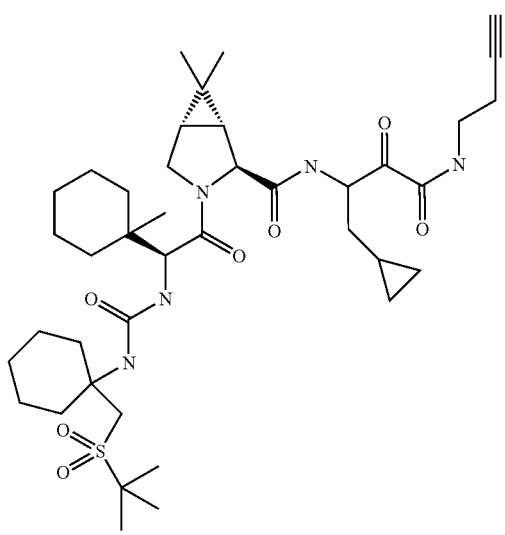 | 17 | 758.0414 |

| Sulfone Compounds | | |
|---|---|---|
| 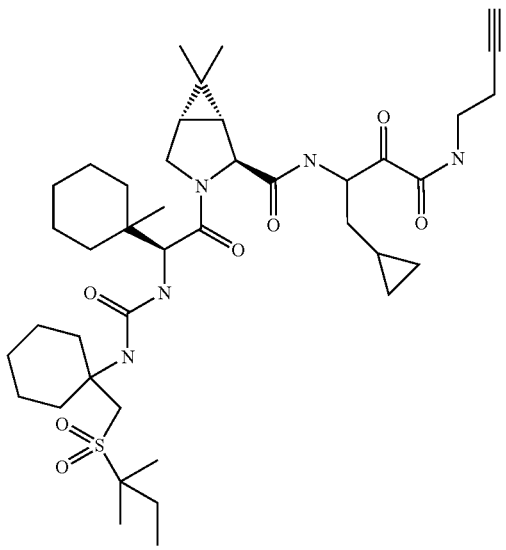 | 20 | 772.0685 |
| 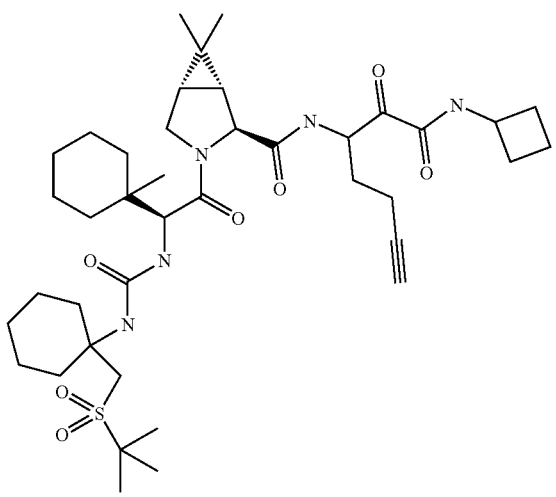 | 10 | 758.0414 |
| 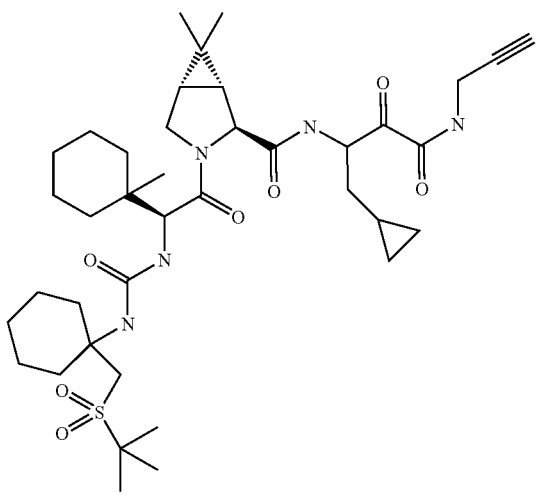 | 8 | 744.0143 |

-continued
| Sulfone Compounds | | |
|---|---|---|
| 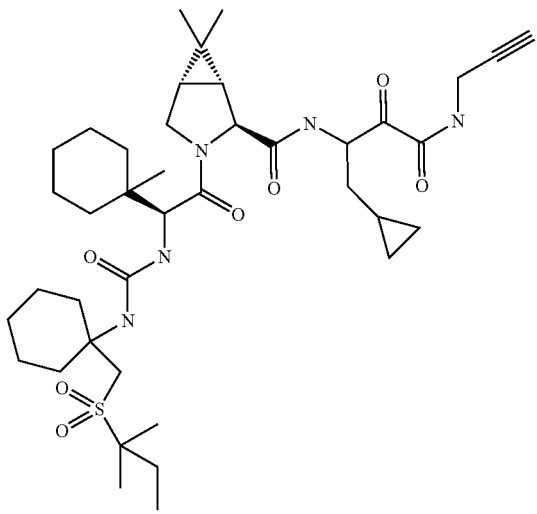 | 17 | 758.0414 |
| 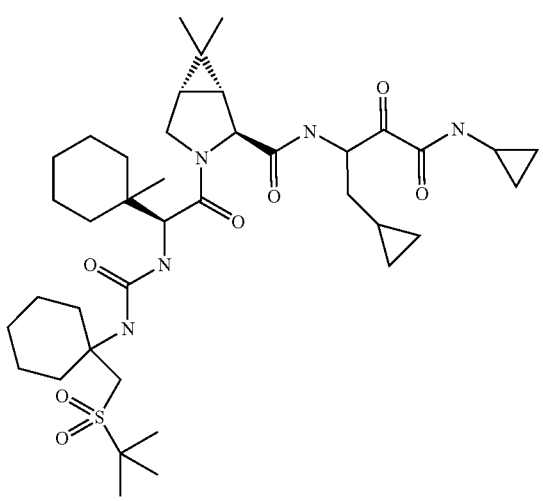 | 12 | 746.0303 |
| 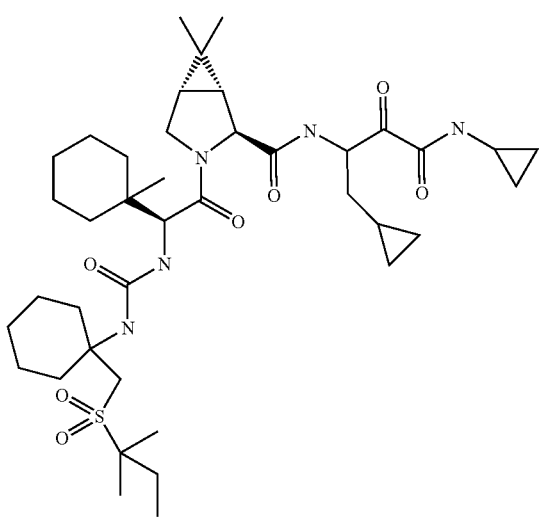 | 13 | 760.0574 |

Sulfone Compounds
| | | |
|---|---|---|
| 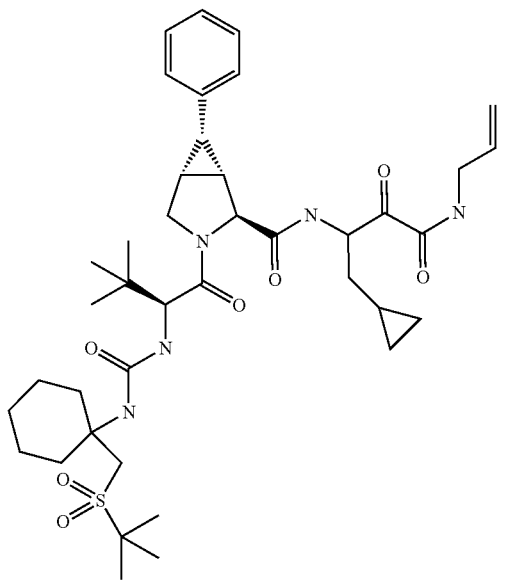 | C | 754.0095 |
| 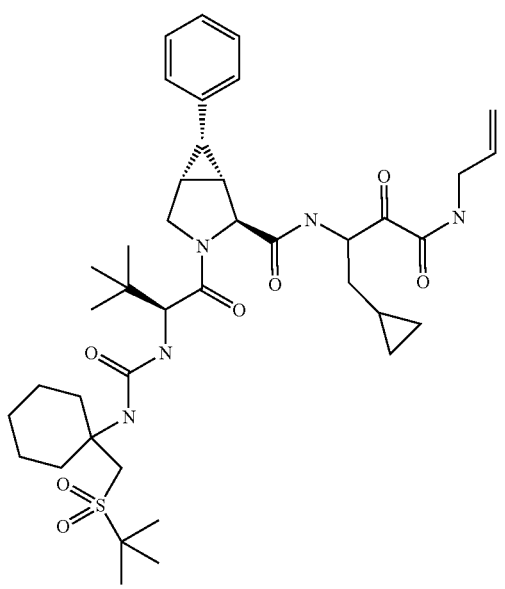 | C | 754.0095 |
| 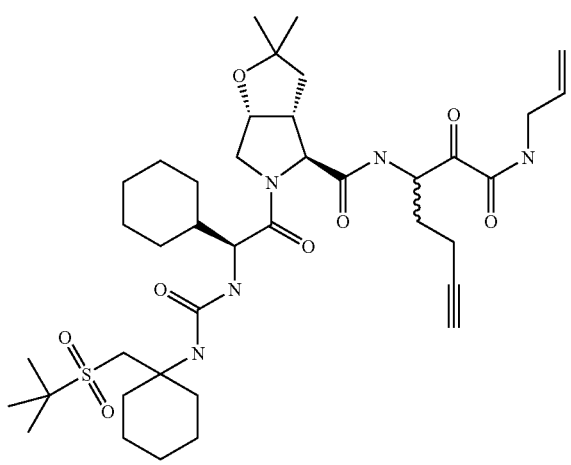 | 23 | 760.0137 |

-continued
Sulfone Compounds
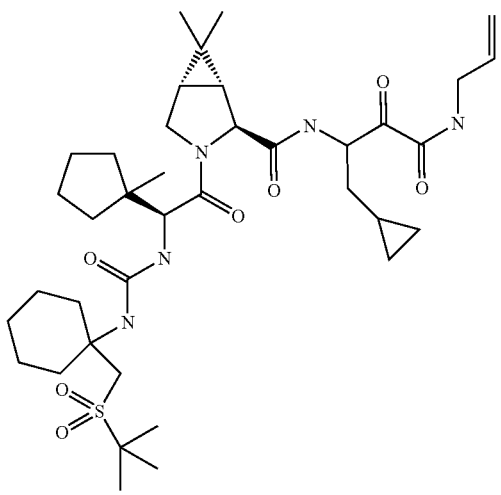
12    732.0032
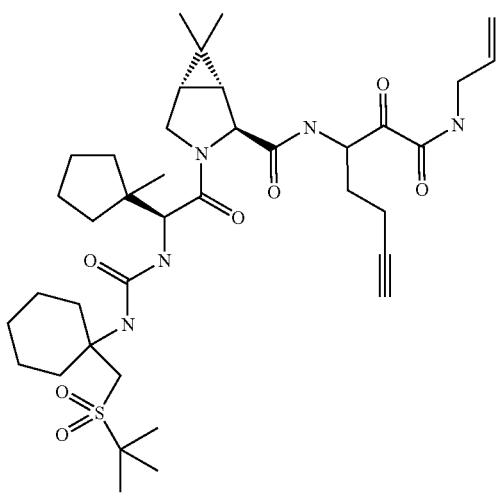
2.4   729.9872
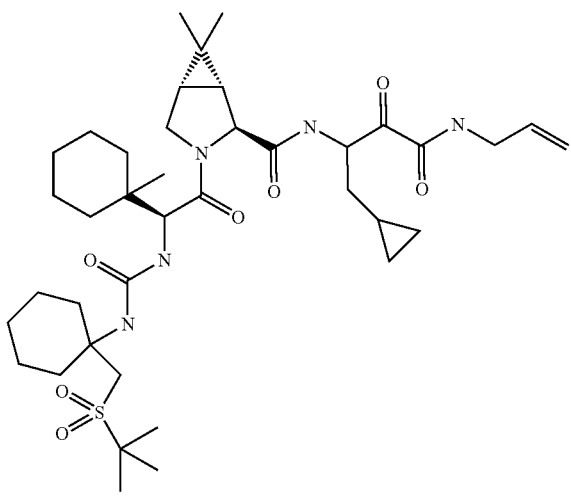
B     786.8661

-continued
Sulfone Compounds
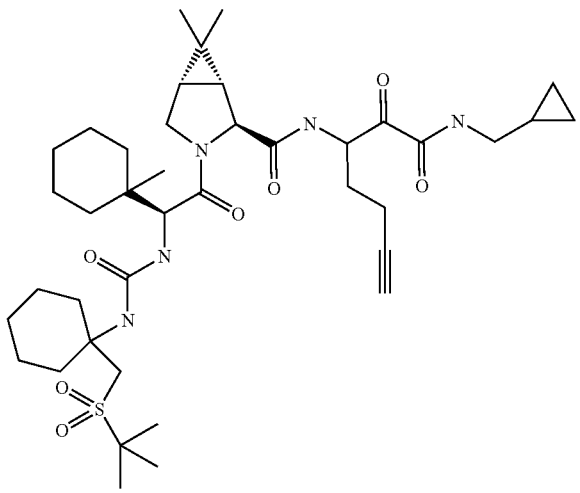
4    758.0414
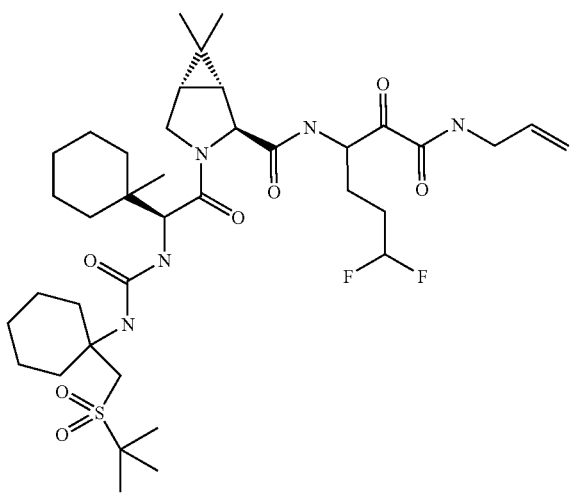
6    770
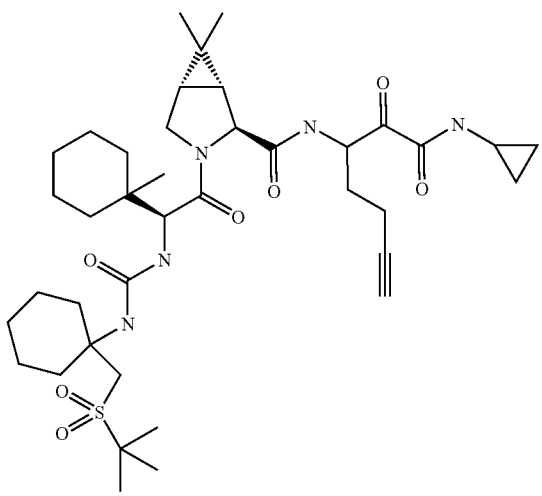
6    744.0143

-continued
Sulfone Compounds
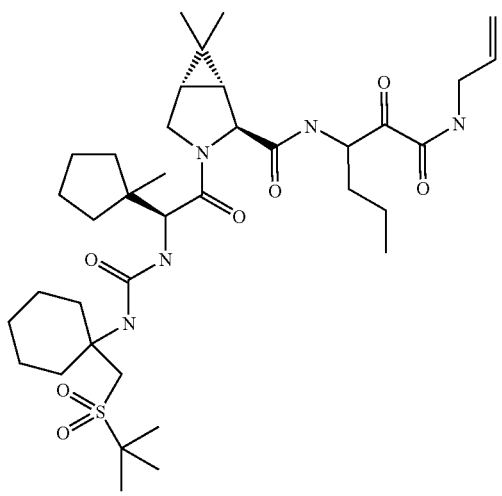
22  719.992
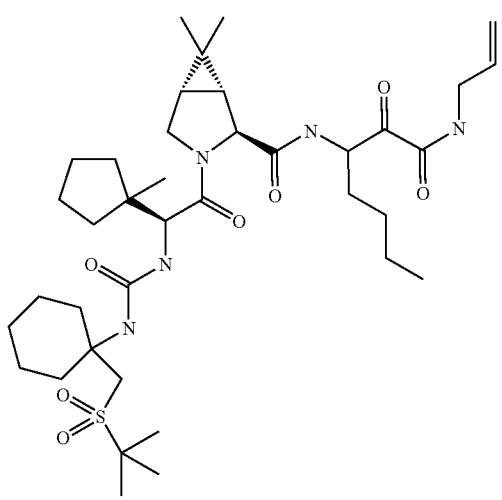
22  734.0191
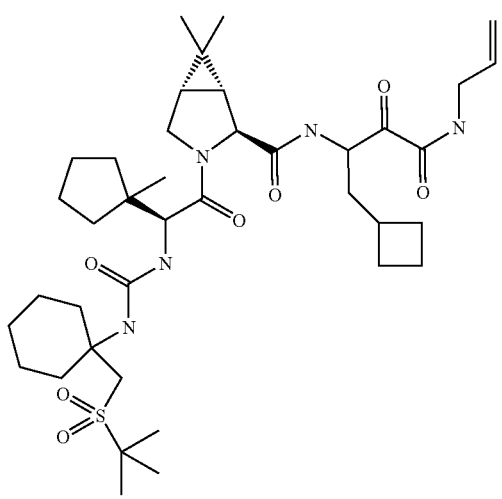
34  746.0303

-continued
Sulfone Compounds
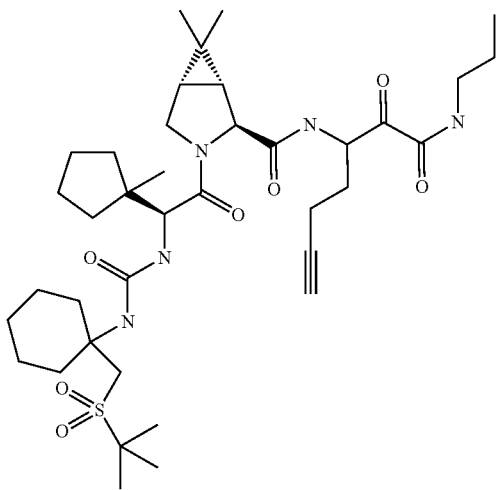
13   732.0032
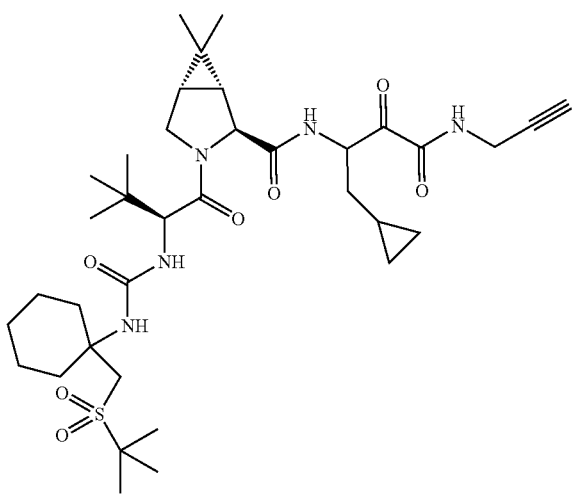
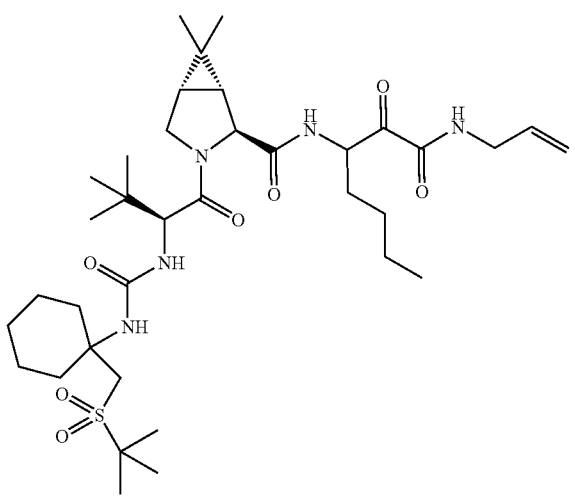

371

-continued

Sulfone Compounds

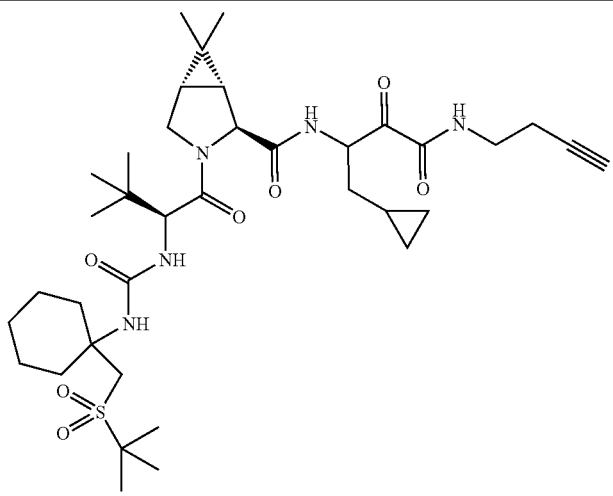

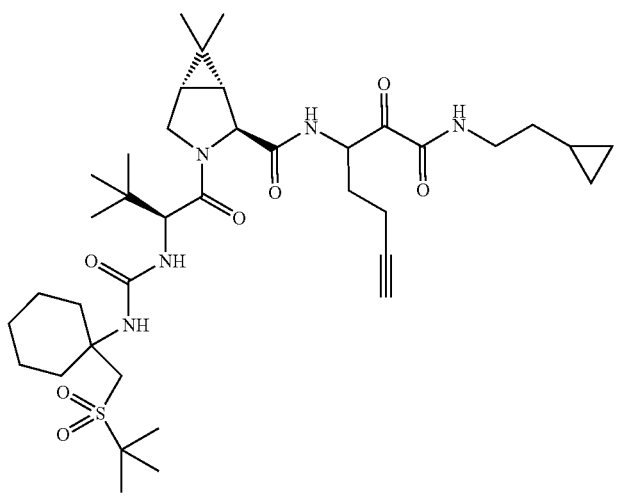

[Ki* ranges are: A = <75 nM;
B = 75-250 nM; C = >250 nM]

Table 3A lists additional compounds made in accordance with this invention. The following experimental procedures describe the preparation of the compounds shown in Table 3A which follows the experimentals.

Example 792

792 (Isomer A)

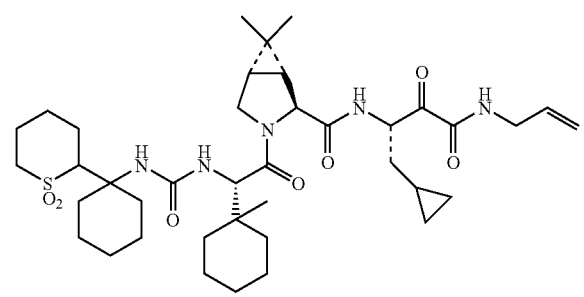

372

Step 1

To a solution of pentamethylene sulfide (10.09 g) in dry benzene (120 ml) was added, portionwise (over a period of 40 min.), N-chlorosuccinimide (13.02 g) while maintaining the internal temperature below 9° C. The resulting reaction mixture was stirred below 15° C. for 45 min. The precipitate was filtered and the supernatant was concentrated under reduced pressure. The residue was diluted with cold hexane, filtered and the supernatant concentrated under reduced pressure to provide the chloride as a yellow oil (11.88 g).

To diisopropylamine (12.5 ml) in anhydrous THF (15 ml) was added n-BuLi (53 ml of a 1.6M solution in hexanes) at −78° C., under an atmosphere of nitrogen, and the resulting mixture was maintained at this temperature for a period of 15 min., before the addition of methyl cyclohexanecarboxylic acid (12.47 ml) and the reaction was maintained at −78° C. for a further 40 min. The chloride in anhydrous THF (50 ml) was added to the reaction mixture and the flask was removed from the cooling bath and allowed to warm slowly to room temperature. The reaction was quenched with 5% aq. $KH_2PO_4$ (100 ml) containing conc. aq. HCl (2.7 ml). The organics were extracted into $Et_2O$/EtOAc, dried ($MgSO_4$) and concentrated under reduced pressure to yield a residue which was purified by silica gel column chromatography using 0-2% EtOAc in hexanes as eluent. Gave the bicycle (792A; 8.12 g) as a yellow oil.

Step 2

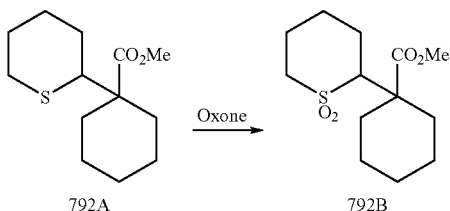

A solution of the sulfide (792A; 0.780 g) in 50% aq. MeOH (8 ml) was cooled to 0° C. and added to a cooled (0° C.) suspension of oxone (5.97 g) in 50% aq. MeOH (8 ml) and the reaction was allowed to warm to room temperature overnight before partitioning between methylene chloride and water. The aqueous layer was further extracted with methylene chloride and the combined organic phases were dried ($MgSO_4$) and concentrated under reduced pressure. The residue was purified by silica gel column chromatography using (25-35%) EtOAc in hexanes to give the sulfone (792B; 0.1598 g). The reaction was repeated using the sulfide (792A; 8.12 g), oxone (62.06 g), methanol (30 ml), water (30 ml) to give the sulfone (792B; 4.73 g).

The racemic mixture (792B; 0.4925 g) was further purified by chiral HPLC using a preparatory Chiralpak AS column using 40% i-PrOH in hexanes (45 ml/min; monitored at 218 nm. Gave (792B-enantiomer A; 0.247 g; retention time 37 min.) followed by (792B-enantiomer B; 0.249 g; retention time 63 min).

Steps 3 and 4:

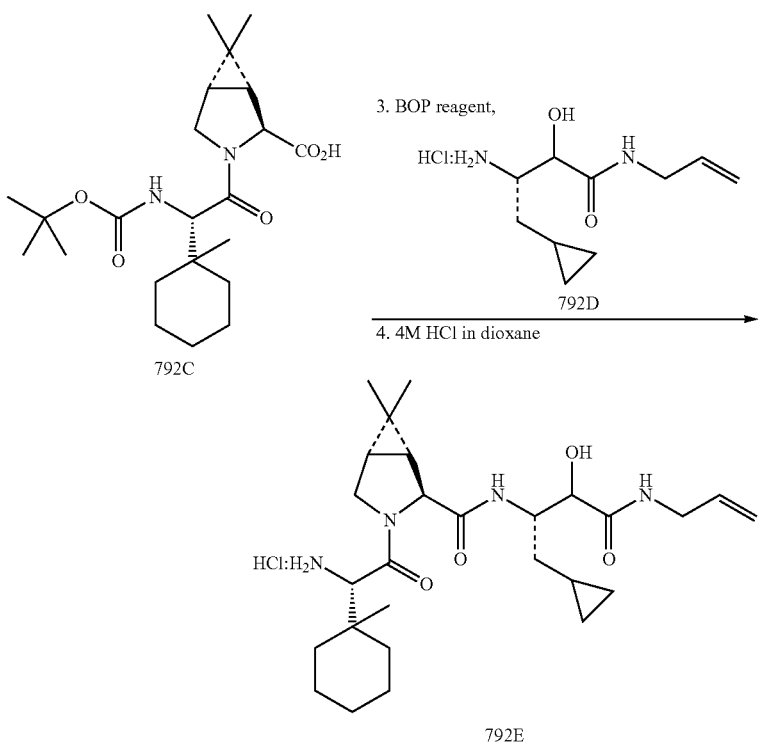

Step 3

To a solution of the carboxylic acid (792C, 0.172 g) and the hydrochloride salt (792D) in dichloromethane (5 ml) was added BOP reagent (0.246 g) followed by triethylamine (0.232 ml) and the resulting reaction mixture was stirred overnight at room temperature. The reaction mixture was partitioned between EtOAc and 10% aq. HCl. The organic phase was separated, washed with sat. aq. $NaHCO_3$, water, dried ($MgSO_4$) and the volatiles were removed under reduced pressure to yield a residue which was used in step 4 without purification.

Step 4

To the residue from step 3 was added 4M HCl in dioxane (10 ml) and the solution was allowed to stand at room temperature for a period of 2 h. The volatiles were removed under reduced pressure to yield the hydrochloride salt (792E), used without purification.

Steps 5 and 6

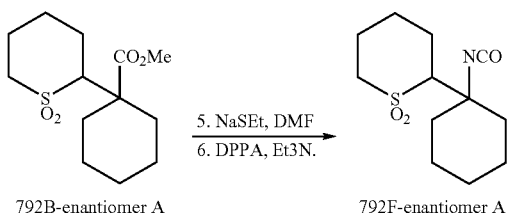

792B-enantiomer A → 792F-enantiomer A

Step 5

To a solution of the methyl ester (792B-enantiomer A; 0.100 g) was dissolved in anhydrous DMF (1 ml) and sodium ethanethiolate (0.122 g) was added and the reaction mixture was allowed to stir at room temperature for approx 72 h. The reaction was partitioned between EtOAc and 10% aq. HCl. The organic phase was separated, washed with water (×4), dried (MgSO$_4$) and the volatiles were removed under reduced pressure.

Step 6

To the residue from step 5 was dissolved in anhydrous toluene (2 ml) and DPPA (0.083 ml) and Et$_3$N (0.054 ml) were added and the reaction was heated to 120° C., under an atmosphere of nitrogen for 1 h. After cooling, the reaction was partitioned between EtOAc and sat. aq. NaHCO$_3$ The organic phase was separated, dried (MgSO$_4$) and the volatiles were removed under reduced pressure to provide the isocyanate (792F-enantiomer A), used without purification.

Steps 7 and 8

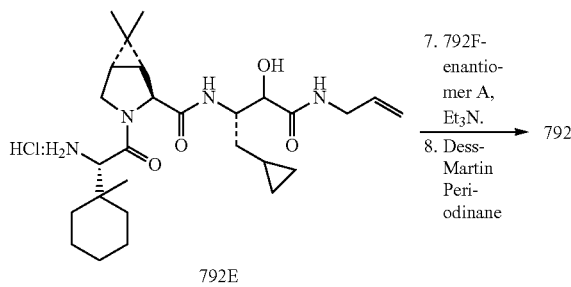

792E

Step 7

To the hydrochloride salt (792E; 0.050 g) in dichloromethane (3 ml) was added triethylamine (0.100 ml) followed by the isocyanate (792F; approx. 0.040 g) in toluene (1 ml) and the reaction mixture was stirred at room temperature overnight. The reaction mixture was partitioned between EtOAc and 10% aq. HCl. The organic phase was separated, washed with sat. aq. sodium bicarbonate, water, dried (MgSO$_4$). The volatiles were removed under reduced pressure to yield a residue which was used without purification in step 8.

Step 8

The residue from step 7 was dissolved in dichloromethane (3 ml) and Dess-Martin peridinane (0.100 g) was added and the reaction was stirred at room temperature for 1 h. The reaction was partitioned between EtOAc and 10% aq. sodium thiosulfate. The organic phase was separated, washed with sat. aq. sodium bicarbonate, dried (MgSO$_4$) and the volatiles removed under reduced pressure. The residue was purified by silica gel column chromatography using EtOAc-hexanes (1:1) as eluent to give the keto-amide (792; 0.0436 g) as a white solid.

Example 795

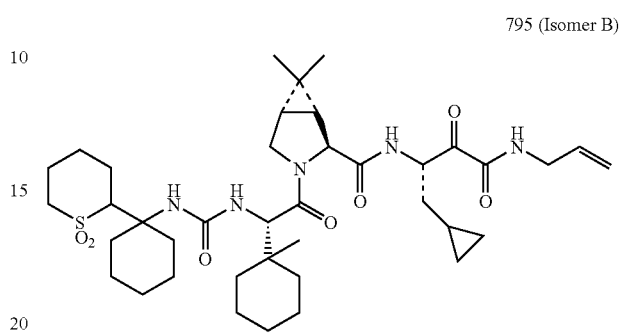

795 (Isomer B)

Using the procedures described for the preparation of 792, 792B-enantiomer B was transformed into the corresponding isocyanate as described in steps 5 and 6. Further by utilizing 792E and steps 7 and 8 and the isocyanate derived from 792B-enantiomer B, 795 was produced.

Example 621

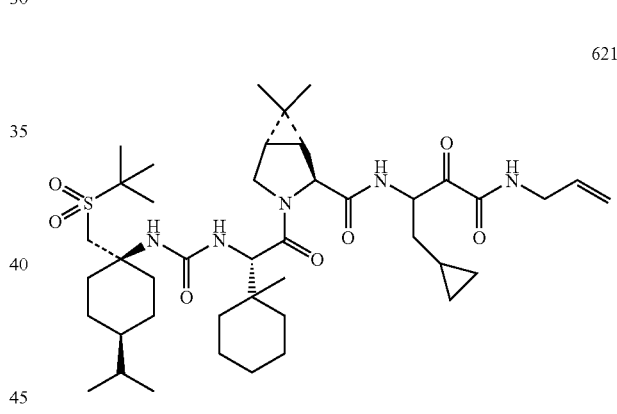

621

Steps 1

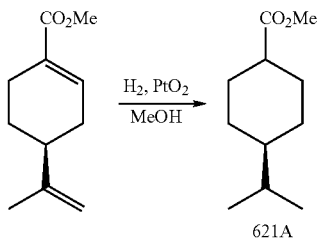

621A

To Methyl Perillate (3 g) in methanol (20 ml) was added PtO$_2$ (0.3 g) and the resulting suspension was placed under an atmosphere of hydrogen (balloon) overnight. The suspension was filtered through a pad of celite and the solid was washed thoroughly with methanol. The filtrate was concentrated under reduced pressure to yield the cyclohexane (621A; 2.93 g), a mixture of diastereomers, as a colorless oil.

Steps 2 and 3

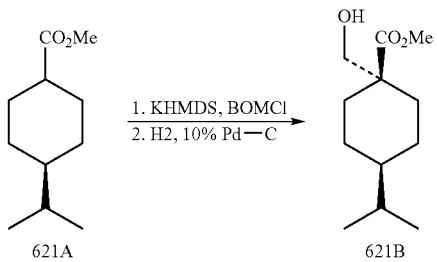

Step 2

The carboxylic esters (621A; 3.75 g) were dissolved in anhydrous diethyl ether (50 ml) and cooled to −78° C., under an atmosphere of nitrogen. KHMDS (69 ml of a 0.5M solution in toluene) was added dropwise and the resulting mixture was stirred for a further 15 min., before the addition of BOMCl (1.7 eq.) and the reaction flask was removed from the cooling vessel and allowed to warm slowly to room temperature. Water (approx. 10 ml) was added and the mixture was partitioned between EtOAc and 10% aq. HCl. The organic phase was separated, washed with sat. aq. sodium bicarbonate, water, dried (MgSO$_4$), and the volatiles removed under reduced pressure. The residue was purified by silica gel column chromatography using EtOAc:Hexanes (1:20) as eluent, providing the intermediate benzyl ether (3.01 g), a colorless oil.

Step 3

To the benzyl ether from step 2 (2 g) was added methanol (10 ml) followed by 10% Pd—C (1 g) and the black suspension was placed under an atmosphere of hydrogen (balloon) overnight. The reaction was filtered through a pad of celite and the solid was washed thoroughly with methanol. The filtrate was concentrated to provide the desired alcohol (621B; 1.362 g) as a colorless oil.

Steps 4 and 5

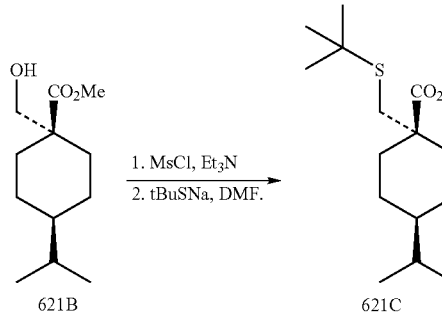

Step 4

The alcohol (621B; 0.32 g) was dissolved in dichloromethane (5 ml) and methane sulfonyl chloride (0.166 ml) followed by triethylamine (0.37 ml) were added and the resulting reaction was stirred for 0.5 h before partitioning between EtOAc and 10% aq. HCl. The organic phase was separated washed with sat. aq. sodium bicarbonate, water, dried (MgSO4) and the volatiles removed under reduced pressure to yield a residue which was used in step 5 without purification.

Step 5

The residue from step 4 was dissolved in DMF (10 ml) and sodium tert-butyl thiolate was added and the resulting reaction mixture was stirred at room temperature under an atmosphere of nitrogen overnight. The reaction mixture was partitioned between EtOAc and aq. 10% HCl. The organic phase was separated, washed with water (×4), dried (MgSO$_4$) and the volatiles removed under reduced pressure. The residue was purified by silica gel column chromatography using EtOAc-Hexanes (3:7) as eluent to give the carboxylic acid (621C, 0.214 g).

Step 6

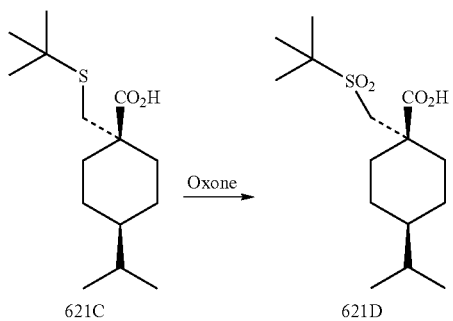

Using the sulfide (621C, 0.090 g), oxone (0.61 g), methanol (2 ml), water (2 ml) and the procedure set forth in example 792 (Step 2), the sulfone (621 D; 0.091 g) was obtained as a white solid.

As described above (Example 792; Steps 6 through 8), the sulfone-carboxylic acid was converted to compound 621.

Example 749

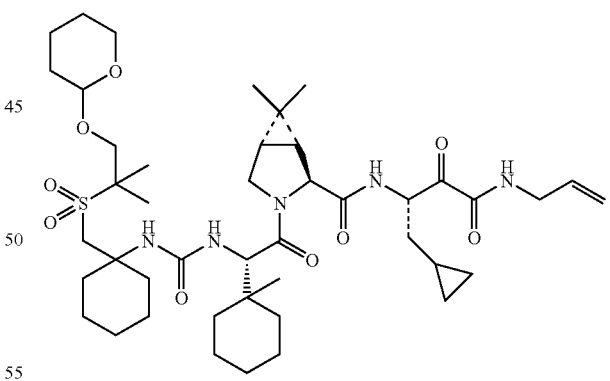

Step 1

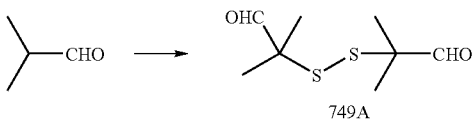

Procedure: To Isobutyraldehyde (59 g, 0.69 mol) in CCl4 was added sulfur monochloride (27.6 mL, 0.345 mol, 0.5 eq.) dropwise at 50° C. After a short lag (10 min), evolution of HCl gas began. After HCl evolution ceased, the mixture was stirred at 55° C. for 2.5 hrs, which TLC indicated the reaction almost completed. Then cooled to room temperature. Crude was concentrated it to dryness. The oily residue, the disulfide (749A), was used without purification.

Step 2

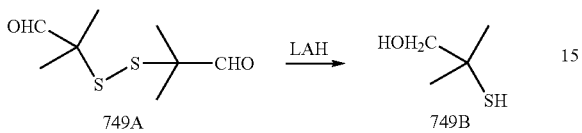

To the disulfide (749A; 7.5 g, 36 mmol) in THF was added LiAlH$_4$ (2.76 g, 72.7 mmol, 2 eq.) at 0° C. very slowly. The mixture was stirred at RT for 3 hrs then Sat. Na2SO4 was added dropwise until white grey solid appeared. Stirred at RT for 10 min. Diltued it with CH$_2$Cl$_2$. Dried over MgSO$_4$. Filtered and concentrated to dryness. Purified it by HPFC with 2~20% EtOAc in hexane to give the alcohol (749B; 6.81 g). Yield 89%.

Step 3

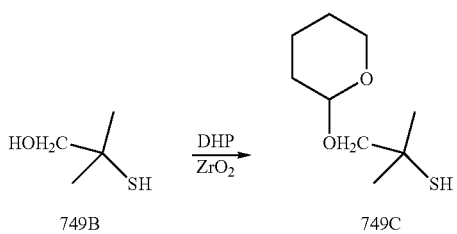

To the alcohol (749B; 10 g, 94.2 mmol) was added 3,4-dihydro-2H-pyran (8.8 mL, 94.2 mmol, 1 equiv) and ZrO$_2$. (2.0 g, 20% w/w). The mixture was stirred at 80° C. for 2 hrs. reaction was diluted it with CH$_2$Cl$_2$ and filtered. The filtrate was concentrated to dryness and purified by HPFC with 2~10% EtOAc in hexane to give 14.3 g of product (749C). Yield 80%.

Step 4

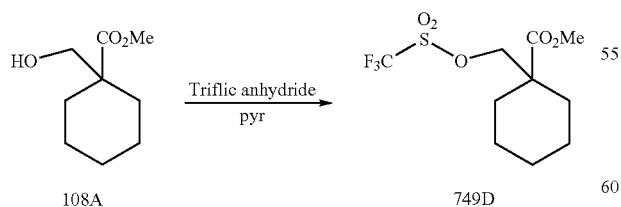

To the alcohol (108A; 3.0 g, 17.4 mmol, 1 equiv) in CH$_2$Cl$_2$ was added pyridine (2.4 mL, 29.6 mmol, 1.7 equiv) and triflic anhydride (3.8 mL, 22.6 mmol, 1.3 equiv) at −20° C. The reaction was stirred at −20~10° C. for 2 hr which MS and TLC indicated the reaction completed. Diluted it with EtOAc, Washed with sat. NH4Cl and brine. Dried over MgSO4. Concentrated it to dryness to give the sulfonate (749D; 5.21 g). Yield 98%.

Step 5

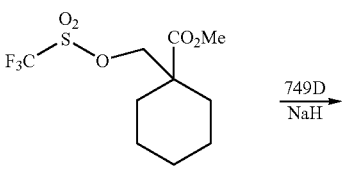

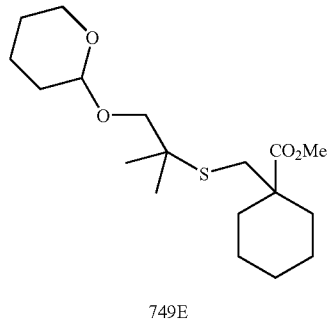

To THF at 0° C. was added NaH (1.02 g, 25.6 mmol, 1.5 eq.), then (749C, 4.88 g, 25.6 mmol, 1.5 eq.). The mixture was stirred at 0° C. for 10 min, then (749D; 5.21 g, 17.1 mmol) was added at 0° C. The reaction was stirred at RT for 1 hr, which TLC indicated no starting materials. Diluted it with EtOAc and water. Extracted aqueous layer with EtOAc. Combined organic layer was washed with H$_2$O and brine. Organic layer was dried over MgSO$_4$. Concentrated it to dryness. Purified it by HPFC with 2~8% EtOAc in hexane to give (749E; 5.89 g) of product. Yield 100%.

Step 6

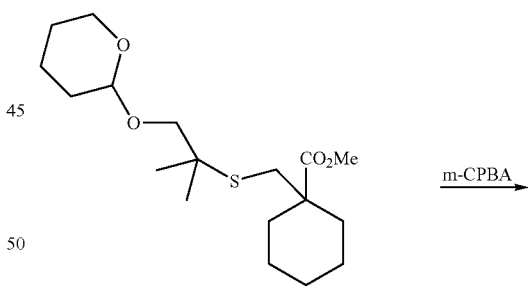

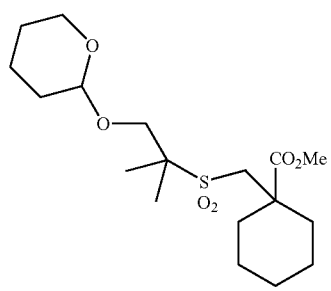

To the sulfide (749E; 0.17 g, 0.49 mmol) in CH$_2$Cl$_2$ was added NaHCO$_3$ (0.205 g, 2.45 mmol, 5 equiv), mCPBA (0.304 g, 1.23 mmol, 2.5 eq.) at 0° C. The reaction was stirred at RT for 2 hrs, which TLC and MS showed the reaction completed. Diluted with CH2Cl2. Washed with sat. NaHCO3 and brine. Dried over MgSO4. Purified it by HPFC with 5~20% EtOAc in hexane to give 0.14 g of the sulfone (749F). Yield 76%.

The methyl ester (749F) can be converted to the corresponding carboxylic acid and subsequently the isocyanate (Example 108; Steps 5 and 6) and converted to 749 (Example 792; Steps 7 and 8).

Example 811

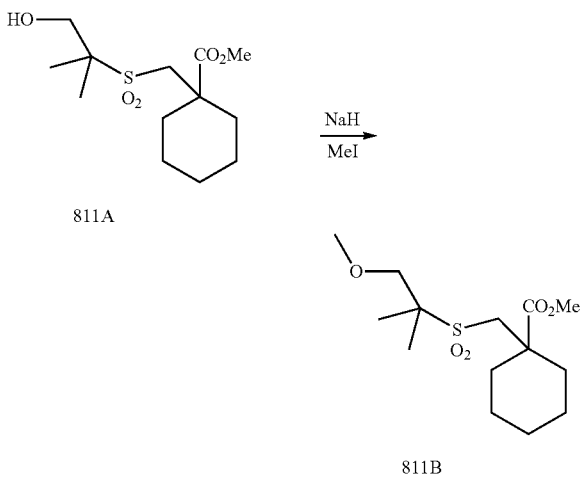

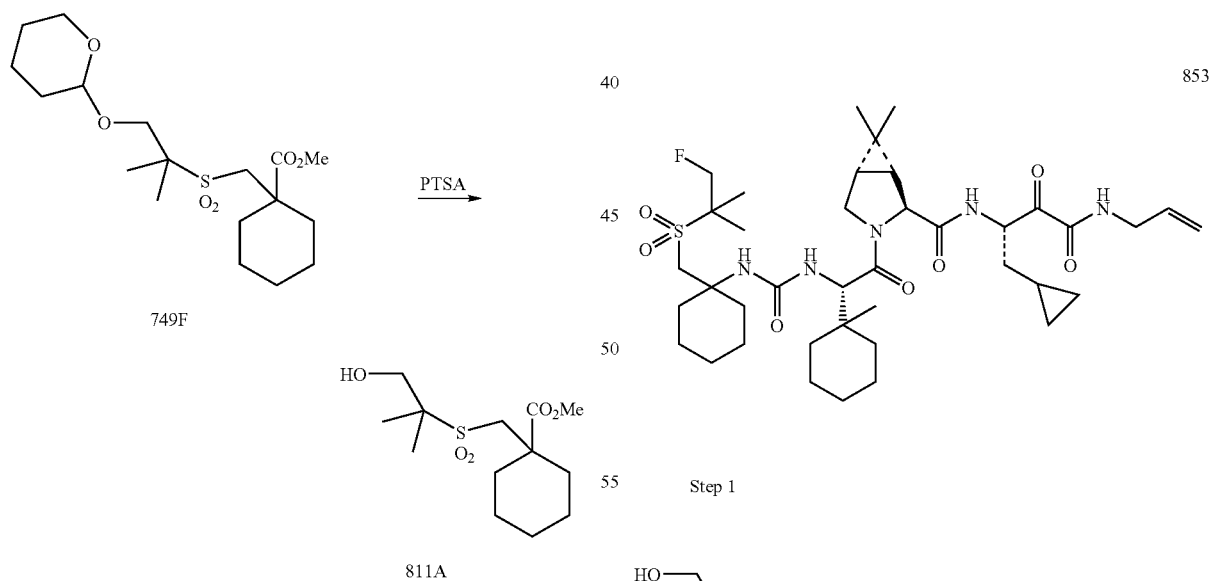

To 749F (70 mg, 0.18 mmol) in MeOH was added pTsOH. The reaction was stirred at RT for overnight. MS showed the reaction almost completed. Concentrated it to dryness. Diluted with EtOAc. Washed with sat NaHCO$_3$, brine. Purified by HPFC with 10~40% EtOAc in hexane to give 52 mg of the alcohol (811A) Yield 99%.

To NaH (88 mg, 2.21 mmol, 1.3 equiv) in DMF at 0° C. was added the alcohol (811A; 0.5 g, 1.7 mmol) and MeI (0.16 mL, 2.56 mmol, 1.5 equiv). The reaction was stirred at RT for 2 hrs which TLC indicated the reaction didn't completed. 1 equiv MeI was added again. The reaction was stirred at RT for overnight. Diluted it with EtOAc. Washed with water, brine. Dried over MgSO4. Purified it by HPFC with 2~10~40% EtOAc in hexane to give the ether (811B; 0.283 g) Yield 54%.

The methyl ester (811B) can be converted to the corresponding carboxylic acid and subsequently the isocyanate (Example 108; Steps 5 and 6) and converted to 749 (Example 792; Steps 7 and 8).

Example 853

383

-continued

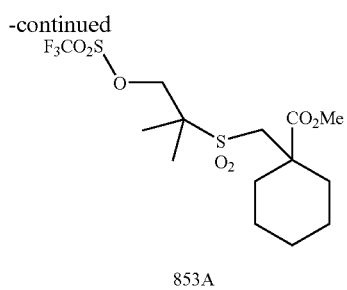

853A

To the alcohol (811A; 56 mg, 0.19 mmol, 1 equiv) in CH$_2$Cl$_2$ was added pyridine (0.026 mL, 0.32 mmol, 1.7 equiv) and triflic anhydride (0.042 mL, 0.25 mmol, 1.3 equiv) at −20° C. The reaction was stirred at −20~10° C. for 2 hr which MS and TLC indicated the reaction completed. Diluted it with EtOAc, Washed with sat. NH4Cl and brine. Dried over MgSO4. Concentrated it to dryness to give 75.9 mg of crude product (853A)

Step 2

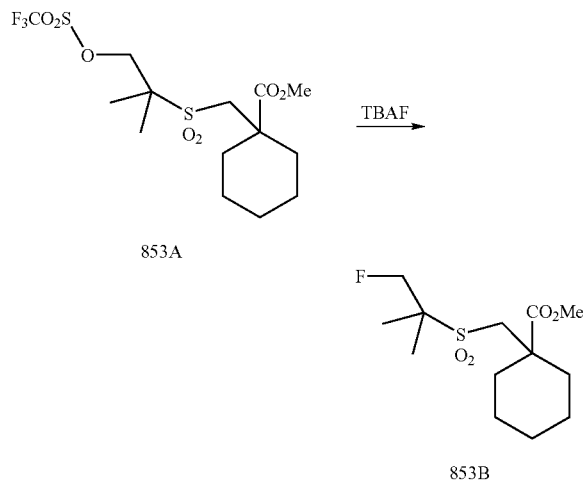

To 853A (75.9 mg, 0.18 mmol, 1 equiv) in ether was added tetra-n-butyl ammonium fluoride (0.23 mL, 0.23 mmol, 1.3 equiv) dropwise at −15° C. The reaction was stirred at RT for over night. Diluted it with ether, washed with sat. NH4Cl and brine. Dried over MgSO$_4$. Purified it with 2~10% EtOAc in hexane to give 32 mg of the fluoride (853B). Yield 60%.

The methyl ester (853B) can be converted to the corresponding carboxylic acid and subsequently the isocyanate (Example 108; Steps 5 and 6) and converted to 749 (Example 792; Steps 7 and 8).

Example 455

455

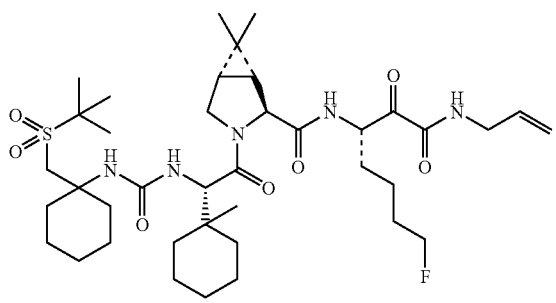

384

Steps 1 and 2

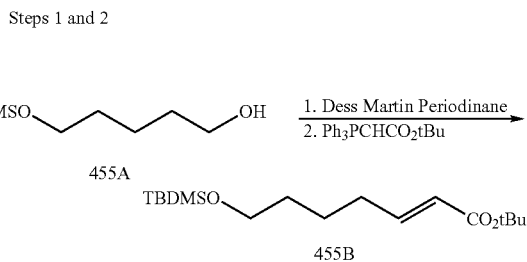

Steps 1 and 2 ('one-pot')

Dess-Martin Periodinane (21.35 g) was added to a solution of the alcohol (455A; 10.00 g) in dichloromethane (100 ml) and stirred for 45 min., before the addition of the phosphorane (17.42 g) and stirred overnight. The reaction mixture was partitioned between 5% aq. sodium thiosulfate and EtOAc and the organic phase was separated, washed with sat. aq. sodium bicarbonate, water, dried (MgSO$_4$) and concentrated under reduced pressure. Hexanes was added to the residue and the resulting suspension was stirred vigorously for 2 h and filtered. The filtrate was concentrated under reduced pressure and purified by silica gel ciolumn chromatography using EtOAc-hexanes (1:99) as eluent to give the desired alkene (455B; 7.33 g) as a yellow oil.

Step 3

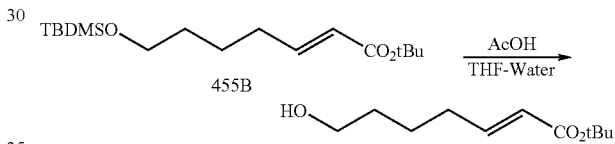

Acetic acid (26 ml) was added to a solution of the silyl ether in THF (6 ml) and water (14 ml) and the resulting mixture was stirred at room temperature overnight. The reaction was partitioned between EtOAc and sat. aq. sodium bicarbonate. The organic phase was separated, washed with water, dried (MgSO$_4$) and the volatiles removed under reduced-pressure. The residue was purified by silica gel column chromatography using EtOAc-hexanes (1:5) as eluent to give the alcohol (455C, 4.46 g) as a colorless oil.

Step 4

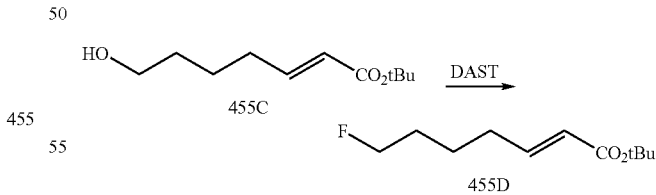

DAST (1.32 ml) was added to a stirred solution of the alcohol (455C; 2.00 g) in dichloromethane (50 ml) at −78 C, under an atmosphere of nitrogen. When the addition was complete the cooling bath was removed and the reaction allowed to stir at room temperature for 2 h., before partitioning between EtOAc and water. The organic phase was separated, dried (MgSO$_4$) and the volatiles removed under reduced pressure before purification by column chromatography. Gave the fluoride (455D; 0.758 g).

Step 5

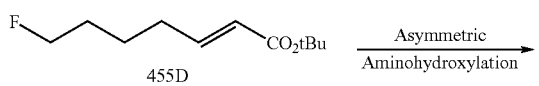

Using benzylcarbamate (2.06 g) in n-PrOH (18 ml), the alkene (455D; 0.881 g), NaOH (0.537 g), freshly prepared tBuOCl (1.54 ml), (DHQ)₂PHAL (0.176 g) in nPrOH (16 ml), potassium osmate (0.065 g) and the procedure set for in Angewandte Int. Ed. (Engl), 1996, 35, 2813 a crude product was formed which was purified by silica gel column chromatography using EtOAc-Hexanes (1:5) as eluent to give the desired hydroxyamide (455E; 0.892 g).

Step 6

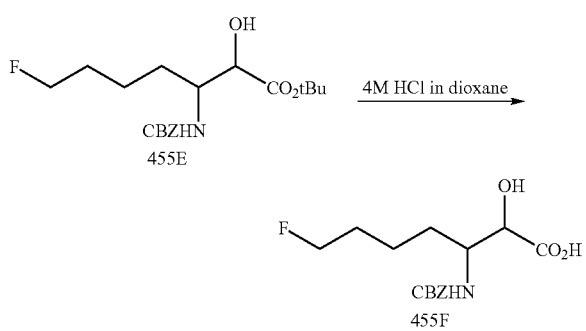

4M HCl in dioxane (25 ml) (ex. Aldrich) was added to the t-Bu ester (455E; 0.69 g) and the resulting solution was allowed to stand at room temperature for 2 h. The volatiles were removed under reduced pressure to yield the carboxylic acid (455F; 0.613 g), used in subsequent reactions without purification.

Step 7

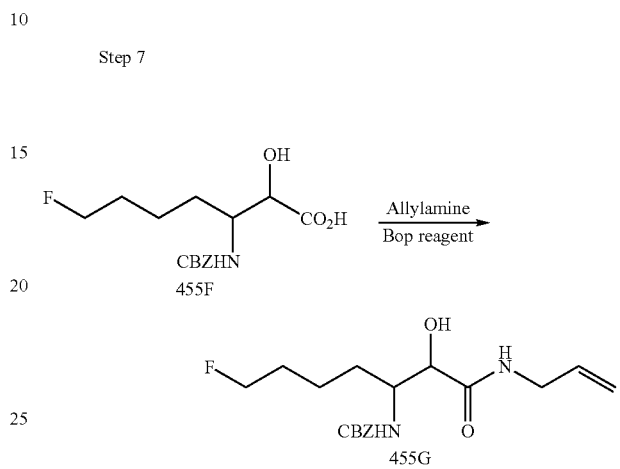

Bop reagent (0.254 g) followed by triethylamine (0.240 ml) were added to a mixture of the carboxylic acid (455F; 0.15 g) and allylamine (0.043 ml) in dichloromethane (5 ml) and the resulting reaction mixture was stirred at room temperature overnight. The reaction was partitioned between EtOAc and 10% aq. HCl. The organic phase was separated, washed with sat. aq. sodium bicarbonate, waster, dried (MgSO₄) and the volatiles removed under reduced pressure. The residue was purified by silica gel column chromatography on silica gel using EtOAc:Hexanes (7:3) as eluent to give the amide (455G; 0.151 g) as a white solid.

Steps 8, 9 and 10

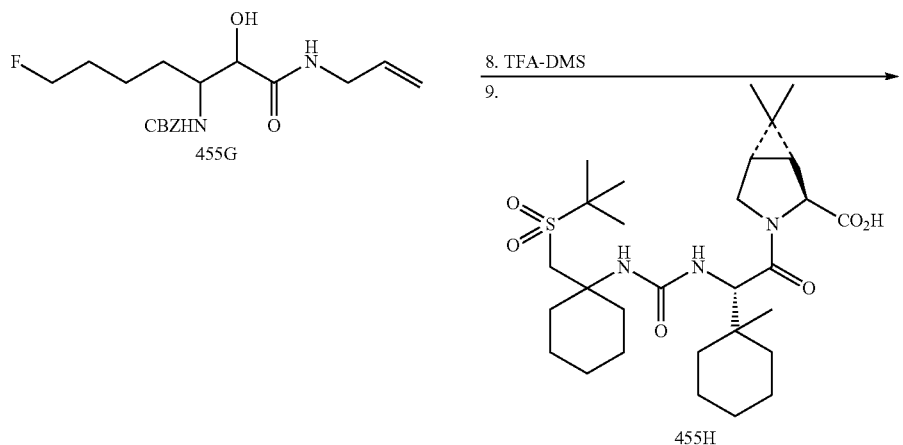

10. Dess-Martin Periodinane

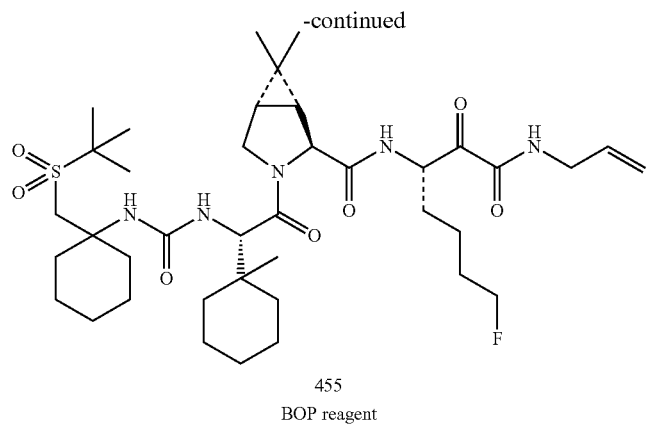

455
BOP reagent

Step 8

To the benzylcarbamate (455G; 0.037 g) was added TFA (2 ml) followed by methylsulfide (0.5 ml) and the resulting solution was allowed to stand at room temperature for 3 h., before removal of the volatiles. The crude reaction product was used in step 9, below, without purification.

Step 9

To the residue from step 8 was added dichloromethane (3 ml), the carboxylic acid (455H, 0.050 g), Bop reagent (0.047 g) and finally triethylamine (0.044 ml) and the resulting mixture was stirred at room temperature overnight. The reaction was partitioned between EtOAc and 10% aq. HCl. The organic phase was separated, washed with sat. aq. sodium bicarbonate, dried (MgSO$_4$) and the volatiles removed under reduced pressure to yield a residue which was used, in step 10, below, without purification.

Step 10

To the residue from step 9, was added dichloromethane (3 ml) followed by Dess-Martin periodinane (0.075 g) and the suspension was stirred at room temperature for 2 h., before partitioning between EtOAc and 5% aq. sodium thiosulfate. The organic phase was separated, washed with sat. aq. sodium bicarbonate, water, dried (MgSO$_4$) and the volatiles removed under reduced pressure. The crude reaction product was purified by silica gel column chromatography to give the desired keto-amide (455; 0.0467 g) as a white solid.

Example 458

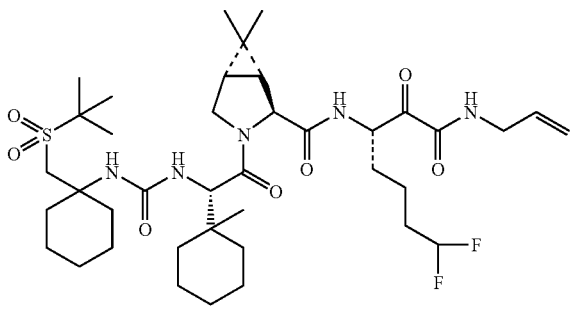

458

Step 1

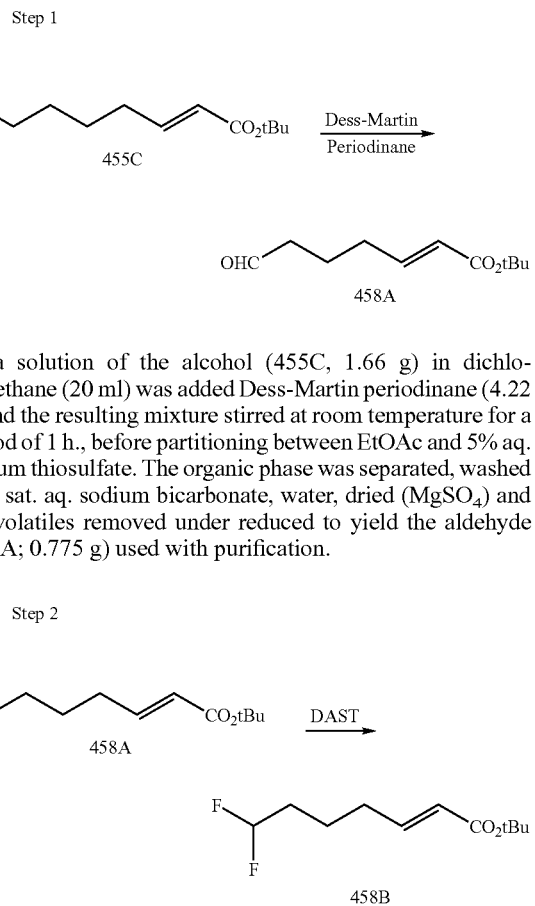

To a solution of the alcohol (455C, 1.66 g) in dichloromethane (20 ml) was added Dess-Martin periodinane (4.22 g) and the resulting mixture stirred at room temperature for a period of 1 h., before partitioning between EtOAc and 5% aq. sodium thiosulfate. The organic phase was separated, washed with sat. aq. sodium bicarbonate, water, dried (MgSO$_4$) and the volatiles removed under reduced to yield the aldehyde (458A; 0.775 g) used with purification.

Step 2

DAST (1.11 ml) was added dropwise to a stirred solution of the aldehyde (458A; 0.755 g) in dichloromethane (50 ml) while cooled in an ice bath, under an atmosphere of nitrogen. After completion of the addition the resulting mixture was stirred at room temperature for a period of 2 h., before partitioning between EtOAc and water. The organic phase was separated, dried (MgSO$_4$) and the volatiles removed under reduced pressure. The residue was purified by silica gel column chromatography to give the desired difluoride (458B; 0.758 g).

Using 458B and the procedures outlined in example 455 (Steps 5 through 10) target 458 was produced.

Example 423

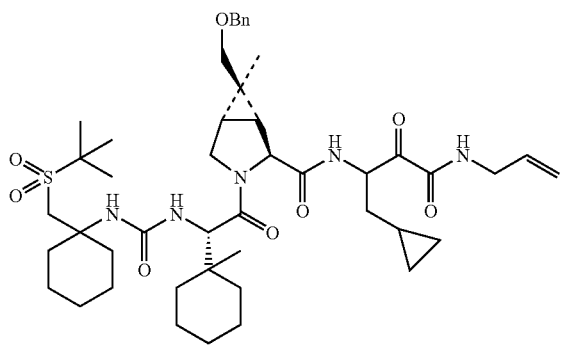

Step 1

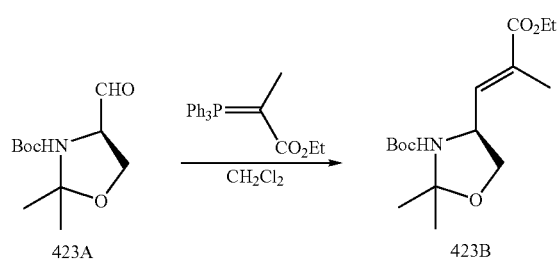

To a solution of Garner aldehyde (423A; 10.7 g) in dichloromethane (110 ml) was added (carbethoxyethylidene)triphenylphosphorane (28.75 g) the resulting solution was stirred at room temperature overnight. The volatiles were removed under reduced pressure and the residue purified by silica gel column chromatography using 4-10% EtOAc in hexanes to give the desired alkene (423B; 12.7 g), as a colorless oil.

Step 2

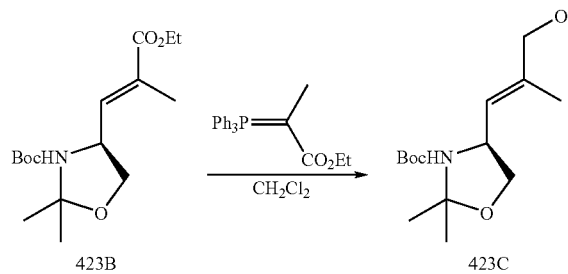

To a solution of the ethyl ester (423B; 12.72 g) in dichloromethane (20 ml) was added DIBAL-H (90 ml of a 1M solution in dichloromethane) at −78 C, under an atmosphere of nitrogen. When the addition was complete the reaction was maintained at this temperature for a further 30 min the at room temperature for 1 h., before the addition of MeOH (3 ml) and sat aq. potassium sodium tartrate (3 ml) and EtOAc. The organic phase was separated, washed with 1M aq HCl, brine, dried ($MgSO_4$). The volatiles were removed under reduced pressure and the residue purified by silica gel column chromatography using 6-35% EtOAc in hexanes to give the alcohol (9.06 g), as a colorless oil.

Step 3

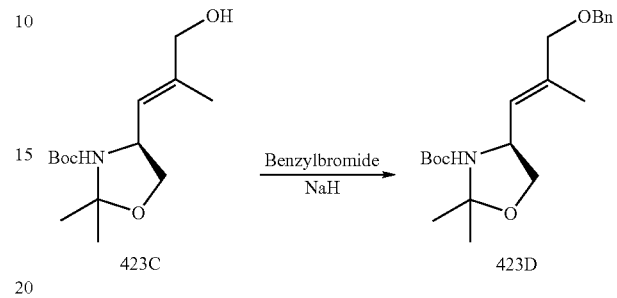

To a solution of the alcohol (423C, 8.66 g) in anhydrous DMF (30 ml), while cooled in an ice bath, was added NaH (1.38 g) and the resulting mixture was maintained at that temperatue for 45 min., before the addition of benzyl bromide (5 ml). The reaction was allowed to warm to room temperature overnight befor the addition of ether followed bt 10% aq. HCl. The organic phase was separated, washed with sat aq. sodium bicarbonate, brine, dried ($Na_2SO_4$). The volatiles were removed under reduced pressure to yield a residue which was purified by silica gel column chromatography using 8% EtOAc in hexanes to yield the benzyl ether (8.10 g) as a yellow oil.

Using analogous procedures described above for the conversion of 22.03 to 22.01, 423D was transformed into 423E

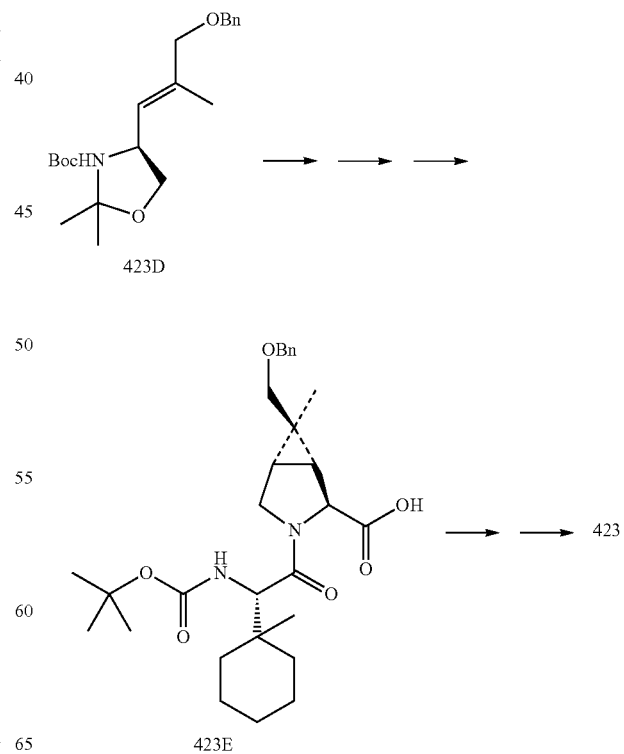

Example 397

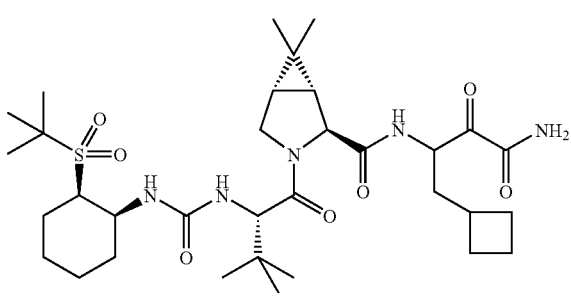

397

Step A

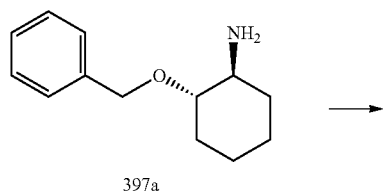

397a

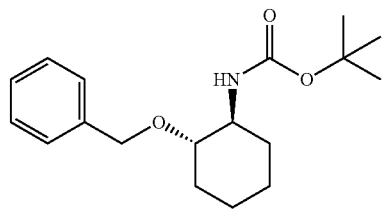

397b

A solution of benzyloxycyclohexyl amine 397a (10.6 g, Lancaster) and N-methylmorpholine (8.5 mL, d 0.920) in 200 mL of dry dichloromethane was cooled to −78° C. Boc-anhydride in 100 mL of dry dichloromethane was added over 15 min using an addition funnel. After addition was completed, the cooling bath was removed and the mixture was stirred of further 30 min. The reaction mixture was partitioned between 300 mL of ether and 100 mL of aqueous 1N HCl. The organic layer was dried over magnesium sulfate, filtered, and concentrated under reduced pressure to afford the product 397b (15.7 g; 99%) as a white solid which was used without further purification.

Step B

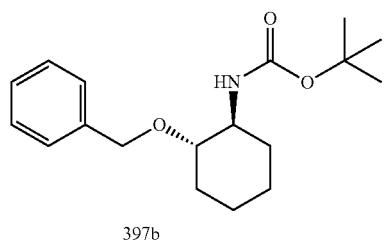

397b

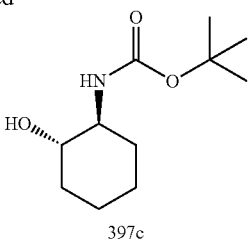

397c

20% palladium dihydroxide on carbon (30 mol %; 10.8 g) was added to a solution of benzyl ether 397b (15.7 g) in 300 mL of methanol. The heterogeneous mixture was subjected to hydrogenation at 40 psi until no more starting material was detected by TLC (ethyl acetate/hexanes; 2:8). The mixture was filtered thru celite and the filtrate was concentrated under reduced pressure. No further purification was carried out for the product 397c (11.1 g; 99%).

Step C

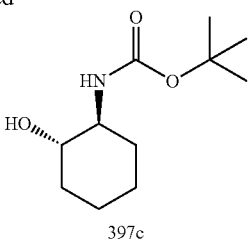

397c

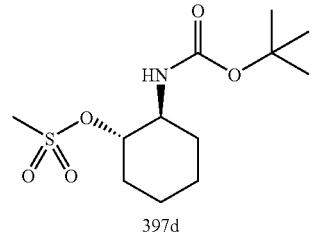

397d

Pyridine (25.0 mL) was added to a solution of cyclohexanol 397c in 300 mL of dry dichloromethane at 0° C. Methanesulfonyl chloride (8.0 mL) in 100 mL of dry dichloromethane was added over 15 min. The reaction mixture turned to a homogeneous yellow solution. The reaction mixture was stirred at 0° C. for 15 min and then the cooling bath was removed. Reaction was stirred at room temp for about 3 h. The mixture was partitioned between ether (500 mL) and aqueous 1N HCl (100 mL). The organic layer was washed with aqueous saturated sodium bicarbonate (100 mL), brine (100 mL), dried over magnesium sulfate, filtered, and concentrated under reduced pressure. The residue was chromatographed on silica gel (gradient: ethyl acetate/(hexanes-dichloromethane, 1:1); 0:10 to 2:8) to afford the product 397d (9.7 g; 64%) as a white solid.

Step D

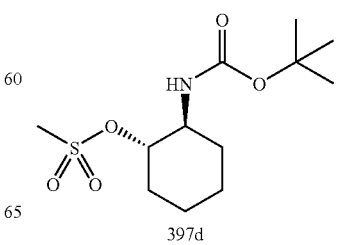

397d

-continued

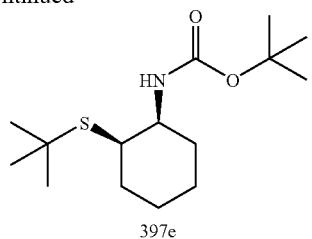

397e

A 250 mL-flask was charged with mesylate 397d (3.0 g) and t-butylthiol sodium salt (3.44 g). The flask was flushed with nitrogen and 100 mL of dry DMF were added. The resulting solution was degassed (vacuum/nitrogen-flush) and heated to 70° C. The flow of the reaction was monitored by TLC (ethyl acetate/hexanes; 2:8). All the starting material was consumed in about 3 h. The reaction mixture was dissolved in 300 mL of ethyl acetate and washed with water (3×50 mL) and brine (1×50 mL). The organic layer was dried over magnesium sulfate, filtered and concentrated. No further purification was done for the product 397e (2.78 g; 95%).

Step E

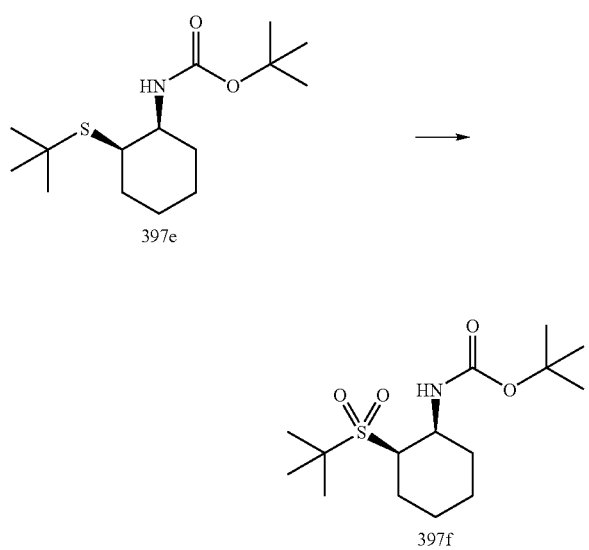

A solution of sulfide 397e (10.22 mmol) in dry dichloromethane (60 mL) was treated with m-CPBA (5.28 g; 60%). The homogeneous mixture was heated at 45° C. for about 3 h. TLC analysis (ethyl acetate/hexanes; 1:9) showed that all the starting material had been consumed. The mixture was concentrated under reduced pressure and the residue was dissolved in 20 mL of ether and treated with aqueous sodium thiosulfate solution at 0° C. The mixture was diluted with ether (350 mL) and washed with aqueous saturated sodium bicarbonate (5×30 mL). The organic layer was dried over magnesium sulfate, filtered, and concentrated. The residue was chromatographed on silica gel (gradient: acetone/hexane; 3:97 to 2:8) to afford the product 397f (2.45 g; 75%) as a white solid.

Step F

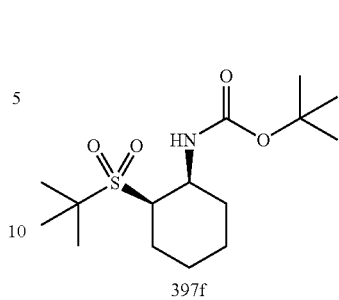

397f

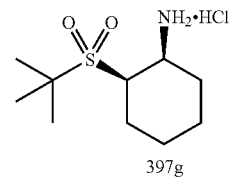

397g

The N—Boc protected amine 397f (2.43 g) was dissolved in 20 mL of 4M HCl in dioxanes. The mixture was stirred at room temperature until all the starting material had been consumed as determined by TLC analysis (ethyl acetate/hexanes; 2:8). After 3 h, all the volatiles were removed under reduced pressure to afford the product 397g (1.90 g; 98%) as a white solid.

Step G

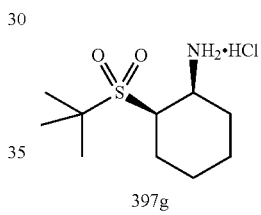

397g

+

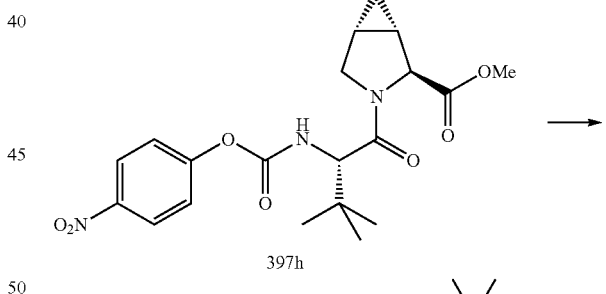

397h

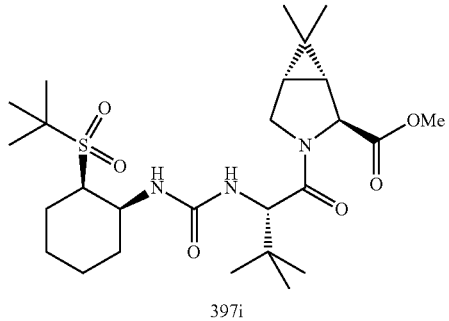

397i

A solution of the p-nitrophenylcarbamate 397h (640 mg) in 10 mL of acetonitrile was treated with amine hydrochloride 397g (350 mg). N-methylmorpholine (0.37 mL, d 0.920) was added to the heterogeneous mixture and the reaction mixture was stirred at room temperature. The reaction was completed after 7 h as determined by TLC analysis (acetone/hexanes; 2:8). The reaction mixture was concentrated under reduced pressure. The residue was dissolved in 150 mL of dichloromethane and washed with aqueous 1N HCl (1×30 mL), and aqueous saturated sodium bicarbonate (2×30 mL). The organic layer was dried over magnesium sulfate, filtered, and concentrated under reduced pressure. The product was purified on silica gel (gradient: acetone/hexanes; 1:9 to 4:6) to afford the product 397i (625 mg; 87%) as a white solid.

Step H

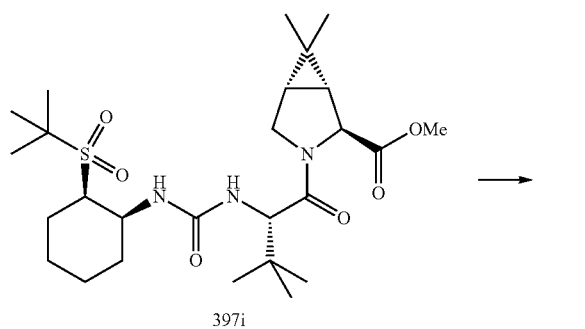

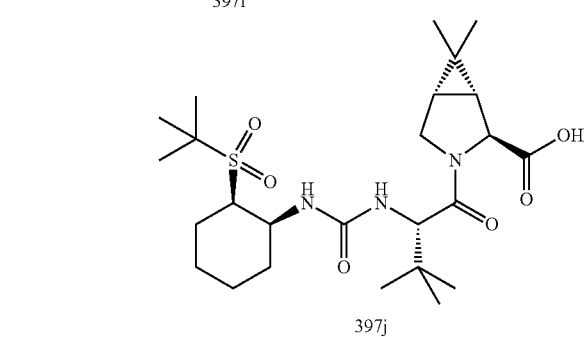

A solution of methyl ester 397i (610 mg) in 15 mL of a mixture of THF/MeOH/water (1:1:1) was treated with lithium hydroxyde monohydrate (121 mg). Reaction was stirred at room temperature and monitored by TLC (acetone/hexanes; 3:7). After 3 h, all the volatiles were removed under reduced pressure. The residue was partitioned between 30 mL of aqueous 1N HCl and 100 mL of dichloromethane. The aqueous layer was back extracted with dichloromethane (2×30 mL). The combined organic layers were dried over magnesium sulfate, filtered, and concentrated under reduced pressure to afford the product 397j (570 mg; 96%) as a white solid.

Step I

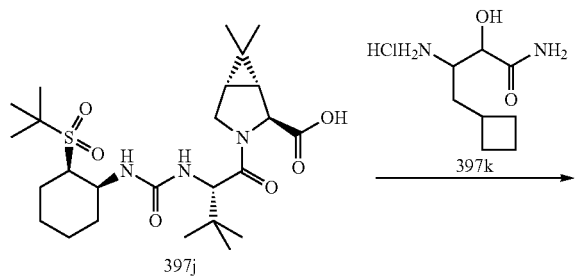

-continued

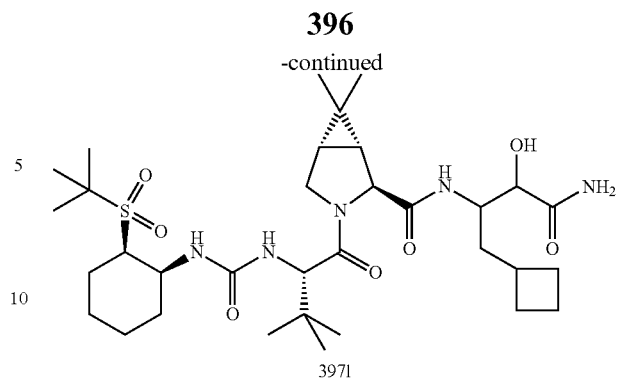

A solution of acid 397j (120 mg) in 2 mL of dry dichloromethane and 2 mL of dry DMF was stirred at 0° C. and treated with HATU (124 mg). The amine hydrochloride 397k (63 mg) was added followed by addition of N-methyl morpholine (0.10 mL, d 0.920). The reaction mixture was gradually warmed to room temperature and stirred overnight. All the volatiles were removed under vacuum and the residue was taken into 100 mL of ethyl acetate. The organic layer was washed with aqueous 1N HCl (15 mL), aqueous saturated sodium bicarbonate (15 mL), and brine (15 mL). The organic layer was dried over magnesium sulfate, filtered, and concentrated under reduced pressure to afford the desired product 397l (150 mg; 96%) which was used without further purification.

Step J

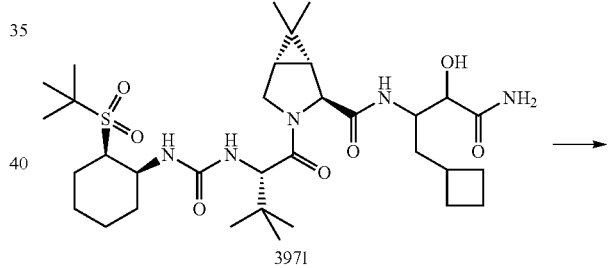

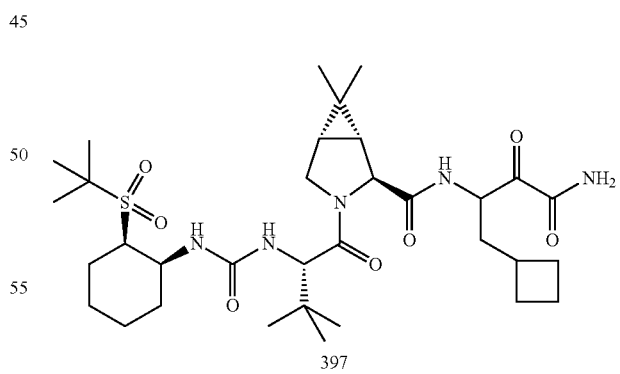

A solution of 397l (150 mg) in 6 mL of a 1:1 mixture of toluene/DMSO was treated with EDCl (430 mg) and dichloroacetic acid (0.09 mL, d 1.563). Reaction mixture was stirred at room temperature for about 2 h. The reaction mixture was diluted with dichloromethane (100 mL) and washed with aqueous saturated sodium bicarboante (15 mL), aqueous 1N HCl (15 mL), and brine (15 mL). The organic layer was dried over magnesium sulfate, filtrated, and concentrated under reduced pressure. The residue was chromatographed on silica gel (gradient: acetone/hexanes; 2:8 to 5:5) to afford the product 397 (94 mg; 64%) as a white solid. HRMS calcd for $C_{33}H_{56}N_5O_7S$ [M+H]$^+$: 666.3900, found 666.3883.

Example 398

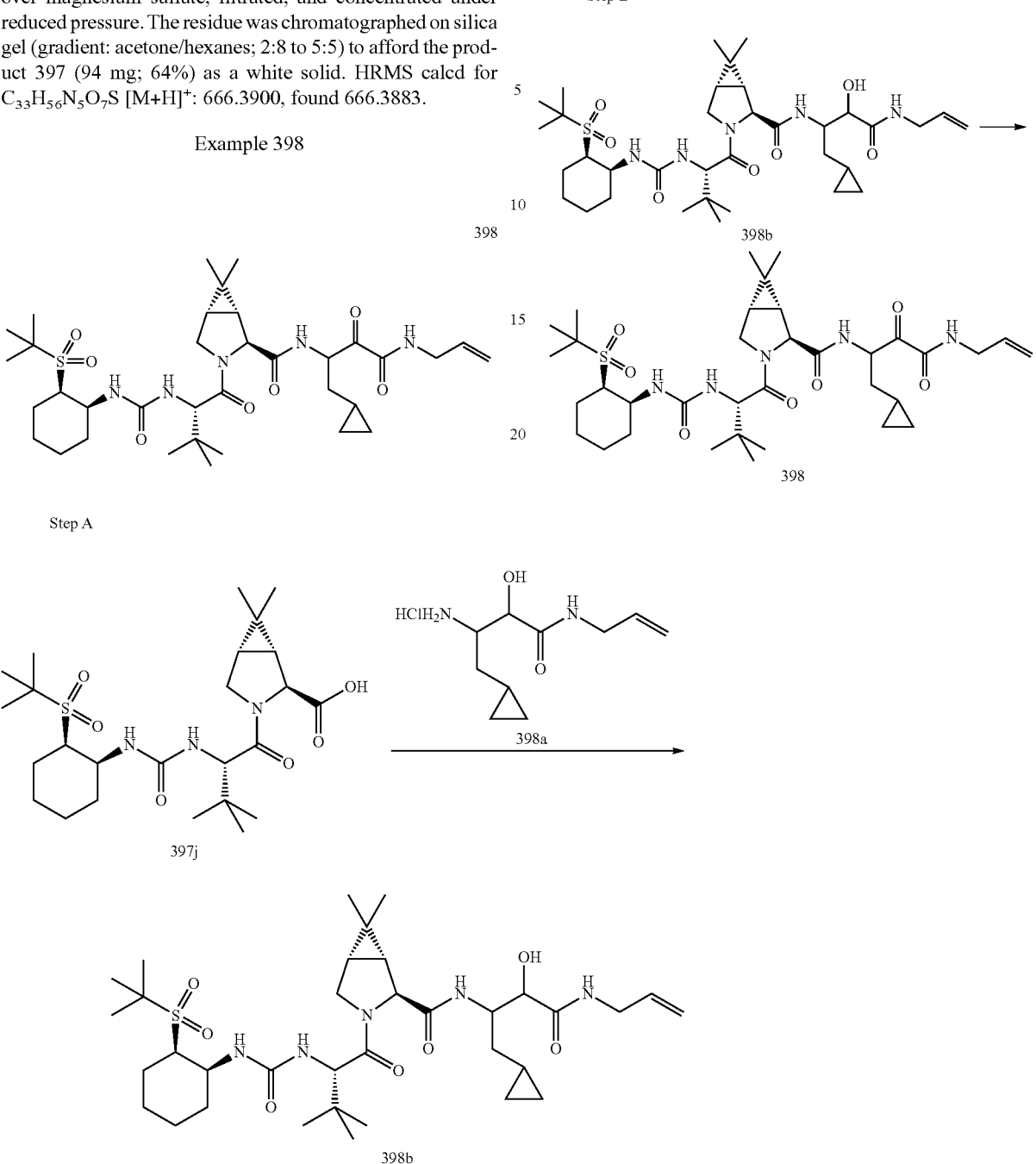

A solution of acid 397j (100 mg) in 2 mL of dry dichloromethane and 2 mL of dry DMF was stirred at 0° C. and treated with HATU (103 mg). The amine hydrochloride 398a (60 mg) was added followed by addition of N-methyl morpholine (0.09 mL, d 0.920). The reaction mixture was gradually warmed to room temperature and stirred overnight. All the volatiles were removed under vacuum and the residue was taken into 100 mL of ethyl acetate. The organic layer was washed with aqueous 1N HCl (15 mL), aqueous saturated sodium bicarbonate (15 mL), and brine (15 mL). The organic layer was dried over magnesium sulfate, filtered, and concentrated under reduced pressure to afford the desired product 398b (115 mg; 86%).

A solution of hydroxyamide 398b (115 mg) in 10 mL of dry dichloromethane was treated with Dess-Martin periodinane (210 mg). Reaction mixture was stirred at room temperature for 1 h. The mixture was treated with aqueous 1M sodium sulfite solution (10 mL) and aqueous saturated sodium bicarbonate (10 mL) and stirred for 15 min. The mixture was extracted with dichloromethane (3×30 mL). The combined organic layers were dried over magnesium sulfate, filtered, and concentrated. The residue was chromatographed on silica gel (gradient: acetone/hexanes; 2:8 to 5:5) to afford the product 398 (60 mg; 53%) as a white solid. HRMS calcd for $C_{35}H_{58}N_5O_7S$ [M+H]$^+$: 692.4057, found 692.4081.

Example 399

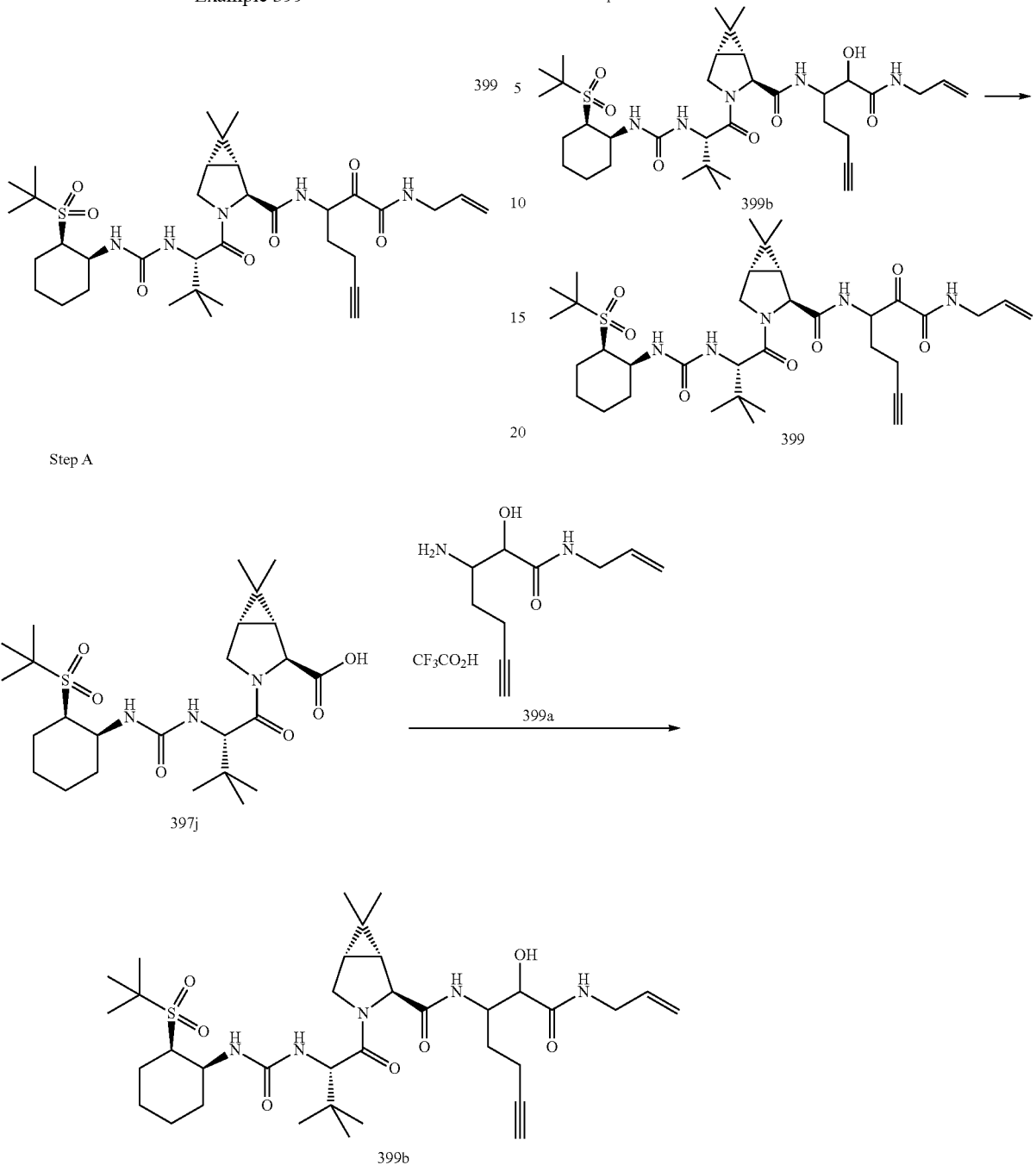

Step A

A solution of acid 397j (100 mg) in 2 mL of dry dichloromethane and 2 mL of dry DMF was stirred at 0° C. and treated with HATU (106 mg). A solution of the amine salt 399a (0.252 mmol) and N-methyl morpholine (0.09 mL, d 0.920) in 1 mL of dichloromethane was added dropwise. The reaction mixture was gradually warmed to room temperature and stirred overnight. All the volatiles were removed under vacuum and the residue was taken into 100 mL of ethyl acetate. The organic layer was washed with aqueous 1N HCl (15 mL), aqueous saturated sodium bicarbonate (15 mL), and brine (15 mL). The organic layer was dried over magnesium sulfate, filtered, and concentrated under reduced pressure to afford the desired product 399b (85 mg; 63%).

Step B

A solution of hydroxyamide 399b (85 mg) in 10 mL of dry dichloromethane was treated with Dess-Martin periodinane (157 mg). Reaction mixture was stirred at room temperature for 1 h. The mixture was treated with aqueous 1M sodium thiosulfate solution (10 mL) and aqueous saturated sodium bicarbonate (10 mL) and stirred for 15 min. The mixture was extracted with dichloromethane (3×30 mL). The combined organic layers were dried over magnesium sulfate, filtered, and concentrated. The residue was chromatographed on silica gel (gradient: acetone/hexanes; 2:8 to 4:6) to afford the product 399 (50 mg; 60%) as a white solid. HRMS calcd for $C_{33}H_{55}N_6O_7S$ [M+H]$^+$: 679.3853, found 679.3834.

Example 473

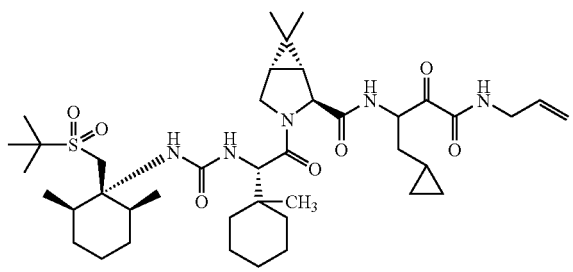

Step A

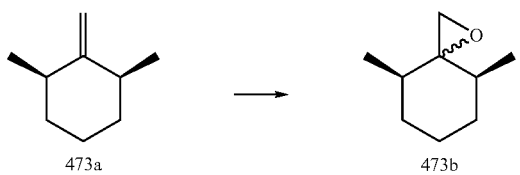

Cis-2,6-dimethyl-1-methylene cyclohexane (3.0 g, Chem-Samp Co.) was added to a stirred suspension of solid sodium bicarbonate (6 eq, 12.19 g) in 150 mL of dichloromethane. The mixture was cooled to 0° C. and a slurry of 70% m-CPBA (3 eq, 17.4 g) in 150 mL of dichloromethane was added in small portions. After addition was completed, the cooling bath was removed and the mixture was stirred for about 2 h. The excess m-CPBA was quenched at 0° C. by careful addition of aqueous saturated sodium thiosulfate solution.

The mixture was washed with aqueous saturated sodium bicarbonate solution (100 mL). The organic layer was concentrated in the rotavap (ice-water bath was used). The residue was dissolved in ether (80 mL) and hexanes (120 mL) and washed several times with aqueous saturated sodium bicarbonate solution. The organic layer was dried over magnesium sulfate, filtered, and concentrated under reduced pressure (ice-water bath). The residue was chromatographed on silica gel (gradient: ether/hexanes; 0:10 to 8:92) to afford the product 473b (3.0 g; 90%) as a colorless oil.

Step B

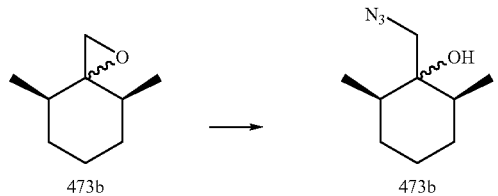

A heterogeneous mixture of epoxide 473b (3 g) and ammonium chloride (5 eq, 5.72 g) in 80 mL of methanol was treated with sodium azide (5 eq, 7.17 g) and heated at 65° C. for 3 h. TLC analysis showed some starting material left and more ammonium chloride (1.5 eq, 1.71 g) and sodium azide (1.5 eq, 2.15 g) were added. The mixture was heated (65° C.) overnight. The reaction mixture was diluted with 30 mL of water and extracted with ether (3×100 mL). The combined organic extracts were dried over magnesium sulfate, filtered and concentrated under reduced pressure. The residue was chromatographed on silica gel (gradient: ether/hexanes; 0:10 to 2:8) to afford the corresponding diastereomeric product 473b (2.73 g; 71%) as a colorless oil.

Step C

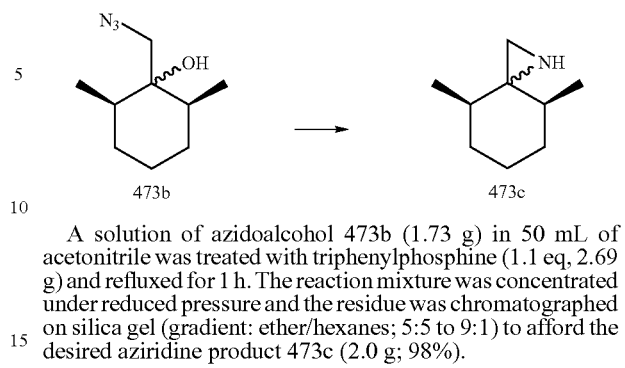

A solution of azidoalcohol 473b (1.73 g) in 50 mL of acetonitrile was treated with triphenylphosphine (1.1 eq, 2.69 g) and refluxed for 1 h. The reaction mixture was concentrated under reduced pressure and the residue was chromatographed on silica gel (gradient: ether/hexanes; 5:5 to 9:1) to afford the desired aziridine product 473c (2.0 g; 98%).

Step D

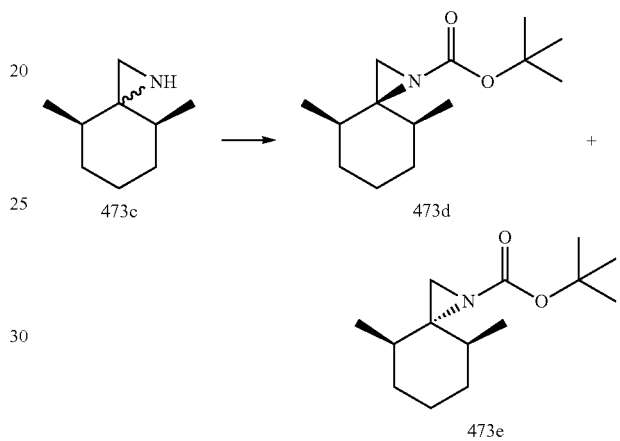

A solution of aziridine 473c (aprox 1.5 g) in dry dichloromethane (50 mL) was cooled to 0° C. and treated with di-tert-butyldicarbonate (1.3 eq, 3.0 g) in 50 mL of dry dichloromethane. N-methylmorpholine (2.5 eq, 2.9 mL, d 0.920) was added dropwise and the mixture was stirred overnight (temp: 0 to 25° C.). The mixture was diluted with ether (300 mL) and washed with aqueous 1M HCl (100 mL), aqueous saturated sodium bicarbonate (80 mL) and brine (80 mL). The organic layer was dried over magnesium sulfate, filtered and concentrated under reduced pressure. The residue was chromatographed on silica gel (gradient: ether/hexanes; 0:10 to 1:9) to afford the products 473d and 473e as clear oils (970 mg).

Step E

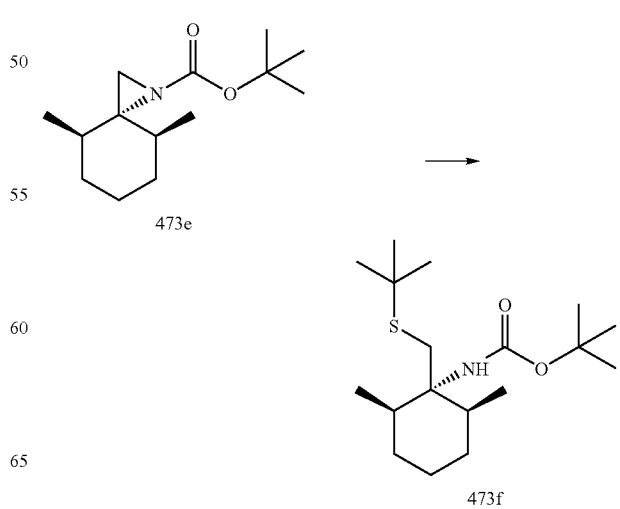

A 20 mL vial was charged with a solution of N—Boc-aziridine 473e (469 mg) in 20 mL of dry DMF and sodium tert-butylthiolate (2 eq, 438 mg). The reaction was carried out in a microwave oven at 130° C. for 30 min. The reaction mixture was diluted with 100 mL of ether and washed with water (3×30 mL) and brine (20 mL). The organic layer was dried over magnesium sulfate, filtered and concentrated under reduced pressure. The residue was chromatographed on silica gel (gradient: hexanes to ether/hexanes, 4:96) to afford the product 473e (140 mg) as a white solid and unreacted starting material (120 mg).

Step F

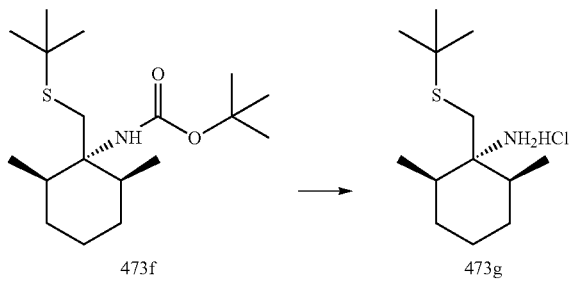

The N—Boc protected amine 473f (140 mg) was dissolved in 10 mL of 4M HCl solution in dioxanes. The resulting solution was stirred at room temperature for 30 min until all the starting material had been consumed as determined by TLC analysis (ether/hexanes; 5:95). All the volatiles were removed under reduced pressure and the residue was placed under high vacuum for 3 h to afford the product 473g (112 mg; 98%) as a white solid.

Step G

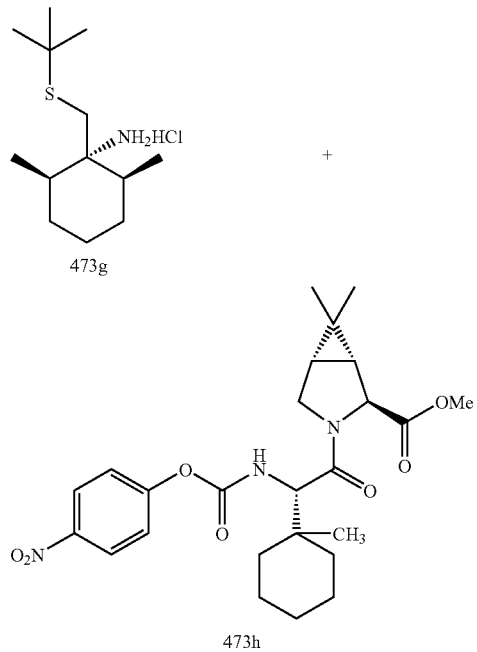

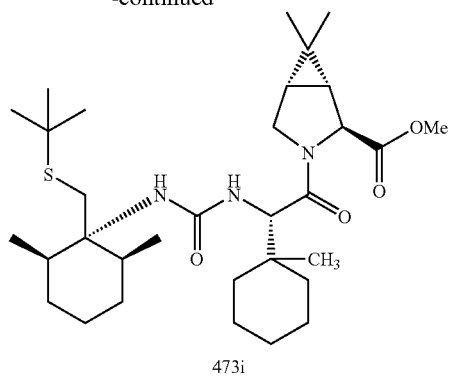

A solution of the p-nitrophenylcarbamate 473h (1.05 eq, 212 mg) in 3 mL of acetonitrile was treated with amine hydrochloride 473g (110 mg) in 2 mL of acetonitrile. N-methylmorpholine (2.5 eq, 0.11 mL, d 0.920) was added and the resulting yellow solution was stirred at room temperature for 8 h. The reaction mixture was concentrated under reduced pressure and the residue was dissolved in 100 mL of dichloromethane and washed with aqueous 1N HCl (1×20 mL), and aqueous saturated sodium bicarbonate solution (2×20 mL). The organic layer was dried over magnesium sulfate, filtered, and concentrated under reduced pressure. The product was purified on silica gel (gradient: hexanes to acetone/hexanes, 2:8) to afford the product 473i (150 mg; 63%).

Step H

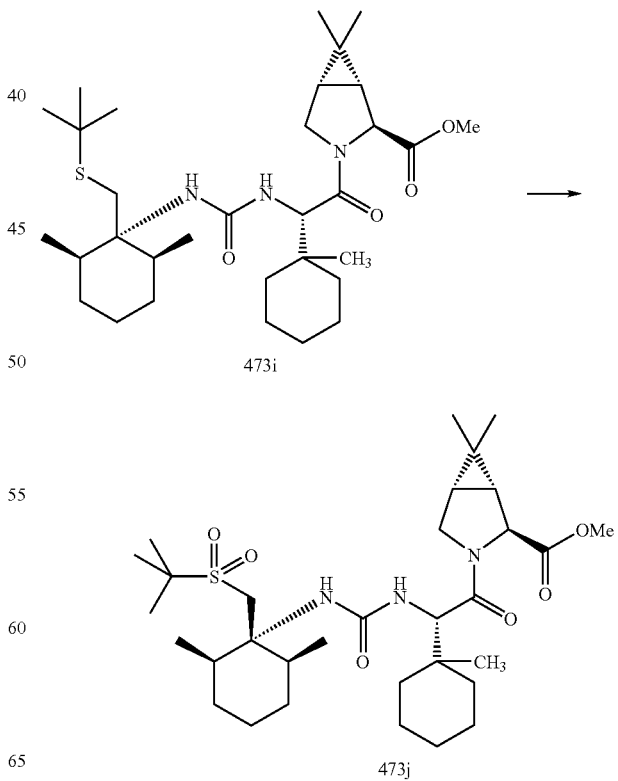

A solution of sulfide 473i (150 mg) in dry dichloromethane (15 mL) was treated with 60% m-CPBA (3 eq, 134 mg). The homogeneous mixture was heated at 45° C. for about 1.5 h. Excess m-CPBA was quenched by addition of aqueous sodium thiosulfate solution (20 mL) and stirring was continued for 10 min. Aqueous saturated sodium bicarbonate solution (20 mL) was added and the product was taken into ethyl acetate (100 mL). The organic layer was concentrated and the residue was dissolved in ethyl acetate (80 mL). The organic layer was washed with aqueous saturated sodium bicarbonate solution (3×10 mL) and brine (10 mL). The organic layer was dried over magnesium sulfate, filtered and concentrated. The residue was chromatographed on silica gel (gradient: ethyl acetate/hexanes; 1:3 to 5:5) to afford the product 473j (120 mg; 76%) as a colorless oil.

Step I

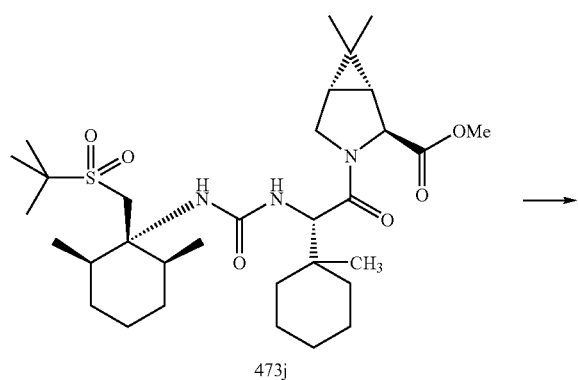

473j

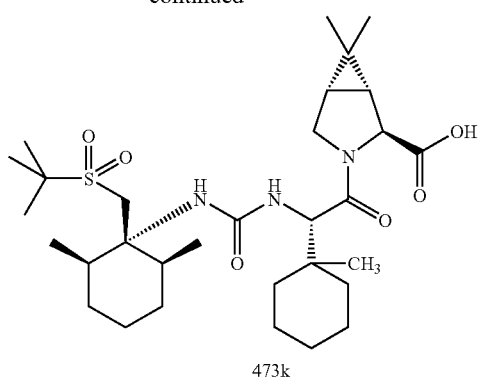

473k

A solution of methyl ester 473j (110 mg) in 10 mL of a 1:1:1 mixture of THF/water/MeOH was cooled to 0° C. and treated with lithium hydroxide monohydrate (2.5 eq, 19 mg). The cooling bath was removed after 30 min and the mixture was stirred at room temp for further 2 h until all the starting material had been consumed as determined by TLC analysis (ethyl acetate/hexanes; 3:7). The reaction mixture was treated with 20 mL of aqueous 1M HCl (pH of mixture=1) and the organic solvents were removed under reduced pressure. The aqueous residue was extracted with dichloromethane (3×50 mL). The combined organic extracts were dried over magnesium sulfate, filtered and concentrated under reduced pressure to afford the product 473k (105 mg; 98%) as a clear oil.

Step J

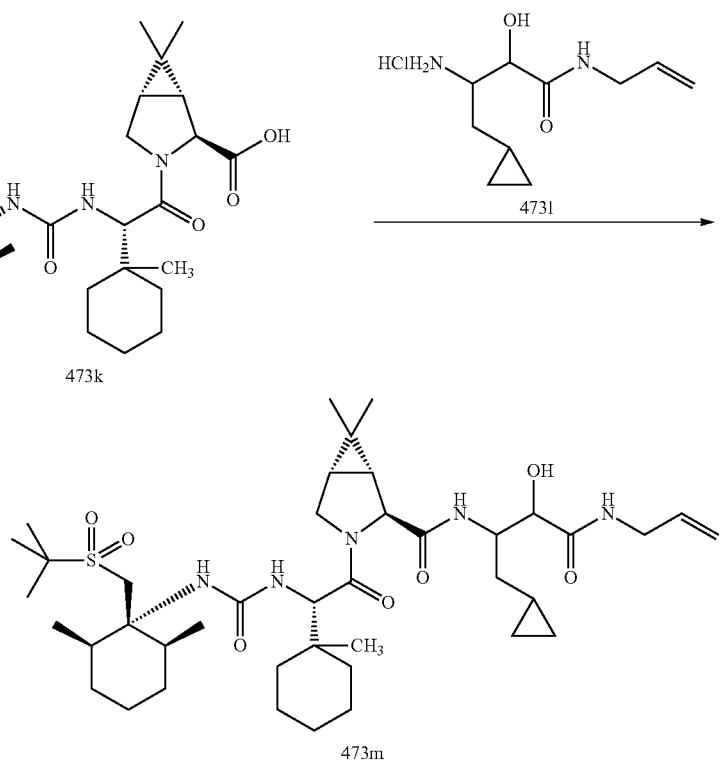

473k

473l

473m

A solution of acid 473k (50 mg) in 2 mL of dry dichloromethane and 1 mL of dry DMF was stirred at 0° C. and treated with HATU (1.4 eq, 44 mg). The amine salt (1.3 eq, 25 mg) was added followed by N-methylmorpholine (4 eq, 0.036 mL, d 0.920). The reaction mixture was stirred overnight (temp 0 to 25° C.). All the volatiles were removed under vacuum and the residue was dissolved in 50 mL of ethyl acetate. The organic layer was washed with water (20 mL), aqueous 1M HCl (10 mL), aqueous saturated sodium bicarbonate solution (10 mL), and brine (10 mL). The organic layer was dried over magnesium sulfate, filtered and concentrated under reduced pressure. The product 473m (64 mg) was used without further purification.

Step K

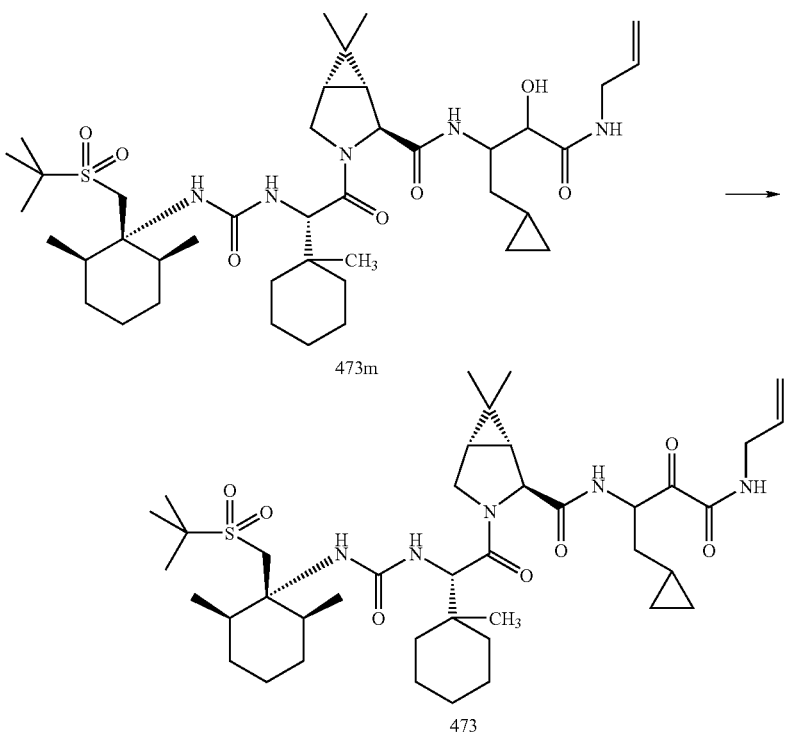

A solution of hydroxyamide 473m (0.083 mmol) in 10 mL of dry dichloromethane was treated with Dess-Martin periodinane (2.0 eq, 70 mg). The reaction mixture was stirred at room temperature for 30 min. The mixture was treated with aqueous 1M sodium thiosulfate solution (10 mL) and stirred for 5 min. Aqueous saturated sodium bicarbonate solution (20 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 1:9 to 4:6) to afford the product 473 (40 mg; 62% for two steps) as white solid. HRMS calcd for $C_{41}H_{68}N_5O_7S$ $[M+H]^+$: 774.4839, found 774.4834.

Example 474

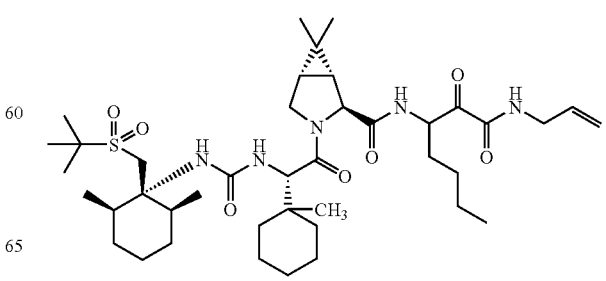

Step A

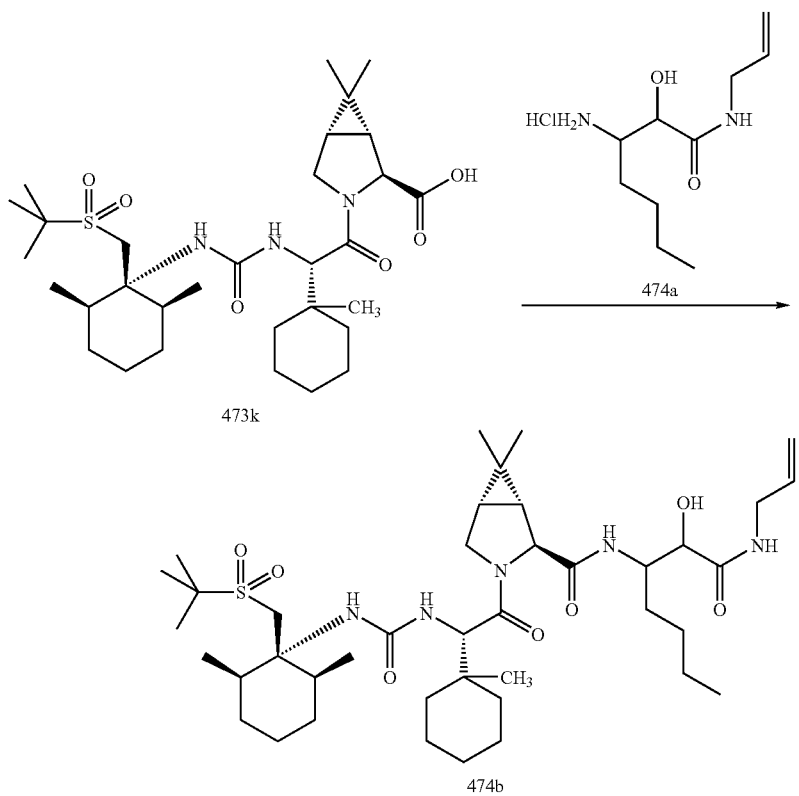

A solution of acid 473k (50 mg) in 2 mL of dry dichloromethane and 1 mL of dry DMF was stirred at 0° C. and treated with HATU (1.4 eq, 44 mg). The amine salt 474a (1.3 eq, 25 mg) was added followed by N-methylmorpholine (4 eq, 0.036 mL, d 0.920). The reaction mixture was stirred overnight (temp 0 to 25° C.). All the volatiles were removed under vacuum and the residue was dissolved in 50 mL of ethyl acetate. The organic layer was washed with water (20 mL), aqueous 1M HCl (10 mL), aqueous saturated sodium bicarbonate solution (10 mL), and brine (10 mL). The organic layer was dried over magnesium sulfate, filtered and concentrated under reduced pressure. The product 474b (65 mg) was used without further purification.

Step B

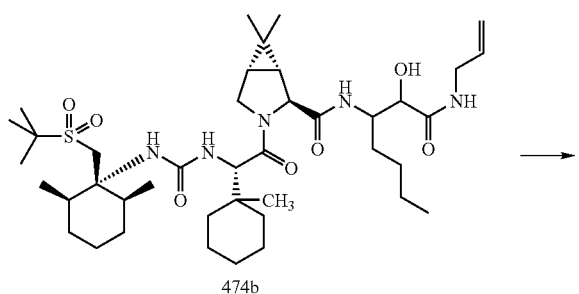

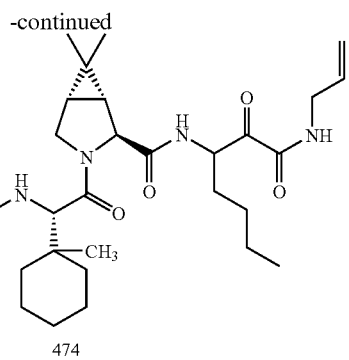

A solution of hydroxyamide 474b (0.083 mmol) in 10 mL of dry dichloromethane was treated with Dess-Martin periodinane (2.0 eq, 70 mg). The reaction mixture was stirred at room temperature for 30 min. The mixture was treated with aqueous 1M sodium thiosulfate solution (10 mL) and stirred for 5 min. Aqueous saturated sodium bicarbonate solution (20 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 1:9 to 4:6) to afford the product 474 (40 mg; 62% for two steps) as white solid. HRMS calcd for $C_{41}H_{70}N_5O_7S$ $[M+H]^+$: 776.4995, found 776.5005.

Example 696

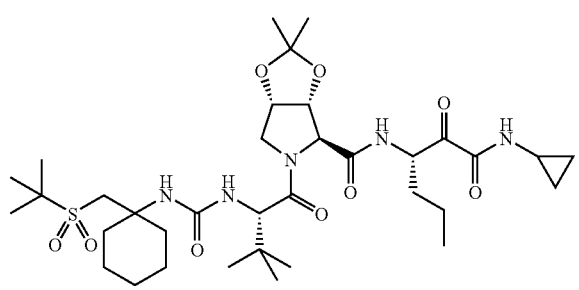

Step A

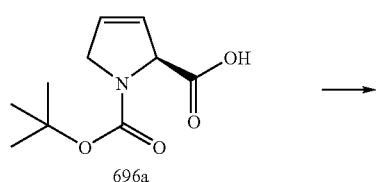

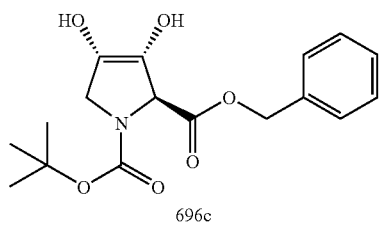

Step C

A solution of N-methylmorpholine-N-oxide (1.3 eq, 1.9 g) in tert-butanol (20 mL), THF (7 mL) and water (3.5 mL) under argon atmosphere was treated with osmium tetroxide (0.1 eq, 318 mg). The resulting pale yellow solution was stirred for 5 min followed by dropwise addition of benzylester 696b (3.8 g) in 30 mL of THF. The reaction mixture was stirred at room temperature for 20 h. The mixture was filtered thru a short path of silica gel and the solids were washed with ethyl acetate (500 mL). The organic layer was washed with brine (80 mL), dried over magnesium sulfate, filtered and concentrated under reduced pressure. The residue was chromatographed on silica gel (gradient: acetone/hexanes; 2:8 to 55:45) to afford the product 696c (3.5 g; 83%) as a paste.

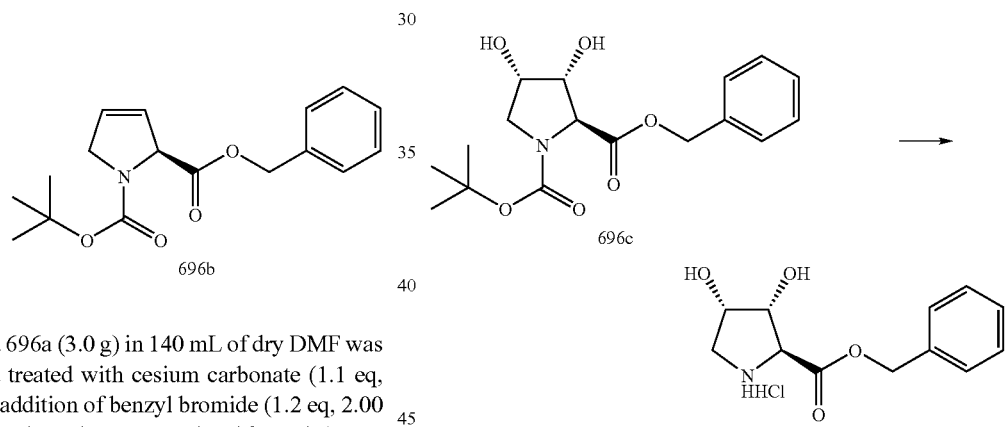

A solution of acid 696a (3.0 g) in 140 mL of dry DMF was cooled to 0° C. and treated with cesium carbonate (1.1 eq, 5.04 g) followed by addition of benzyl bromide (1.2 eq, 2.00 mL, d 1.438). The reaction mixture was stirred for 24 h (temp: 0 to 25° C.). The mixture was diluted with ethyl acetate (350 mL) and washed with water (3×50 mL). The organic layer was dried over magnesium sulfate, filtered and concentrated under reduced pressure. The residue was chromatographed on silica gel (gradient: hexanes to ethyl acetate/hexanes 25:75) to afford the product 696b (3.82 g; 90%) as a clear oil.

The N—Boc amine 696c (3.5 g) was dissolved in 60 mL of 4M HCl in dioxane. The resulting solution was stirred at room temperature for about 2 h. All the volatiles were removed under reduced pressure to afford the product 696d (2.8 g; 98%) which was used without further purification.

Step B

Step D

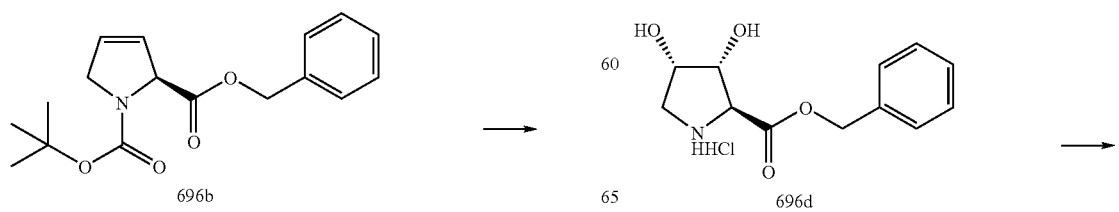

-continued

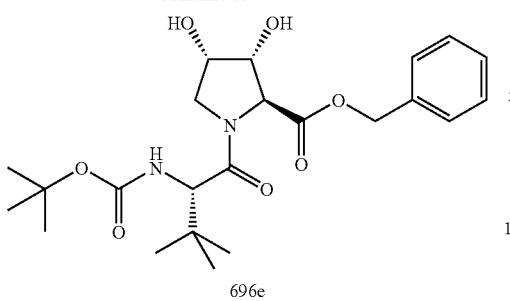

696e

A solution of N—Boc-tert-butyl glycine (2.15 g) in 100 mL of dry dichloromethane and 20 mL of dry DMF was stirred at 0° C. and treated with HATU (1.4 eq, 4.96 g). The amine salt 696d (1.1 eq, 2.8 g) was added in 30 mL of DMF followed by addition of N-methylmorpholine (4 eq, 4.08 mL, d 0.920). The reaction mixture was stirred at 0° C. overnight. All the volatiles were removed under vacuum and the residue was dissolved in 300 mL of ethyl acetate. The organic layer was washed with water (1×100 mL), aqueous 1M HCl (100 mL), aqueous saturated sodium bicarbonate solution (100 mL), and brine (100 mL). The organic layer was dried over magnesium sulfate, filtered and concentrated under reduced pressure. The residue was chromatographed on silica gel (ethyl acetate/hexanes; 6:4) to afford the product 696e (3.29 g; 79%) as a colorless oil.

Step E

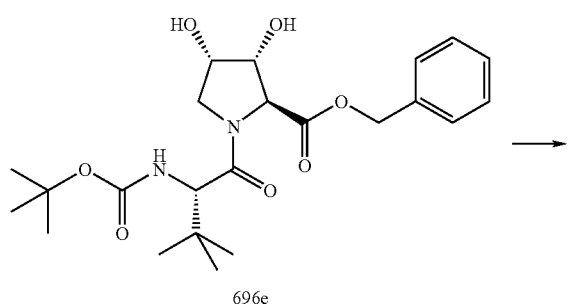

696e

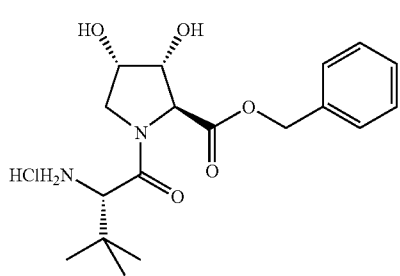

696f

The N—Boc amine 696e (1.24 g) was dissolved in 30 mL of 4M HCl in dioxane. The resulting solution was stirred at room temperature for about 2 h. All the volatiles were removed under reduced pressure to afford the product 696f (1.06 g; 98%) as a white solid.

Step F

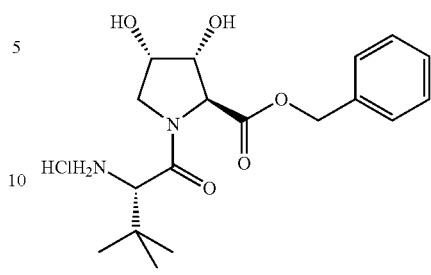

696f

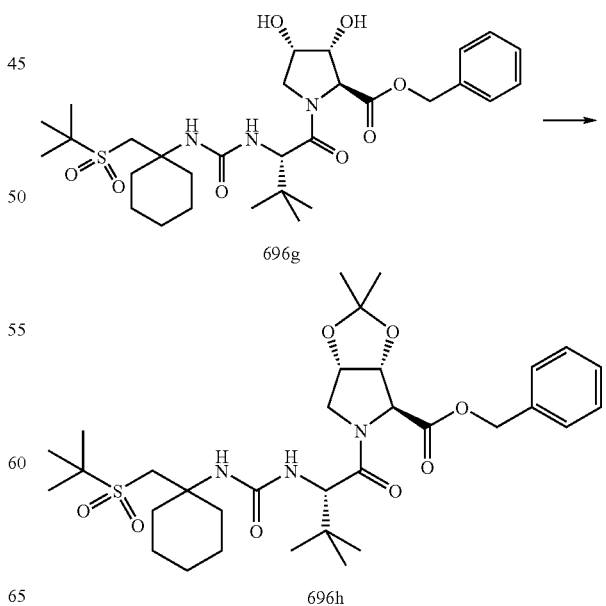

696g

N-methyl morpholine (1.3 eq, 0.39 mL, d 0.920) was added to a heterogeneous mixture of amine-diol 696f (1.06 g) in 50 mL of dichloromethane. After 5 min, a solution of isocyanate (1.05 eq, 9.63 mL of a 0.3M soln in toluene) was added. DMF (5 mL) was also added and the slurry was stirred at room temperature. The mixture gradually converted (over 4 h) to a clear homogeneous solution. The mixture was diluted with ethyl acetate (300 mL) and washed with aqueous 1M HCl. The aqueous layer was back extracted with 100 mL of ethyl acetate. The combined organic layers were dried over magnesium sulfate, filtered, and concentrated under reduced pressure. The residue was chromatographed on silica gel (gradient: acetone/hexanes; 3:7 to 6:4) to give the product 696g (1.6 g; 98%) as a colorless oil.

Step G

A solution of diol 696g (1.5 g) was treated with 2,2-dimethoxypropane (2 eq, 0.6 mL, d 0.847) and a catalytic amount of pyridinium p-toluenesulfonic acid (0.1 eq, 62 mg). The mixture was stirred overnight at 50° C. The mixture was diluted with 200 mL of ethyl acetate and washed with 50 mL of aqueous saturated sodium bicarbonate soln. The aqueous layer was extracted with ethyl acetate (100 mL). The combined organic layers were dried over magnesium sulfate, filtered and concentrated. The residue was chromatographed on silica gel (gradient: acetone/hexanes; 5:95 to 35:65) to afford the product 696h (1.33 g; 83%) as a white solid.

Step H

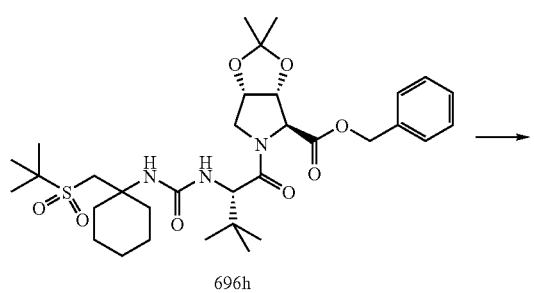

696h

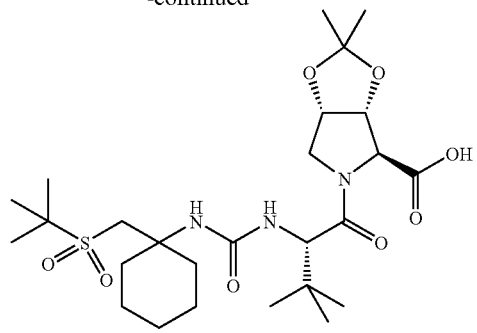

696i

The benzyl ester 696h (1.33 g) was dissolved in 70 mL of ethyl acetate and treated with 20% palladium dihydroxide on carbon (0.1 mol %; 144 mg). The heterogeneous mixture was hydrogenated at 50 psi for 3 h. The mixture was diluted with 200 mL of dichloromethane and filtered thru a short path of celite. The filtrate was concentrated under reduced pressure to afford the product 696i (1.14 g; 98%) as a white solid.

Step I

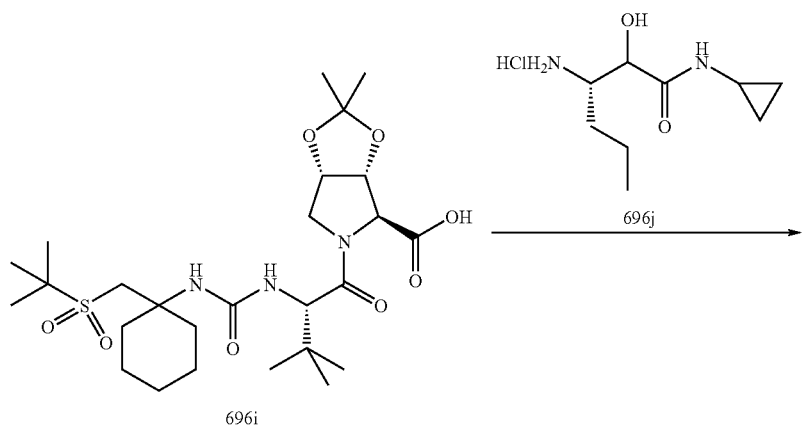

696i 696j

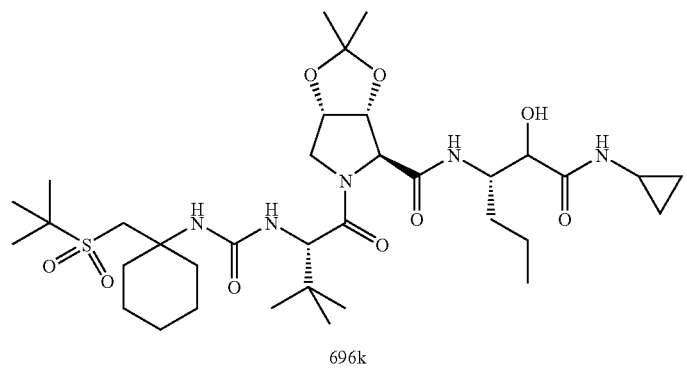

696k

A solution of acid 696i (100 mg) in 3 mL of dry dichloromethane and 3 mL of dry DMF was stirred at 0° C. and treated with HATU (1.4 eq, 93 mg). The amine salt 696j (1.2 eq, 47 mg) was added followed by N-methylmorpholine (4 eq, 0.08 mL, d 0.920). The reaction mixture was stirred overnight (temp 0 to 25° C.). All the volatiles were removed under vacuum and the residue was dissolved in 50 mL of ethyl acetate. The organic layer was washed with water (10 mL), aqueous 1M HCl (10 mL), aqueous saturated sodium bicarbonate solution (10 mL), and brine (10 mL). The organic layer was dried over magnesium sulfate, filtered and concentrated under reduced pressure. The product 696k was used without further purification.

Step J

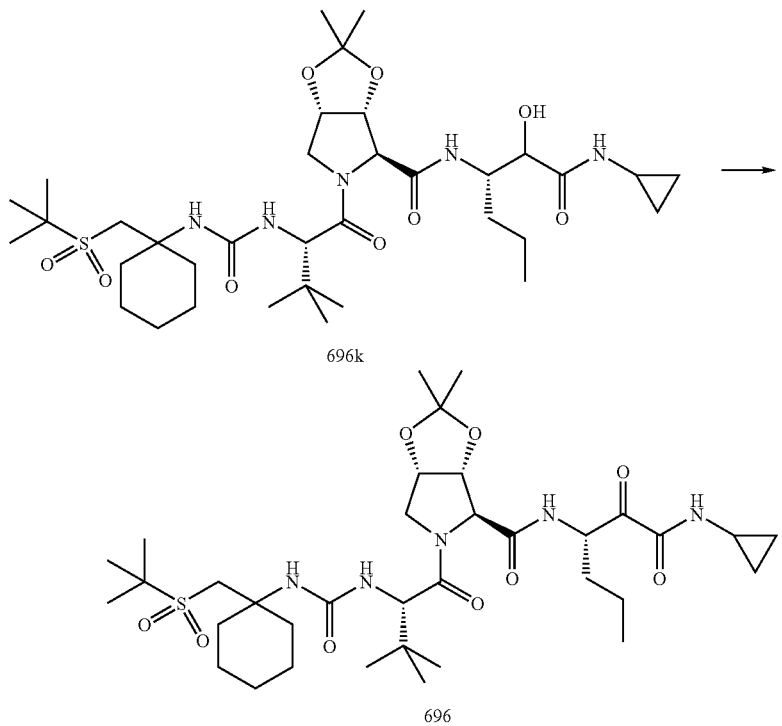

A solution of hydroxyamide 696k (0.178 mmol) in 10 mL of dry dichloromethane was treated with Dess-Martin periodinane (2.0 eq, 150 mg). The reaction mixture was stirred at room temperature for 30 ml. The mixture was treated with aqueous 1M sodium thiosulfate solution (10 mL) and stirred for 5 min. Aqueous saturated sodium bicarbonate solution (10 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 15:85 to 1:1) to afford the product 696 (120 mg; 93%) as white solid. HRMS calcd for $C_{35}H_{60}N_5O_9S$ $[M+H]^+$: 726.4112, found 726.4128.

Example 697

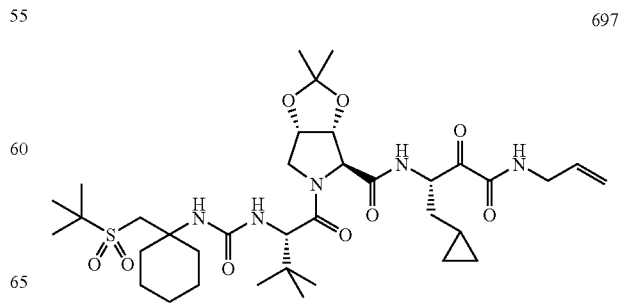

Step A

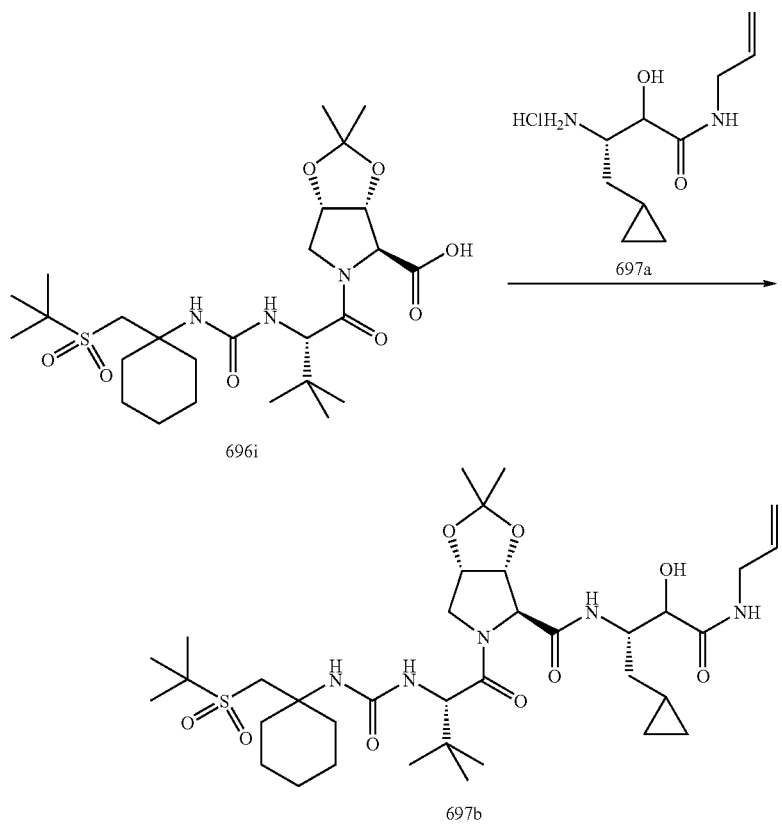

A solution of acid 696i (100 mg) in 3 mL of dry dichloromethane and 3 mL of dry DMF was stirred at 0° C. and treated with HATU (1.4 eq, 93 mg). The amine salt 697a (1.2 eq, 50 mg) was added followed by N-methylmorpholine (4 eq, 0.08 mL, d 0.920). The reaction mixture was stirred overnight (temp 0 to 25° C.). All the volatiles were removed under vacuum and the residue was dissolved in 50 mL of ethyl acetate. The organic layer was washed with water (10 mL), aqueous 1M HCl (10 mL), aqueous saturated sodium bicarbonate solution (10 mL), and brine (10 mL). The organic layer was dried over magnesium sulfate, filtered and concentrated under reduced pressure. The product 697b was used without further purification.

Step B

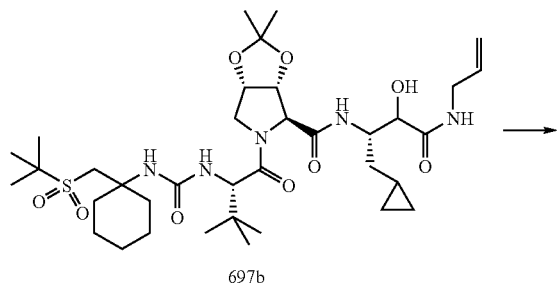

-continued

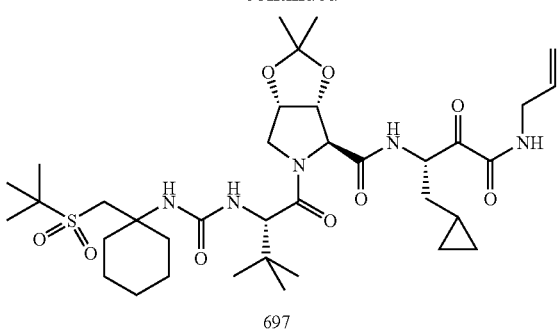

A solution of hydroxyamide 697b (0.178 mmol) in 10 mL of dry dichloromethane was treated with Dess-Martin periodinane (2.0 eq, 150 mg). The reaction mixture was stirred at room temperature for 30 min. The mixture was treated with aqueous 1M sodium thiosulfate solution (10 mL) and stirred for 5 min. Aqueous saturated sodium bicarbonate solution (10 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 15:85 to 1:1) to afford the product 697 (120 mg; 91%) as white solid. HRMS calcd for $C_{36}H_{60}N_5O_9S$ [M+H]$^+$: 738.4112, found 738.4092.

Example 837

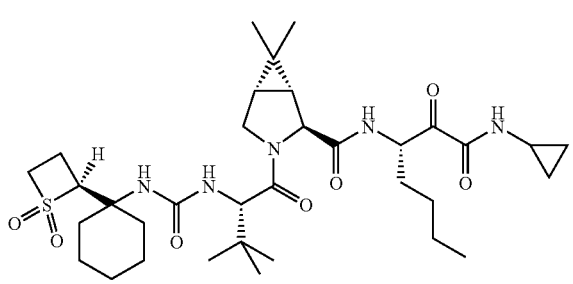

Step A

A solution of thietane (10 g, 9.727 mL, d 1.028, Aldrich) in 200 mL of dichloromethane was treated with a slurry of m-chloroperoxybenzoic acid (2.3 eq, 76 g of 70% m-CPBA) in dichloromethane (400 mL) at 0° C. The cooling bath was removed and the mixture was stirred for 3 h. The solids were removed by filtration and the filtrate was concentrated under reduced pressure. The residue was dissolved in ethyl acetate (400 mL) and the solution was extensively washed with aqueous saturated sodium bicarbonate solution. The organic layer was dried over magnesium sulfate, filtered and concentrated. The residue was purified by column chromatography to afford the product 837b as a white solid.

Step B

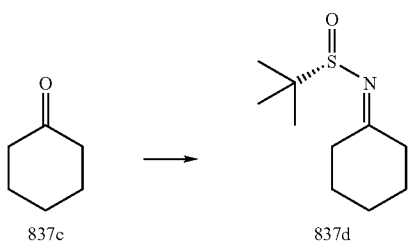

Titanium tetraethoxide (2 eq, 24.2 mL, d 1.088) was added to a solution of cyclohexanone (1.2 eq, 7.18 mL, d 0.947) in 150 mL of dry THF under nitrogen atmosphere. After 5 min, t-butanesulfinamide (7.0 g, Aldrich) in 50 mL of THF was added dropwise. The mixture was heated to 60° C. overnight. The reaction mixture was poured into an equal volume of aqueous saturated sodium bicarbonate solution with rapid stirring and immediately filtered through filter paper whatman #1. The filter cake was washed with ethyl acetate (100 mL). The layers in the filtrate were separated and the aqueous layer was extracted with ethyl acetate (100 mL). The combined organic layers were washed with aqueous saturated sodium bicarbonate solution (100 mL), dried over magnesium sulfate, filtered and concentrated. The residue was chromatographed on silica gel (ethyl acetate/hexanes; 3:7) to afford the product 837d (7.5 g; 55%) as a colorless oil. The product is kept under inert atmosphere at −20° C.

Step C

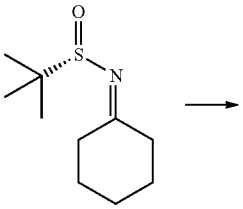

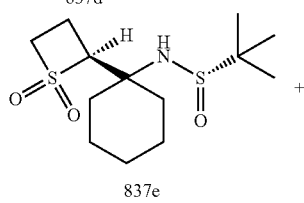

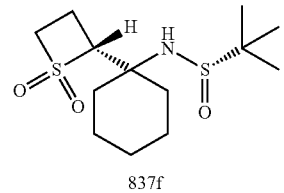

n-Butyl lithium (1.1 eq, 7.6 mL of a 1.6M soln in cyclohexane) was added dropwise to a cooled (−78° C.) solution of sulfone 837b (1.15 eq, 1.35 g) in 100 mL of dry THF under anhydrous atmosphere. The mixture was stirred for 1 h at that temperature and then transferred via cannula to a pre-cooled (−78° C.) solution of sulfinylimine 837d (2.23 g) in 100 mL of dry THF. The resulting mixture was stirred at −78° C. and monitored by TLC (acetone/hexanes; 3:7). All the sulfinylimine 837d starting material was consumed in 2 h. The reaction was quenched by addition of aqueous saturated ammonium chloride solution (5 mL). The mixture was allowed to reach room temperature and partitioned between ethyl acetate (200 mL) and aqueous saturated sodium bicarbonate (80 mL). The aqueous layer was back extracted with ethyl acetate (2×60 mL). The combined organic layers were washed with brine, dried over magnesium sulfate, filtered and concentrated under reduced pressure. The residue was chromatographed on silica gel (gradient: dichloromethane to acetone/dichloromethane; 3:7) to afford the corresponding diastereomeric products 837e and 837f as a 1.4:1 mixture (1.64 g; 50% comb.yield).

Step D

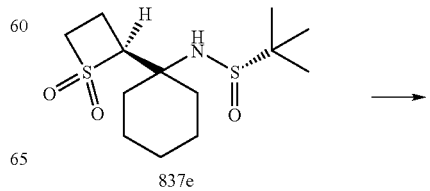

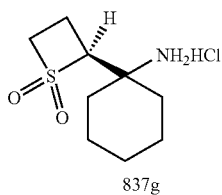

837g

The sulfinamide 837e (910 mg) was dissolved in 50 mL of methanol and treated with 20 mL of 4M HCl solution in dioxane. The mixture was stirred for about 1 h until all the starting material had been consumed as determined by TLC (acetone/hexanes; 1:9). The mixture was concentrated to dryness. Dichloromethane (10 mL) was added to make a homogeneous solution then ether was added (80 mL) and a white precipitate was formed. The amine hydrochloride product 837g (700 mg; 98%) was recovered by filtration as a white solid.

Step E

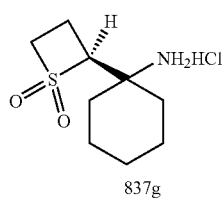 

837g

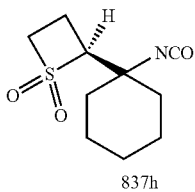

837h

A solution of amine hydrochloride 837g (2.960 mmol) in 40 mL of dichloromethane was treated with 20 mL of aqueous saturated sodium bicarbonate solution and stirred vigorously for 10 min at 0° C. Stirring was stopped and layers were allowed to separate. Phosgene (10 mL of 20% soln in toluene) was added through a needle to the organic layer (lower layer) in one portion. The mixture was vigorously stirred immediately after addition for 10 min at 0° C. and further stirred at room temp for 3 h. The mixture was diluted with 100 mL of dichloromethane and layers were separated. The organic layer was washed with 50 mL of cold aqueous saturated sodium bicarbonate solution and dried over magnesium sulfate. The organic layer was filtered and diluted with 50 mL of toluene. The resulting solution was concentrated and kept as a 0.118M solution in toluene.

Step F

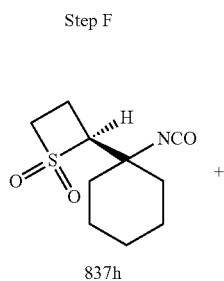

837h

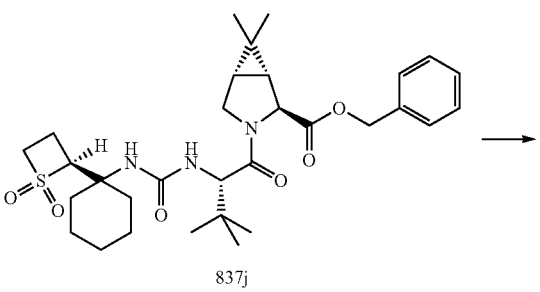

837i

837j

A solution of amine hydrochloride 837i (1.5 mmol) in 30 mL of dichloromethane was treated with 5 mL of aqueous saturated sodium bicarbonate. The mixture was stirred for 10 min followed by addition of the isocyanate 837h (1.03 eq, 13.1 mL of a 0.118M solution in toluene. The reaction mixture was stirred overnight. The reaction mixture was diluted with dichloromethane (200 mL) and washed with aqueous saturated sodium bicarbonate solution (40 mL). The organic layer was dried over magnesium sulfate, filtered and concentrated under reduced pressure. The residue was chromatographed on silica gel (gradient: acetone/hexanes; 1:9 to 1:1) to afford the product 837j (740 mg; 84%) as a white solid.

Step G

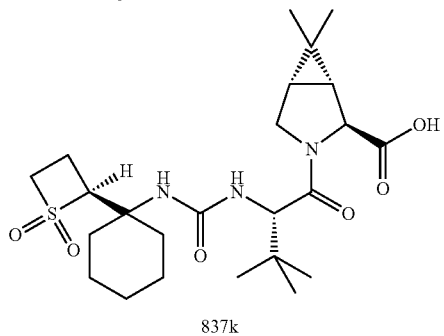

837j

837k

The benzyl ester 837j (740 mg) was dissolved in 20 mL of methanol and treated with 20% palladium dihydroxide on carbon (0.1 mol %; 90 mg). The heterogeneous mixture was hydrogenated at 50 psi for 2 h. TLC (acetone/hexanes; 35:65) showed that all the starting material had been consumed. The mixture was diluted with 100 mL of dichloromethane and filtered thru a short path of celite. The filtrate was concentrated under reduced pressure to afford the product 837k (620 mg; 98%) as a white solid.

Step H

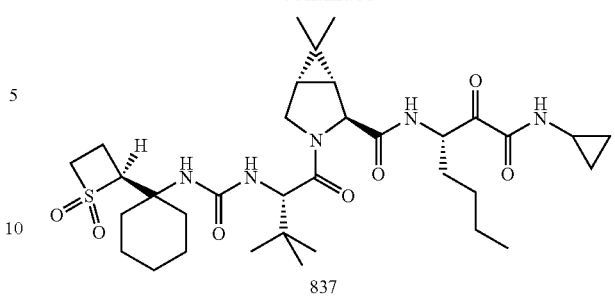

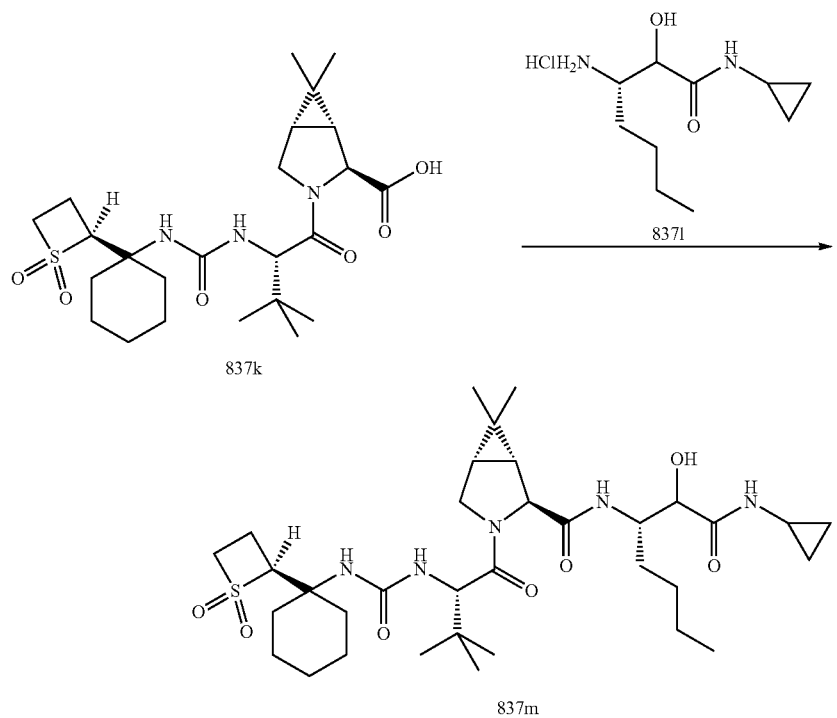

A solution of acid 837k (69 mg) in 2 mL of dry dichloromethane and 2 mL of dry DMF was stirred at 0° C. and treated with HATU (1.4 eq, 74 mg). The amine salt 837l (1.2 eq, 39 mg) was added followed by N-methylmorpholine (4 eq, 0.06 mL, d 0.920). The reaction mixture was stirred overnight (temp 0 to 25° C.). All the volatiles were removed under vacuum and the residue was dissolved in 50 mL of ethyl acetate. The organic layer was washed with water (10 mL), aqueous 1M HCl (10 mL), aqueous saturated sodium bicarbonate solution (10 mL), and brine (10 mL). The organic layer was dried over magnesium sulfate, filtered and concentrated under reduced pressure. The product 837m was used without further purification.

Step I

A solution of hydroxyamide 837m (0.138 mmol) in 10 mL of dry dichloromethane was treated with Dess-Martin periodinane (2.0 eq, 117 mg). The reaction mixture was stirred at room temperature for 30 min. The mixture was treated with aqueous 1M sodium thiosulfate solution (10 mL) and stirred for 5 min. Aqueous saturated sodium bicarbonate solution (10 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 2:8 to 1:1) to afford the product 837 (66 mg; 70%) as white solid. HRMS calcd for $C_{34}H_{56}N_5O_7S$ [M+H]$^+$: 678.3900, found 678.3883.

Example 838

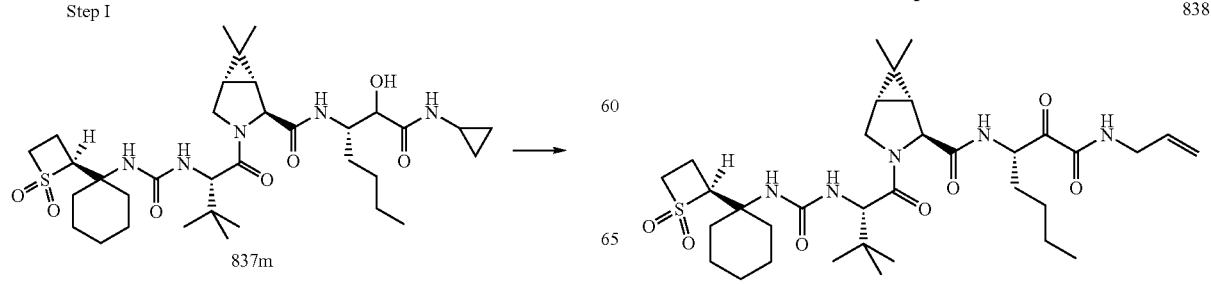

Step A

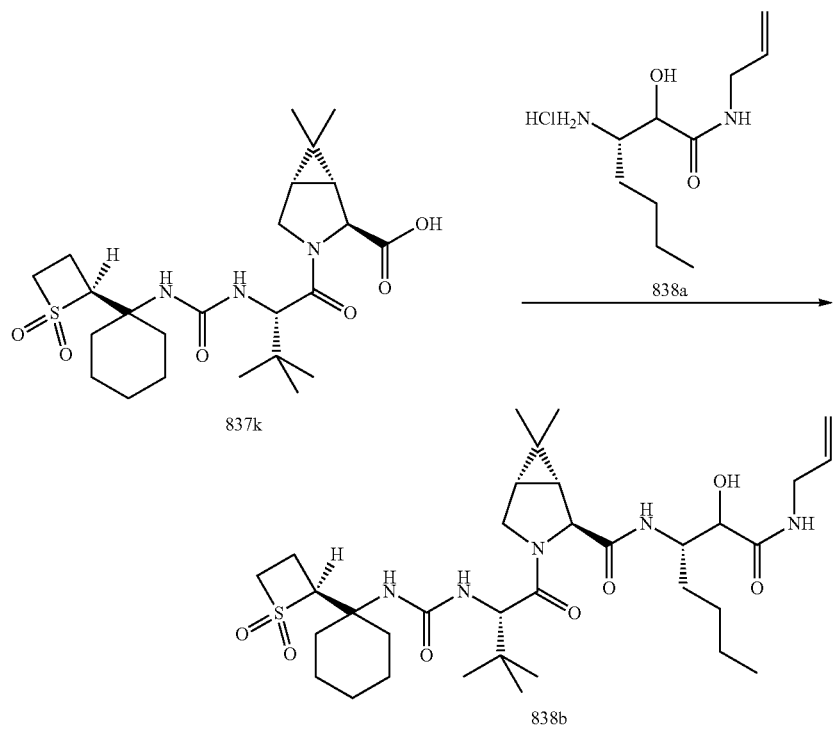

A solution of acid 837k (69 mg) in 2 mL of dry dichloromethane and 2 mL of dry DMF was stirred at 0° C. and treated with HATU (1.4 eq, 74 mg). The amine salt 838a (1.2 eq, 39 mg) was added followed by N-methylmorpholine (4 eq, 0.06 mL, d 0.920). The reaction mixture was stirred overnight (temp 0 to 25° C.). All the volatiles were removed under vacuum and the residue was dissolved in 50 mL of ethyl acetate. The organic layer was washed with water (10 mL), aqueous 1M HCl (10 mL), aqueous saturated sodium bicarbonate solution (10 mL), and brine (10 mL). The organic layer was dried over magnesium sulfate, filtered and concentrated under reduced pressure. The product 838b was used without further purification.

A solution of hydroxyamide 838b (0.138 mmol) in 10 mL of dry dichloromethane was treated with Dess-Martin periodinane (2.0 eq, 117 mg). The reaction mixture was stirred at room temperature for 30 min. The mixture was treated with aqueous 1M sodium thiosulfate solution (10 mL) and stirred for 5 min. Aqueous saturated sodium bicarbonate solution (10 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 1:9 to 4:6) to afford the product 838 (71 mg; 76%) as white solid. HRMS calcd for $C_{34}H_{56}N_5O_7S$ [M+H]$^+$: 678.3900, found 678.3883.

Example 869

Step B

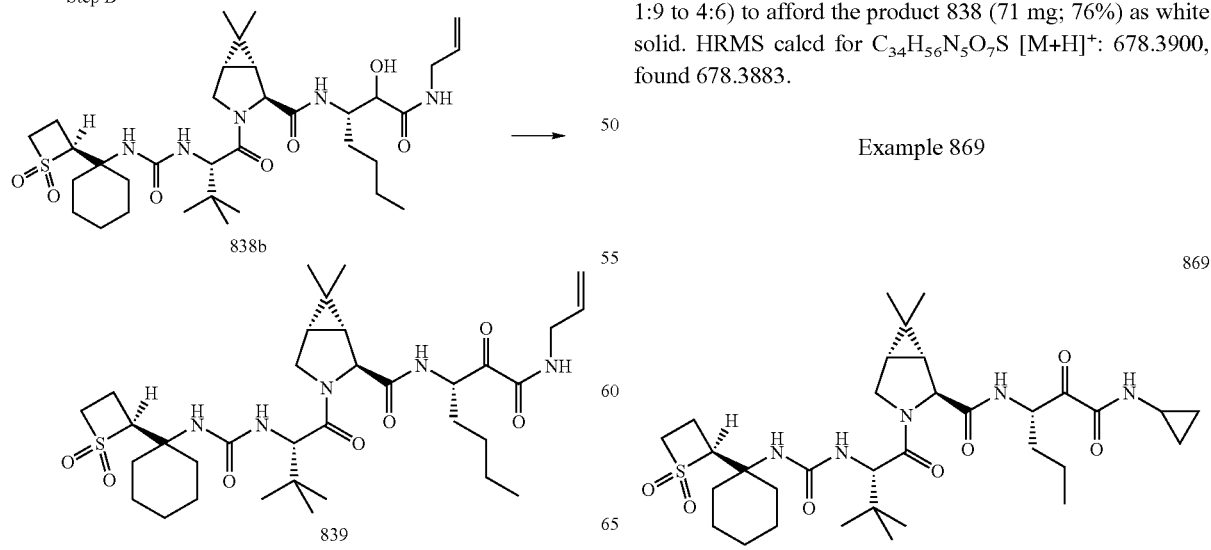

Step A

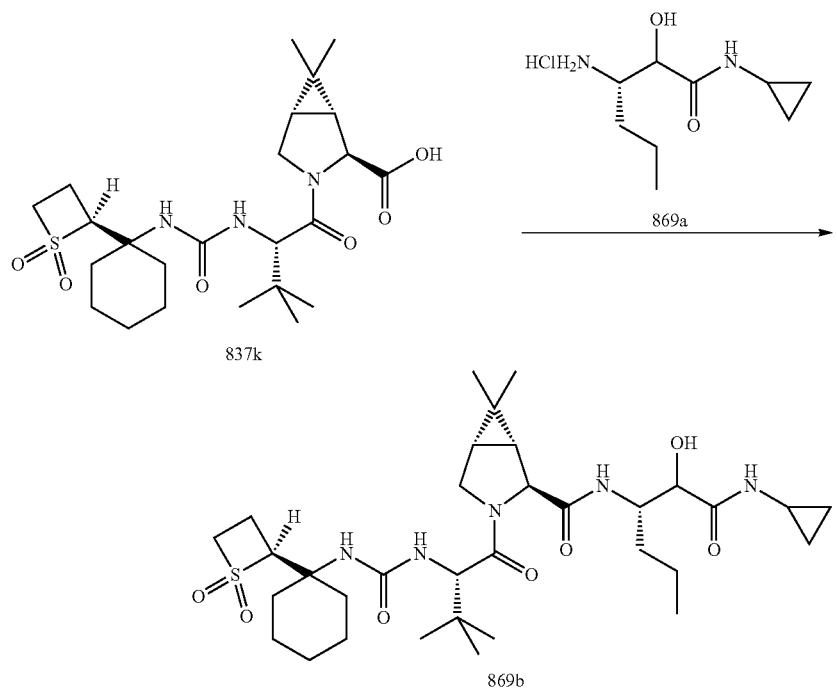

A solution of acid 837k (69 mg) in 2 mL of dry dichloromethane and 2 mL of dry DMF was stirred at 0° C. and treated with HATU (1.4 eq, 74 mg). The amine salt 869a (1.2 eq, 37 mg) was added followed by N-methylmorpholine (4 eq, 0.06 mL, d 0.920). The reaction mixture was stirred overnight (temp 0 to 25° C.). All the volatiles were removed under vacuum and the residue was dissolved in 50 mL of ethyl acetate. The organic layer was washed with water (10 mL), aqueous 1M HCl (10 mL), aqueous saturated sodium bicarbonate solution (10 mL), and brine (10 mL). The organic layer was dried over magnesium sulfate, filtered and concentrated under reduced pressure. The product 869b was used without further purification.

Step B

A solution of hydroxyamide 869b (0.138 mmol) in 10 mL of dry dichloromethane was treated with Dess-Martin periodinane (2.0 eq, 117 mg). The reaction mixture was stirred at room temperature for 30 min. The mixture was treated with aqueous 1M sodium thiosulfate solution (10 mL) and stirred for 5 min. Aqueous saturated sodium bicarbonate solution (10 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 18:85 to 45:55) to afford the product 869 (69 mg; 75%) as white solid.

Preparative Example 868

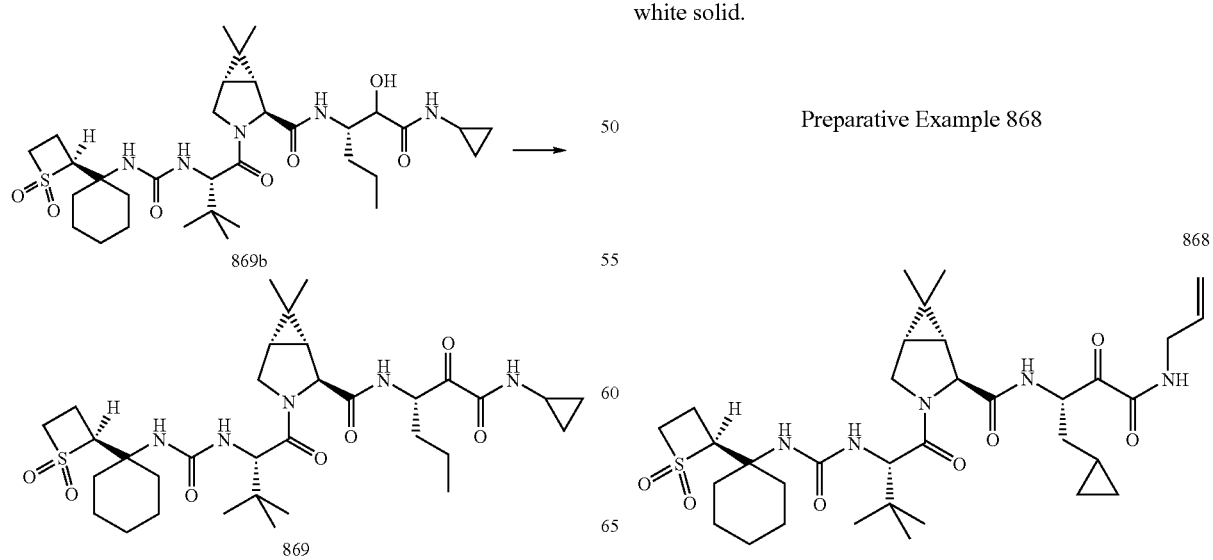

Step A

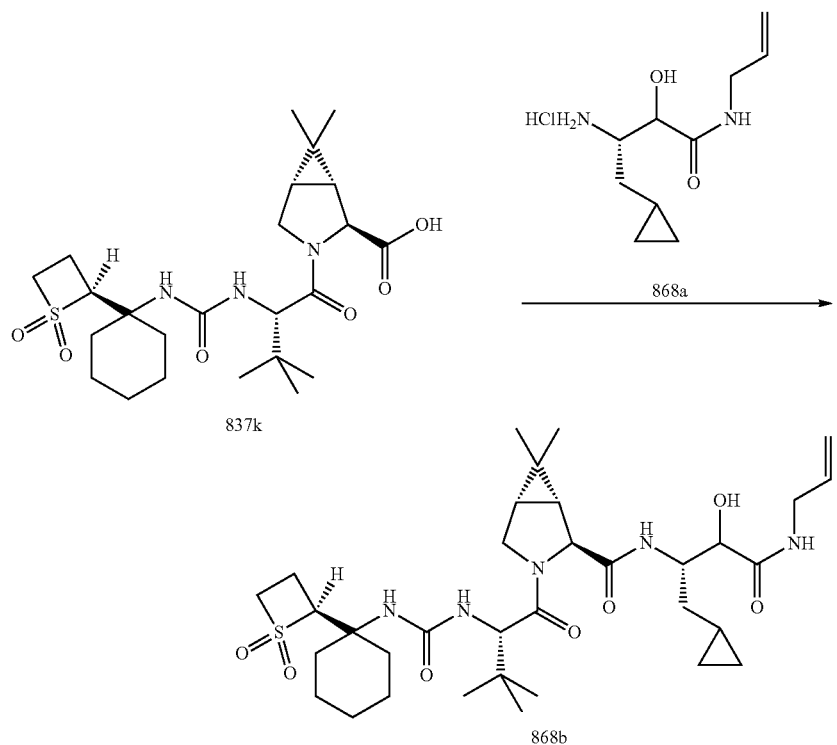

A solution of acid 837k (69 mg) in 2 mL of dry dichloromethane and 2 mL of dry DMF was stirred at 0° C. and treated with HATU (1.4 eq, 74 mg). The amine salt 868a (1.2 eq, 39 mg) was added followed by N-methylmorpholine (4 eq, 0.06 mL, d 0.920). The reaction mixture was stirred overnight (temp 0 to 25° C.). All the volatiles were removed under vacuum and the residue was dissolved in 50 mL of ethyl acetate. The organic layer was washed with water (10 mL), aqueous 1M HCl (10 mL), aqueous saturated sodium bicarbonate solution (10 mL), and brine (10 mL). The organic layer was dried over magnesium sulfate, filtered and concentrated under reduced pressure. The product 868b was used without further purification.

A solution of hydroxyamide 868b (0.138 mmol) in 10 mL of dry dichloromethane was treated with Dess-Martin periodinane (2.0 eq, 117 mg). The reaction mixture was stirred at room temperature for 30 min. The mixture was treated with aqueous 1M sodium thiosulfate solution (10 mL) and stirred for 5 min. Aqueous saturated sodium bicarbonate solution (10 mL) was also added and stirring was continued for further 10 min. The mixture was extracted with dichloromethane (3×30 mL). The combined organic layers were dried over magnesium sulfate, filtered, and concentrated. The residue was chromatographed on silica gel (gradient: acetone/hexanes; 1:9 to 4:6) to afford the product 868 (73 mg; 78%) as white solid.

Example 833

Step B

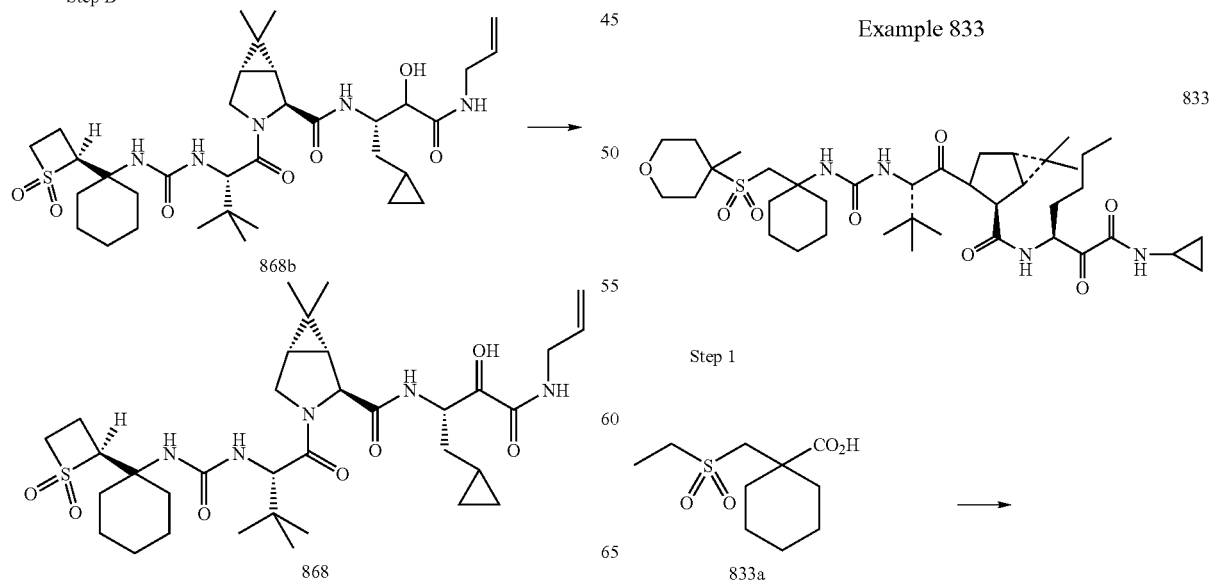

Step 1

433

-continued

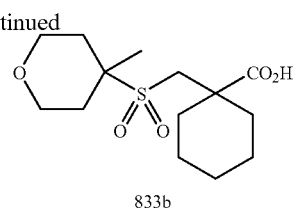

833b

To a solution of ethylsulfone acid 833a (2.06 g, 8.79 mmol) in anhydrous THF at −78° C. under N₂ was added LiHMDS solution (19.3 mL, 1.0 Min THF). The mixture was stirred at −78° C. for 30 min before it was allowed to warmed to 0° C. along with a cold acetone bath. It was then re-cooled to −78° C. and to it was added 2-bromoethyl ether (1.8 mL, 13.2 mmol). After stirred at −78° C. for 30 min, the mixture was warmed to rt and stirred for 2 h. It was again re-cooled to −78° C. and to it was added LiHMDS solution (10.6 mL, 10.6 mmol). After stirred at −78° C. for 30 min, the mixture was warmed to rt and stirred for 3 h before it was quenched with 1N aqueous HCl solution until the pH is about 1-2. The solution was extracted with CH₂Cl₂ (2×450 mL). Combined organic solution was dried (MgSO₄), filtered and concentrated. The crude product was dissolved in 1 N NaOH solution (300 mL) and extracted with EtOAc (100 mL). After layers were separated, the organic solution was washed with 1 N NaOH (2×150 mL). The combined aqueous solution was acidified to pH~1 using 6 N HCl solution. It was extracted with EtOAc (3×300 mL). The organic solutions were combined, dried (MgSO₄), filtered and concentrated to give 2.3 g product (833b; 7.56 mmol, 89%).

Step 2

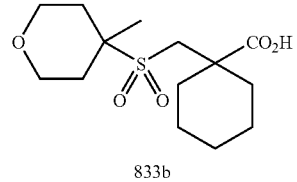

833b

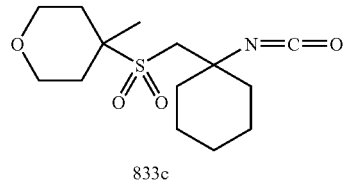

833c

To the acid 833b (2.30 g, 7.56 mmol) in toluene at rt under N₂ was added triethylamine (1.15 mL, 8.32 mmol) and diphenylphosphoryl azide (1.79 mL, 8.32 mmol). The resulting mixture was stirred at rt for 30 min and heated to reflux for 5.5 h. After it was cooled to rt, more toluene was added to make up a 0.19 M solution of the isocyanate 833c, which was used without further purification.

Using the aforementioned procedures 833c was transformed into 833.

TABLE 3A

| Compound # | structure | mol weight structure | Select LC-MS Data (M + H) | Ki* Range |
|---|---|---|---|---|
| 397 | 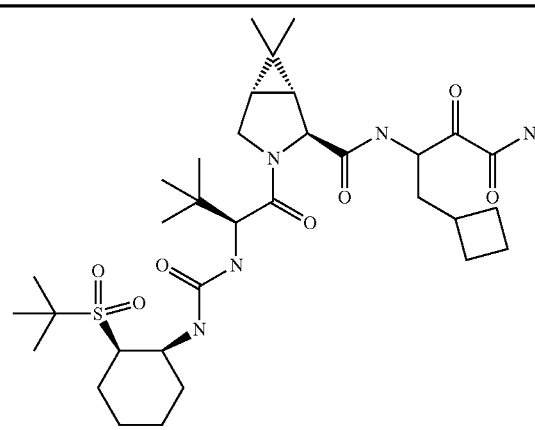 | 665.887 | 666.3 | B |
| 398 | 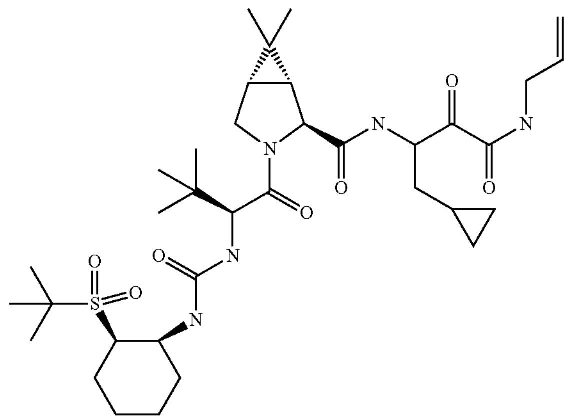 | 691.925 | 692.4 | C |

TABLE 3A-continued
| Compound # | structure | mol weight structure | Select LC-MS Data (M + H) | Ki* Range |
|---|---|---|---|---|
| 399 | 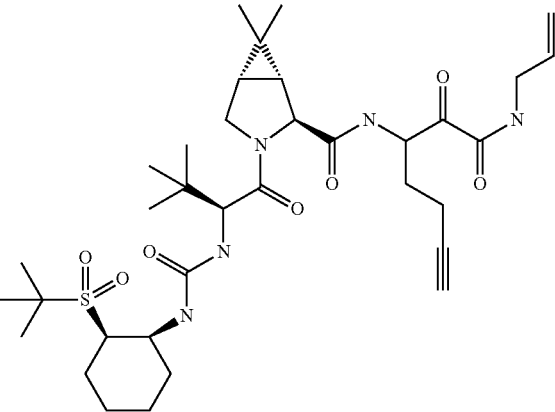 | 689.909 | 690.3 | B |
| 400 | 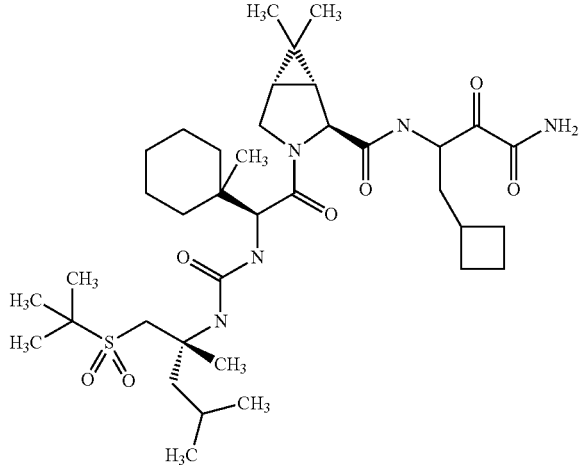 | 722.008 | 722.4 | A |
| 401 | 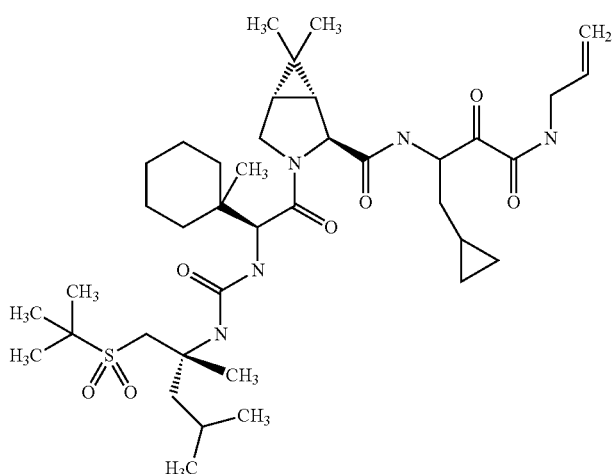 | 748.0462 | 748.4 | A |

TABLE 3A-continued

| Compound # | structure | mol weight structure | Select LC-MS Data (M + H) | Ki* Range |
|---|---|---|---|---|
| 402 | 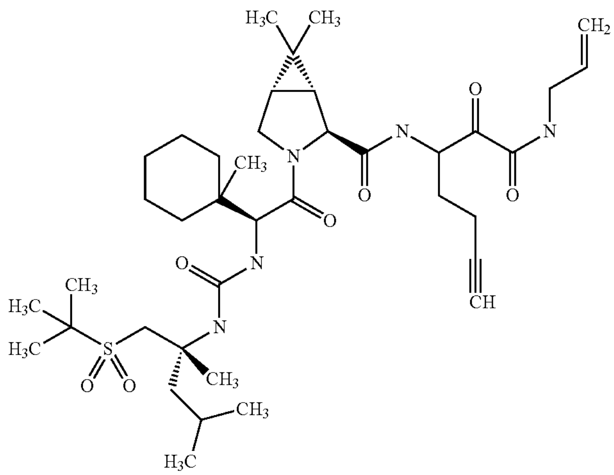 | 746.0303 | 746.2 | A |
| 403 | 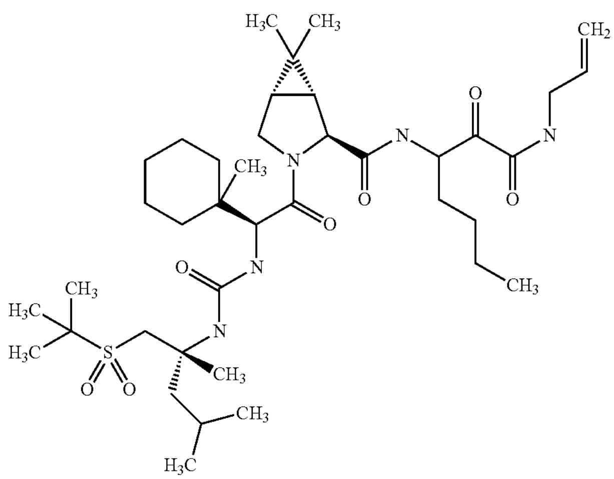 | 750.0621 | 750.4 | A |
| 404 | 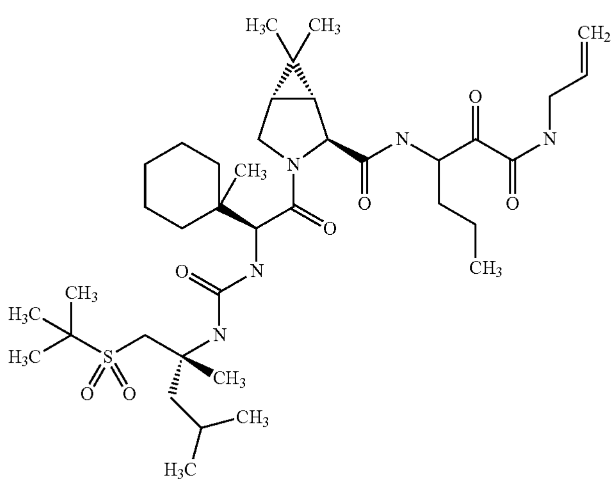 | 736.0351 | 736.4 | A |

TABLE 3A-continued
| Compound # | structure | mol weight structure | Select LC-MS Data (M + H) | Ki* Range |
|---|---|---|---|---|
| 405 | 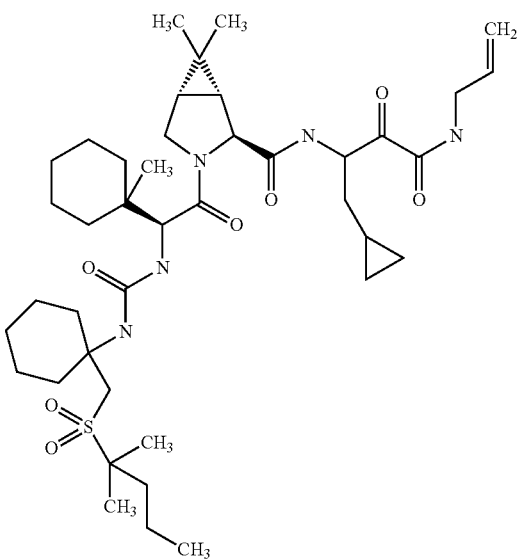 | 774.0844 | | A |
| 406 | 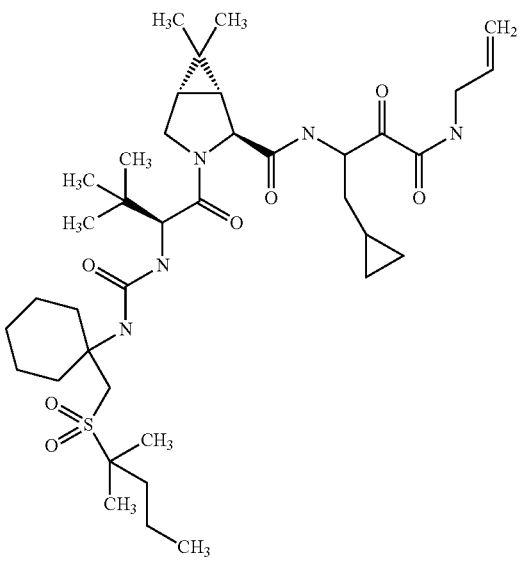 | 734.0191 | | A |

TABLE 3A-continued

| Compound # | structure | mol weight structure | Select LC-MS Data (M + H) | Ki* Range |
|---|---|---|---|---|
| 407 | 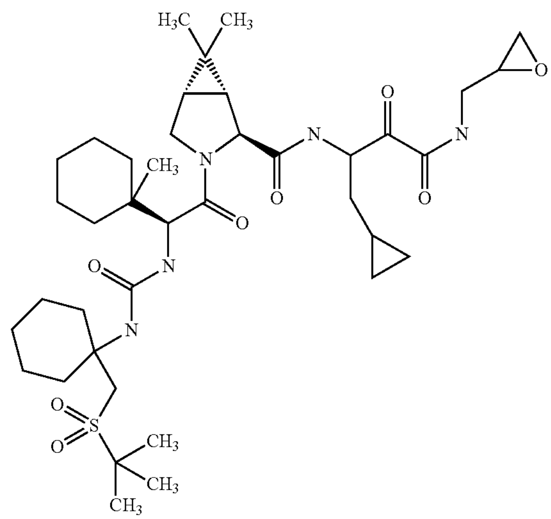 | 762.0297 | | A |
| 408 | 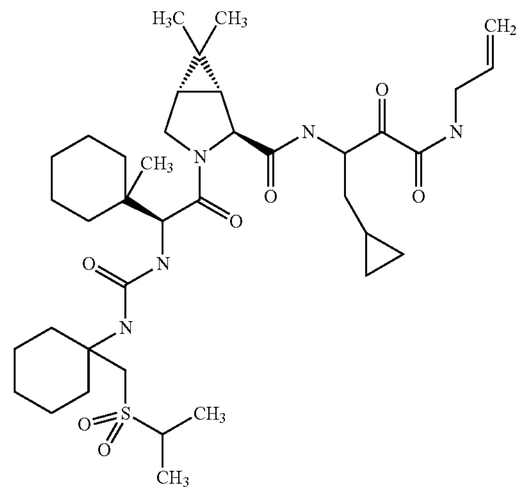 | 732.0032 | | A |
| 409 | 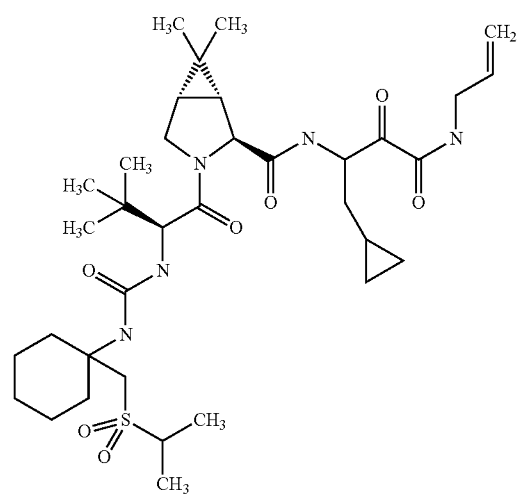 | 691.9378 | | A |

TABLE 3A-continued

| Compound # | structure | mol weight structure | Select LC-MS Data (M + H) | Ki* Range |
|---|---|---|---|---|
| 410 | 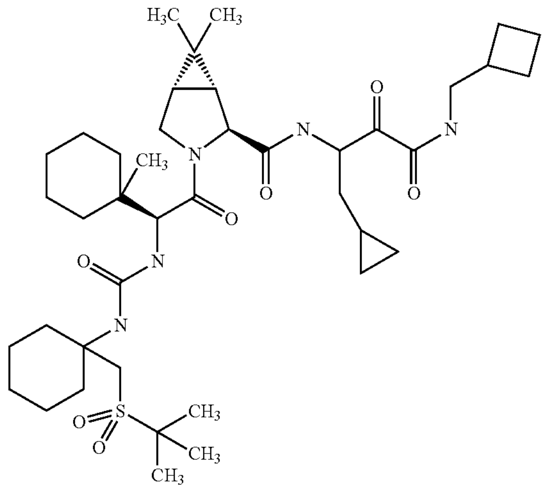 | 774.0844 | | A |
| 411 | 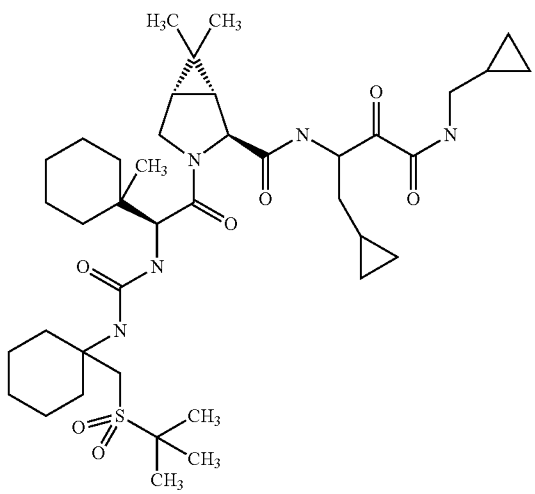 | 760.0574 | | A |
| 412 | 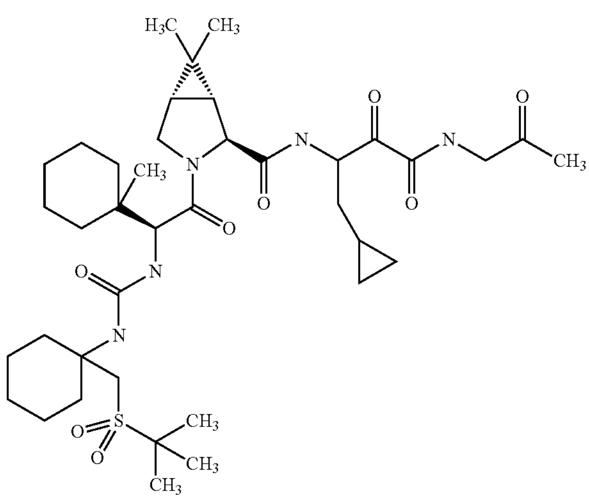 | 762.0297 | | A |

TABLE 3A-continued

| Compound # | structure | mol weight structure | Select LC-MS Data (M + H) | Ki* Range |
|---|---|---|---|---|
| 413 | 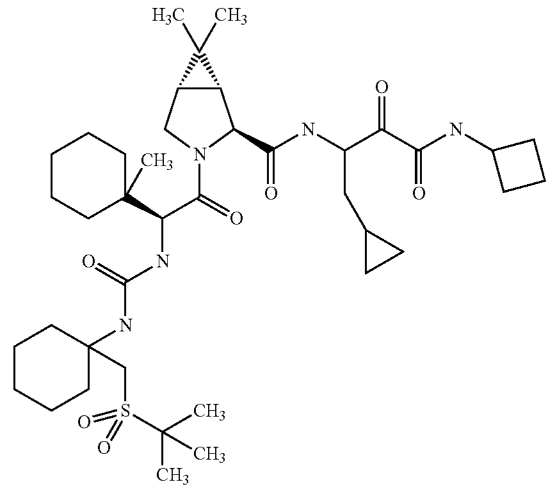 | 760.0574 | | A |
| 414 | 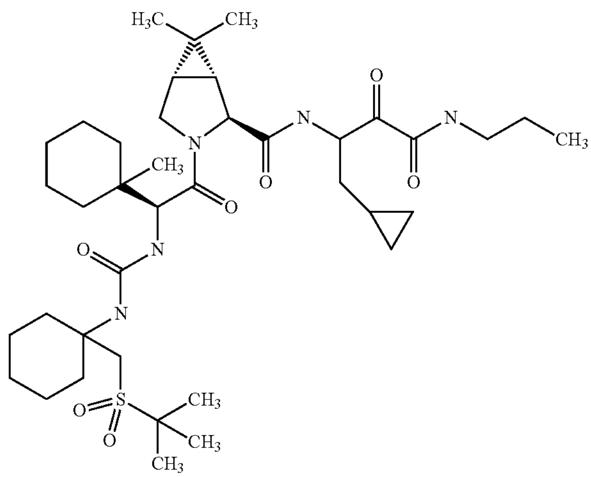 | 748.0462 | | A |
| 415 | 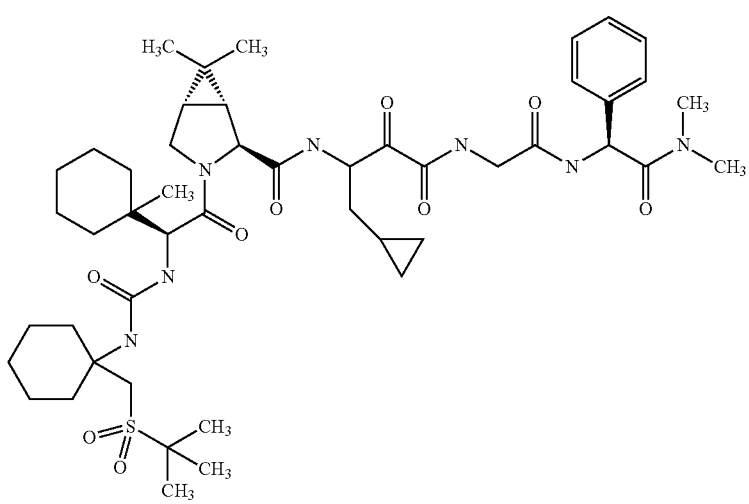 | 924.2225 | | B |

TABLE 3A-continued

| Compound # | structure | mol weight structure | Select LC-MS Data (M + H) | Ki* Range |
|---|---|---|---|---|
| 416 | 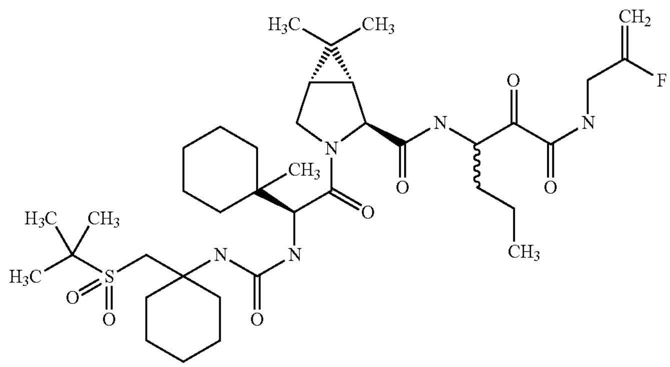 | 752.0095 | | A |
| 417 | 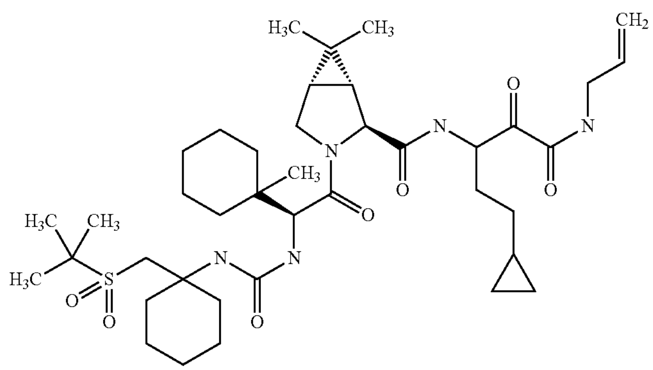 | 760.0574 | | A |
| 418 | 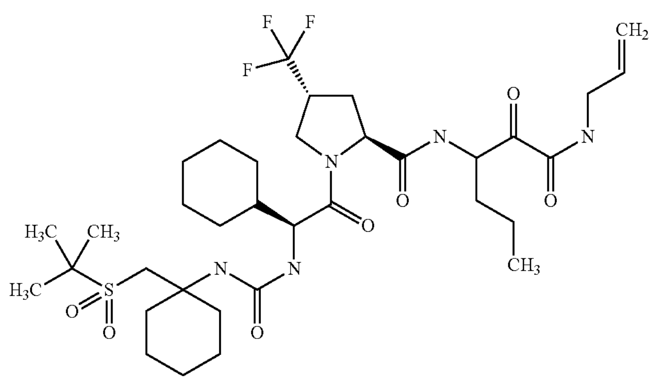 | 747.9251 | | A |
| 419 | 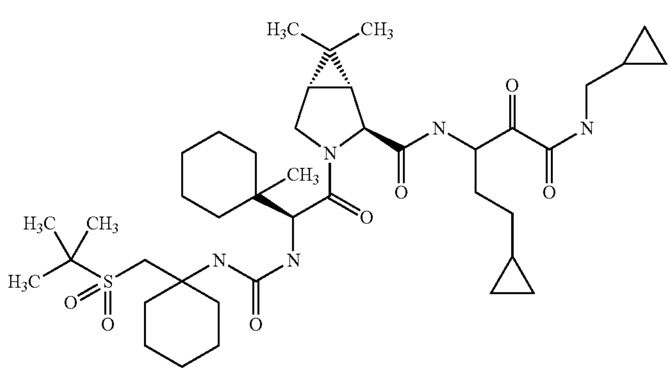 | 774.0844 | | A |

TABLE 3A-continued

| Compound # | structure | mol weight structure | Select LC-MS Data (M + H) | Ki* Range |
|---|---|---|---|---|
| 420 | 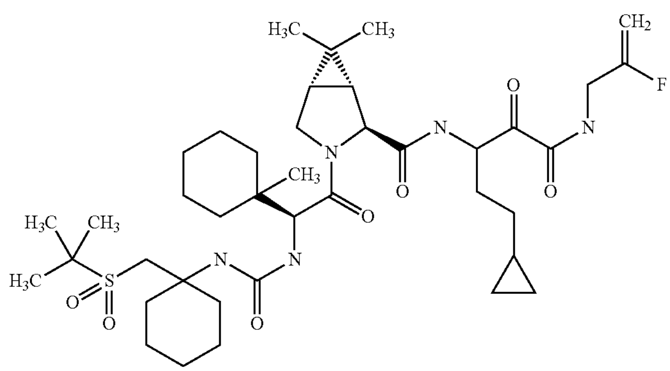 | 778.0478 | | A |
| 421 | 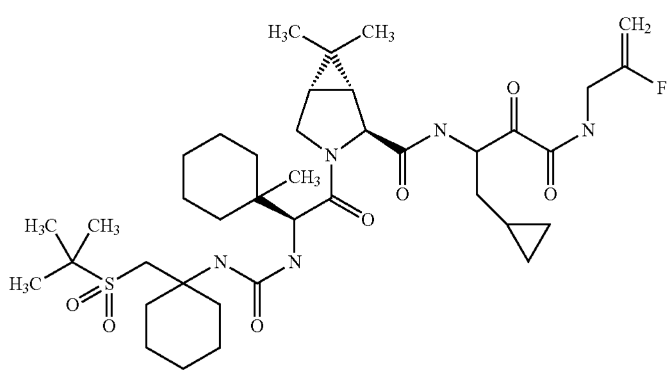 | 764.0207 | | A |
| 422 | 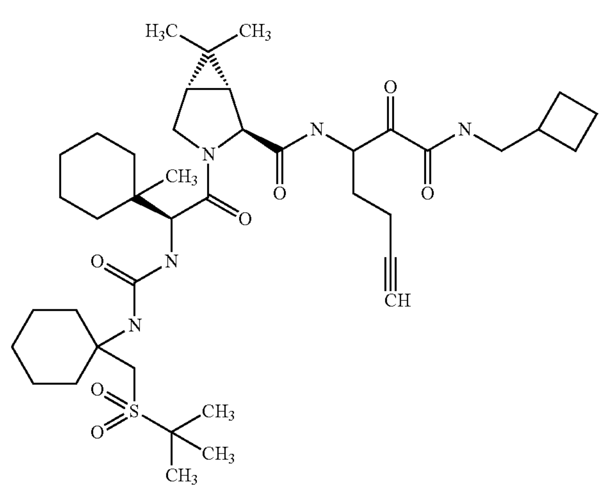 | 772.0685 | | A |

TABLE 3A-continued

| Compound # | structure | mol weight structure | Select LC-MS Data (M + H) | Ki* Range |
|---|---|---|---|---|
| 423 | 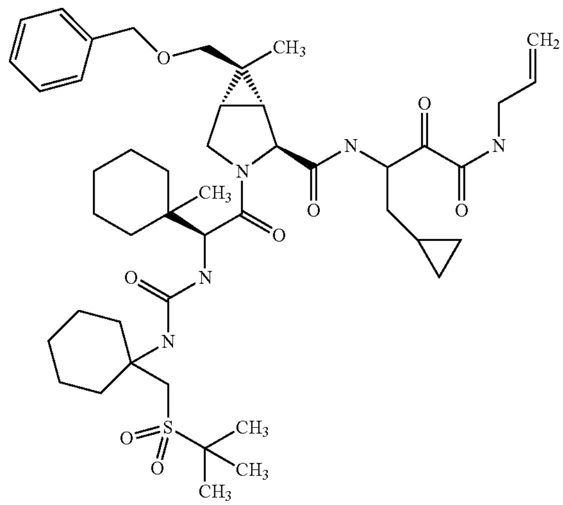 | 852.1555 | 852.5 | A |
| 424 | 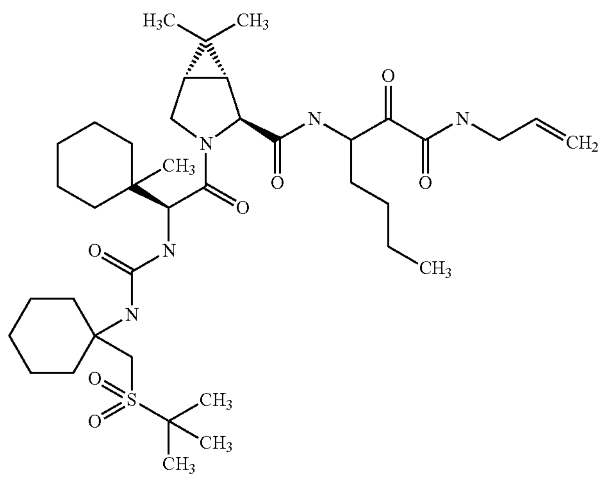 | 748.0462 | | A |
| 425 | 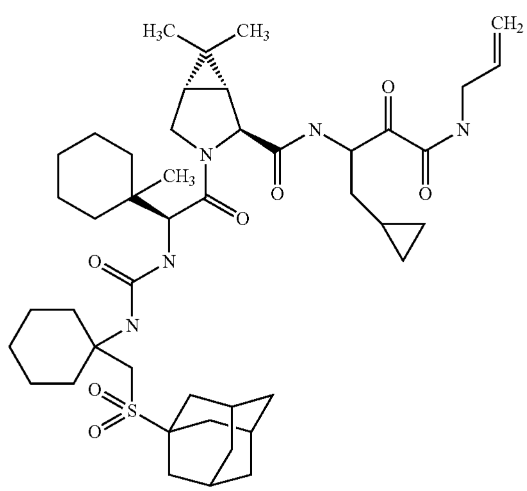 | 824.145 | | A |

TABLE 3A-continued

| Compound # | structure | mol weight structure | Select LC-MS Data (M + H) | Ki* Range |
|---|---|---|---|---|
| 426 | 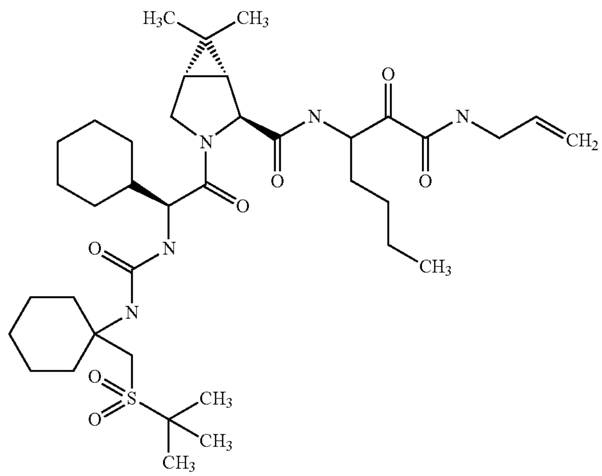 | 734.0191 | | A |
| 427 | 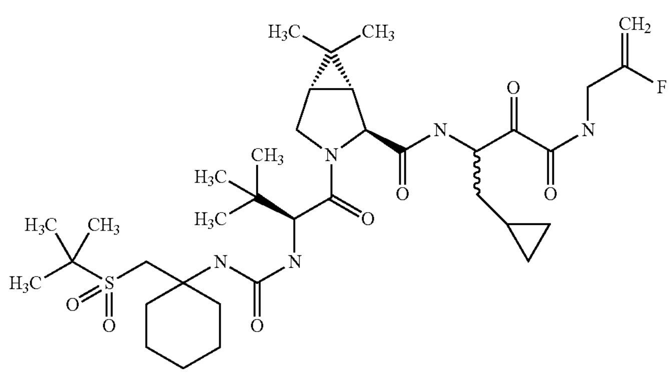 | 723.9554 | | A |
| 428 | 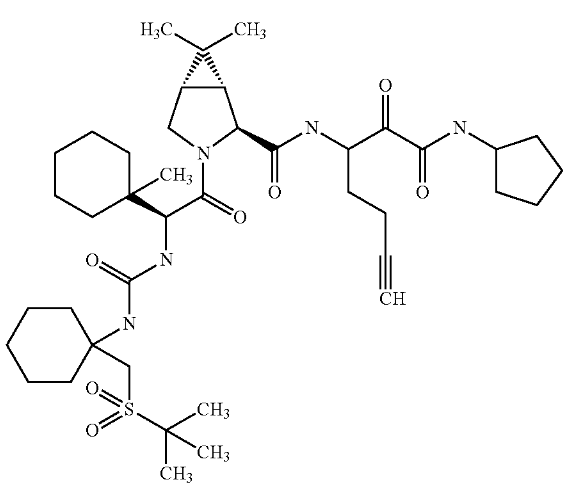 | 772.0685 | | A |

TABLE 3A-continued

| Compound # | structure | mol weight structure | Select LC-MS Data (M + H) | Ki* Range |
|---|---|---|---|---|
| 429 | 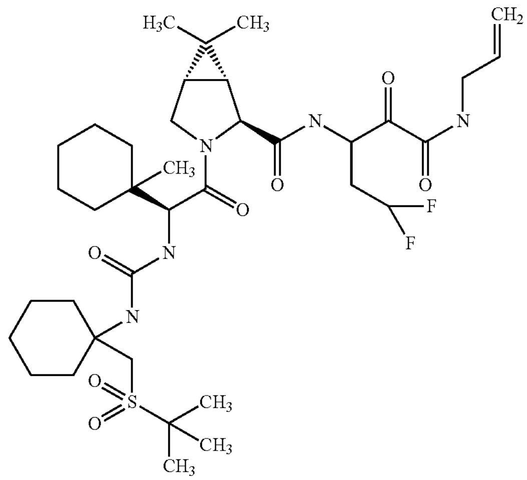 | 755.9729 | | A |
| 430 | 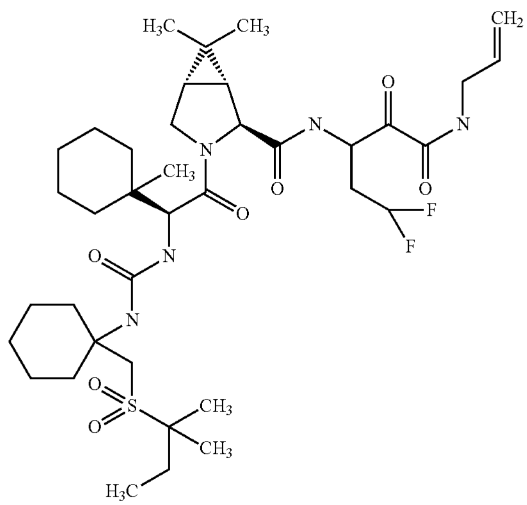 | 770 | | A |
| 431 | 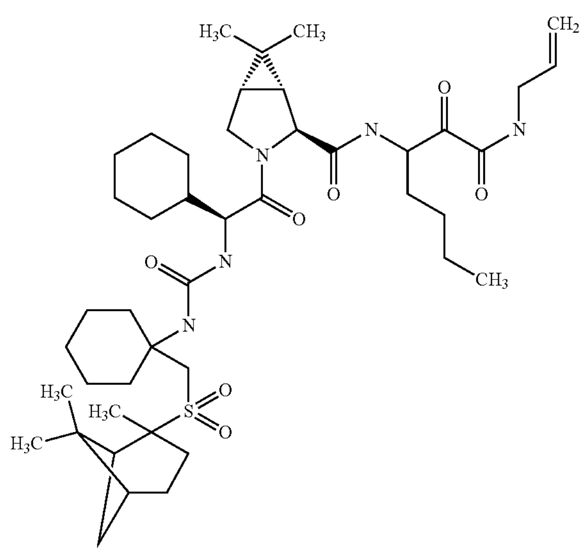 | 814.1498 | | A |

TABLE 3A-continued

| Compound # | structure | mol weight structure | Select LC-MS Data (M + H) | Ki* Range |
|---|---|---|---|---|
| 432 | 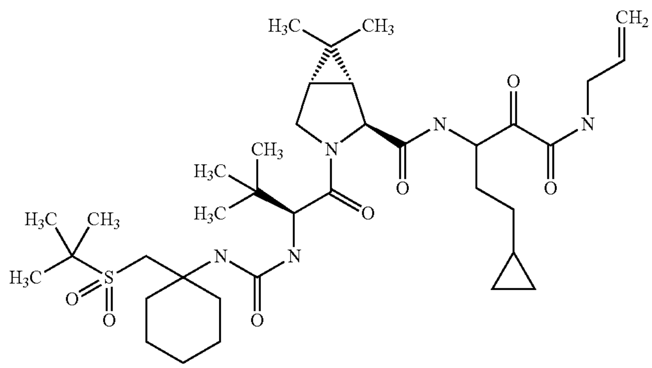 | 719.992 | | A |
| 433 | 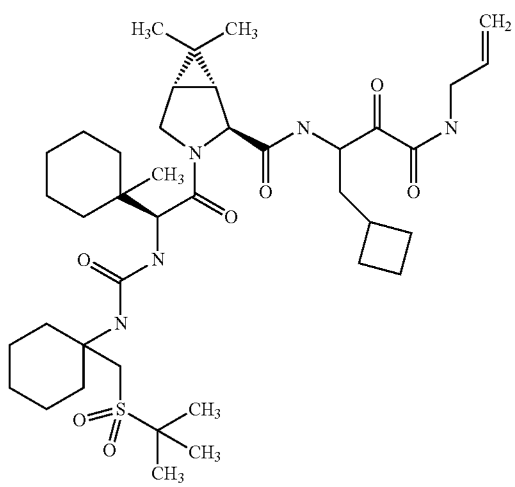 | 760.0574 | | A |
| 434 | 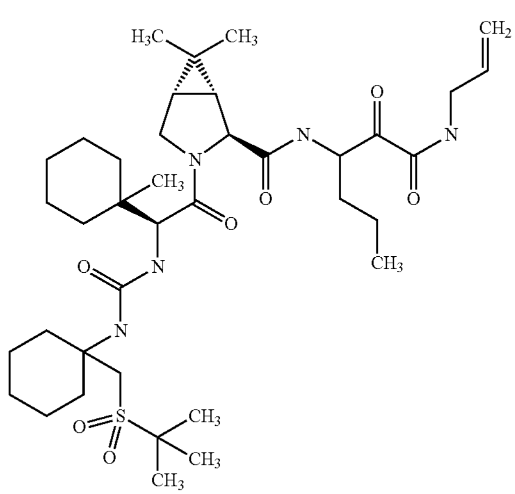 | 734.0191 | | A |

TABLE 3A-continued

| Compound # | structure | mol weight structure | Select LC-MS Data (M + H) | Ki* Range |
|---|---|---|---|---|
| 435 | 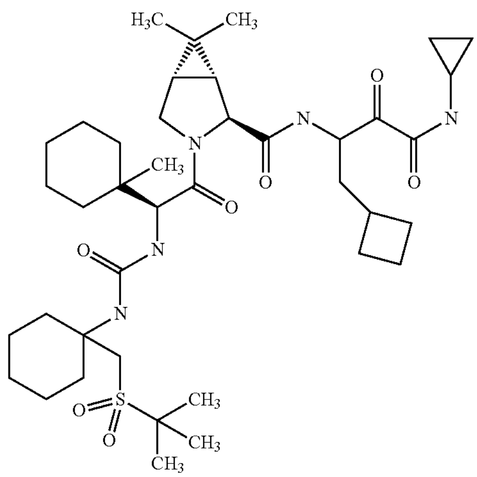 | 760.0574 | | A |
| 436 | 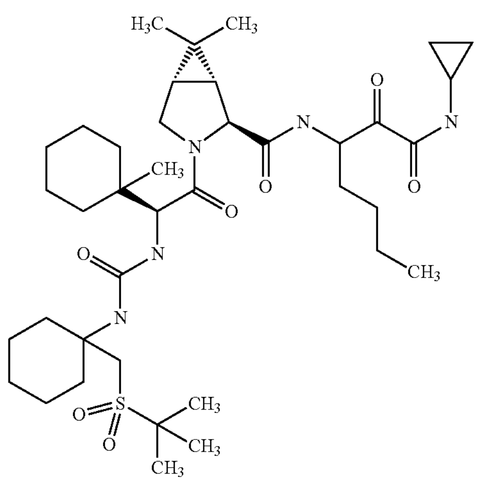 | 748.0462 | | A |
| 437 | 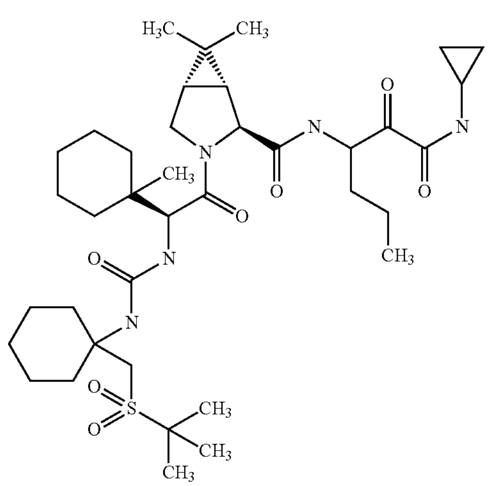 | 734.0191 | | A |

TABLE 3A-continued

| Compound # | structure | mol weight structure | Select LC-MS Data (M + H) | Ki* Range |
|---|---|---|---|---|
| 438 | 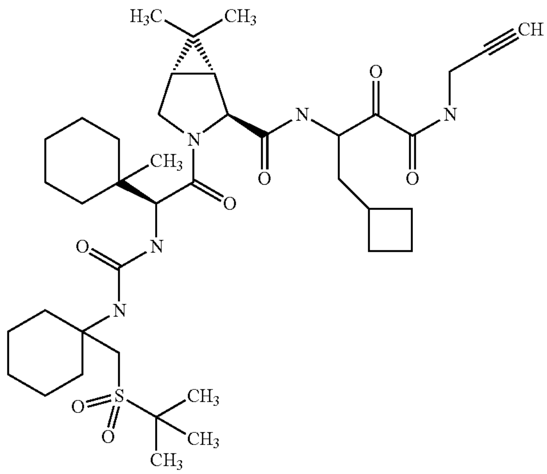 | 758.0414 | | A |
| 439 | 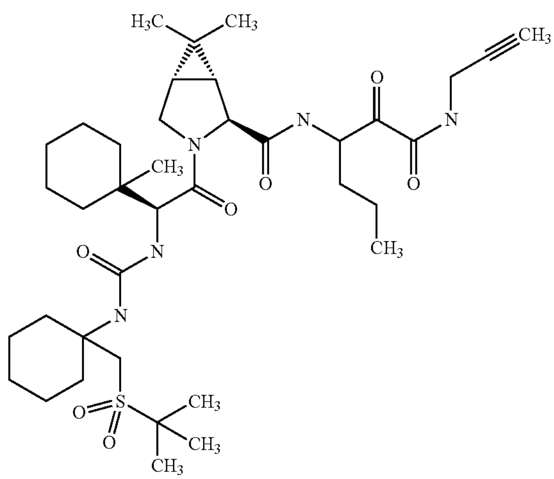 | 732.0032 | | A |
| 440 | 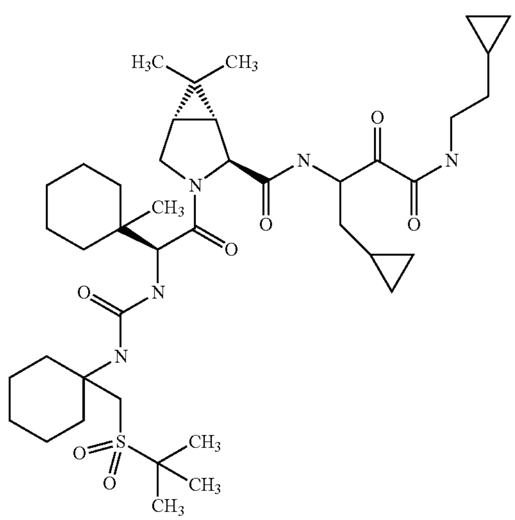 | 774.0844 | 774.2 | A |

TABLE 3A-continued

| Compound # | structure | mol weight structure | Select LC-MS Data (M + H) | Ki* Range |
|---|---|---|---|---|
| 441 | 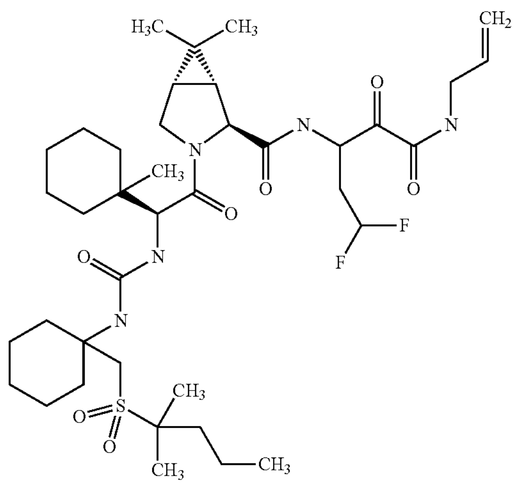 | 784.0271 | 784.2 | A |
| 442 | 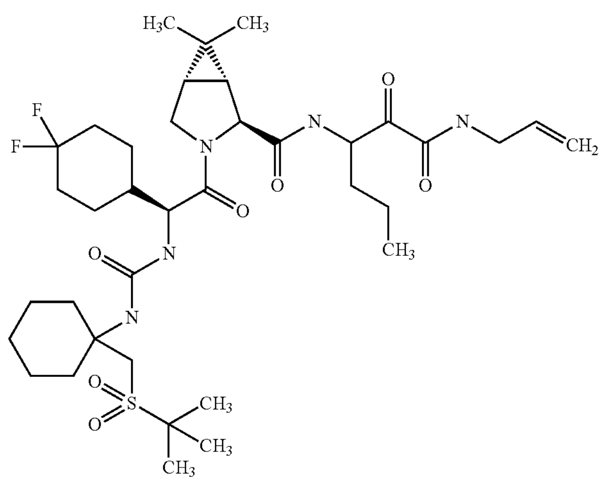 | 755.9729 | 756.2 | A |
| 443 | 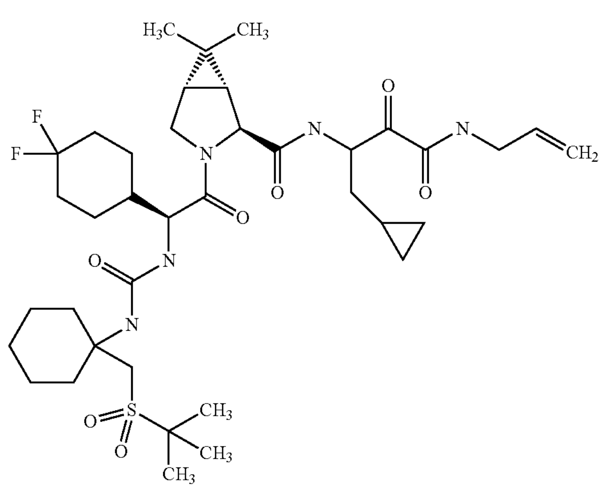 | 767.984 | 768.4 | A |

TABLE 3A-continued

| Compound # | structure | mol weight structure | Select LC-MS Data (M + H) | Ki* Range |
|---|---|---|---|---|
| 444 | 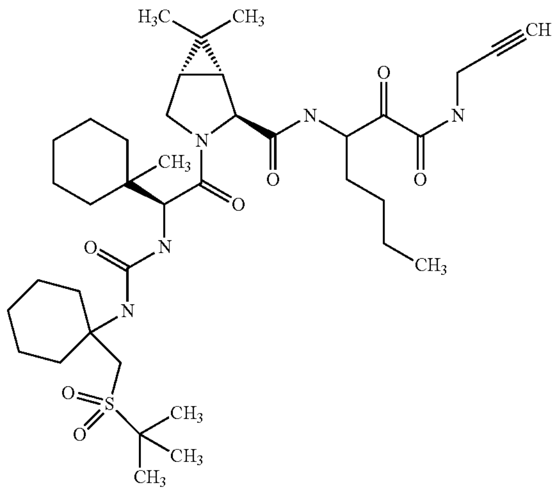 | 746.0303 | | A |
| 445 | 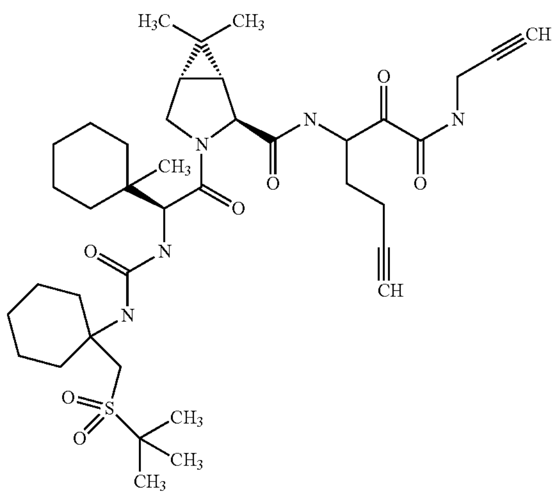 | 741.9984 | | A |
| 446 | 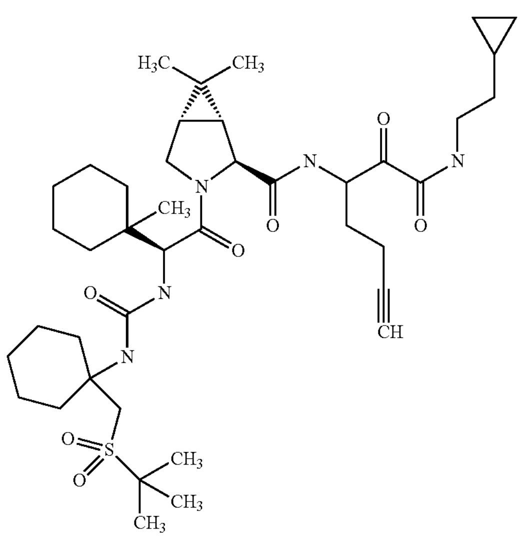 | 772.0685 | | A |

TABLE 3A-continued

| Compound # | structure | mol weight structure | Select LC-MS Data (M + H) | Ki* Range |
|---|---|---|---|---|
| 447 | 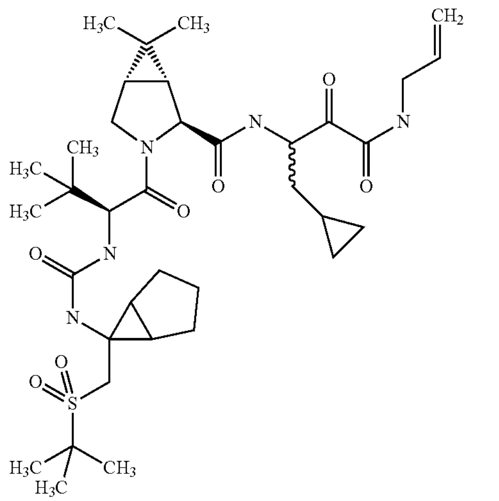 | 703.949 | 704.4 | A |
| 448 | 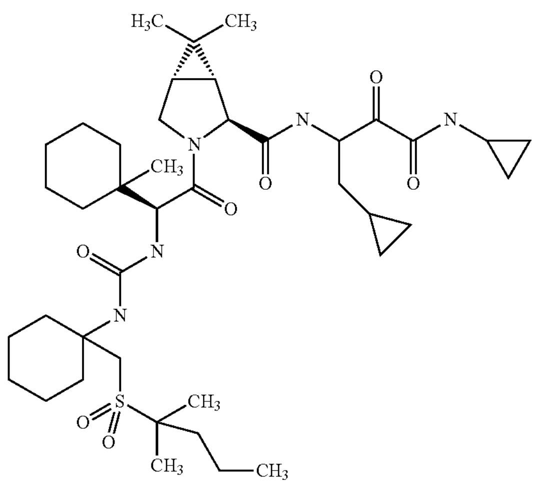 | 774.0844 | | A |
| 449 | 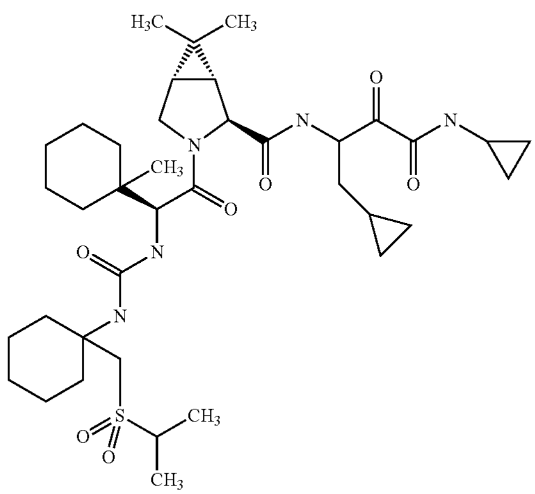 | 732.0032 | | A |

TABLE 3A-continued

| Compound # | structure | mol weight structure | Select LC-MS Data (M + H) | Ki* Range |
|---|---|---|---|---|
| 450 | 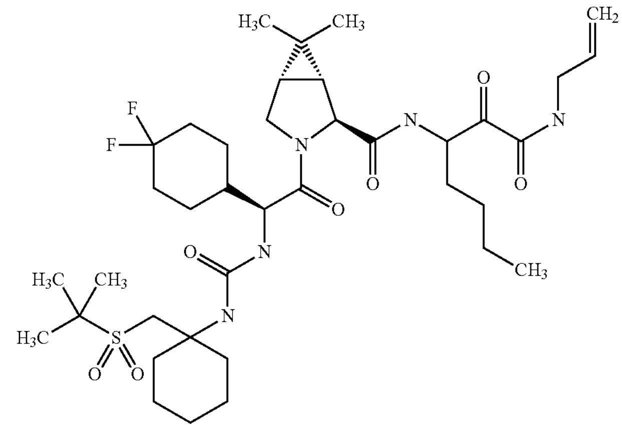 | 770 | 770.2 | A |
| 451 | 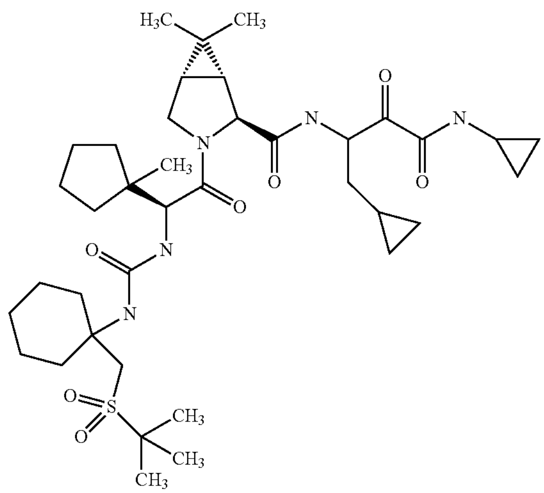 | 732.0032 | 732.2 | A |
| 452 | 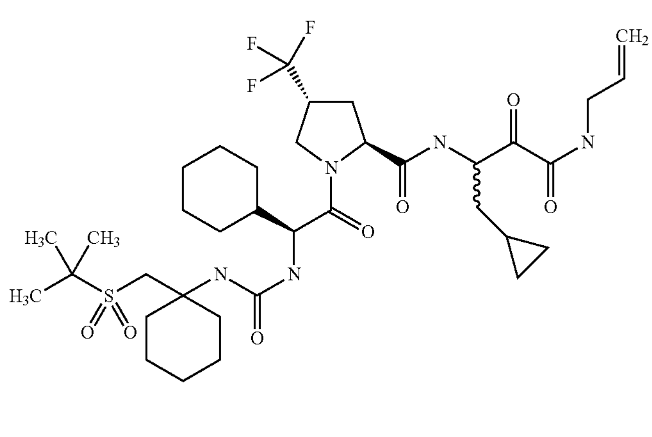 | 759.9362 | | A |

TABLE 3A-continued

| Compound # | structure | mol weight structure | Select LC-MS Data (M + H) | Ki* Range |
|---|---|---|---|---|
| 453 | 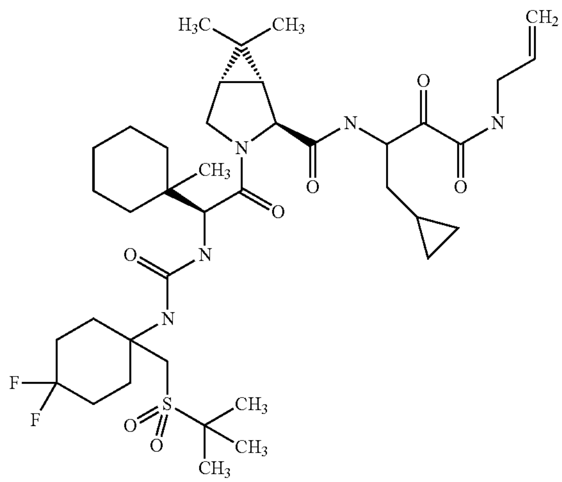 | | 782.0111 | A |
| 454 | 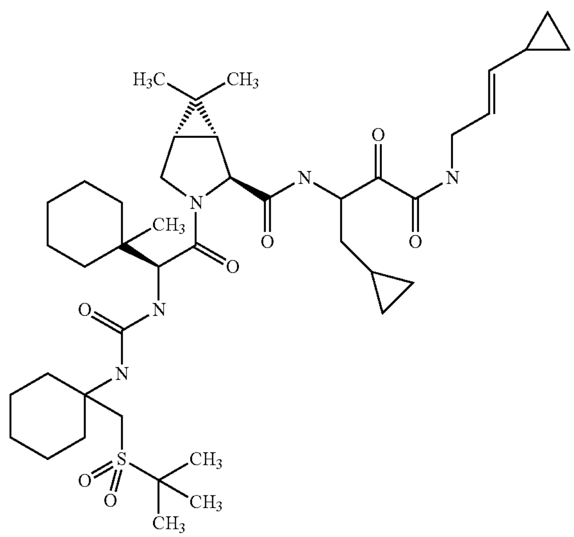 | | 786.0956 | A |
| 455 | 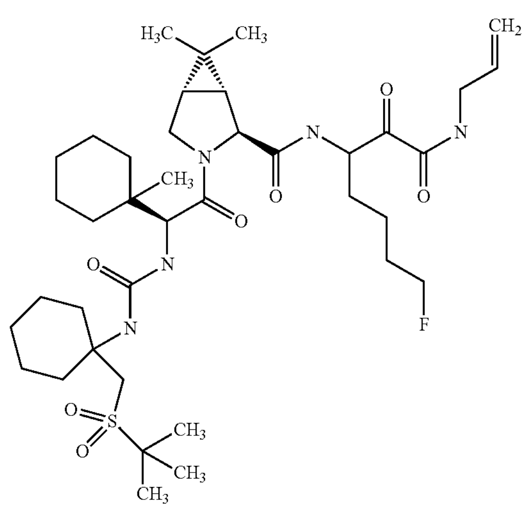 | | 766.0366 | A |

TABLE 3A-continued

| Compound # | structure | mol weight structure | Select LC-MS Data (M + H) | Ki* Range |
|---|---|---|---|---|
| 456 | 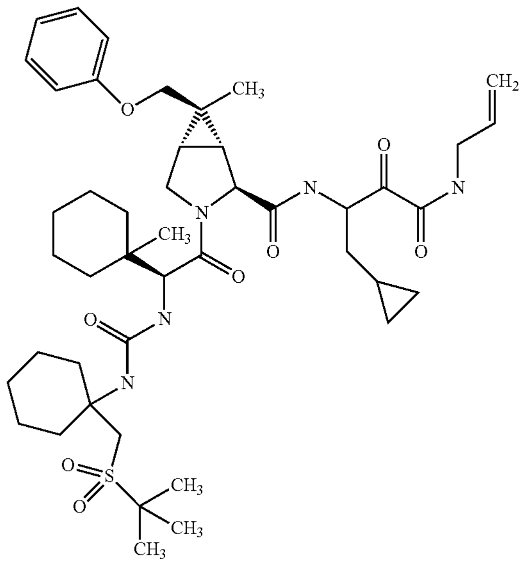 | 838.1284 | | B |
| 457 | 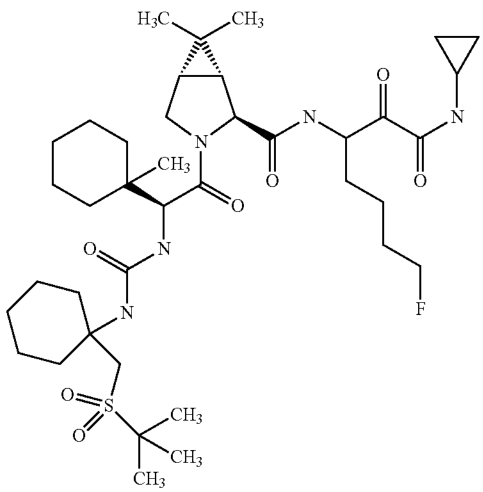 | 766.0366 | 766.4 | A |
| 458 | 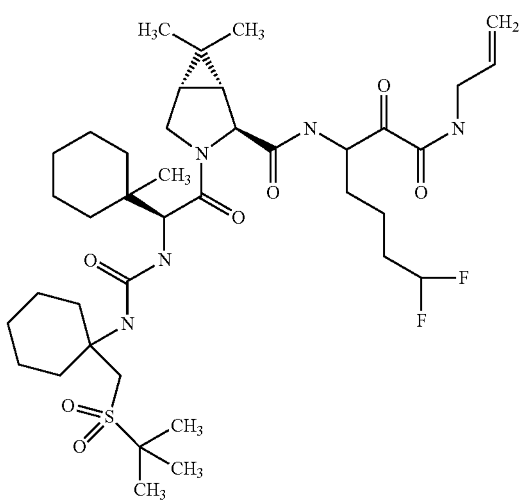 | 784.0271 | 784.4 | A |

TABLE 3A-continued
| Compound # | structure | mol weight structure | Select LC-MS Data (M + H) | Ki* Range |
|---|---|---|---|---|
| 459 | 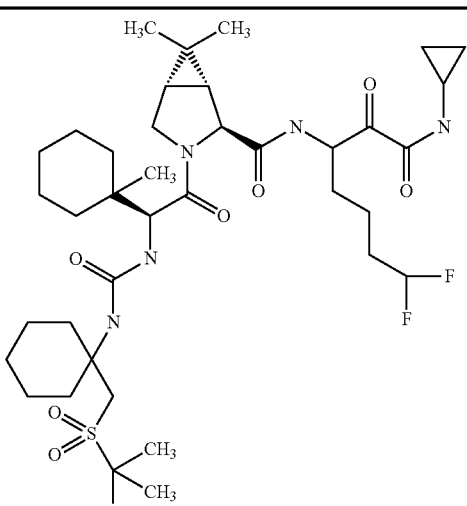 | 784.0271 | 784.2 | A |
| 460 | 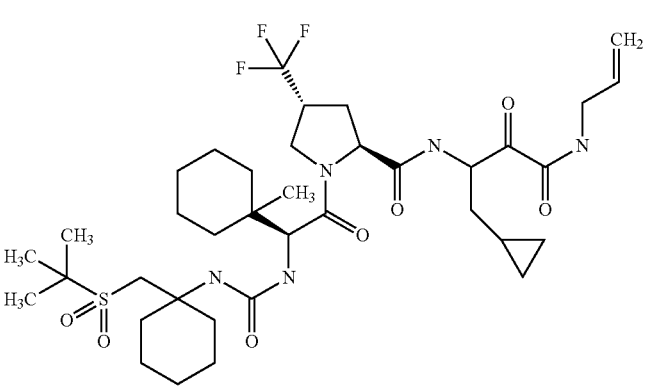 | 773.9633 | | A |
| 461 | 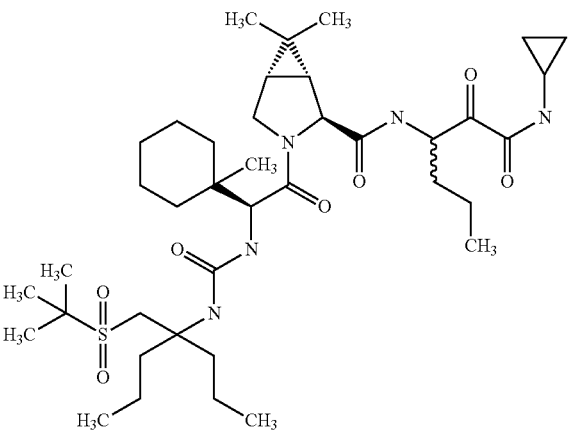 | 750.0621 | 750.9 | B |

TABLE 3A-continued
| Compound # | structure | mol weight structure | Select LC-MS Data (M + H) | Ki* Range |
|---|---|---|---|---|
| 462 | 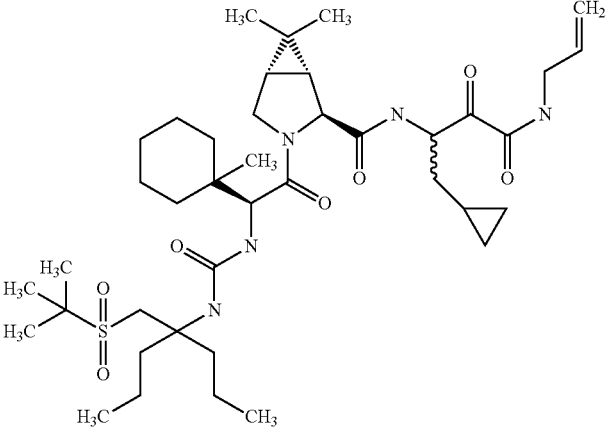 | 762.0733 | 762.41 | C |
| 463 | 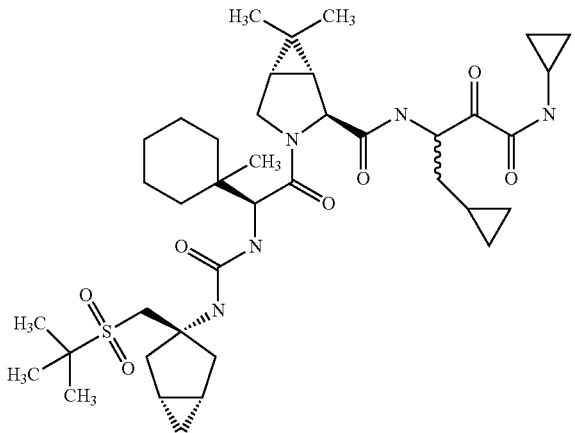 | 744.0143 | 744.2 | B |
| 464 | 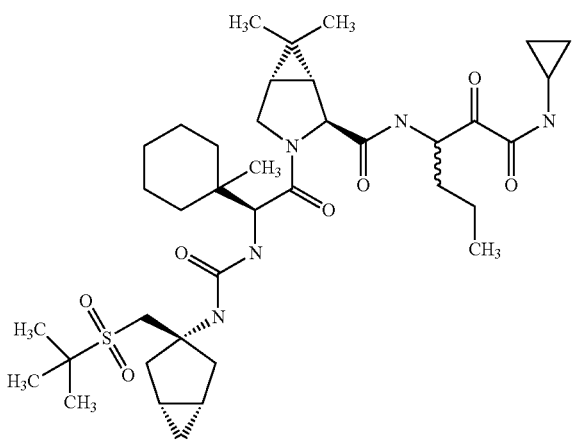 | 732.0032 | 732.4 | A |

TABLE 3A-continued
| Compound # | structure | mol weight structure | Select LC-MS Data (M + H) | Ki* Range |
|---|---|---|---|---|
| 465 | 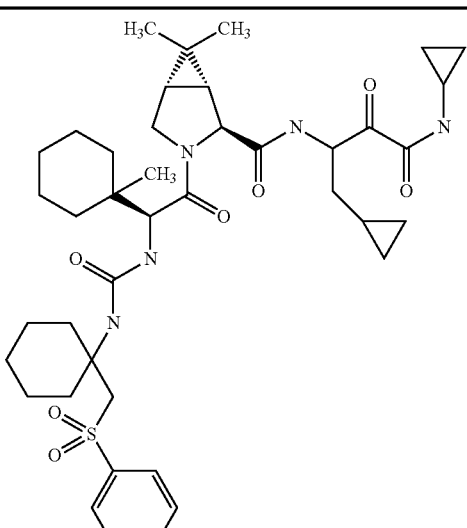 | 766.0207 | | B |
| 466 | 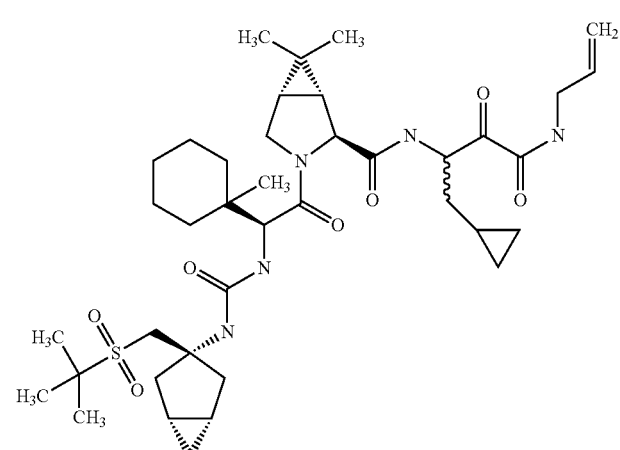 | 744.0143 | 744.4 | A |
| 467 | 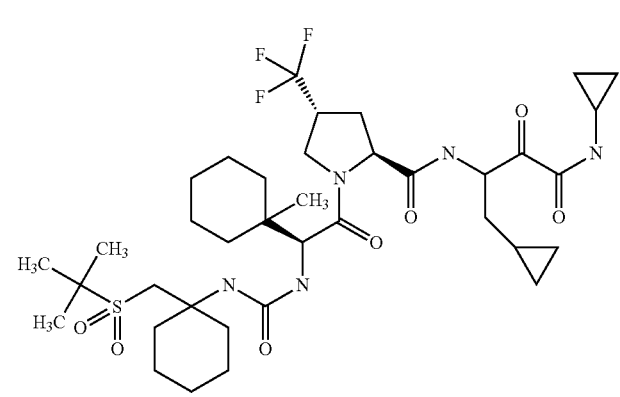 | 773.9633 | | B |

TABLE 3A-continued
| Compound # | structure | mol weight structure | Select LC-MS Data (M + H) | Ki* Range |
|---|---|---|---|---|
| 468 | 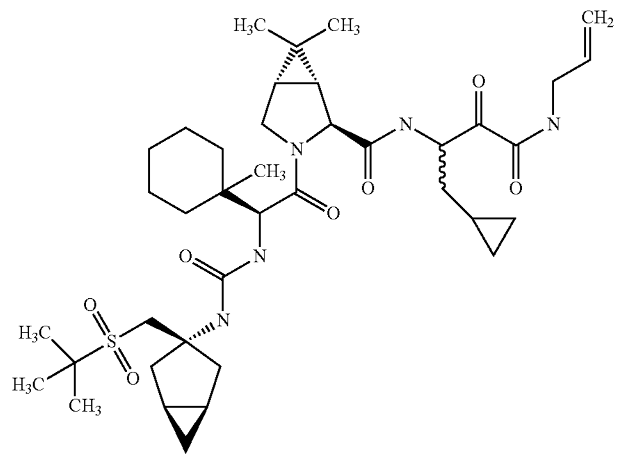 | 744.0143 | 744.70 | B |
| 469 | 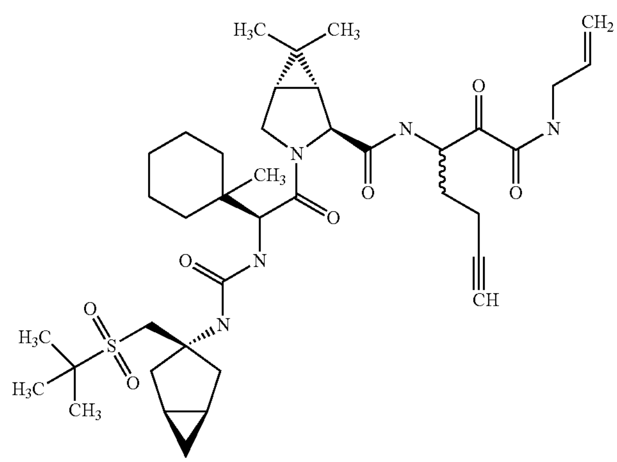 | 741.9984 | 742.40 | A |
| 470 | 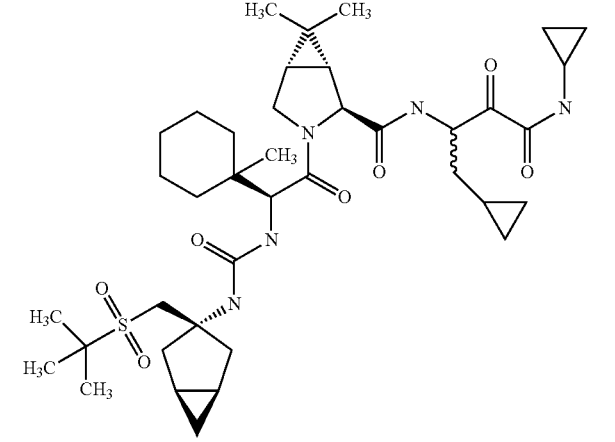 | 744.0143 | 744.38 | B |

TABLE 3A-continued

| Compound # | structure | mol weight structure | Select LC-MS Data (M + H) | Ki* Range |
|---|---|---|---|---|
| 471 | 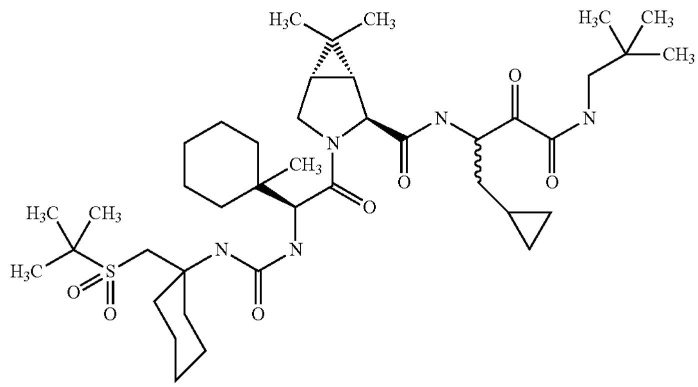 | 778.0727 | 778.7 | B |
| 472 | 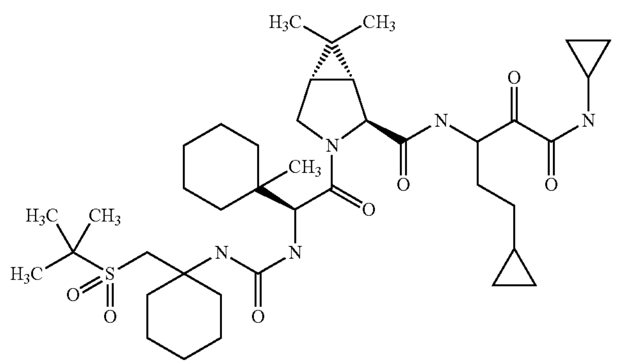 | 760.0574 | | A |
| 473 | 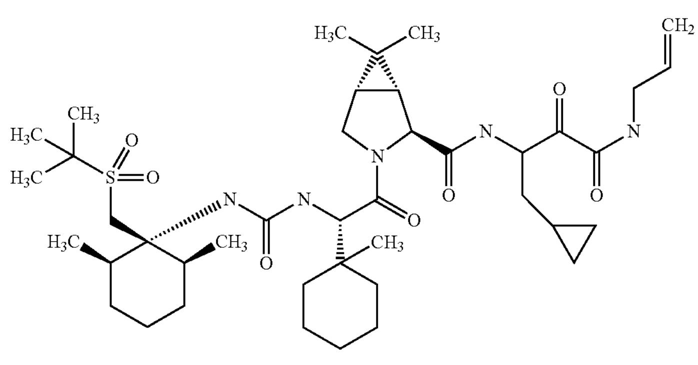 | 774.0844 | 774.4 | A |
| 474 | 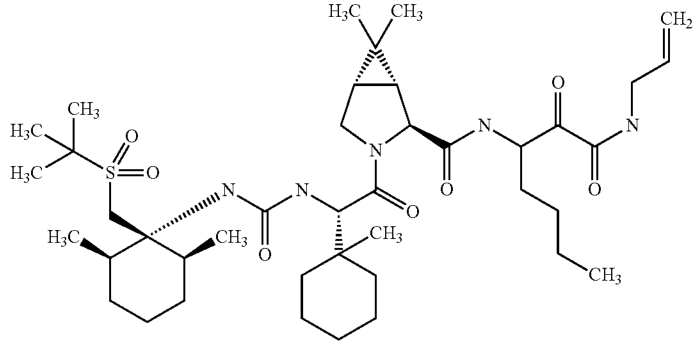 | 776.1004 | 776.5 | A |

TABLE 3A-continued

| Compound # | structure | mol weight structure | Select LC-MS Data (M + H) | Ki* Range |
|---|---|---|---|---|
| 475 | 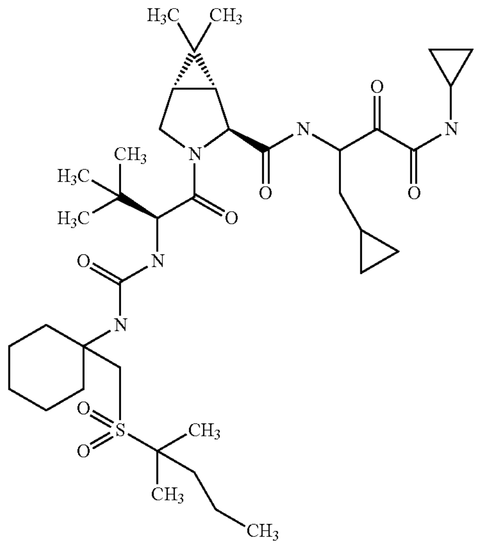 | 734.0191 | | A |
| 476 | 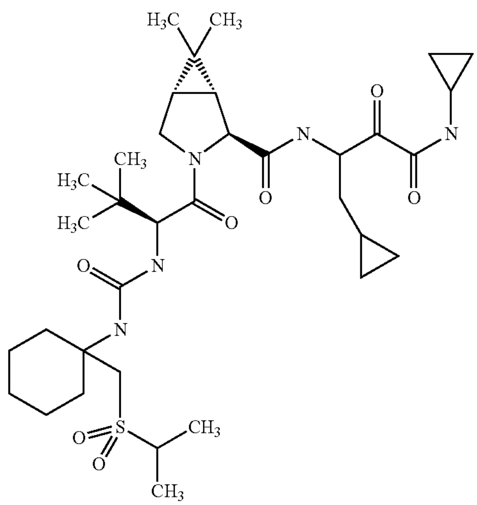 | 691.9378 | | B |
| 477 | 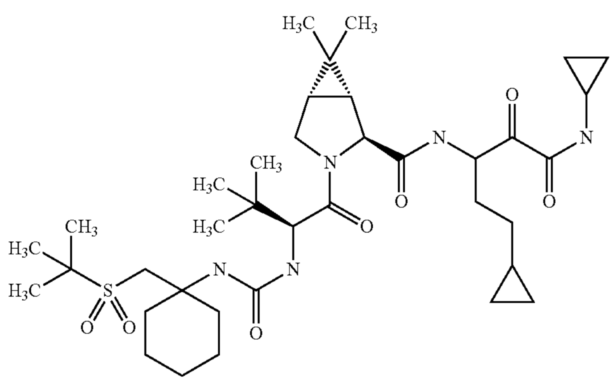 | 719.992 | | A |

TABLE 3A-continued

| Compound # | structure | mol weight structure | Select LC-MS Data (M + H) | Ki* Range |
|---|---|---|---|---|
| 478 | 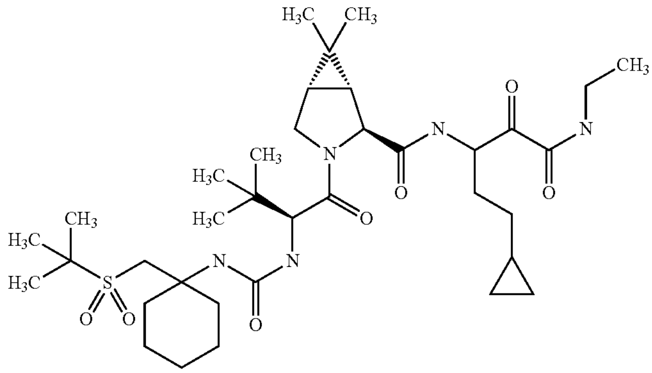 | 707.9809 | | A |
| 479 | 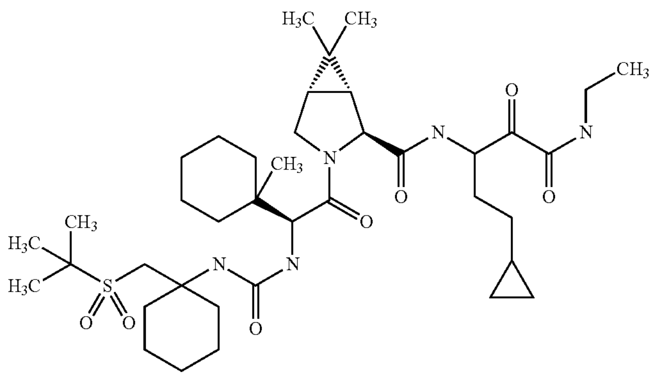 | 748.0462 | | A |
| 480 | 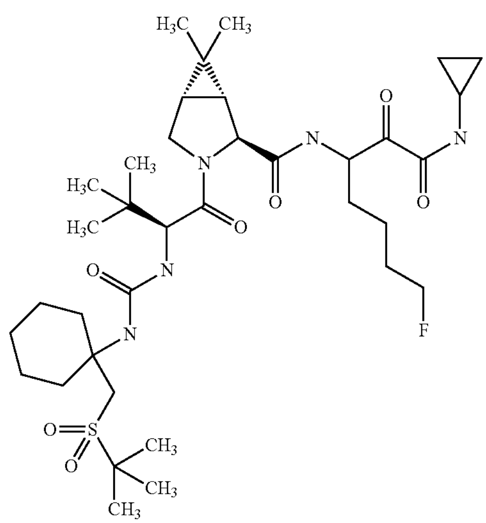 | 725.9713 | 726.4 | A |

TABLE 3A-continued

| Compound # | structure | mol weight structure | Select LC-MS Data (M + H) | Ki* Range |
|---|---|---|---|---|
| 481 | 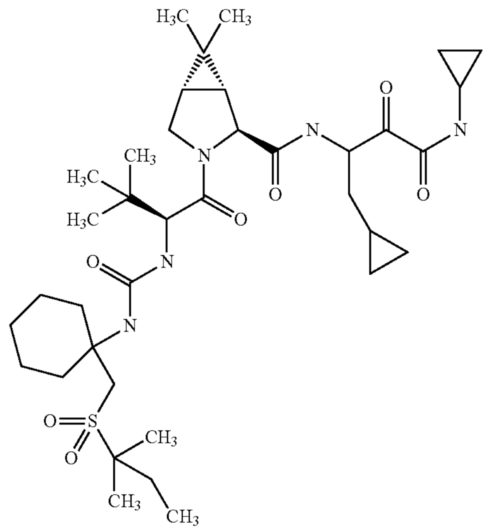 | 719.992 | | A |
| 482 | 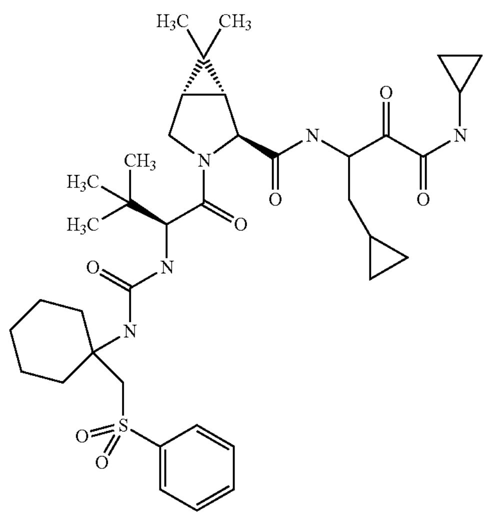 | 725.9554 | | B |
| 483 | 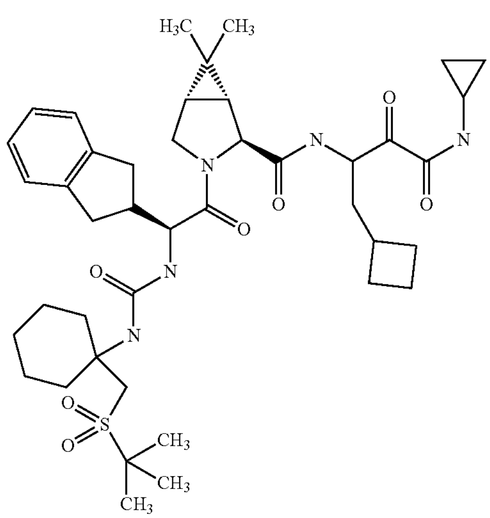 | 780.0478 | | B |

TABLE 3A-continued

| Compound # | structure | mol weight structure | Select LC-MS Data (M + H) | Ki* Range |
|---|---|---|---|---|
| 484 | 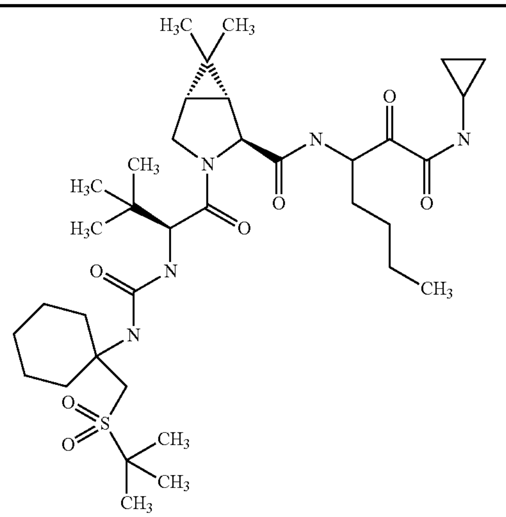 | 707.9809 | | A |
| 485 | 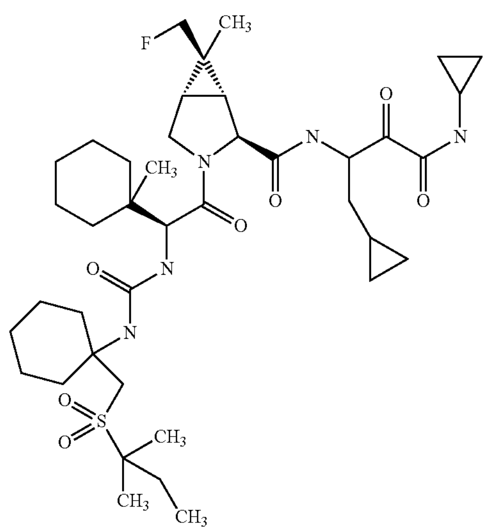 | 778.0478 | | B |
| 486 | 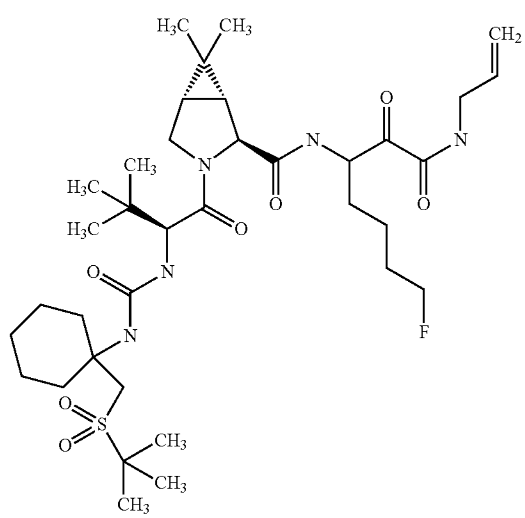 | 725.9713 | | A |

TABLE 3A-continued
| Compound # | structure | mol weight structure | Select LC-MS Data (M + H) | Ki* Range |
|---|---|---|---|---|
| 487 | 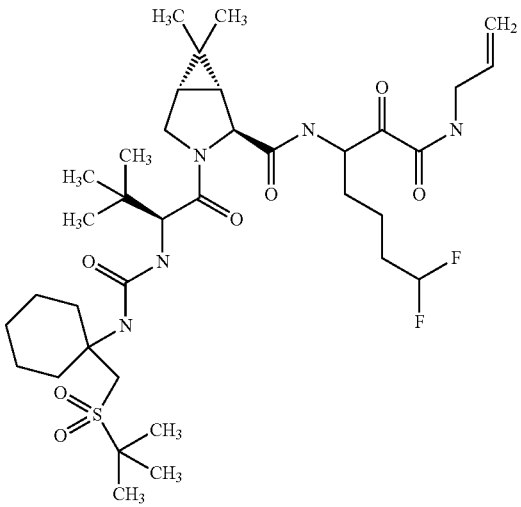 | 743.9617 | | A |
| 488 | 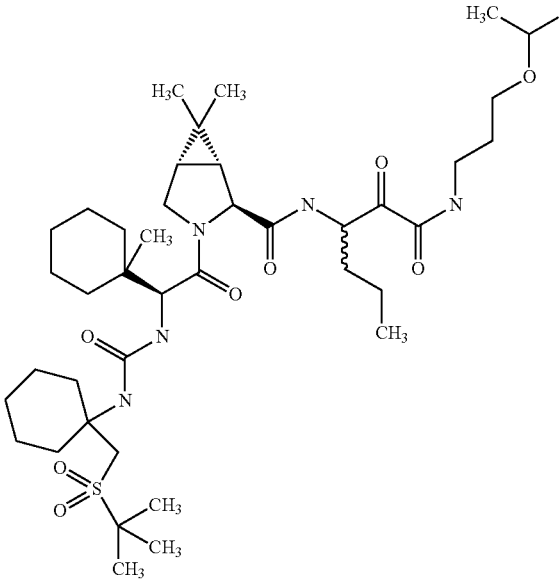 | 794.1157 | 794.2 | B |
| 489 | 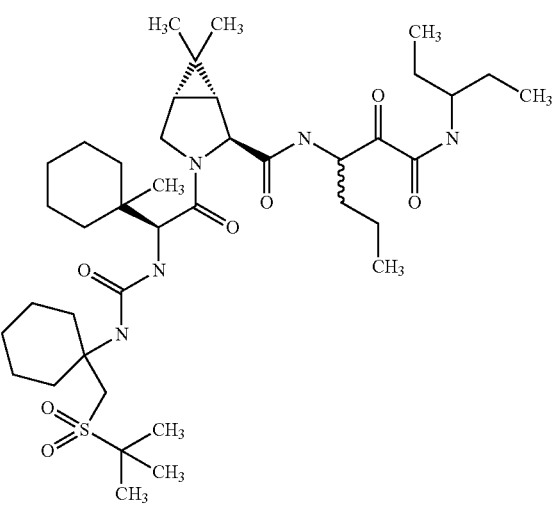 | 764.0892 | 764.1 | B |

TABLE 3A-continued
| Compound # | structure | mol weight structure | Select LC-MS Data (M + H) | Ki* Range |
|---|---|---|---|---|
| 490 | 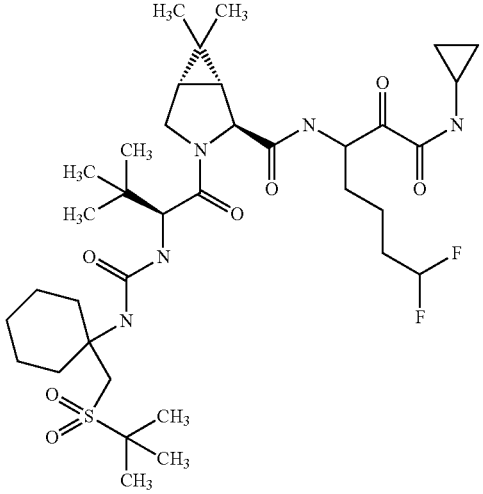 | 743.9617 | 744.4 | A |
| 491 | 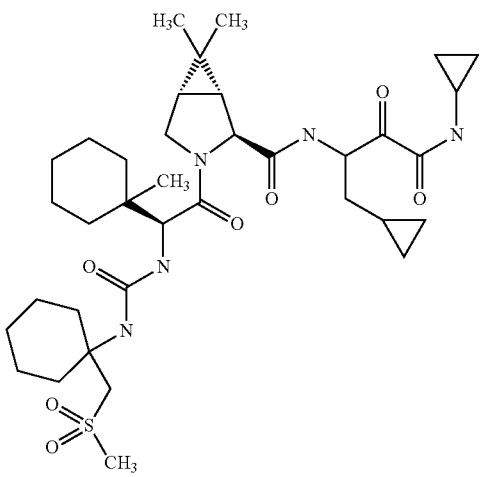 | 703.949 | | A |
| 492 | 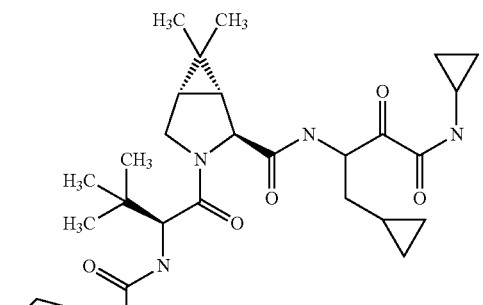 | 663.8837 | | A |

TABLE 3A-continued

| Compound # | structure | mol weight structure | Select LC-MS Data (M + H) | Ki* Range |
|---|---|---|---|---|
| 493 | 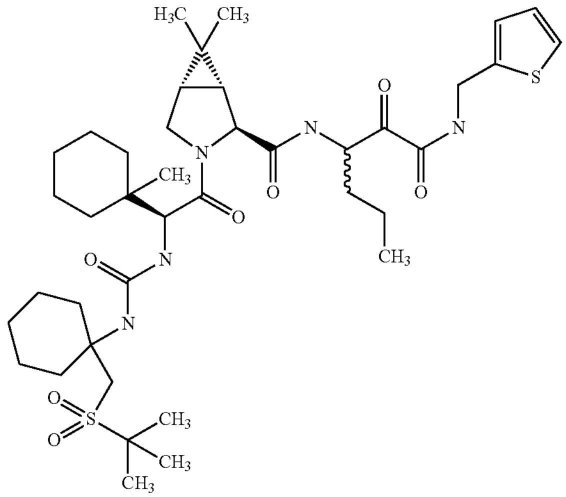 | 790.1054 | 791.4 | A |
| 494 | 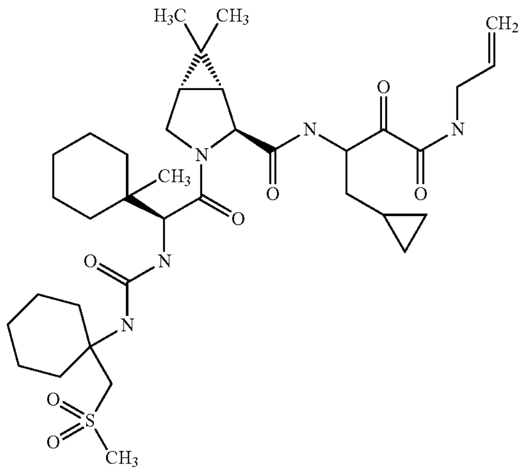 | 703.949 | | A |
| 495 | 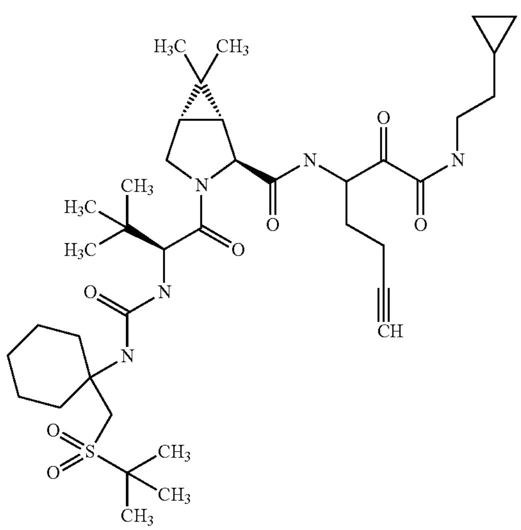 | 732.0032 | | A |

TABLE 3A-continued

| Compound # | structure | mol weight structure | Select LC-MS Data (M + H) | Ki* Range |
|---|---|---|---|---|
| 496 | 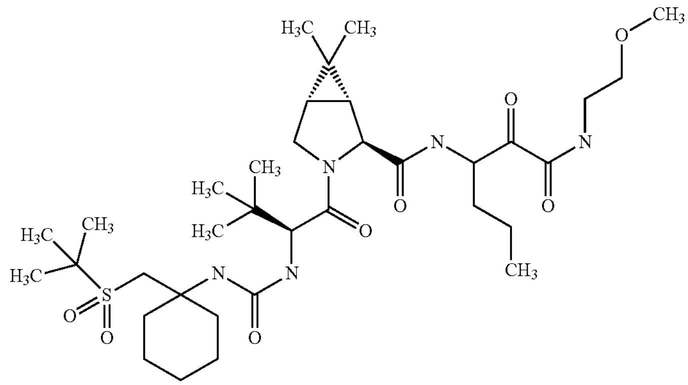 | 712 | | A |
| 497 | 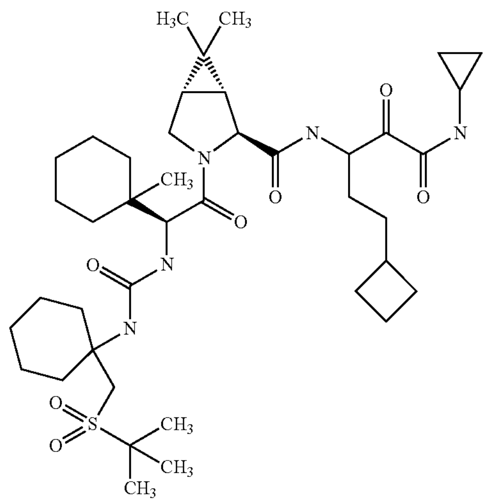 | 774 | 774.2 | A |
| 498 | 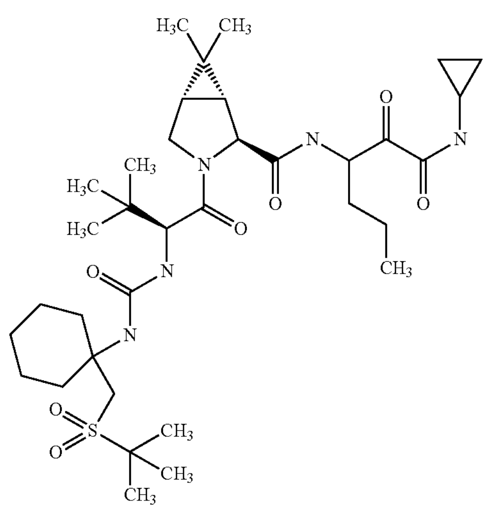 | 693.9538 | | A |

TABLE 3A-continued

| Compound # | structure | mol weight structure | Select LC-MS Data (M + H) | Ki* Range |
|---|---|---|---|---|
| 499 | 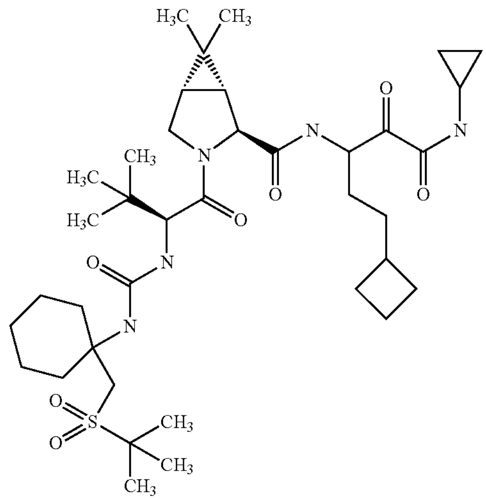 | 734 | 735.2 | A |
| 500 | 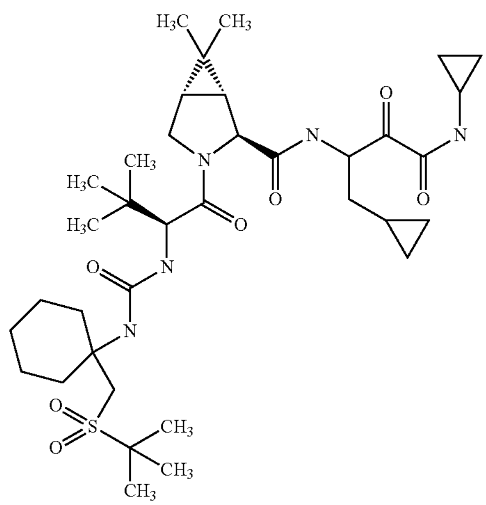 | 706 | | A |
| 501 | 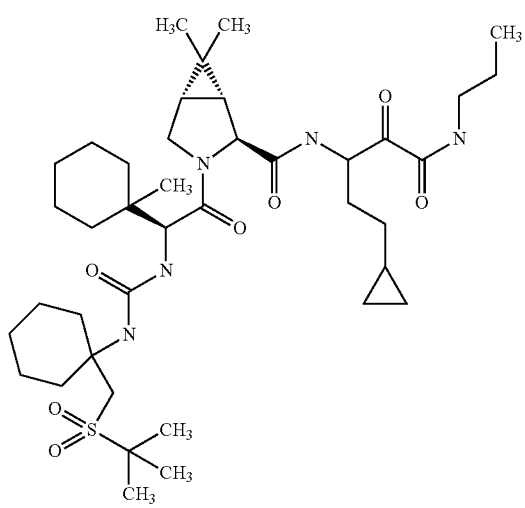 | 762 | | A |

TABLE 3A-continued

| Compound # | structure | mol weight structure | Select LC-MS Data (M + H) | Ki* Range |
|---|---|---|---|---|
| 502 | 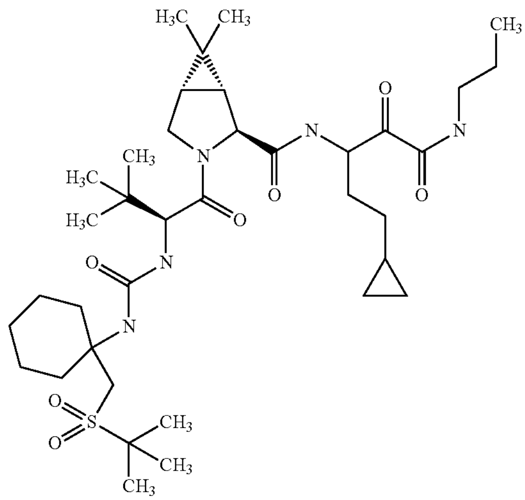 | 722 | | A |
| 503 | 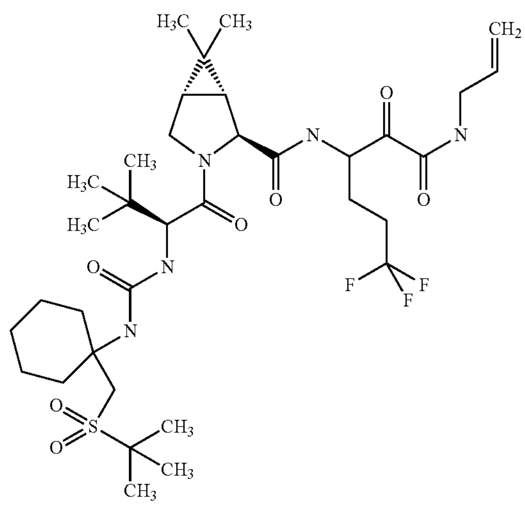 | 748 | | A |
| 504 | 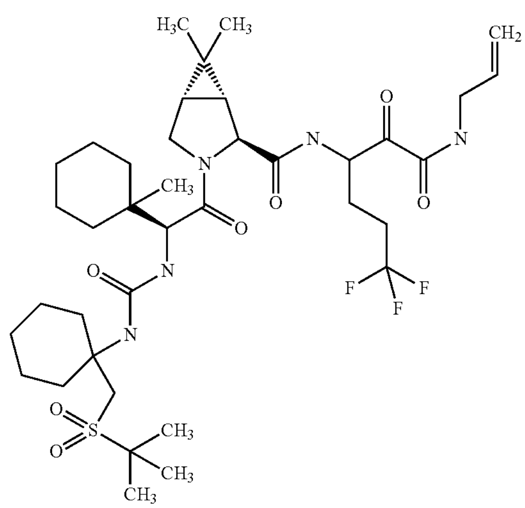 | 788 | | A |

TABLE 3A-continued
| Compound # | structure | mol weight structure | Select LC-MS Data (M + H) | Ki* Range |
|---|---|---|---|---|
| 505 | 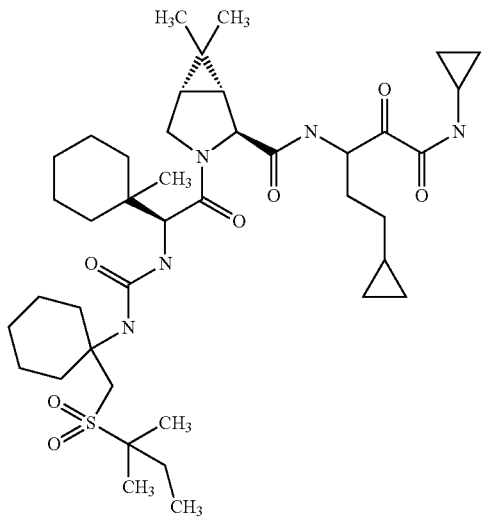 | 774 | | A |
| 506 | 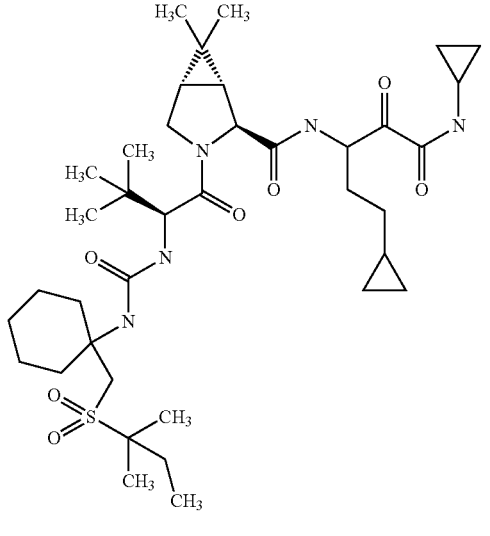 | 734 | | A |
| 507 | 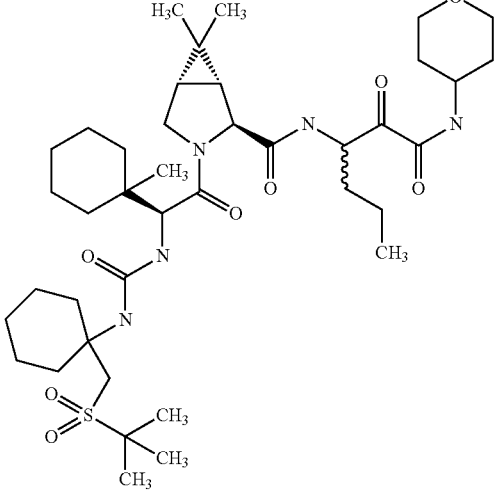 | 778 | 778.2 | C |

TABLE 3A-continued

| Compound # | structure | mol weight structure | Select LC-MS Data (M + H) | Ki* Range |
|---|---|---|---|---|
| 508 | 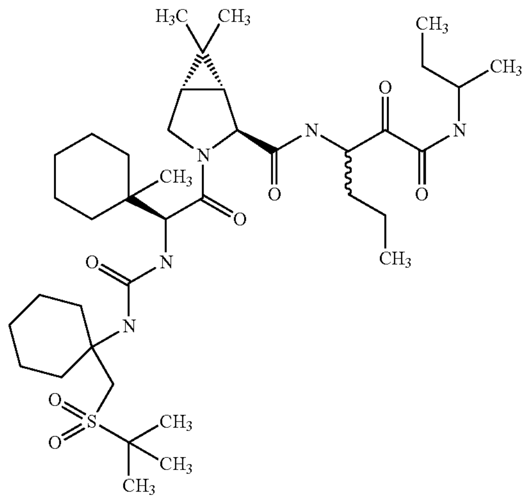 | 750 | 750.5 | B |
| 509 | 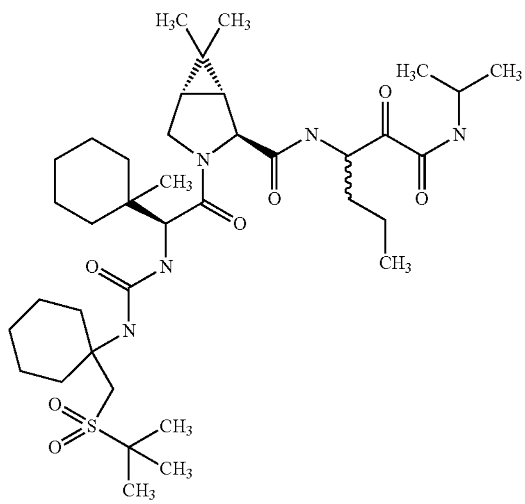 | 736 | 736.2 | A |
| 510 | 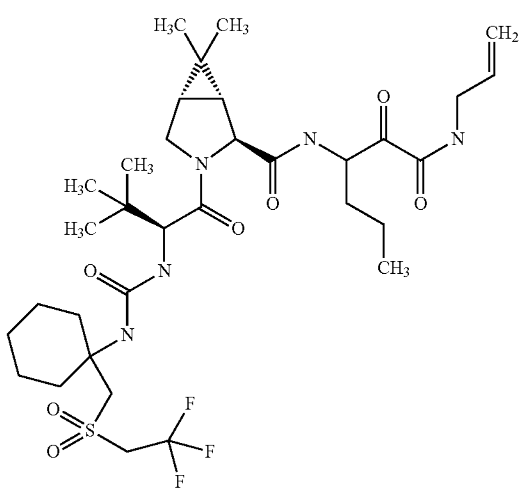 | 720 | | A |

TABLE 3A-continued
| Compound # | structure | mol weight structure | Select LC-MS Data (M + H) | Ki* Range |
|---|---|---|---|---|
| 511 | 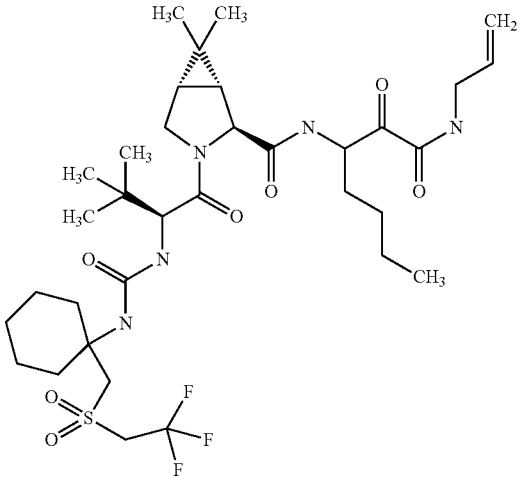 | 734 | | A |
| 512 | 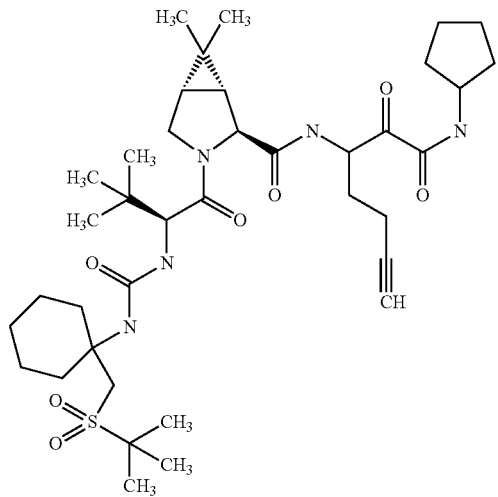 | 732 | 733.4 | A |
| 513 | 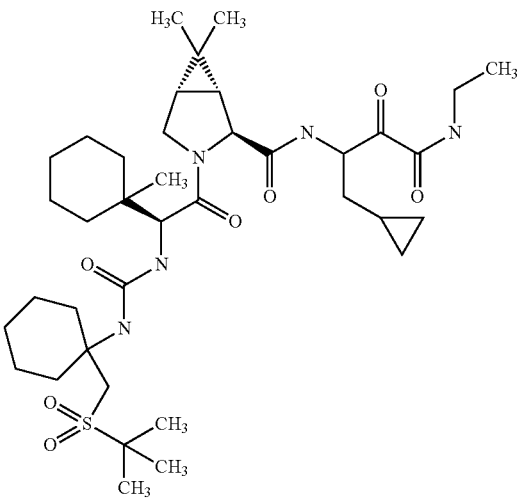 | 734 | 734.4 | A |

TABLE 3A-continued

| Compound # | structure | mol weight structure | Select LC-MS Data (M + H) | Ki* Range |
|---|---|---|---|---|
| 514 | 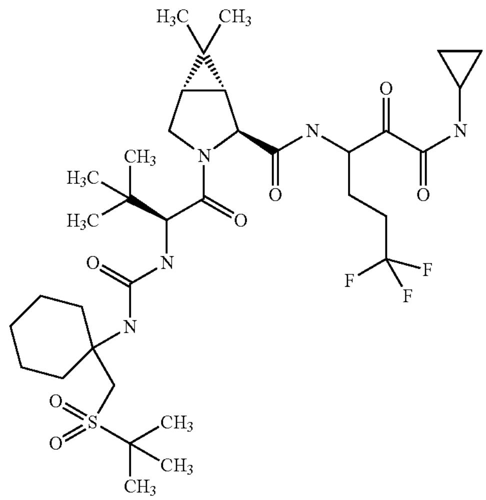 | 748 | | A |
| 515 | 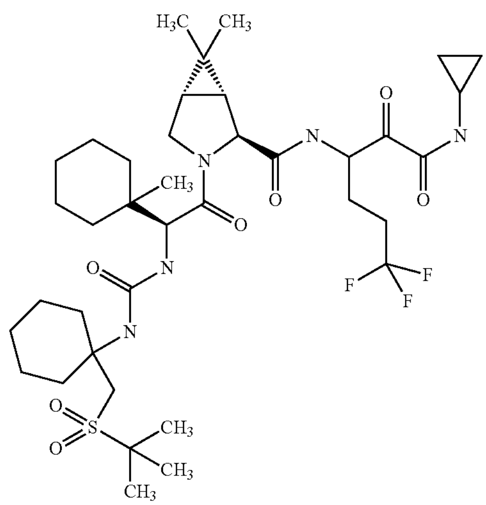 | 788 | | A |
| 516 | 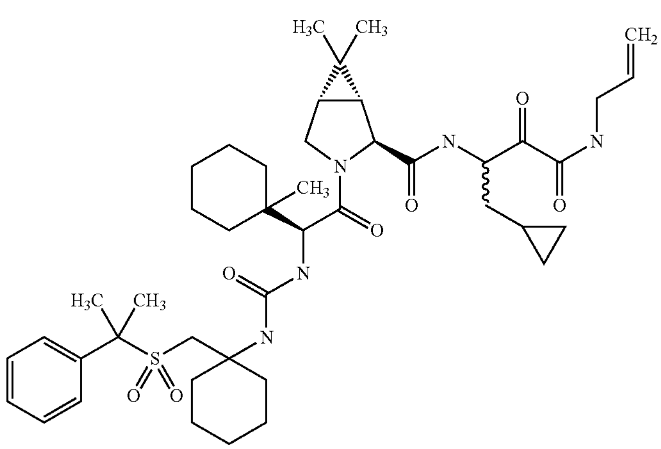 | 808.102 | 809.1 | A |

TABLE 3A-continued
| Compound # | structure | mol weight structure | Select LC-MS Data (M + H) | Ki* Range |
|---|---|---|---|---|
| 517 | 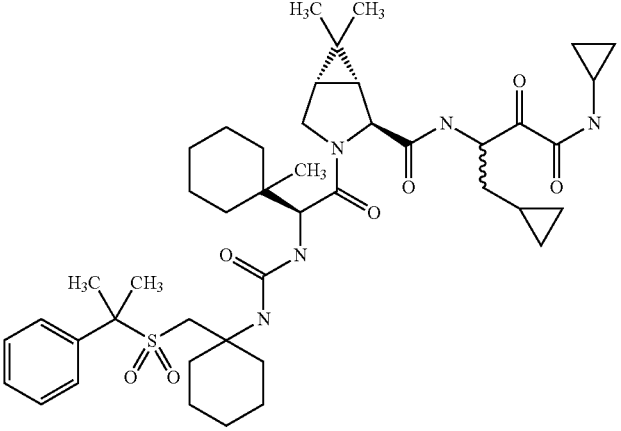 | 808.102 | 809.1 | B |
| 518 | 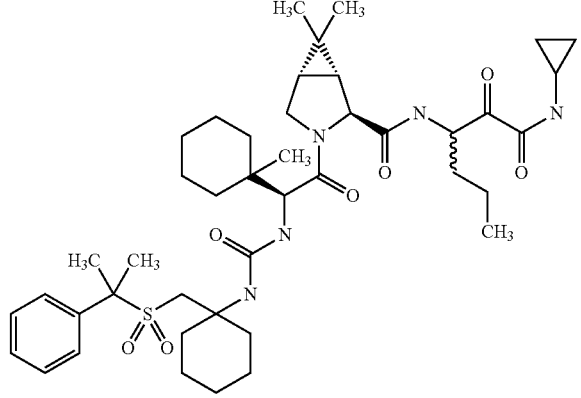 | 796.0908 | 797.1 | A |
| 519 | 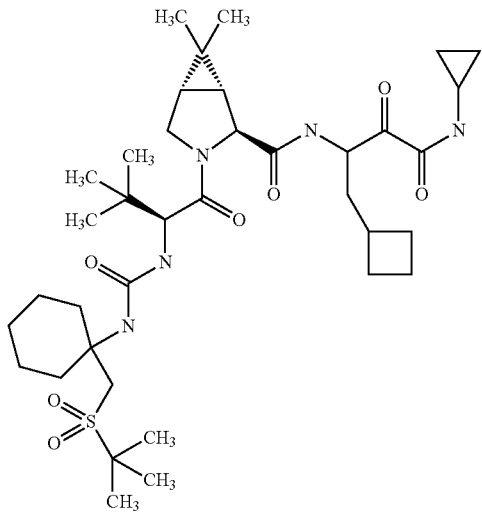 | 719.992 | | A |

TABLE 3A-continued
| Compound # | structure | mol weight structure | Select LC-MS Data (M + H) | Ki* Range |
|---|---|---|---|---|
| 520 | 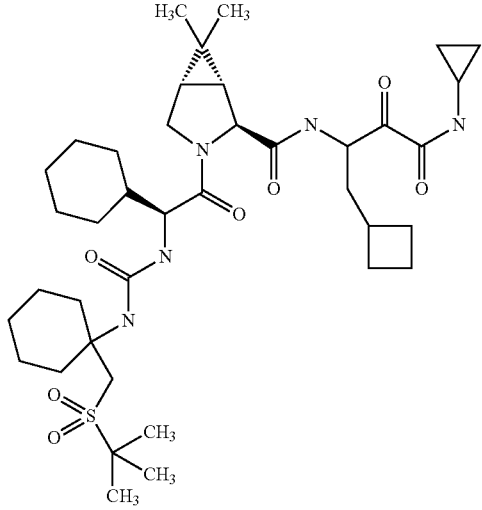 | | 746.0303 | B |
| 521 | 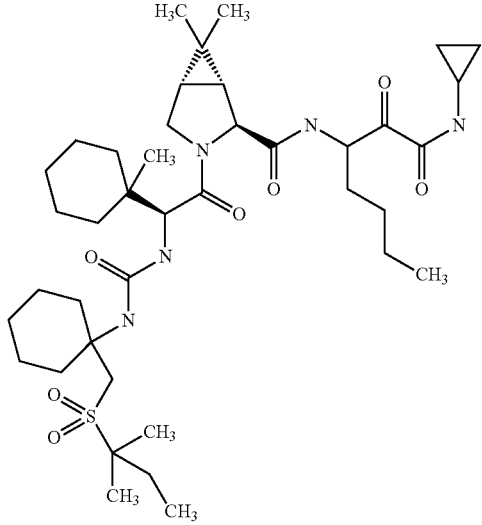 | | 762.0733 | A |
| 522 | 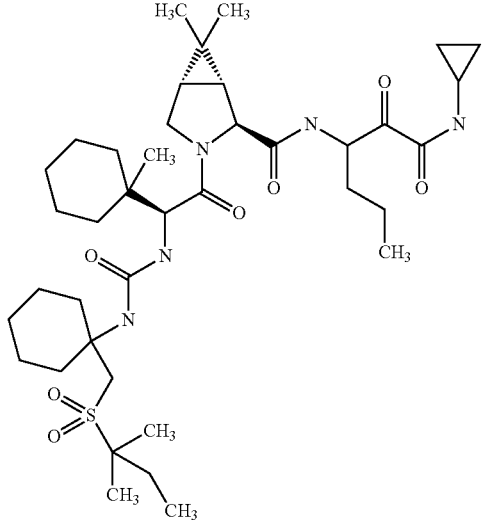 | | 748.0462 | A |

TABLE 3A-continued
| Compound # | structure | mol weight structure | Select LC-MS Data (M + H) | Ki* Range |
|---|---|---|---|---|
| 523 | 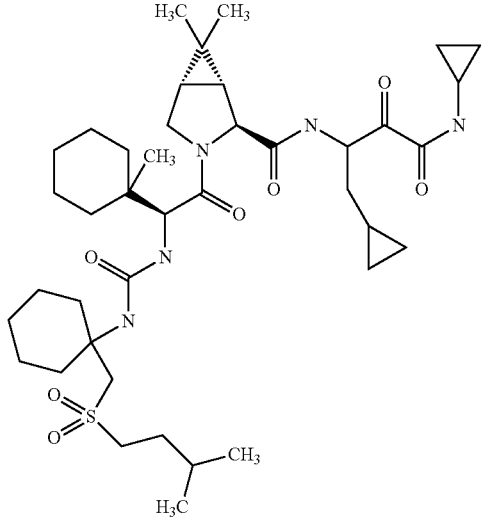 | 760.0574 | | A |
| 524 | 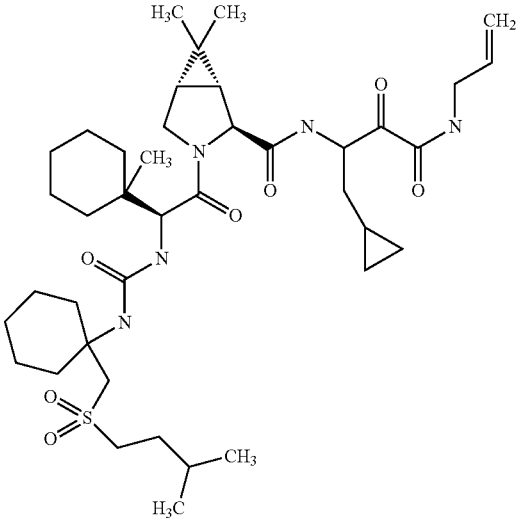 | 760.0574 | | A |
| 525 | 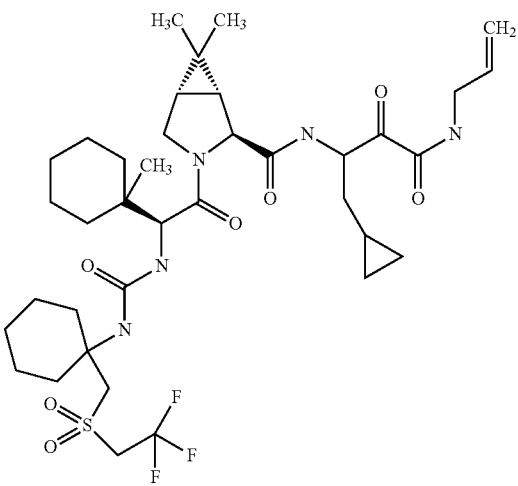 | 771.9474 | | A |

TABLE 3A-continued

| Compound # | structure | mol weight structure | Select LC-MS Data (M + H) | Ki* Range |
|---|---|---|---|---|
| 526 | | 693.9538 | A |
| 527 | | 734.0191 | A |
| 528 | | 734.0191 | A |

TABLE 3A-continued

| Compound # | structure | mol weight structure | Select LC-MS Data (M + H) | Ki* Range |
|---|---|---|---|---|
| 529 | 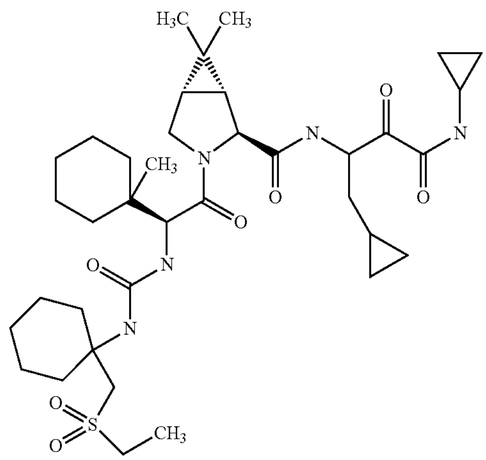 | 717.9761 | | A |
| 530 | 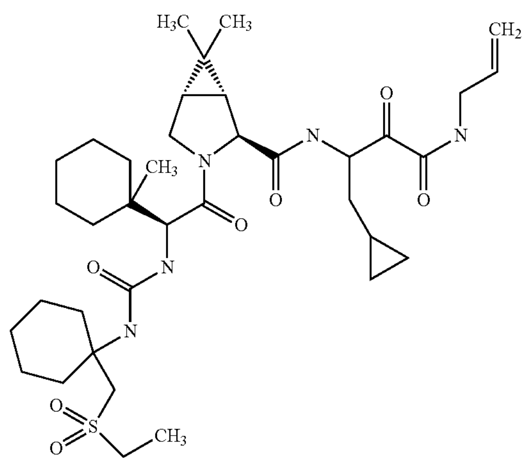 | 717.9761 | | A |
| 531 | 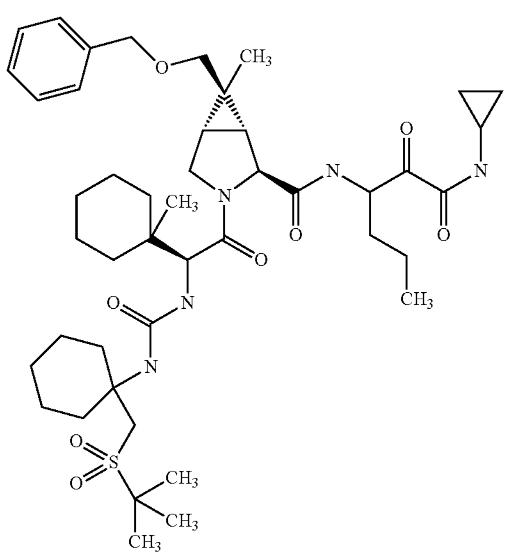 | 840.1444 | | A |

TABLE 3A-continued

| Compound # | structure | mol weight structure | Select LC-MS Data (M + H) | Ki* Range |
|---|---|---|---|---|
| 532 | 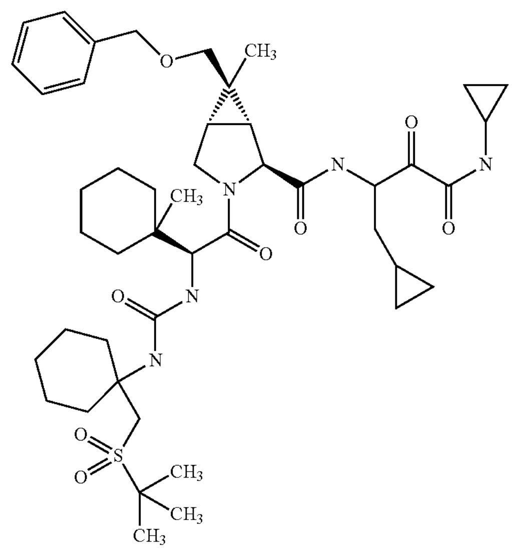 | 852.1555 | | A |
| 533 | 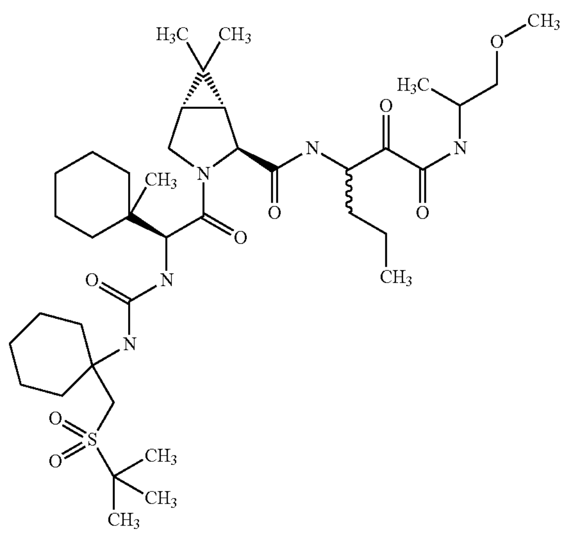 | 766.0615 | 766.4 | B |
| 534 | 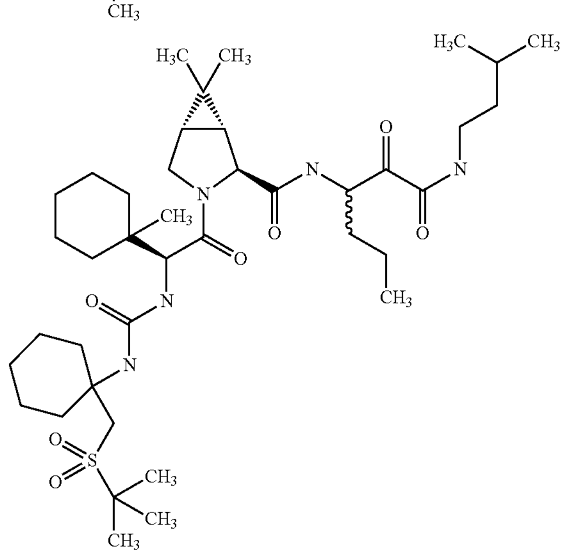 | 764.0892 | 764.4 | C |

TABLE 3A-continued

| Compound # | structure | mol weight structure | Select LC-MS Data (M + H) | Ki* Range |
|---|---|---|---|---|
| 535 | 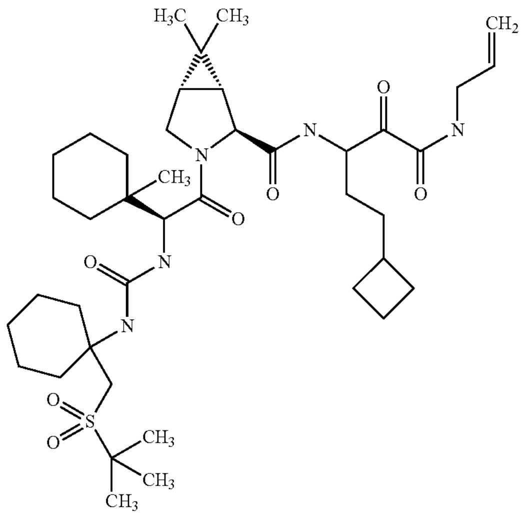 | 774.0844 | | A |
| 536 | 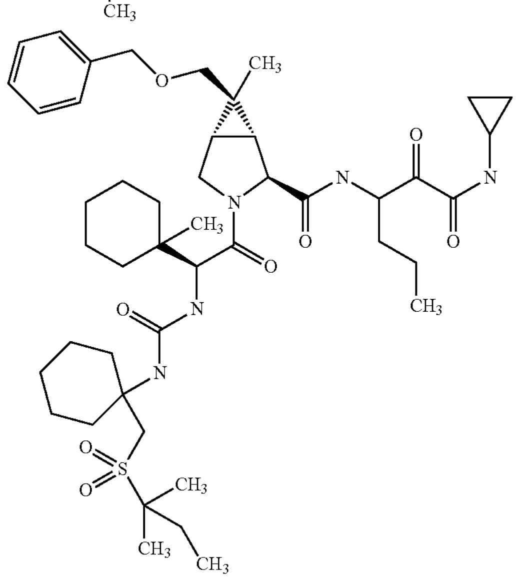 | 854.1715 | | A |
| 537 | 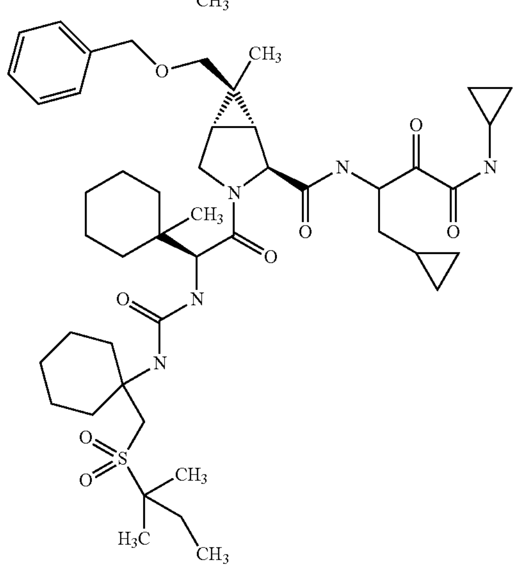 | 866.1826 | | A |

TABLE 3A-continued

| Compound # | structure | mol weight structure | Select LC-MS Data (M + H) | Ki* Range |
|---|---|---|---|---|
| 538 | 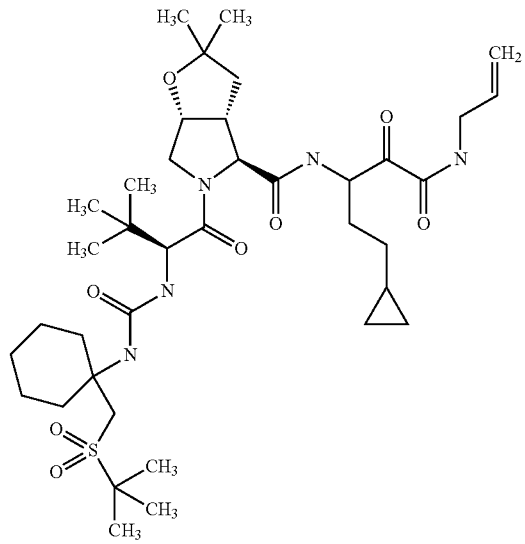 | 750.0185 | 750.4 | A |
| 539 | 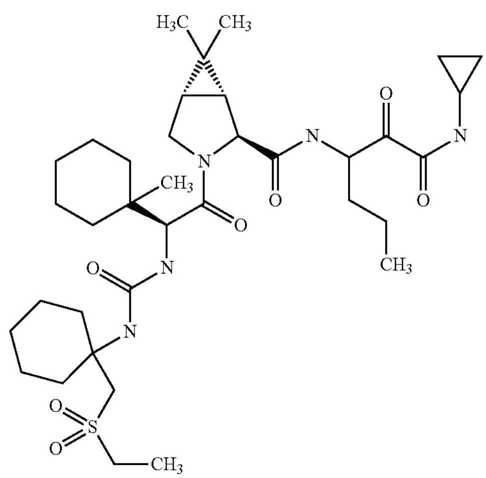 | 705.9649 | | A |
| 540 | 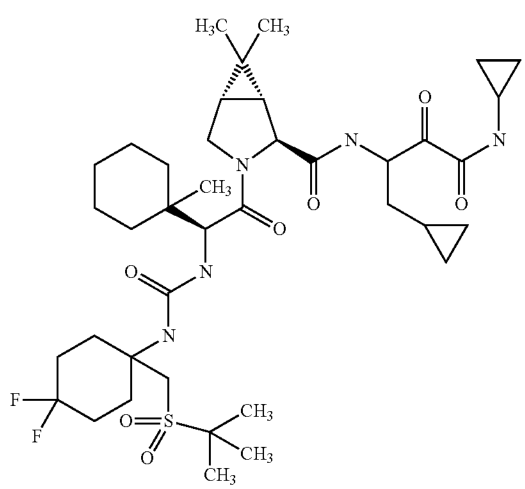 | 782.0111 | | A |

TABLE 3A-continued

| Compound # | structure | mol weight structure | Select LC-MS Data (M + H) | Ki* Range |
|---|---|---|---|---|
| 541 | 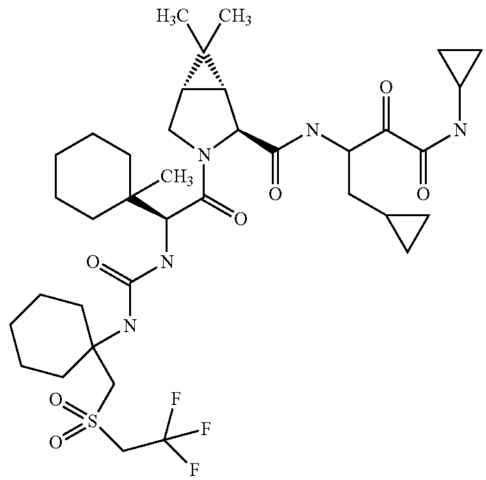 | 771.9474 | | A |
| 542 | 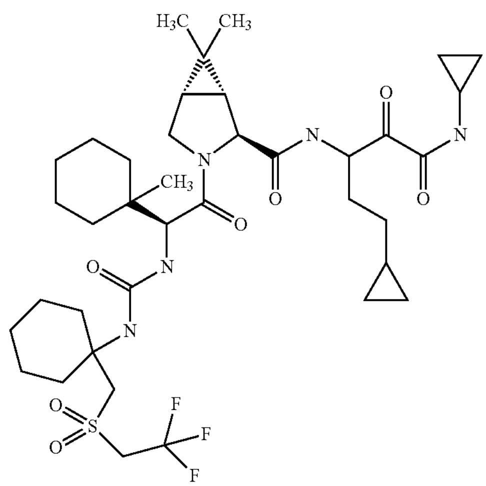 | 785.9745 | | A |
| 543 | 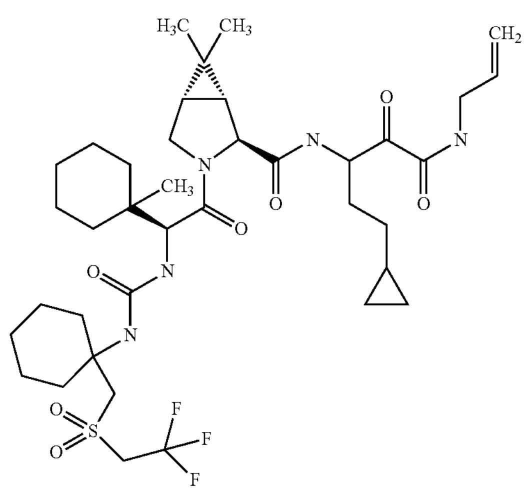 | 785.9745 | | A |

TABLE 3A-continued
| Compound # | structure | mol weight structure | Select LC-MS Data (M + H) | Ki* Range |
|---|---|---|---|---|
| 544 | 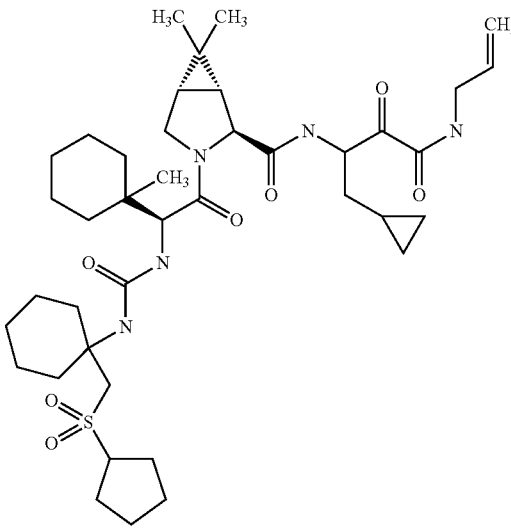 | 758.0414 | | A |
| 545 | 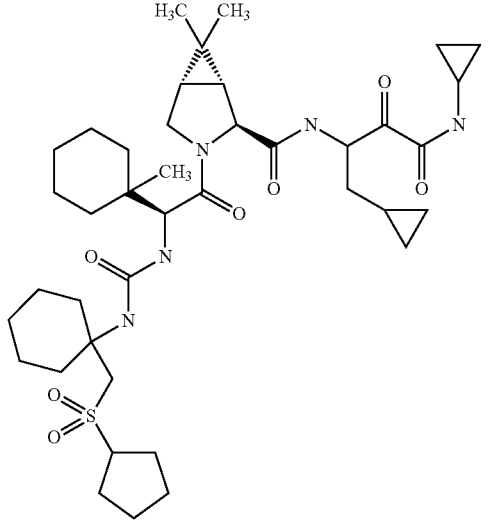 | 758.0414 | | A |
| 546 | 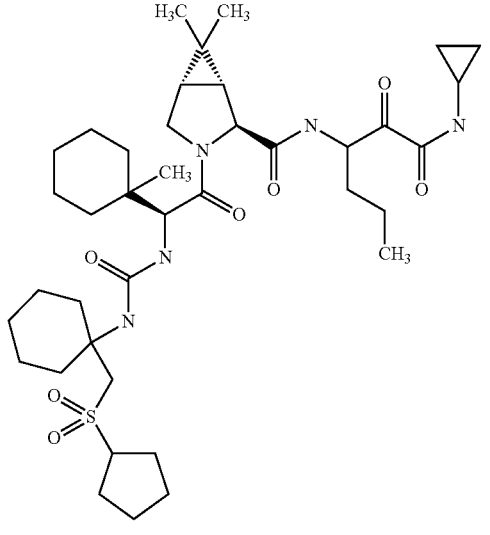 | 746.0303 | | A |

TABLE 3A-continued
| Compound # | structure | mol weight structure | Select LC-MS Data (M + H) | Ki* Range |
|---|---|---|---|---|
| 547 | 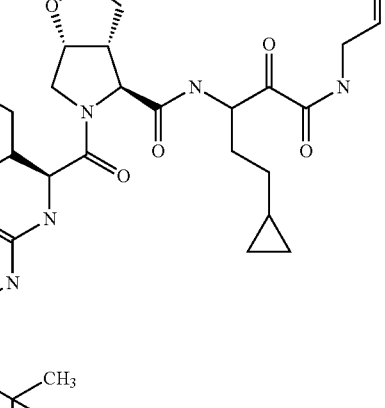 | 776.0568 | 776.4 | A |
| 548 | 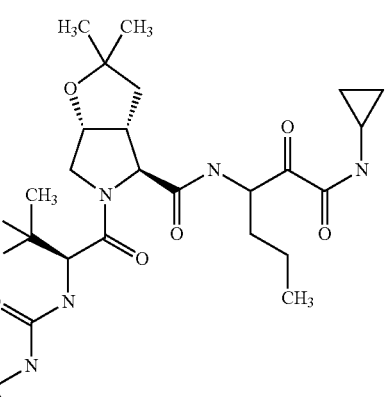 | 723.9803 | 724.4 | B |
| 549 | 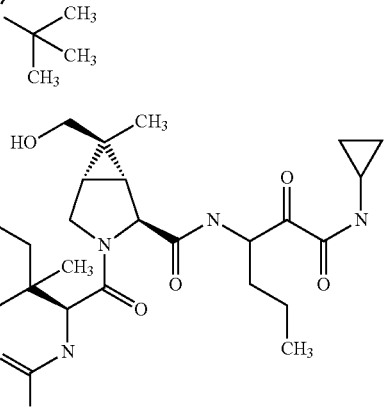 | 764.0456 | | A |

TABLE 3A-continued

| Compound # | structure | mol weight structure | Select LC-MS Data (M + H) | Ki* Range |
|---|---|---|---|---|
| 550 | 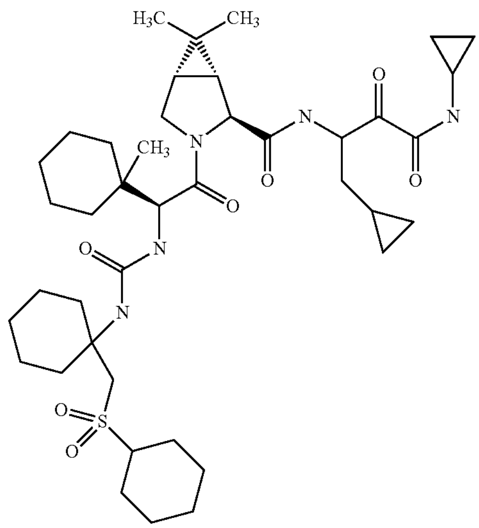 | 772.0685 | | A |
| 551 | 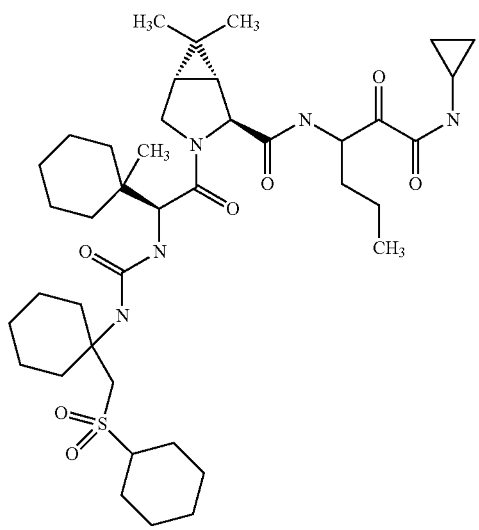 | 760.0574 | | A |
| 552 | 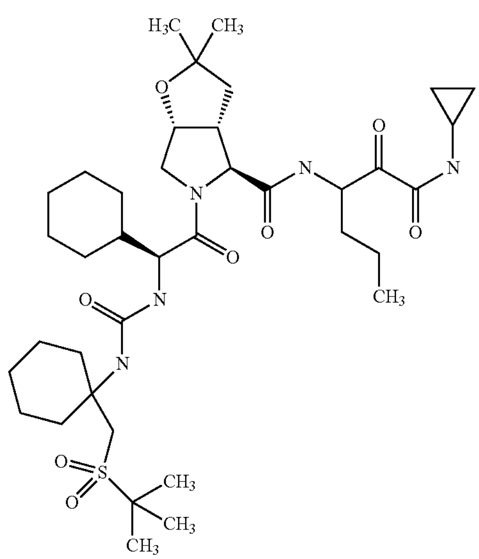 | 750.0185 | 750.1 | B |

TABLE 3A-continued

| Compound # | structure | mol weight structure | Select LC-MS Data (M + H) | Ki* Range |
|---|---|---|---|---|
| 553 | 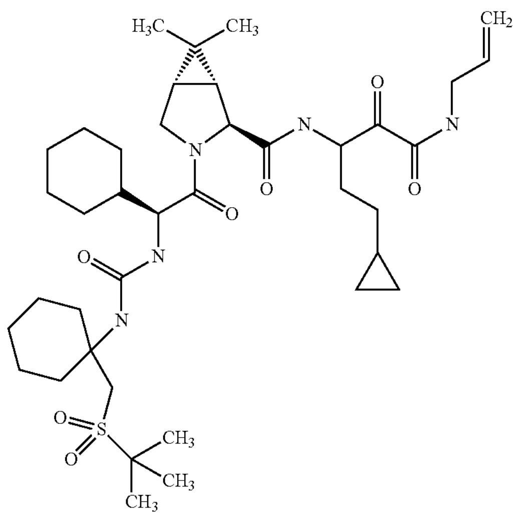 | 746.0303 | | A |
| 554 | 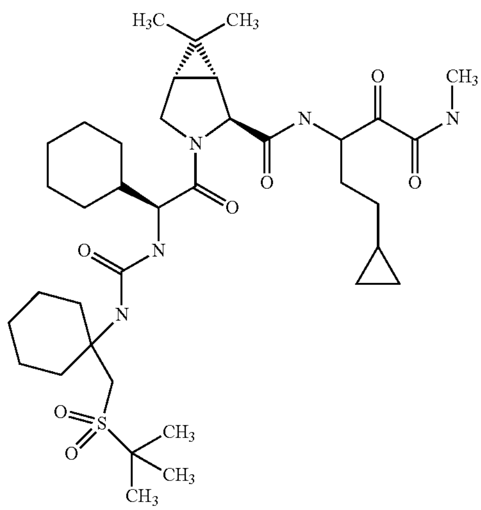 | 719.992 | | A |
| 555 | 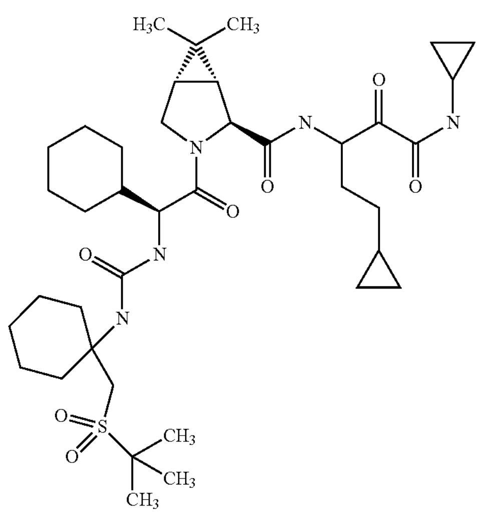 | 746.0303 | | A |

TABLE 3A-continued

| Compound # | structure | mol weight structure | Select LC-MS Data (M + H) | Ki* Range |
|---|---|---|---|---|
| 556 | 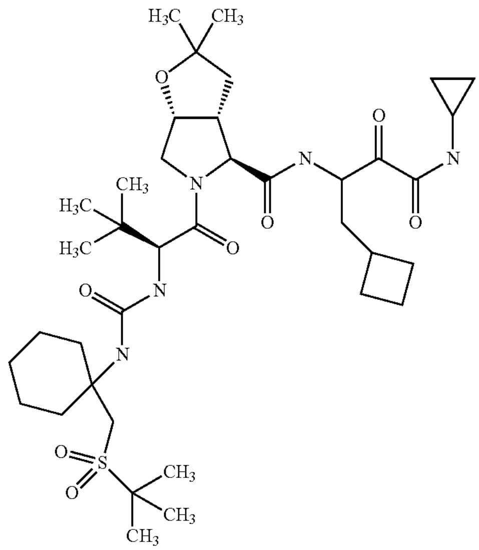 | 750.0185 | 750.1 | B |
| 557 | 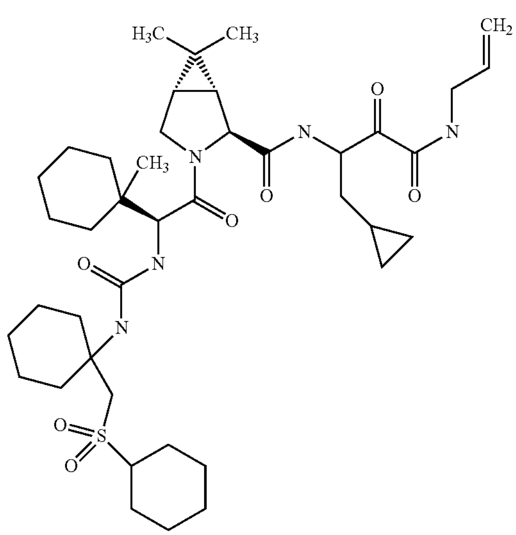 | 772.0685 | | A |

TABLE 3A-continued

| Compound # | structure | mol weight structure | Select LC-MS Data (M + H) | Ki* Range |
|---|---|---|---|---|
| 558 | 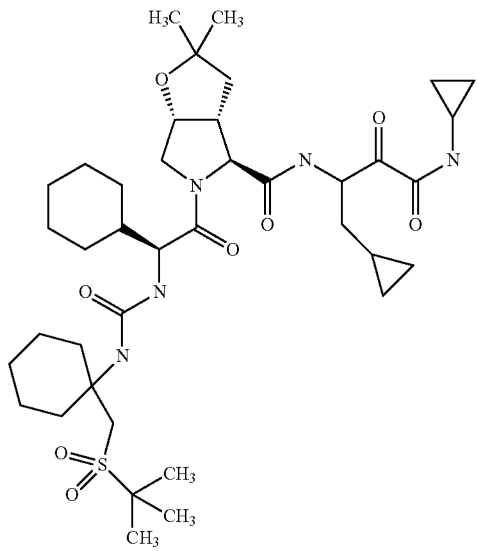 | | 762.0297 | B |
| 559 | 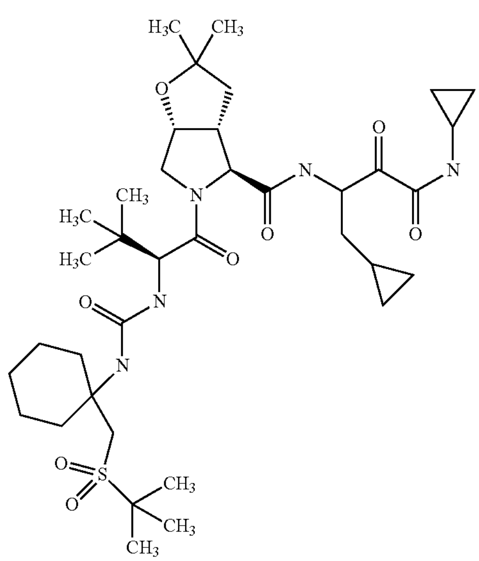 | | 735.9914 | B |

| Compound # | structure | mol weight structure | Select LC-MS Data (M + H) | Ki* Range |
|---|---|---|---|---|
| 560 | 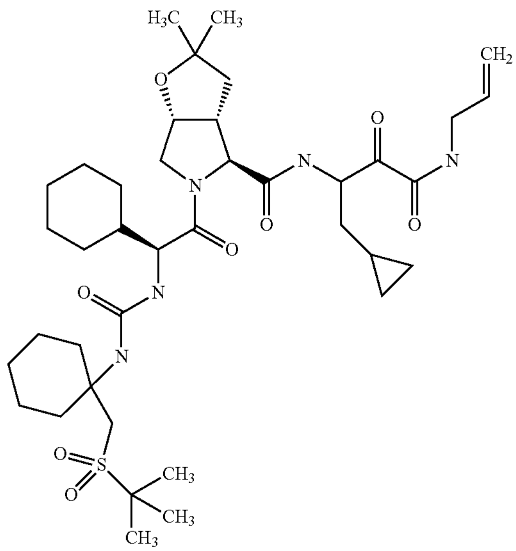 | 762.0297 | | A |
| 561 | 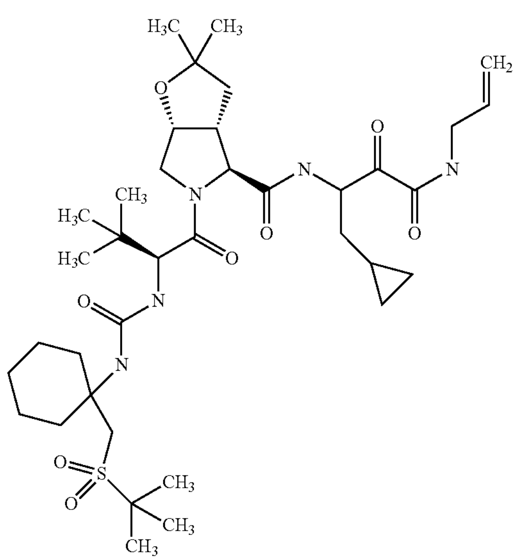 | 735.9914 | | A |

TABLE 3A-continued

| Compound # | structure | mol weight structure | Select LC-MS Data (M + H) | Ki* Range |
|---|---|---|---|---|
| 562 | 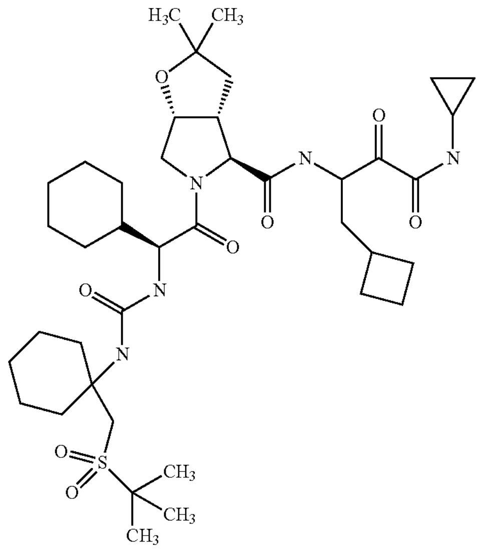 | 776.0568 | | B |
| 563 | 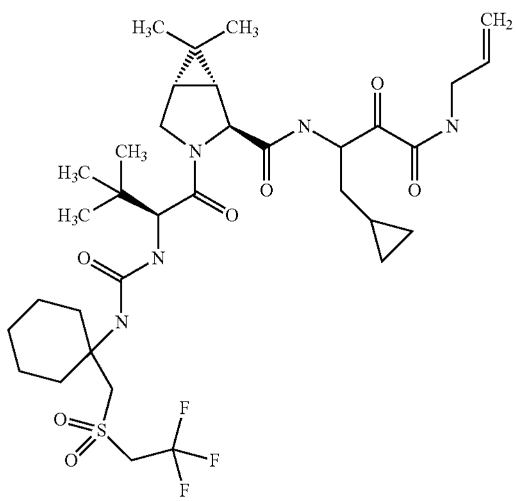 | 731.882 | | A |
| 564 | 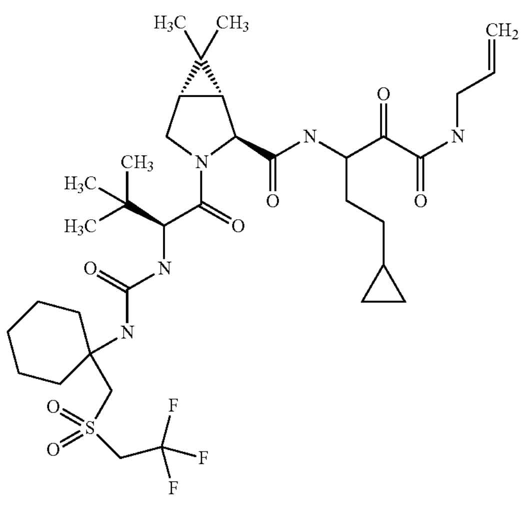 | 745.9091 | | A |

TABLE 3A-continued

| Compound # | structure | mol weight structure | Select LC-MS Data (M + H) | Ki* Range |
|---|---|---|---|---|
| 565 | 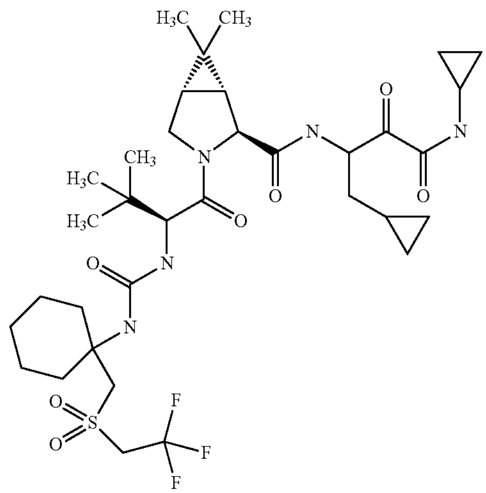 | 731.882 | | A |
| 566 | 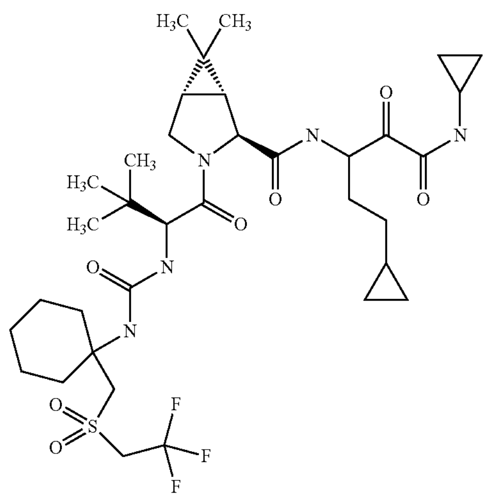 | 745.9091 | | 1A |
| 567 | 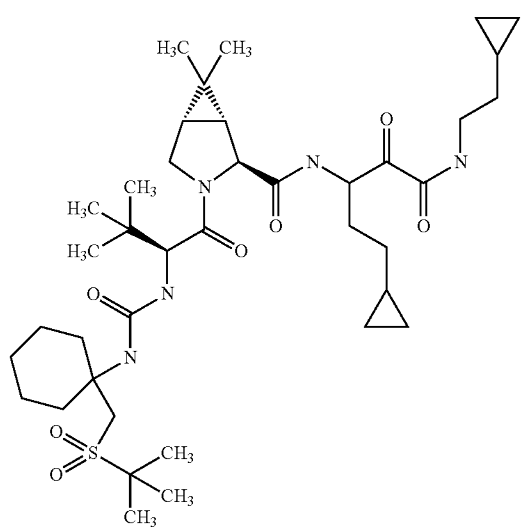 | 748.0462 | | A |

TABLE 3A-continued

| Compound # | structure | mol weight structure | Select LC-MS Data (M + H) | Ki* Range |
|---|---|---|---|---|
| 568 | 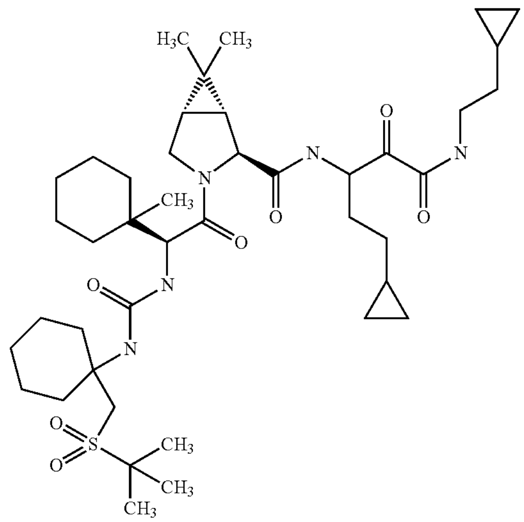 | 788.1115 | | A |
| 569 | 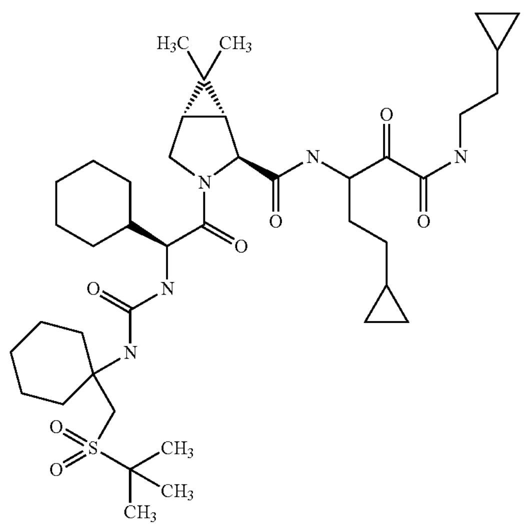 | 774.0844 | | A |
| 570 | 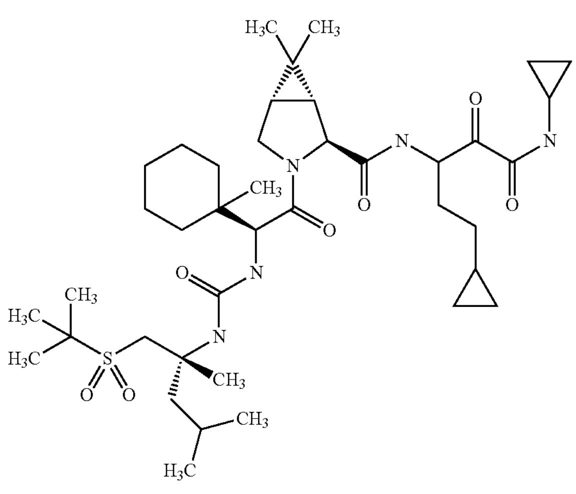 | 762.0733 | 763.1 | A |

TABLE 3A-continued

| Compound # | structure | mol weight structure | Select LC-MS Data (M + H) | Ki* Range |
|---|---|---|---|---|
| 571 | 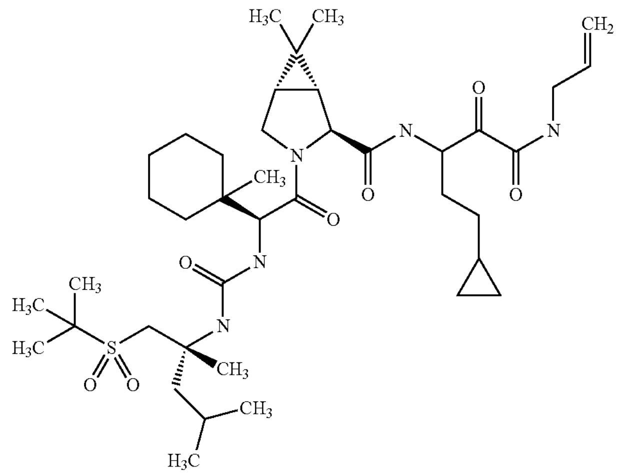 | 762.0733 | 763.1 | A |
| 572 | 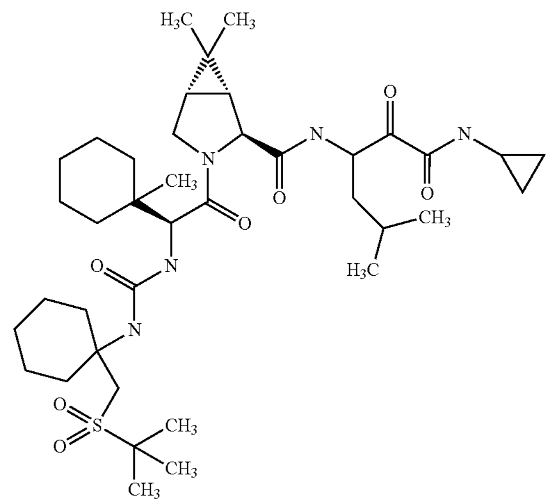 | 748.0462 | | B |
| 573 | 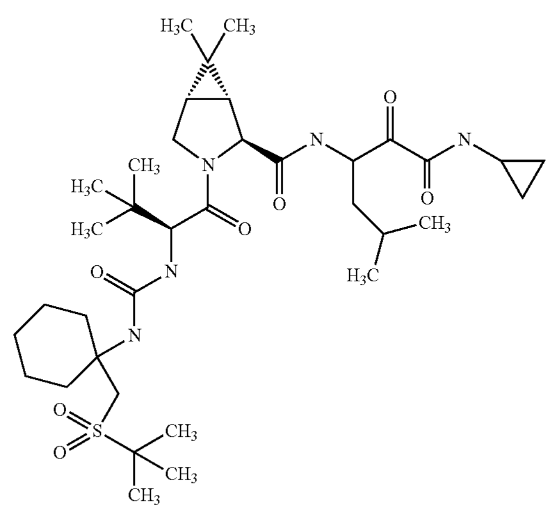 | 707.9809 | | B |

TABLE 3A-continued

| Compound # | structure | mol weight structure | Select LC-MS Data (M + H) | Ki* Range |
|---|---|---|---|---|
| 574 | 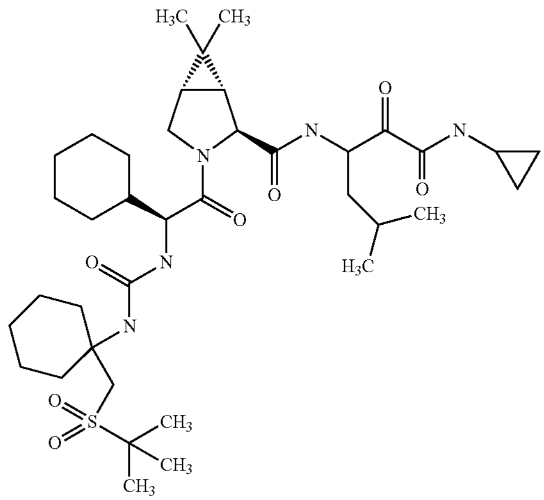 | 734.0191 | | B |
| 575 | 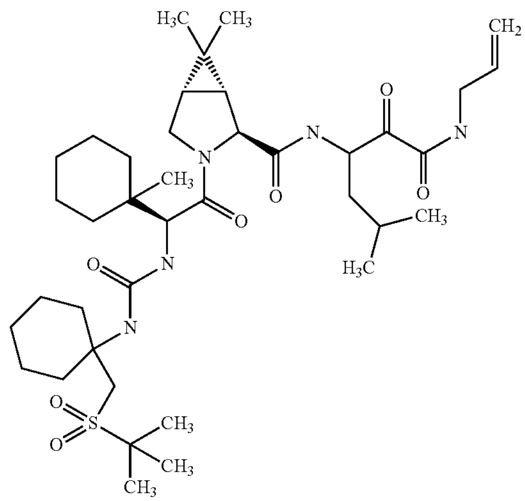 | 748.0462 | | B |
| 576 | 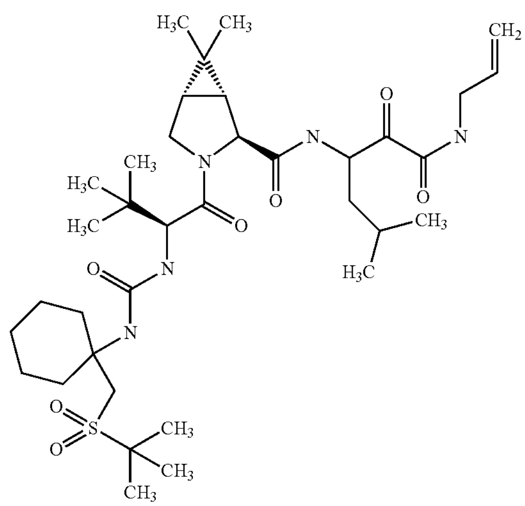 | 707.9809 | | B |

TABLE 3A-continued

| Compound # | structure | mol weight structure | Select LC-MS Data (M + H) | Ki* Range |
|---|---|---|---|---|
| 577 | 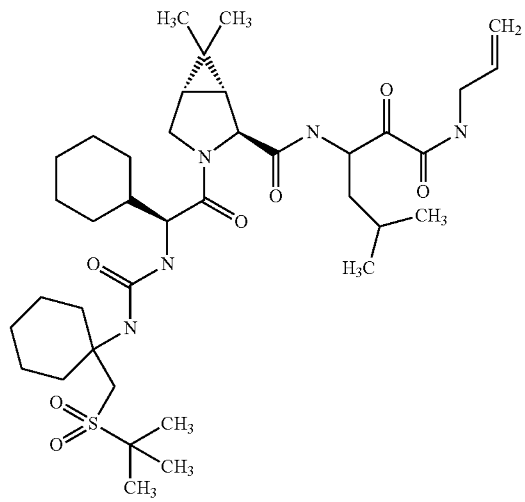 | 734.0191 | | C |
| 578 | 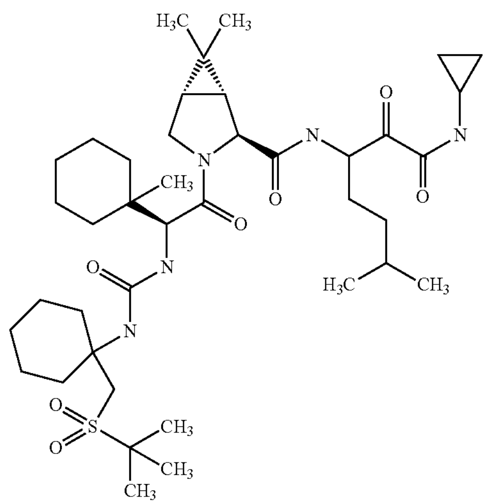 | 762.0733 | 762.4 | B |
| 579 | 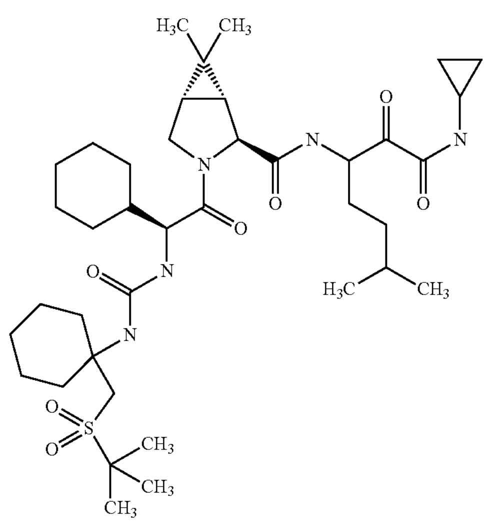 | 748.0462 | 748.4 | A |

TABLE 3A-continued

| Compound # | structure | mol weight structure | Select LC-MS Data (M + H) | Ki* Range |
|---|---|---|---|---|
| 580 | 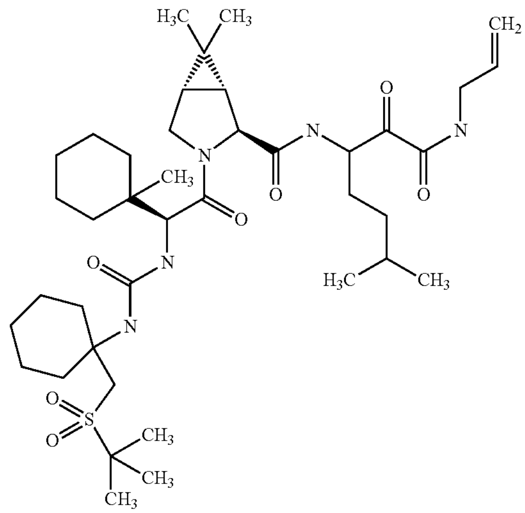 | 762.0733 | | A |
| 581 | 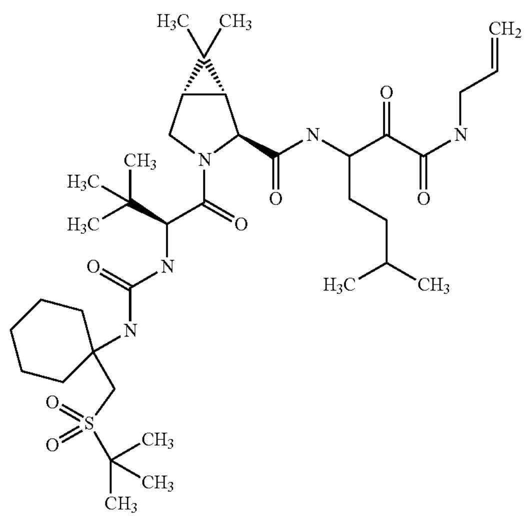 | 722.008 | | A |
| 582 | 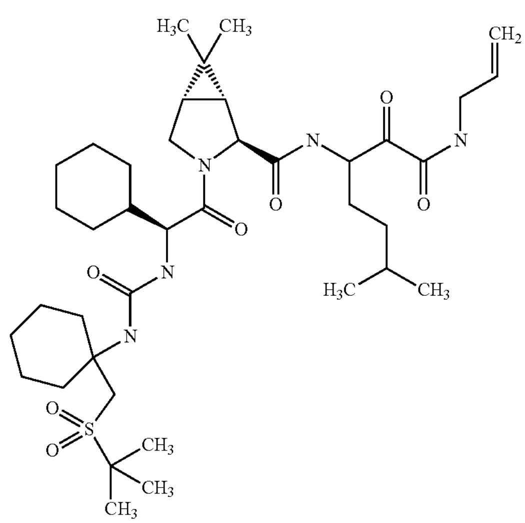 | 748.0462 | | A |

TABLE 3A-continued

| Compound # | structure | mol weight structure | Select LC-MS Data (M + H) | Ki* Range |
|---|---|---|---|---|
| 583 | 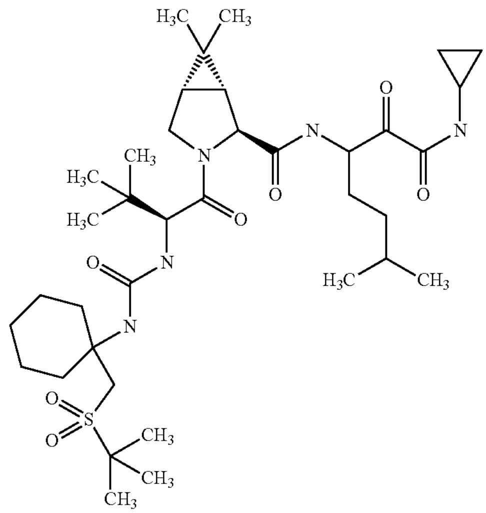 | 722.008 | 722.4 | A |
| 584 | 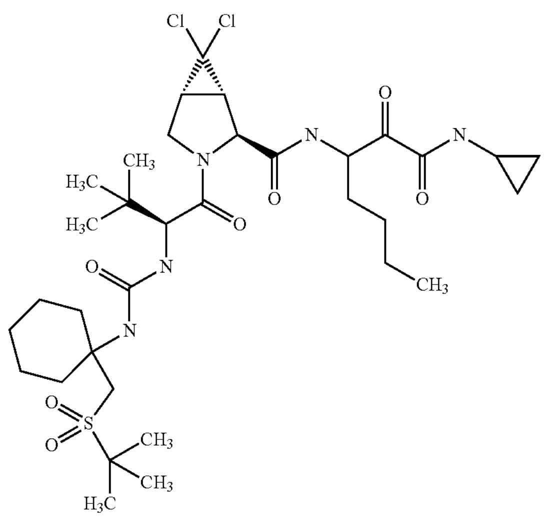 | 748.8168 | 748.4 | A |
| 585 | 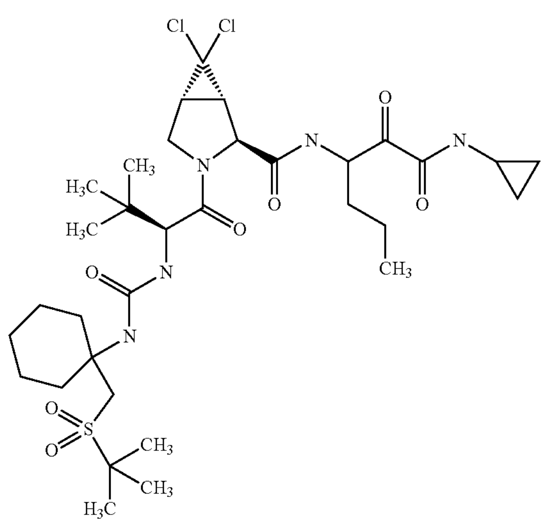 | 734.7897 | 734.4 | A |

TABLE 3A-continued

| Compound # | structure | mol weight structure | Select LC-MS Data (M + H) | Ki* Range |
|---|---|---|---|---|
| 586 | 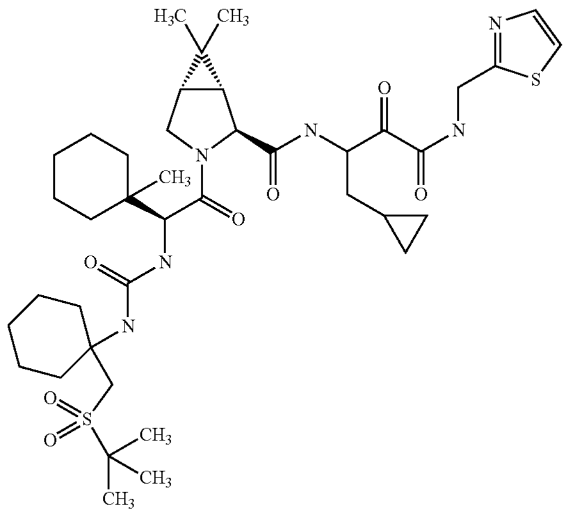 | 803.1041 | 803.4 | A |
| 587 | 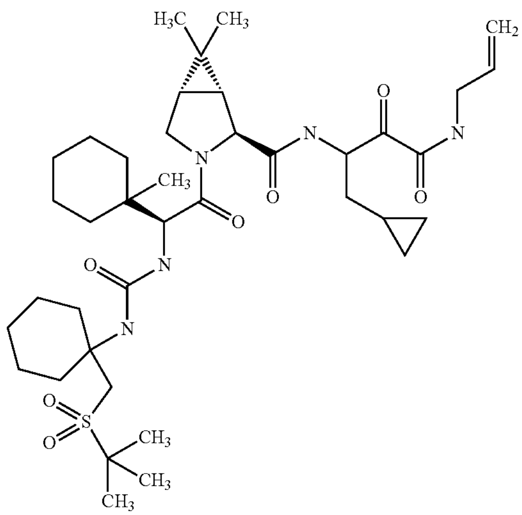 | 746.0303 | | C |
| 588 | 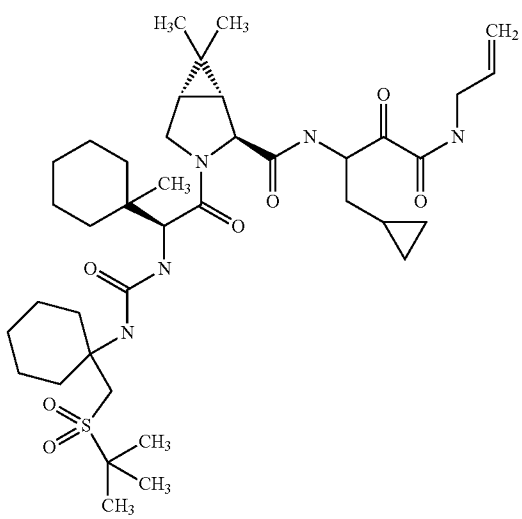 | 746.0303 | | 6 |

TABLE 3A-continued

| Compound # | structure | mol weight structure | Select LC-MS Data (M + H) | Ki* Range |
|---|---|---|---|---|
| 589 | 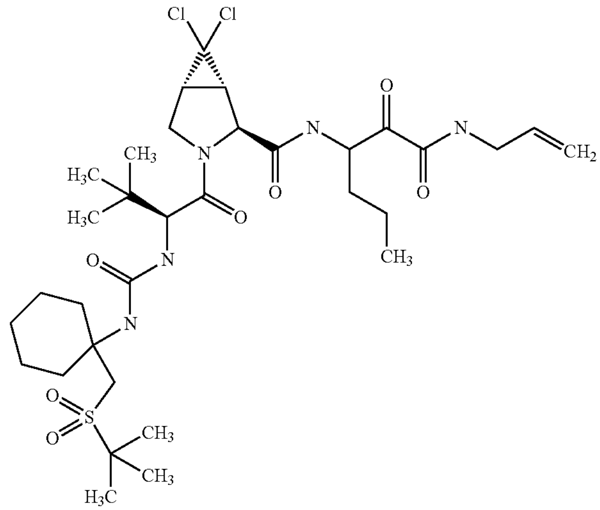 | 734.7897 | 734.1 | A |
| 590 | 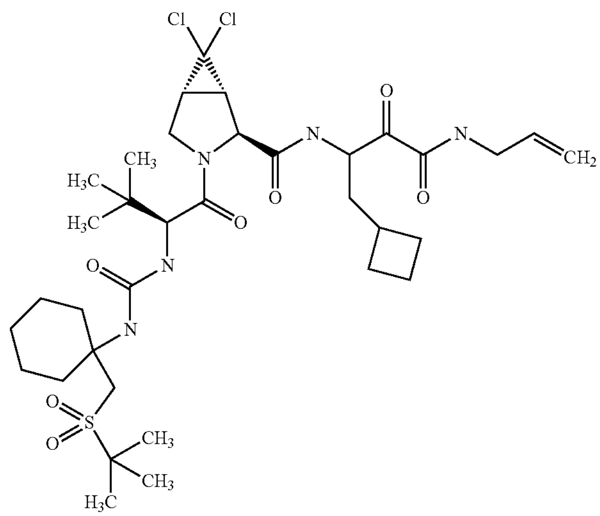 | 760.8279 | 760.1 | A |
| 591 | 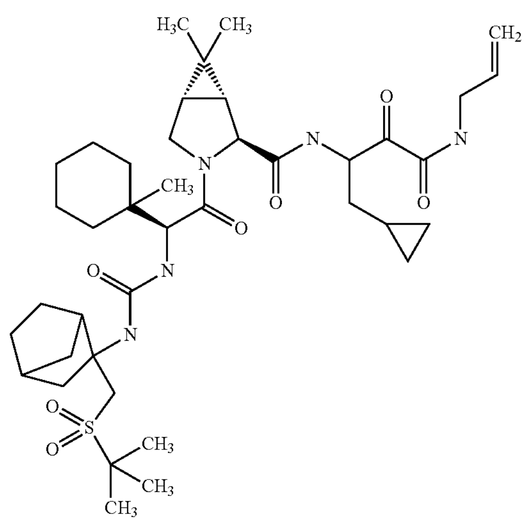 | 758.0414 | | A |

TABLE 3A-continued

| Compound # | structure | mol weight structure | Select LC-MS Data (M + H) | Ki* Range |
|---|---|---|---|---|
| 592 | 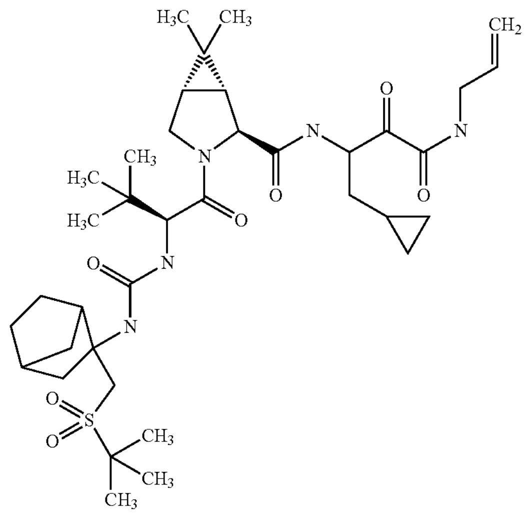 | 717.9761 | | A |
| 593 | 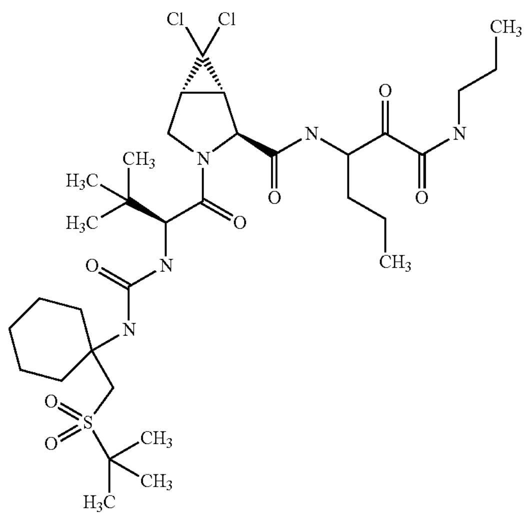 | 736.8056 | 736.1 | A |
| 594 | 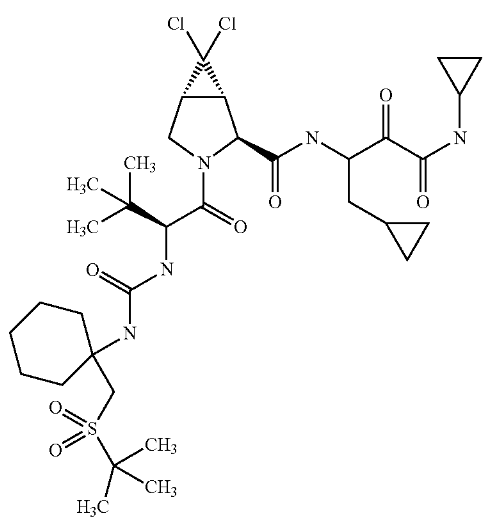 | 746.8008 | 746.1 | A |

TABLE 3A-continued

| Compound # | structure | mol weight structure | Select LC-MS Data (M + H) | Ki* Range |
|---|---|---|---|---|
| 595 | 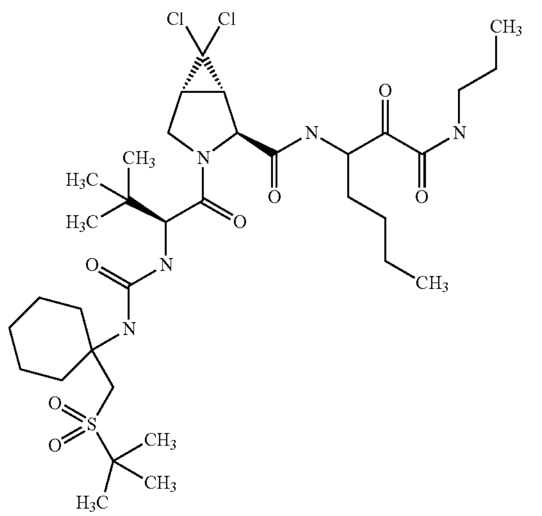 | 750.8327 | 750.4 | A |
| 596 | 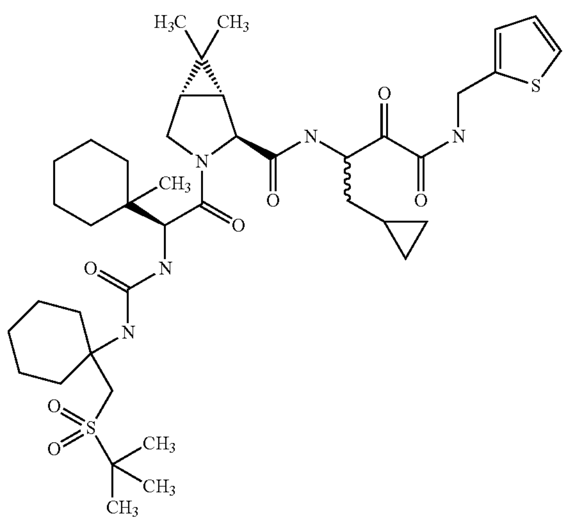 | 802.1166 | 802.5 | A |
| 597 | 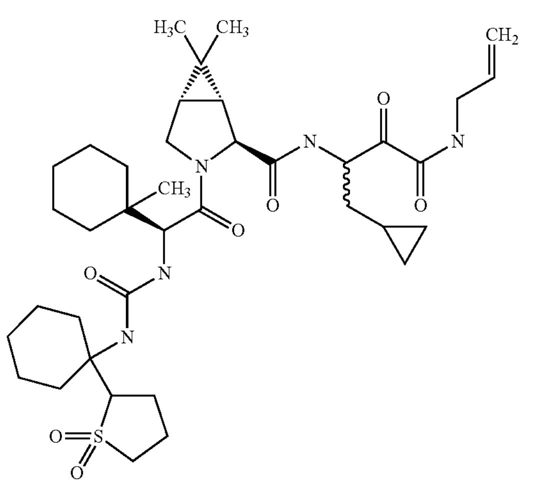 | 729.9872 | 731.4 | A |

TABLE 3A-continued

| Compound # | structure | mol weight structure | Select LC-MS Data (M + H) | Ki* Range |
|---|---|---|---|---|
| 598 | 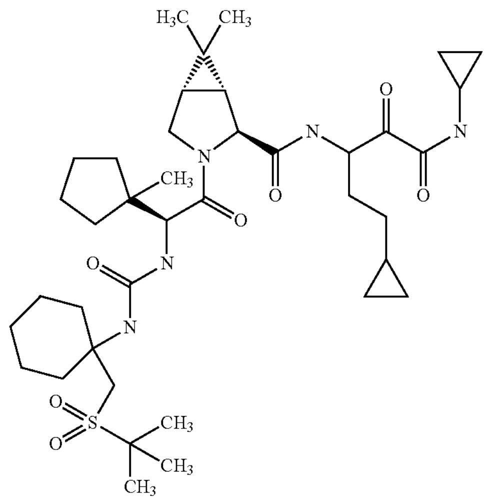 | 746.0303 | 746.4 | A |
| 599 | 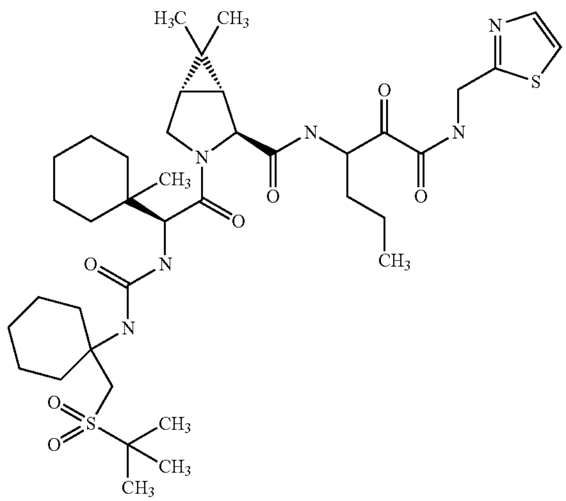 | 791.093 | 791.4 | A |
| 600 | 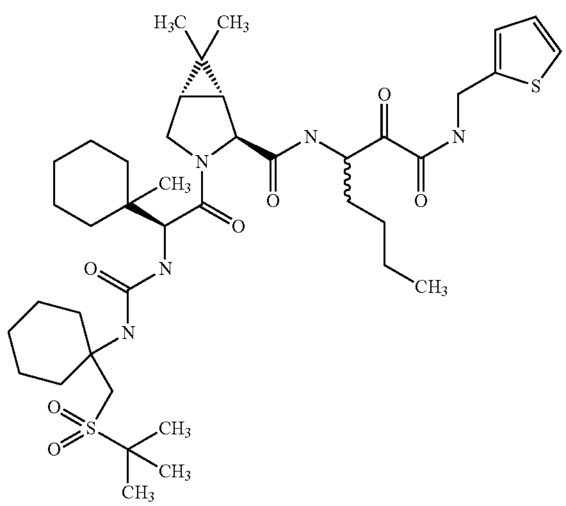 | 804.1325 | 804.5 | A |

TABLE 3A-continued

| Compound # | structure | mol weight structure | Select LC-MS Data (M + H) | Ki* Range |
|---|---|---|---|---|
| 601 | 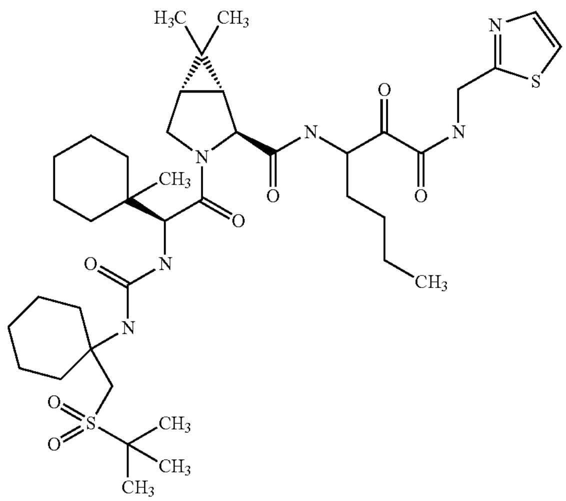 | 805.1201 | 805.4 | A |
| 602 | 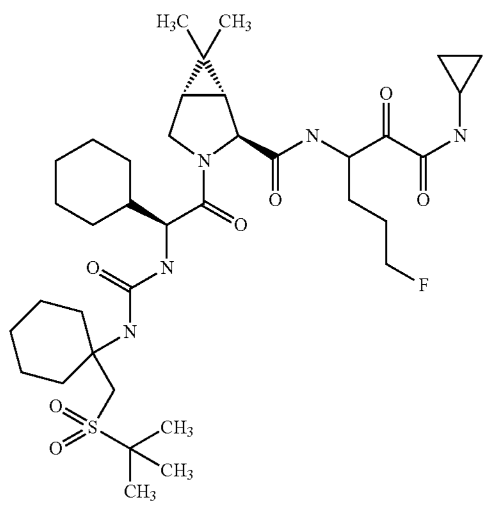 | 737.9825 | | A |
| 603 | 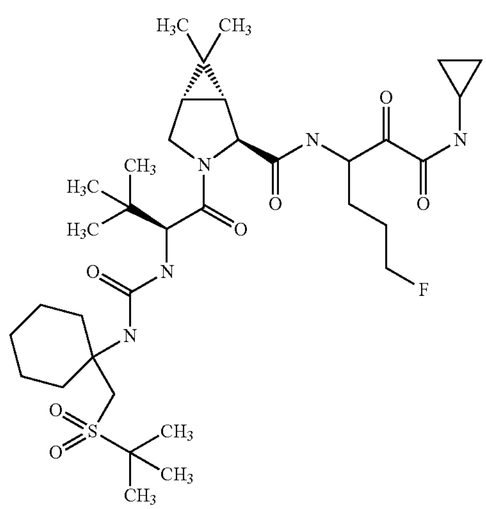 | 711.9442 | | A |

TABLE 3A-continued

| Compound # | structure | mol weight structure | Select LC-MS Data (M + H) | Ki* Range |
|---|---|---|---|---|
| 604 | 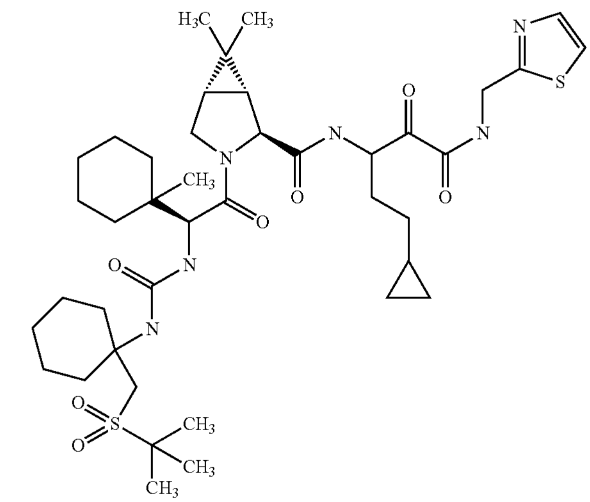 | 817.1312 | 817.4 | A |
| 605 | 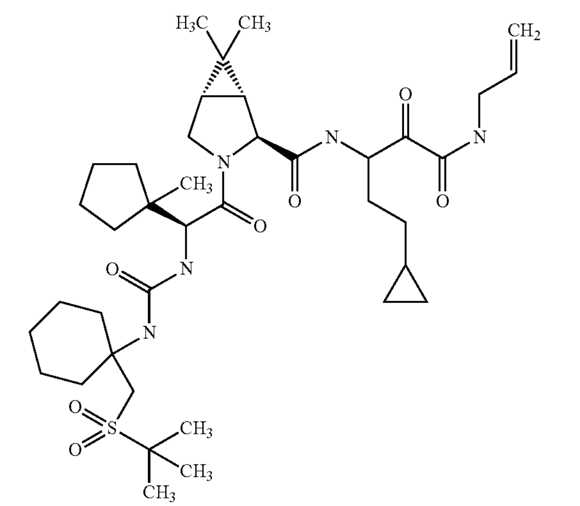 | 746.0303 | 746.4 | A |
| 606 | 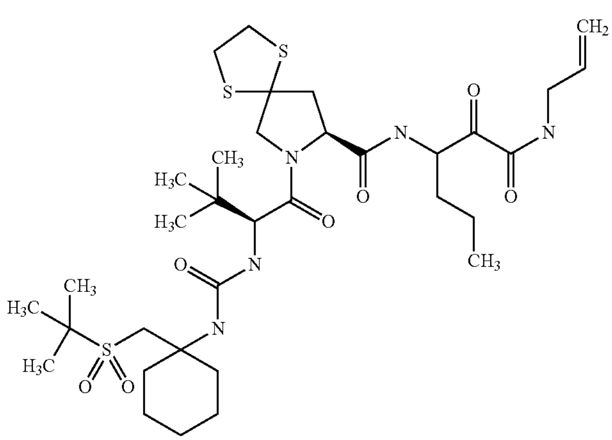 | 744.0547 | 745.1 | A |

TABLE 3A-continued

| Compound # | structure | mol weight structure | Select LC-MS Data (M + H) | Ki* Range |
|---|---|---|---|---|
| 607 | 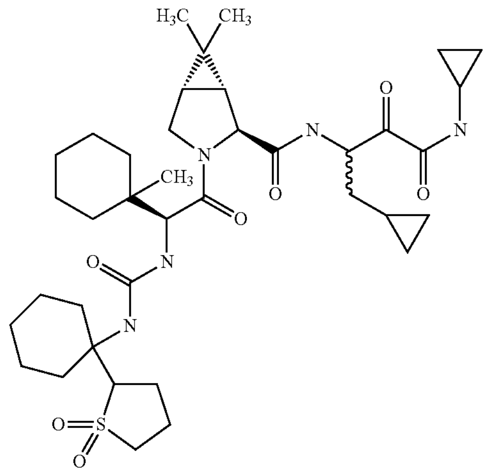 | 729.9872 | | A |
| 608 | 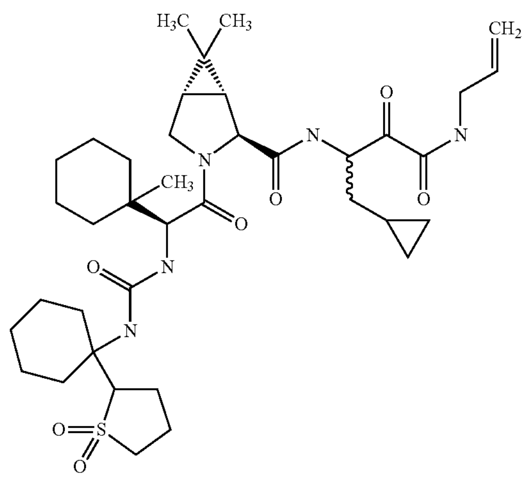 | 729.9872 | 730.4 | A |
| 609 | 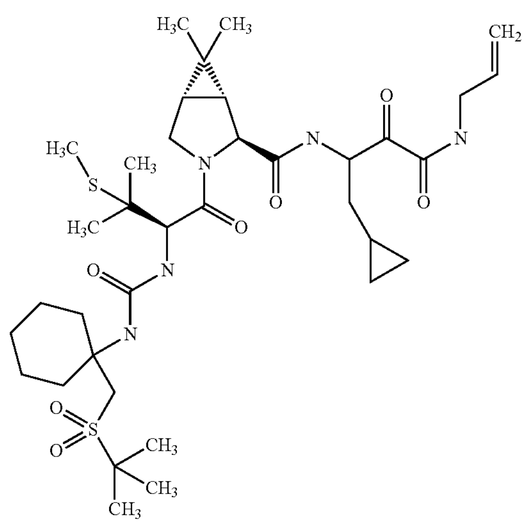 | 738.0289 | 738.1 | A |

TABLE 3A-continued

| Compound # | structure | mol weight structure | Select LC-MS Data (M + H) | Ki* Range |
|---|---|---|---|---|
| 610 | 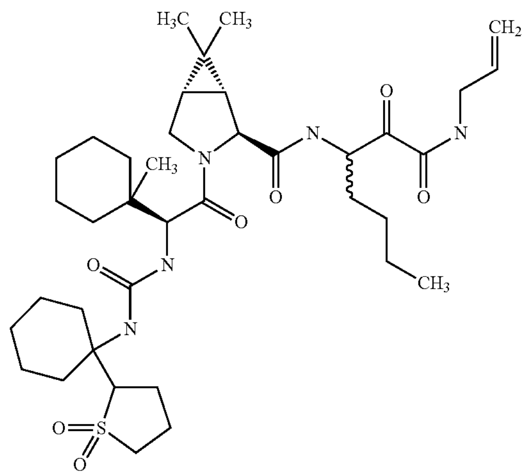 | 732.0032 | 732.1 | A |
| 611 | 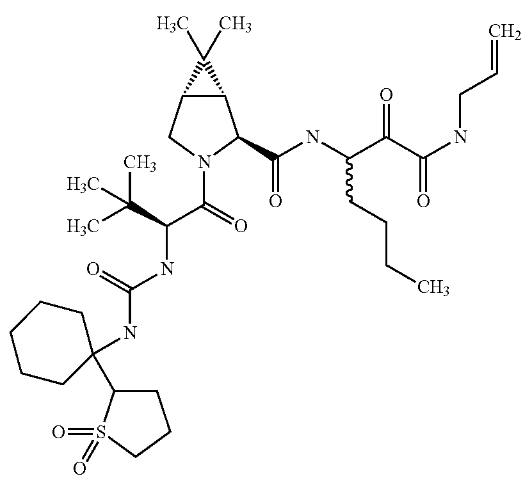 | 691.9378 | 692.1 | 3.8 |
| 612 | 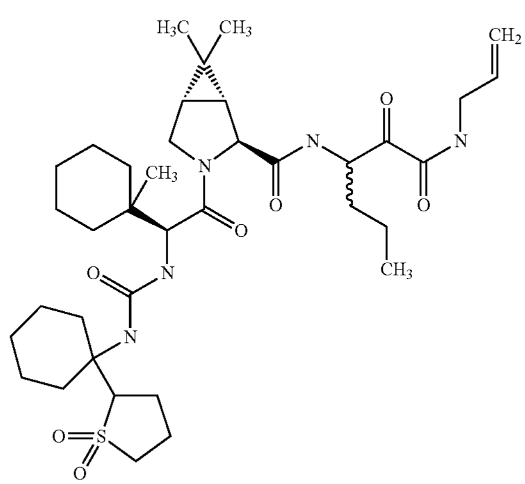 | 717.9761 | 718.1 | A |

TABLE 3A-continued

| Compound # | structure | mol weight structure | Select LC-MS Data (M + H) | Ki* Range |
|---|---|---|---|---|
| 613 | 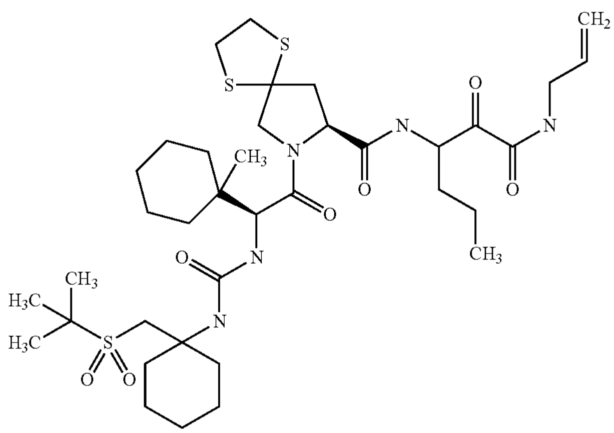 | 784.12 | 784.2 | A |
| 614 | 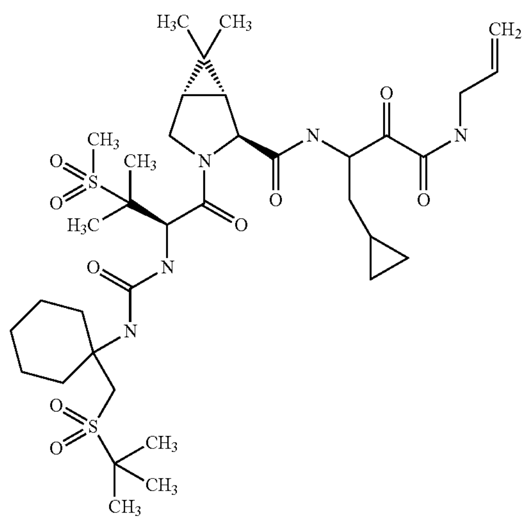 | 770.0277 | 770.2 | B |
| 615 | 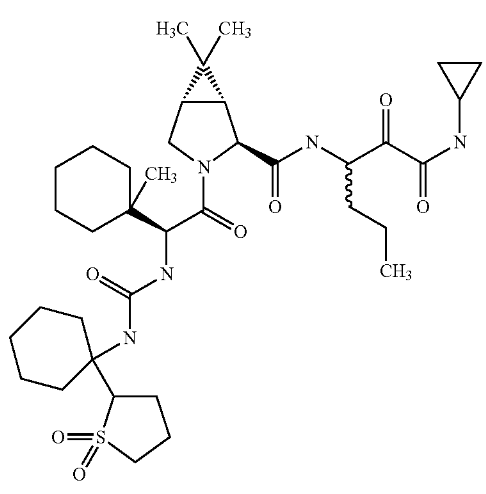 | 717.9761 | | A |

TABLE 3A-continued
| Compound # | structure | mol weight structure | Select LC-MS Data (M + H) | Ki* Range |
|---|---|---|---|---|
| 616 | 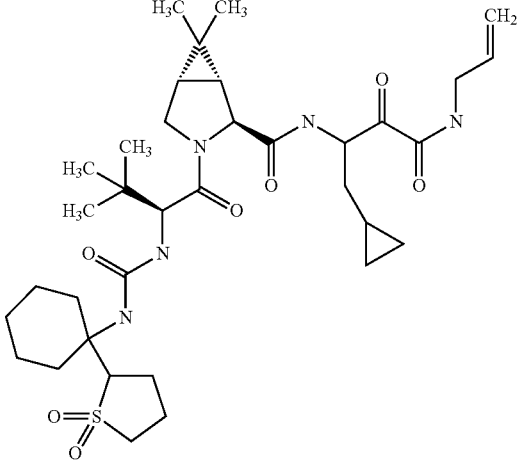 | 689.9219 | | A |
| 617 | 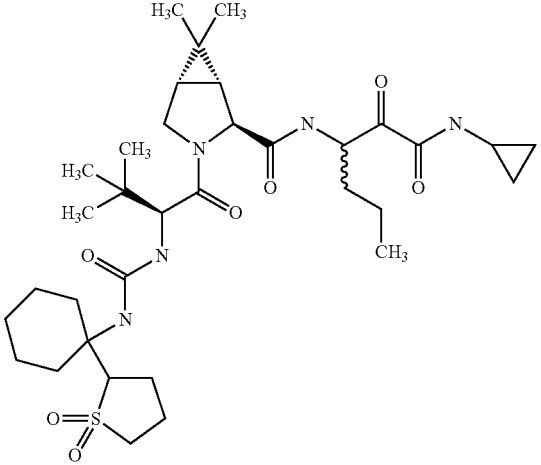 | 677.9108 | 678.4 | A |
| 618 | 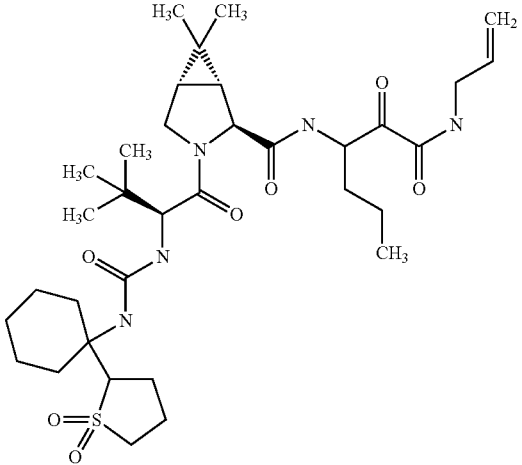 | 677.9108 | 678.4 | A |

TABLE 3A-continued

| Compound # | structure | mol weight structure | Select LC-MS Data (M + H) | Ki* Range |
|---|---|---|---|---|
| 619 | 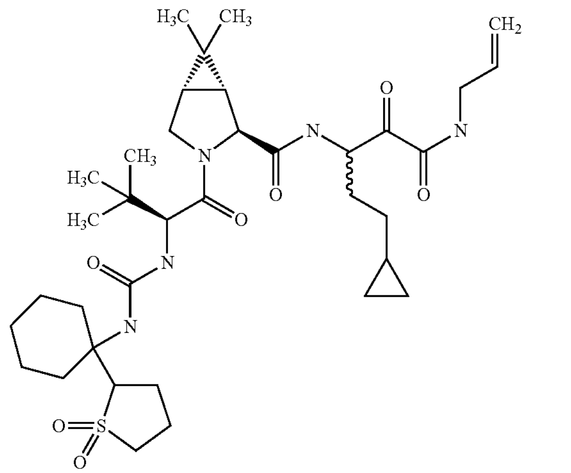 | 703.949 | 704.4 | A |
| 620 | 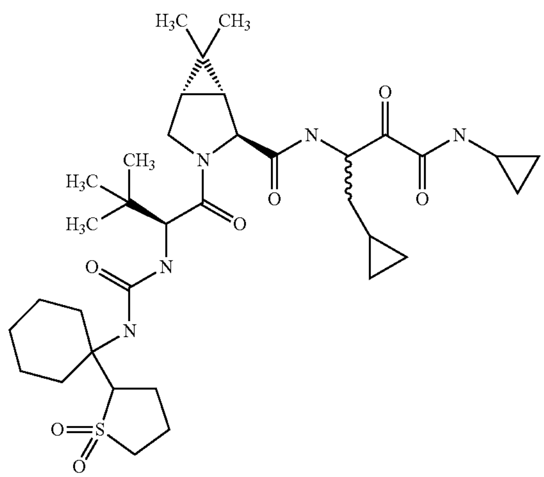 | 689.9219 | 690.4 | A |
| 621 | 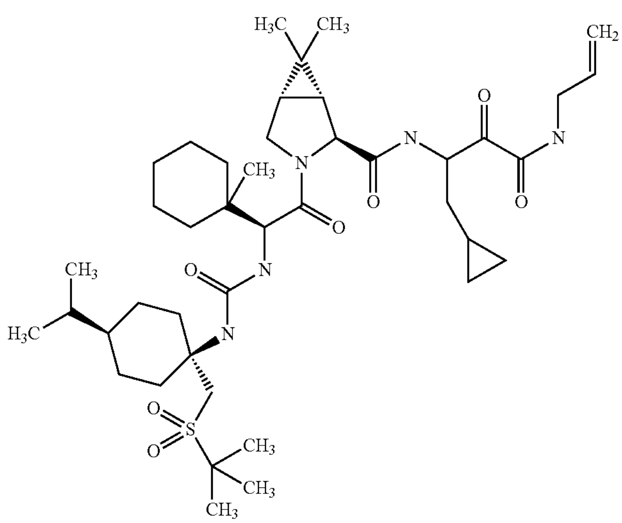 | 788.1115 | 789.4 | C |

TABLE 3A-continued

| Compound # | structure | mol weight structure | Select LC-MS Data (M + H) | Ki* Range |
|---|---|---|---|---|
| 622 | 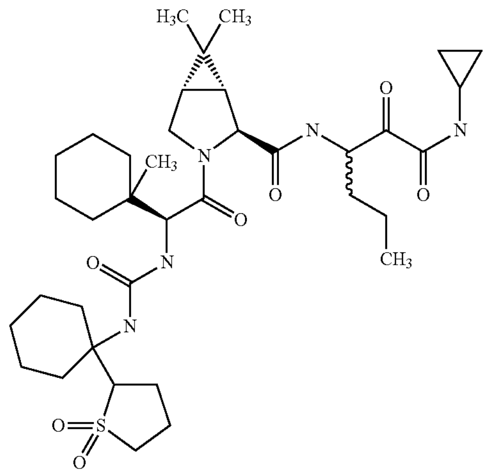 | 717.9761 | 718.1 | A |
| 623 | 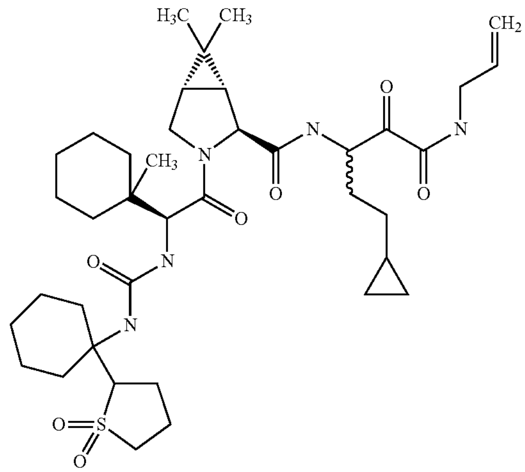 | 744.0143 | 744.1 | A |
| 624 | 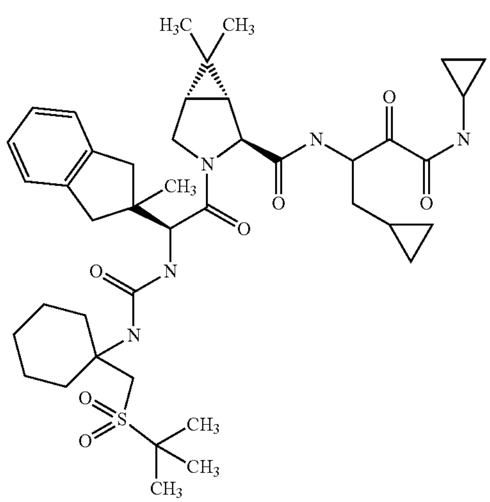 | 780.0478 | 780.5 | B |

TABLE 3A-continued

| Compound # | structure | mol weight structure | Select LC-MS Data (M + H) | Ki* Range |
|---|---|---|---|---|
| 625 | 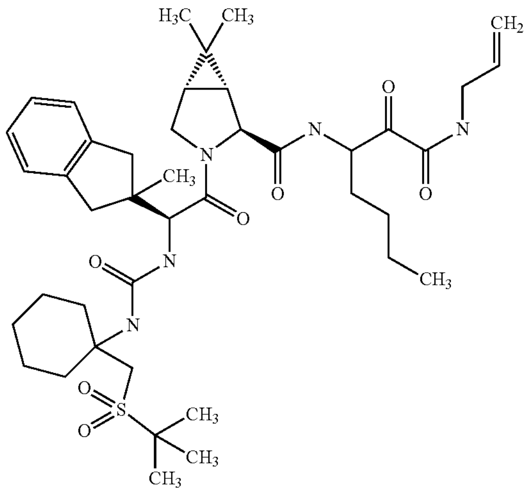 | 782.0637 | 782.5 | A |
| 626 | 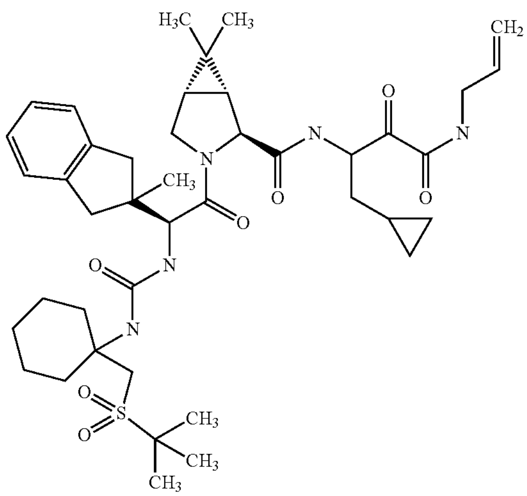 | 780.0478 | 780.5 | A |
| 627 | 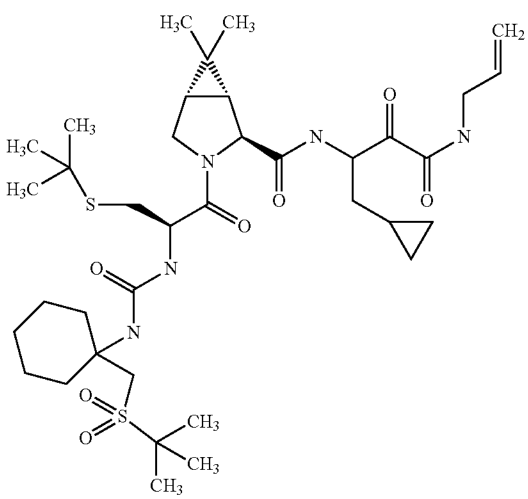 | 752.056 | 752.1 | C |

TABLE 3A-continued

| Compound # | structure | mol weight structure | Select LC-MS Data (M + H) | Ki* Range |
|---|---|---|---|---|
| 628 | 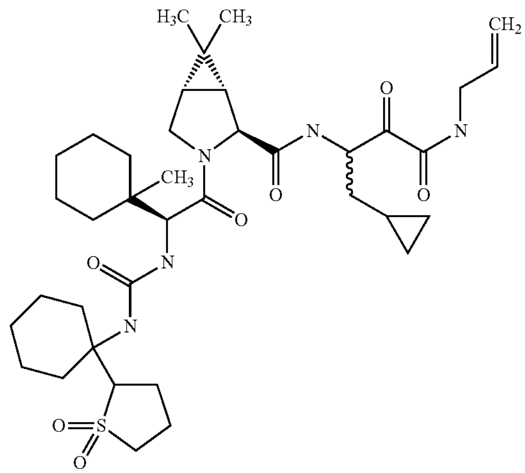 | 729.9872 | 730.4 | A |
| 629 | 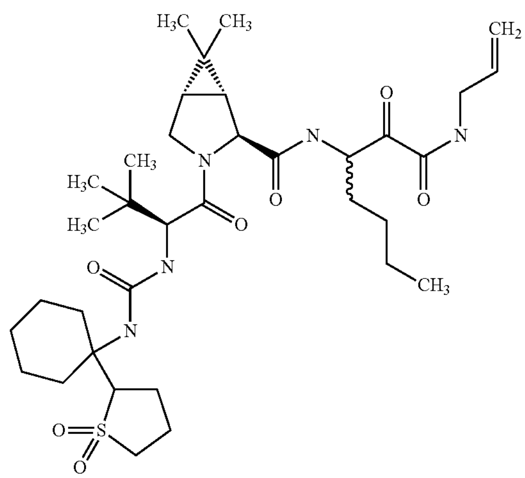 | 691.9378 | 692.4 | A |
| 630 | 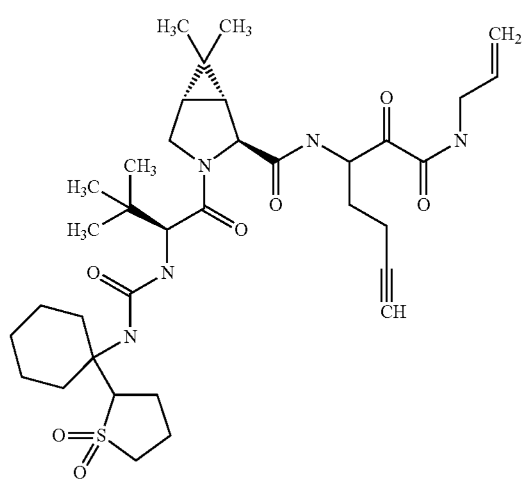 | 687.906 | 688.4 | A |

TABLE 3A-continued

| Compound # | structure | mol weight structure | Select LC-MS Data (M + H) | Ki* Range |
|---|---|---|---|---|
| 631 | 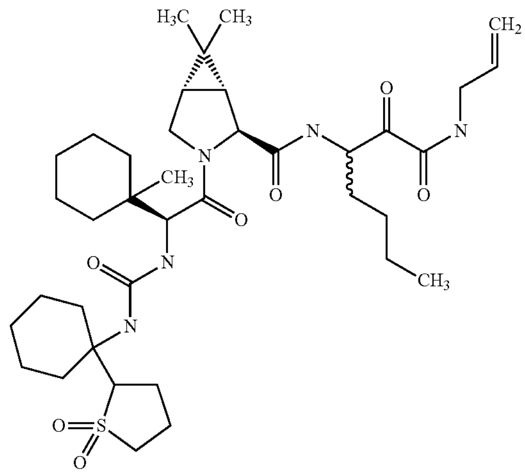 | 732.0032 | 732.4 | A |
| 632 | 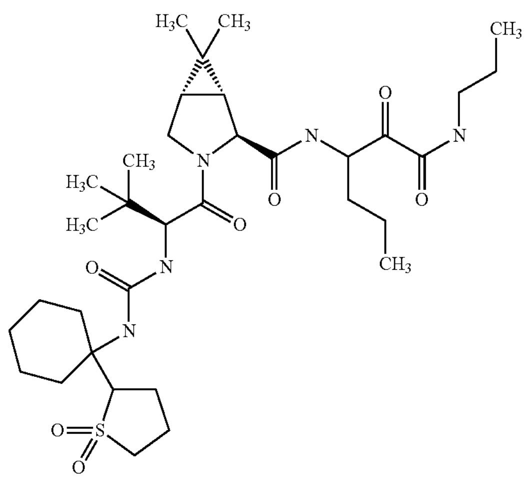 | 679.9267 | 680.4 | A |
| 633 | 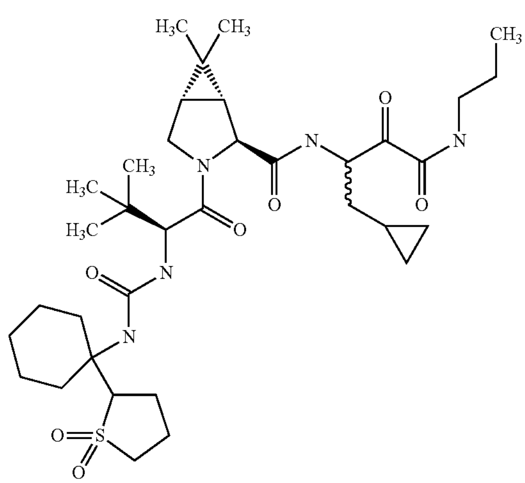 | 691.9378 | 692.4 | A |

TABLE 3A-continued
| Compound # | structure | mol weight structure | Select LC-MS Data (M + H) | Ki* Range |
|---|---|---|---|---|
| 634 | 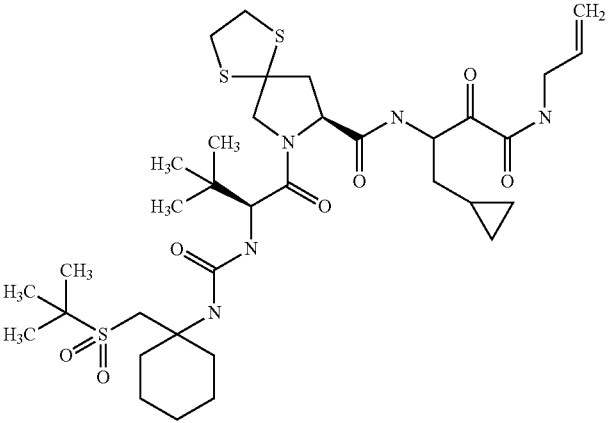 | 756.0658 | 756.1 | A |
| 635 | 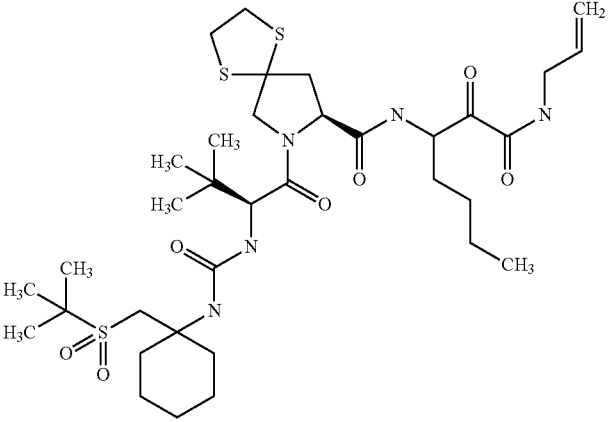 | 758.0818 | 758.1 | A |
| 636 | 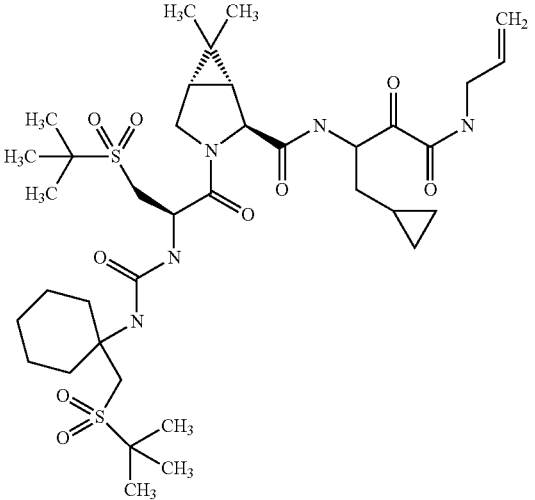 | 784.0548 | 784.2 | C |

TABLE 3A-continued

| Compound # | structure | mol weight structure | Select LC-MS Data (M + H) | Ki* Range |
|---|---|---|---|---|
| 637 | 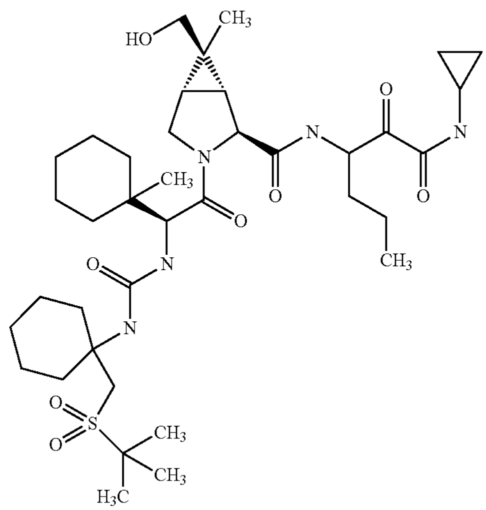 | 750.0185 | | B |
| 638 | 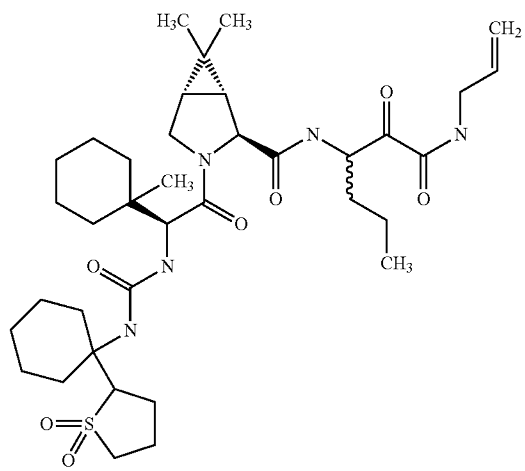 | 717.9761 | 718.4 | A |
| 639 | 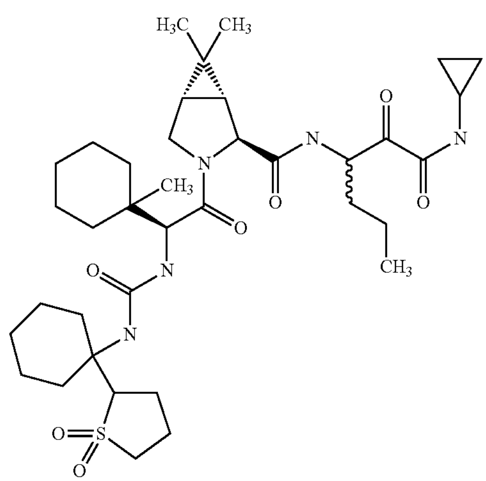 | 717.9761 | 718.4 | A |

TABLE 3A-continued

| Compound # | structure | mol weight structure | Select LC-MS Data (M + H) | Ki* Range |
|---|---|---|---|---|
| 640 | 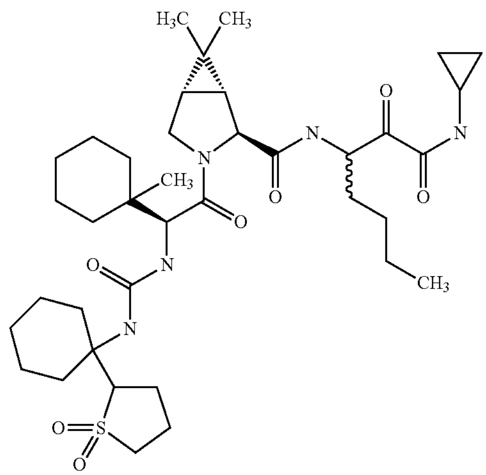 | 732.0032 | 732.4 | A |
| 641 | 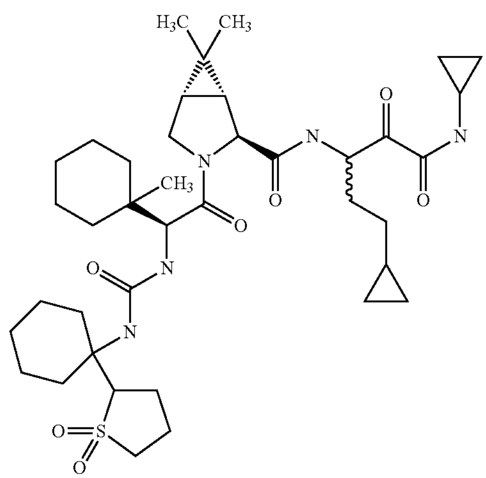 | 744.0143 | 744.4 | A |
| 642 | 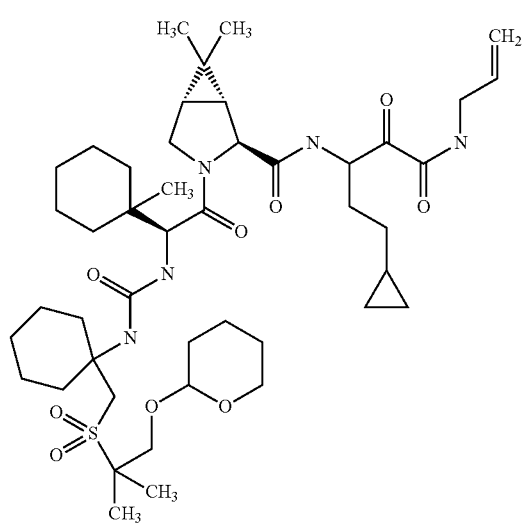 | 860.1757 | | A |

TABLE 3A-continued

| Compound # | structure | mol weight structure | Select LC-MS Data (M + H) | Ki* Range |
|---|---|---|---|---|
| 643 | 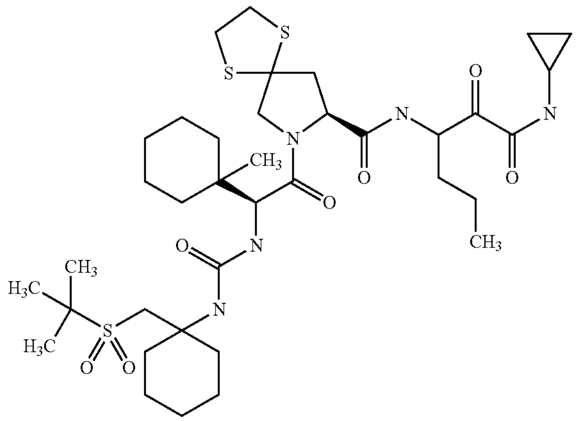 | 784.12 | | B |
| 644 | 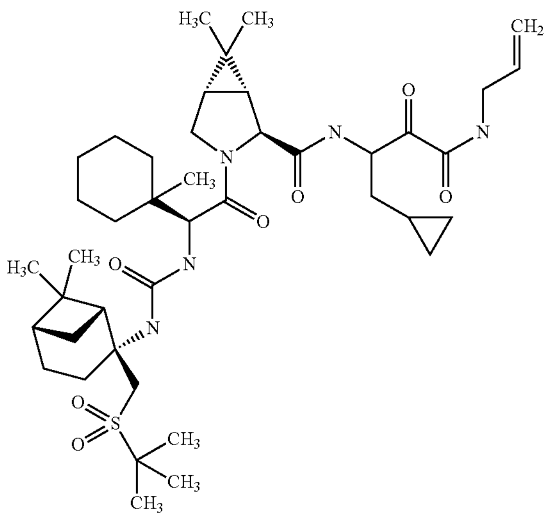 | 786.0956 | | B |
| 645 | 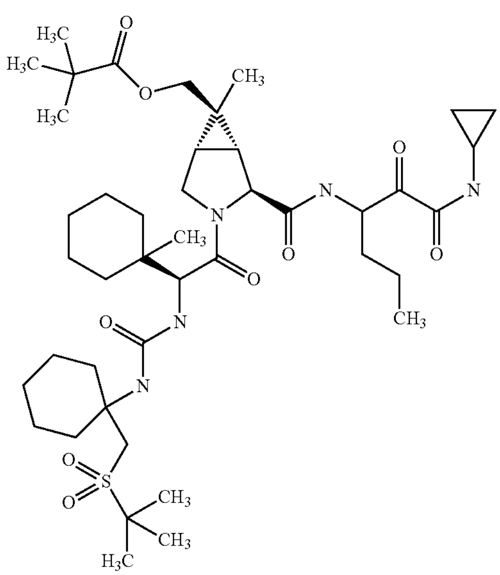 | 834.1374 | | B |

TABLE 3A-continued

| Compound # | structure | mol weight structure | Select LC-MS Data (M + H) | Ki* Range |
|---|---|---|---|---|
| 646 | 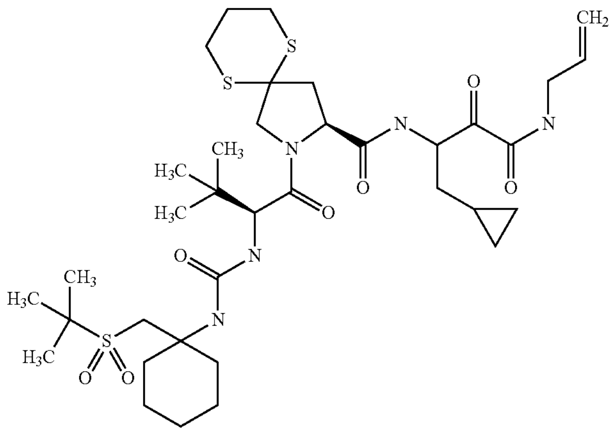 | 770.0929 | 770.2 | A |
| 647 | 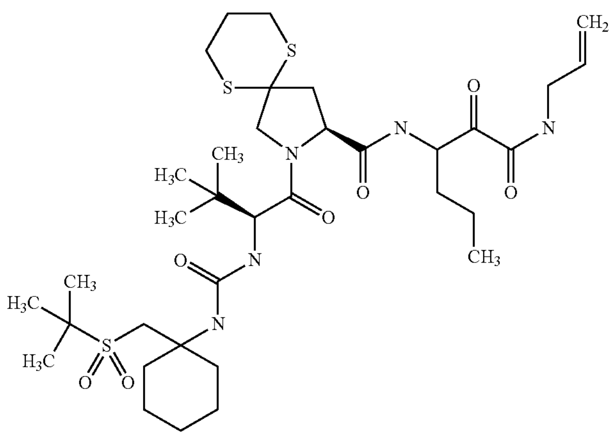 | 758.0818 | 758.2 | A |
| 648 | 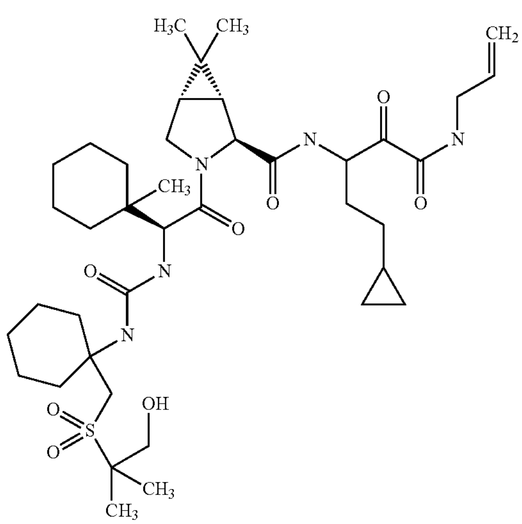 | 776.0568 | | A |

TABLE 3A-continued

| Compound # | structure | mol weight structure | Select LC-MS Data (M + H) | Ki* Range |
|---|---|---|---|---|
| 649 | 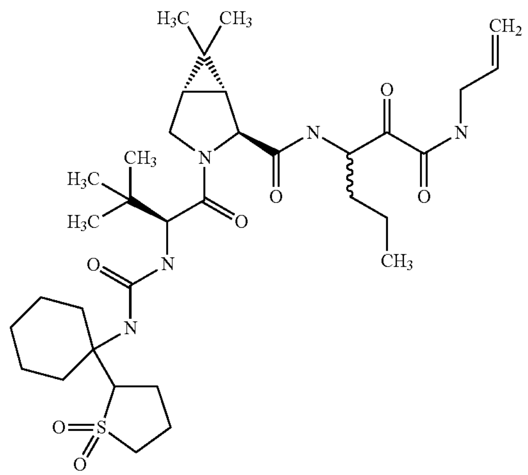 | 677.9108 | 678.2 | A |
| 650 | 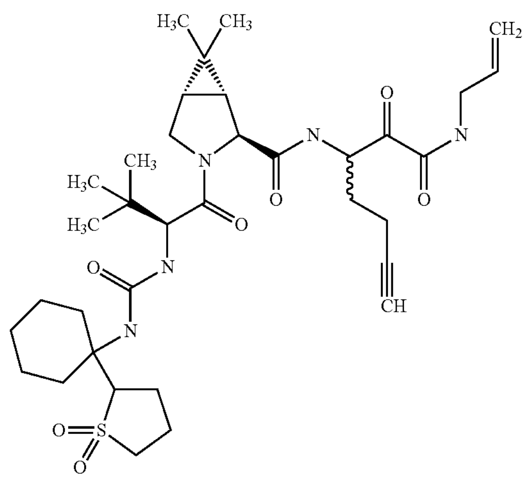 | 687.906 | 688.2 | A |
| 651 | 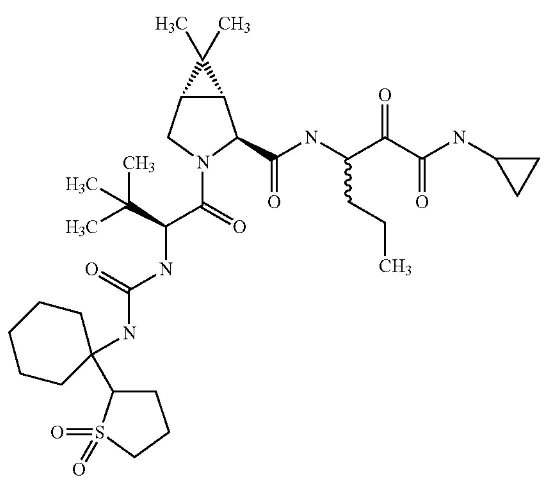 | 677.9108 | 678.2 | A |

TABLE 3A-continued

| Compound # | structure | mol weight structure | Select LC-MS Data (M + H) | Ki* Range |
|---|---|---|---|---|
| 652 | 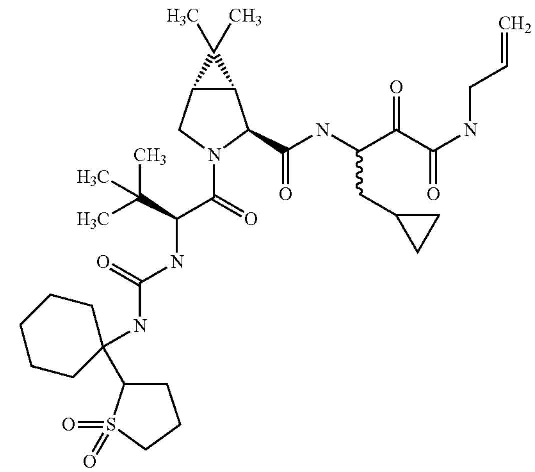 | 689.9219 | 690.2 | A |
| 653 | 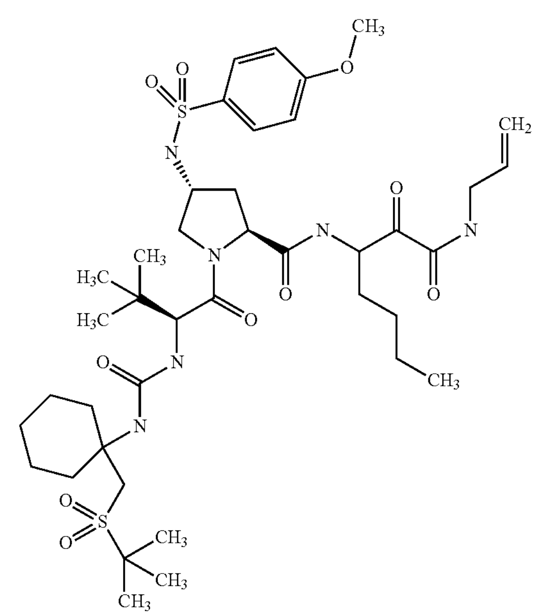 | 853.1183 | 853.4 | C |

TABLE 3A-continued

| Compound # | structure | mol weight structure | Select LC-MS Data (M + H) | Ki* Range |
|---|---|---|---|---|
| 654 | 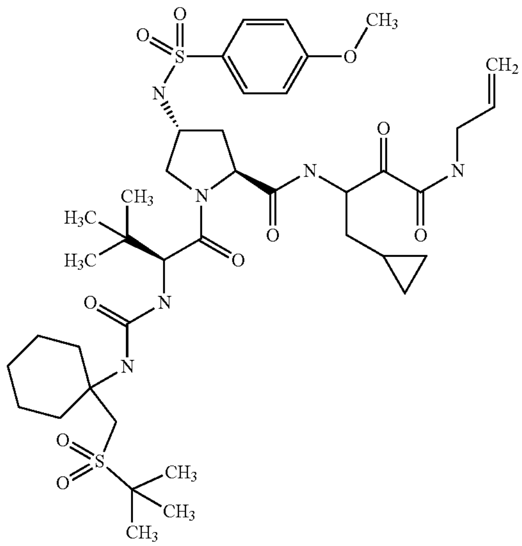 | 851.1023 | 851.4 | C |
| 655 | 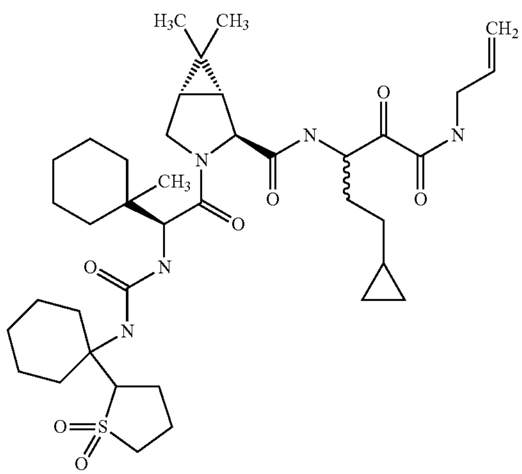 | 744.0143 | 744.1 | A |
| 656 | 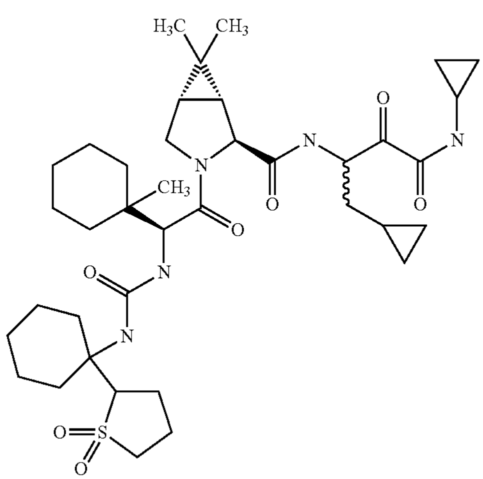 | 729.9872 | 730.1 | A |

TABLE 3A-continued

| Compound # | structure | mol weight structure | Select LC-MS Data (M + H) | Ki* Range |
|---|---|---|---|---|
| 657 | 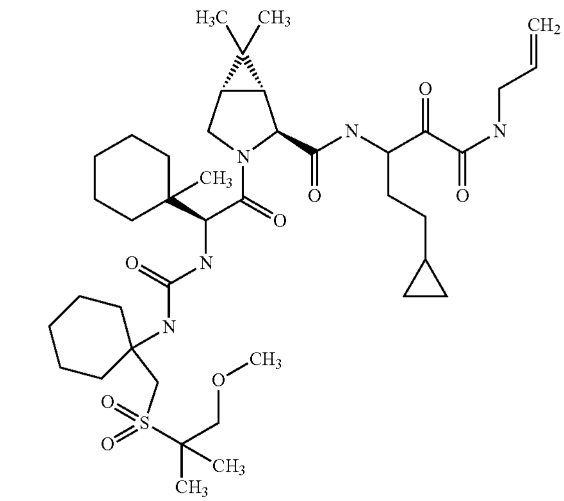 | 790.0838 | | A |
| 658 | 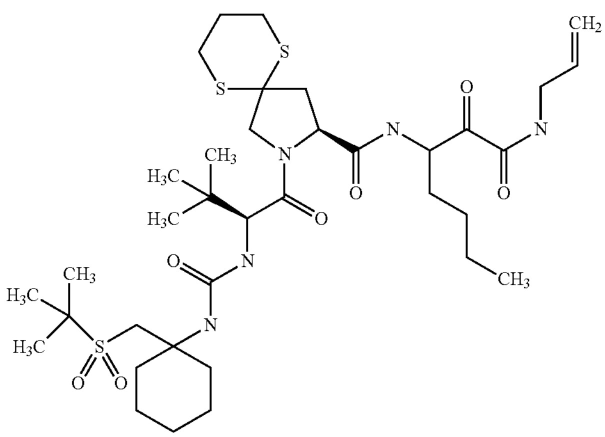 | 772.1089 | 772.2 | A |
| 659 | 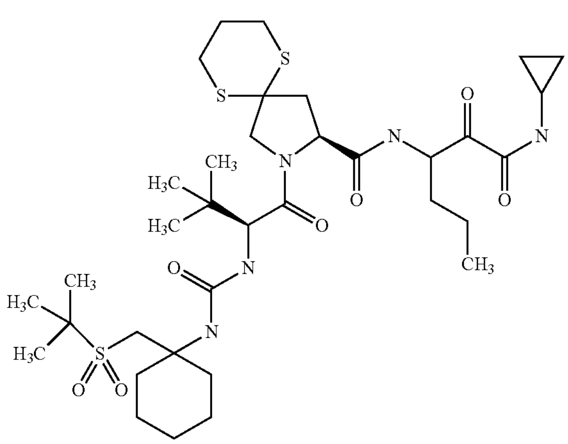 | 758.0818 | 758.2 | A |

TABLE 3A-continued

| Compound # | structure | mol weight structure | Select LC-MS Data (M + H) | Ki* Range |
|---|---|---|---|---|
| 660 | 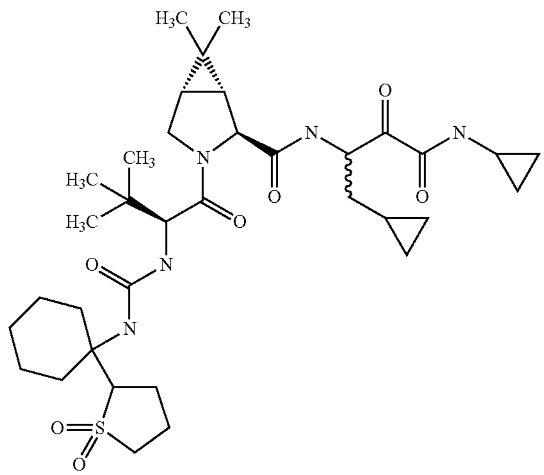 | 689.9219 | 690.1 | A |
| 661 | 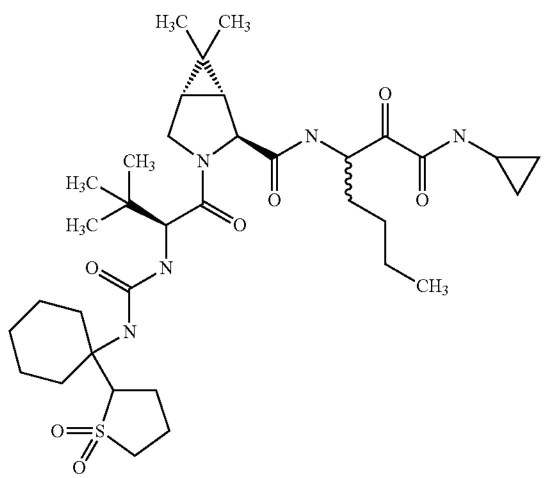 | 691.9378 | 692.1 | A |
| 662 | 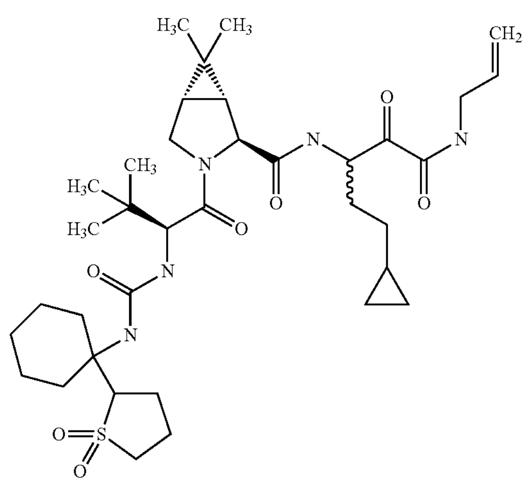 | 703.949 | 704.1 | A |

TABLE 3A-continued

| Compound # | structure | mol weight structure | Select LC-MS Data (M + H) | Ki* Range |
|---|---|---|---|---|
| 663 | 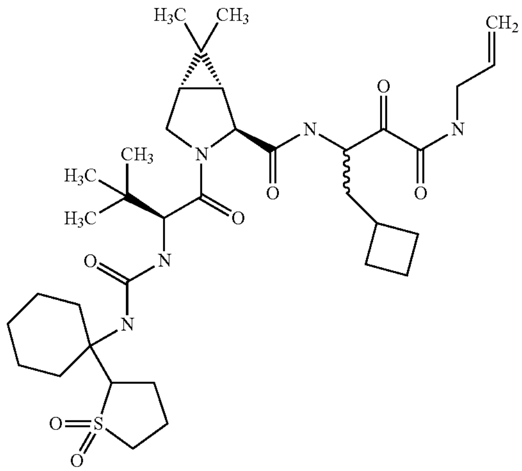 | 703.949 | 704.1 | A |
| 664 | 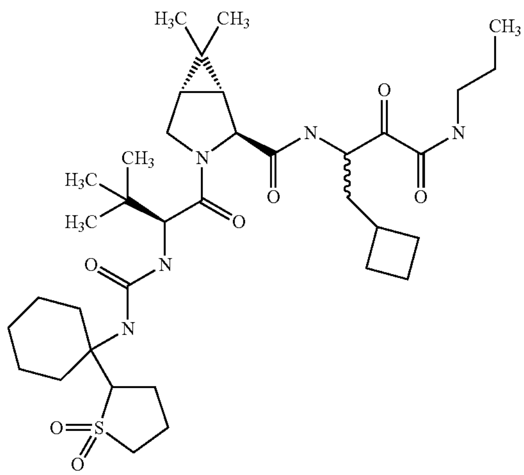 | 705.9649 | 706.2 | A |
| 665 | 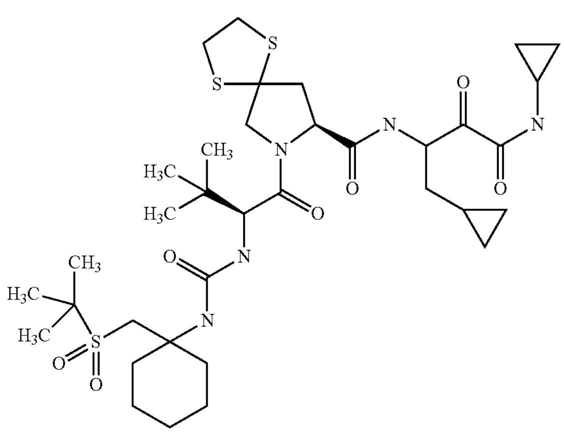 | 756.0658 | | B |

TABLE 3A-continued

| Compound # | structure | mol weight structure | Select LC-MS Data (M + H) | Ki* Range |
|---|---|---|---|---|
| 666 | 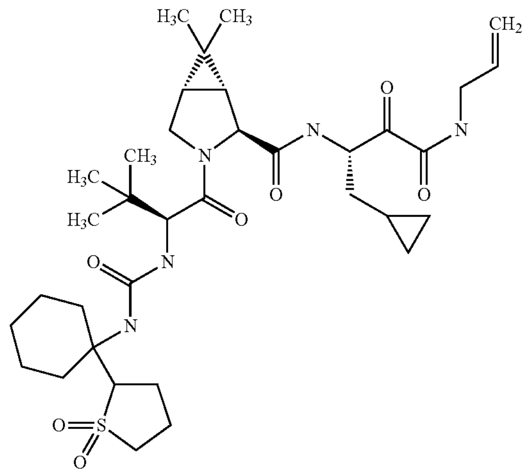 | 689.9219 | | A |
| 667 | 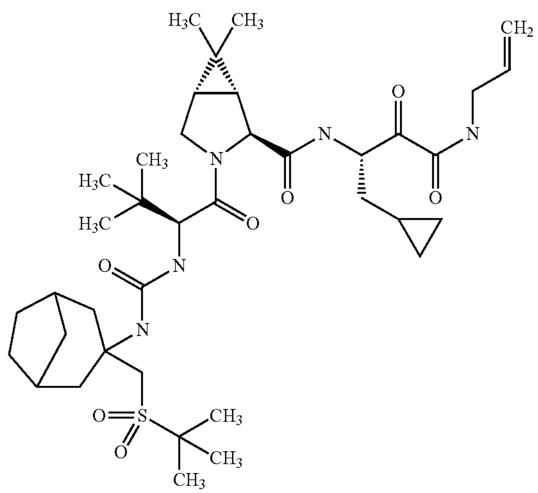 | 732.0032 | | A |
| 668 | 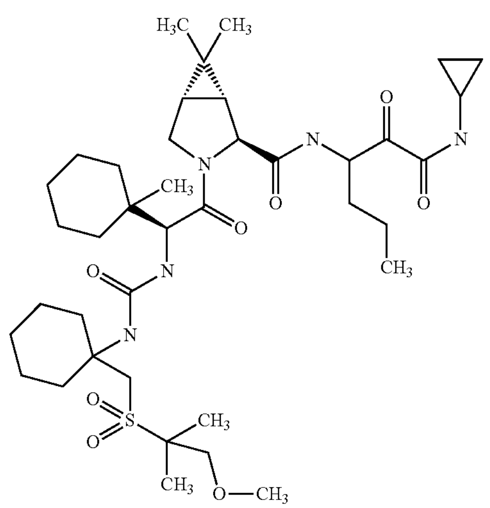 | 764.0456 | | A |

TABLE 3A-continued

| Compound # | structure | mol weight structure | Select LC-MS Data (M + H) | Ki* Range |
|---|---|---|---|---|
| 669 | 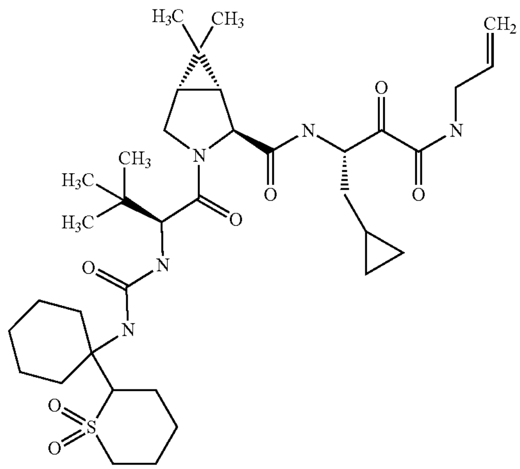 | 703.949 | | A |
| 670 | 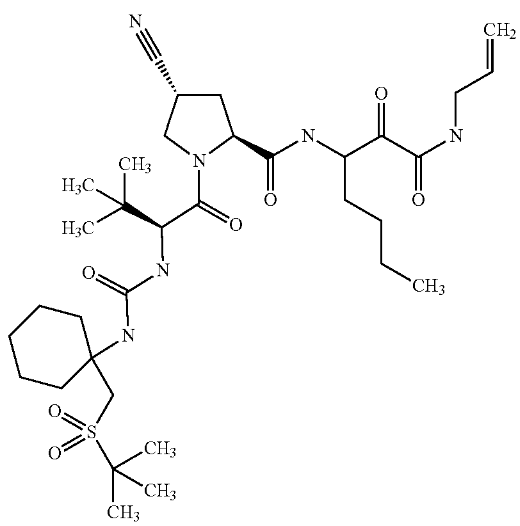 | 692.9254 | 693.3 | C |
| 671 | 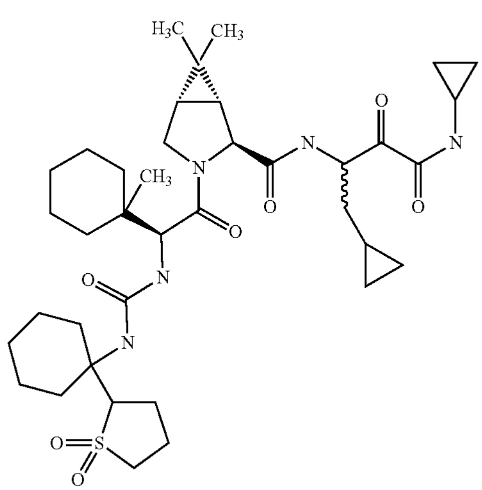 | 729.9872 | 730.1 | A |

TABLE 3A-continued

| Compound # | structure | mol weight structure | Select LC-MS Data (M + H) | Ki* Range |
|---|---|---|---|---|
| 672 | 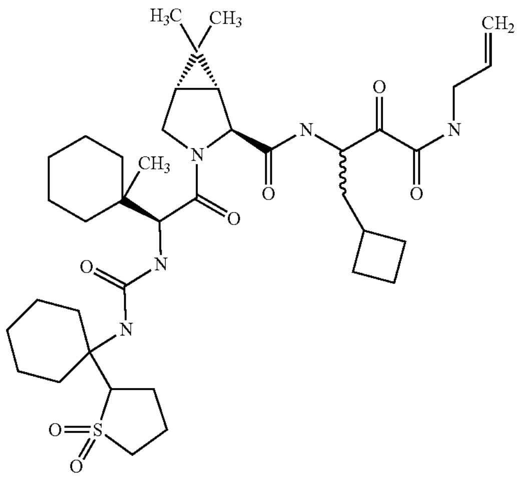 | 744.0143 | 744.1 | A |
| 673 | 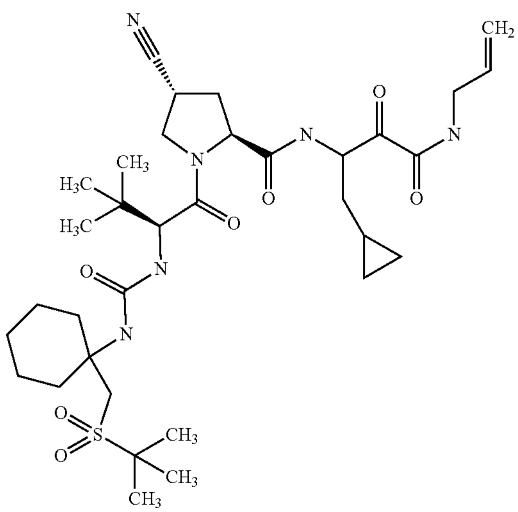 | 690.9095 | 691.35 | C |
| 674 | 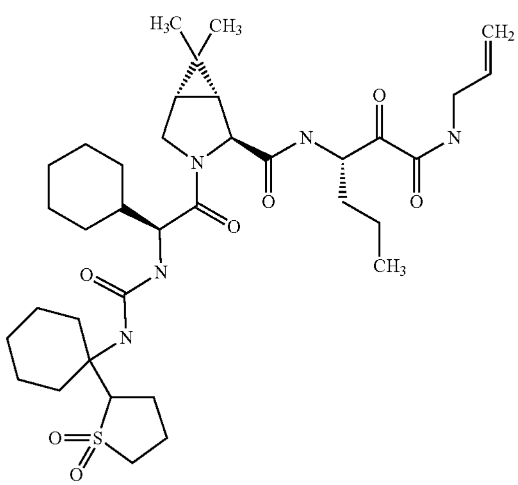 | 703.949 | | A |

TABLE 3A-continued
| Compound # | structure | mol weight structure | Select LC-MS Data (M + H) | Ki* Range |
|---|---|---|---|---|
| 675 | 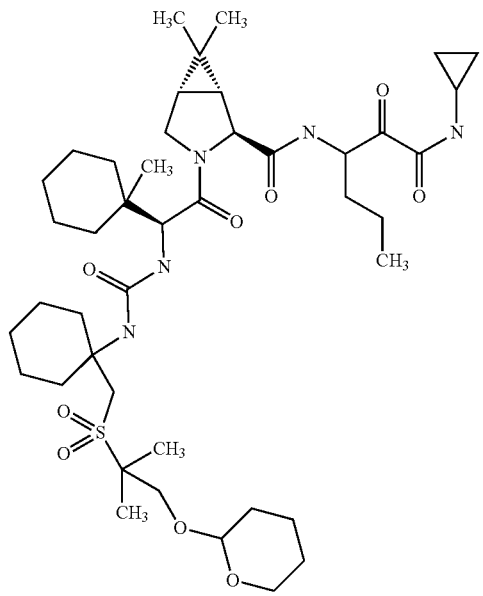 | 834.1374 | | A |
| 676 | 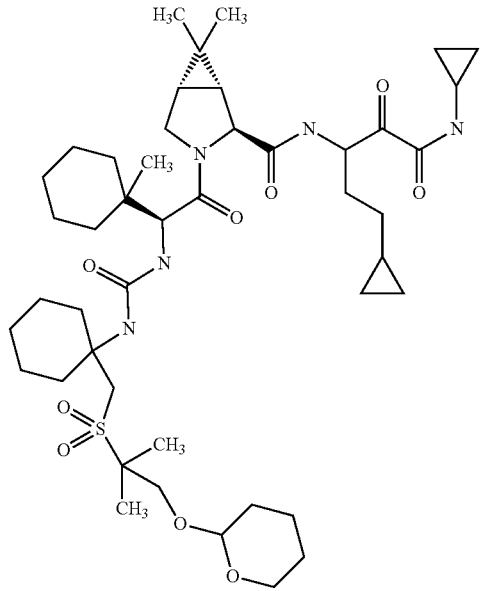 | 860.1757 | | A |

TABLE 3A-continued

| Compound # | structure | mol weight structure | Select LC-MS Data (M + H) | Ki* Range |
|---|---|---|---|---|
| 677 | 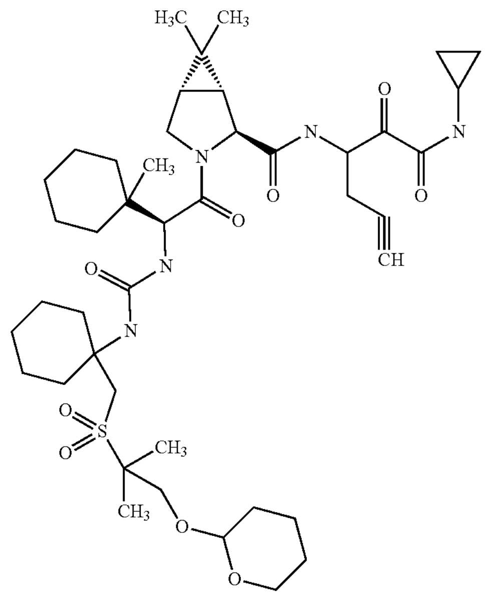 | | 844.1326 | A |
| 678 | 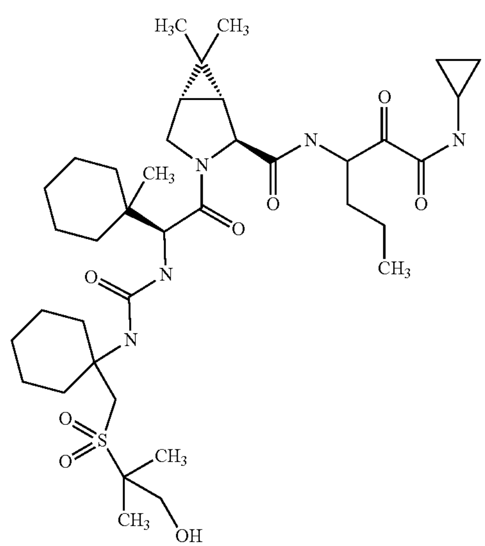 | | 750.0185 | A |

TABLE 3A-continued

| Compound # | structure | mol weight structure | Select LC-MS Data (M + H) | Ki* Range |
|---|---|---|---|---|
| 679 | 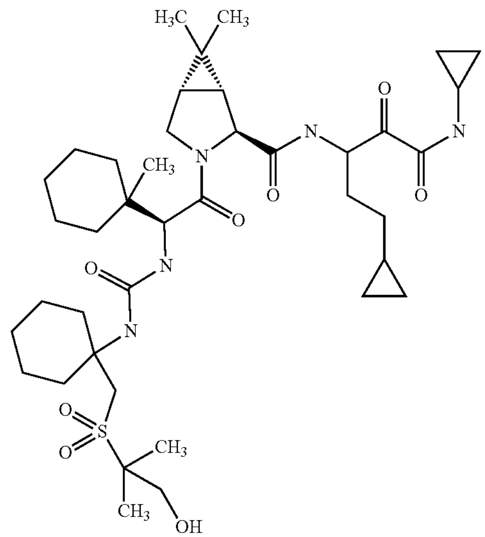 | 776.0568 | | A |
| 680 | 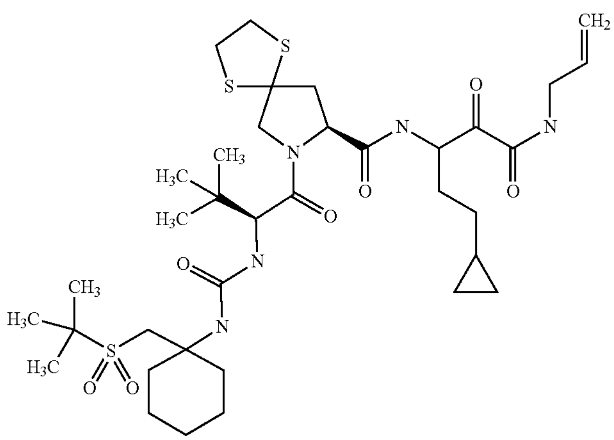 | 770.0929 | 770.4 | A |
| 681 | 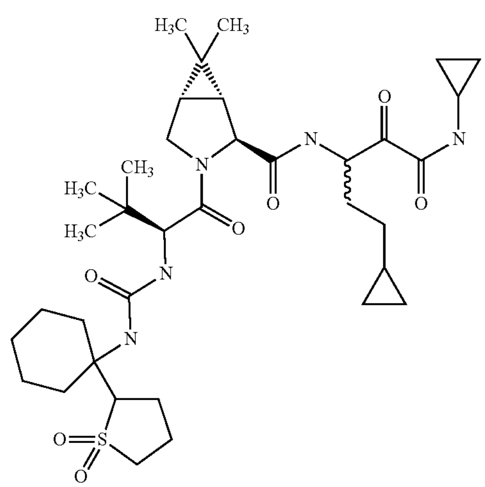 | 703.949 | 704.2 | A |

TABLE 3A-continued

| Compound # | structure | mol weight structure | Select LC-MS Data (M + H) | Ki* Range |
|---|---|---|---|---|
| 682 | 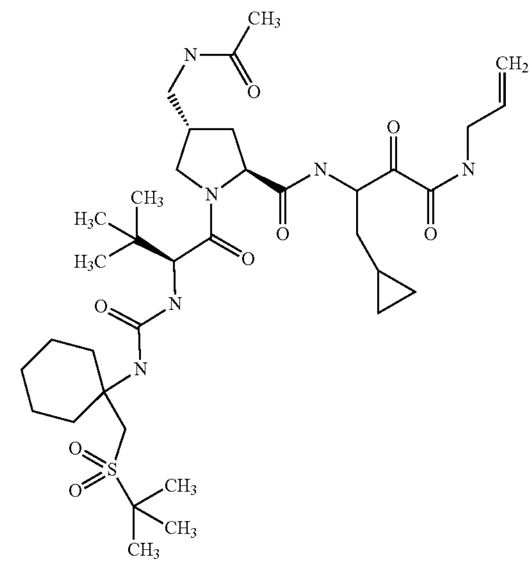 | 736.979 | 737.5 | C |
| 683 | 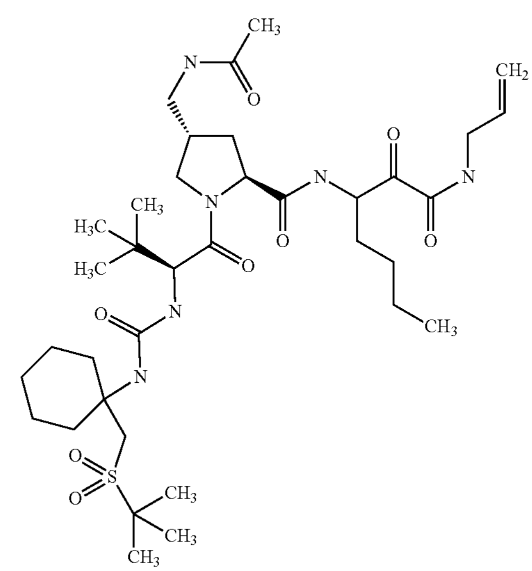 | 738.9949 | 739.4 | C |

TABLE 3A-continued

| Compound # | structure | mol weight structure | Select LC-MS Data (M + H) | Ki* Range |
|---|---|---|---|---|
| 684 | 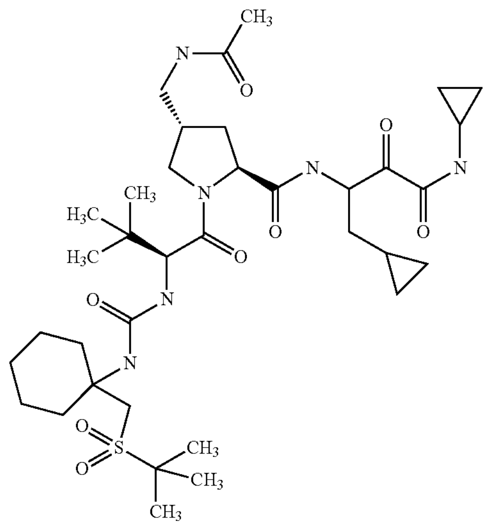 | 736.979 | 737.4 | C |
| 685 | 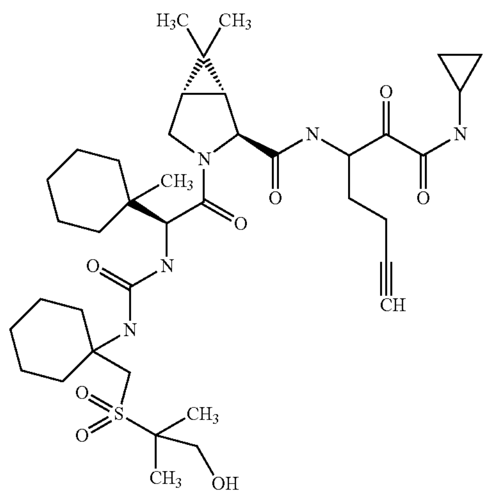 | 760.0137 | | A |
| 686 | 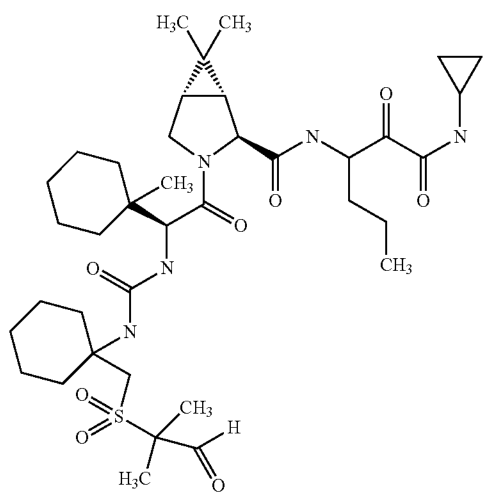 | 748.0026 | | A |

TABLE 3A-continued

| Compound # | structure | mol weight structure | Select LC-MS Data (M + H) | Ki* Range |
|---|---|---|---|---|
| 687 | 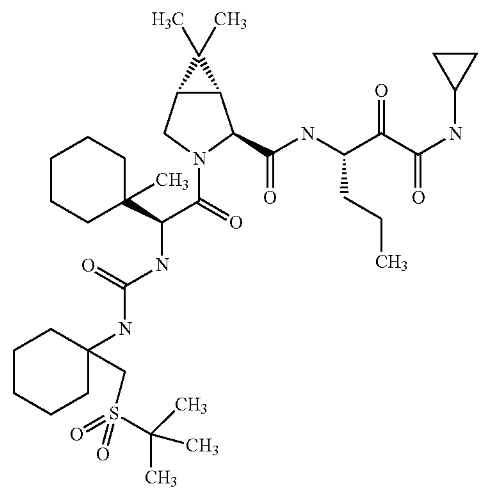 | 734.0191 | | A |
| 688 | 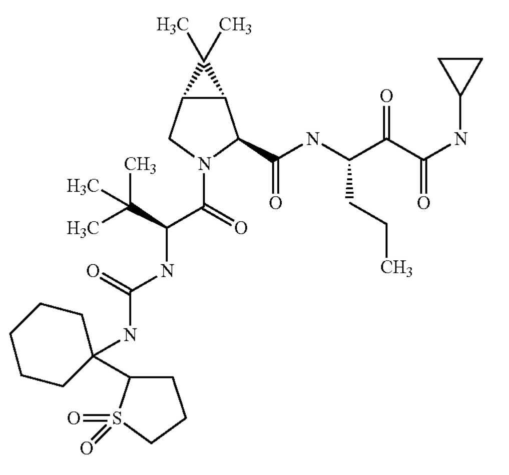 | 677.9108 | 678.2 | A |
| 689 | 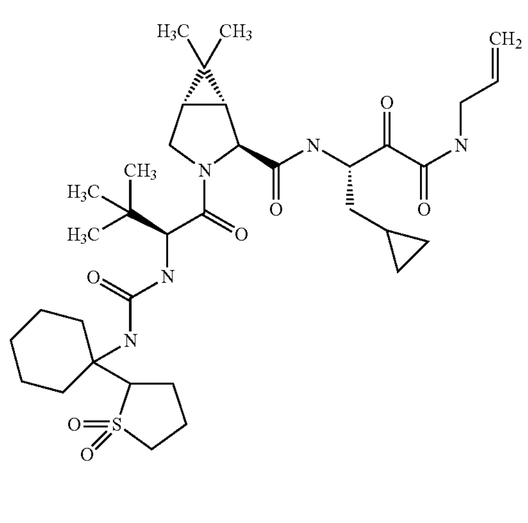 | 689.9219 | 690.2 | A |

TABLE 3A-continued

| Compound # | structure | mol weight structure | Select LC-MS Data (M + H) | Ki* Range |
|---|---|---|---|---|
| 690 | 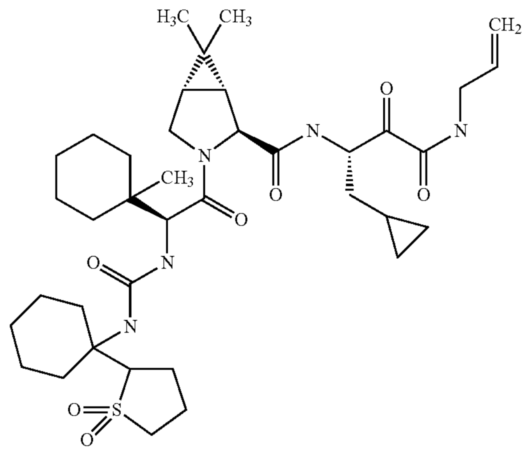 | 729.9872 | 730.2 | A |
| 691 | 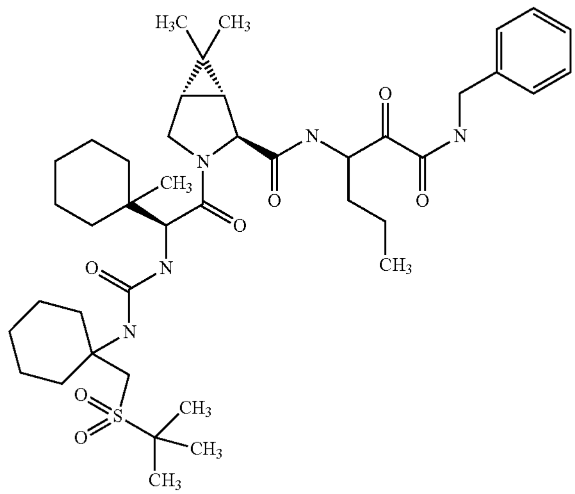 | 784.0797 | 784.2 | A |
| 692 | 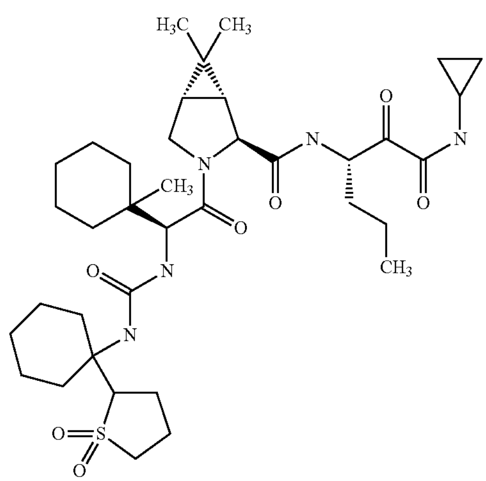 | 717.9761 | | A |

TABLE 3A-continued

| Compound # | structure | mol weight structure | Select LC-MS Data (M + H) | Ki* Range |
|---|---|---|---|---|
| 693 | 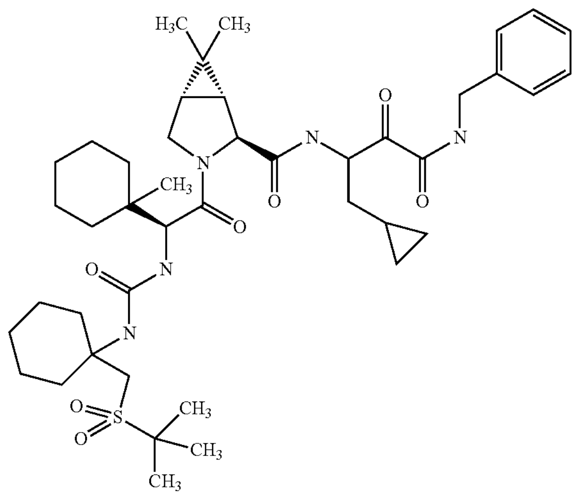 | 796.0908 | 796.2 | A |
| 694 | 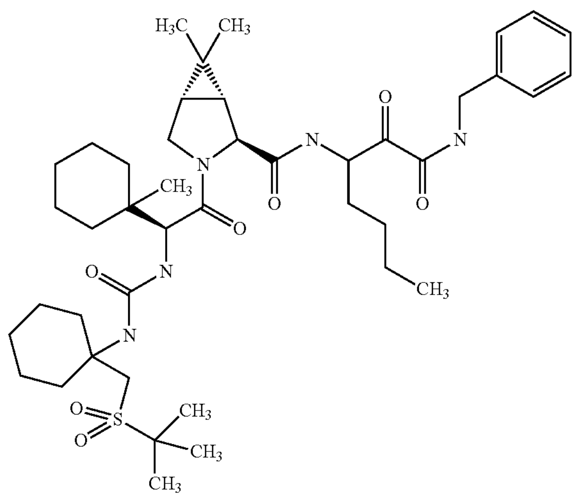 | 798.1067 | 798.2 | A |
| 695 | 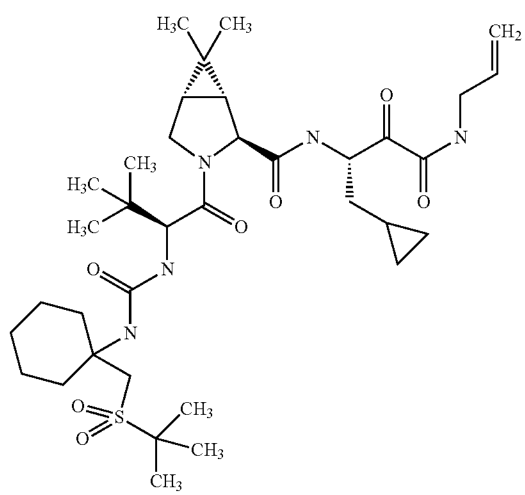 | 705.9649 | | 5 |

TABLE 3A-continued

| Compound # | structure | mol weight structure | Select LC-MS Data (M + H) | Ki* Range |
|---|---|---|---|---|
| 696 | 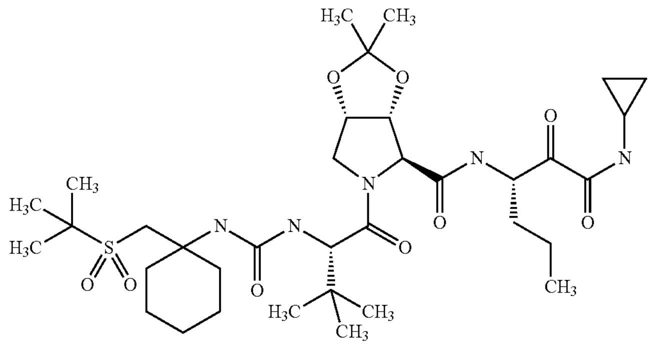 | 725.9526 | 726.4 | A |
| 697 | 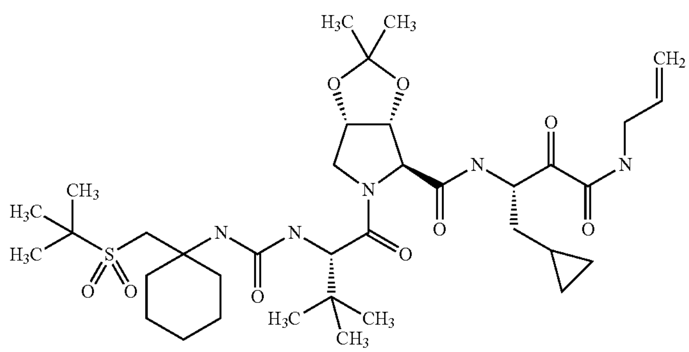 | 737.9637 | 738.4 | A |
| 698 | 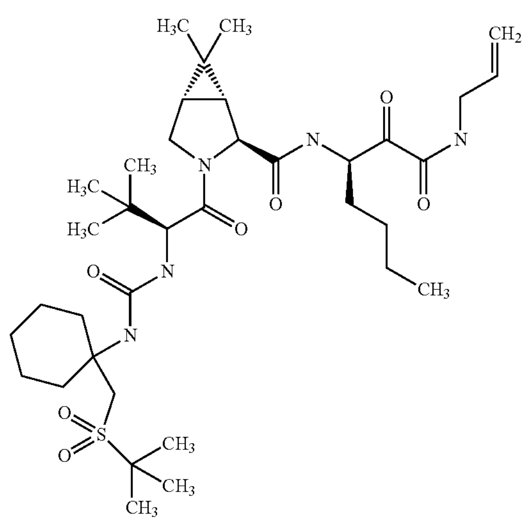 | 707.9809 | 708.4 | B |

TABLE 3A-continued

| Compound # | structure | mol weight structure | Select LC-MS Data (M + H) | Ki* Range |
|---|---|---|---|---|
| 699 | 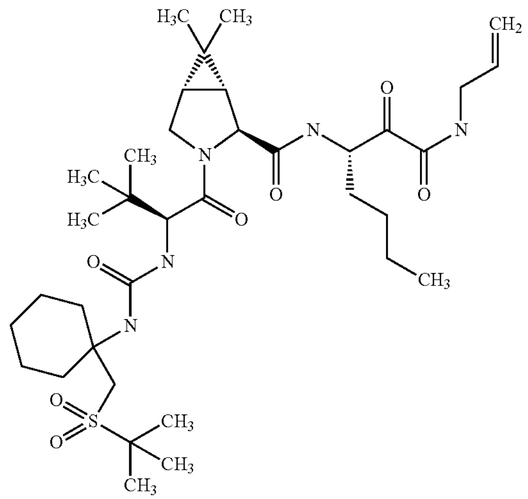 | 707.9809 | 708.4 | A |
| 700 | 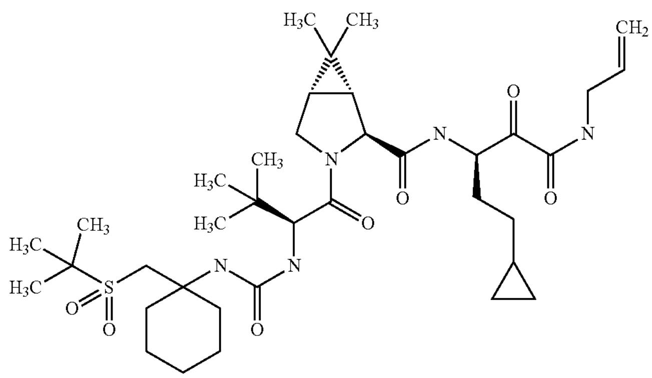 | 719.992 | | A |
| 701 | 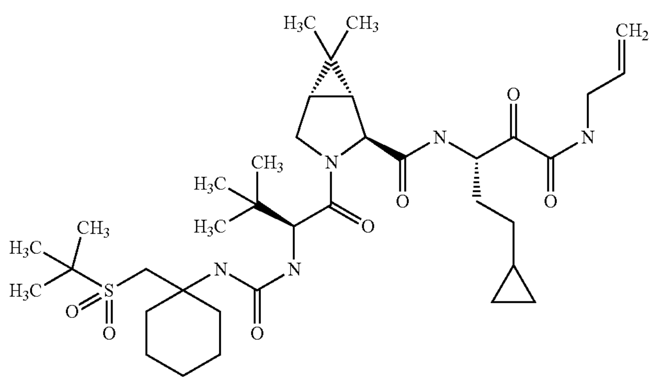 | 719.992 | | 6 |

TABLE 3A-continued

| Compound # | structure | mol weight structure | Select LC-MS Data (M + H) | Ki* Range |
|---|---|---|---|---|
| 702 | 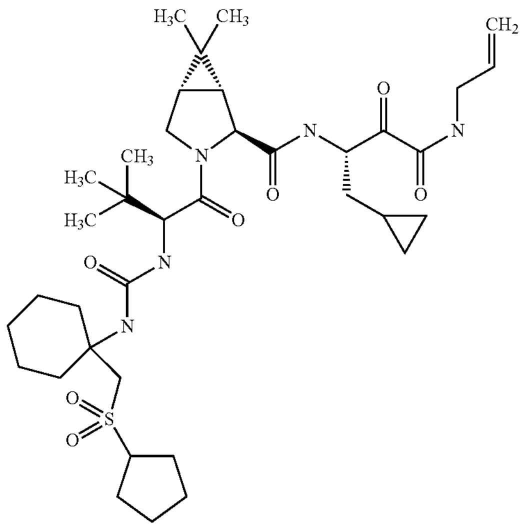 | 717.9761 | 718.60 | A |
| 703 | 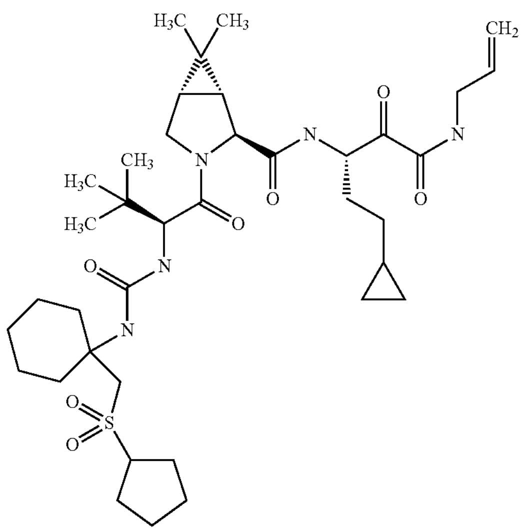 | 732.0032 | 732.6 | A |
| 704 | 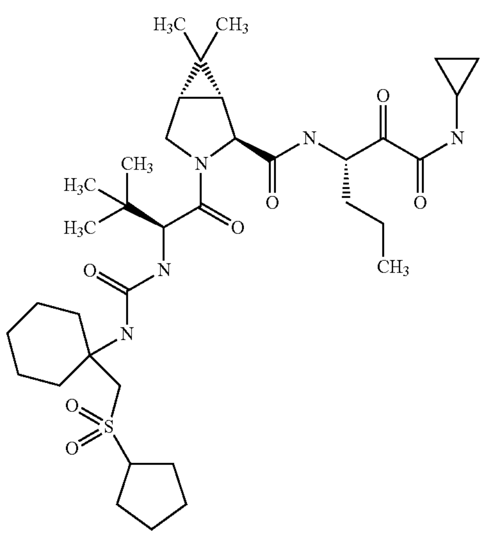 | 705.9649 | 706.6 | A |

TABLE 3A-continued

| Compound # | structure | mol weight structure | Select LC-MS Data (M + H) | Ki* Range |
|---|---|---|---|---|
| 705 | 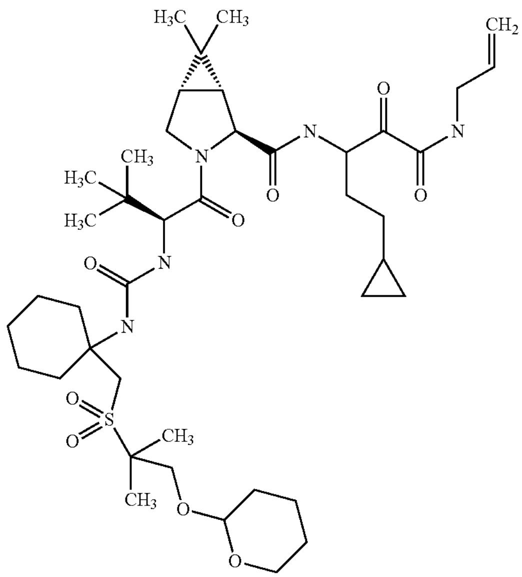 | 820.1103 | | A |
| 706 | 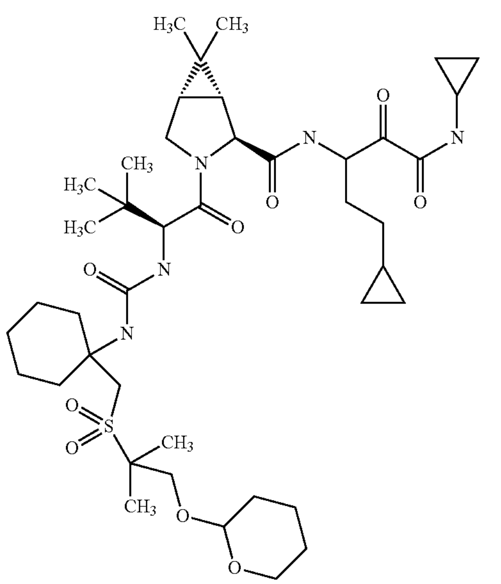 | 820.1103 | | A |

TABLE 3A-continued
| Compound # | structure | mol weight structure | Select LC-MS Data (M + H) | Ki* Range |
|---|---|---|---|---|
| 707 | 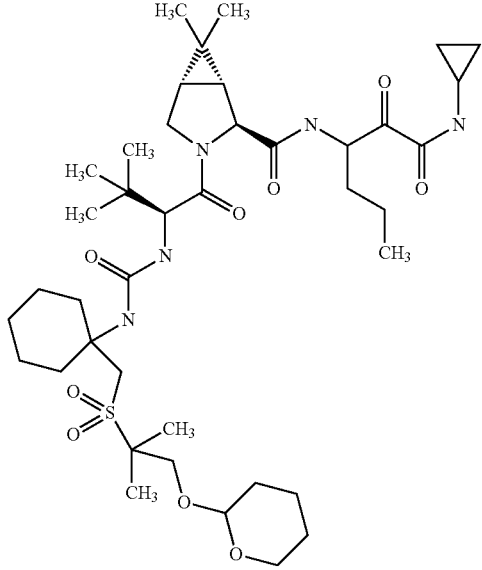 | 794.0721 | | A |
| 708 | 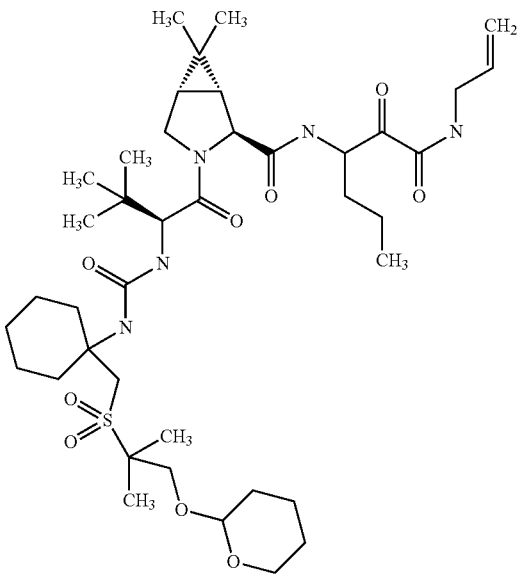 | 794.0721 | | A |

TABLE 3A-continued
| Compound # | structure | mol weight structure | Select LC-MS Data (M + H) | Ki* Range |
|---|---|---|---|---|
| 709 | 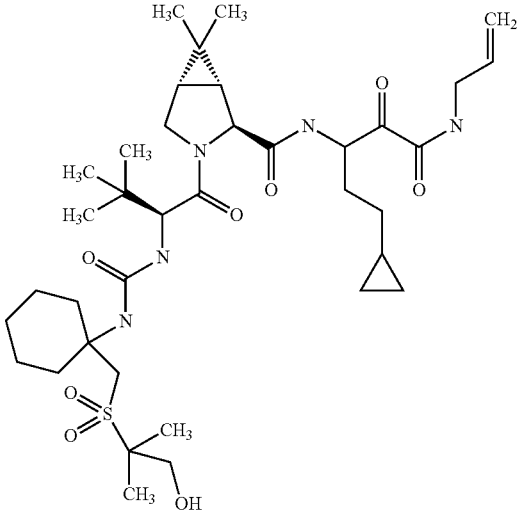 | 735.9914 | | A |
| 710 | 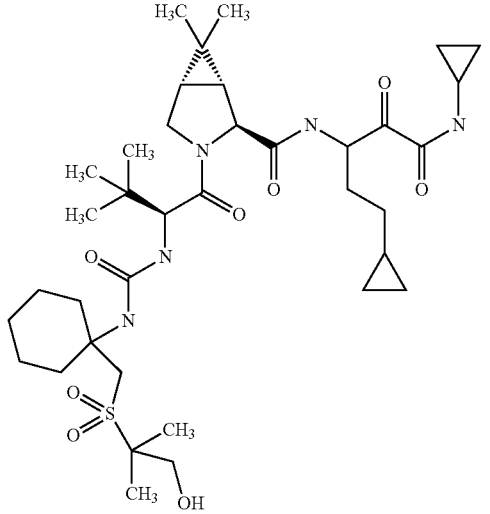 | 735.9914 | | A |
| 711 | 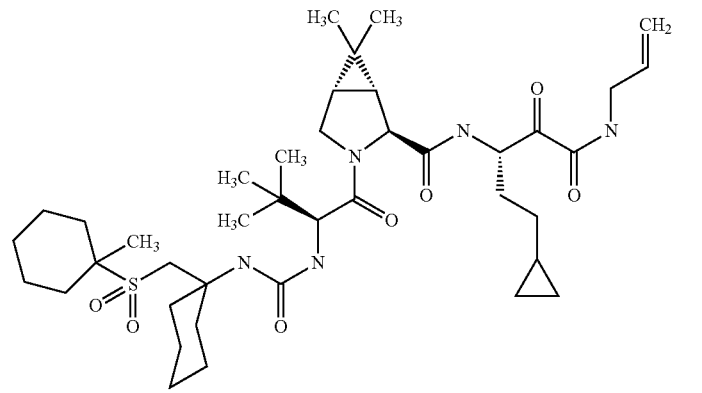 | 760.0574 | | A |

TABLE 3A-continued

| Compound # | structure | mol weight structure | Select LC-MS Data (M + H) | Ki* Range |
|---|---|---|---|---|
| 712 | 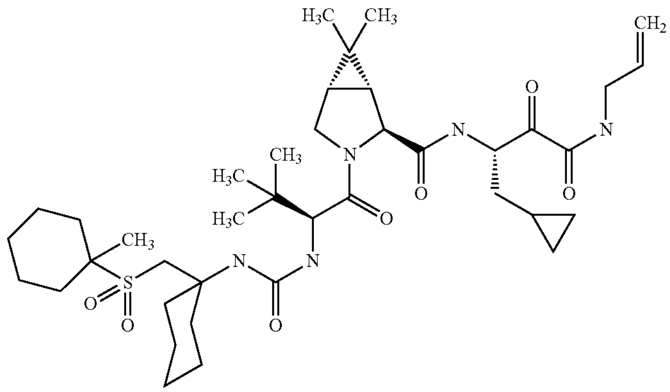 | 746.0303 | | A |
| 713 | 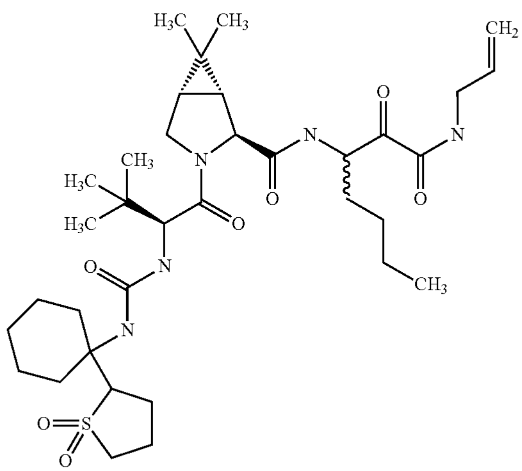 | 691.9378 | 692.2 | B |
| 714 | 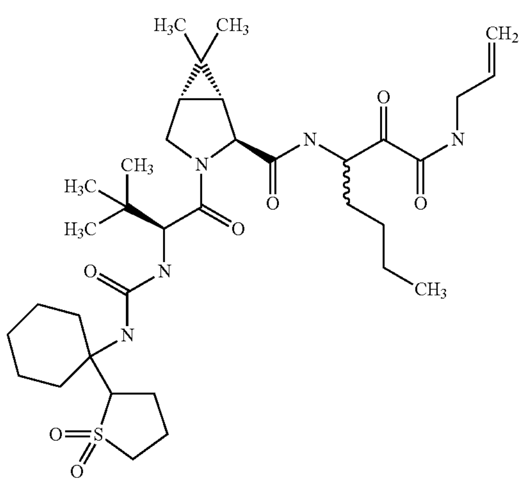 | 691.9378 | 692.2 | A |

TABLE 3A-continued

| Compound # | structure | mol weight structure | Select LC-MS Data (M + H) | Ki* Range |
|---|---|---|---|---|
| 715 | 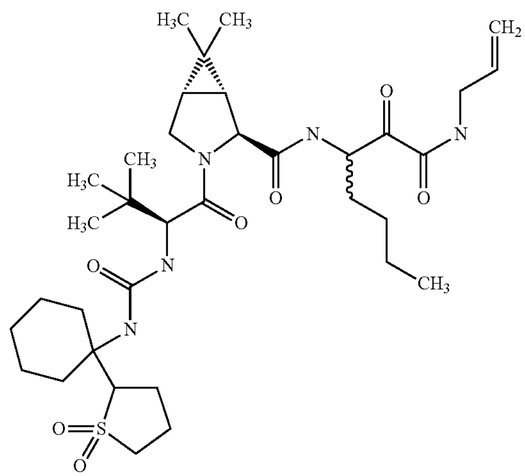 | 691.9378 | 692.2 | A |
| 716 | 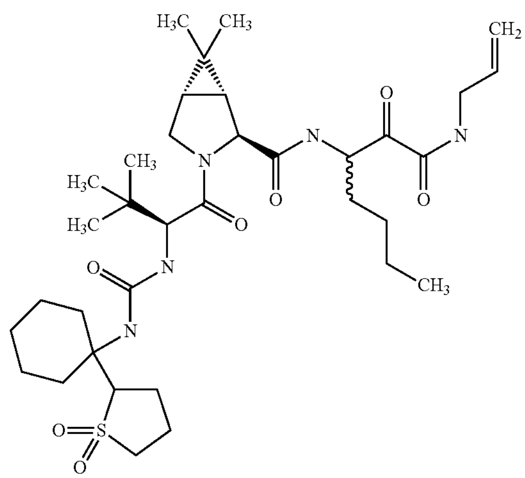 | 691.9378 | 692.2 | A |
| 717 | 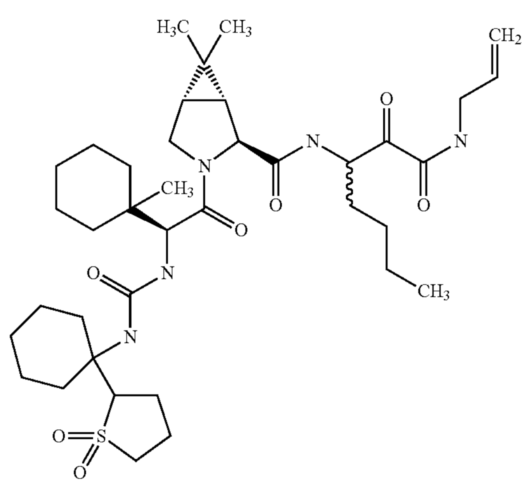 | 732.0032 | 732.2 | B |

TABLE 3A-continued

| Compound # | structure | mol weight structure | Select LC-MS Data (M + H) | Ki* Range |
|---|---|---|---|---|
| 718 | 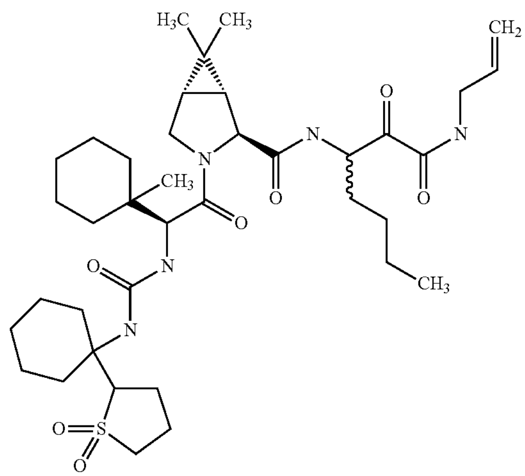 | 732.0032 | 732.2 | B |
| 719 | 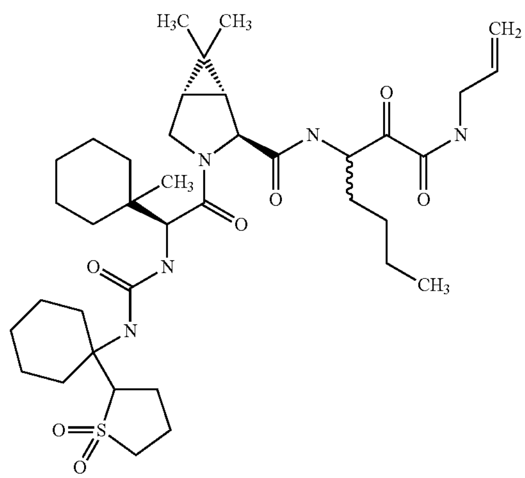 | 732.0032 | 732.2 | A |
| 720 | 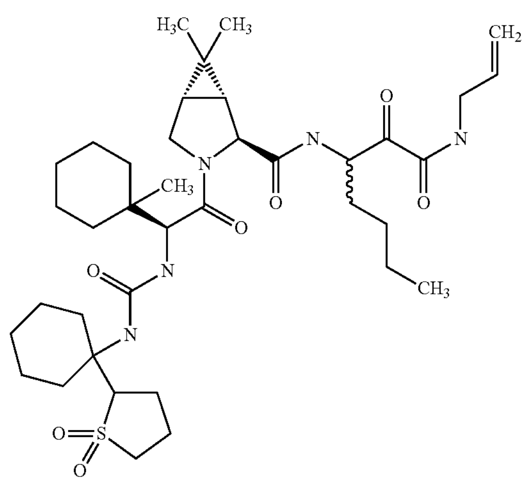 | 732.0032 | 732.2 | A |

TABLE 3A-continued

| Compound # | structure | mol weight structure | Select LC-MS Data (M + H) | Ki* Range |
| --- | --- | --- | --- | --- |
| 721 | 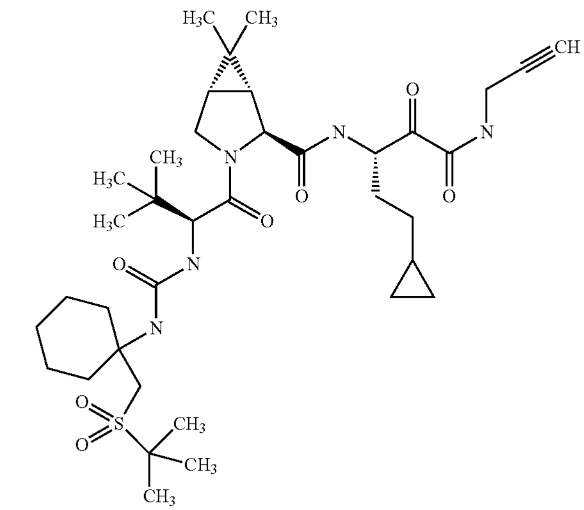 | 717.9761 | 718.1 | A |
| 722 | 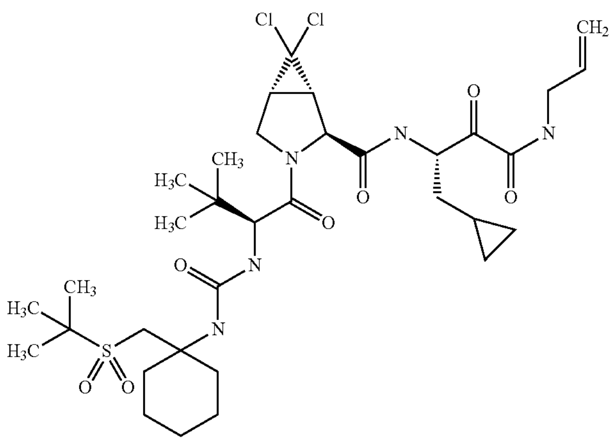 | 746.8008 | | A |
| 723 | 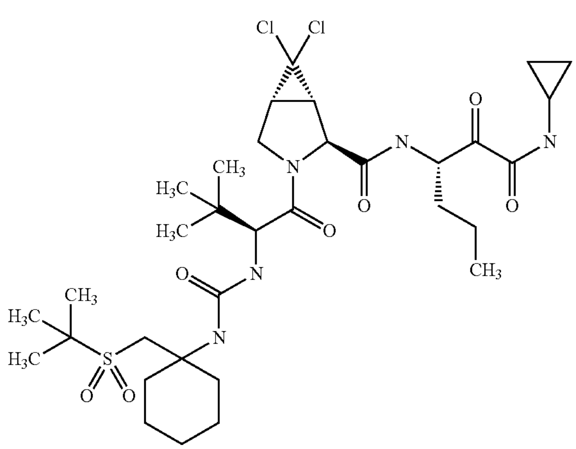 | 734.7897 | | A |

TABLE 3A-continued

| Compound # | structure | mol weight structure | Select LC-MS Data (M + H) | Ki* Range |
|---|---|---|---|---|
| 724 | 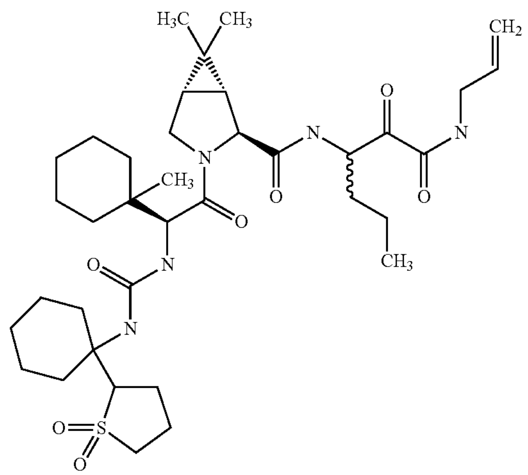 | 717.9761 | 718.2 | B |
| 725 | 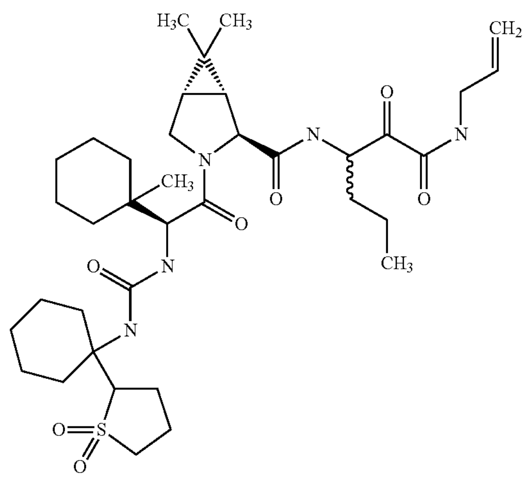 | 717.9761 | 718.2 | A |
| 726 | 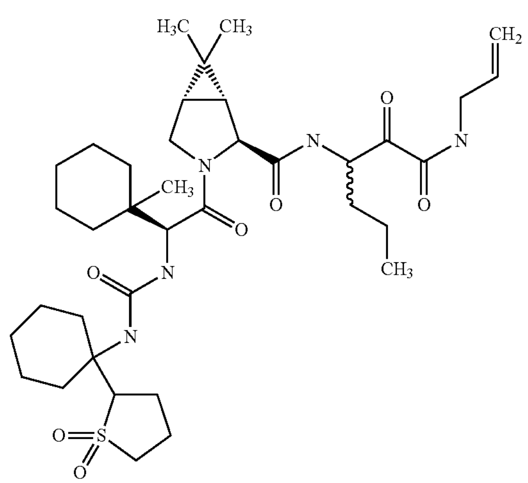 | 717.9761 | 718.2 | A |

TABLE 3A-continued

| Compound # | structure | mol weight structure | Select LC-MS Data (M + H) | Ki* Range |
|---|---|---|---|---|
| 727 | 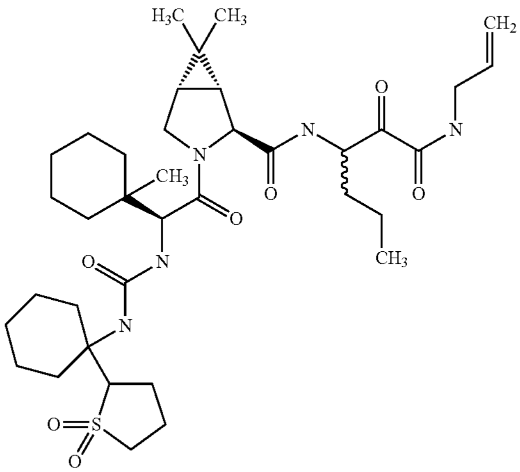 | 717.9761 | 718.2 | A |
| 728 | 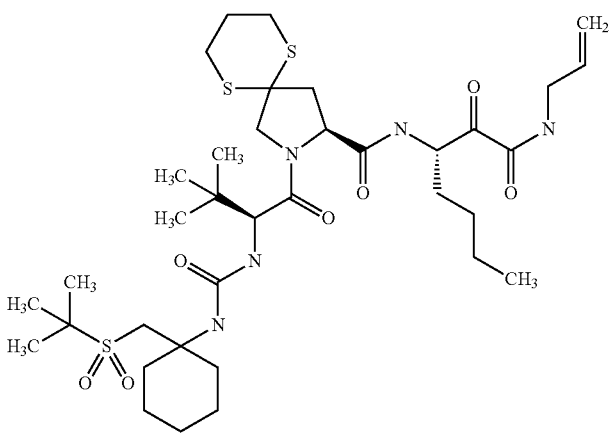 | 772.1089 | | A |
| 729 | 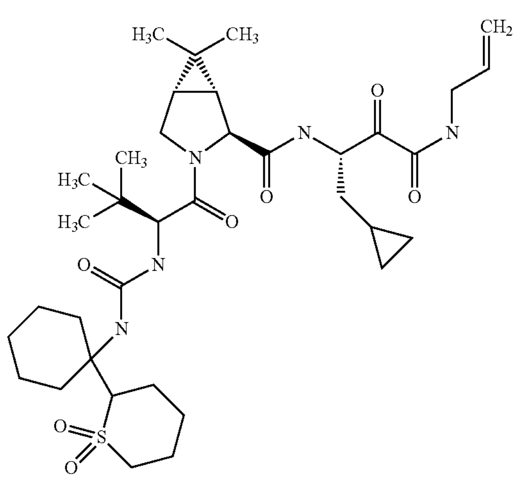 | 703.949 | 704.2 | A |

TABLE 3A-continued

| Compound # | structure | mol weight structure | Select LC-MS Data (M + H) | Ki* Range |
|---|---|---|---|---|
| 730 | 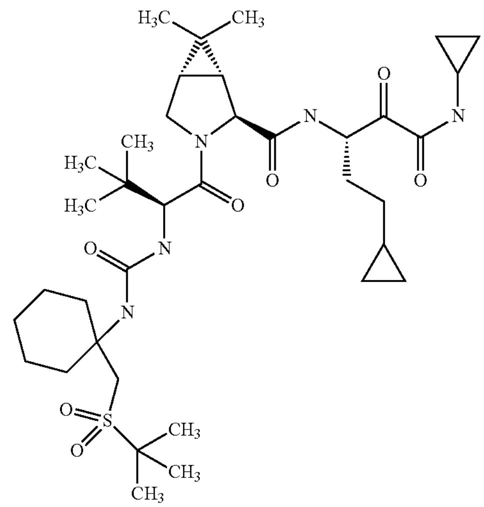 | 719.992 | | 5.6 |
| 731 | 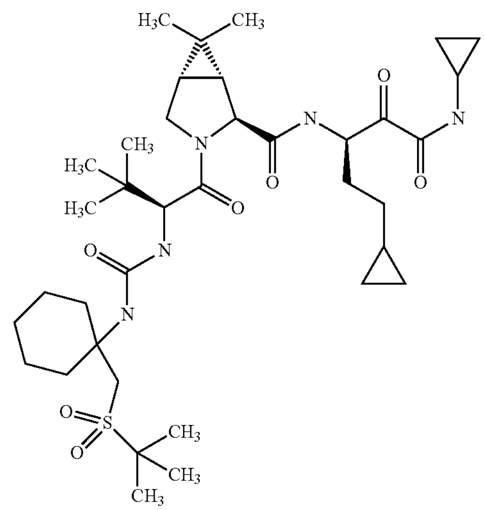 | 719.992 | | 64 |
| 732 | 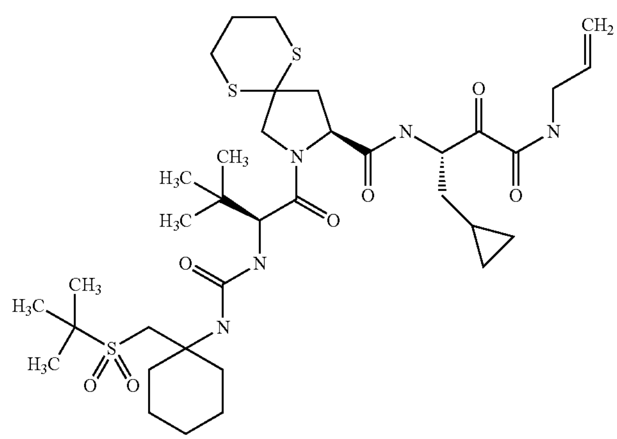 | 770.0929 | 770.2 | A |

TABLE 3A-continued

| Compound # | structure | mol weight structure | Select LC-MS Data (M + H) | Ki* Range |
|---|---|---|---|---|
| 733 | 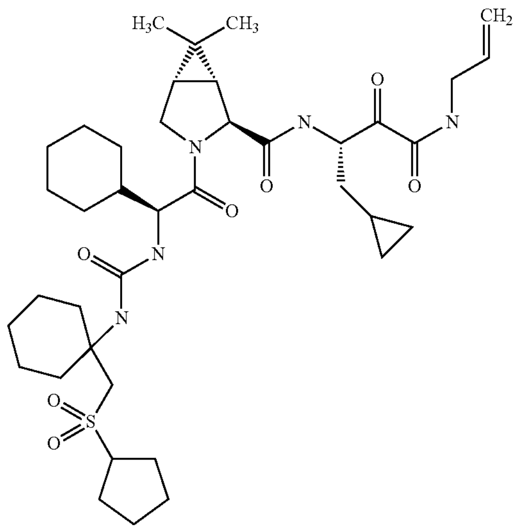 | 744.0143 | 744.3 | A |
| 734 | 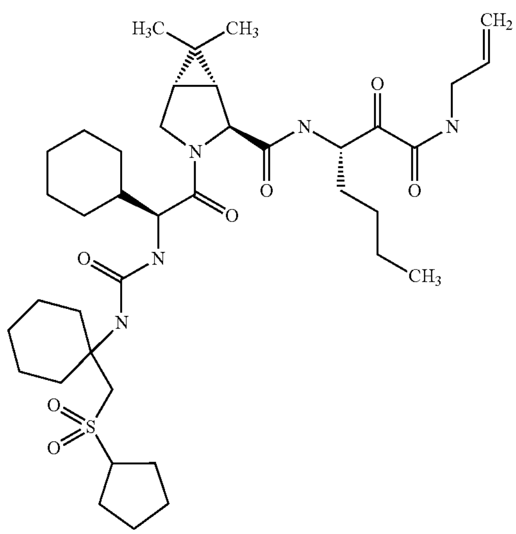 | 746.0303 | 746.2 | A |
| 735 | 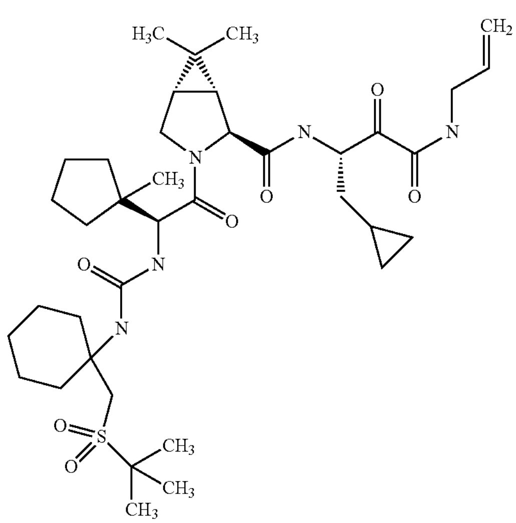 | 732.0032 | 732.4 | A |

TABLE 3A-continued

| Compound # | structure | mol weight structure | Select LC-MS Data (M + H) | Ki* Range |
|---|---|---|---|---|
| 736 | 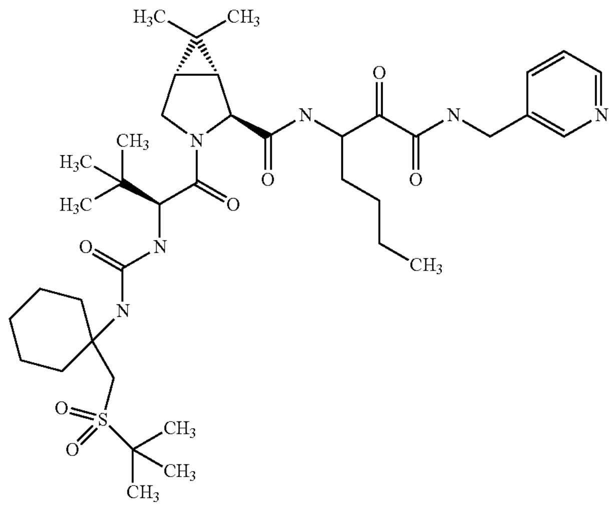 | 759.029 | 759.4 | A |
| 737 | 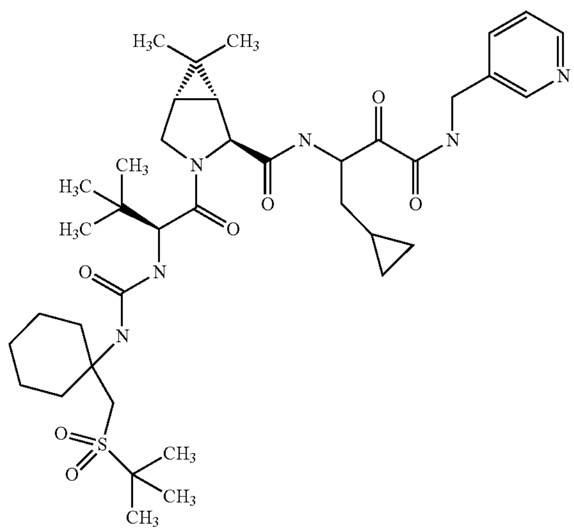 | 757.0131 | 757.4 | A |
| 738 | 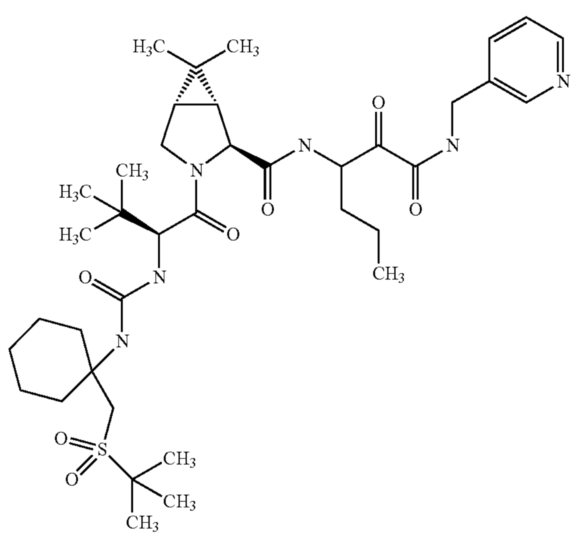 | 745.0019 | 745.4 | A |

TABLE 3A-continued

| Compound # | structure | mol weight structure | Select LC-MS Data (M + H) | Ki* Range |
|---|---|---|---|---|
| 739 | 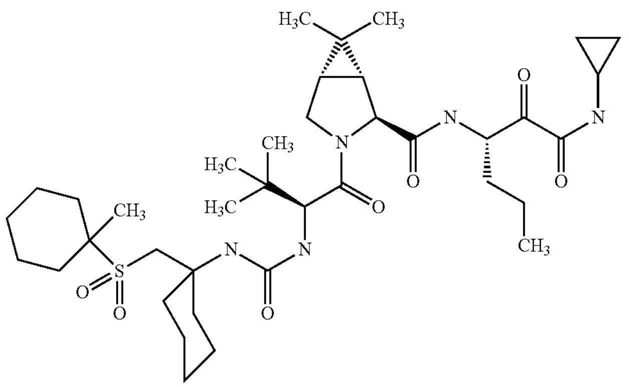 | 734.0191 | 734.3 | 18 |
| 740 | 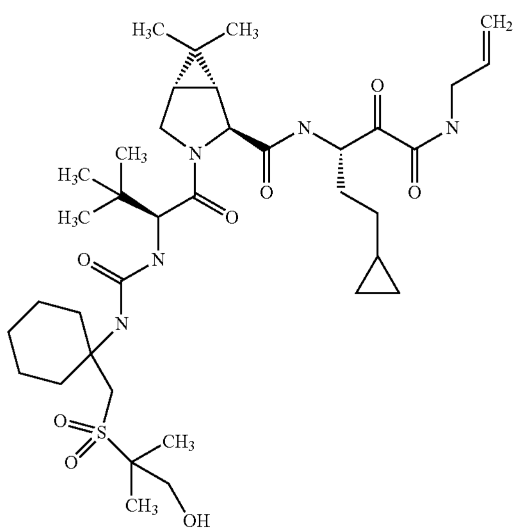 | 735.9914 | | A |
| 741 | 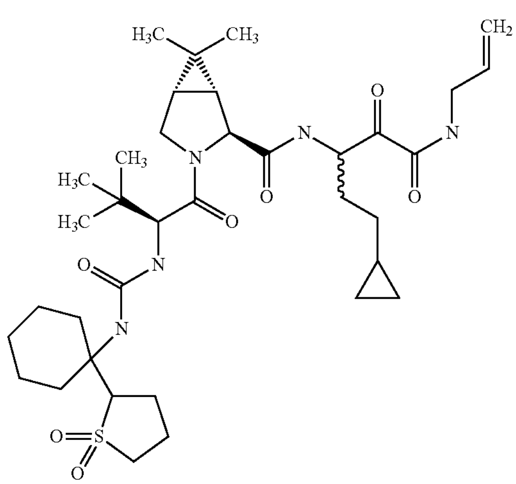 | 703.949 | 704.2 | A |

TABLE 3A-continued

| Compound # | structure | mol weight structure | Select LC-MS Data (M + H) | Ki* Range |
|---|---|---|---|---|
| 742 | 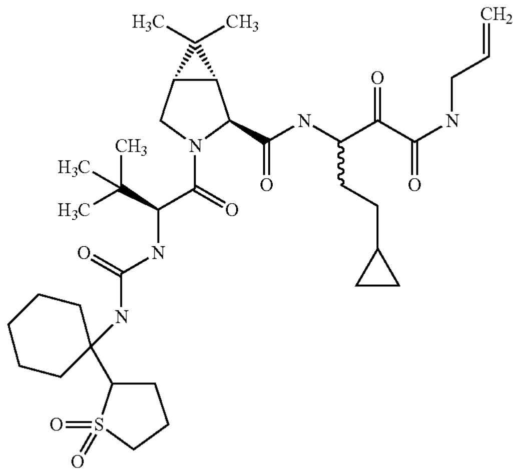 | 703.949 | 704.2 | A |
| 743 | 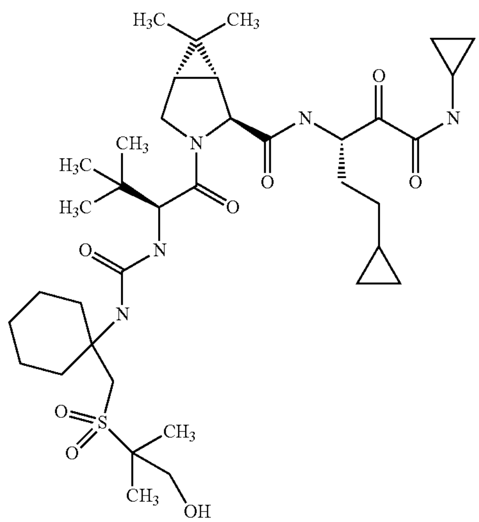 | 735.9914 | | A |
| 744 | 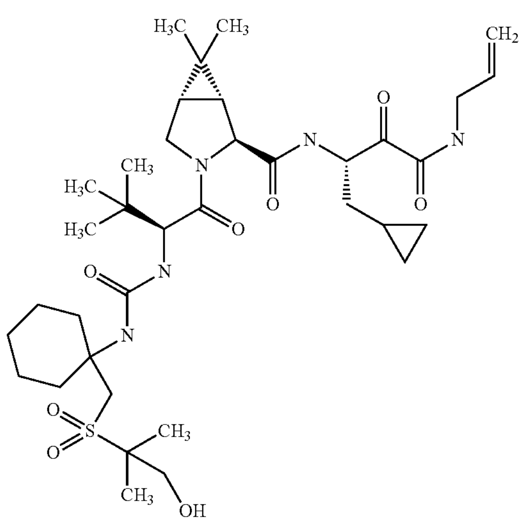 | 721.9643 | | A |

TABLE 3A-continued

| Compound # | structure | mol weight structure | Select LC-MS Data (M + H) | Ki* Range |
|---|---|---|---|---|
| 745 | 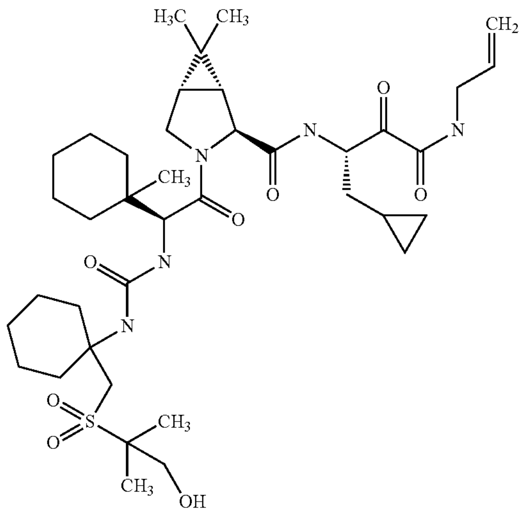 | 762.0297 | | A |
| 746 | 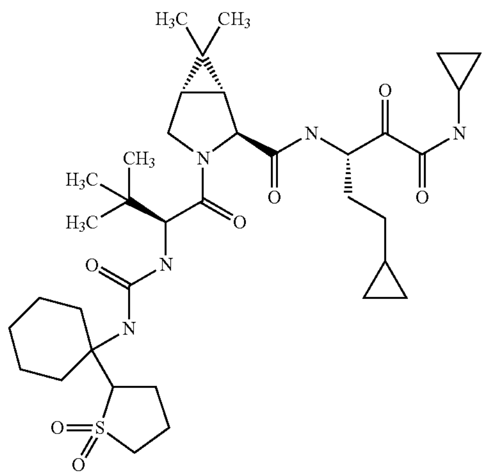 | 703.949 | 704.2 | A |
| 747 | 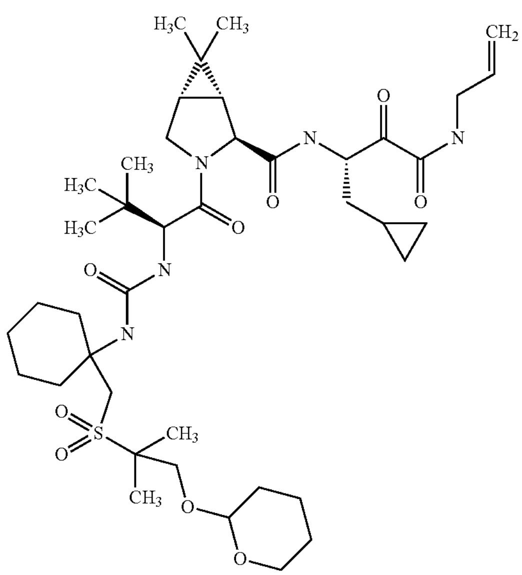 | 806.0832 | | A |

TABLE 3A-continued
| Compound # | structure | mol weight structure | Select LC-MS Data (M + H) | Ki* Range |
|---|---|---|---|---|
| 748 | 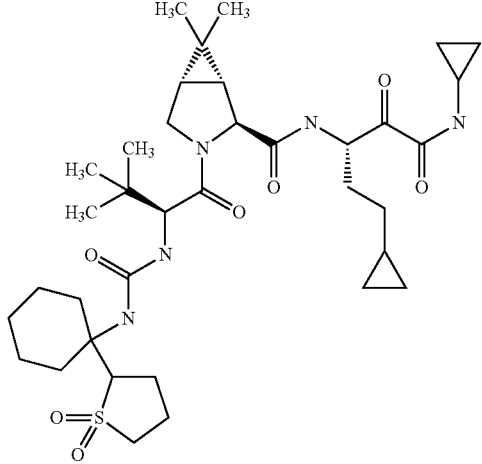 | 703.949 | 704.2 | A |
| 749 | 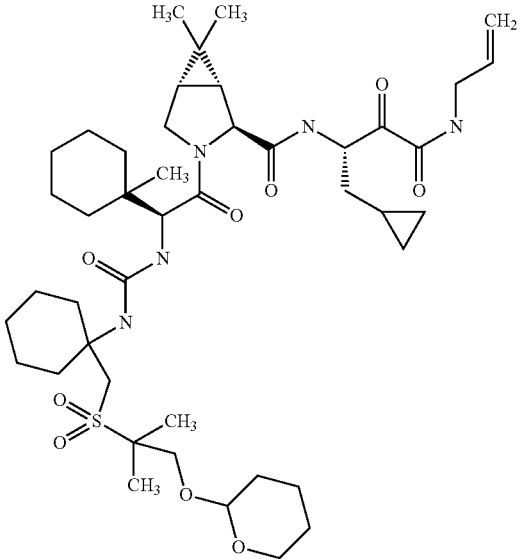 | 846.1486 | | A |
| 750 | 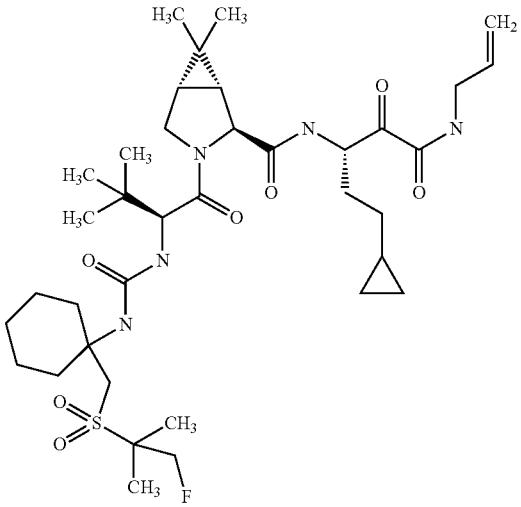 | 737.9825 | | A |

TABLE 3A-continued

| Compound # | structure | mol weight structure | Select LC-MS Data (M + H) | Ki* Range |
|---|---|---|---|---|
| 751 | 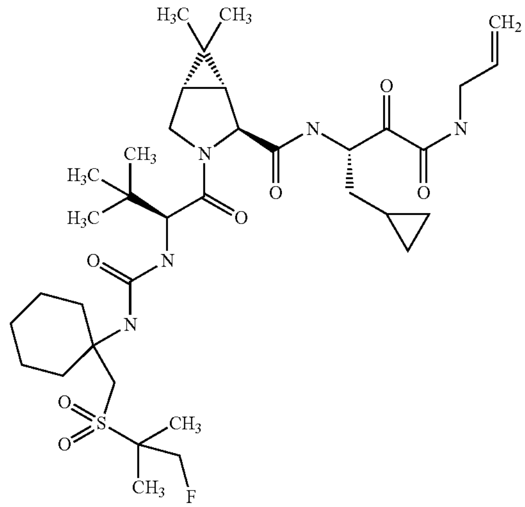 | 723.9554 | | A |
| 752 | 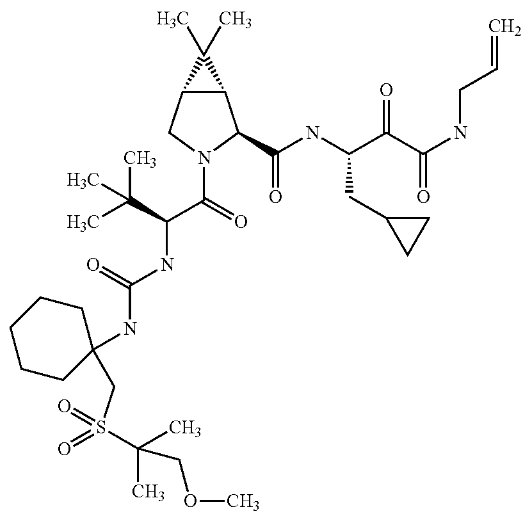 | 735.9914 | | A |
| 753 | 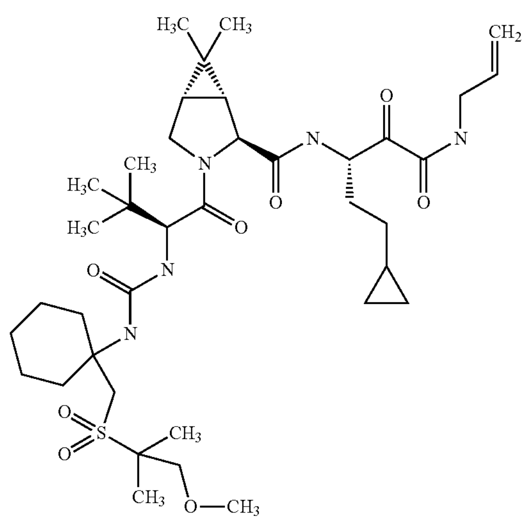 | 750.0185 | | A |

TABLE 3A-continued

| Compound # | structure | mol weight structure | Select LC-MS Data (M + H) | Ki* Range |
|---|---|---|---|---|
| 754 | 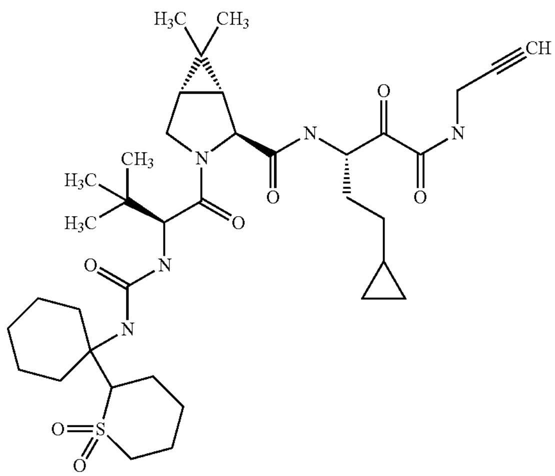 | 715.9601 | 716.1 | A |
| 755 | 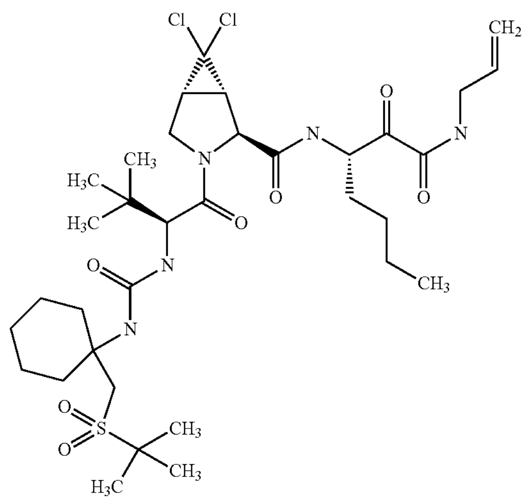 | 748.8168 | 748.1 | A |
| 756 | 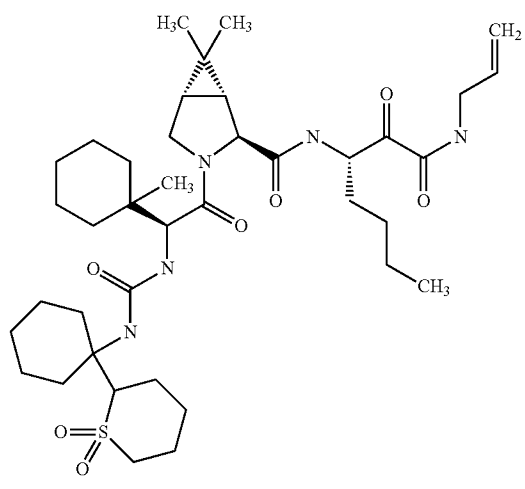 | 746.0303 | 746.1 | A |

TABLE 3A-continued

| Compound # | structure | mol weight structure | Select LC-MS Data (M + H) | Ki* Range |
|---|---|---|---|---|
| 757 | 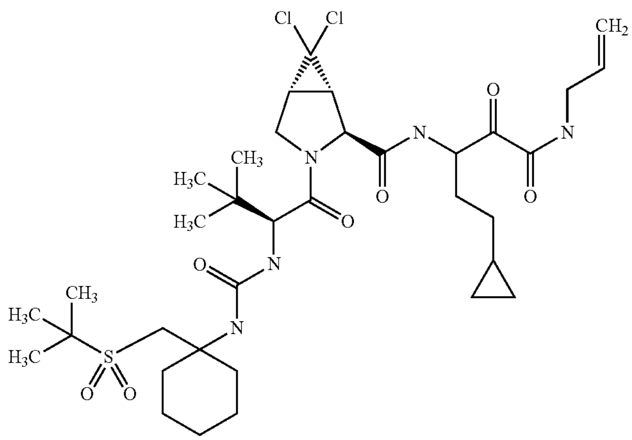 | 760.8279 | 760.1 | A |
| 758 | 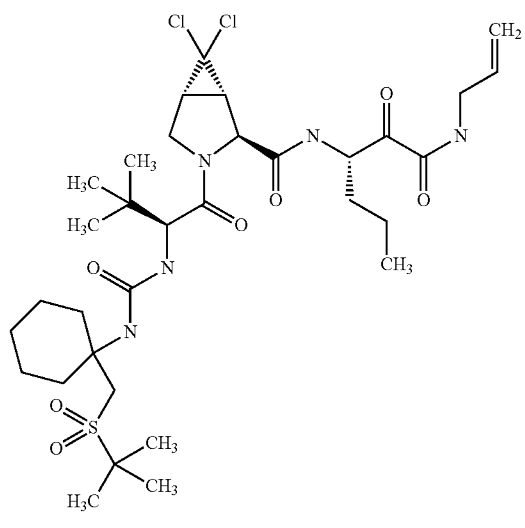 | 734.7897 | 734.1 | A |
| 759 | 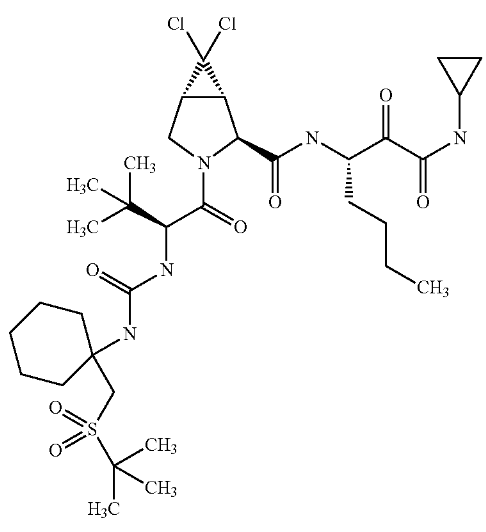 | 748.8168 | 748.1 | A |

TABLE 3A-continued

| Compound # | structure | mol weight structure | Select LC-MS Data (M + H) | Ki* Range |
|---|---|---|---|---|
| 760 | 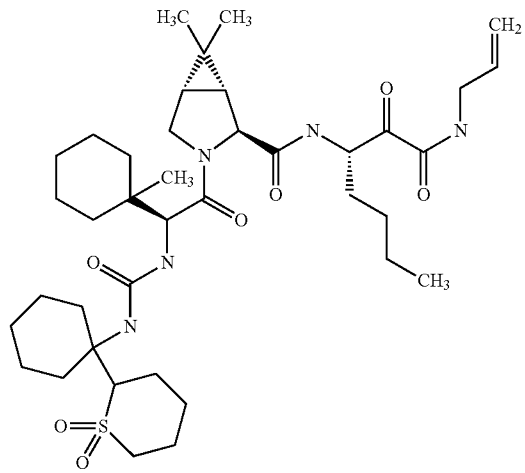 | | 746.0303 | A |
| 761 | 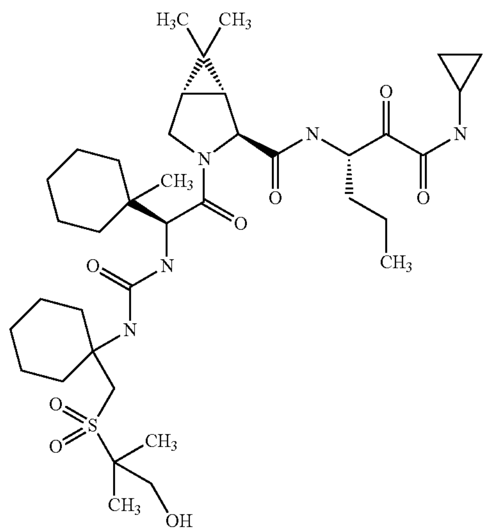 | | 750.0185 | A |
| 762 | 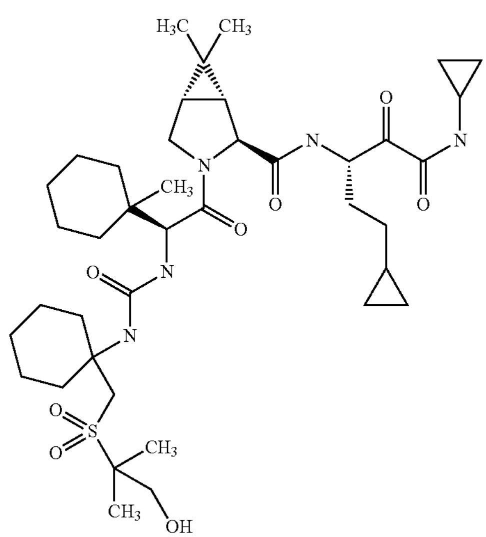 | | 776.0568 | A |

TABLE 3A-continued

| Compound # | structure | mol weight structure | Select LC-MS Data (M + H) | Ki* Range |
|---|---|---|---|---|
| 763 | 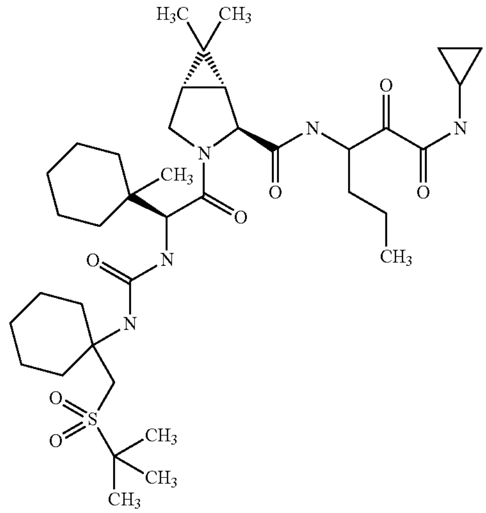 | 734.0191 | | B |
| 764 | 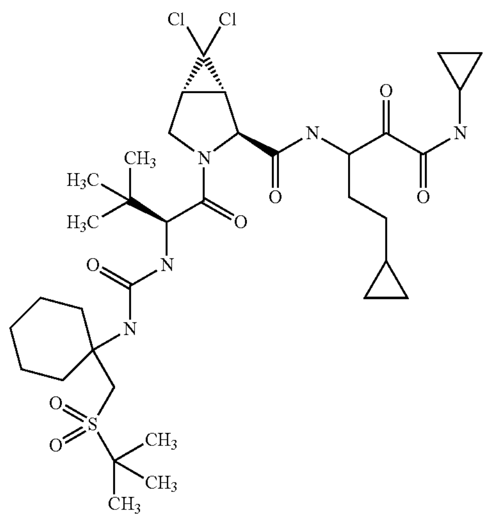 | 760.8279 | 760.1 | A |
| 765 | 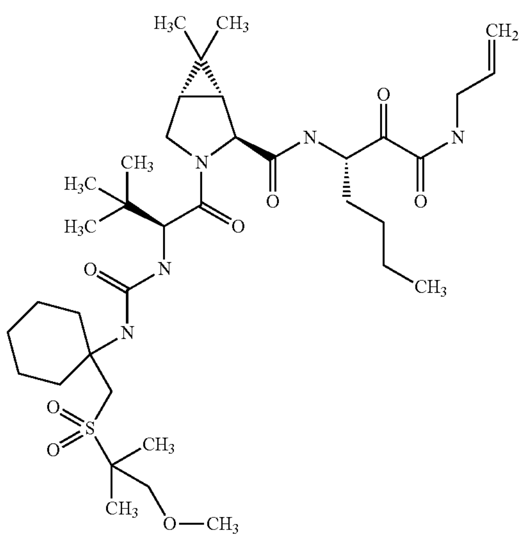 | 738.0074 | | A |

TABLE 3A-continued

| Compound # | structure | mol weight structure | Select LC-MS Data (M + H) | Ki* Range |
|---|---|---|---|---|
| 766 | 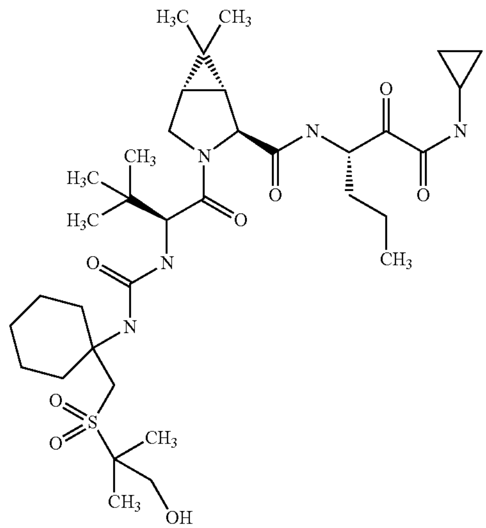 | 709.9532 | | A |
| 767 | 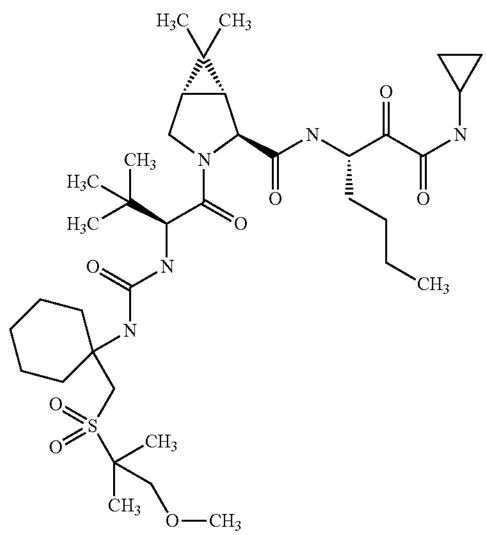 | 738.0074 | | A |
| 768 | 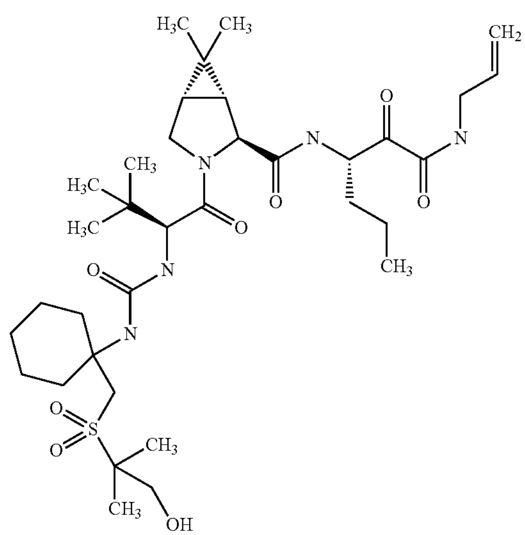 | 709.9532 | | A |

TABLE 3A-continued

| Compound # | structure | mol weight structure | Select LC-MS Data (M + H) | Ki* Range |
|---|---|---|---|---|
| 769 | 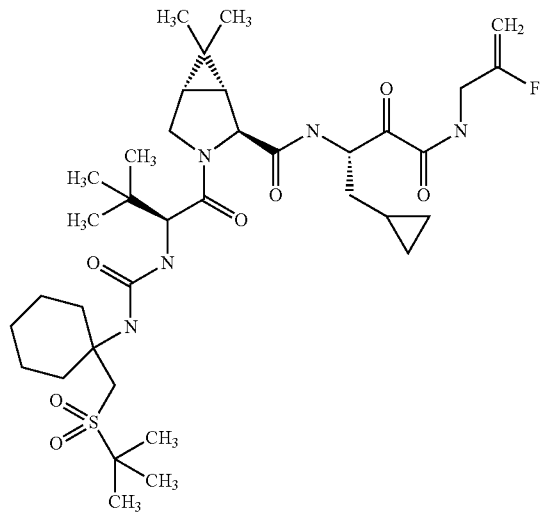 | 723.9554 | | A |
| 770 | 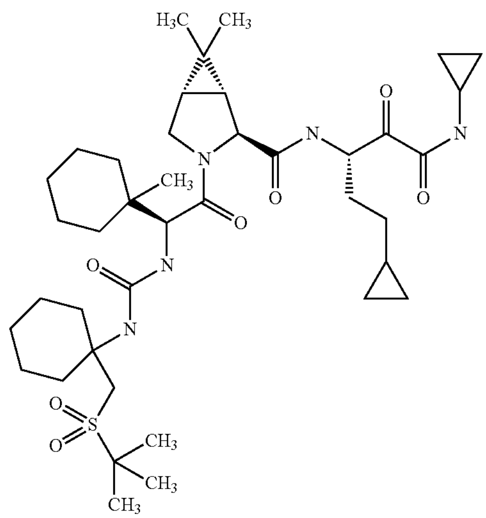 | 760.0574 | | A |
| 771 | 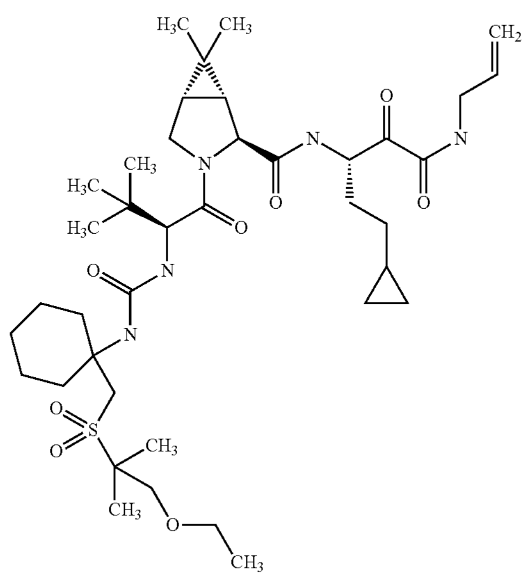 | 764.0456 | | A |

TABLE 3A-continued

| Compound # | structure | mol weight structure | Select LC-MS Data (M + H) | Ki* Range |
|---|---|---|---|---|
| 772 | 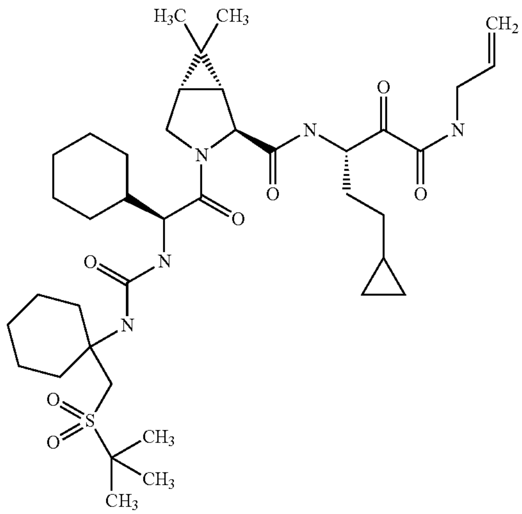 | 746.0303 | | A |
| 773 | 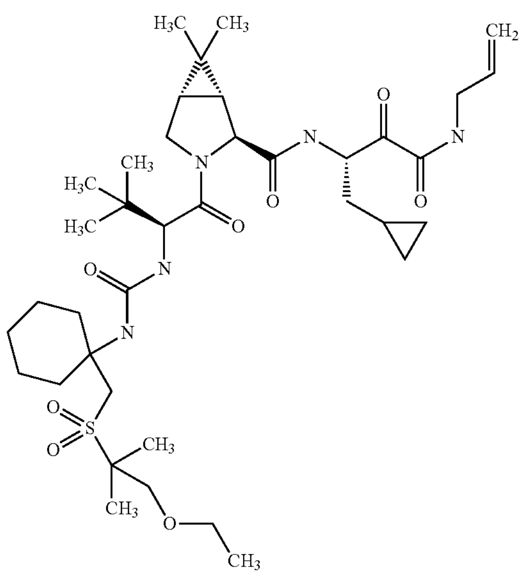 | 750.0185 | | A |

TABLE 3A-continued
| Compound # | structure | mol weight structure | Select LC-MS Data (M + H) | Ki* Range |
|---|---|---|---|---|
| 774 | 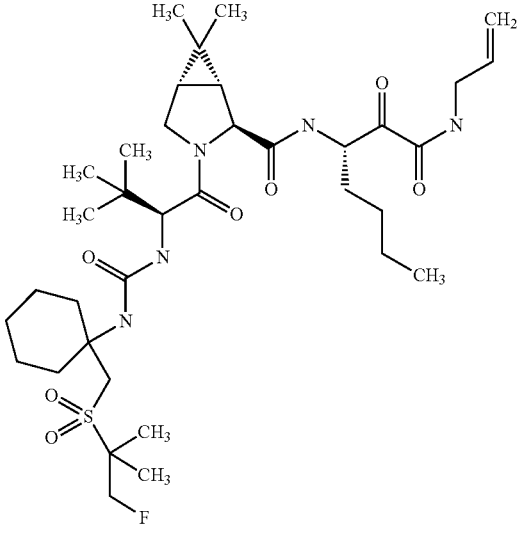 | | 725.9713 | A |
| 775 | 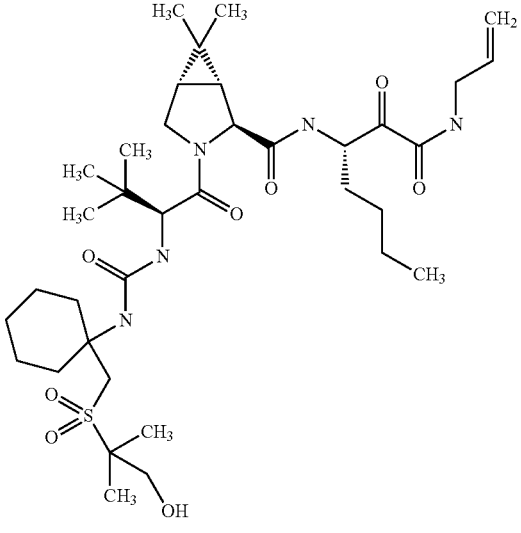 | | 723.9803 | A |

TABLE 3A-continued

| Compound # | structure | mol weight structure | Select LC-MS Data (M + H) | Ki* Range |
|---|---|---|---|---|
| 776 | 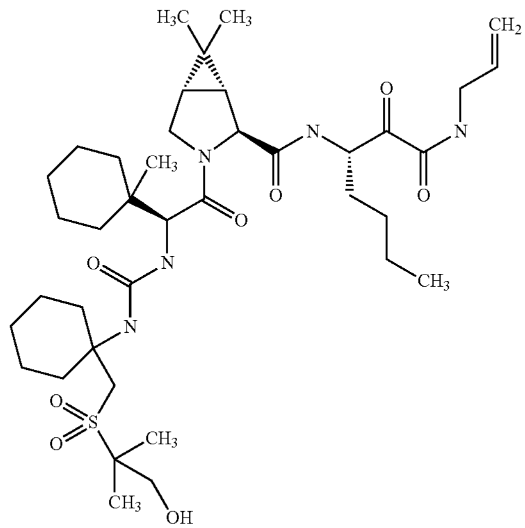 | 764.0456 | | A |
| 777 | 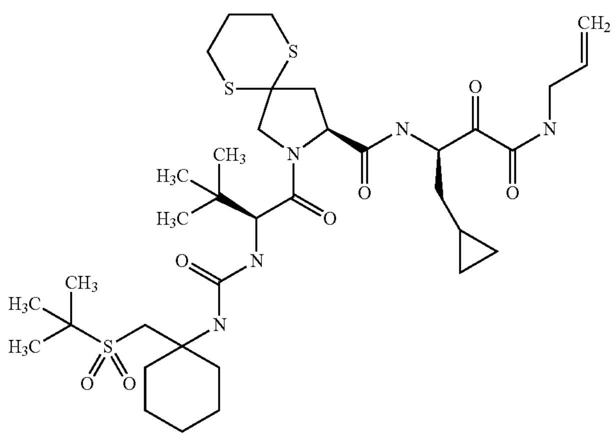 | 770.0929 | 770.2 | B |
| 778 | 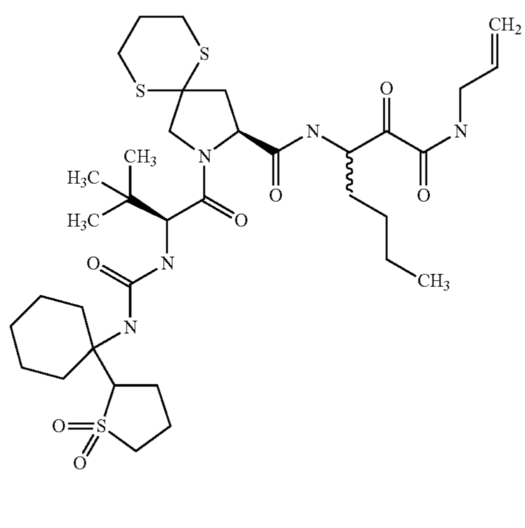 | 756.0658 | 756.1 | A |

TABLE 3A-continued

| Compound # | structure | mol weight structure | Select LC-MS Data (M + H) | Ki* Range |
|---|---|---|---|---|
| 779 | 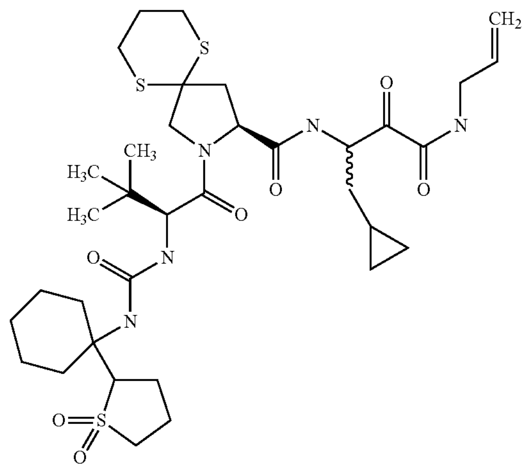 | 754.0499 | 754.1 | A |
| 780 | 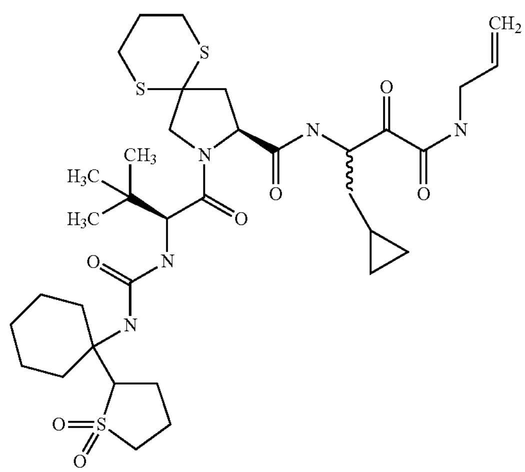 | 754.0499 | 754.1 | A |
| 781 | 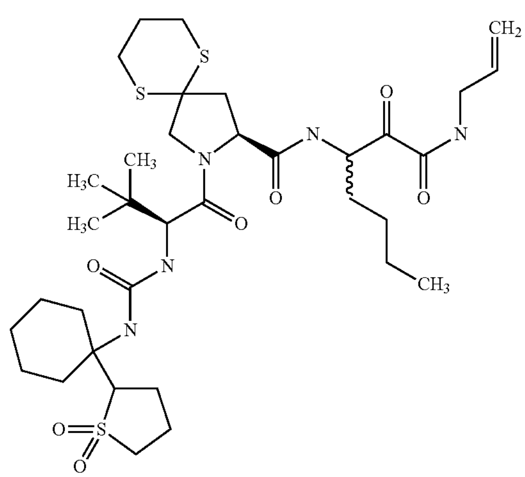 | 756.0658 | 756.1 | A |

TABLE 3A-continued

| Compound # | structure | mol weight structure | Select LC-MS Data (M + H) | Ki* Range |
|---|---|---|---|---|
| 782 | 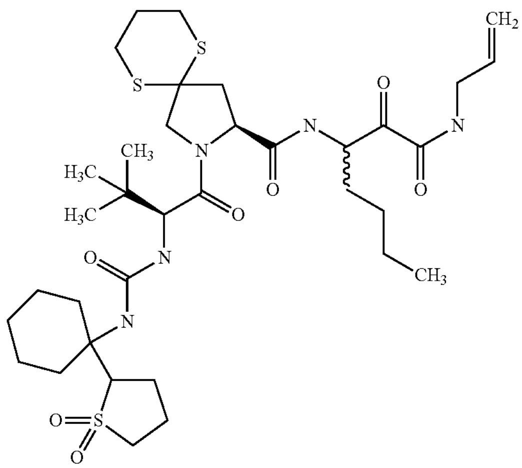 | 756.0658 | 756.1 | A |
| 783 | 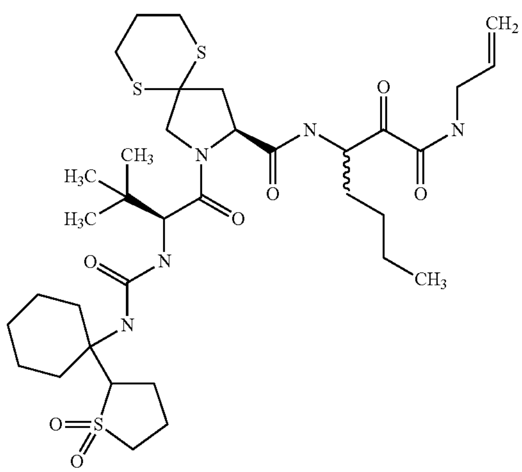 | 756.0658 | 756.1 | A |
| 784 | 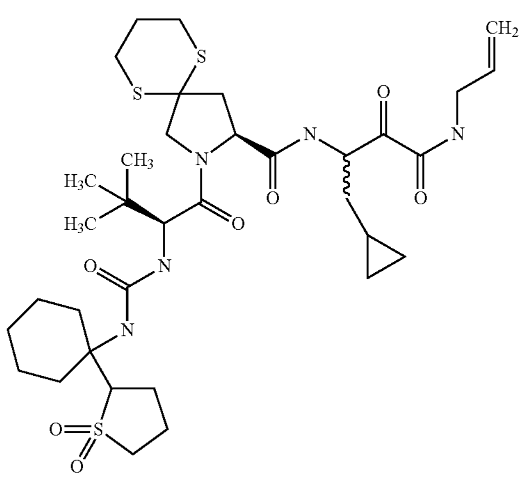 | 754.0499 | 754.1 | A |

TABLE 3A-continued

| Compound # | structure | mol weight structure | Select LC-MS Data (M + H) | Ki* Range |
|---|---|---|---|---|
| 785 | 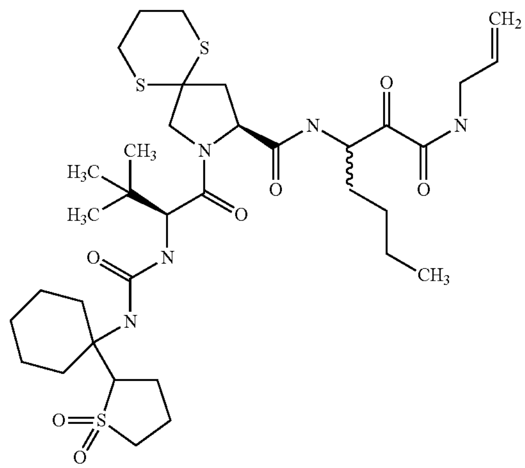 | 756.0658 | 756.1 | A |
| 786 | 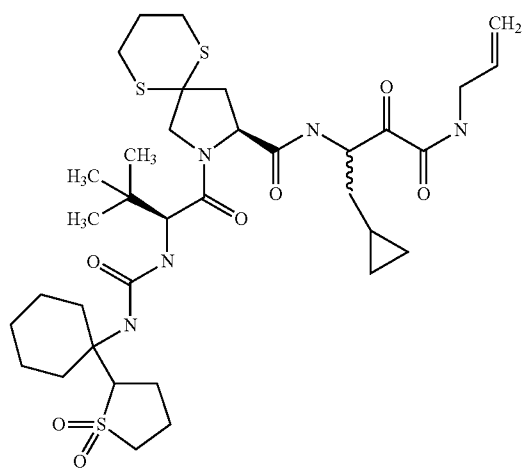 | 754.0499 | 754.1 | A |
| 787 | 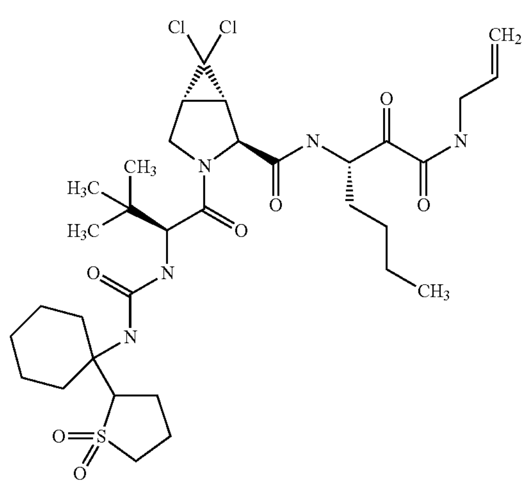 | 732.7737 | 732.1 | A |

TABLE 3A-continued

| Compound # | structure | mol weight structure | Select LC-MS Data (M + H) | Ki* Range |
|---|---|---|---|---|
| 788 | 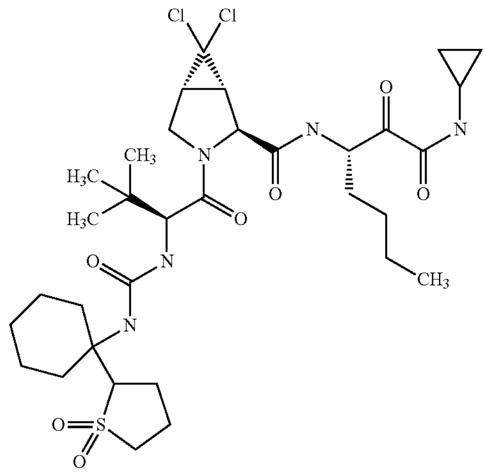 | 732.7737 | 732.1 | A |
| 789 | 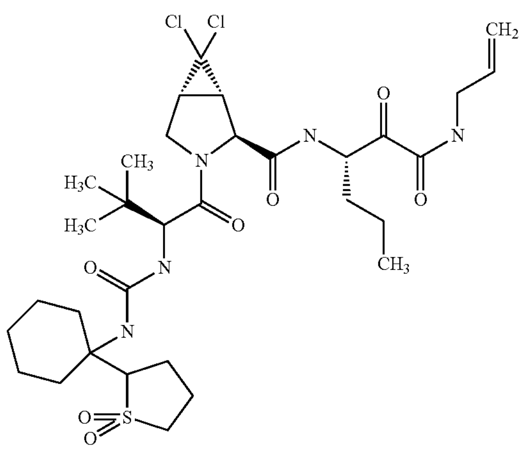 | 718.7466 | 718.2 | A |
| 790 | 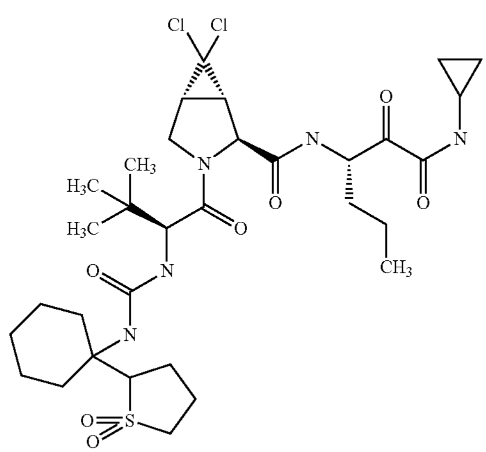 | 718.7466 | 718.2 | A |

TABLE 3A-continued

| Compound # | structure | mol weight structure | Select LC-MS Data (M + H) | Ki* Range |
|---|---|---|---|---|
| 791 | 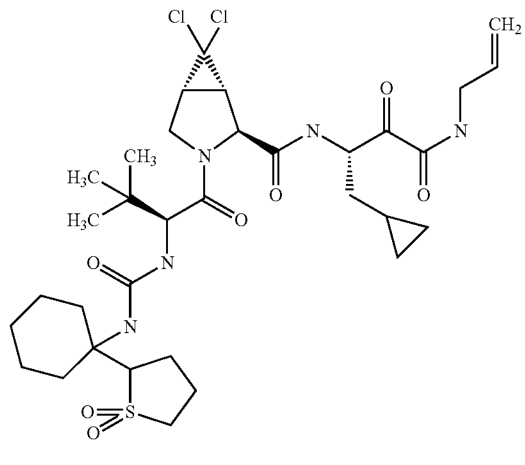 | 730.7578 | 730.2 | A |
| 792 | 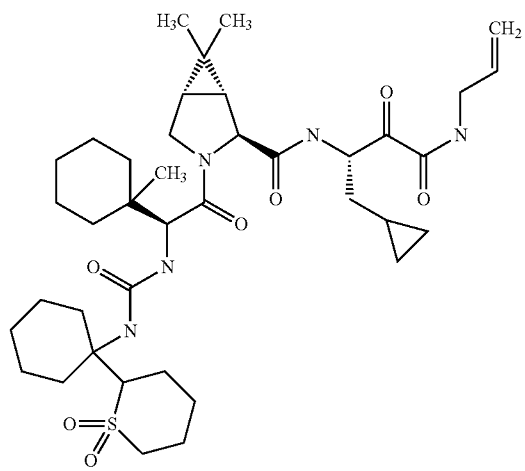 | 744.0143 | | A |
| 793 | 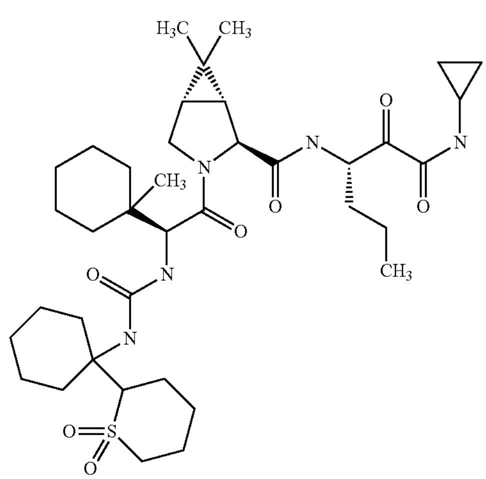 | 732.0032 | 732.1 | A |

TABLE 3A-continued

| Compound # | structure | mol weight structure | Select LC-MS Data (M + H) | Ki* Range |
|---|---|---|---|---|
| 794 | 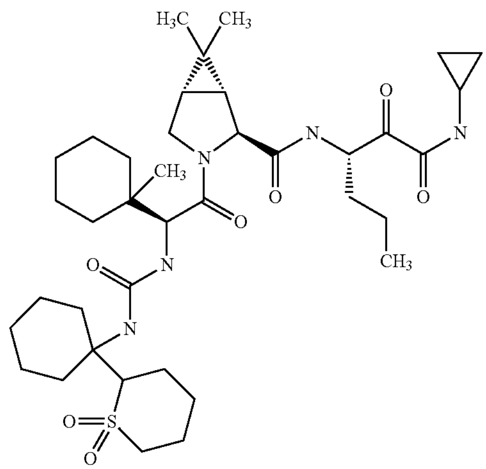 | 732.0032 | | A |
| 795 | 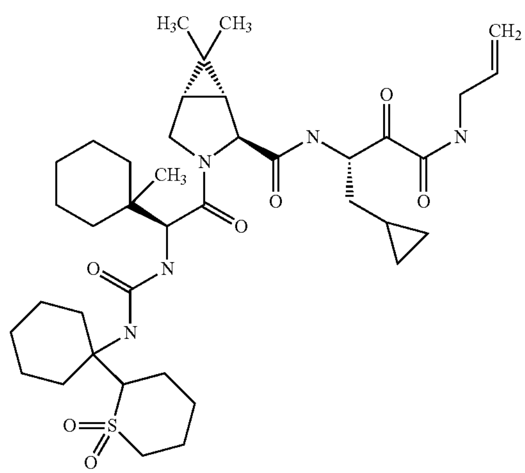 | 744.0143 | | A |
| 796 | 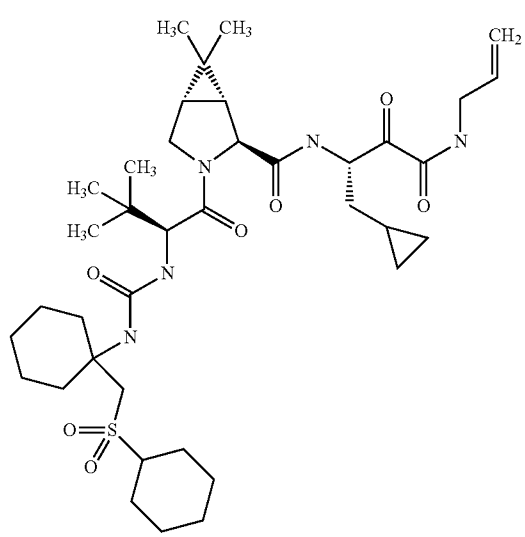 | 732.0032 | 732.1 | A |

TABLE 3A-continued

| Compound # | structure | mol weight structure | Select LC-MS Data (M + H) | Ki* Range |
|---|---|---|---|---|
| 797 | 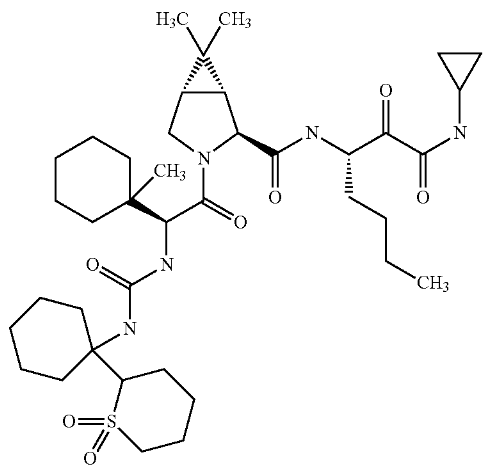 | 746.0303 | | A |
| 798 | 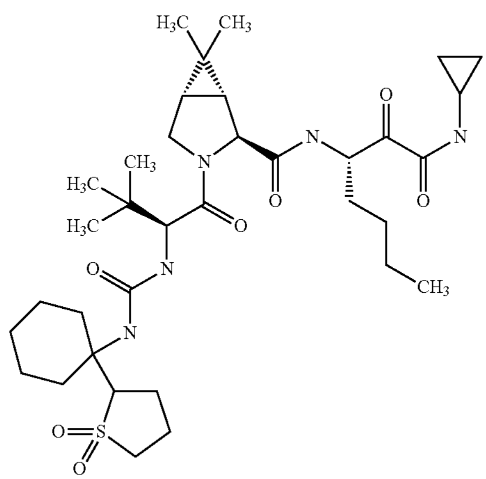 | 677.9108 | 678.1 | A |
| 799 | 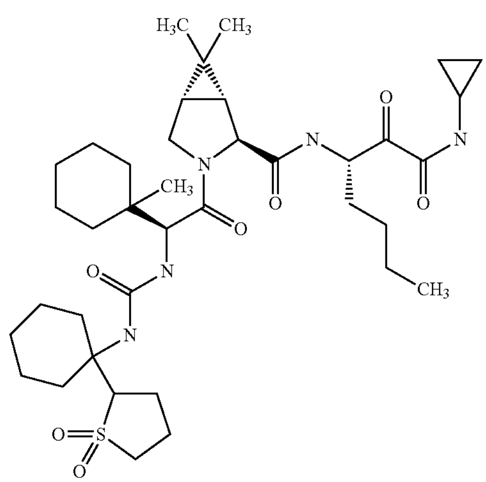 | 732.0032 | 732.2 | A |

TABLE 3A-continued

| Compound # | structure | mol weight structure | Select LC-MS Data (M + H) | Ki* Range |
|---|---|---|---|---|
| 800 | 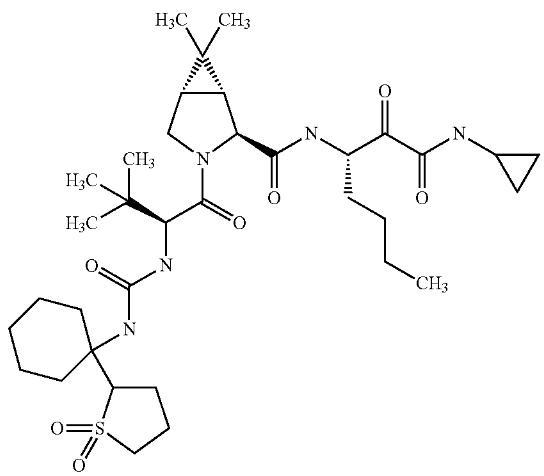 | 691.9378 | 692.2 | A |
| 801 | 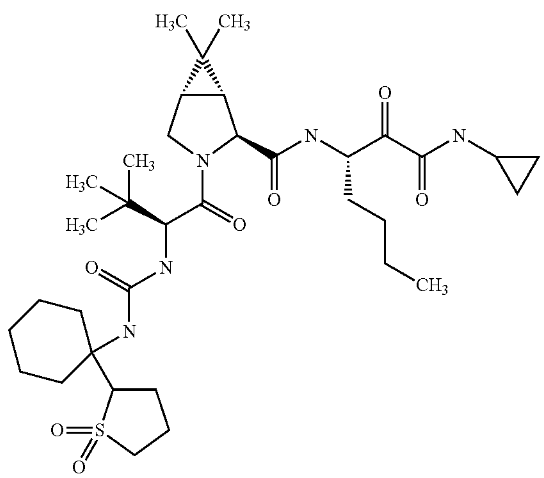 | 692 | 692.2 | A |
| 802 | 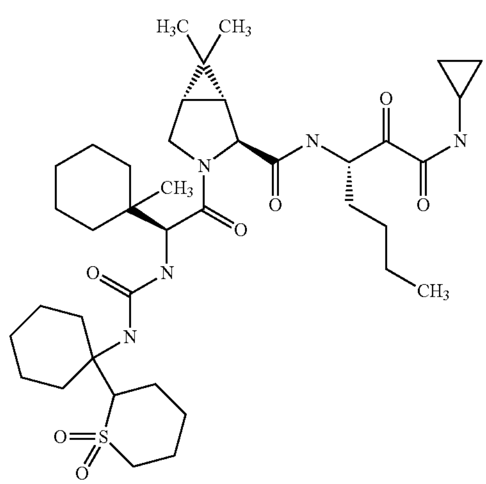 | 746.0303 | | A |

TABLE 3A-continued
| Compound # | structure | mol weight structure | Select LC-MS Data (M + H) | Ki* Range |
|---|---|---|---|---|
| 803 | 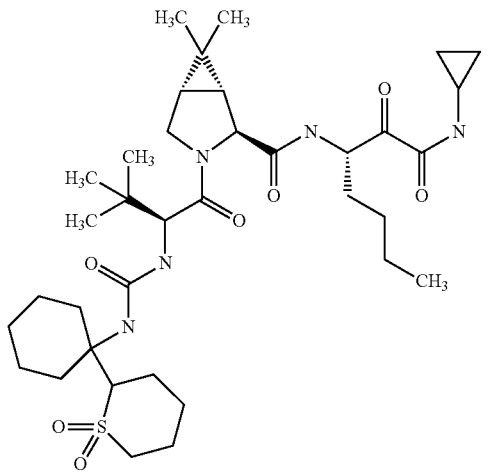 | | 705.9649 | A |
| 804 | 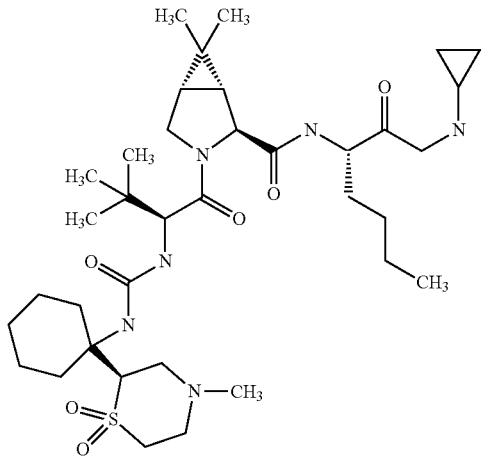 | | 720.9796 | A |
| 805 | 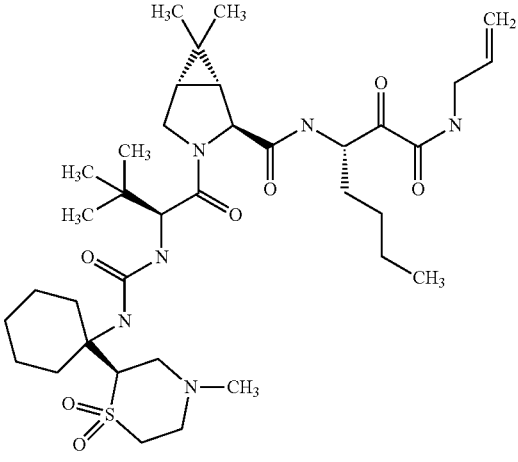 | | 720.9796 | A |

TABLE 3A-continued

| Compound # | structure | mol weight structure | Select LC-MS Data (M + H) | Ki* Range |
|---|---|---|---|---|
| 806 | 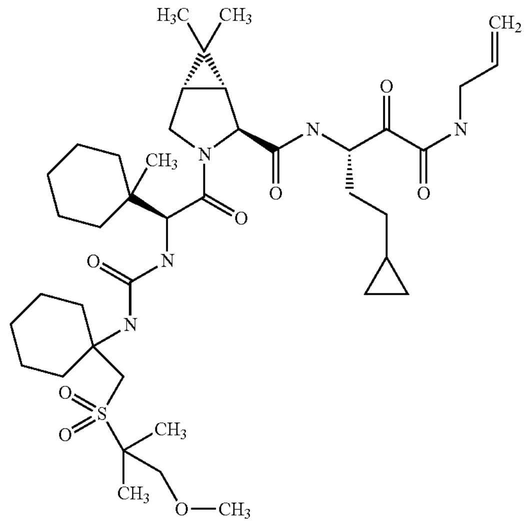 | 790.0838 | | A |
| 807 | 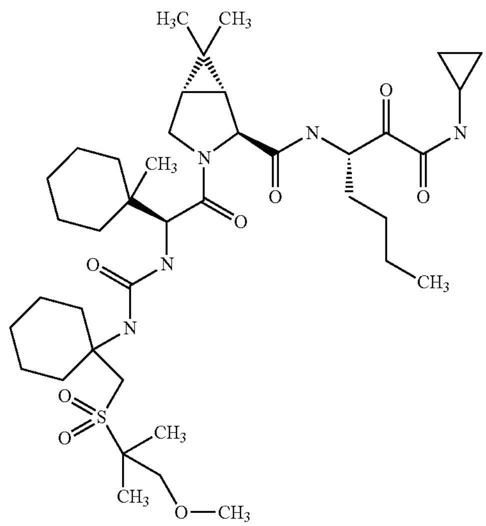 | 778.0727 | | A |
| 808 | 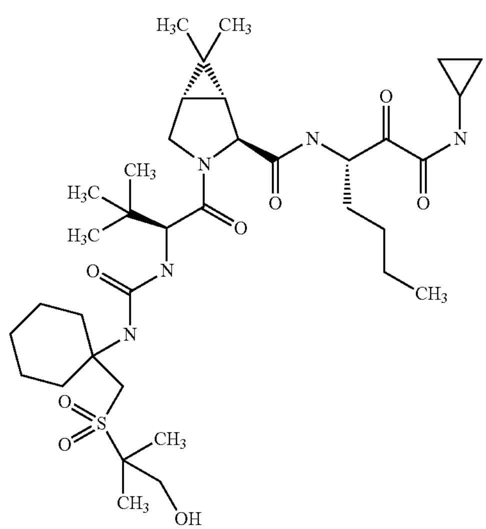 | 723.9803 | | A |

TABLE 3A-continued

| Compound # | structure | mol weight structure | Select LC-MS Data (M + H) | Ki* Range |
|---|---|---|---|---|
| 809 | 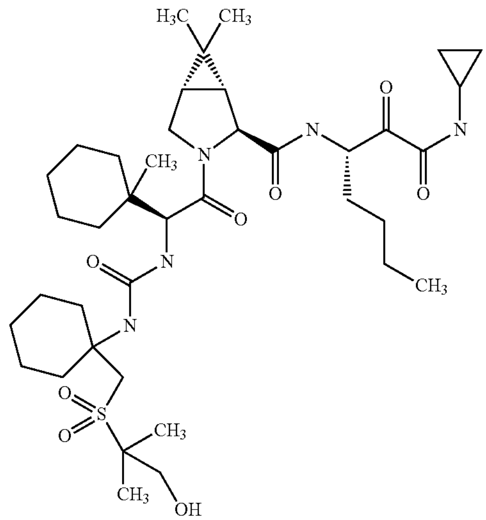 | 764.0456 | | A |
| 810 | 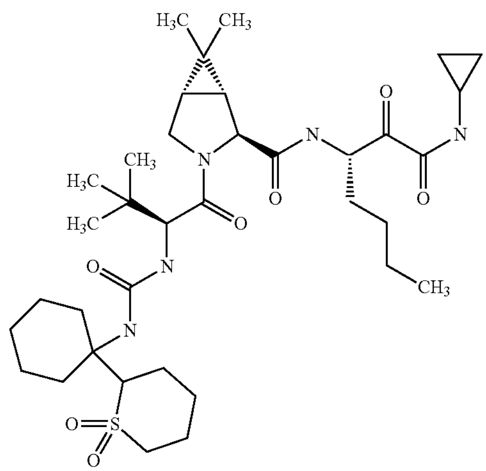 | 705.9649 | 706.4 | A |
| 811 | 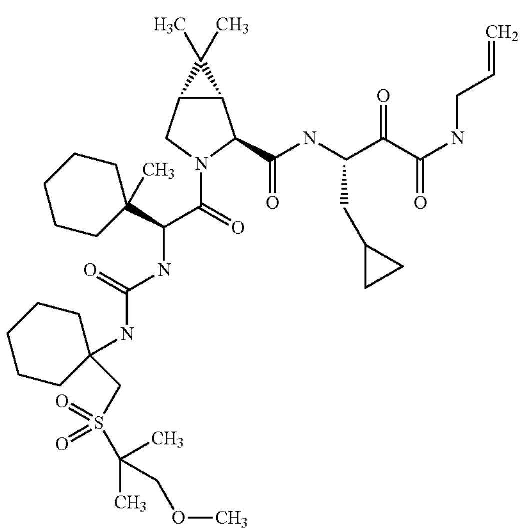 | 776.0568 | | A |

TABLE 3A-continued

| Compound # | structure | mol weight structure | Select LC-MS Data (M + H) | Ki* Range |
|---|---|---|---|---|
| 812 | 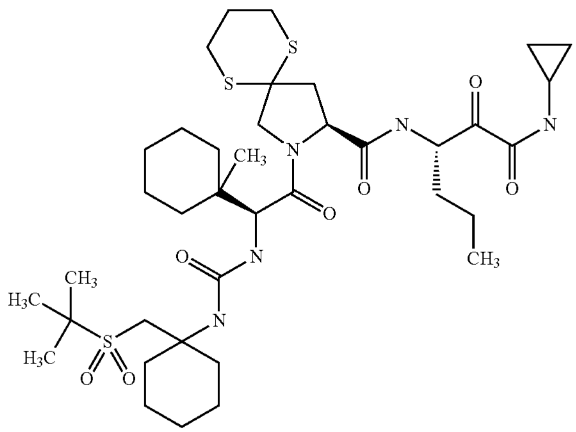 | 798.1471 | 798.4 | A |
| 813 | 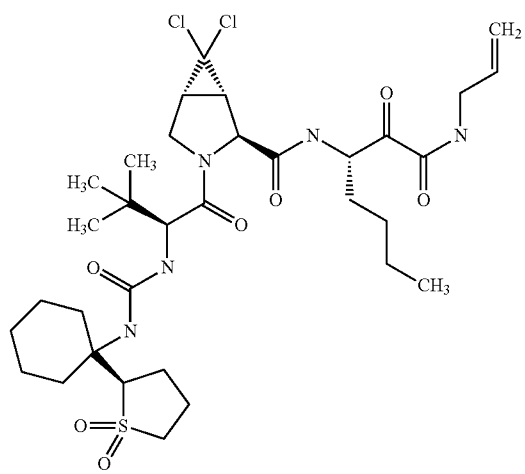 | 732.7737 | 732.1 | A |
| 814 | 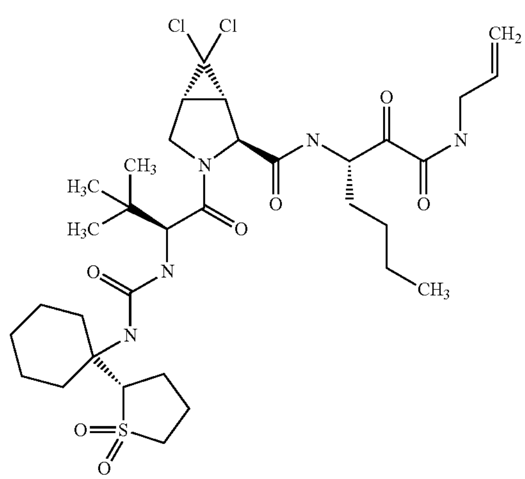 | 732.7737 | 732.1 | A |

TABLE 3A-continued

| Compound # | structure | mol weight structure | Select LC-MS Data (M + H) | Ki* Range |
|---|---|---|---|---|
| 815 | 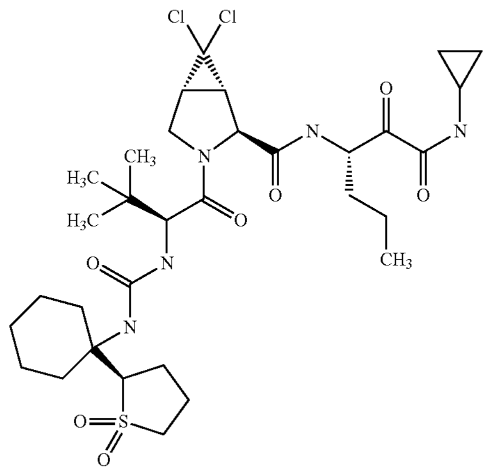 | 718.7466 | 718.1 | A |
| 816 | 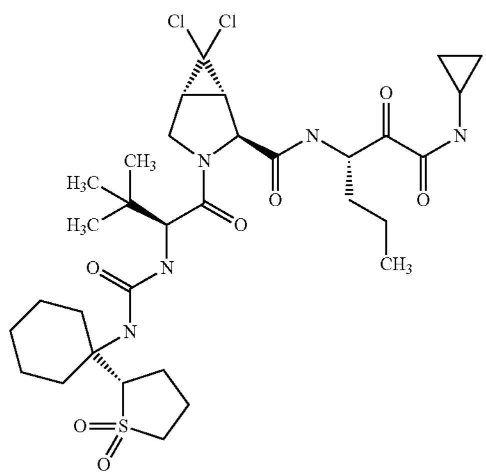 | 718.7466 | 718.1 | A |
| 817 | 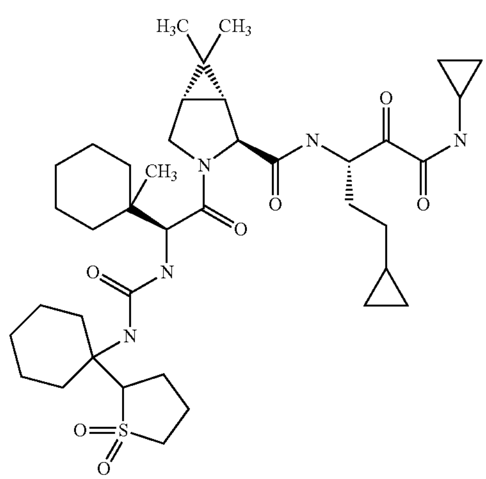 | 744.0143 | 744.1 | A |

TABLE 3A-continued

| Compound # | structure | mol weight structure | Select LC-MS Data (M + H) | Ki* Range |
|---|---|---|---|---|
| 818 | 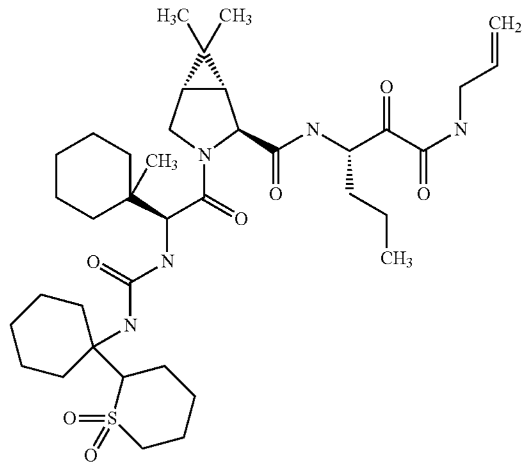 | 732.0032 | 732.1 | A |
| 819 | 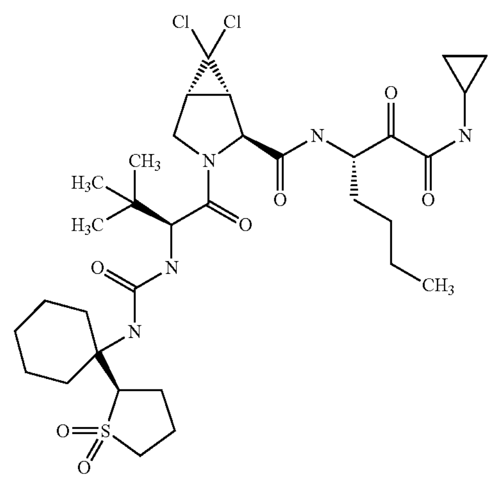 | 732.7737 | 732.1 | A |
| 820 | 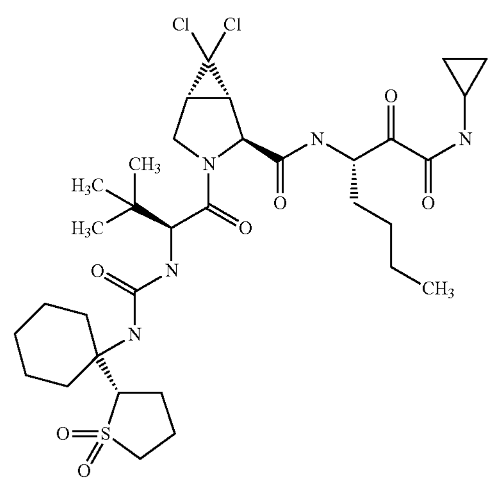 | 732.7737 | 732.1 | A |

TABLE 3A-continued

| Compound # | structure | mol weight structure | Select LC-MS Data (M + H) | Ki* Range |
|---|---|---|---|---|
| 821 | 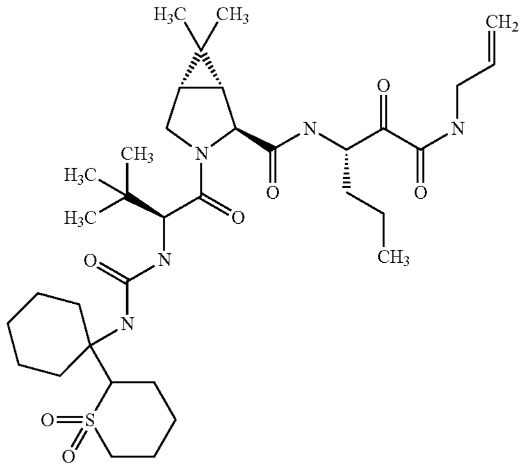 | 691.9378 | 692.1 | A |
| 822 | 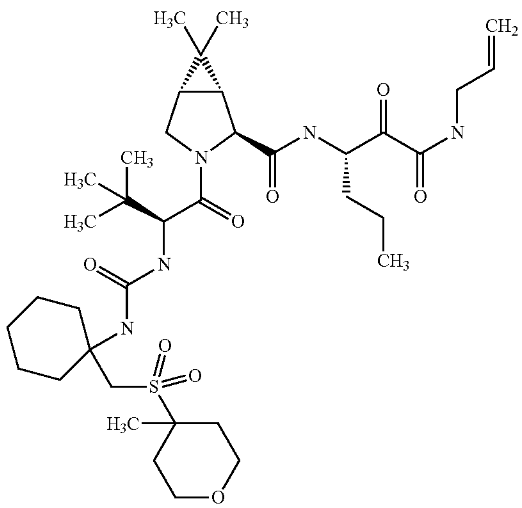 | 735.9914 | 736.1 | A |
| 823 | 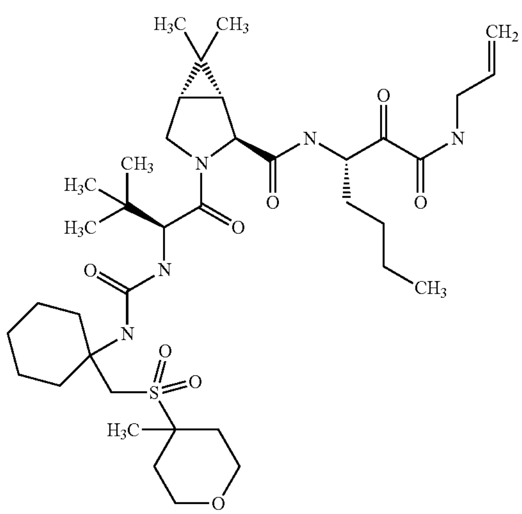 | 750.0185 | 750.1 | A |

TABLE 3A-continued

| Compound # | structure | mol weight structure | Select LC-MS Data (M + H) | Ki* Range |
|---|---|---|---|---|
| 824 | 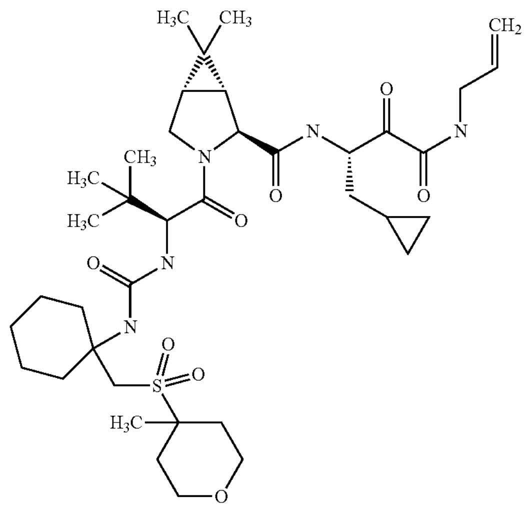 | 748.0026 | 748.1 | A |
| 825 | 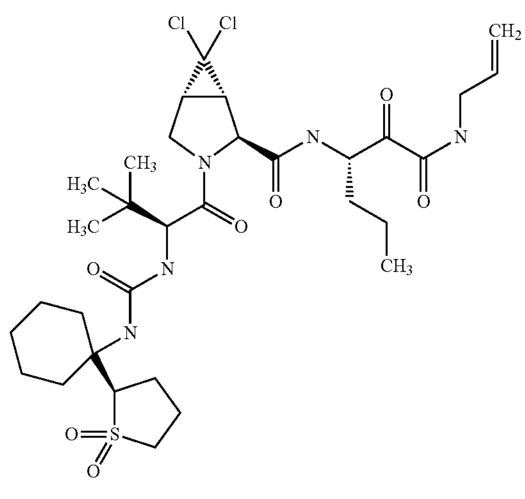 | 718.7466 | 718.2 | A |
| 826 | 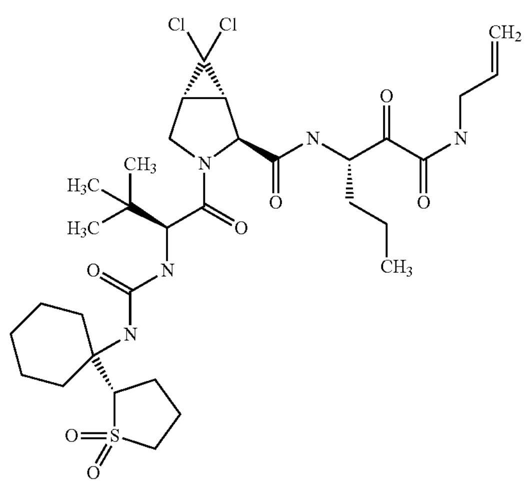 | 718.7466 | 718.2 | A |

TABLE 3A-continued

| Compound # | structure | mol weight structure | Select LC-MS Data (M + H) | Ki* Range |
|---|---|---|---|---|
| 827 | 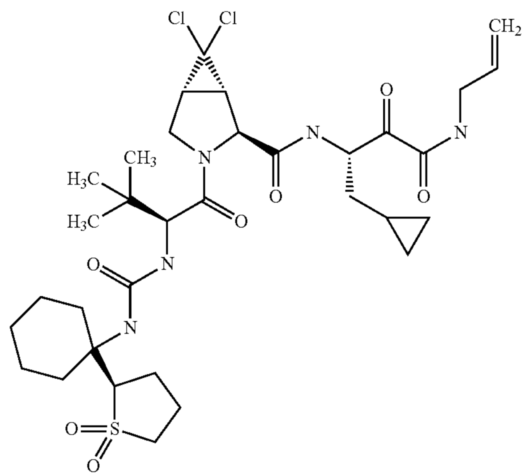 | 730.7578 | 730.2 | A |
| 828 | 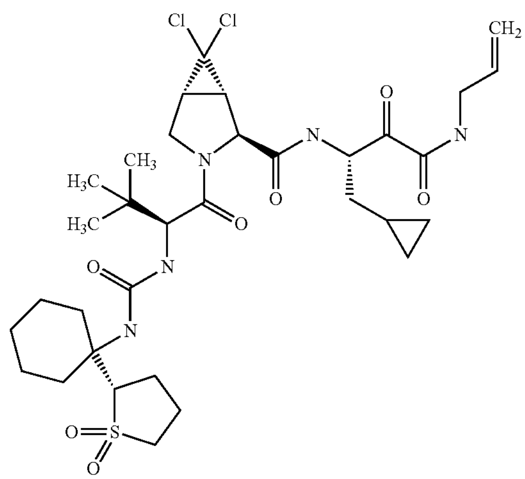 | 730.7578 | 730.2 | A |
| 829 | 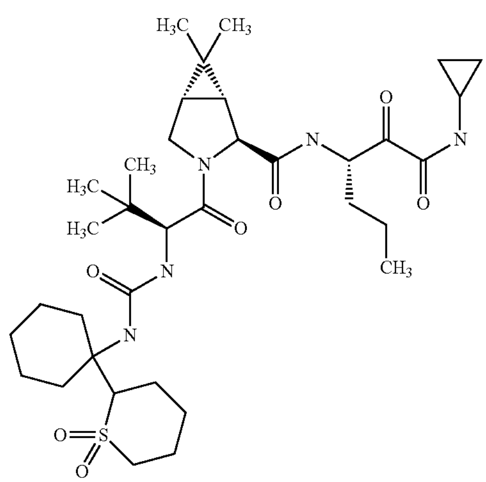 | 691.9378 | | A |

TABLE 3A-continued

| Compound # | structure | mol weight structure | Select LC-MS Data (M + H) | Ki* Range |
|---|---|---|---|---|
| 830 | 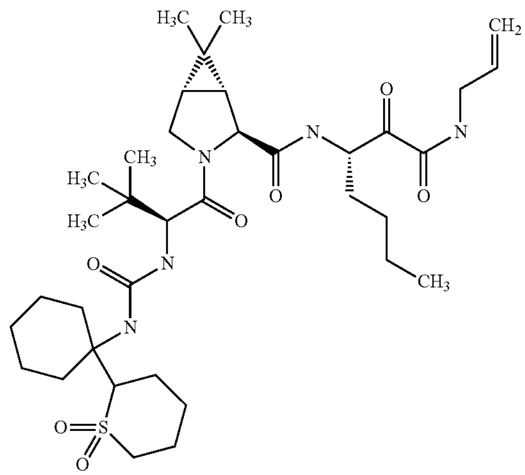 | 705.9649 | 706.1 | A |
| 831 | 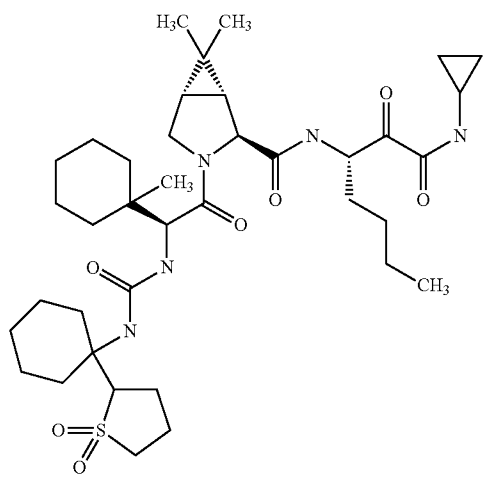 | 732.0032 | 732.2 | A |
| 832 | 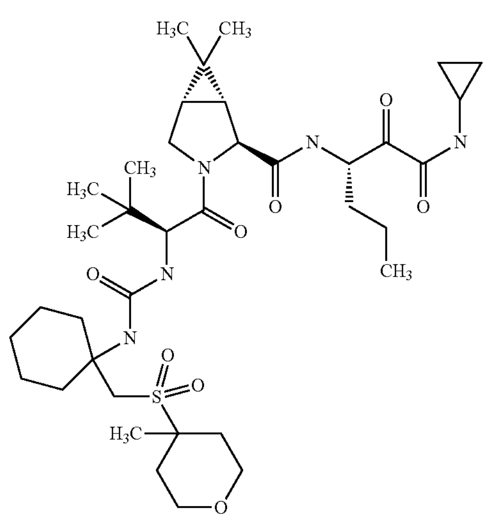 | 735.9914 | 736.1 | A |

TABLE 3A-continued

| Compound # | structure | mol weight structure | Select LC-MS Data (M + H) | Ki* Range |
|---|---|---|---|---|
| 833 | 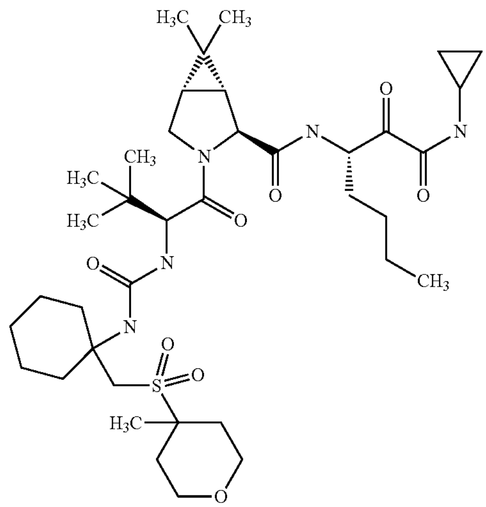 | 750.0185 | 750.1 | A |
| 834 | 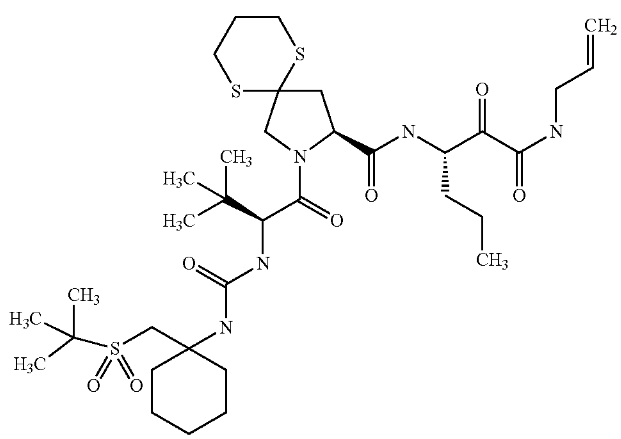 | 758.0818 | 758.2 | A |
| 835 | 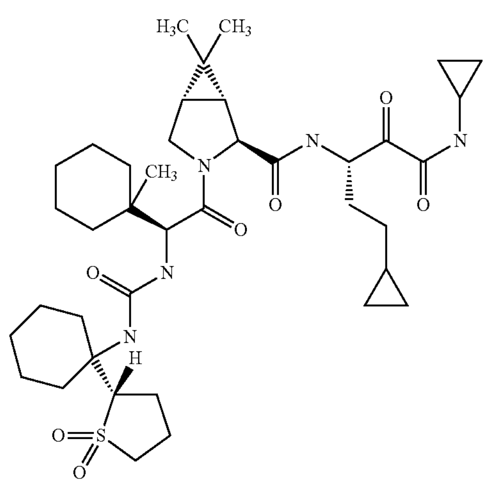 | 744.0143 | 744.1 | A |

TABLE 3A-continued

| Compound # | structure | mol weight structure | Select LC-MS Data (M + H) | Ki* Range |
|---|---|---|---|---|
| 836 | 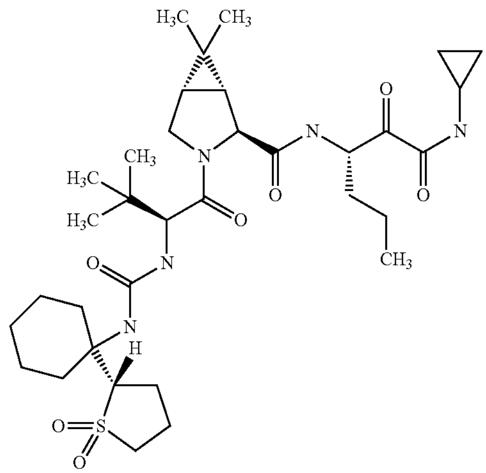 | 677.9108 | | A |
| 837 | 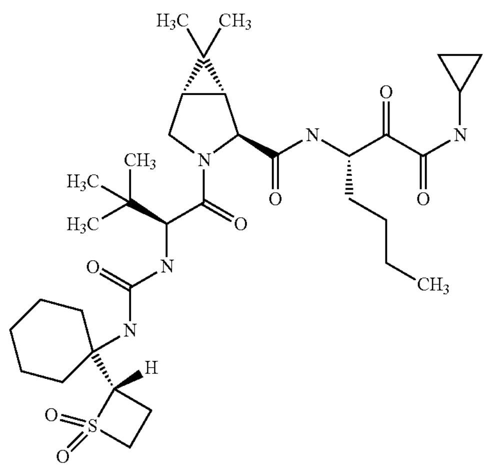 | 677.9108 | 678.3 | A |
| 838 | 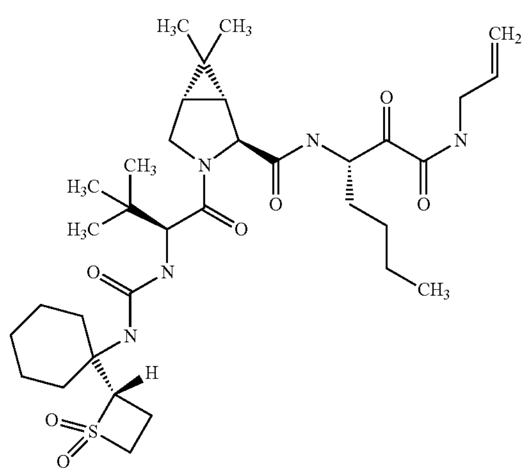 | 677.9108 | 678.3 | A |

TABLE 3A-continued
| Compound # | structure | mol weight structure | Select LC-MS Data (M + H) | Ki* Range |
|---|---|---|---|---|
| 839 | 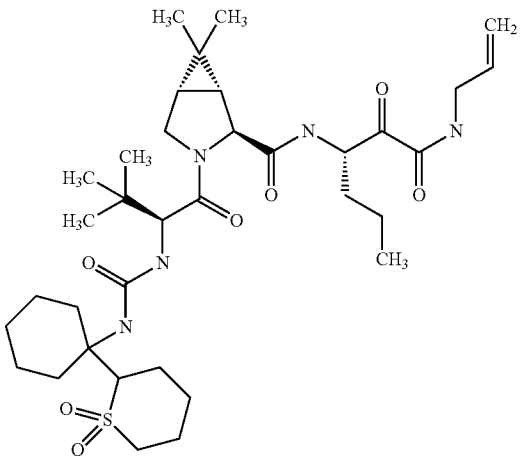 | 691.9378 | | A |
| 840 | 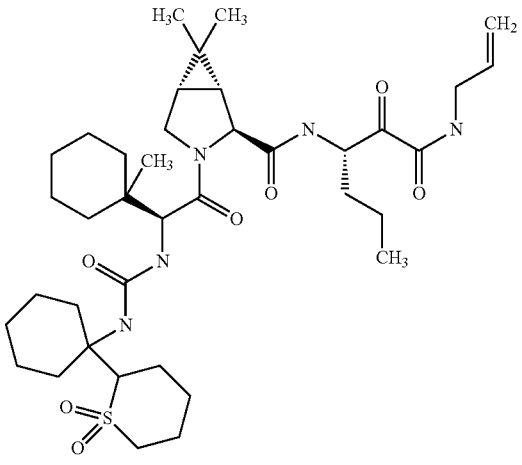 | 732.0032 | | A |
| 841 | 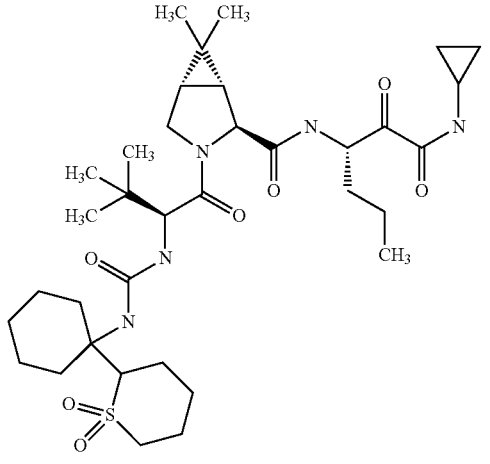 | 691.9378 | | A |

TABLE 3A-continued

| Compound # | structure | mol weight structure | Select LC-MS Data (M + H) | Ki* Range |
|---|---|---|---|---|
| 842 | 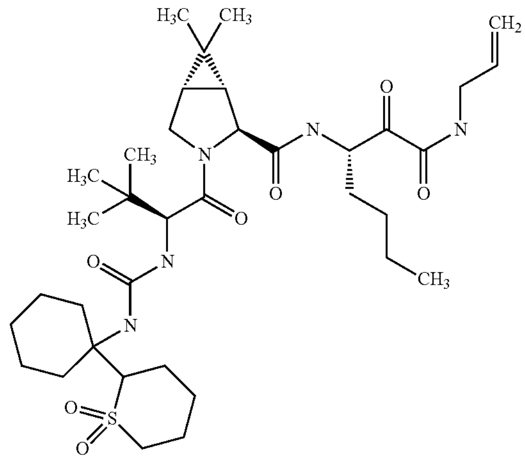 | 705.9649 | | A |
| 843 | 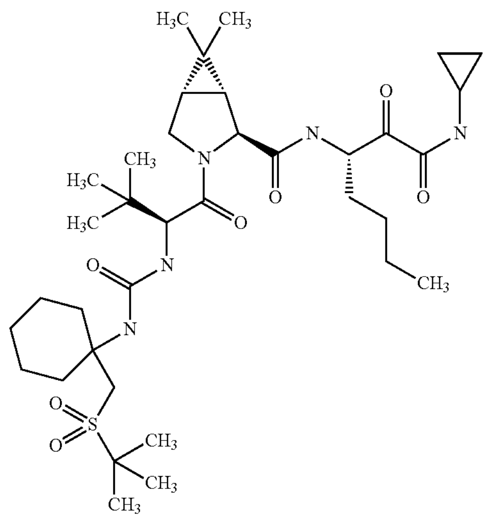 | 707.9809 | 708.4 | 11 |
| 845 | 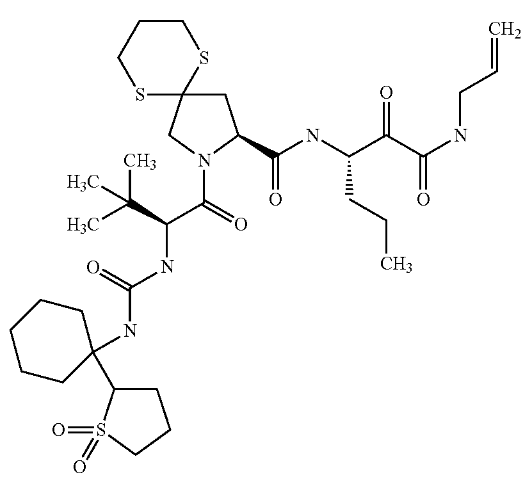 | 742.0388 | 742.4 | A |

TABLE 3A-continued

| Compound # | structure | mol weight structure | Select LC-MS Data (M + H) | Ki* Range |
|---|---|---|---|---|
| 846 | 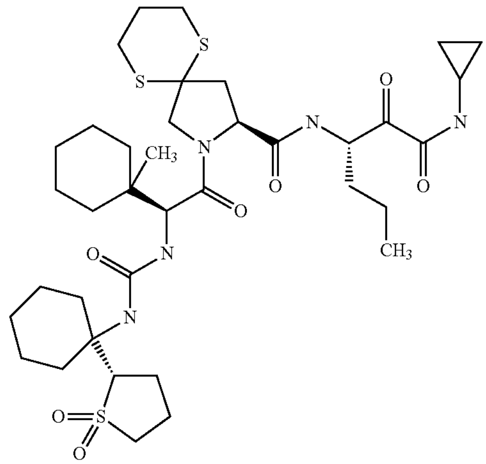 | 782.1041 | 782.4 | A |
| 847 | 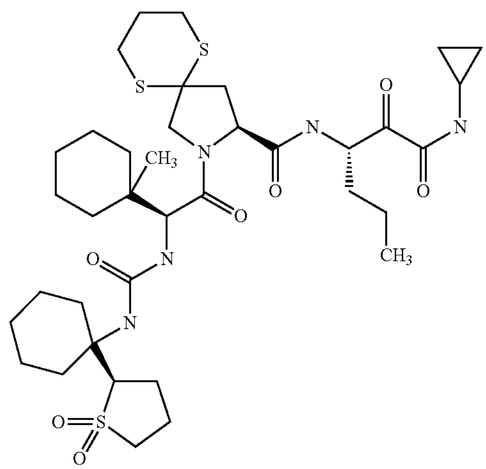 | 782.1041 | 782.4 | A |
| 848 | 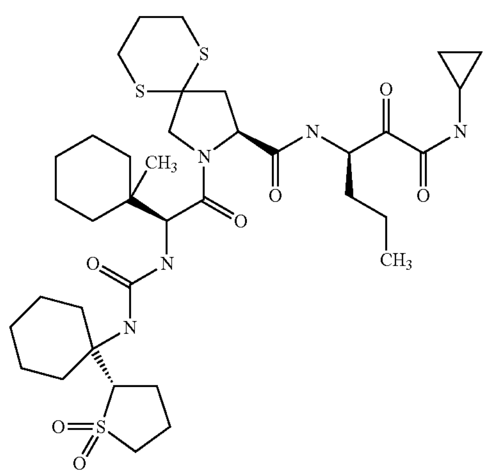 | 782.1041 | 782.4 | B |

TABLE 3A-continued

| Compound # | structure | mol weight structure | Select LC-MS Data (M + H) | Ki* Range |
|---|---|---|---|---|
| 849 | 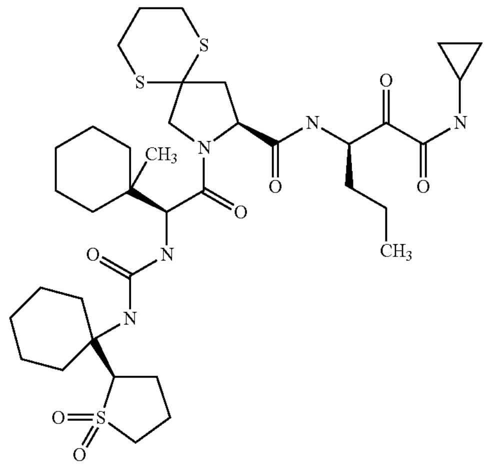 | 782.1041 | 782.4 | B |
| 850 | 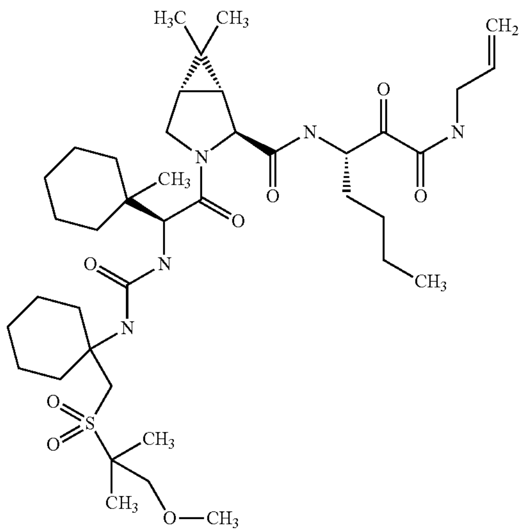 | 778.0727 | | A |
| 851 | 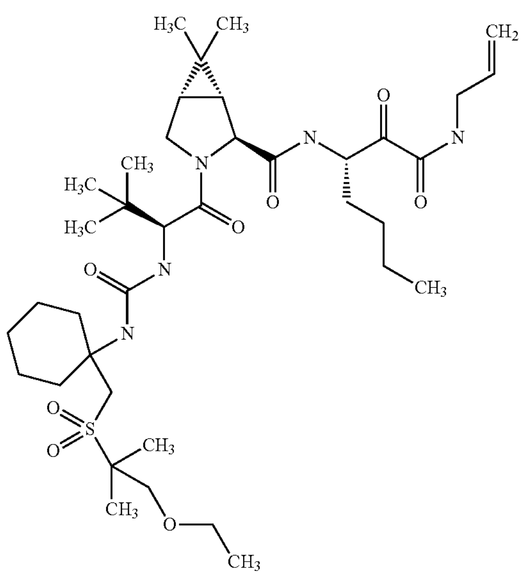 | 752.0345 | | A |

TABLE 3A-continued

| Compound # | structure | mol weight structure | Select LC-MS Data (M + H) | Ki* Range |
|---|---|---|---|---|
| 852 | 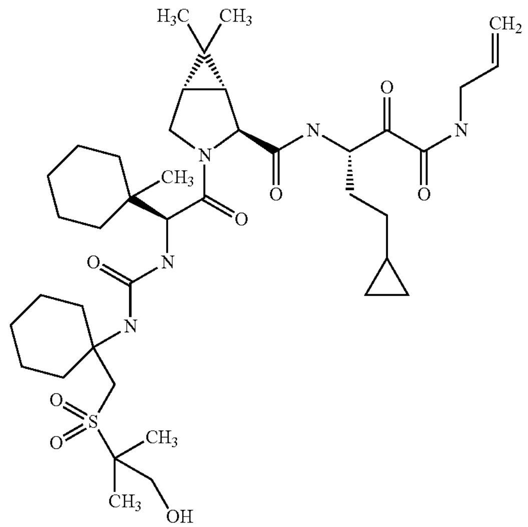 | 776.0568 | | A |
| 853 | 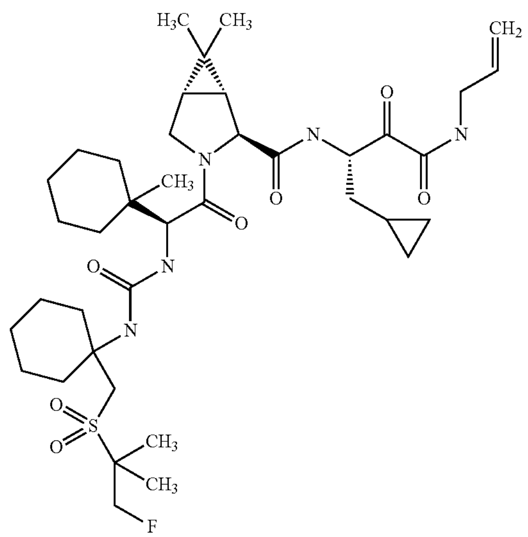 | 764.0207 | | A |
| 854 | 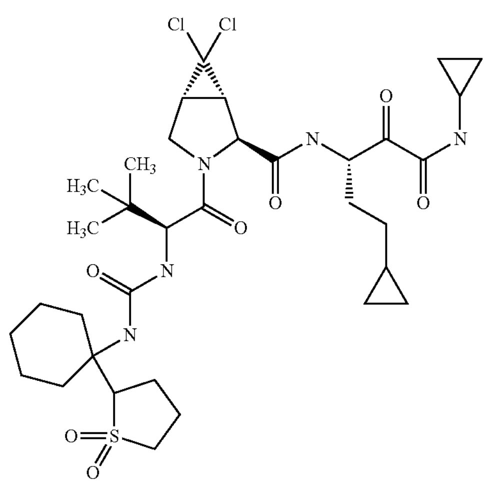 | 744.7849 | 744.4 | A |

TABLE 3A-continued

| Compound # | structure | mol weight structure | Select LC-MS Data (M + H) | Ki* Range |
|---|---|---|---|---|
| 855 | 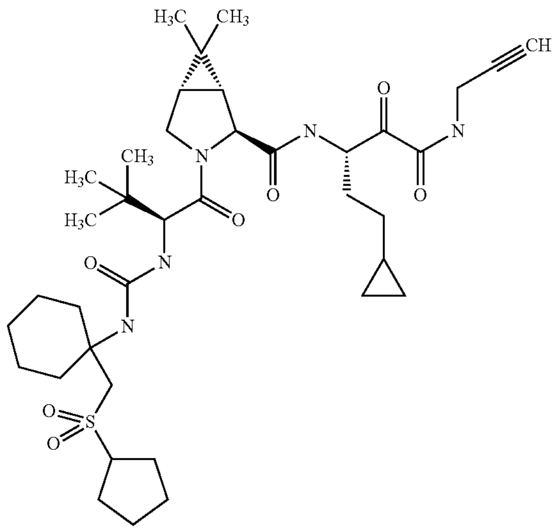 | 729.9872 | 730.2 | A |
| 856 | 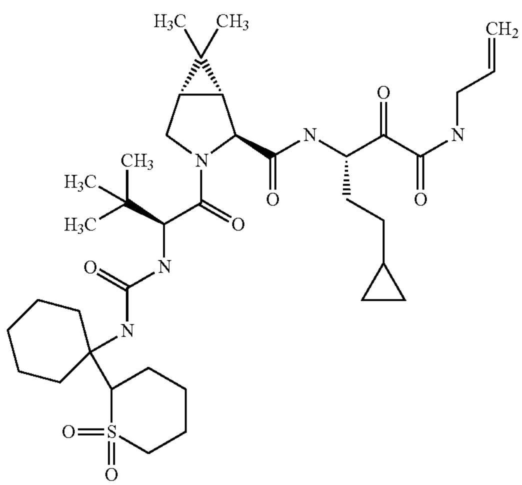 | 717.9761 | | 5 |
| 857 | 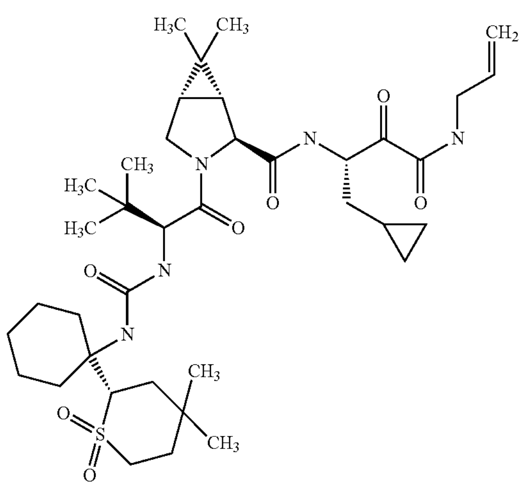 | 732.0032 | 732.4 | A |

TABLE 3A-continued

| Compound # | structure | mol weight structure | Select LC-MS Data (M + H) | Ki* Range |
|---|---|---|---|---|
| 858 | 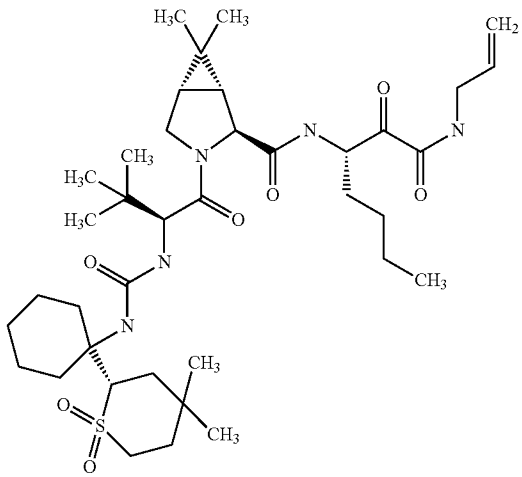 | 734.0191 | 734.4 | A |
| 859 | 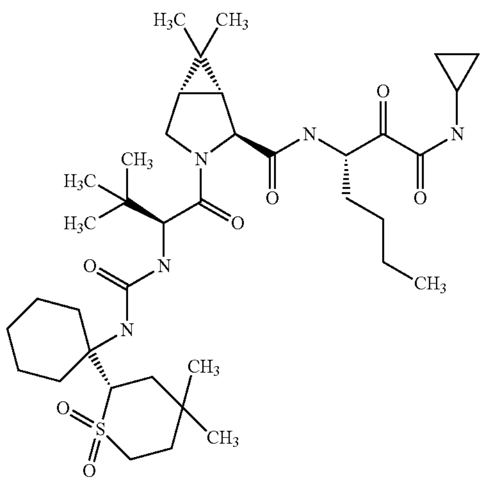 | 734.0191 | 734.41 | A |
| 860 | 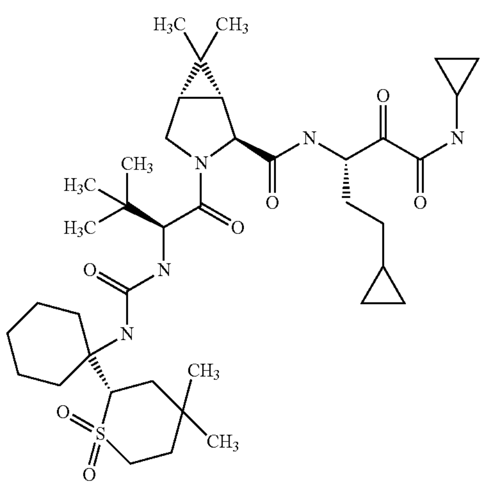 | 746.0303 | 746.5 | A |

TABLE 3A-continued
| Compound # | structure | mol weight structure | Select LC-MS Data (M + H) | Ki* Range |
|---|---|---|---|---|
| 861 | 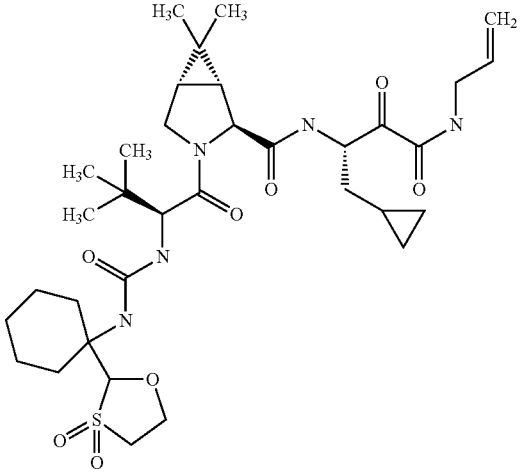 | 691.8942 | 692.4 | A |
| 862 | 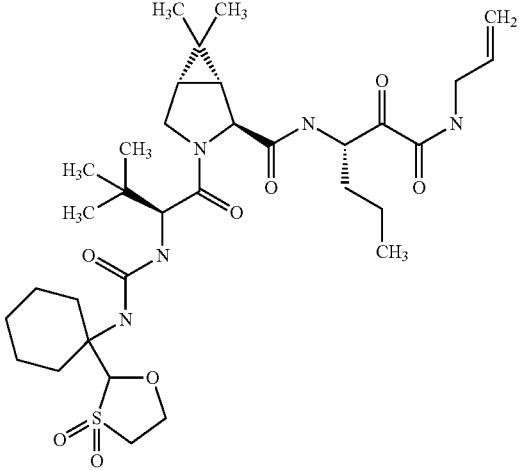 | 679.8831 | 680.38 | A |
| 863 | 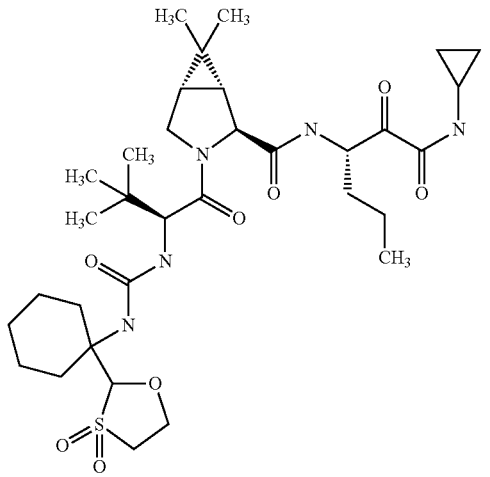 | 679.8831 | 680.4 | A |

TABLE 3A-continued

| Compound # | structure | mol weight structure | Select LC-MS Data (M + H) | Ki* Range |
|---|---|---|---|---|
| 864 | 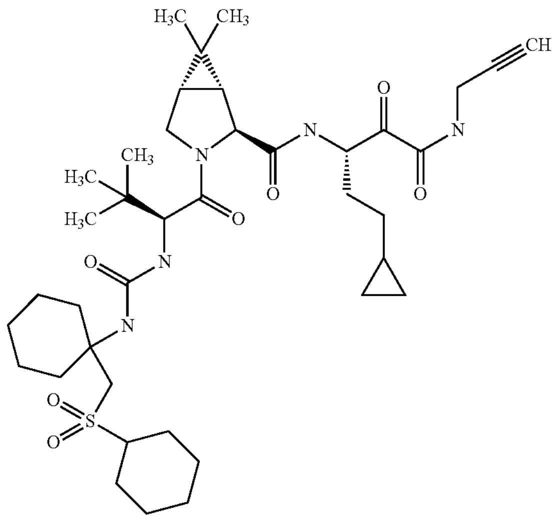 | 744.0143 | 744.1 | A |
| 865 | 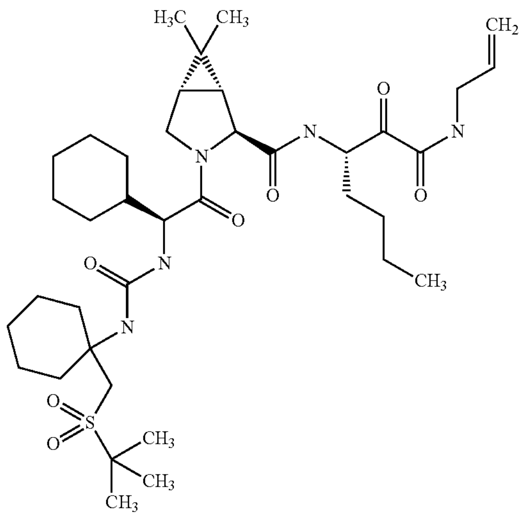 | 734.0191 | 734.4 | A |
| 866 | 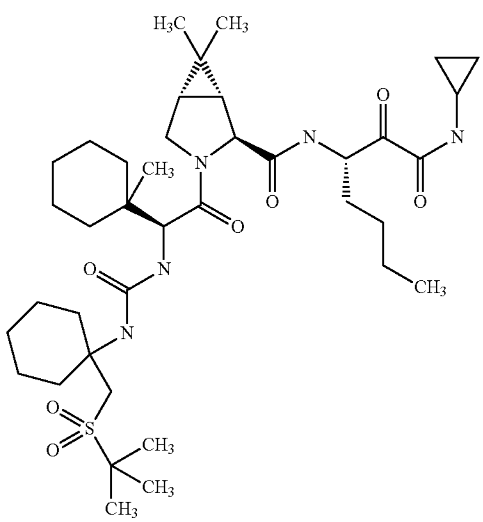 | 748.0462 | 748.4 | A |

TABLE 3A-continued

| Compound # | structure | mol weight | Select LC-MS Data (M + H) structure | Ki* Range |
|---|---|---|---|---|
| 867 | 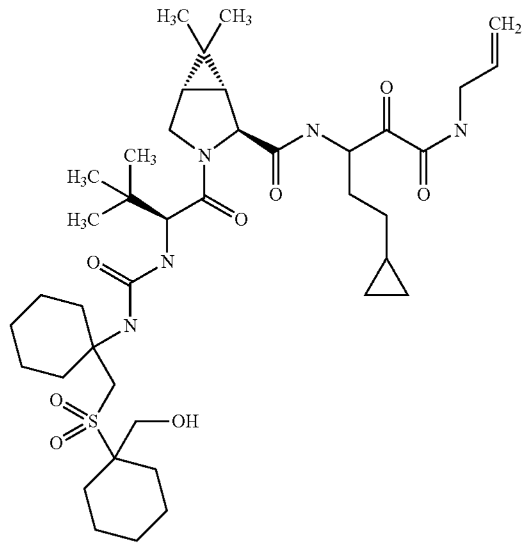 | 776.0568 | | A |
| 868 | 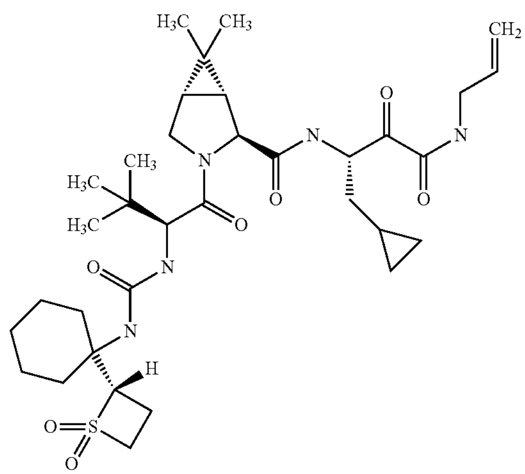 | 675.8948 | | A |
| 869 | 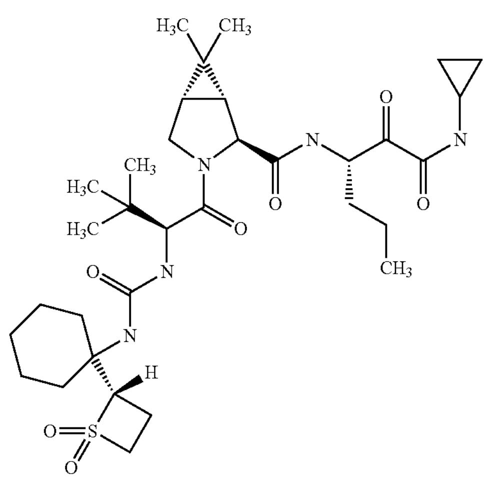 | 663.8837 | | A |

TABLE 3A-continued

| Compound # | structure | mol weight structure | Select LC-MS Data (M + H) | Ki* Range |
|---|---|---|---|---|
| 870 | 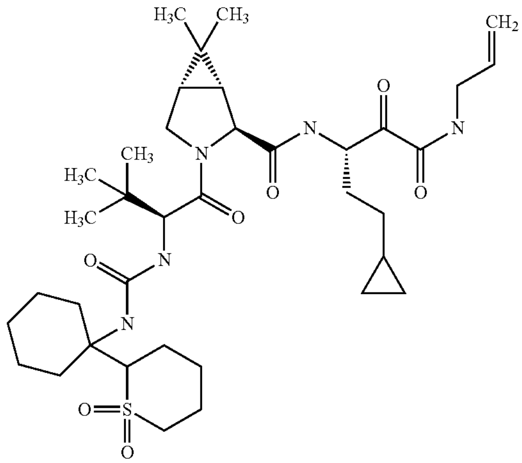 | 717.9761 | | A |
| 871 | 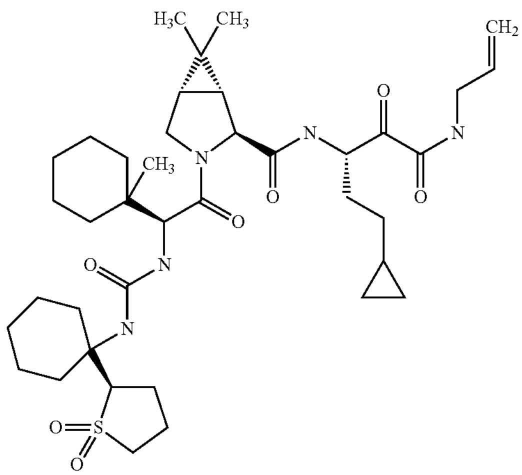 | 744.0143 | | A |
| 872 | 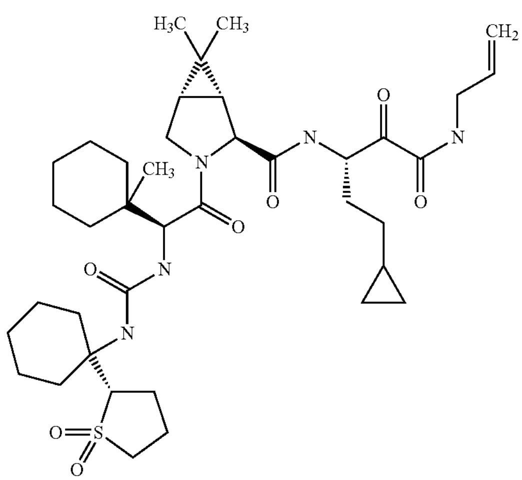 | 744.0143 | | A |

TABLE 3A-continued

| Compound # | structure | mol weight structure | Select LC-MS Data (M + H) | Ki* Range |
|---|---|---|---|---|
| 873 | 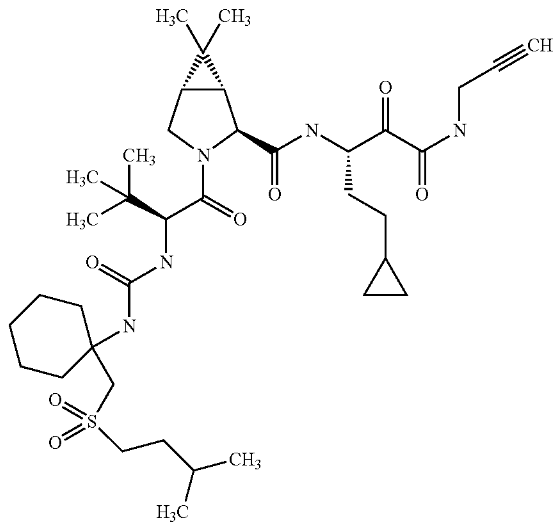 | 732.0032 | 732.1 | A |
| 874 | 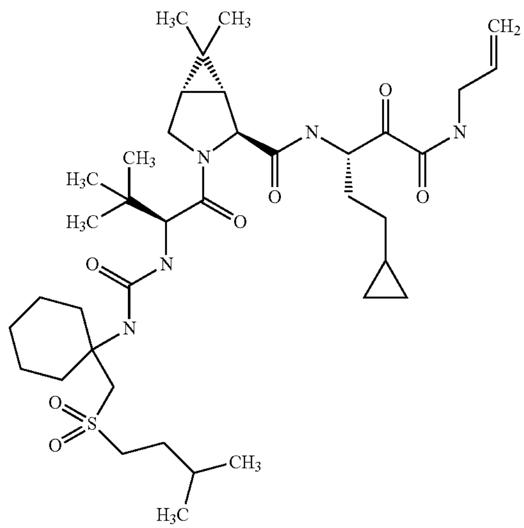 | 734.0191 | 734.1 | A |
| 875 | 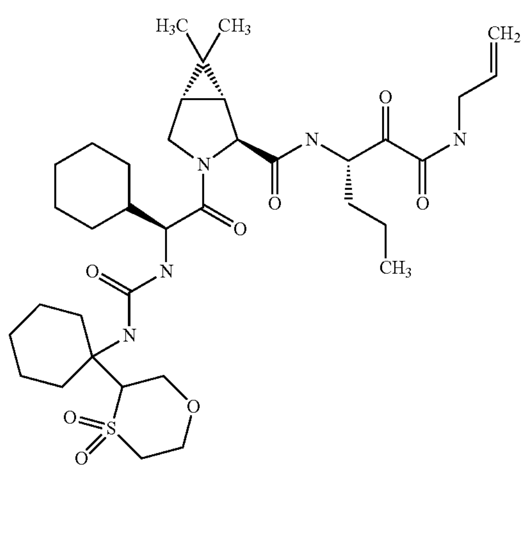 | 719.9484 | | A |

TABLE 3A-continued

| Compound # | structure | mol weight structure | Select LC-MS Data (M + H) | Ki* Range |
|---|---|---|---|---|
| 876 | 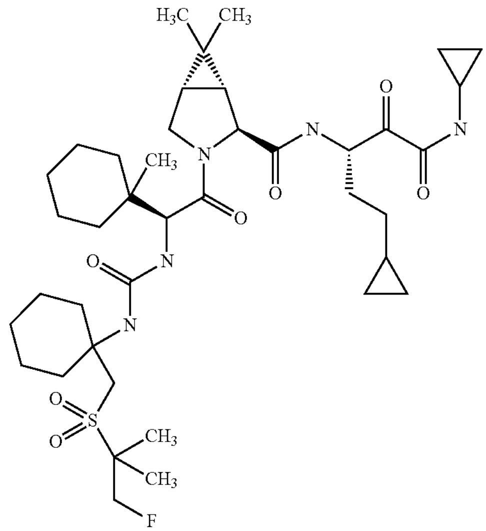 | 778.0478 | | A |
| 877 | 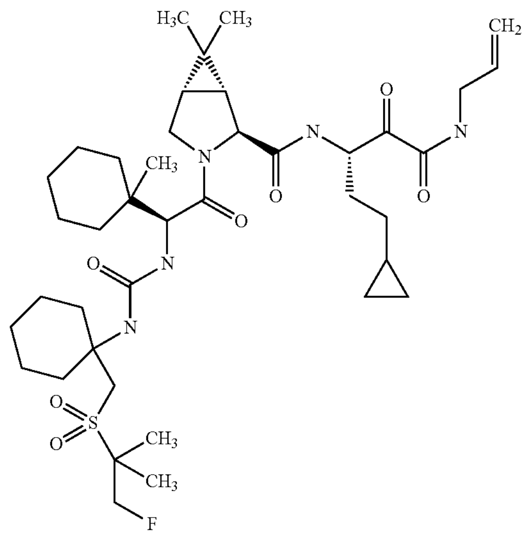 | 778.0478 | | A |
| 878 | 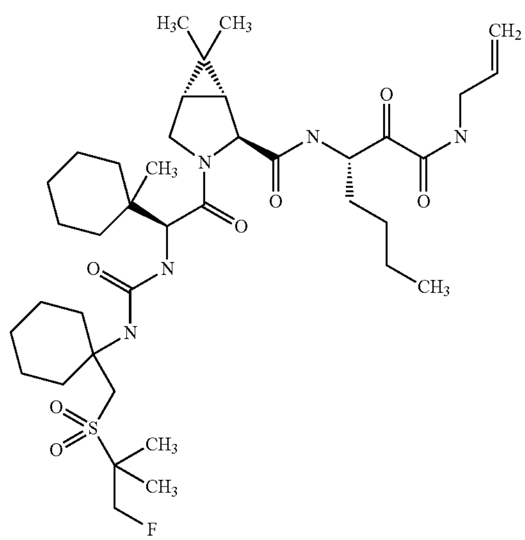 | 766.0366 | | A |

TABLE 3A-continued

| Compound # | structure | mol weight structure | Select LC-MS Data (M + H) | Ki* Range |
|---|---|---|---|---|
| 879 | 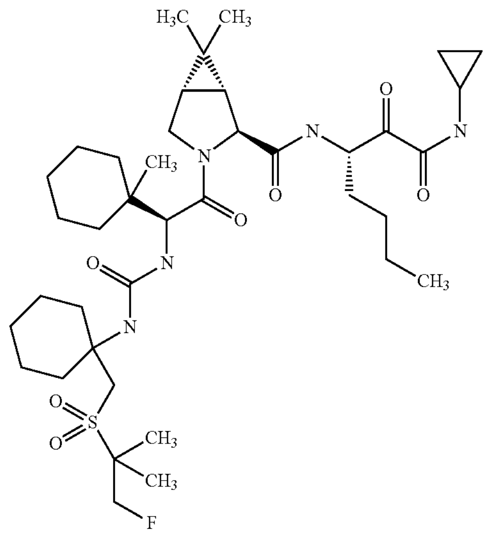 | 766.0366 | | A |
| 880 | 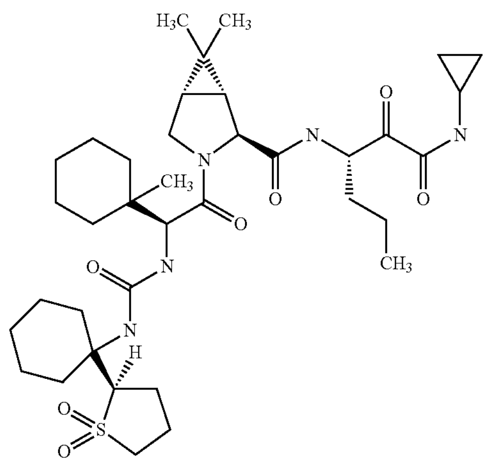 | 717.9761 | 718.1 | A |
| 881 | 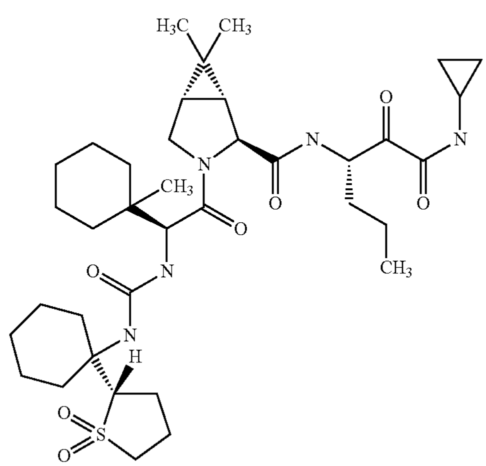 | 717.9761 | 718.1 | A |

TABLE 3A-continued

| Compound # | structure | mol weight structure | Select LC-MS Data (M + H) | Ki* Range |
|---|---|---|---|---|
| 882 | 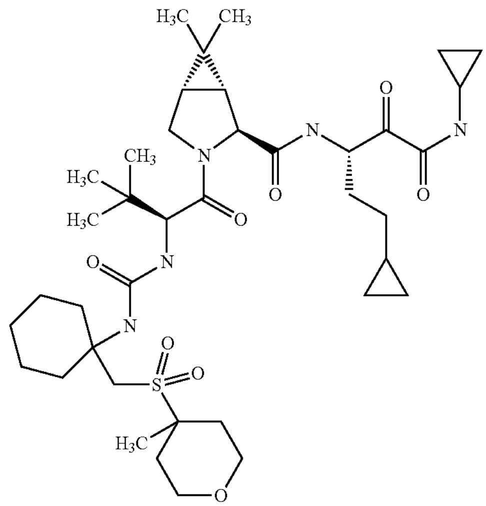 | 762.0297 | 762.1 | A |
| 883 | 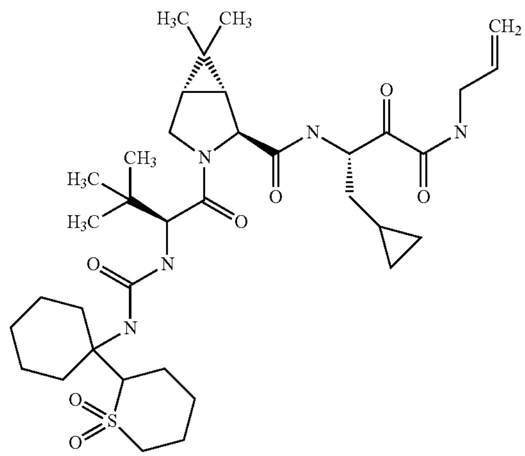 | 703.949 | 704.1 | A |
| 883-a | 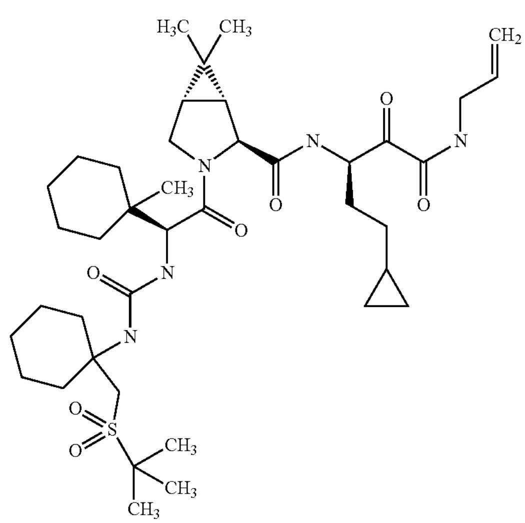 | 760.0574 | | B |

TABLE 3A-continued

| Compound # | structure | mol weight structure | Select LC-MS Data (M + H) | Ki* Range |
|---|---|---|---|---|
| 883-b | 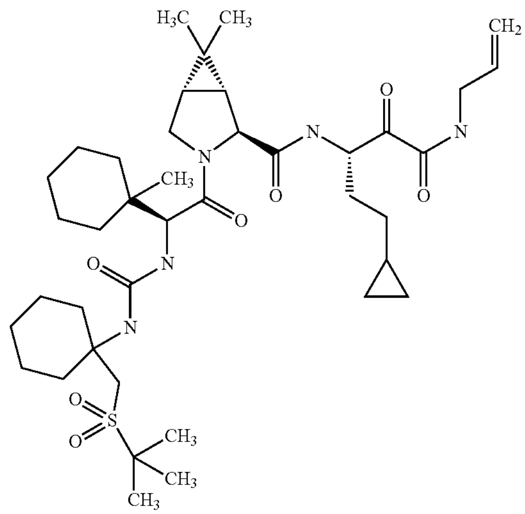 | 760.0574 | | A |
| 883-c | 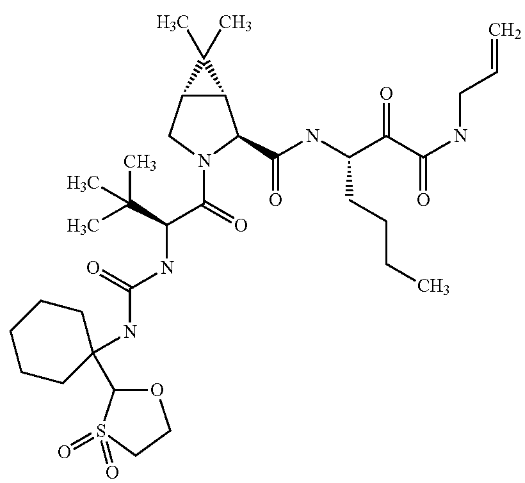 | 693.9102 | | 3 |
| 883-d | 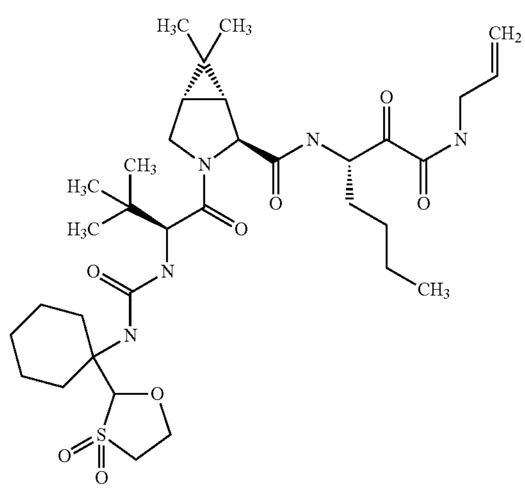 | 693.9102 | | A |

TABLE 3A-continued

| Compound # | structure | mol weight structure | Select LC-MS Data (M + H) | Ki* Range |
|---|---|---|---|---|
| 883-e | 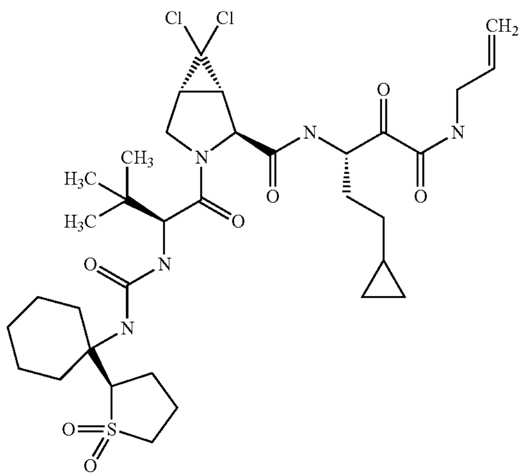 | 744.7849 | | A |
| 883-f | 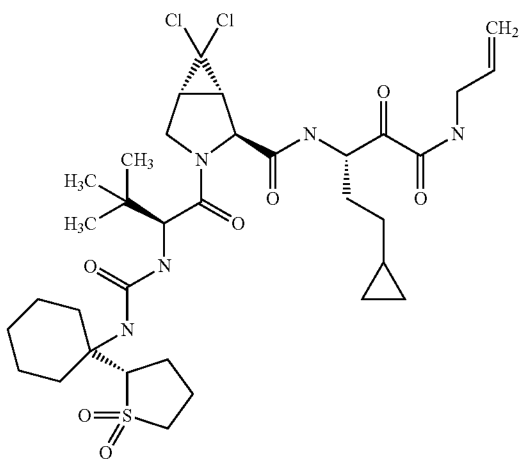 | 744.7849 | | A |
| 883-fa | 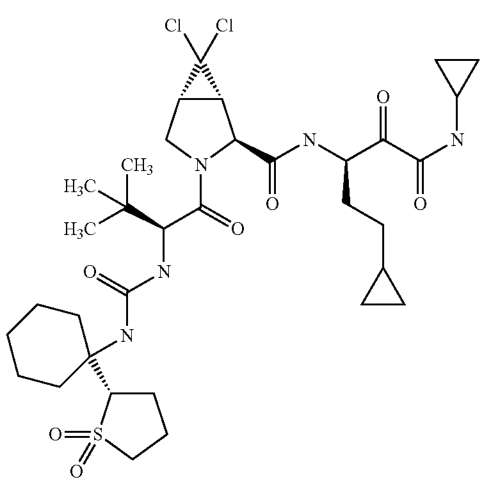 | 744.7849 | | A |

TABLE 3A-continued
| Compound # | structure | mol weight structure | Select LC-MS Data (M + H) | Ki* Range |
|---|---|---|---|---|
| 883-g | 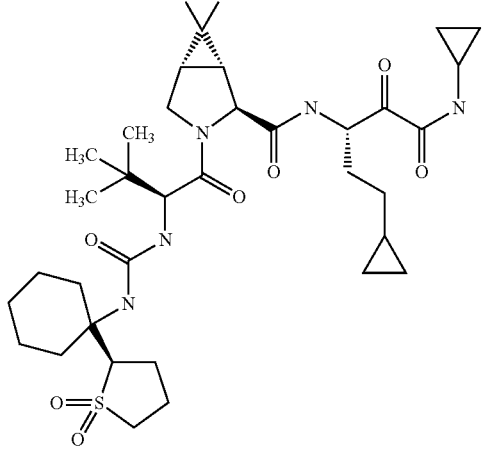 | 744.7849 | | A |
| 883-h | 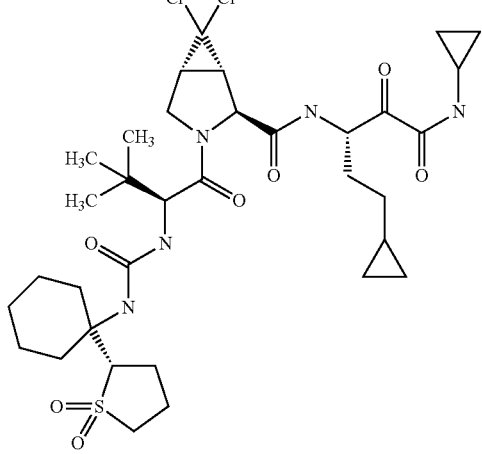 | 744.7849 | | A |
| 883-i | 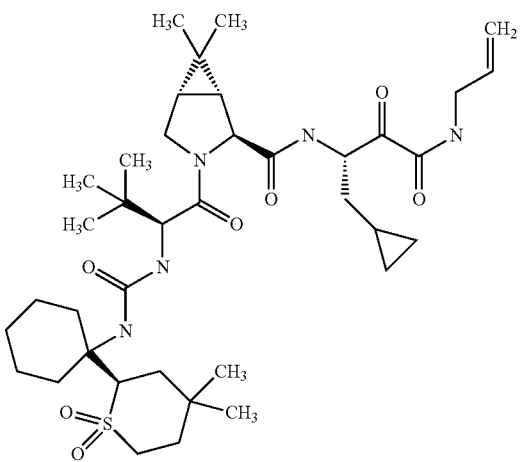 | 732.0032 | | A |

TABLE 3A-continued

| Compound # | structure | mol weight structure | Select LC-MS Data (M + H) | Ki* Range |
|---|---|---|---|---|
| 883-j | 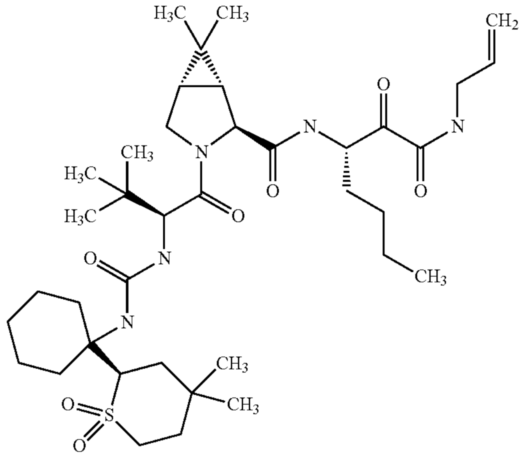 | 734.0191 | | A |
| 883-k | 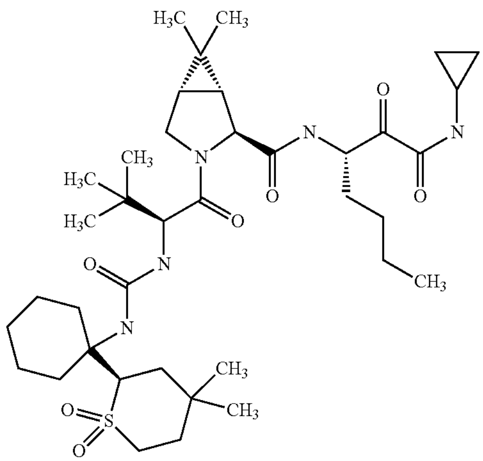 | 734.0191 | | A |
| 883-l | 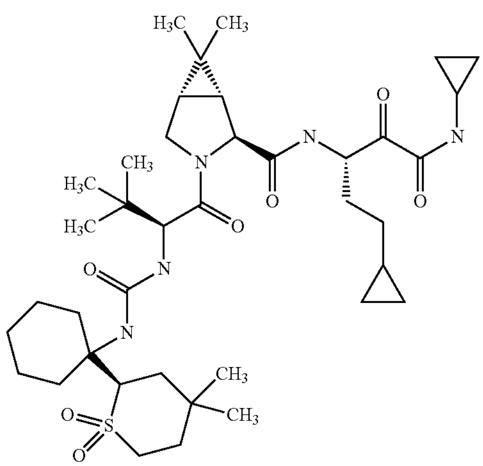 | 746.0303 | | A |

TABLE 3A-continued

| Compound # | structure | mol weight structure | Select LC-MS Data (M + H) | Ki* Range |
|---|---|---|---|---|
| 883-m | 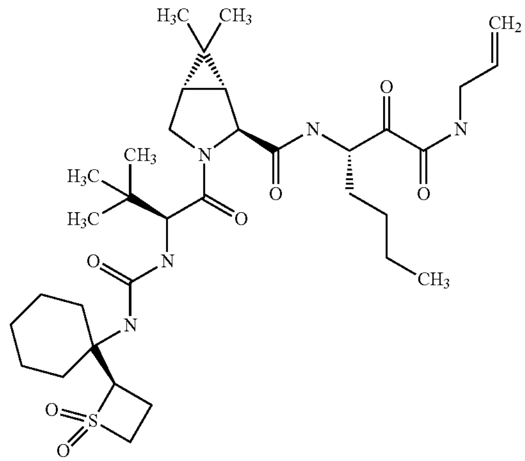 | 677.9108 | | A |
| 883-n | 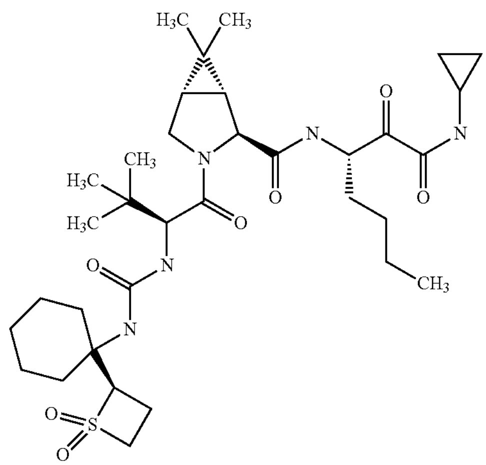 | 677.9108 | | A |
| 883-o | 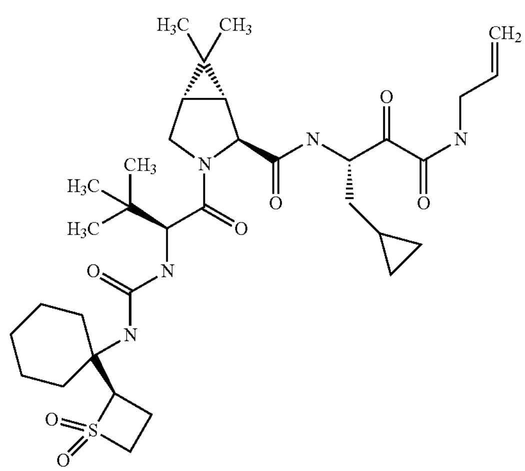 | 675.8948 | | A |

TABLE 3A-continued

| Compound # | structure | mol weight structure | Select LC-MS Data (M + H) | Ki* Range |
|---|---|---|---|---|
| 883-p | 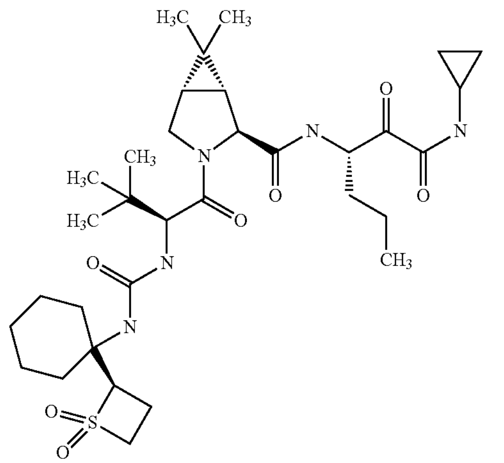 | 693.8837 | | A |
| 883-q | 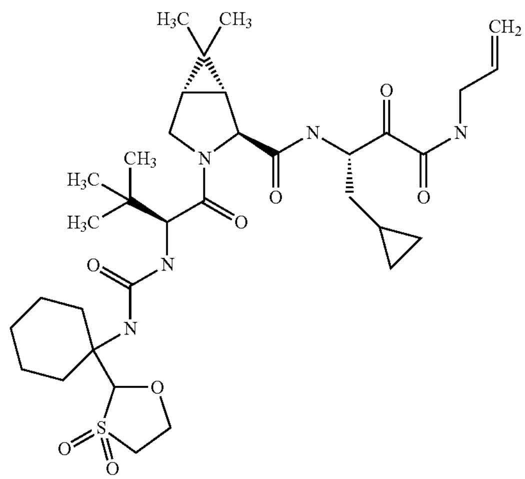 | 691.8942 | | A |
| 883-r | 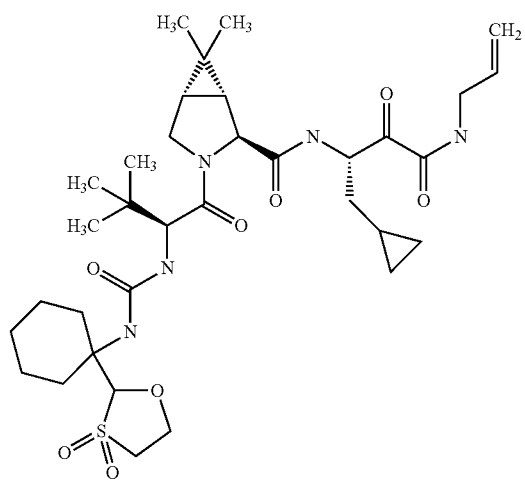 | 691.8942 | | A |

TABLE 3A-continued

| Compound # | structure | mol weight structure | Select LC-MS Data (M + H) | Ki* Range |
|---|---|---|---|---|
| 883-s | 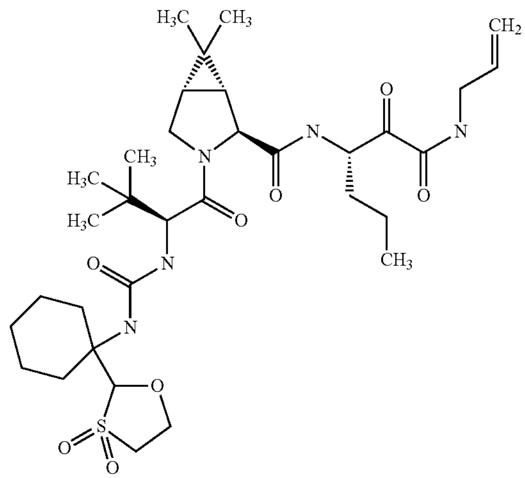 | 679.8831 | | A |
| 883-t | 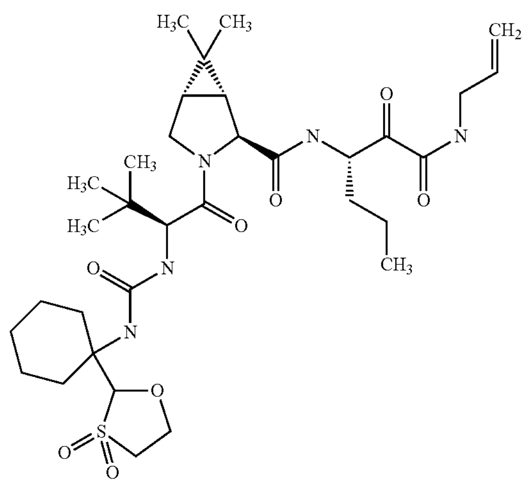 | 679.8831 | | A |
| 883-u | 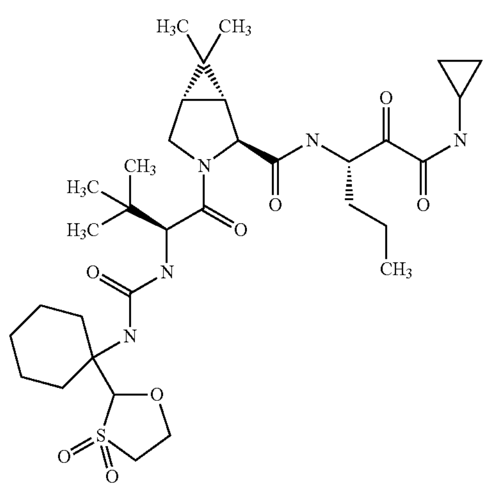 | 679.8831 | | A |

TABLE 3A-continued

| Compound # | structure | mol weight structure | Select LC-MS Data (M + H) | Ki* Range |
|---|---|---|---|---|
| 883-v | 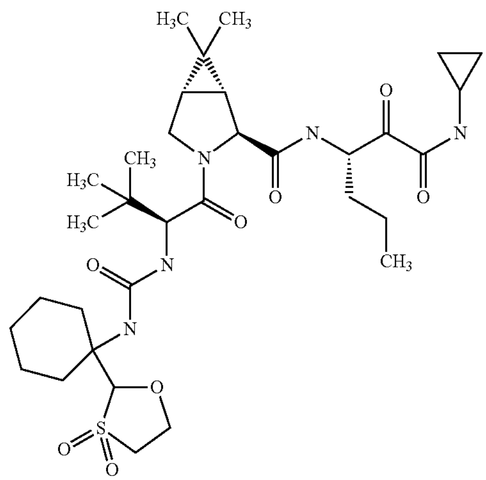 | 679.8831 | | A |
| 883-w | 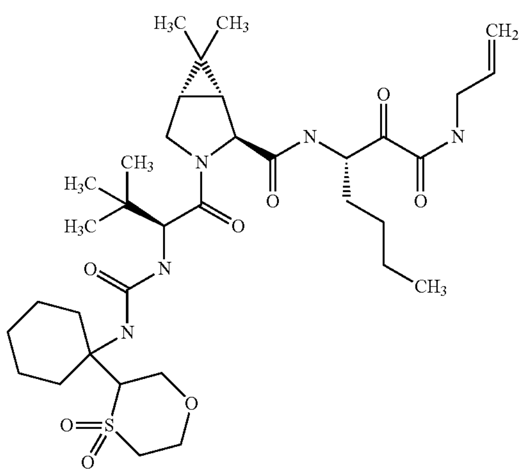 | 707.9372 | | 3 |
| 883-x | 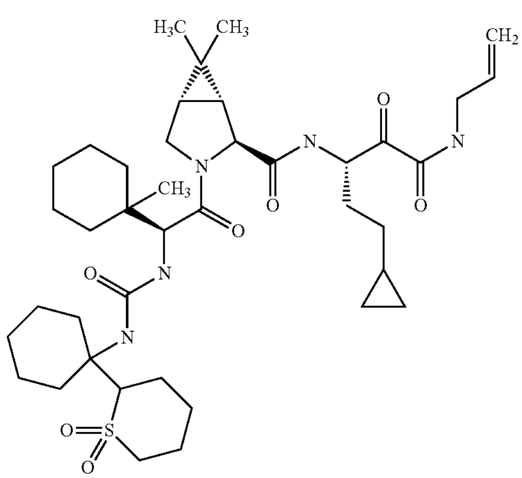 | 758.0414 | | A |

TABLE 3A-continued

| Compound # | structure | mol weight structure | Select LC-MS Data (M + H) | Ki* Range |
|---|---|---|---|---|
| 883-y | 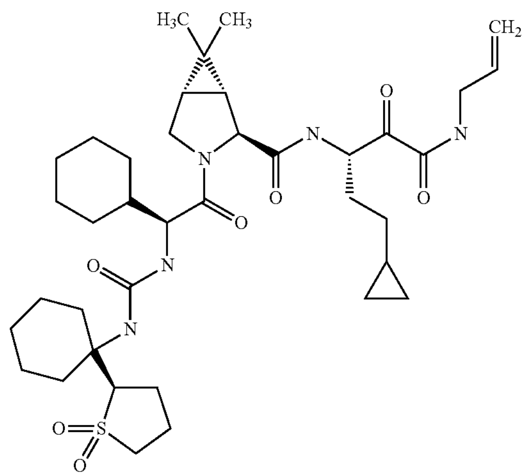 | 729.9872 | | A |
| 883-z | 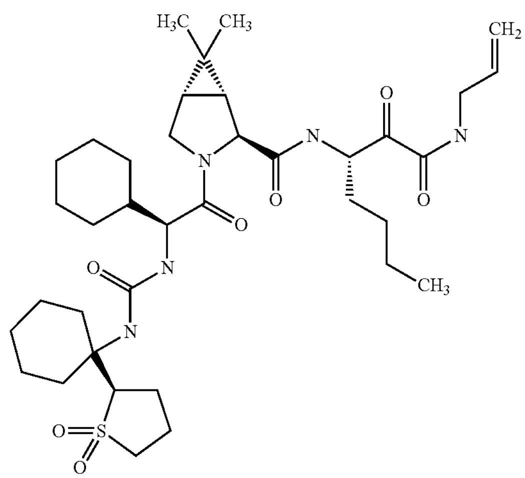 | 717.9761 | | A |
| 883-aa | 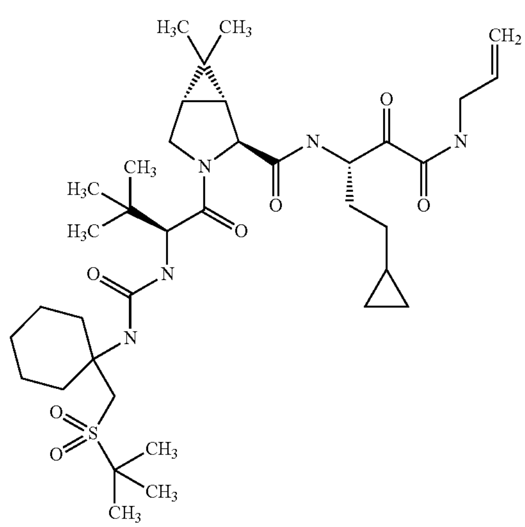 | 760.8279 | | A |

TABLE 3A-continued

| Compound # | structure | mol weight structure | Select LC-MS Data (M + H) | Ki* Range |
|---|---|---|---|---|
| 883-ab | 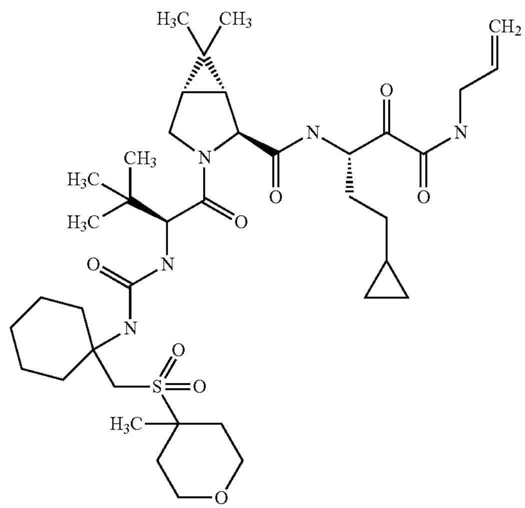 | 762.0297 | | A |
| 883-ac | 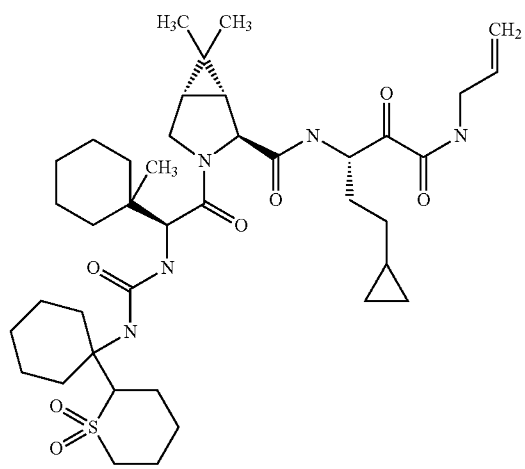 | 758.0414 | | A |
| 883-ad | 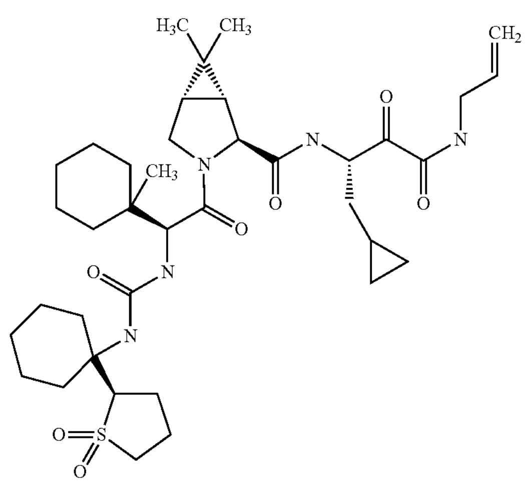 | 729.9872 | | A |

TABLE 3A-continued

| Compound # | structure | mol weight structure | Select LC-MS Data (M + H) | Ki* Range |
|---|---|---|---|---|
| 883-ae | 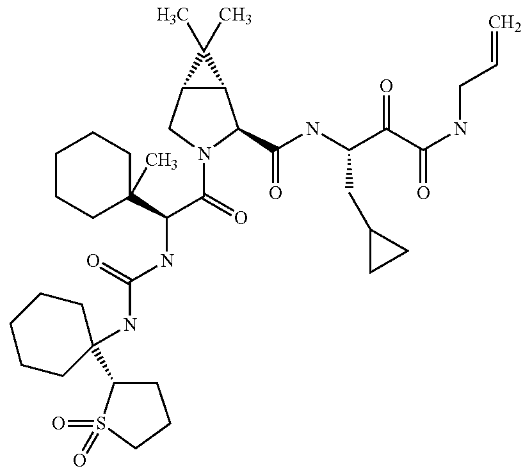 | 729.9872 | | A |
| 883-af | 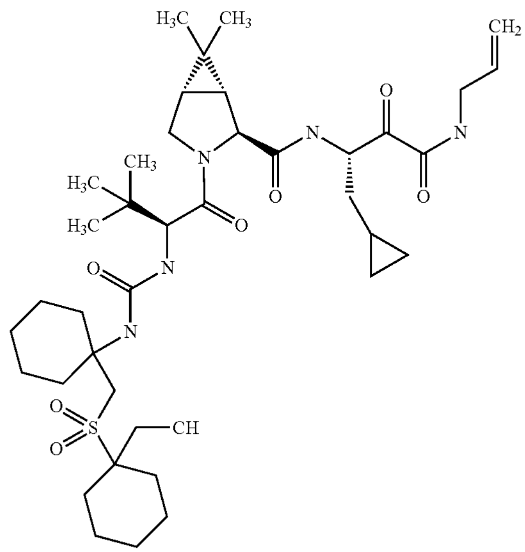 | 762.0297 | | A |
| 883-ag | 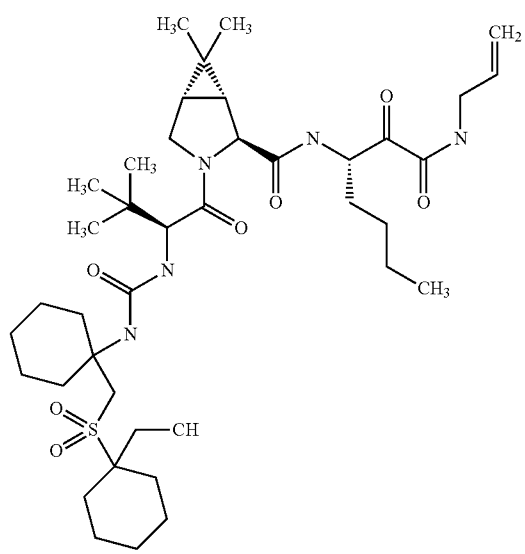 | 764.0456 | | A |

TABLE 3A-continued

| Compound # | structure | mol weight structure | Select LC-MS Data (M + H) | Ki* Range |
|---|---|---|---|---|
| 883-ah | 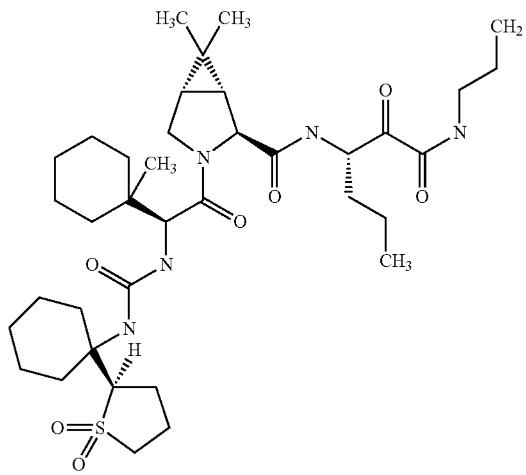 | 719.992 | | A |
| 883-ai | 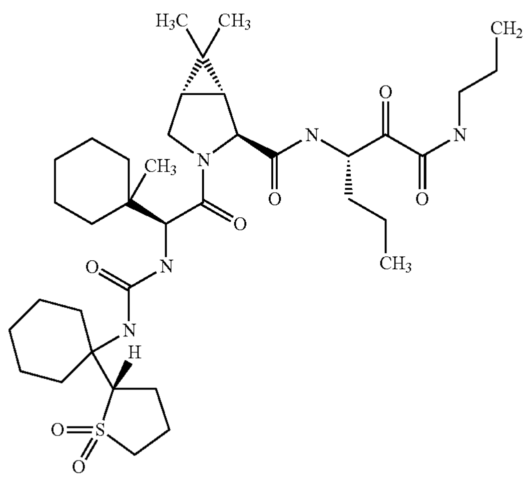 | 719.992 | | A |
| 883-aj | 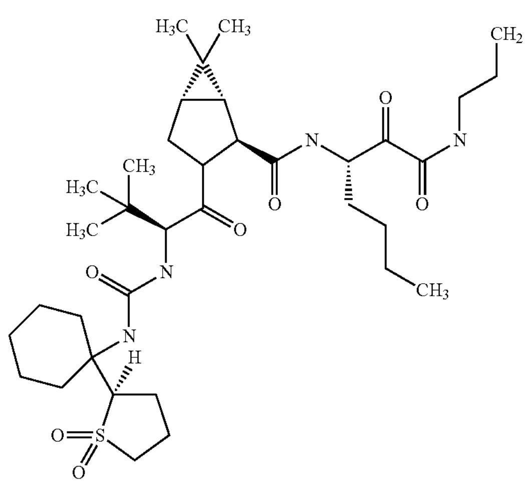 | 693.9538 | | A |

TABLE 3A-continued

| Compound # | structure | mol weight structure | Select LC-MS Data (M + H) | Ki* Range |
|---|---|---|---|---|
| 883-ak | 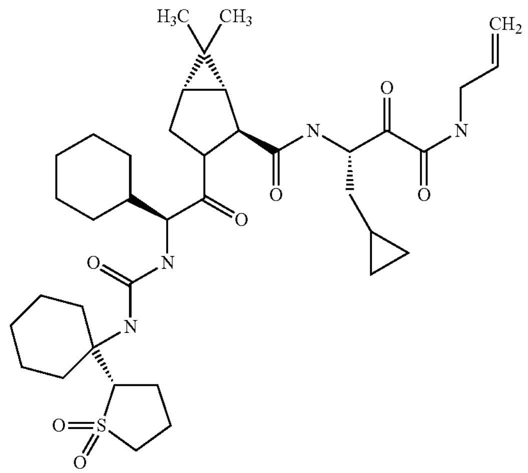 | 715.9601 | | A |
| 883-al | 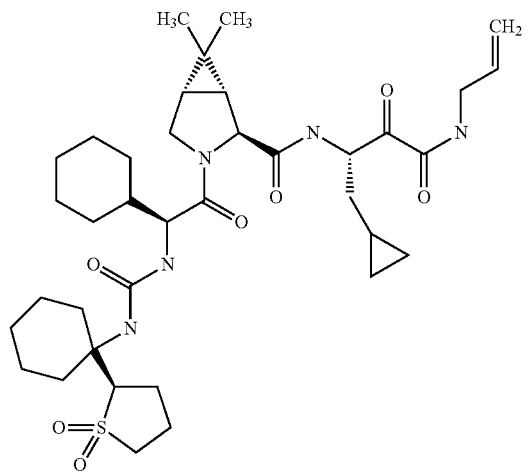 | 715.9601 | | A |
| 883-am | 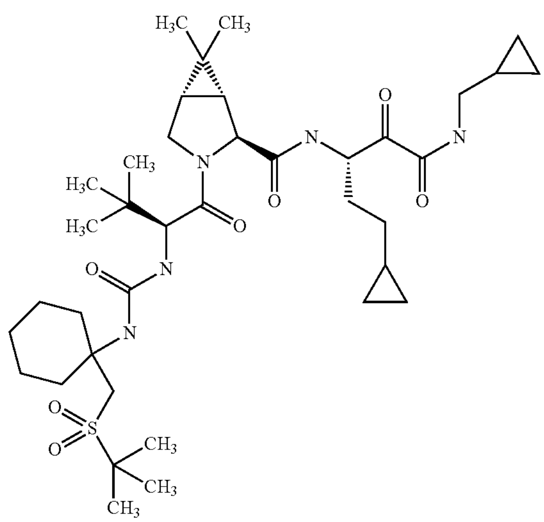 | 734.0191 | | A |

TABLE 3A-continued

| Compound # | structure | mol weight structure | Select LC-MS Data (M + H) | Ki* Range |
|---|---|---|---|---|
| 883-an | 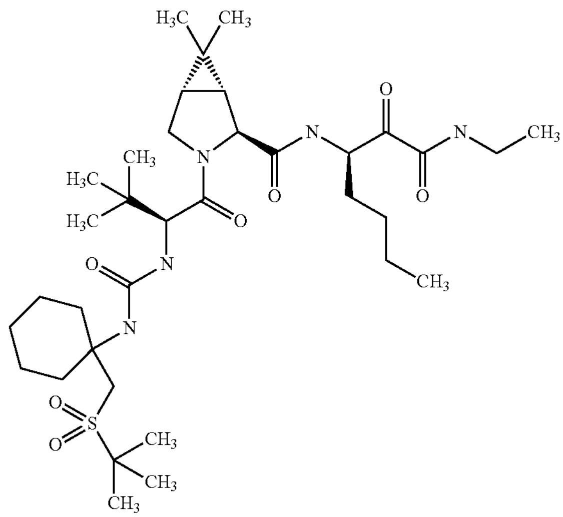 | 695.9697 | | C |
| 883-ao | 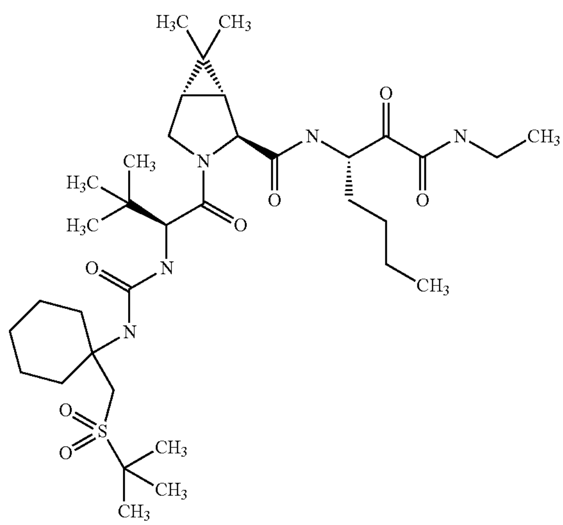 | 695.9697 | | A |
| 883-ap | 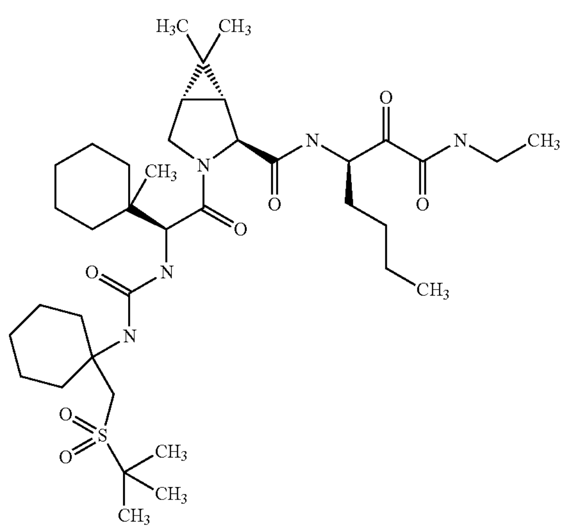 | 736.0351 | | B |

TABLE 3A-continued

| Compound # | structure | mol weight structure | Select LC-MS Data (M + H) | Ki* Range |
|---|---|---|---|---|
| 883-aq | 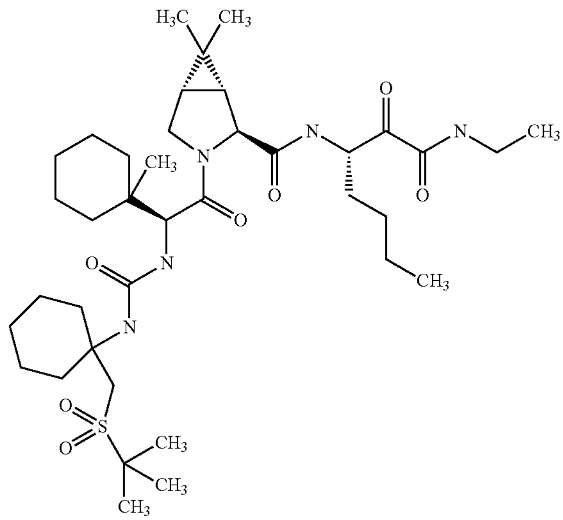 | | 736.0351 | B |
| 883-ar | 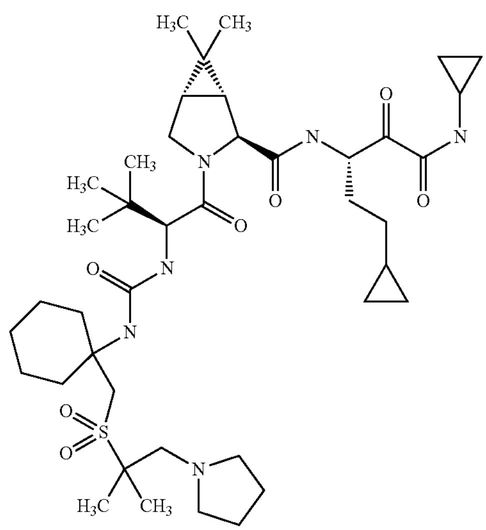 | | 789.0991 | A |
| 883-as | 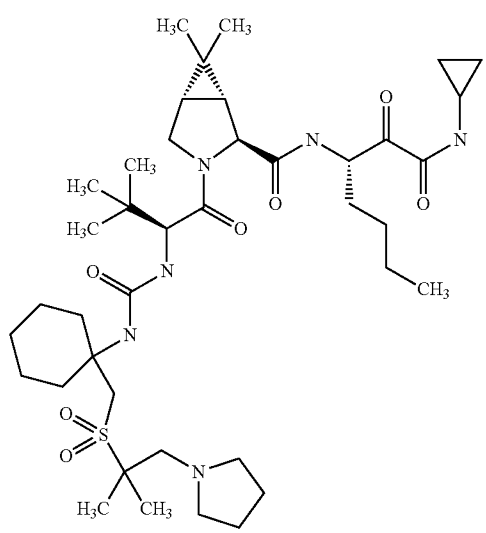 | | 777.088 | A |

TABLE 3A-continued

| Compound # | structure | mol weight structure | Select LC-MS Data (M + H) | Ki* Range |
|---|---|---|---|---|
| 883-at | 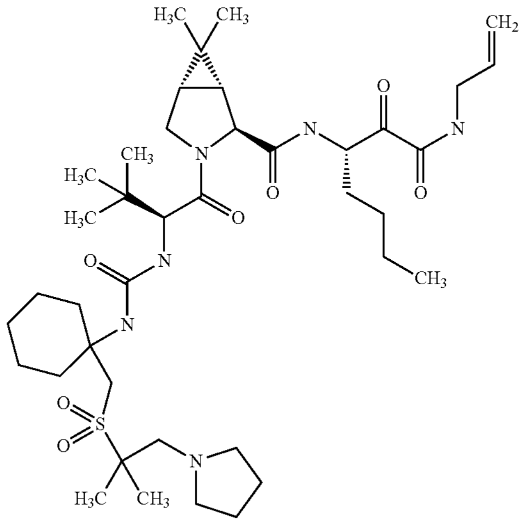 | 777.088 | | A |
| 883-au | 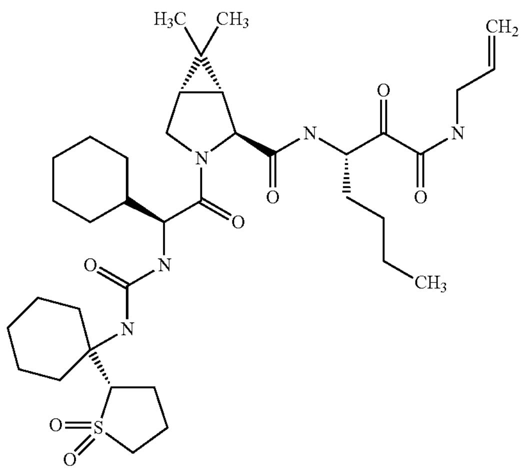 | 717.9761 | | A |
| 883-av | 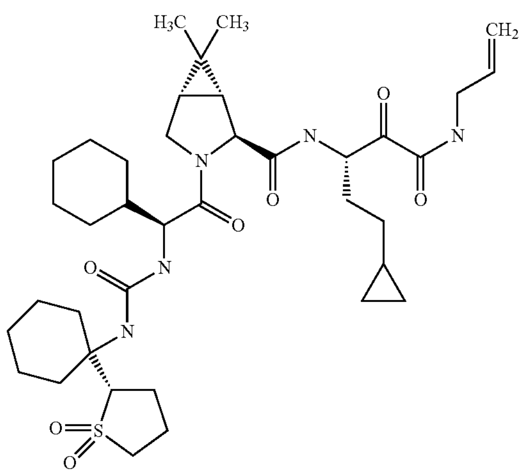 | 729.9872 | | A |

TABLE 3A-continued

| Compound # | structure | mol weight structure | Select LC-MS Data (M + H) | Ki* Range |
|---|---|---|---|---|
| 883-aw | 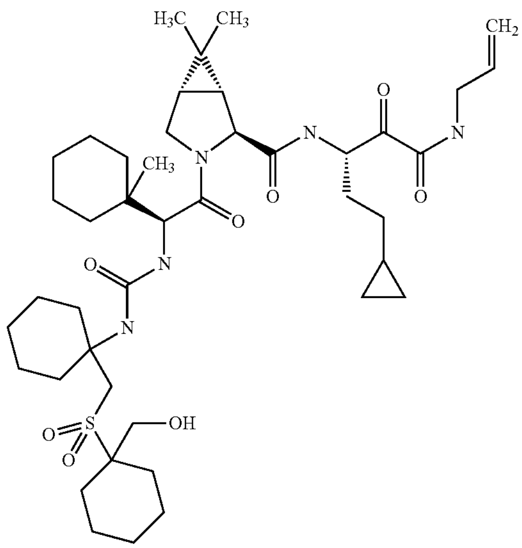 | | 816.1221 | A |
| 883-ax | 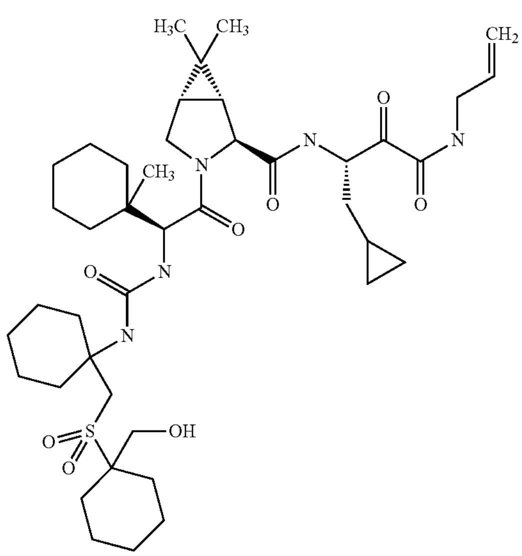 | | 802.095 | A |

TABLE 3A-continued

| Compound # | structure | mol weight structure | Select LC-MS Data (M + H) | Ki* Range |
|---|---|---|---|---|
| 883-ay | 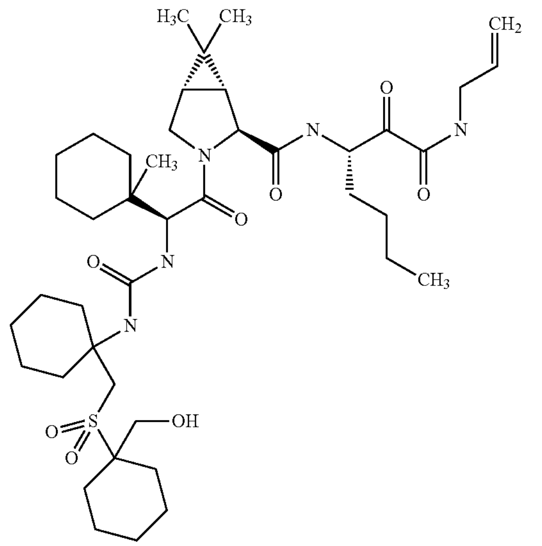 | 804.1109 | | A |
| 883-az | 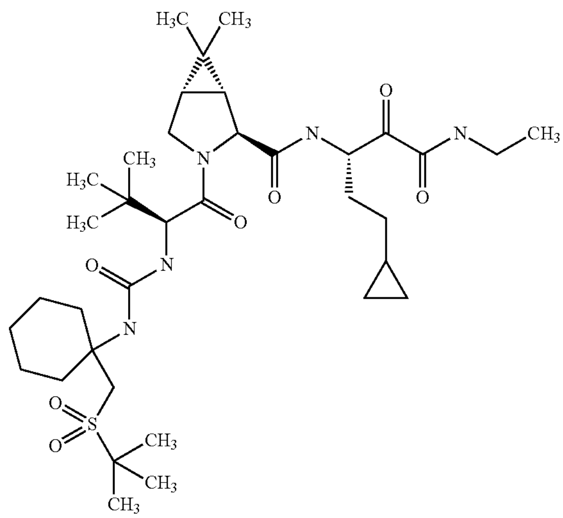 | 707.9809 | | A |
| 883-ba | 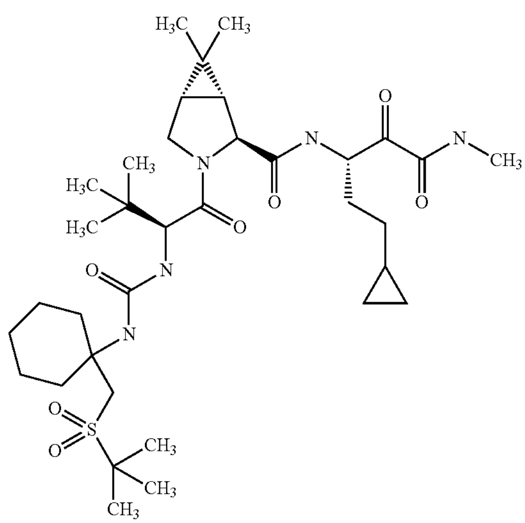 | 693.9538 | | A |

TABLE 3A-continued

| Compound # | structure | mol weight structure | Select LC-MS Data (M + H) | Ki* Range |
|---|---|---|---|---|
| 883-bb | 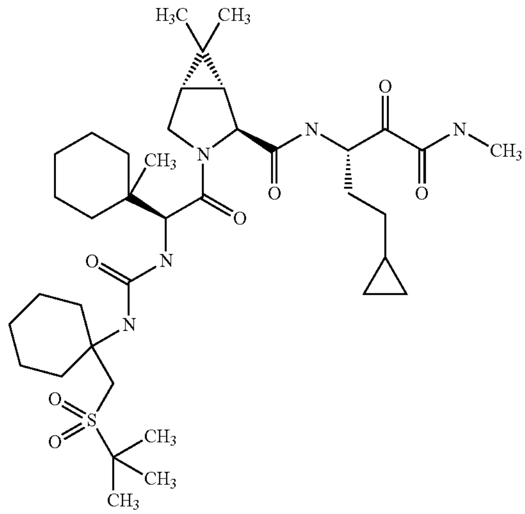 | 734.0191 | | A |
| 883-bc | 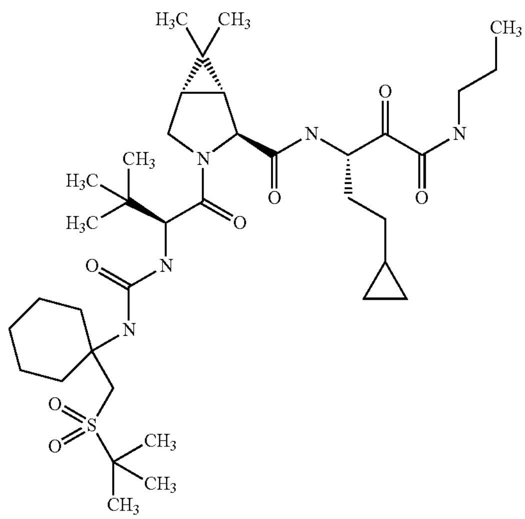 | 722.008 | | A |
| 883-bd | 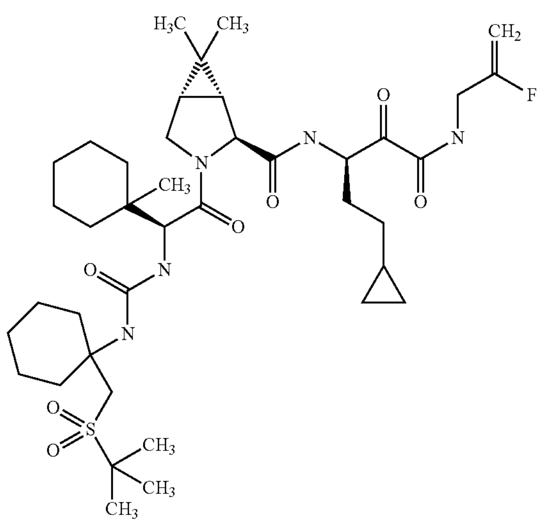 | 778.0478 | | b |

TABLE 3A-continued

| Compound # | structure | mol weight structure | Select LC-MS Data (M + H) | Ki* Range |
|---|---|---|---|---|
| 883-be | 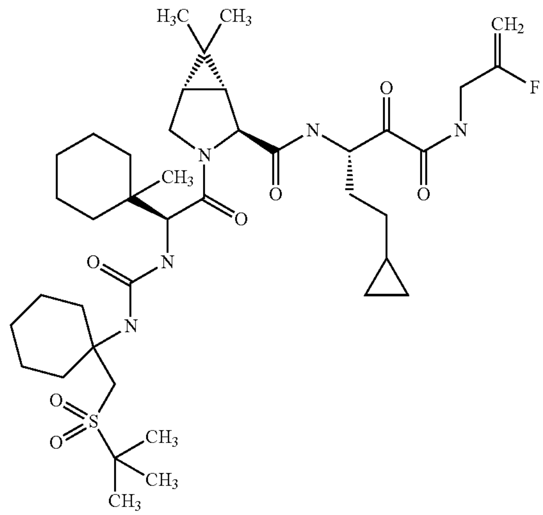 | | 778.0478 | A |
| 883-bf | 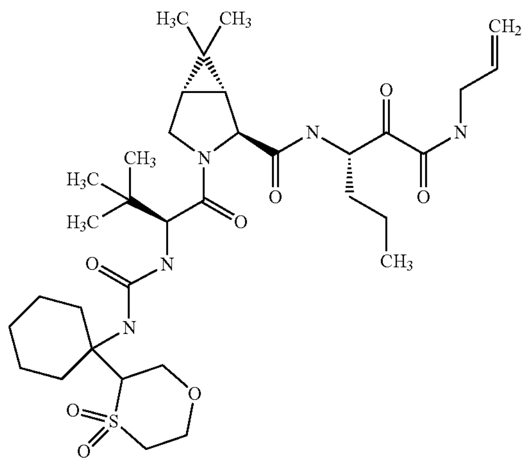 | | 693.9102 | A |
| 883-bg | 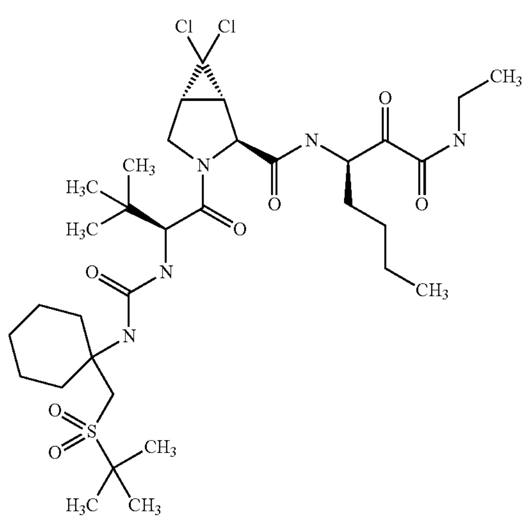 | | 736.8056 | B |

TABLE 3A-continued

| Compound # | structure | mol weight structure | Select LC-MS Data (M + H) | Ki* Range |
|---|---|---|---|---|
| 883-bh | 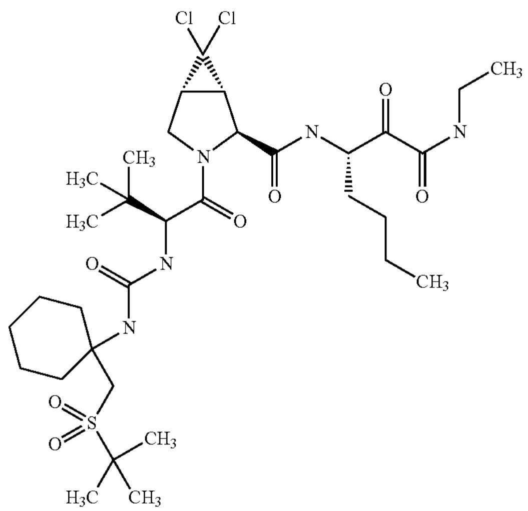 | 736.8056 | | A |
| 883-bi | 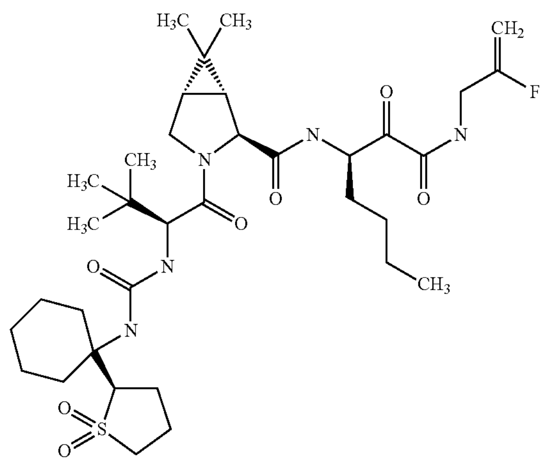 | 709.9283 | | B |
| 883-bj | 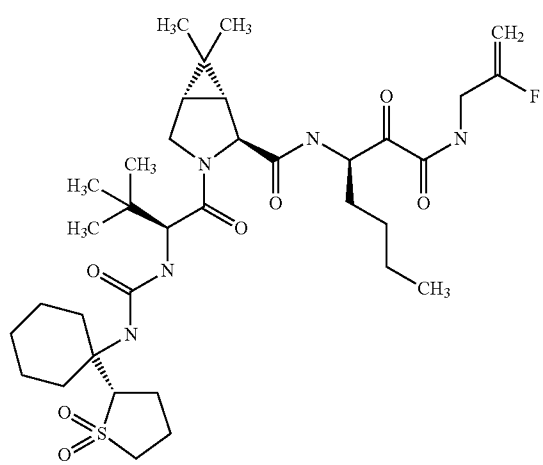 | 709.9283 | | B |

TABLE 3A-continued

| Compound # | structure | mol weight structure | Select LC-MS Data (M + H) | Ki* Range |
|---|---|---|---|---|
| 883-bk | 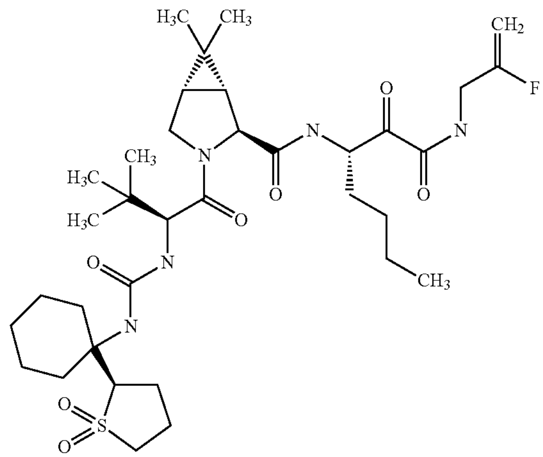 | 709.9283 | | A |
| 883-bl | 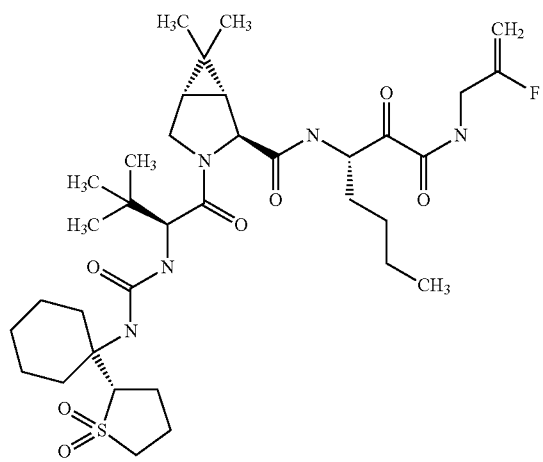 | 709.9283 | | A |
| 883-bm | 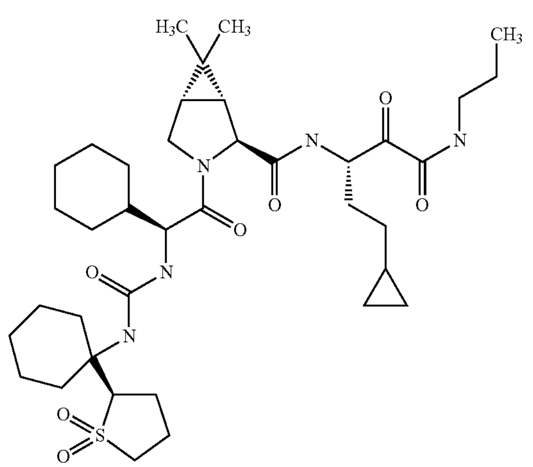 | 732.0032 | | A |

TABLE 3A-continued

| Compound # | structure | mol weight structure | Select LC-MS Data (M + H) | Ki* Range |
|---|---|---|---|---|
| 883-bn | 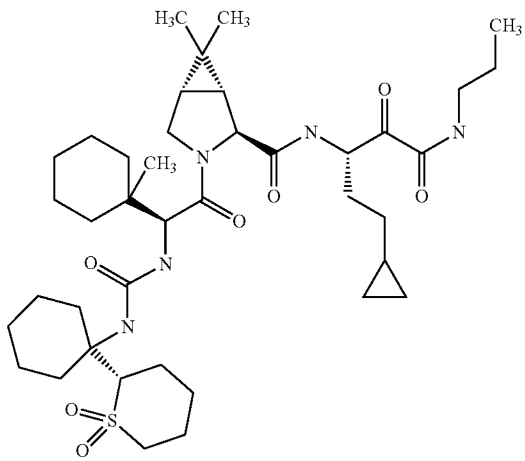 | 760.0574 | | A |
| 883-bo | 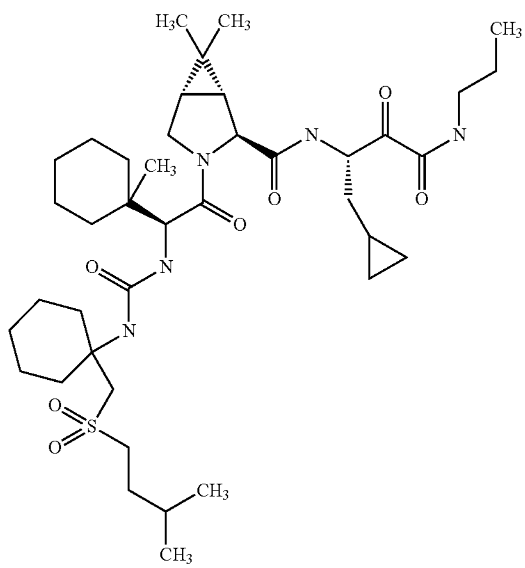 | 762.0733 | | A |
| 883-bp | 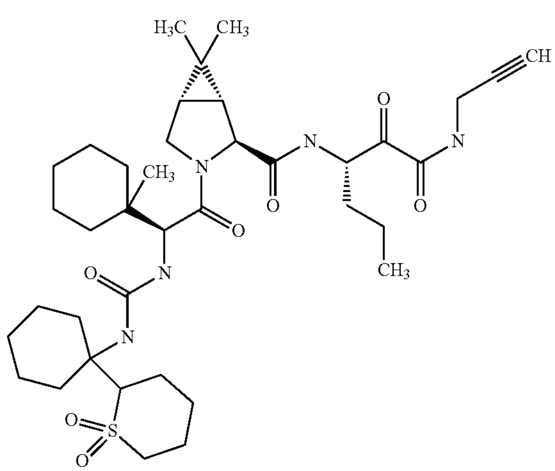 | 729.9872 | | A |

TABLE 3A-continued
| Compound # | structure | mol weight structure | Select LC-MS Data (M + H) | Ki* Range |
|---|---|---|---|---|
| 883-bq | 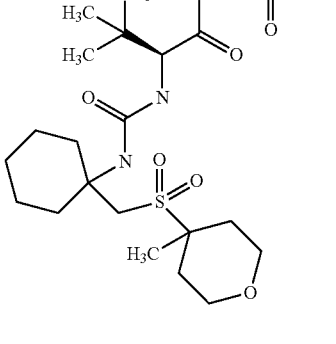 | 738.0074 | | A |
| 883-br | 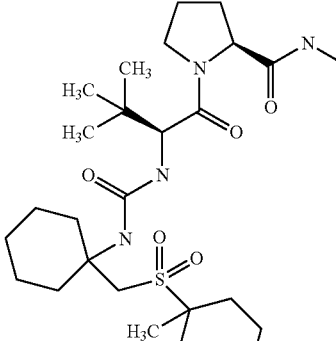 | 752.0345 | | A |
| 883-bs | 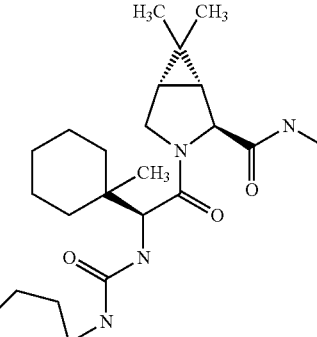 | 748.0462 | | A |

TABLE 3A-continued

| Compound # | structure | mol weight structure | Select LC-MS Data (M + H) | Ki* Range |
|---|---|---|---|---|
| 883-bt | 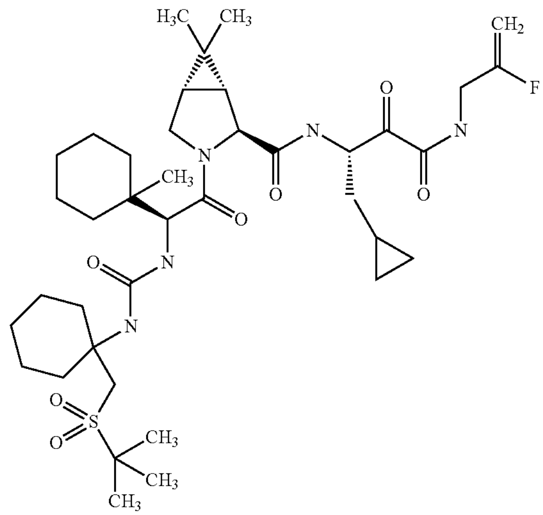 | 764.0207 | | A |
| 883-bu | 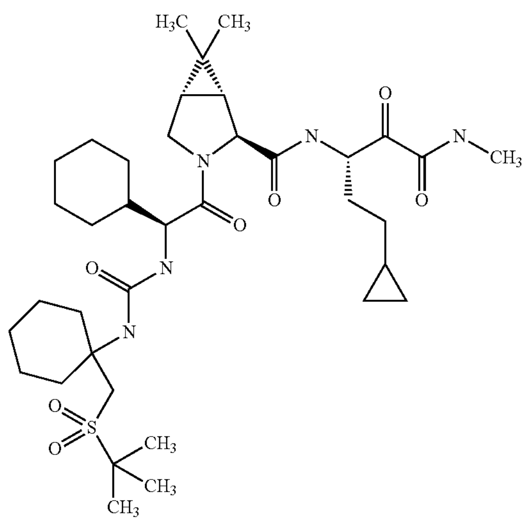 | 719.992 | | A |
| 883-bv | 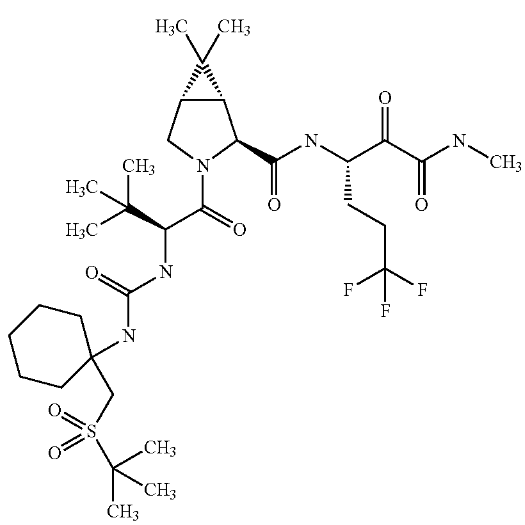 | 721.8868 | | A |

TABLE 3A-continued

| Compound # | structure | mol weight structure | Select LC-MS Data (M + H) | Ki* Range |
|---|---|---|---|---|
| 883-bw | 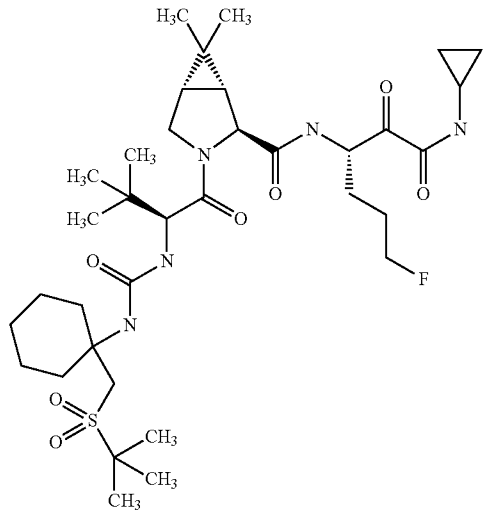 | 711.9442 | | A |
| 883-bx | 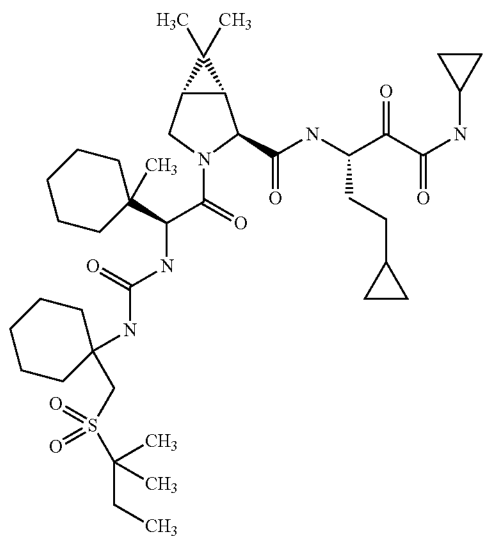 | 774.0844 | | A |
| 883-by | 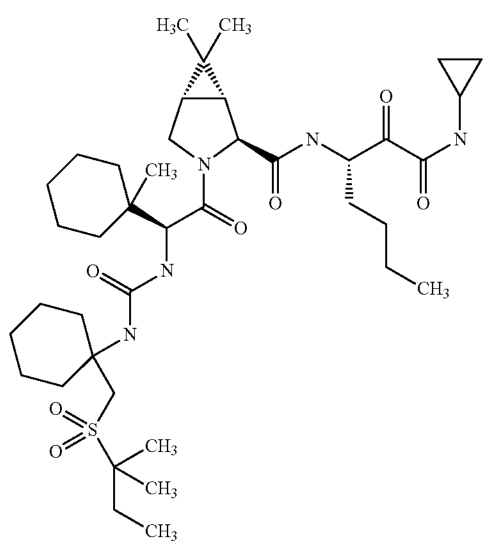 | 762.0733 | | A |

TABLE 3A-continued

| Compound # | structure | mol weight structure | Select LC-MS Data (M + H) | Ki* Range |
|---|---|---|---|---|
| 883-bz | 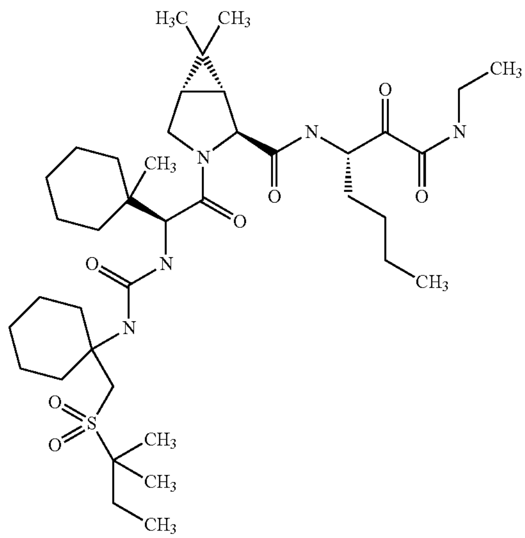 | 750.0621 | | A |
| 883-ca | 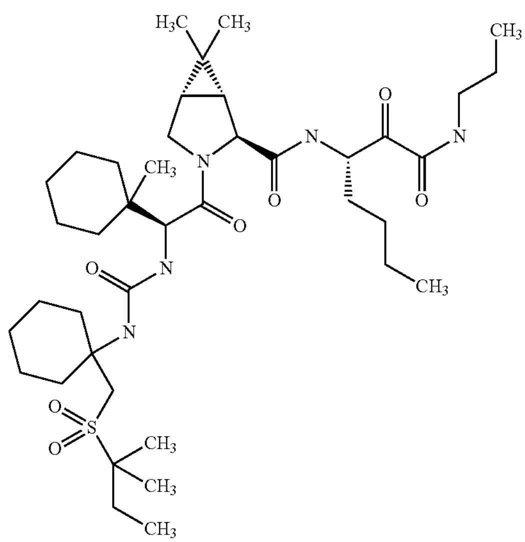 | 764.0892 | | A |
| 883-cb | 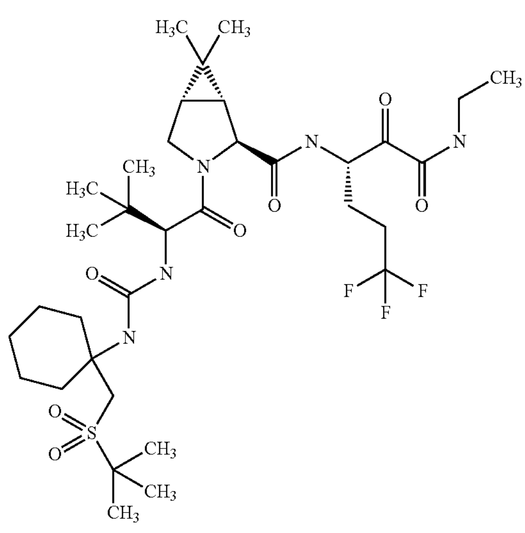 | 735.9139 | | A |

TABLE 3A-continued

| Compound # | structure | mol weight structure | Select LC-MS Data (M + H) | Ki* Range |
|---|---|---|---|---|
| 883-cc | 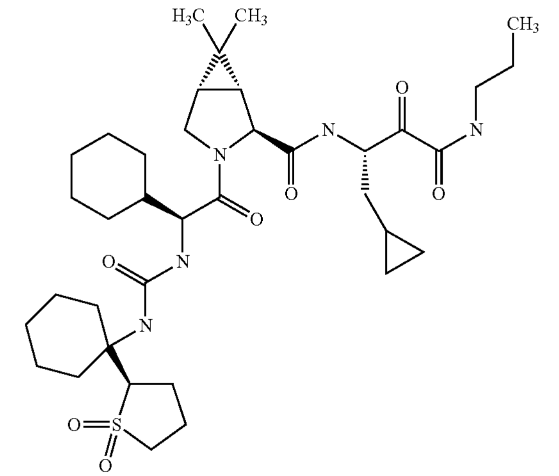 | 717.9761 | | A |
| 883-cd | 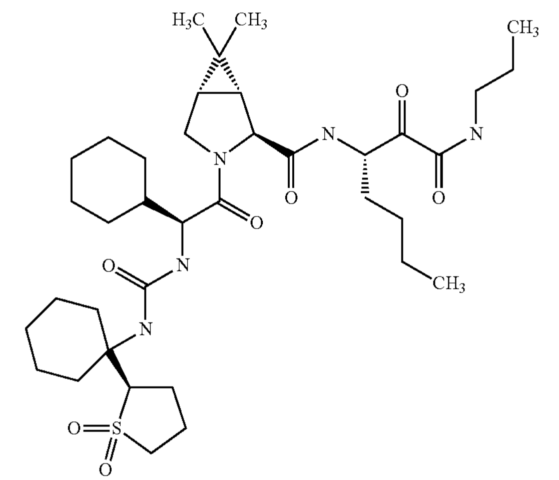 | 719.992 | | A |
| 883-ce | 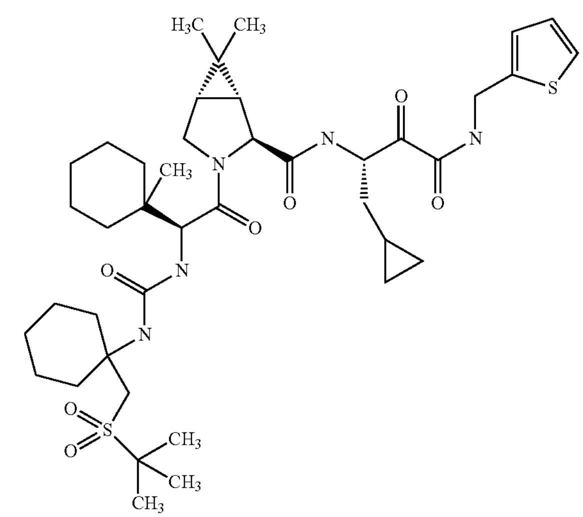 | 802.1166 | | A |

TABLE 3A-continued

| Compound # | structure | mol weight structure | Select LC-MS Data (M + H) | Ki* Range |
|---|---|---|---|---|
| 883-cf | 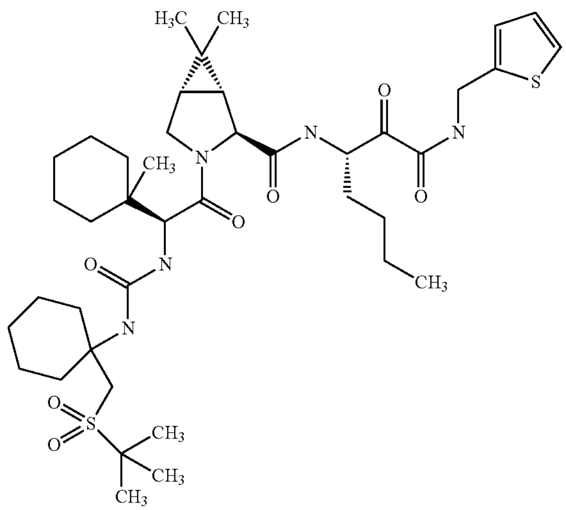 | 804.1325 | | A |
| 883-cg | 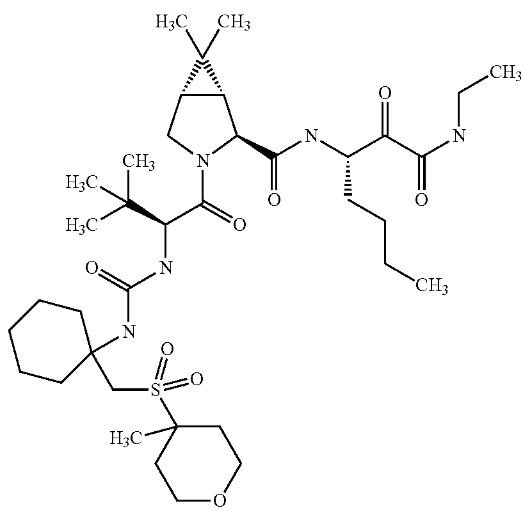 | 738.0074 | | A |
| 883-ch | 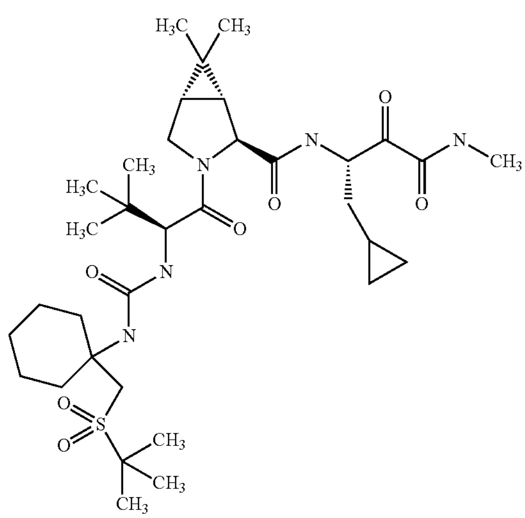 | 679.9267 | | A |

TABLE 3A-continued

| Compound # | structure | mol weight structure | Select LC-MS Data (M + H) | Ki* Range |
|---|---|---|---|---|
| 883-ci | 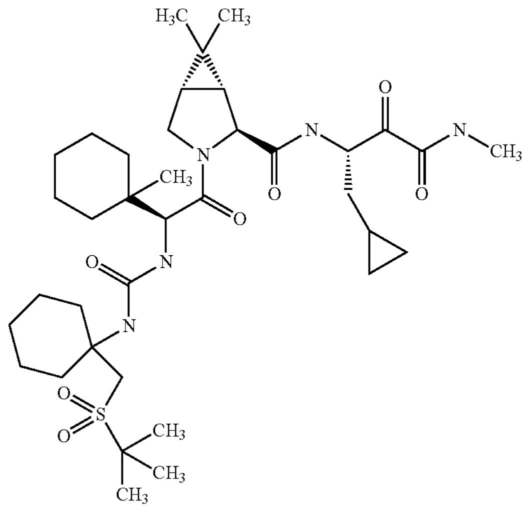 | 719.992 | | A |
| 883-cj | 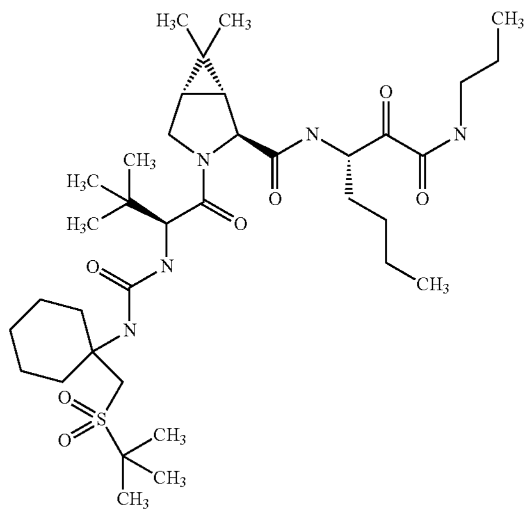 | 709.9968 | | A |
| 883-ck | 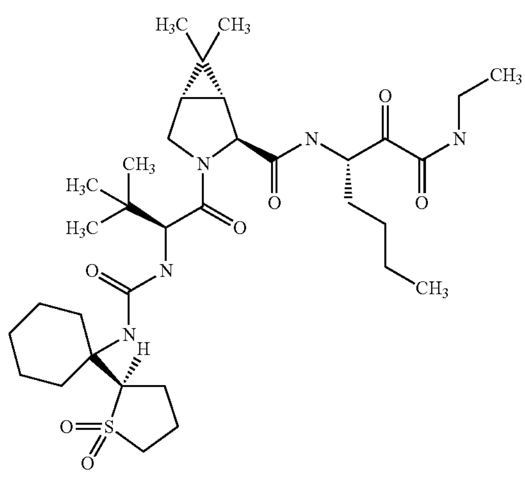 | 679.9267 | | A |

TABLE 3A-continued

| Compound # | structure | mol weight structure | Select LC-MS Data (M + H) | Ki* Range |
|---|---|---|---|---|
| 883-cl | 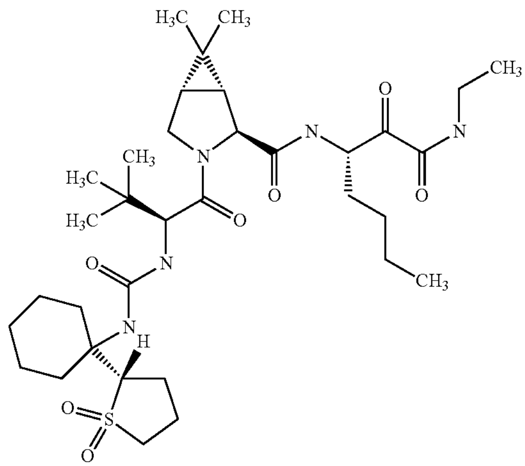 | 679.9267 | | A |
| 883-cm | 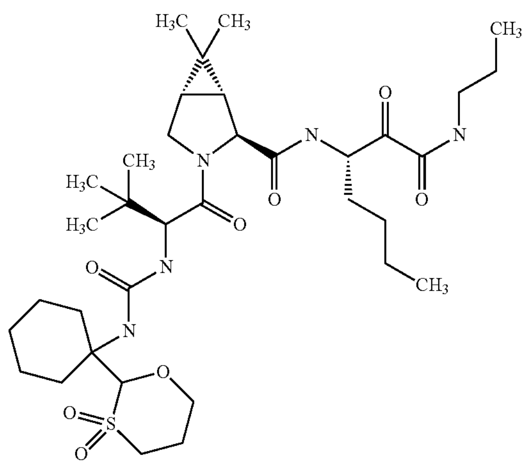 | 709.9532 | | A |
| 883-cn | 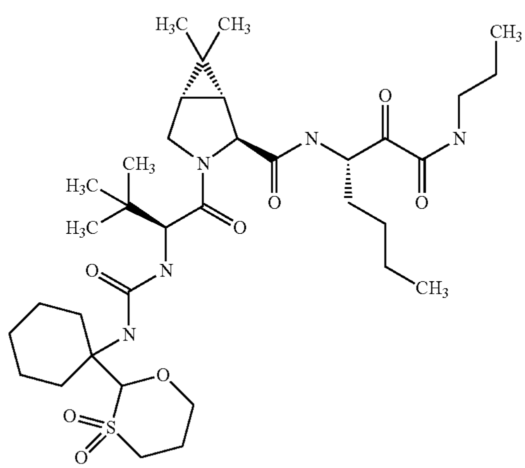 | 709.9532 | | A |

TABLE 3A-continued

| Compound # | structure | mol weight structure | Select LC-MS Data (M + H) | Ki* Range |
|---|---|---|---|---|
| 883-co | 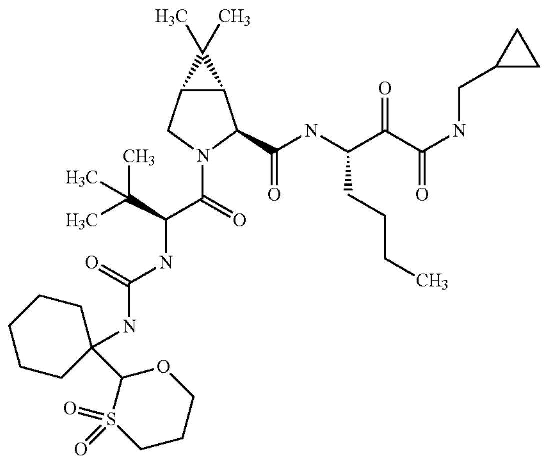 | | 721.9643 | A |
| 883-cp | 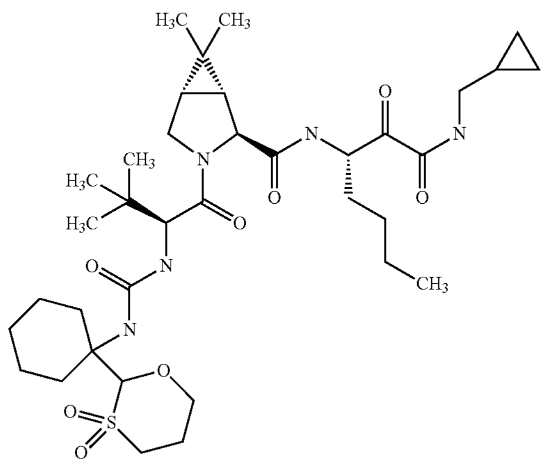 | | 721.9643 | A |
| 883-cq | 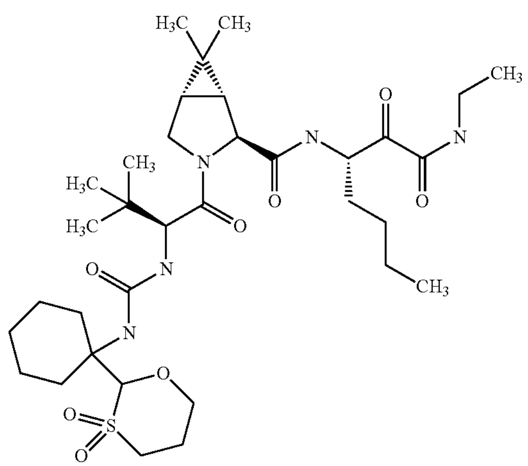 | | 695.9261 | A |

TABLE 3A-continued

| Compound # | structure | mol weight structure | Select LC-MS Data (M + H) | Ki* Range |
|---|---|---|---|---|
| 883-cr | 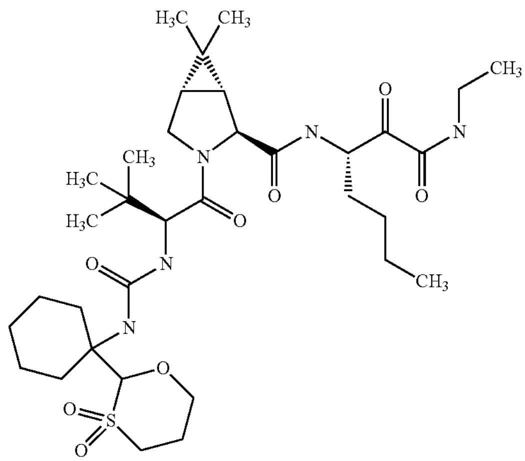 | 695.9261 | | B |
| 883-cs | 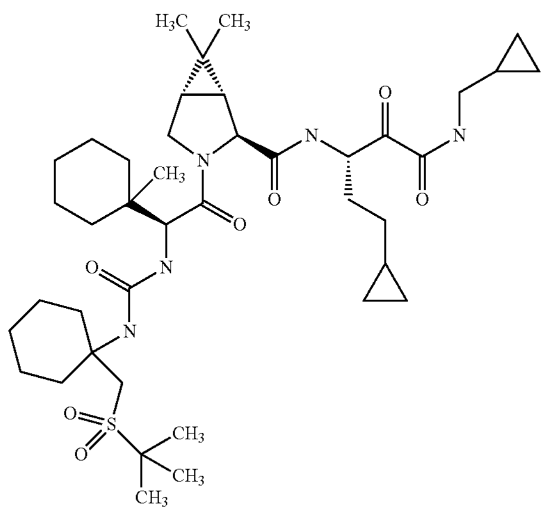 | 774.0844 | | A |
| 883-ct | 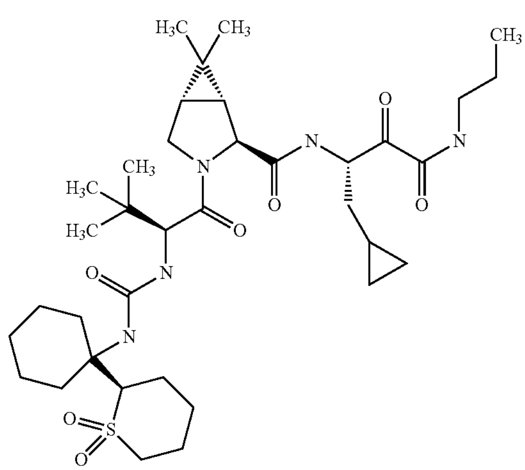 | 705.9649 | | A |

TABLE 3A-continued

| Compound # | structure | mol weight structure | Select LC-MS Data (M + H) | Ki* Range |
|---|---|---|---|---|
| 883-cu | 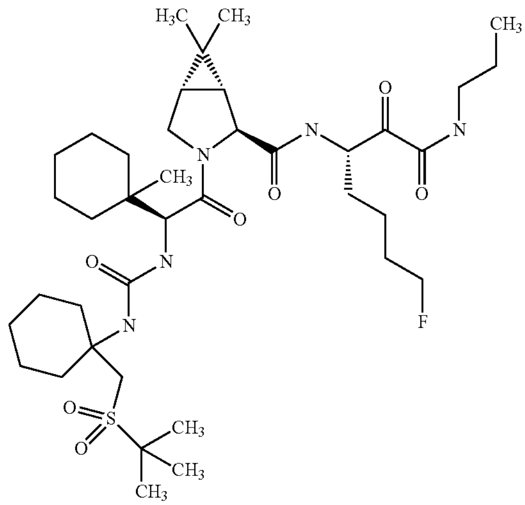 | 768.0526 | | A |
| 883-cv | 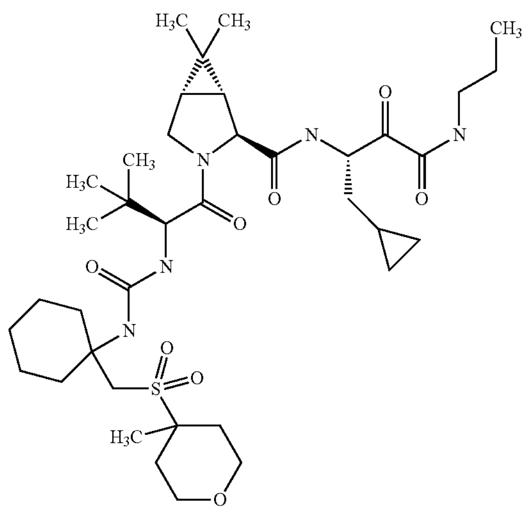 | 750.0185 | | A |
| 883-cw | 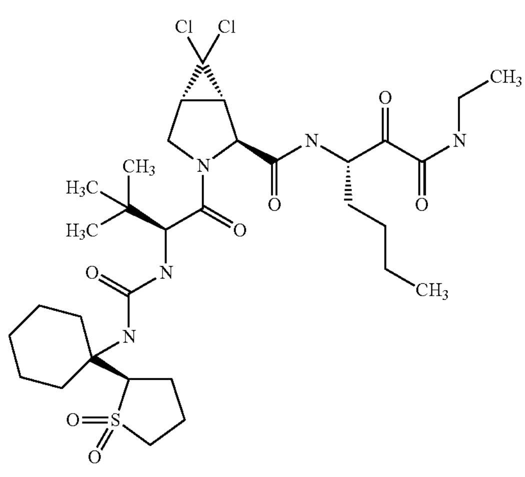 | 720.7626 | | A |

TABLE 3A-continued

| Compound # | structure | mol weight structure | Select LC-MS Data (M + H) | Ki* Range |
|---|---|---|---|---|
| 883-cx | 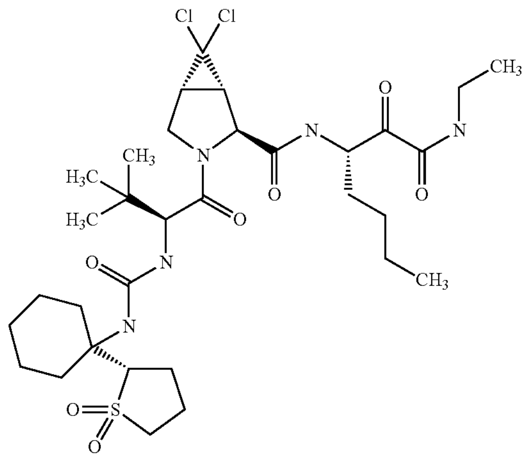 | 720.7626 | | A |
| 883-cy | 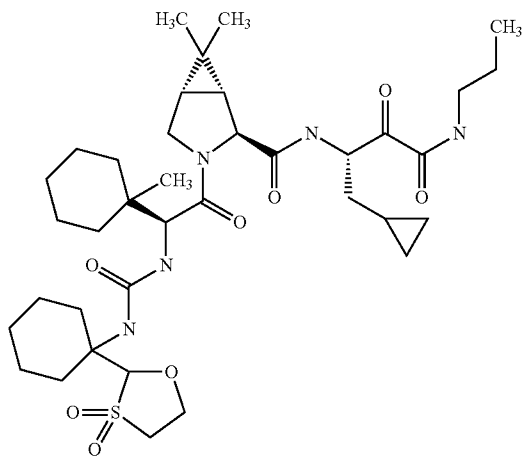 | 733.9755 | | A |
| 883-cz | 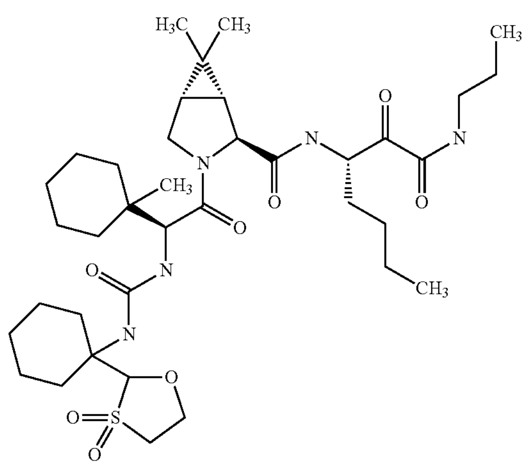 | 735.9914 | | A |

TABLE 3A-continued

| Compound # | structure | mol weight structure | Select LC-MS Data (M + H) | Ki* Range |
|---|---|---|---|---|
| 883-da | 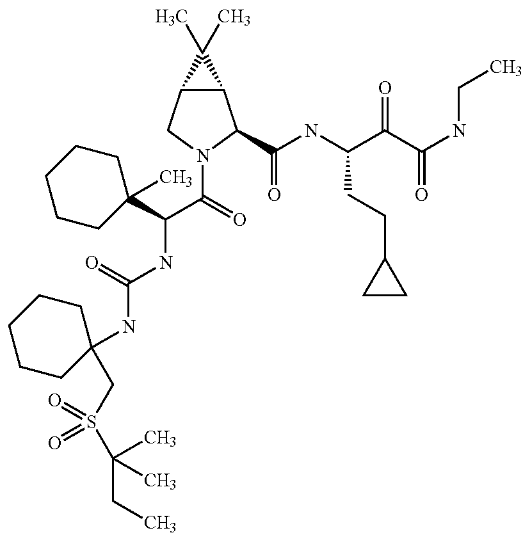 | | 762.0733 | A |
| 883-db | 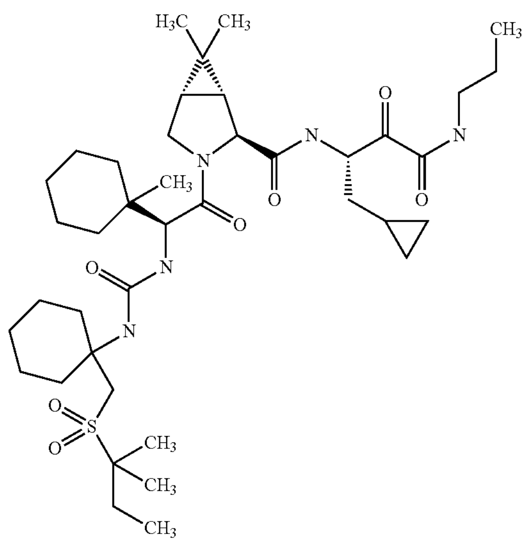 | | 762.0733 | A |
| 883-dc | 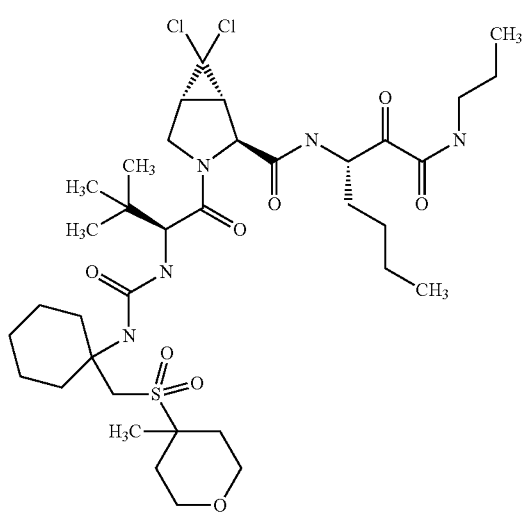 | | 792.8703 | A |

TABLE 3A-continued

| Compound # | structure | mol weight structure | Select LC-MS Data (M + H) | Ki* Range |
|---|---|---|---|---|
| 883-dd | 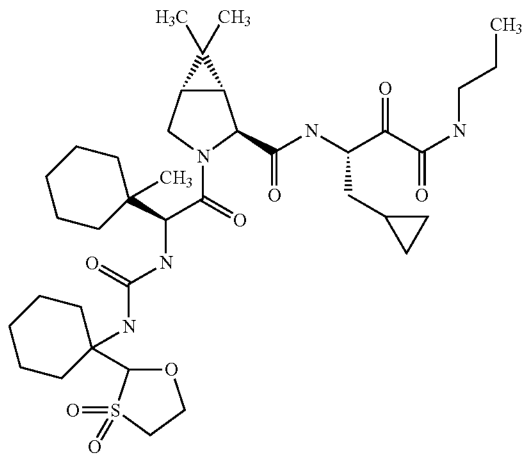 | 733.9755 | | A |
| 883-de | 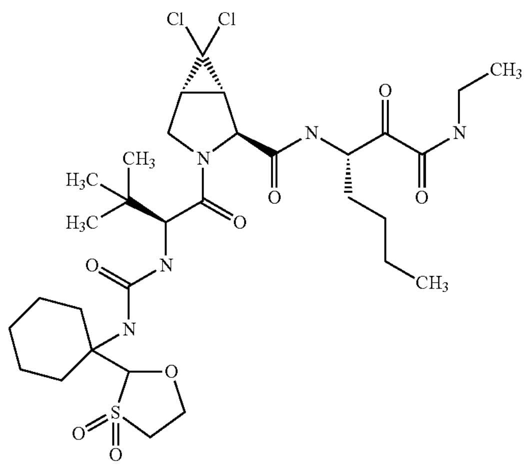 | 722.7349 | | A |
| 883-df | 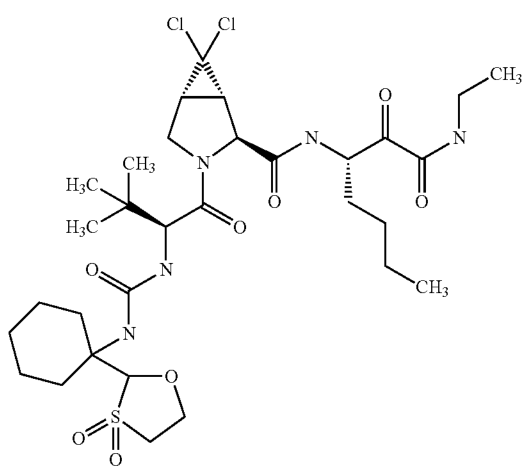 | 722.7349 | | A |

TABLE 3A-continued

| Compound # | structure | mol weight structure | Select LC-MS Data (M + H) | Ki* Range |
|---|---|---|---|---|
| 883-dg | 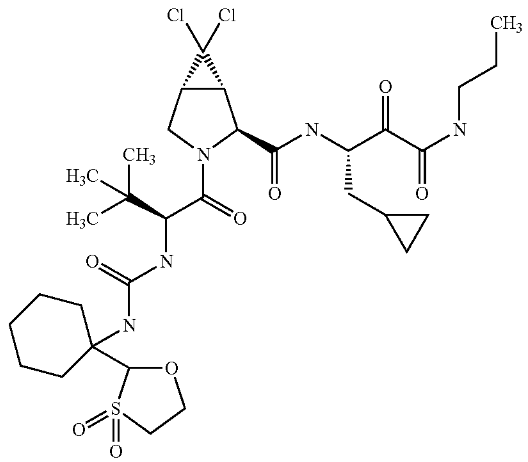 | 734.746 | | A |
| 883-dh | 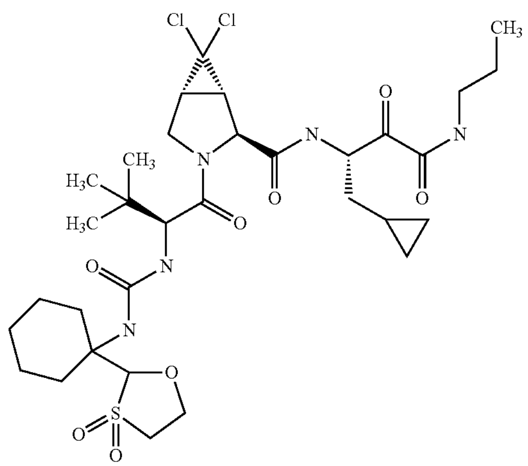 | 734.746 | | A |
| 883-di | 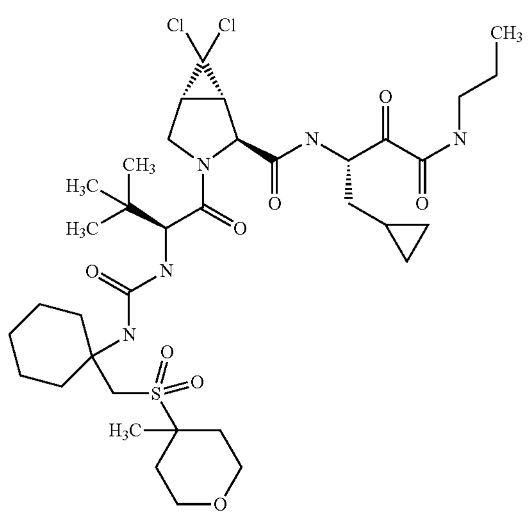 | 790.8544 | | A |

TABLE 3A-continued

| Compound # | structure | mol weight structure | Select LC-MS Data (M + H) | Ki* Range |
|---|---|---|---|---|
| 883-dj | 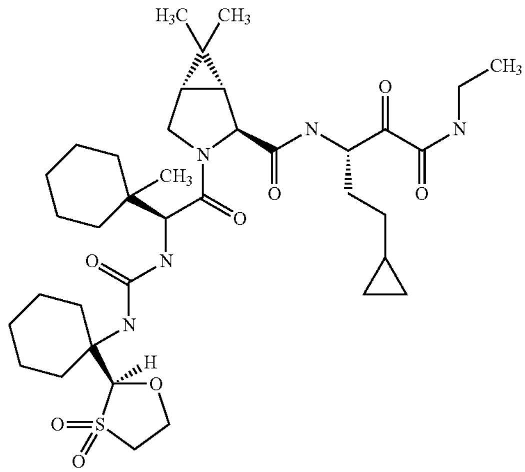 | 733.9755 | | A |
| 883-dk | 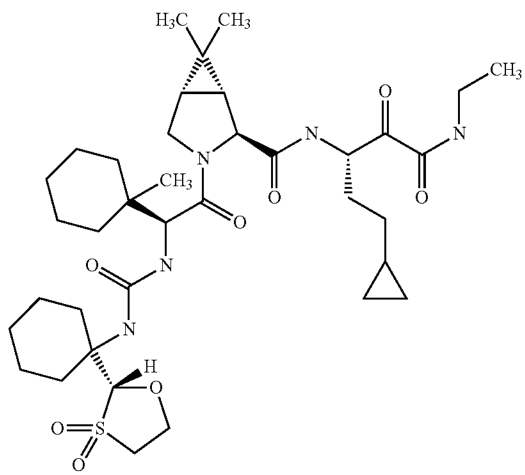 | 733.9755 | | A |
| 883-dl | 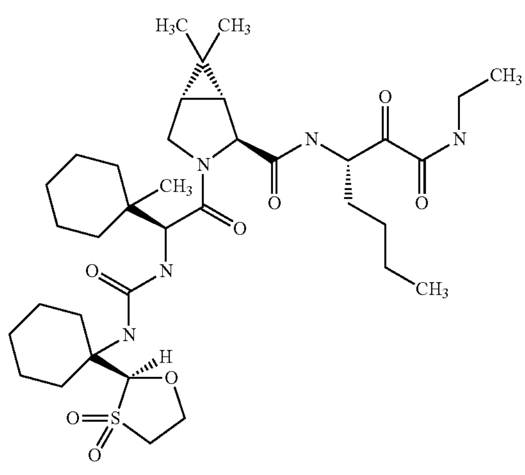 | 721.9643 | | A |

TABLE 3A-continued

| Compound # | structure | mol weight structure | Select LC-MS Data (M + H) | Ki* Range |
|---|---|---|---|---|
| 883-dm | 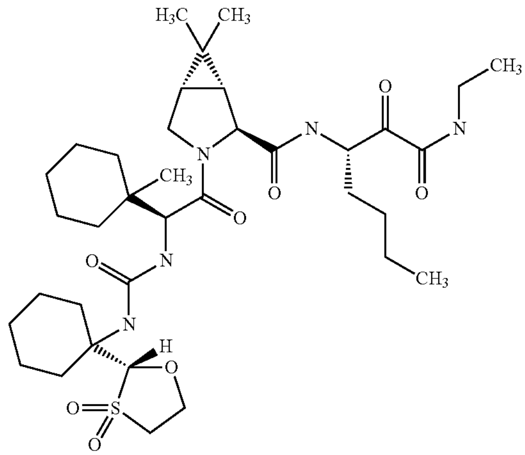 | 721.9643 | | A |
| 883-dn | 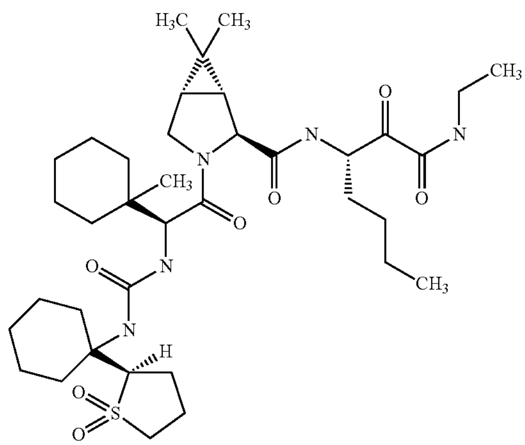 | 719.992 | | A |
| 883-do | 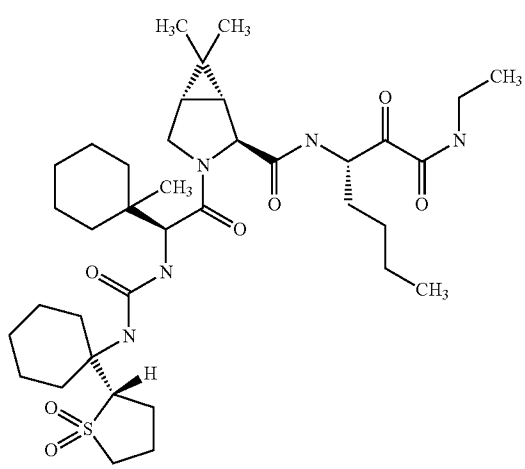 | 719.992 | | A |

TABLE 3A-continued

| Compound # | structure | mol weight structure | Select LC-MS Data (M + H) | Ki* Range |
|---|---|---|---|---|
| 883-dp | 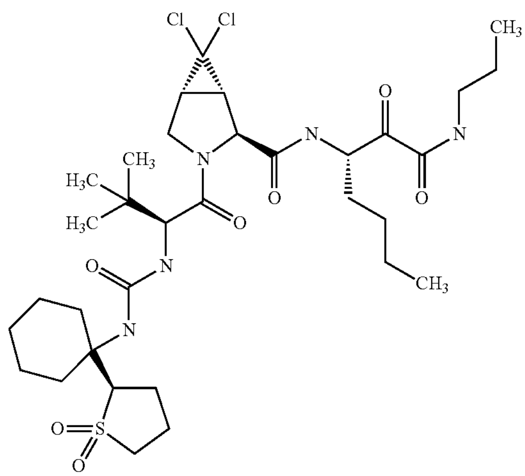 | 734.7897 | | A |
| 883-dq | 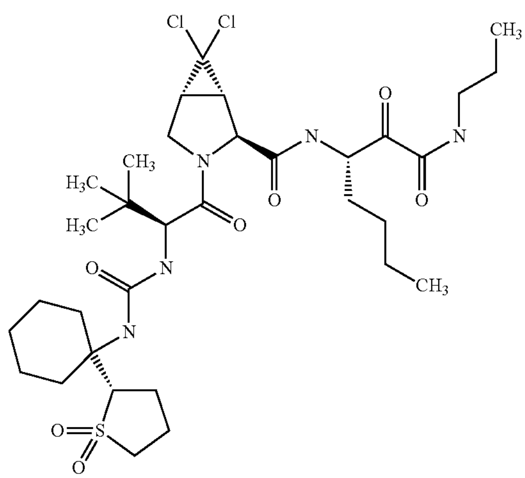 | 734.7897 | | A |
| 883-dr | 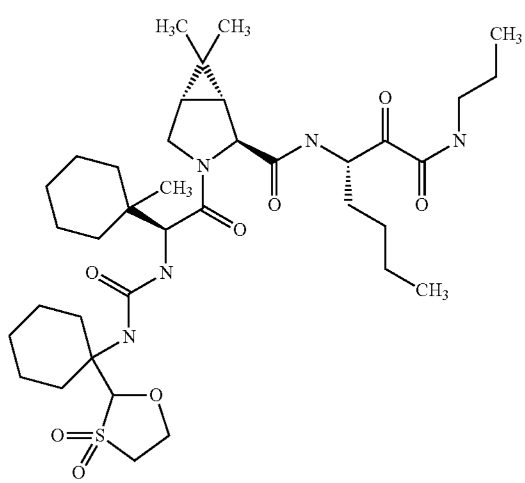 | 735.9914 | | A |

TABLE 3A-continued

| Compound # | structure | mol weight structure | Select LC-MS Data (M + H) | Ki* Range |
|---|---|---|---|---|
| 883-ds | 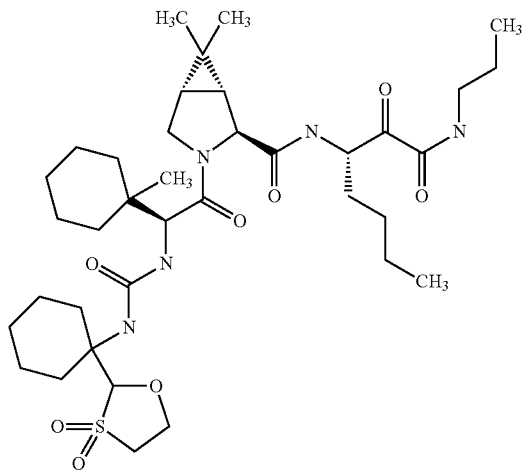 | 735.9914 | | A |
| 883-dt | 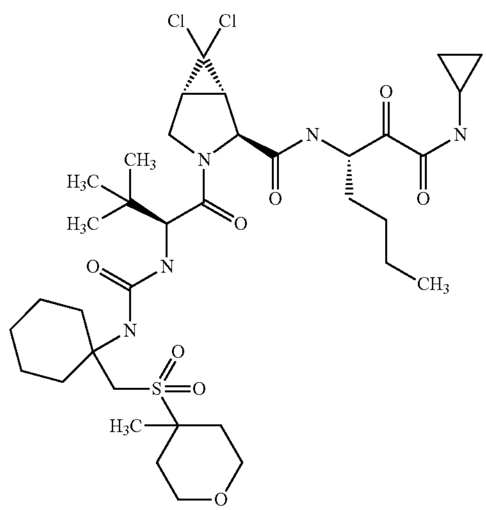 | 790.8544 | | A |
| 883-du | 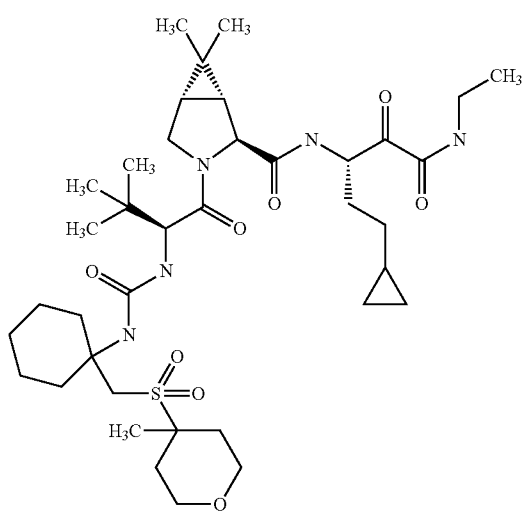 | 750.0185 | | A |

TABLE 3A-continued

| Compound # | structure | mol weight structure | Select LC-MS Data (M + H) | Ki* Range |
|---|---|---|---|---|
| 883-dv | 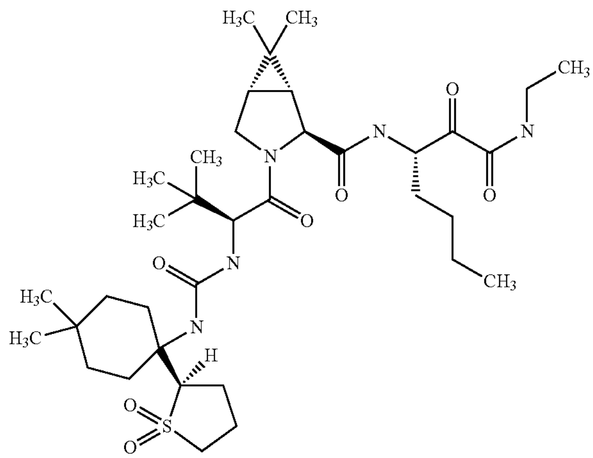 | 707.9809 | | A |
| 883-dw | 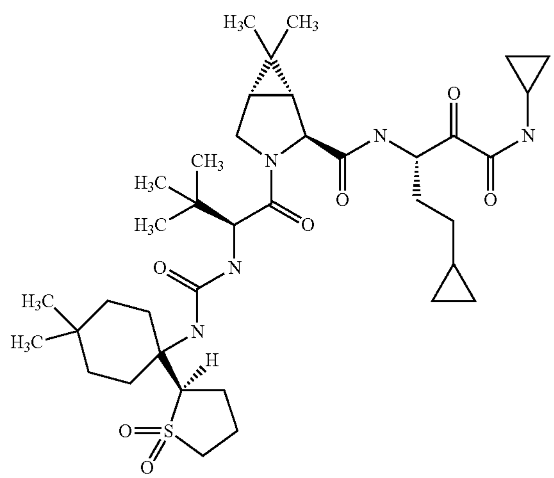 | 732.0032 | | A |
| 883-dx | 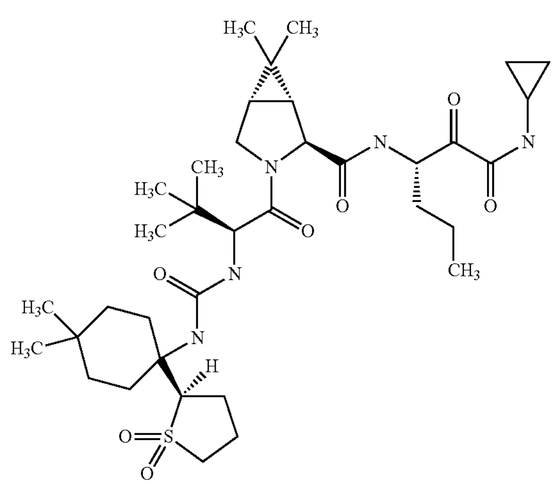 | 705.9649 | | A |

TABLE 3A-continued

| Compound # | structure | mol weight structure | Select LC-MS Data (M + H) | Ki* Range |
|---|---|---|---|---|
| 883-dy | 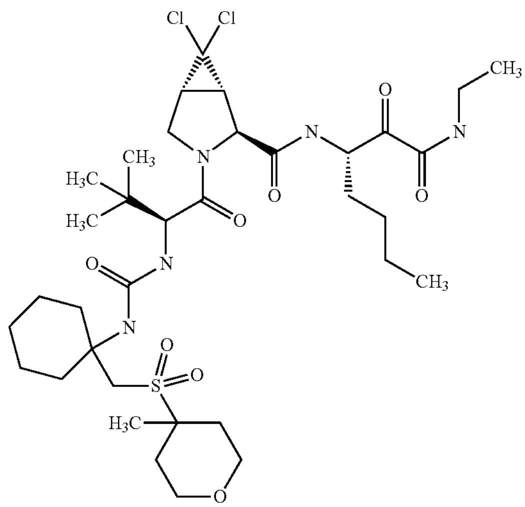 | 778.8432 | | A |
| 883-dz | 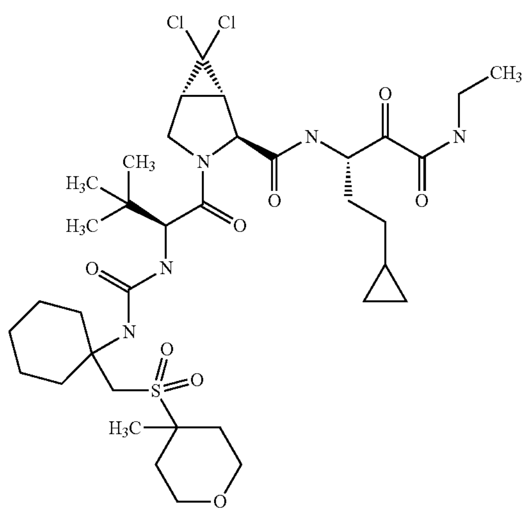 | 790.8544 | | A |
| 883-ea | 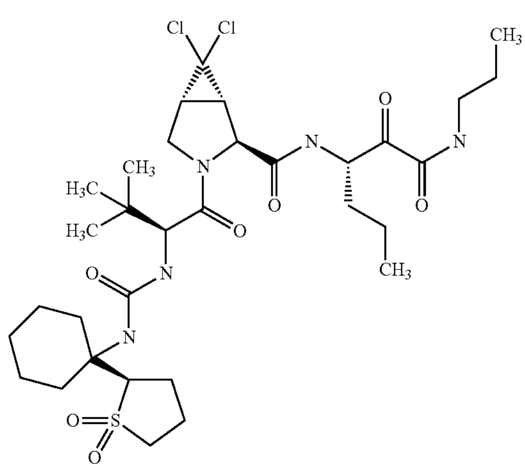 | 720.7626 | | A |

TABLE 3A-continued
| Compound # | structure | mol weight structure | Select LC-MS Data (M + H) | Ki* Range |
|---|---|---|---|---|
| 883-eb | 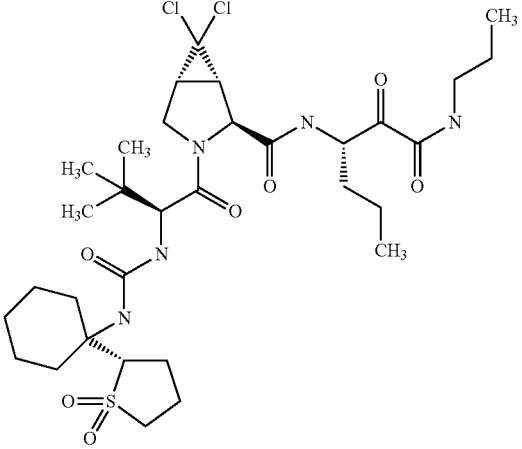 | 720.7626 | | A |
| 883-ec | 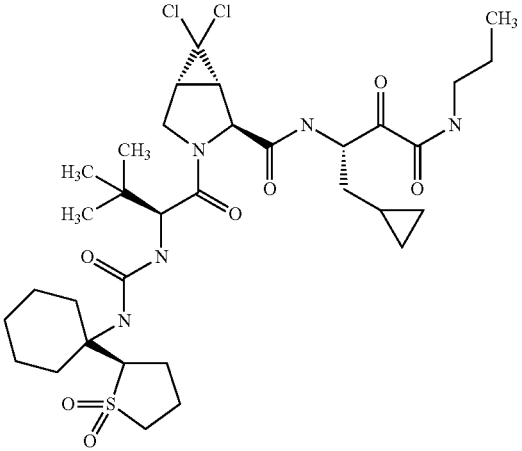 | 732.7737 | | A |
| 883-ed | 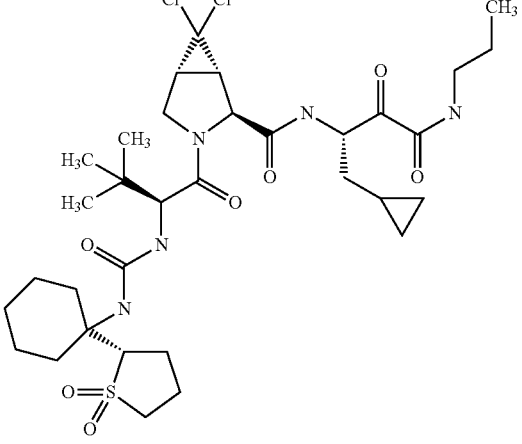 | 732.7737 | | A |

TABLE 3A-continued
| Compound # | structure | mol weight structure | Select LC-MS Data (M + H) | Ki* Range |
|---|---|---|---|---|
| 883-ee | 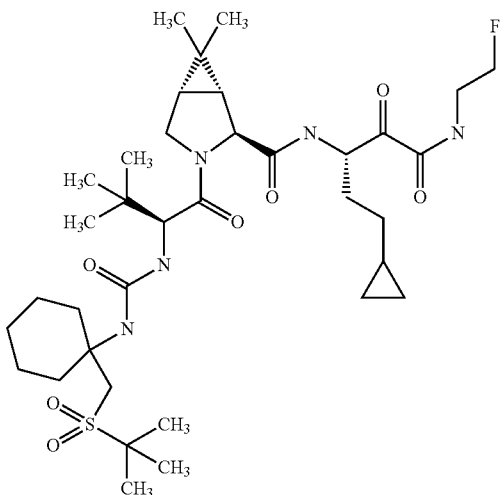 | | 725.9713 | A |
| 883-ef | 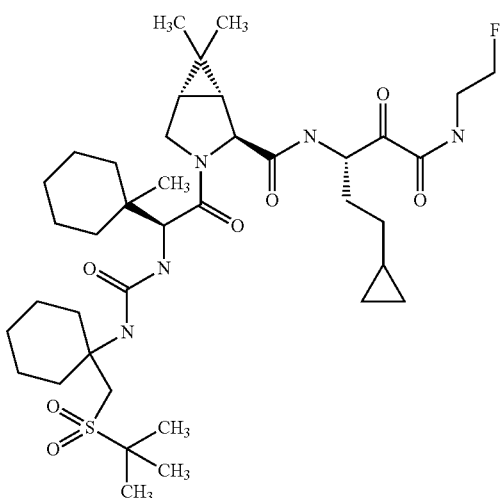 | | 766.0366 | A |
| 883-eg | 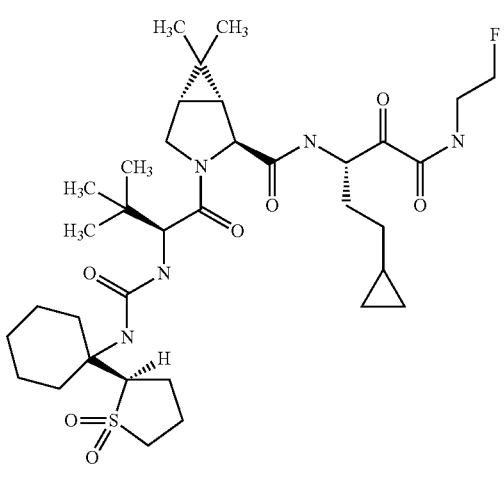 | | 709.9283 | A |

TABLE 3A-continued

| Compound # | structure | mol weight structure | Select LC-MS Data (M + H) | Ki* Range |
|---|---|---|---|---|
| 883-eh | 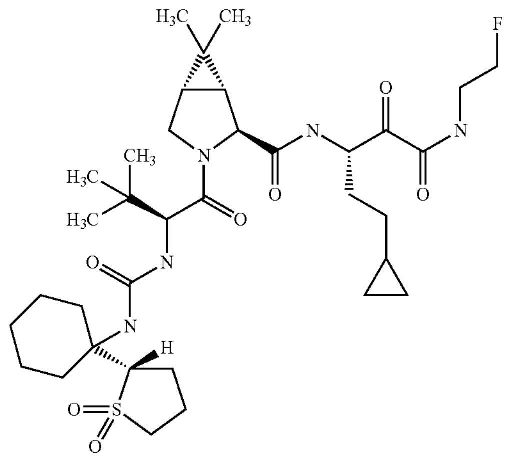 | 709.9283 | | A |
| 883-ei | 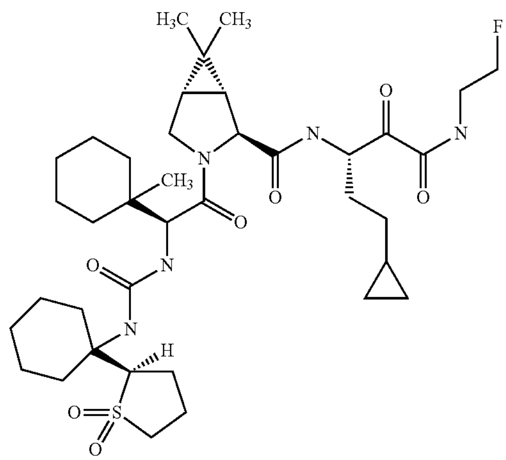 | 749.9936 | | A |
| 883-ej | 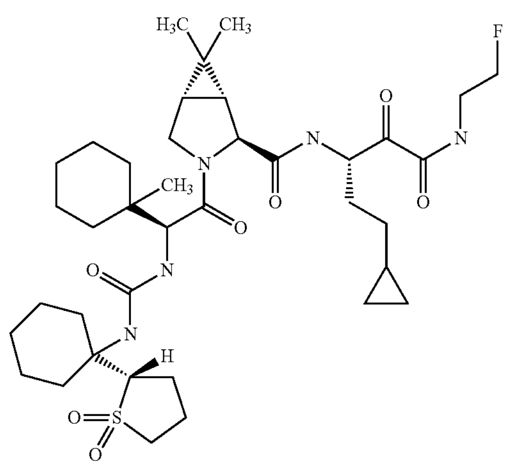 | 749.9936 | | A |

TABLE 3A-continued

| Compound # | structure | mol weight structure | Select LC-MS Data (M + H) | Ki* Range |
|---|---|---|---|---|
| 883-ek | 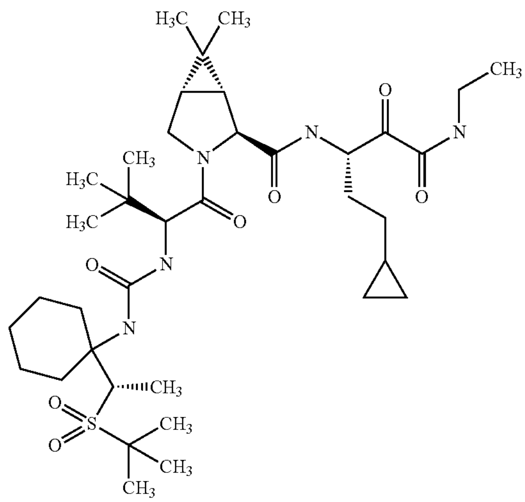 | 722.008 | | A |
| 883-el | 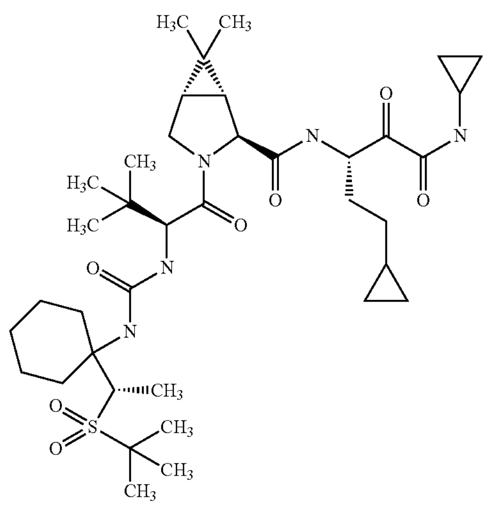 | 734.0191 | | A |
| 883-em | 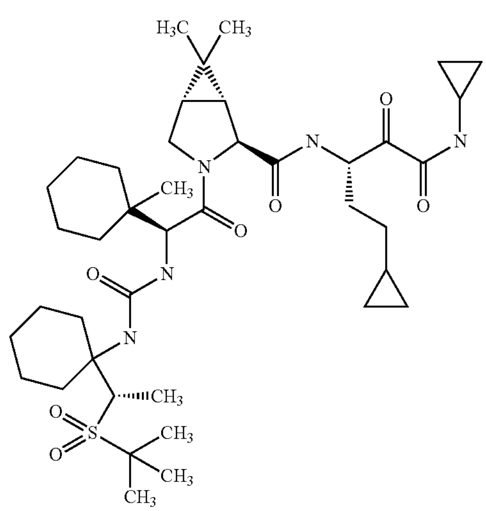 | 774.0844 | | A |

TABLE 3A-continued
| Compound # | structure | mol weight structure | Select LC-MS Data (M + H) | Ki* Range |
|---|---|---|---|---|
| 883-en | 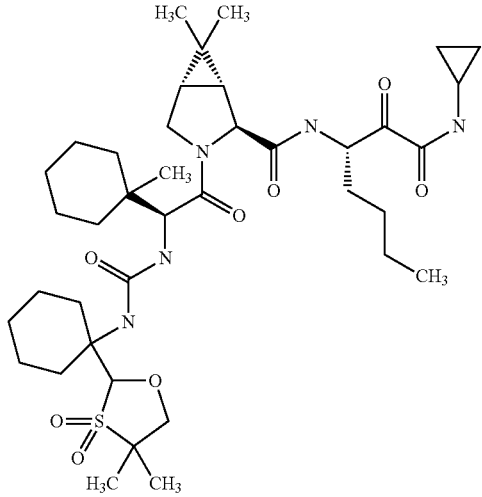 | | 762.0297 | A |
| 883-eo | 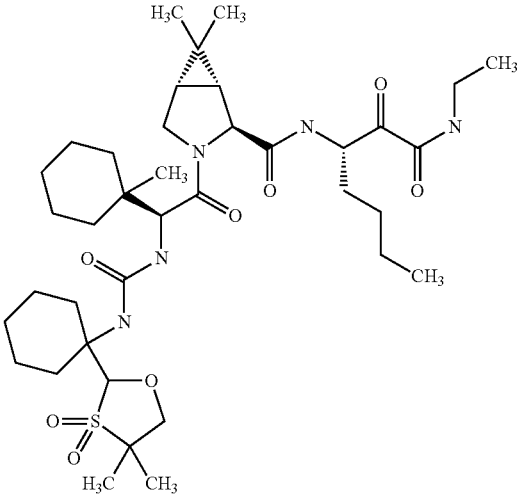 | | 750.0185 | A |
| 883-ep | 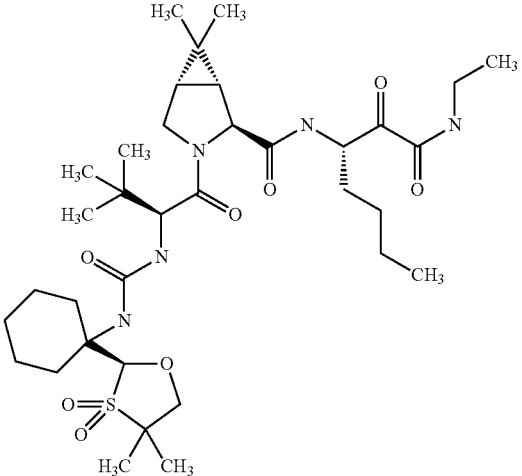 | | 709.9532 | A |

TABLE 3A-continued

| Compound # | structure | mol weight structure | Select LC-MS Data (M + H) | Ki* Range |
|---|---|---|---|---|
| 883-eq | 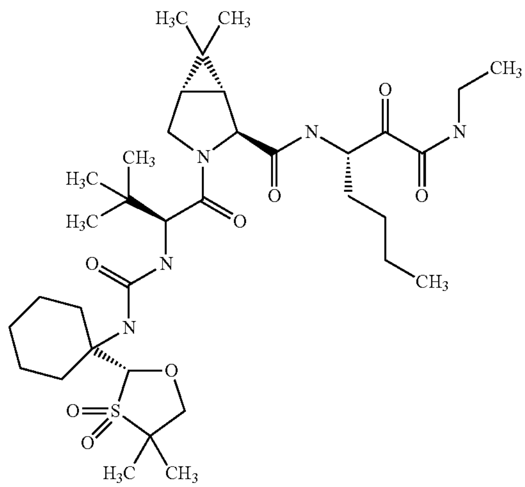 | 709.9532 | | A |
| 883-er | 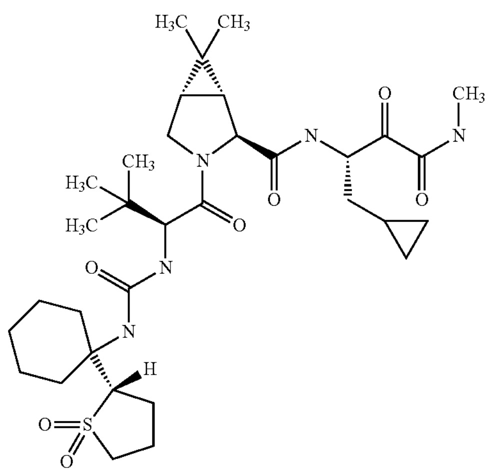 | 663.8837 | | A |
| 883-es | 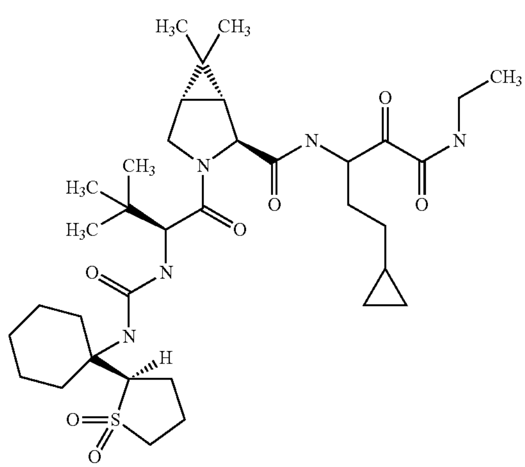 | 691.9378 | | A |

TABLE 3A-continued

| Compound # | structure | mol weight structure | Select LC-MS Data (M + H) | Ki* Range |
|---|---|---|---|---|
| 883-et | 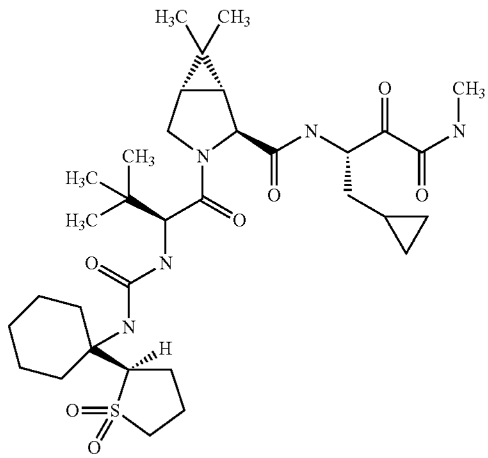 | 663.8837 | | A |
| 883-eu | 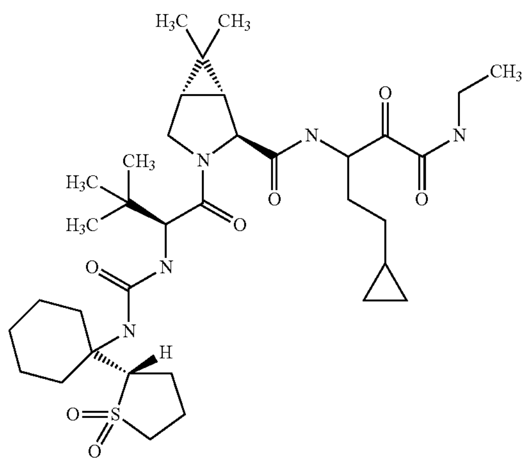 | 691.9378 | | A |
| 883-ev | 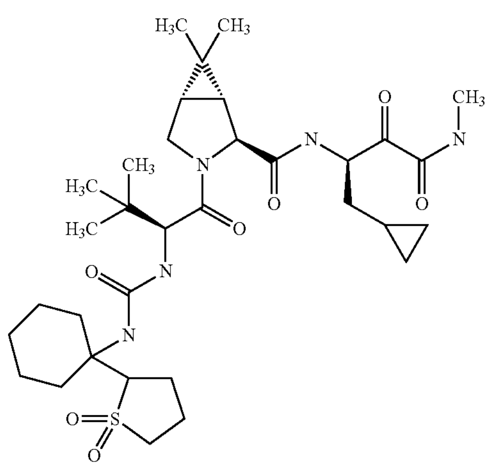 | 663.8837 | | A |

TABLE 3A-continued

| Compound # | structure | mol weight structure | Select LC-MS Data (M + H) | Ki* Range |
|---|---|---|---|---|
| 883-ew | 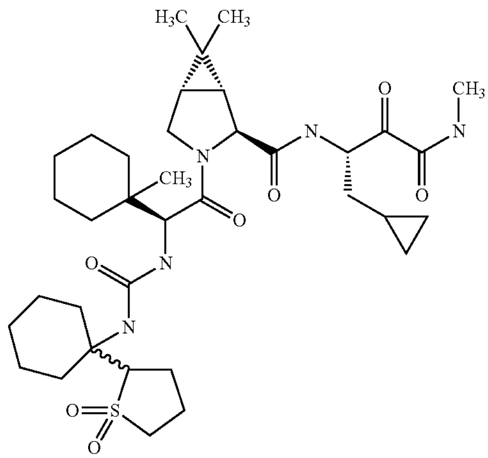 | 703.949 | | A |
| 883-ex | 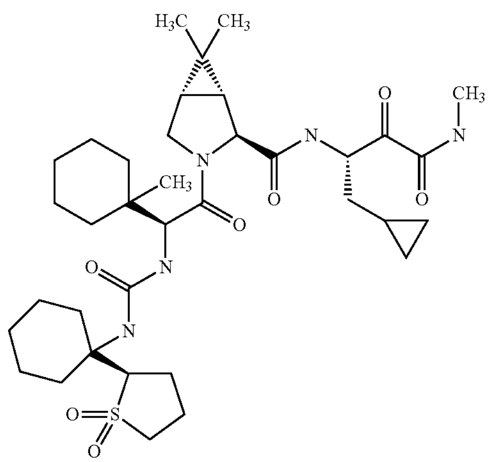 | 703.949 | | A |
| 883-ey | 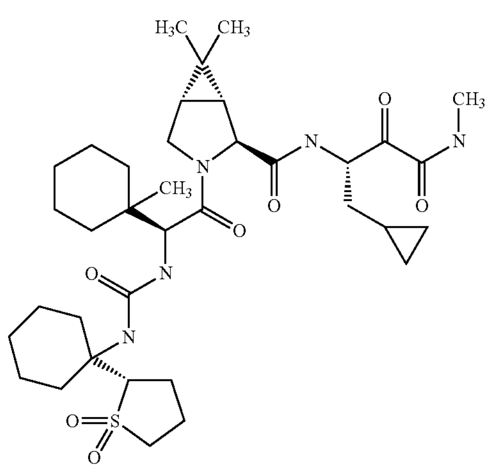 | 703.949 | | A |

TABLE 3A-continued

| Compound # | structure | mol weight structure | Select LC-MS Data (M + H) | Ki* Range |
|---|---|---|---|---|
| 883-ez | 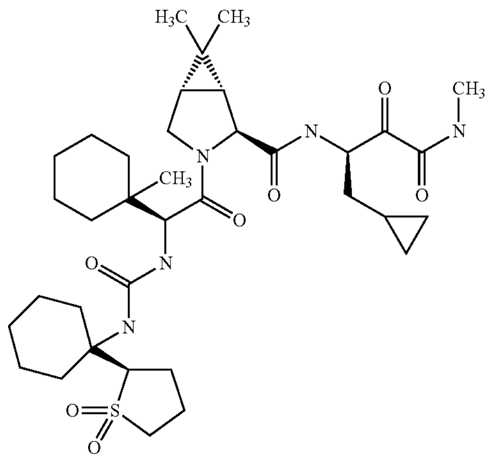 | 703.949 | | A |
| 883-fa | 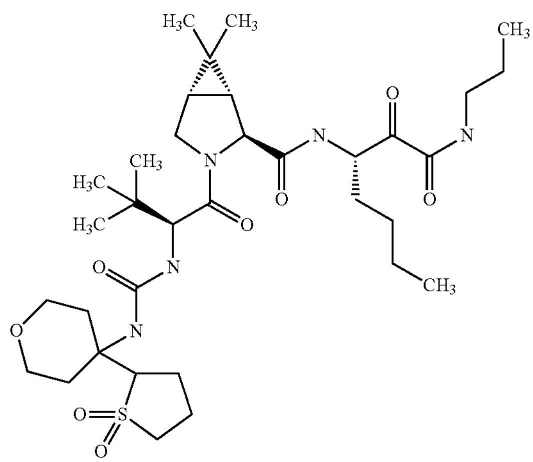 | 695.9261 | | B |
| 883-fb | 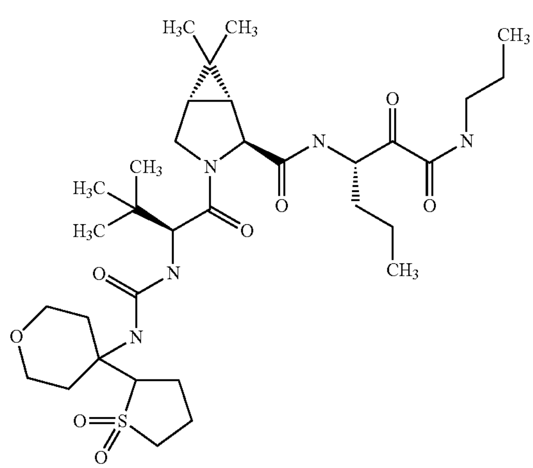 | 681.899 | | A |

TABLE 3A-continued
| Compound # | structure | mol weight structure | Select LC-MS Data (M + H) | Ki* Range |
|---|---|---|---|---|
| 883-fc | 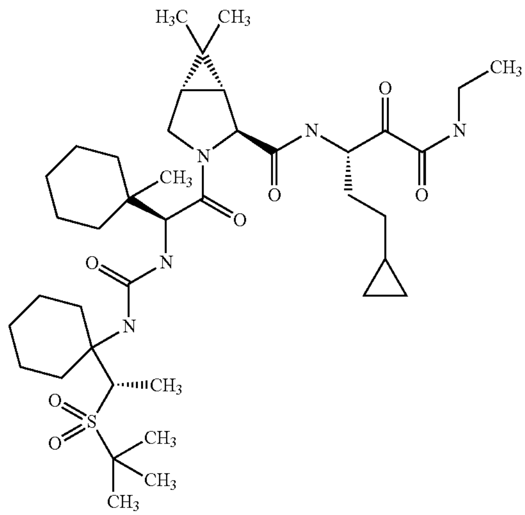 | 762.0733 | | A |
| 883-fd | 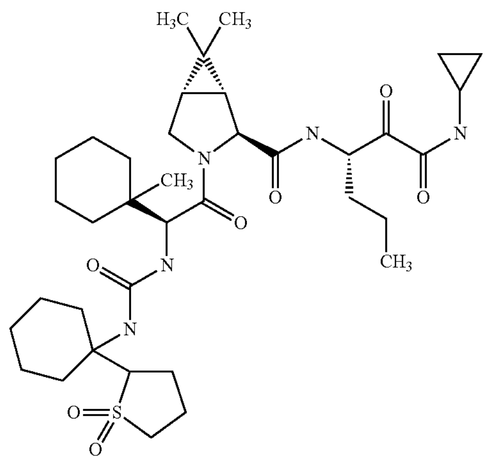 | 717.9761 | | A |
Also disclosed are the following compounds in Table 4 and Table 4A. The preparation of the compounds in Table 4 and Table 4A is described below:
Example 1005
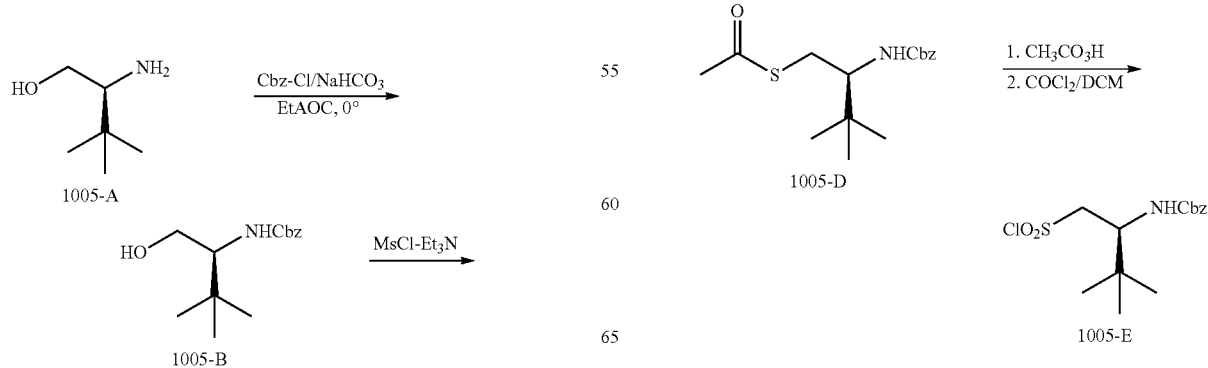

Step 1

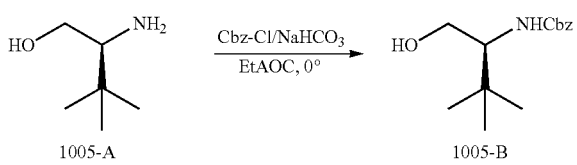

To a solution of 5 g of 1005-A (commercially available from Aldrich) in 100 ml of EtOAc at 0° C. were added 40 ml of saturated NaHCO₃ solution followed by 6.5 ml of Cbz-Cl in one portion. The resulting mixture was stirred for 2 h and layers were separated. The aqueous layer was back extracted with 50 ml of EtOAc. The combined organic layer was washed once with brine, dried over MgSO₄ and concentrated to a colorless liquid which solidified on standing. 10.7 g of 1005-B as white solids were obtained.
MS: 274 [M+Na]⁺.

Step 2

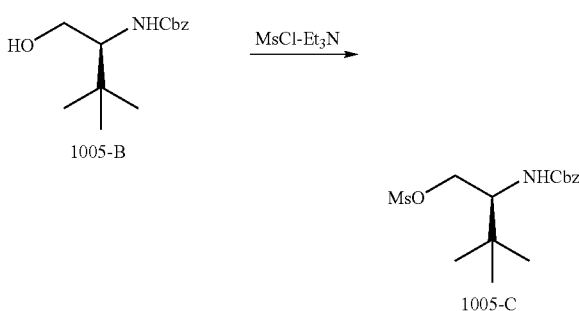

To a solution of 10.7 g of 1005-B in 120 ml of DCM at 0° C. were added 7.04 ml of triethylamine and 4.05 ml of methanesulfonyl chloride. The mixture was stirred at 0° C. for 10 minutes and 1.5 h at room temperature. The mixture was washed with 1M KHSO₄ solution, water, brine and dried over MgSO₄. Concentration of solvent gave the crude product which was purified on silica gel column eluted with DCM. 13 g of 1005-C were obtained as colorless thick oil. MS: 352 [M+Na]⁺.

Step 3

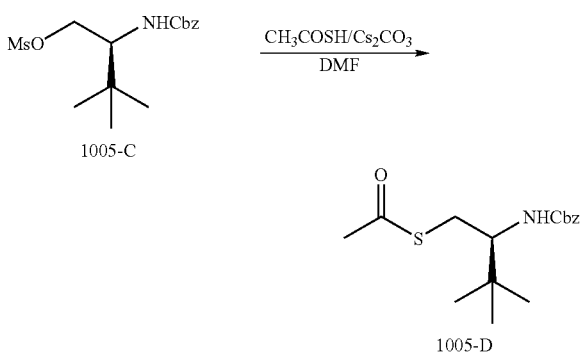

To a suspension of 8.3 g of Cs₂CO₃ in 100 ml of anhydrous DMF were added 3.3 ml of thioacetic acid. To the dark brown slurry was added a solution of 12.97 g of 1005-C in 30 ml of anhydrous DMF. The resulting mixture was stirred overnight at room temperature, diluted with 300 ml of ice-water and extracted with 2×250 ml of EtOAc. The combined organic layer was washed with water, brine and dried over MgSO₄. Evaporation of solvent gave ~10 g of the crude product which was purified over silica gel column with 10% EtOAc in hexane. 4.8 g of 1005-D as white solids were obtained. MS: 310 [M+H]⁺, 332 [M+Na]⁺.

Step 4

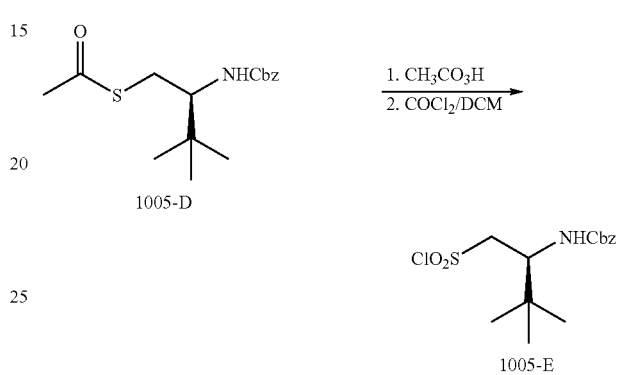

To a solution of 4.4 g of 1005-D in 15 ml of AcOH was added a solution of 15 ml of 30% H₂O₂ and 30 ml of AcOH. The resulting solution was stirred at room temperature for 20 h. 75 mg of 10% Pd/C were added and the mixture was stirred for 1 h, filtered through a celite pad and rinsed with MeOH. The combined filtrate was concentrated and co-evaporated with 3×100 ml of toluene to give solids. 90 ml of anhydrous DCM were added to dissolve solids and to the solution was added 15 ml of 20% phosgene in toluene (Fluka) followed by 1.8 ml of anhydrous DMF. Gas evolved and the mixture was stirred at room temperature for 2 h and concentrated to yield solid residue. Purification on silica gel eluted with DCM gave 3.94 g of 1005-E as solids. MS: 356, 358 [M+Na]⁺.

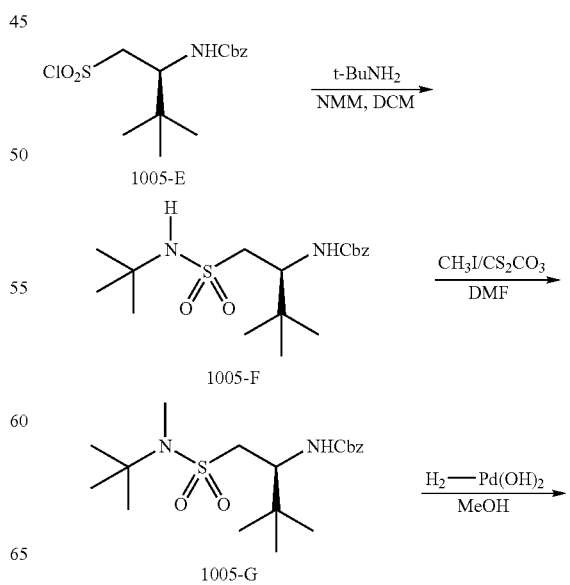

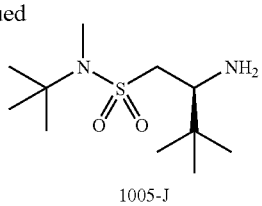

1005-J

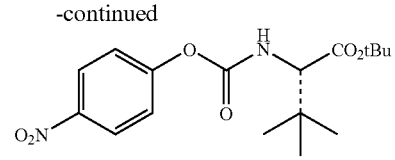

1005-K

Step 5

A mixture of 900 mg of 1005-E, 1.0 ml of t-Butylamine and 0.4 ml of NMM in 40 ml of DCM was stirred at room temperature for 0.5 h, washed with 1M KHSO4 solution, brine and dried over MgSO$_4$. Evaporation of solvent gave 445 mg of the crude product which was purified on silica gel with DCM and 5% EtOAc in DCM. 617 mg of 1005-F were obtained. MS: 379 [M+Na]$^+$.

Step 6

A mixture of 600 mg of 1005-F, 2.64 g of cesium carbonate and 0.5 ml methyl iodide in 10 ml of anhydrous DMF was stirred at room temperature overnight, diluted with 50 ml of ice-cold water and extracted with 2×50 ml EtOAc. The combined organic solution was washed twice with water, once with brine, dried over MgSO4. Removal of solvent under vacuum gave 620 mg of 1005-G as white solids. MS: 385 [M+H]$^+$.

Step 7

A solution of 1005-G (600 mg) and Pd(OH)$_2$ (70 mg) in MeOH was placed under an atmosphere of hydrogen overnight. The solids were filtered and washed thoroughly with MeOH. The volatiles were removed under reduced pressure to give the amine (1005-J; 380 mg). MS: 251 [M+H]$^+$.

Step 8

To a solution of the of the hydrochloride salt (Bachem; 2.24 g) in dichloromethane (50 ml) was added NMM (2.6 ml) followed by the p-nitrophenyl chloroformate (2.42 g) and the resulting mixture was stirred at room temperature overnight. The reaction mixture was washed with cold aq. 1N HCl, sat aq. sodium bicarbonate, dried and the volatiles were removed under reduced pressure. The crude reaction product by silica gel chromatography using EtOAc:hexanes (1:10) as eluent to give the carbamate (1005-K; 2.97 g).

Step 9

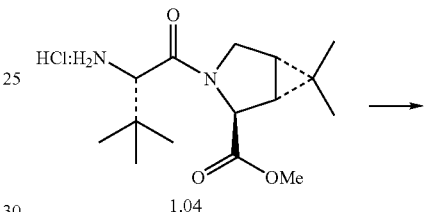

1.04

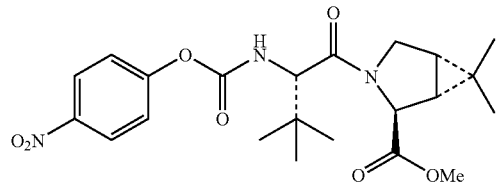

1005-L

Using the procedure set forth in STEP 8 the carbamate 1005-L was prepared from the amine-hydrochloride salt 1.04.

Step 10

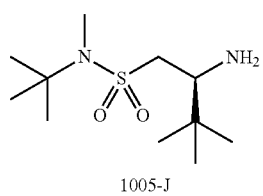

1005-J

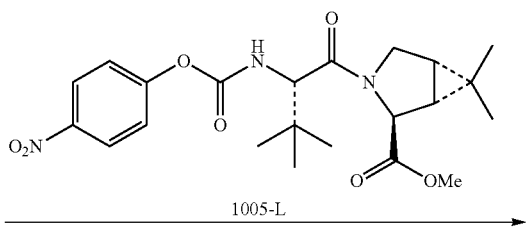

1005-L

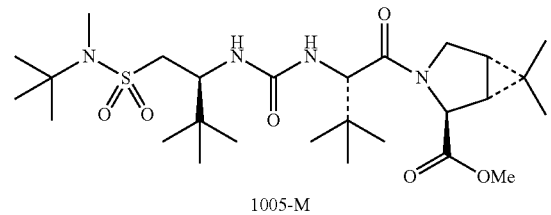

1005-M

NMM (0.12 ml) was added to a mixture of the amine (1005-J; 0.20 g) and the carbamate (1005-L; 0.375 g) in acetonitrile (15 ml) and the resulting mixture was stirred at room temperature, under an atmosphere of nitrogen, overnight. The volatiles were removed under reduced pressure and the residue was partitioned between EtOAc and water. The organic phase was separated, dried and concentrated. The crude reaction product was purified by silica gel column chromatography using EtOAc: Hexanes (2:3) as eluent, providing the desired urea (1005-M; 0.43 g). MS: 559.28 [M+H]$^+$.

Step 11

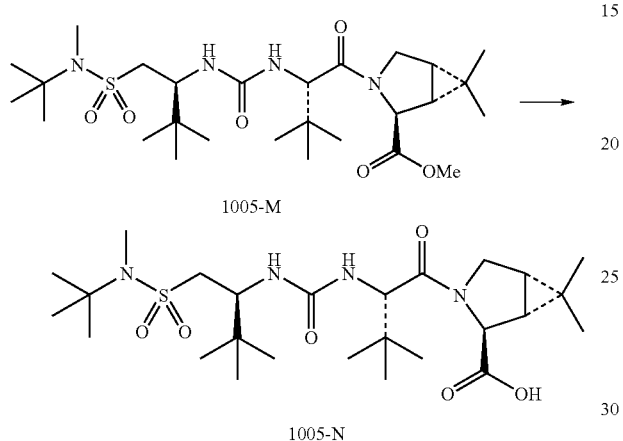

Lithium hydroxide (0.020 g) in water (2 ml) was added to a solution of the methyl ester (1005-M; 0.41 g) in dioxane (15 ml) and the resulting mixture was stirred at room temperature overnight. Aqueous HCl (0.01N) was added and the organics were extracted into EtOAc. The organic phase was separated, dried and concentrated to yield the carboxylic acid (1005-N; 0.395 g). MS: 545.32 [M+H]$^+$.

Step 12

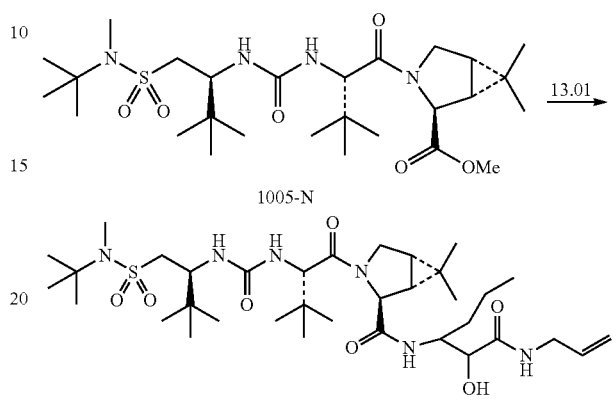

Hunigs base (0.050 ml) was added to a mixture of the carboxylic acid (1005-N, 0.030 g) and the hydrochloride salt (13.01; 0.015 g) in dichloromethane (5 ml) at −20 C, under an atmosphere of nitrogen. The reaction was maintained at this temperature for a period of 20 h. Aqueous work-up gave a crude reaction product (1005-O) which was used in STEP 12, below.

Step 13

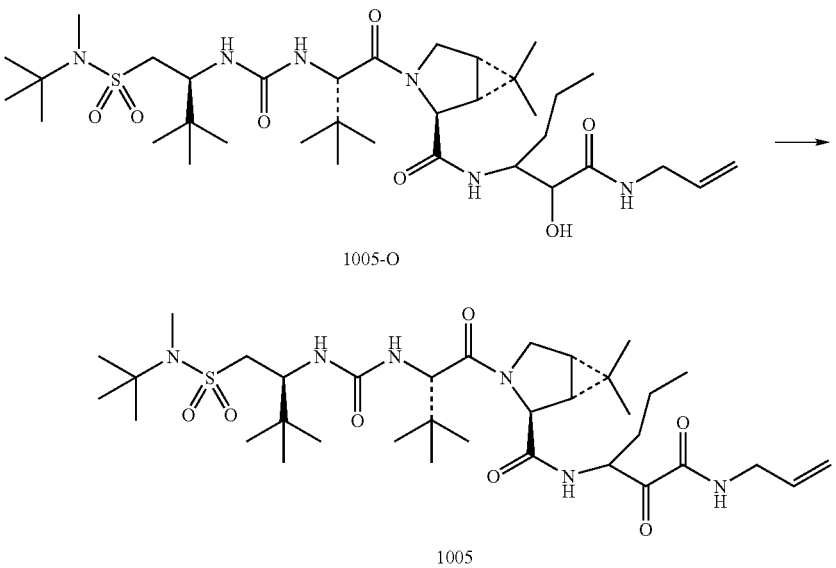

To crude (1005-O; above in STEP 11) in dichloromethane (3 ml) was added Dess-Martin periodinane (0.050 g) and the resulting mixture was stirred at room temperature for a period of 24 h. Aqueous work-up and silica gel plate chromatography using dichloromethane:methanol (20:1) as eluent gave the desired α-keto-amide (0.0282 g), as a white solid. Ki* ranges are: A=<75 nM; B=75-250 nM; C=>250 nM.

TABLE 4
| Prep. Ex. | COMPOUND | FABMS: MH+ | Ki* range |
|---|---|---|---|
| 1000 | | 703.7 | A |
| 1001 | | 729.7 | B |
| 1002 | | 683.3 | C |
| 1003 | | 697.3 | A |
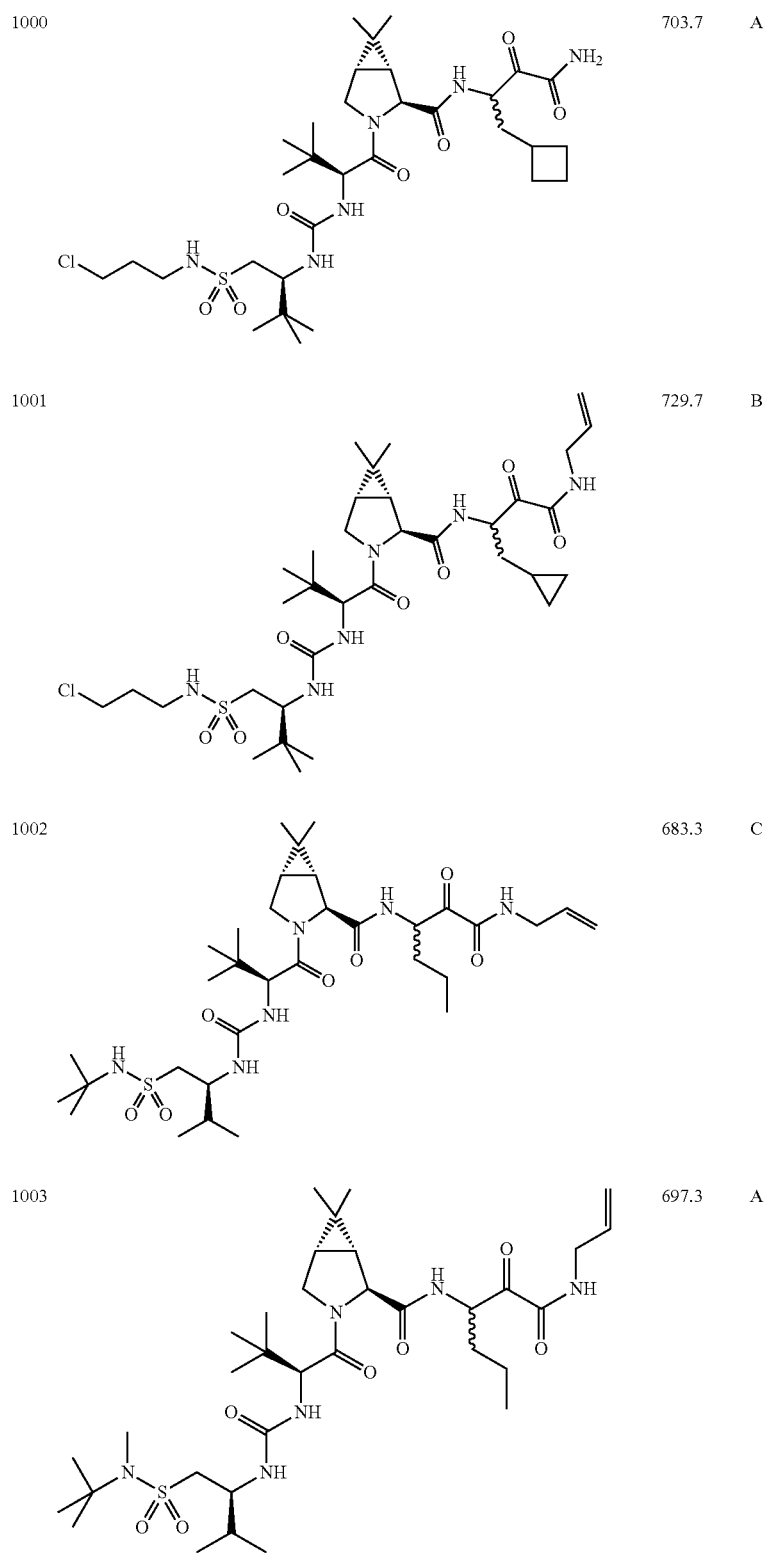

TABLE 4-continued
| Prep. Ex. | COMPOUND | FABMS: MH+ | Ki* range |
|---|---|---|---|
| 1004 | 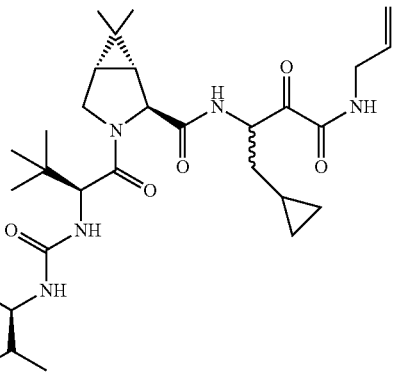 | 709.3 | A |
| 1005 | 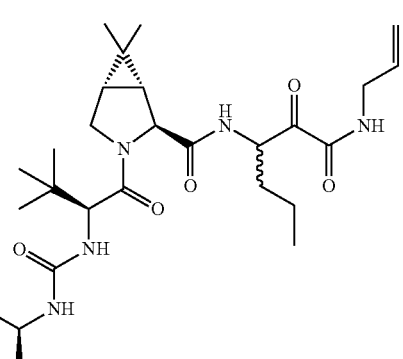 | 711.3 | B |
| 1006 | 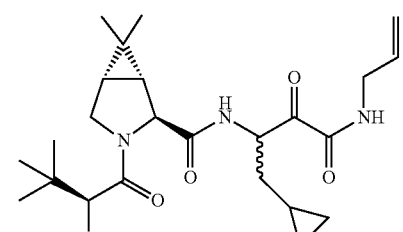 | 723.3 | B |
| 1007 | 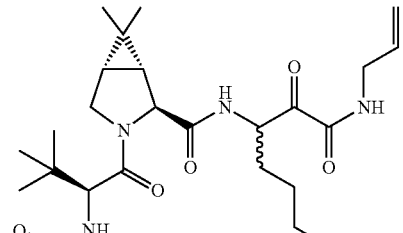 | 725.3 | B |

TABLE 4-continued

| Prep. Ex. | COMPOUND | FABMS: MH+ | Ki* range |
|---|---|---|---|
| 1008 | | 683.3 | B |

Table 4A lists still additional compounds representing the present invention:

TABLE 4A

| Prep. Ex. | Compound | Select Mass Spectra Data | Ki* Range |
|---|---|---|---|
| 1100 | | | A |
| 1101 | | | A |

TABLE 4A-continued

| Prep. Ex. | Compound | Select Mass Spectra Data | Ki* Range |
|---|---|---|---|
| 1102 | | | A |
| 1103 | | | B |
| 1104 | | | B |
| 1105 | | | B |

TABLE 4A-continued

| Prep. Ex. | Compound | Select Mass Spectra Data | Ki* Range |
|---|---|---|---|
| 1106 | | | B |
| 1107 | | | A |
| 1108 | | | A |
| 1109 | | | B |

TABLE 4A-continued
| Prep. Ex. | Compound | Select Mass Spectra Data | Ki* Range |
|---|---|---|---|
| 1110 | 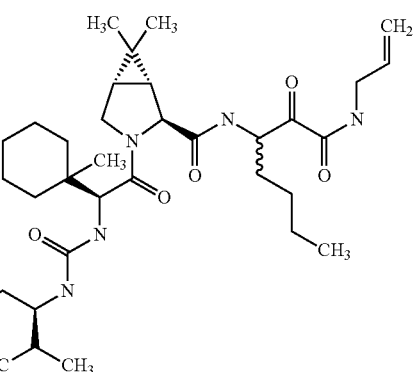 | | A |
| 1111 | 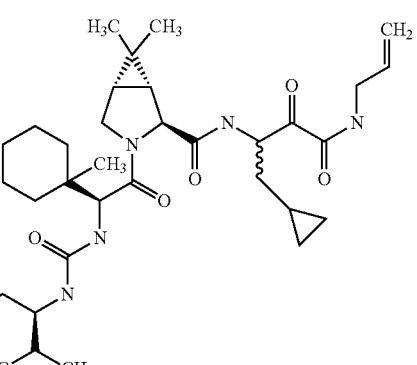 | | C |
| 1112 | 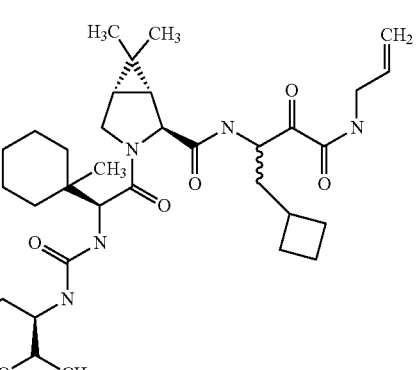 | | A |
| 1113 | 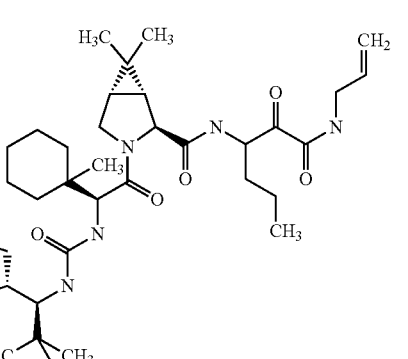 | | C |

TABLE 4A-continued

| Prep. Ex. | Compound | Select Mass Spectra Data | Ki* Range |
|---|---|---|---|
| 1114 | | | C |
| 1115 | | | C |
| 1116 | | | C |
| 1117 | | | C |

TABLE 4A-continued

| Prep. Ex. | Compound | Select Mass Spectra Data | Ki* Range |
|---|---|---|---|
| 1118 | | | C |
| 1119 | | | C |
| 1120 | | | C |
| 1121 | | | C |

The present invention relates to novel HCV protease inhibitors. This utility can be manifested in their ability to inhibit the HCV NS2/NS4a serine protease. A general procedure for such demonstration is illustrated by the following in vitro assay.

Assay for HCV Protease Inhibitory Activity:

Spectrophotometric Assay: Spectrophotometric assay for the HCV serine protease can be performed on the inventive compounds by following the procedure described by R. Zhang et al, *Analytical Biochemistry*, 270 (1999) 268-275, the disclosure of which is incorporated herein by reference. The assay based on the proteolysis of chromogenic ester substrates is suitable for the continuous monitoring of HCV NS3 protease activity. The substrates are derived from the P side of the NS5A-NS5B junction sequence (Ac-DTEDWX(Nva), where X=A or P) whose C-terminal carboxyl groups are esterified with one of four different chromophoric alcohols (3- or 4-nitrophenol, 7-hydroxy-4-methyl-coumarin, or 4-phenylazophenol). Illustrated below are the synthesis, characterization and application of these novel spectrophotometric ester substrates to high throughput screening and detailed kinetic evaluation of HCV NS3 protease inhibitors.

Materials and Methods:

Materials: Chemical reagents for assay related buffers are obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides are synthesized manually or on an automated ABI model 431A synthesizer (from Applied Biosystems). UV/VIS Spectrometer model LAMBDA 12 was from Perkin Elmer (Norwalk, Conn.) and 96-well UV plates were obtained from Corning (Corning, N.Y.). The prewarming block can be from USA Scientific (Ocala, Fla.) and the 96-well plate vortexer is from Labline Instruments (Melrose Park, Ill.). A Spectramax Plus microtiter plate reader with monochrometer is obtained from Molecular Devices (Sunnyvale, Calif.).

Enzyme Preparation: Recombinant heterodimeric HCV NS3/NS4A protease (strain 1a) is prepared by using the procedures published previously (D. L. Sali et al, *Biochemistry*, 37 (1998) 3392-3401). Protein concentrations are determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) is exchanged for the assay buffer (25 mM MOPS pH 6.5, 300 mM NaCl, 10% glycerol, 0.05% lauryl maltoside, 5 µM EDTA and 5 µM DTT) utilizing a Biorad Bio-Spin P-6 prepacked column.

Substrate Synthesis and Purification: The synthesis of the substrates is done as reported by R. Zhang et al, (ibid.) and is initiated by anchoring Fmoc-Nva-OH to 2-chlorotrityl chloride resin using a standard protocol (K. Barlos et al, *Int. J. Pept. Protein Res.*, 37 (1991), 513-520). The peptides are subsequently assembled, using Fmoc chemistry, either manually or on an automatic ABI model 431 peptide synthesizer. The N-acetylated and fully protected peptide fragments are cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash is evaporated azeotropically (or repeatedly extracted by aqueous $Na_2CO_3$ solution) to remove the acid used in cleavage. The DCM phase is dried over $Na_2SO_4$ and evaporated.

The ester substrates are assembled using standard acid-alcohol coupling procedures (K. Holmber et al, *Acta Chem. Scand.*, B33 (1979) 410-412). Peptide fragments are dissolved in anhydrous pyridine (30-60 mg/ml) to which 10 molar equivalents of chromophore and a catalytic amount (0.1 eq.) of para-toluenesulfonic acid (pTSA) were added. Dicyclohexylcarbodiimide (DCC, 3 eq.) is added to initiate the coupling reactions. Product formation is monitored by HPLC and can be found to be complete following 12-72 hour reaction at room temperature. Pyridine solvent is evaporated under vacuum and further removed by azeotropic evaporation with toluene. The peptide ester is deprotected with 95% TFA in DCM for two hours and extracted three times with anhydrous ethyl ether to remove excess chromophore. The deprotected substrate is purified by reversed phase HPLC on a C3 or C8 column with a 30% to 60% acetonitrile gradient (using six column volumes). The overall yield following HPLC purification can be approximately 20-30%. The molecular mass can be confirmed by electrospray ionization mass spectroscopy. The substrates are stored in dry powder form under desiccation.

Spectra of Substrates and Products: Spectra of substrates and the corresponding chromophore products are obtained in the pH 6.5 assay buffer. Extinction coefficients are determined at the optimal off-peak wavelength in 1-cm cuvettes (340 nm for 3-Np and HMC, 370 nm for PAP and 400 nm for 4-Np) using multiple dilutions. The optimal off-peak wavelength is defined as that wavelength yielding the maximum fractional difference in absorbance between substrate and product (product OD−substrate OD)/substrate OD).

Protease Assay: HCV protease assays are performed at 30° C. using a 200 µl reaction mix in a 96-well microtiter plate. Assay buffer conditions (25 mM MOPS pH 6.5, 300 mM NaCl, 10% glycerol, 0.05% lauryl maltoside, 5 µM EDTA and 5 µM DTT) are optimized for the NS3/NS4A heterodimer (D. L. Sali et al, ibid.)). Typically, 150 µl mixtures of buffer, substrate and inhibitor are placed in wells (final concentration of DMSO≦4% v/v) and allowed to preincubate at 30° C. for approximately 3 minutes. Fifty µls of prewarmed protease (12 nM, 30° C.) in assay buffer, is then used to initiate the reaction (final volume 200 µl). The plates are monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore is monitored at the appropriate wavelength against a no enzyme blank as a control for non-enzymatic hydrolysis. The evaluation of substrate kinetic parameters is performed over a 30-fold substrate concentration range (~6-200 µM). Initial velocities are determined using linear regression and kinetic constants are obtained by fitting the data to the Michaelis-Menten equation using non-linear regression analysis (Mac Curve Fit 1.1, K. Raner). Turnover numbers ($k_{cat}$) are calculated assuming the enzyme is fully active.

Evaluation of Inhibitors and Inactivators: The inhibition constants ($K_i$) for the competitive inhibitors Ac-D-(D-Gla)-L-l-(Cha)-C-OH (27), Ac-DTEDWA(Nva)-OH and Ac-DT-EDVVP(Nva)-OH are determined experimentally at fixed concentrations of enzyme and substrate by plotting $v_o/v_i$ vs. inhibitor concentration ($[I]_o$) according to the rearranged Michaelis-Menten equation for competitive inhibition kinetics: $v_o/v_i=1+[I]_o/(K_i(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data are fitted using linear regression and the resulting slope, $1/(K_i(1+[S]_o/K_m))$, is used to calculate the $K_i$ value. The following Table 5 lists the obtained Ki* values (in nanoMolar) for some of the inventive compounds. Several others are noted in the Tables on earlier pages.

TABLE 5
| Structure | Ki* (nM) |
|---|---|
| 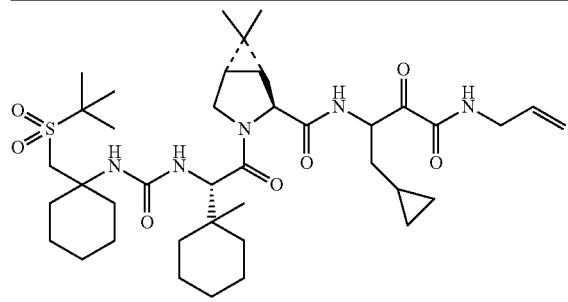 | 10 |
| 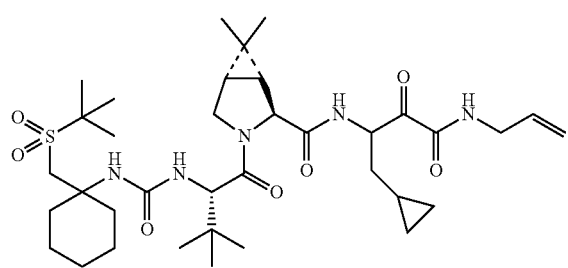 | 14 |
| 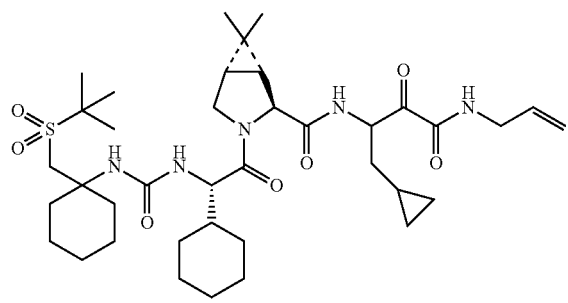 | 4.1 |
| 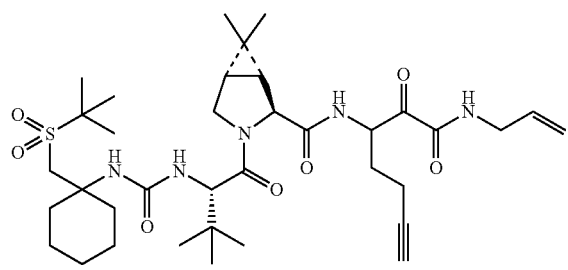 | 2 |
| 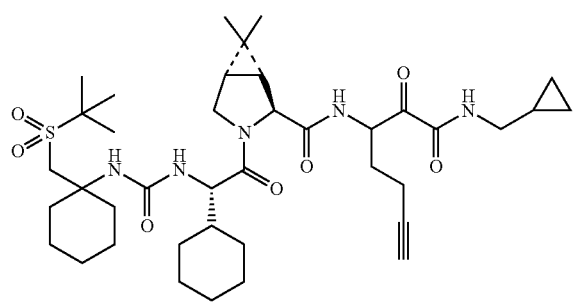 | 19 |

TABLE 5-continued

| Structure | Ki* (nM) |
|---|---|
| 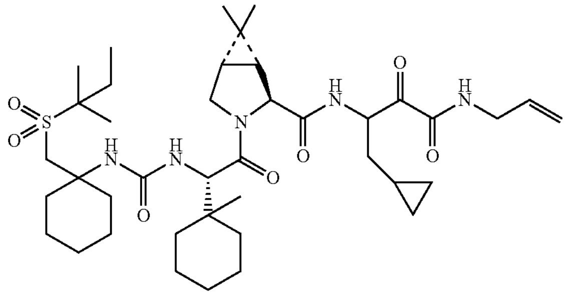 | 9 |
| 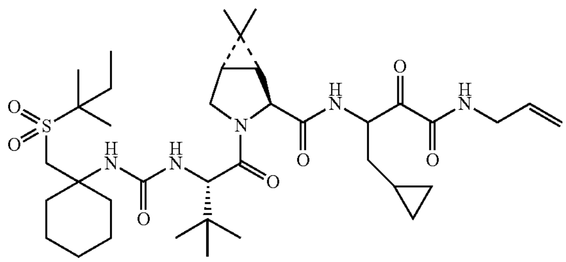 | 14 |
| 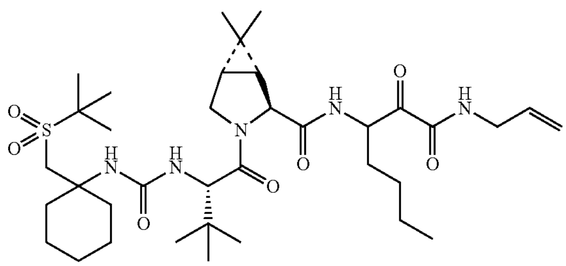 | 11 |
| 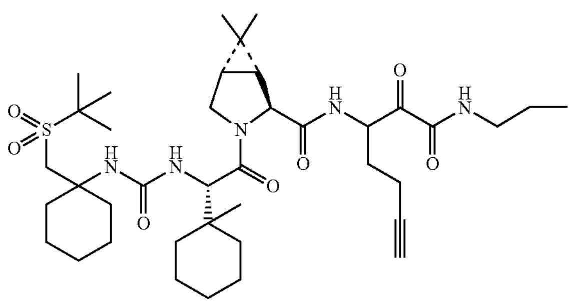 | 4 |
| 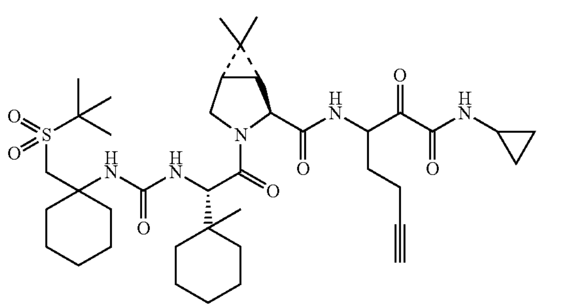 | 6 |

TABLE 5-continued

| Structure | Ki* (nM) |
|---|---|
| 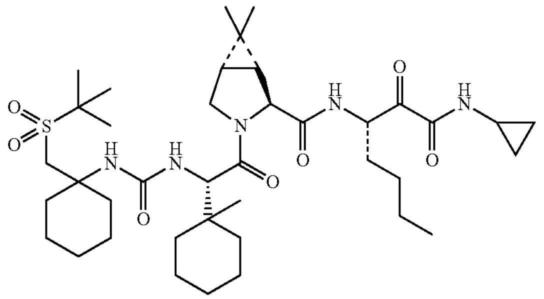 | 5 |
| 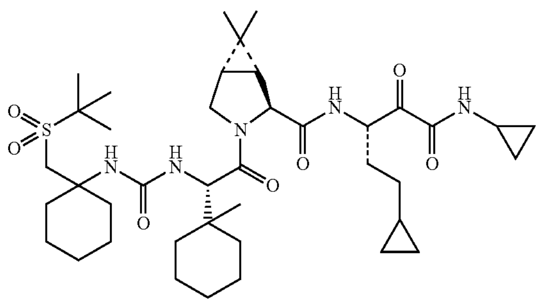 | 3 |

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound, or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having the general structure shown in Formula I:

Formula I wherein:
R¹ is H, OR⁸, NR⁹R¹⁰, or CHR⁹R¹⁰, wherein R⁸, R⁹ and R¹⁰ can be the same or different, each being independently selected from the group consisting of H, alkyl-, alkenyl-, alkynyl-, aryl-, heteroalkyl-, heteroaryl-, cycloalkyl-, heterocyclyl-, arylalkyl-, and heteroarylalkyl;

the moiety:

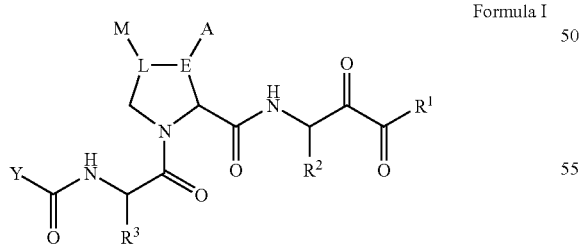

R² and R³ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl;

and Y is selected from the following moieties:

-continued

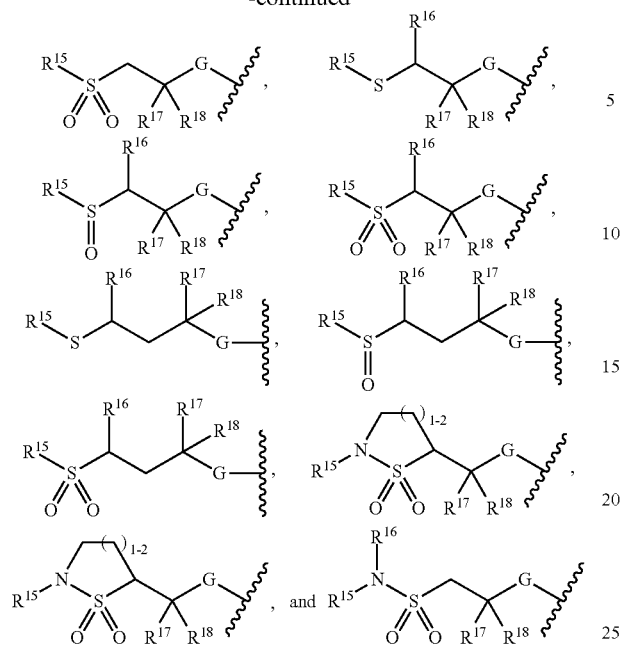

wherein G is NH or O; and $R^{15}$, $R^{16}$, $R^{17}$ and $R^{18}$ can be the same or different, each being independently selected from the group consisting of H, alkyl, heteroalkyl, alkenyl, heteroalkenyl, alkynyl, heteroalkynyl, cycloalkyl, heterocyclyl, aryl, and heteroaryl, or alternately, (i) $R^{15}$ and $R^{16}$ are connected to each other to form a four to eight-membered cyclic structure, and (ii) likewise, independently $R^{17}$ and $R^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkylsulfonamido, arylsulfonamido, alkyl, aryl, heteroaryl, keto, carboxy, carbalkoxy, carboxamido, alkoxycarbonylamino, alkoxycarbonyloxy, alkylureido, arylureido, halo, cyano, and nitro.

2. The compound of claim 1, wherein $R^1$ is $NR^9R^{10}$, and $R^9$ is H, $R^{10}$ is H, or $R^{14}$ wherein $R^{14}$ is alkyl, aryl, heteroalkyl, heteroaryl, cycloalkyl, aryl-alkyl, alkenyl, alkynyl or heteroaryl-alkyl.

3. The compound of claim 2, wherein $R^{14}$ is selected from the group consisting of:

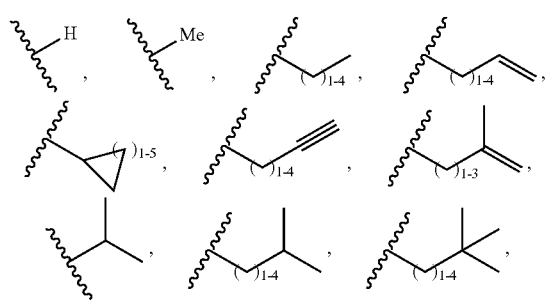

-continued

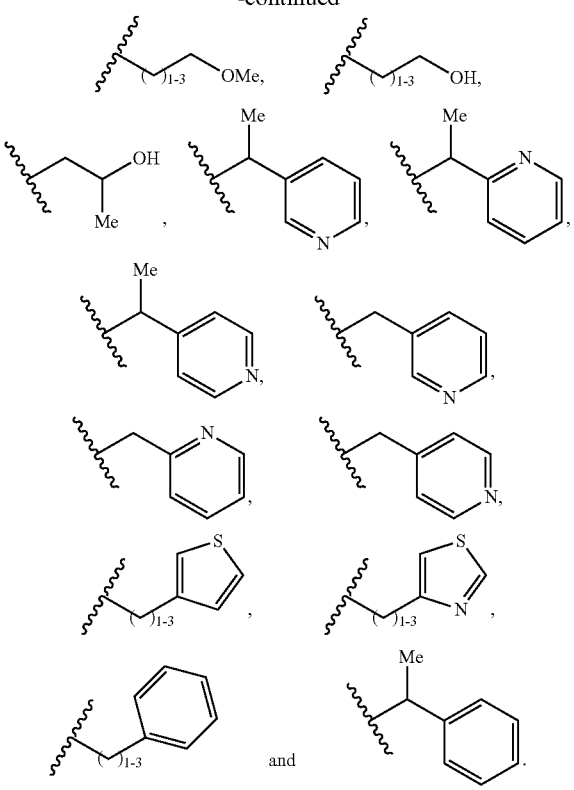

4. The compound of claim 1, wherein $R^2$ is selected from the group consisting of the following moieties:

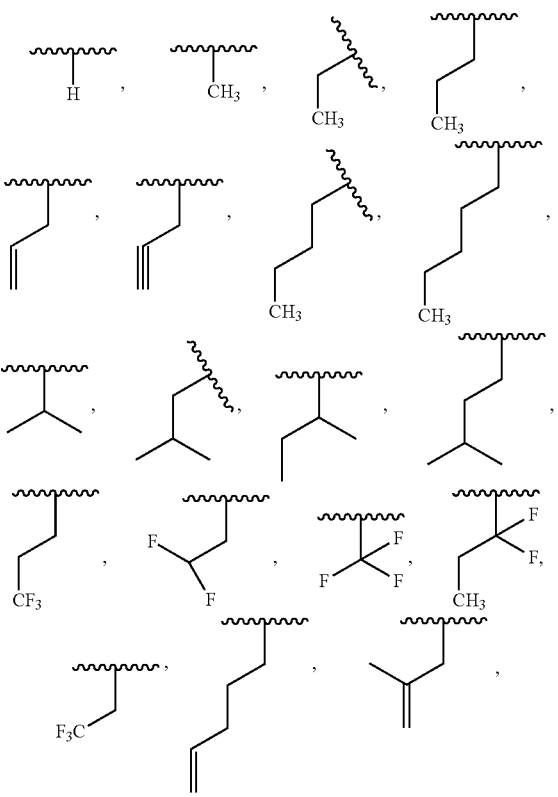

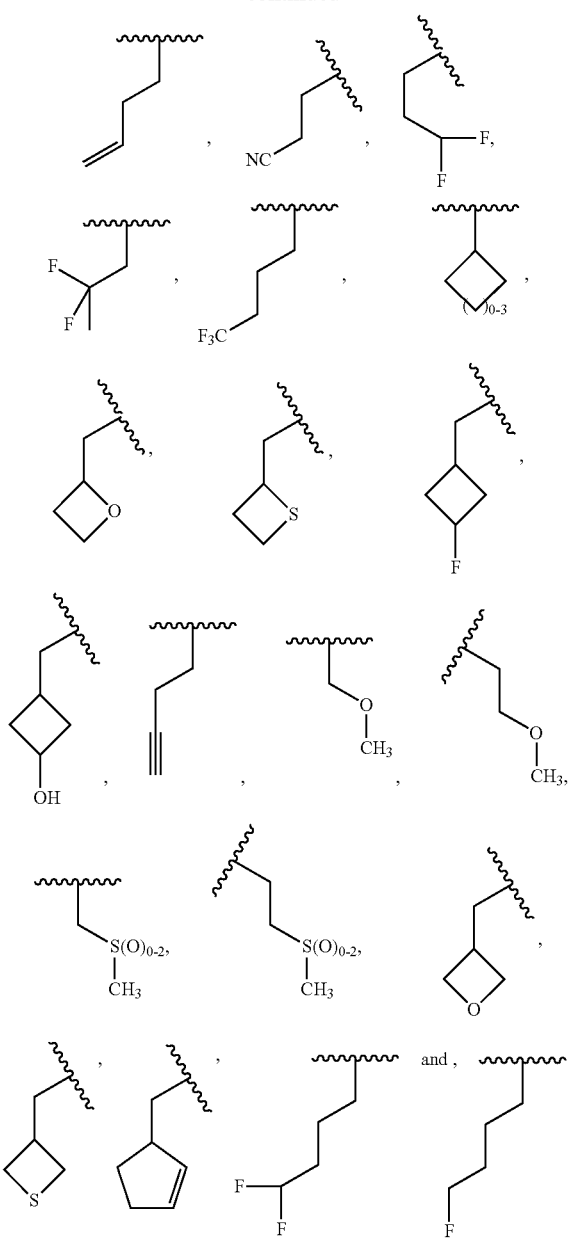
5. The compound of claim 1, wherein $R^3$ is selected from the group consisting of:
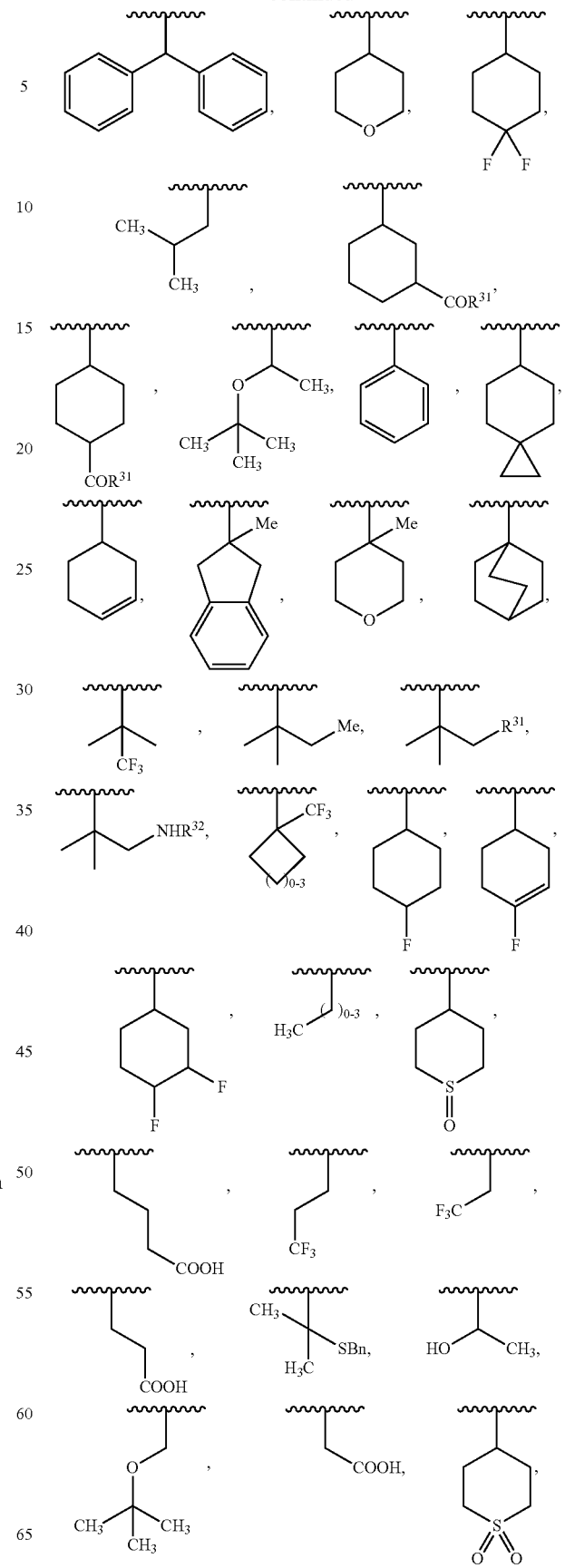

-continued
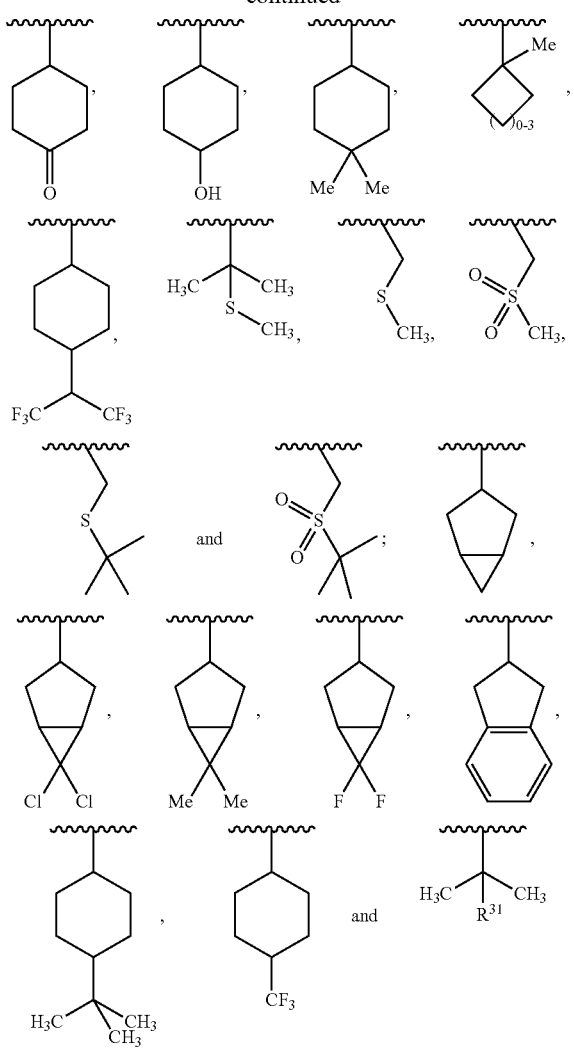
wherein R³¹ is OH or O-alkyl; and
R³² is H, C(O)CH₃, C(O)OtBu or C(O)N(H)tBu.
6. The compound of claim 5, wherein R³ is selected from the group consisting of the following moieties:
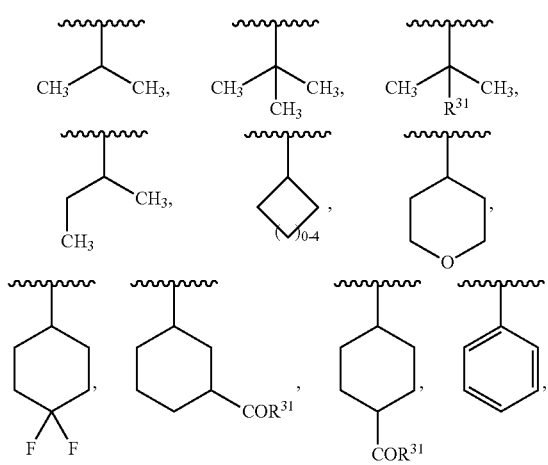
-continued
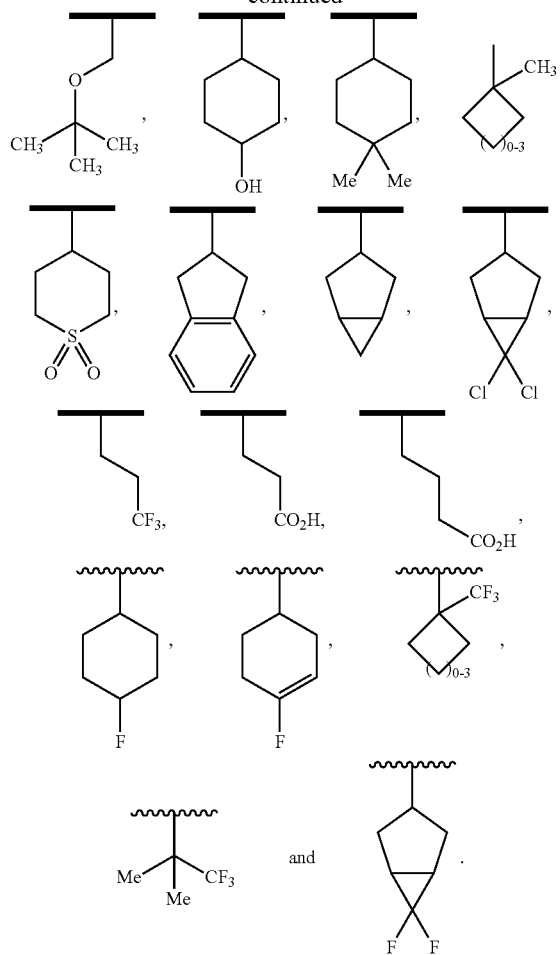
7. The compound of claim 1, wherein Y is selected from the following moieties:
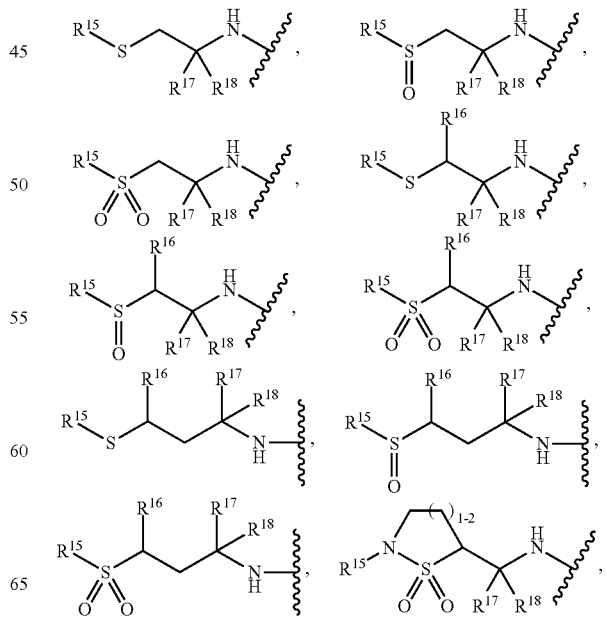

909
-continued

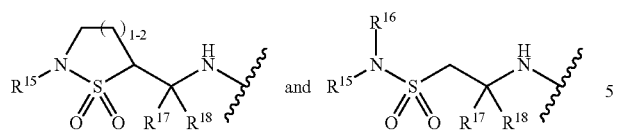

and wherein $R^{15}$ $R^{16}$, $R^{17}$ and $R^{18}$ can be the same or different, each being independently selected from the group consisting of H, alkyl, heteroalkyl, alkenyl, heteroalkenyl, alkynyl, heteroalkynyl, cycloalkyl, heterocyclyl, aryl, and heteroaryl, or alternately, $R^{15}$ and $R^{16}$ are connected to each other to form a four to eight-membered cycloalkyl or heterocyclic structure; $R^{17}$ and $R^{18}$ are connected to each other to form a three to eight-membered cycloalkyl or heterocyclyl, wherein each of said aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkylsulfonamido, arylsulfonamido, alkyl, aryl, heteroaryl, carboxy, carbalkoxy, carboxamido, alkoxycarbonylamino, alkoxycarbonyloxy, alkylureido, arylureido, halo, cyano, and nitro.

8. The compound of claim 7, Y is selected from the group consisting of:

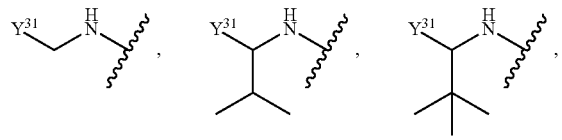

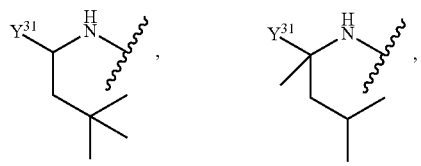

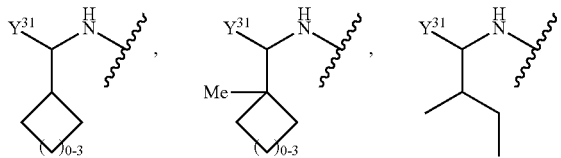

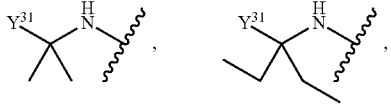

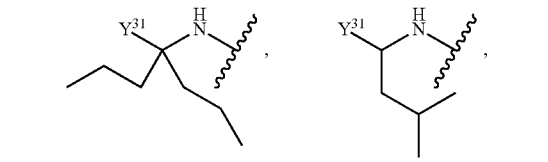

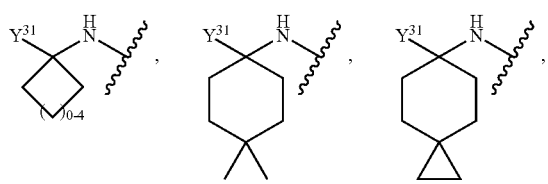

910
-continued

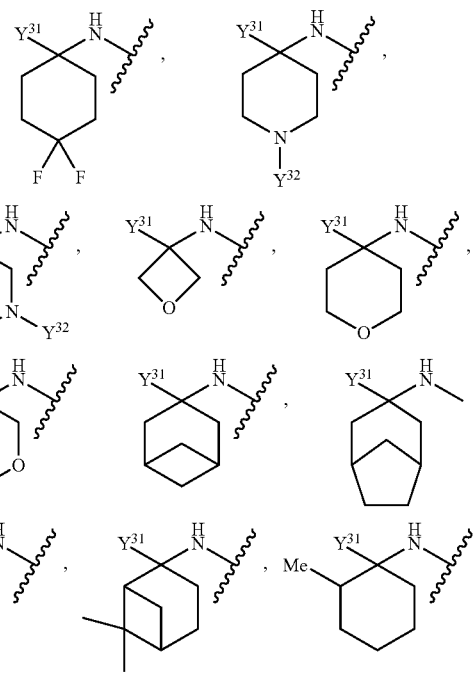

wherein $Y^{31}$ is selected from the group consisting of:

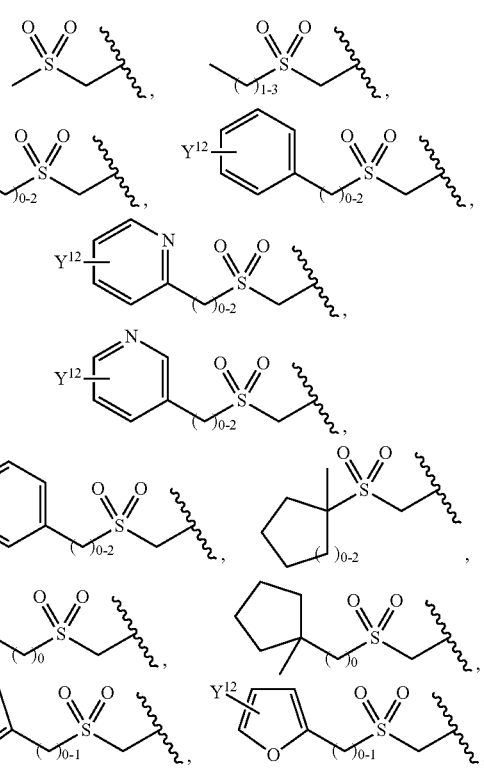

911
-continued
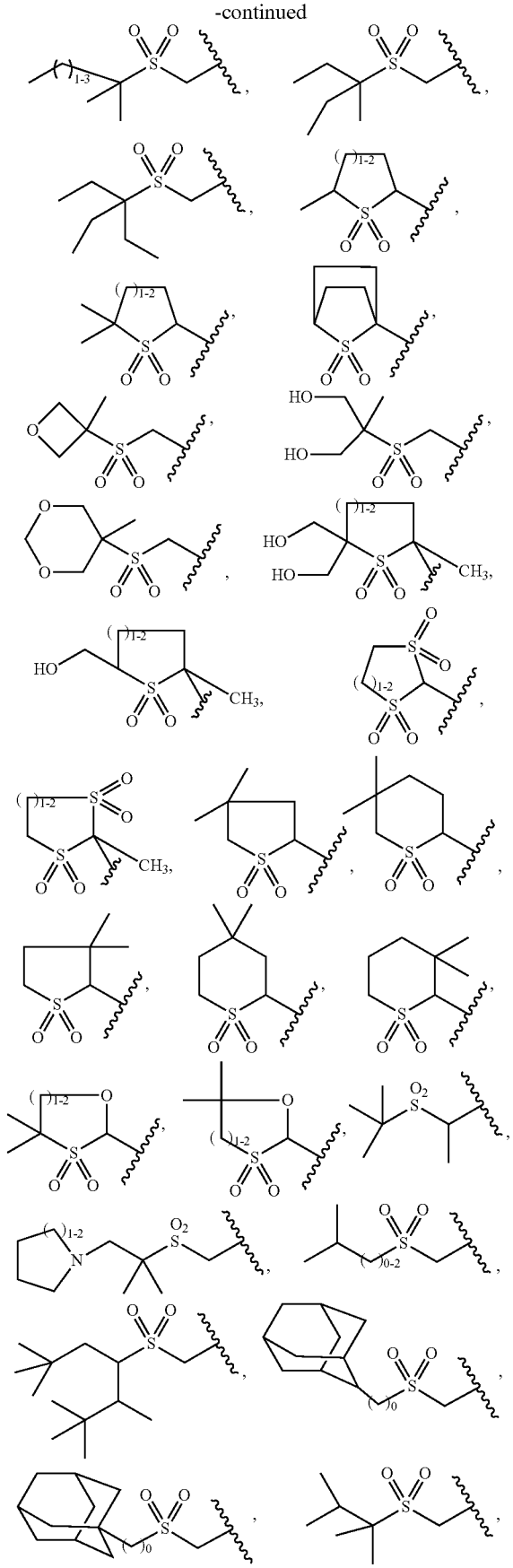
912
-continued
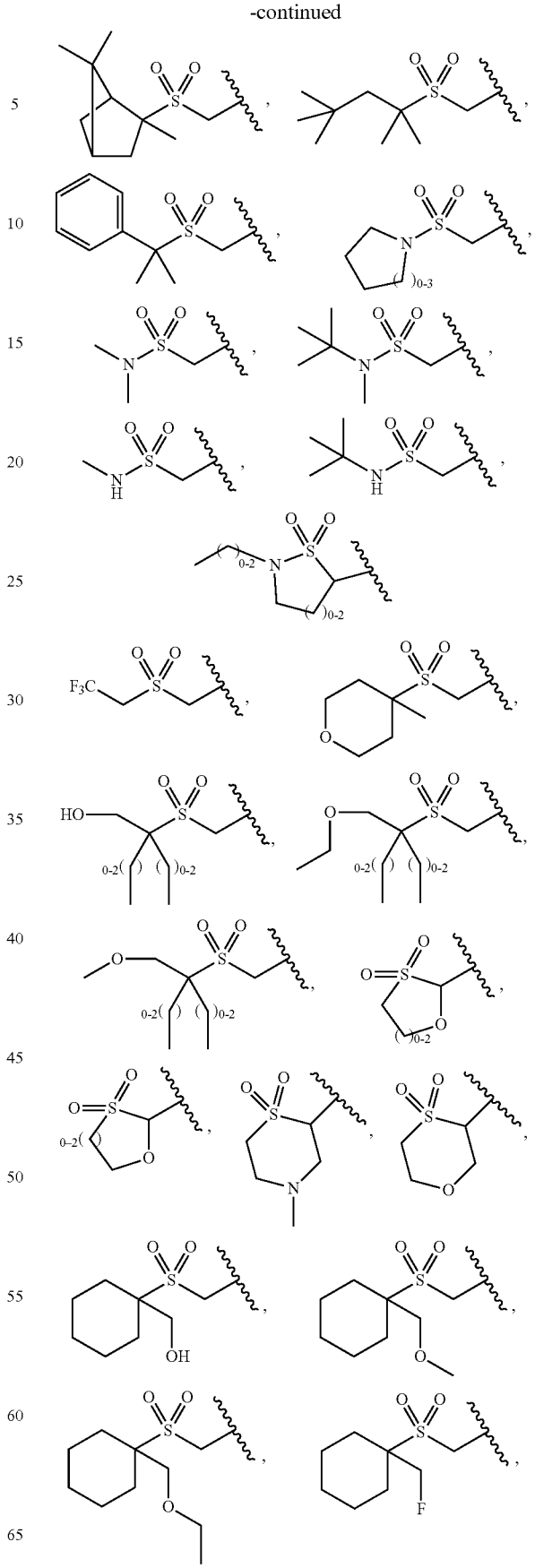

913
-continued

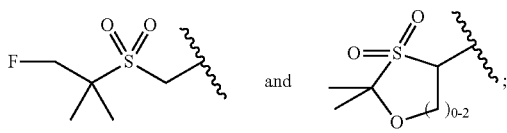

and $Y^{32}$ is selected from the group consisting of:

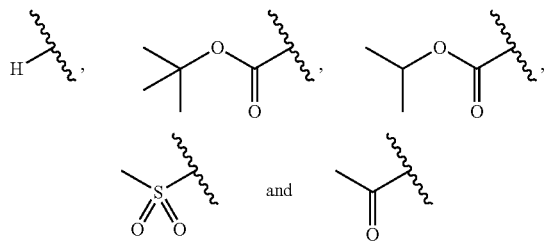

and $Y^{12}$ is selected from the group consisting of H, $CO_2H$, $CO_2Me$, OMe, F, Cl, Br, $NH_2$, $N(H)S(O_2)CH_3$, $N(H)C(O)CH_3$, $NO_2$, $S(O_2)NH_2$, $CF_3$, Me, OH, $OCF_3$, and $C(O)NH_2$.

9. The compound of claim 1, wherein:
$R^1$ is $NHR^{14}$, where $R^{14}$ is selected from the group consisting of:

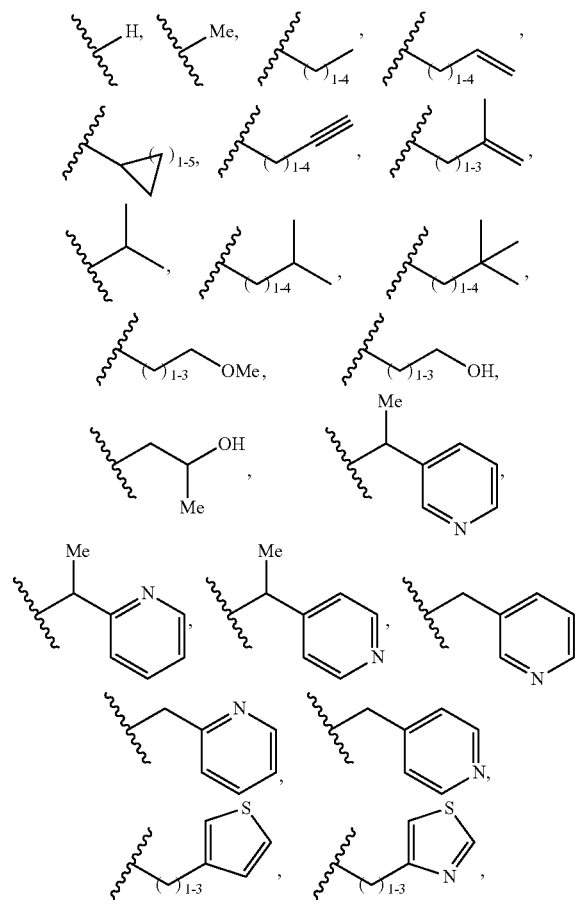

914
-continued

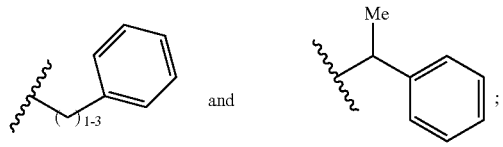

$R^2$ is selected from the group consisting of the following moieties:

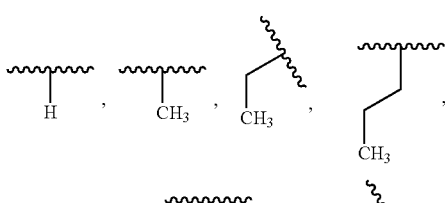

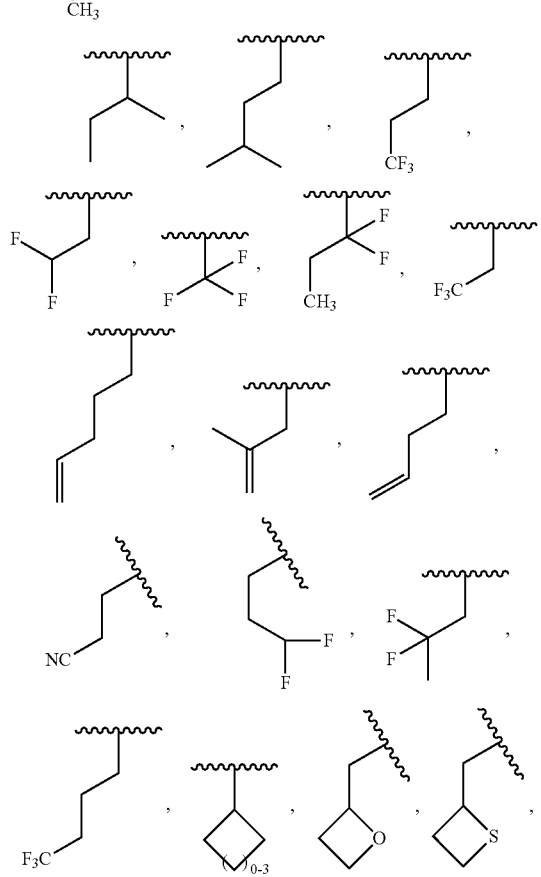

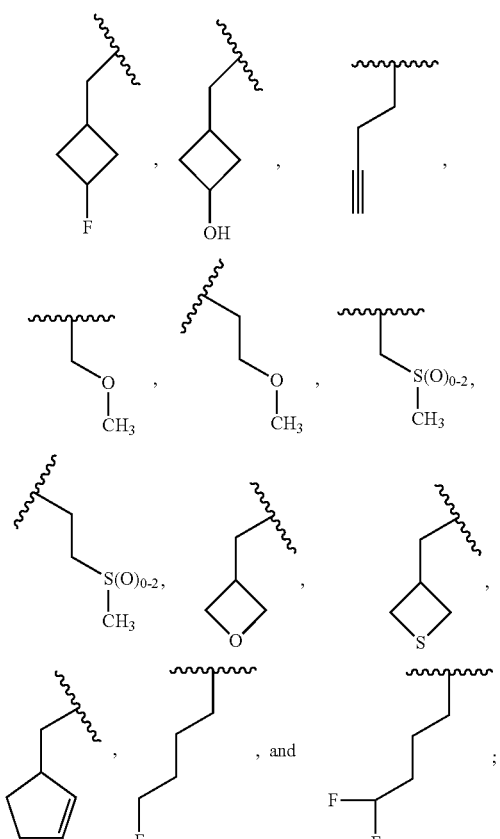
$R^3$ is selected from the group consisting of the following moieties:
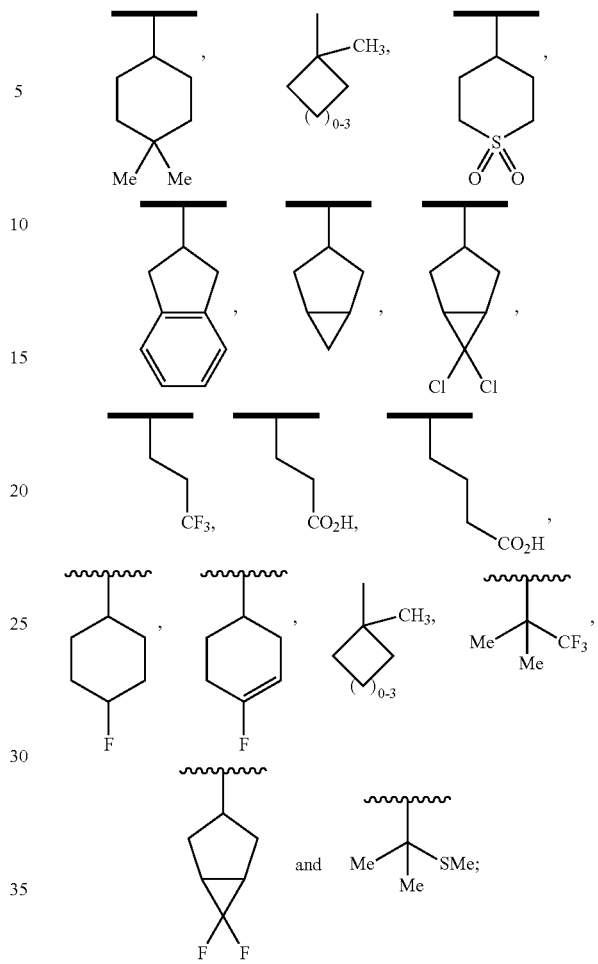
Y is selected from the group consisting of:
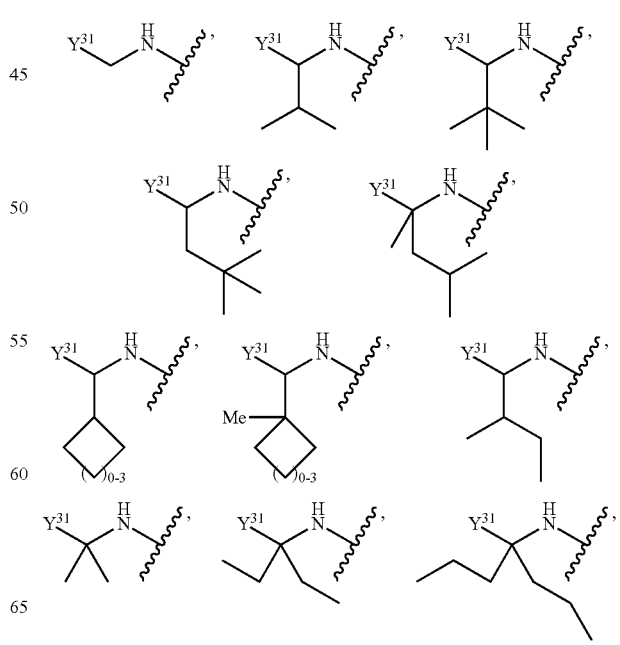

-continued

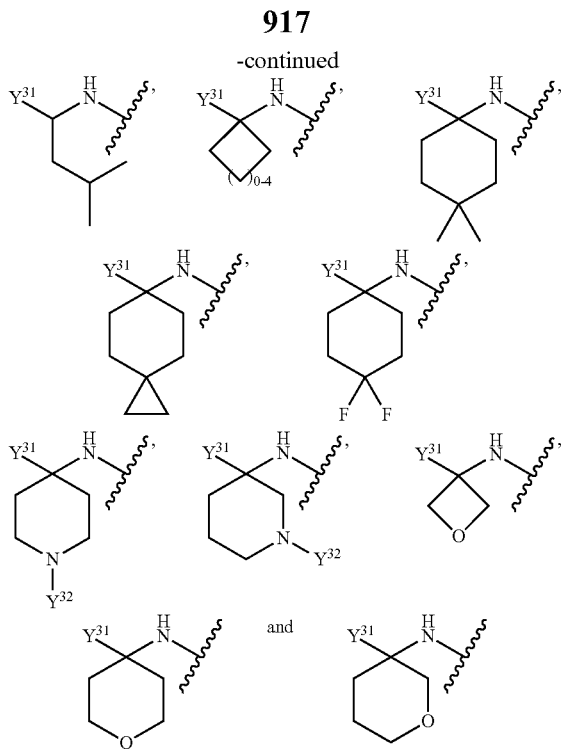

wherein $Y^{31}$ is selected from the group consisting of:

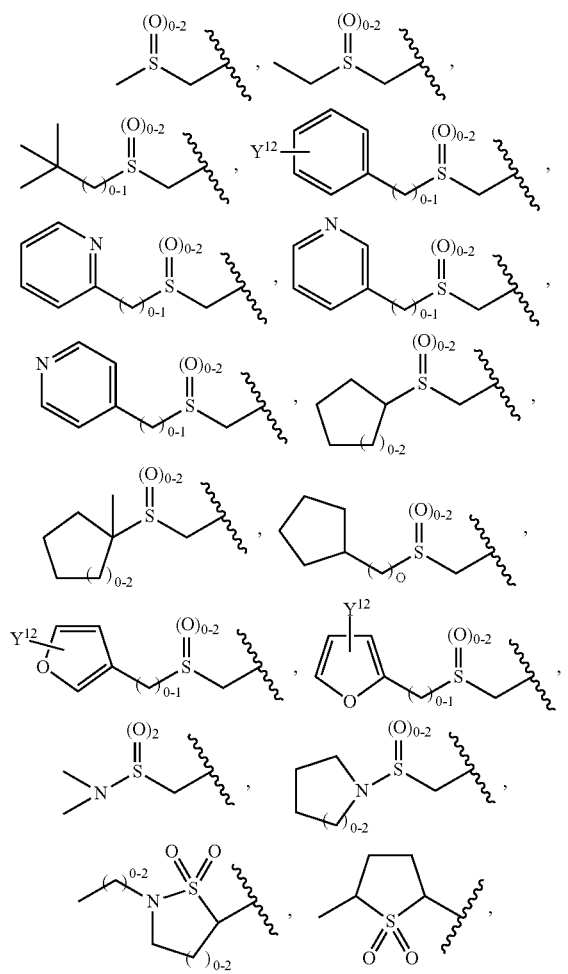

-continued

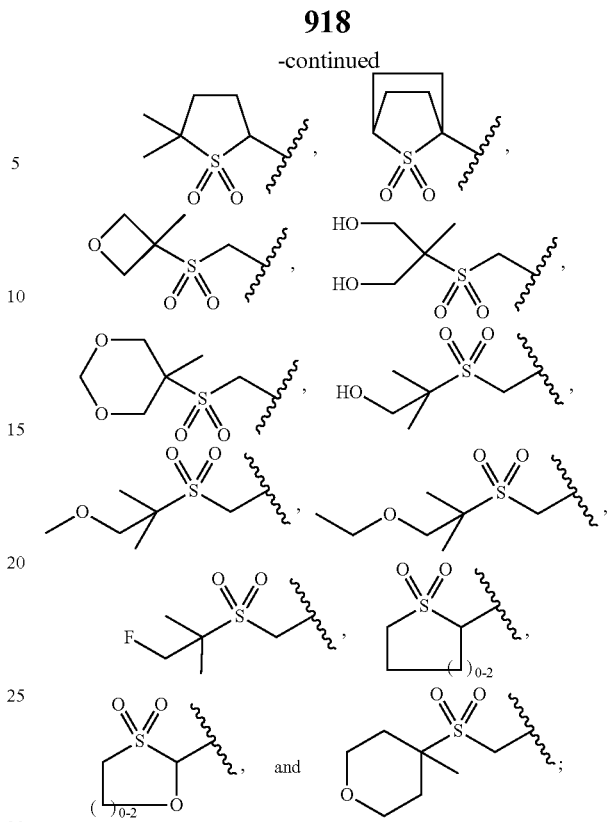

$Y^{32}$ is selected from the group consisting of:

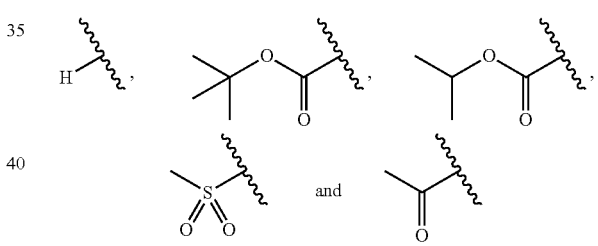

and $Y^{12}$ is selected from the group consisting of H, $CO_2H$, $CO_2Me$, OMe, F, Cl, Br, $NH_2$, $N(H)S(O_2)CH_3$, $N(H)C(O)CH_3$, $NO_2$, $S(O_2)NH_2$, $CF_3$, Me, OH, $OCF_3$, and $C(O)NH_2$.

10. A pharmaceutical composition comprising as an active ingredient at least one compound of claim 1.

11. The pharmaceutical composition of claim 10 additionally comprising at least one pharmaceutically acceptable carrier.

12. The pharmaceutical composition of claim 11, additionally containing at least one antiviral agent.

13. The pharmaceutical composition of claim 12, still additionally containing at least one interferon.

14. The pharmaceutical composition of claim 13, wherein said at least one antiviral agent is ribavirin and said at least one interferon is α-interferon or pegylated interferon.

15. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound being selected from the compounds of structures listed below:

| 919 | 920 |
|---|---|
| 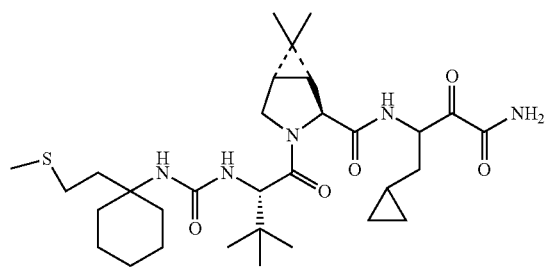 | 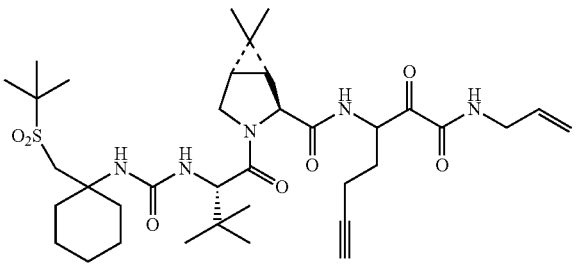 |
| 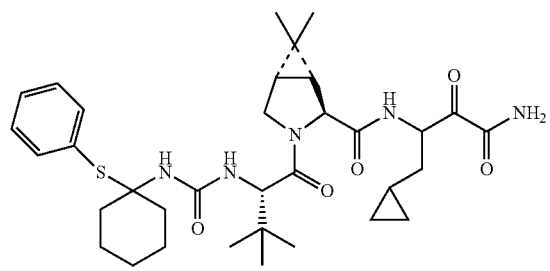 | 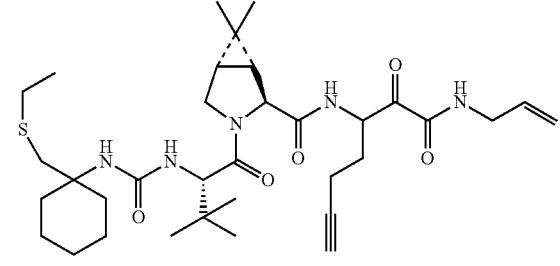 |
| 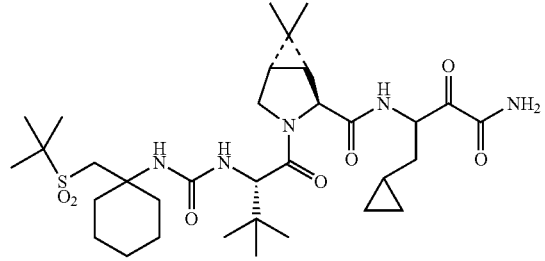 | 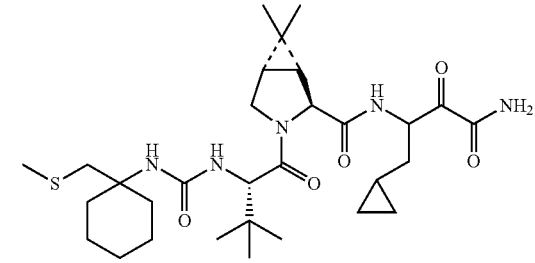 |
| 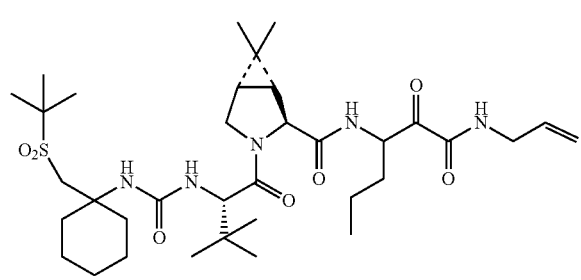 | 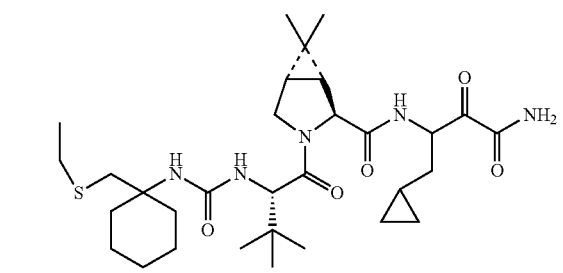 |
| 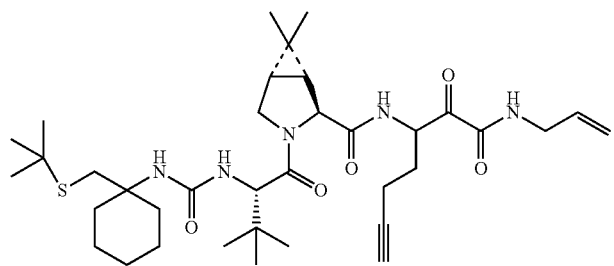 | 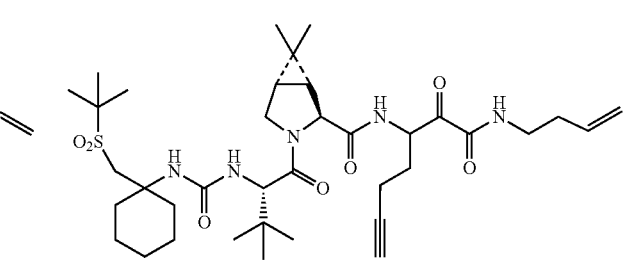 |
| 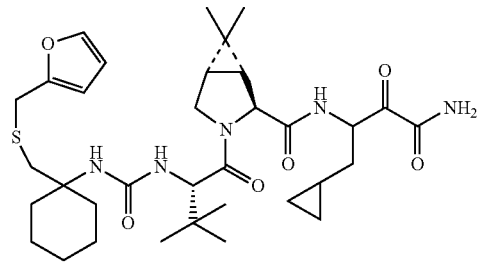 | 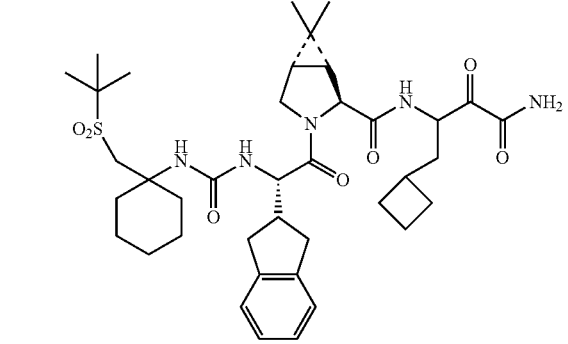 |

921
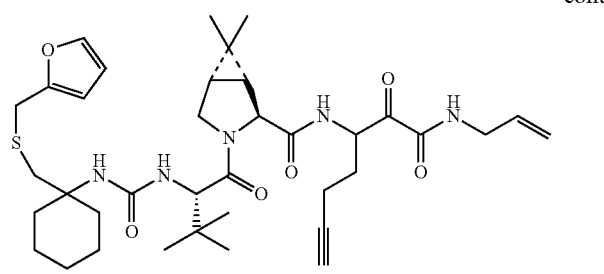
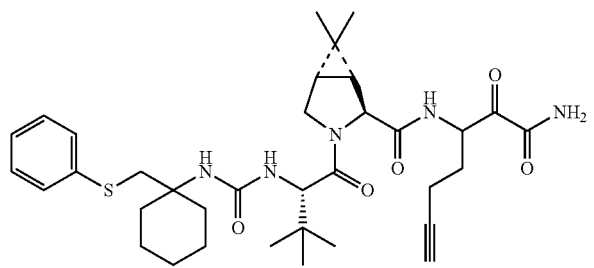
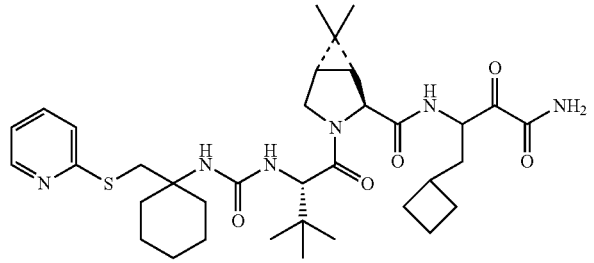
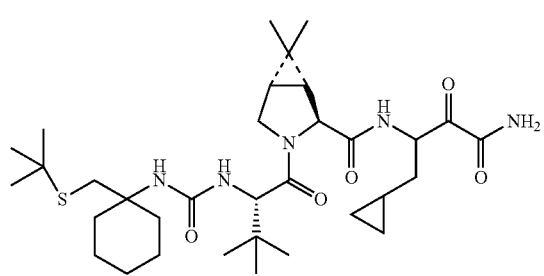
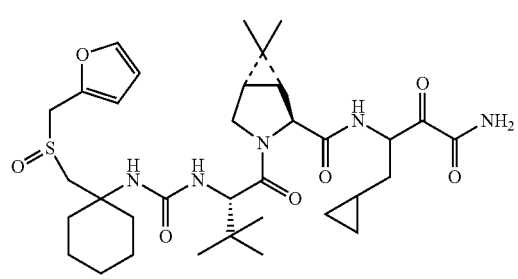
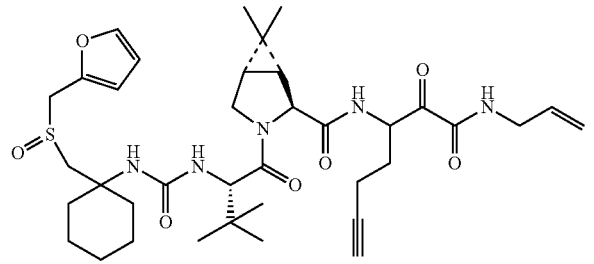
922
-continued
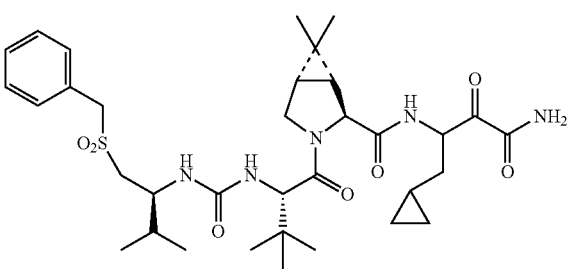
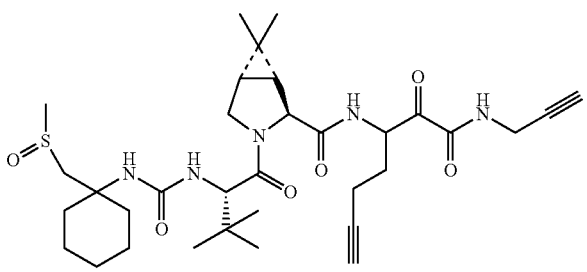
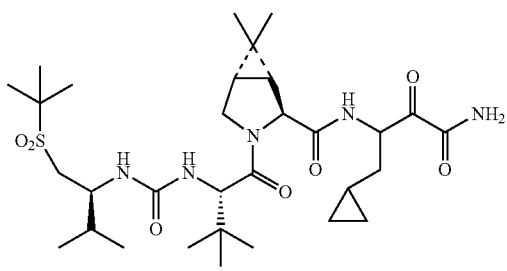
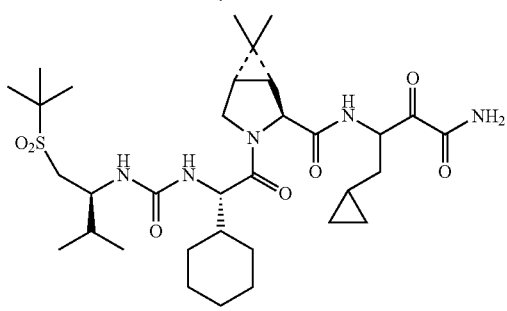
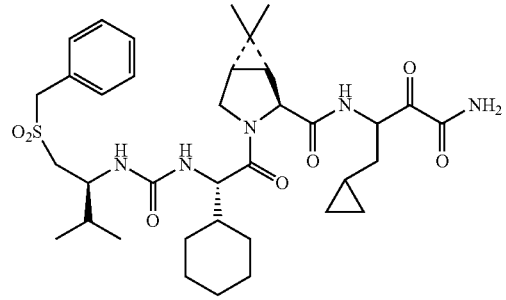
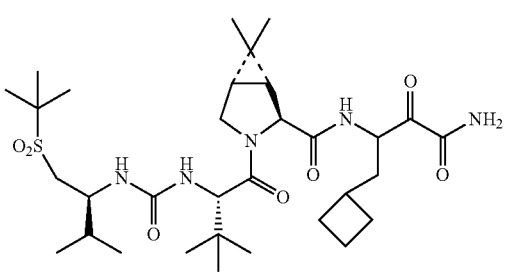

923
924
-continued
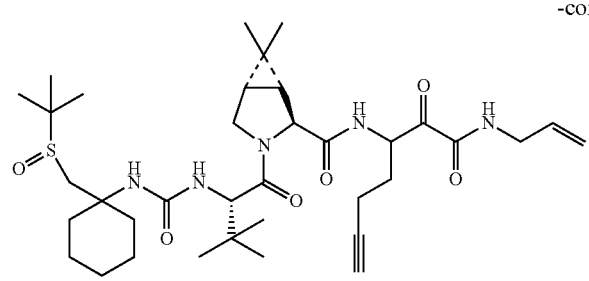
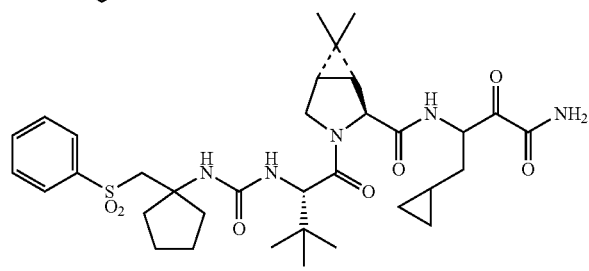
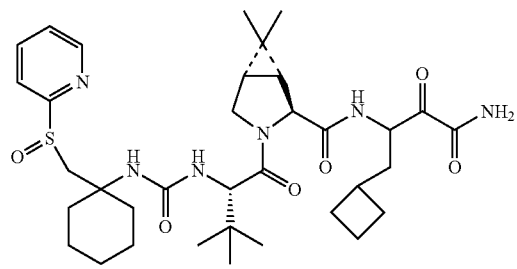
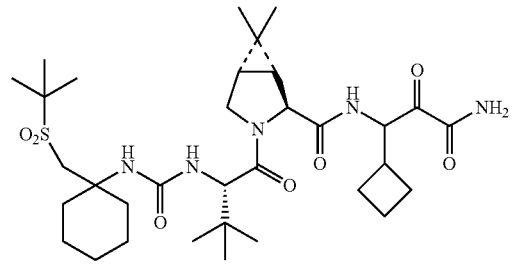
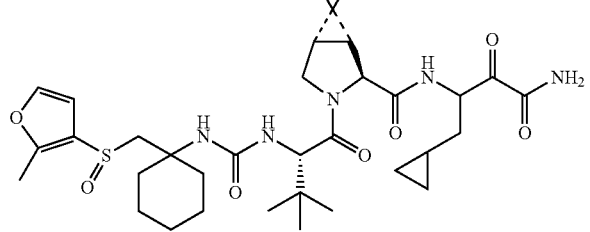
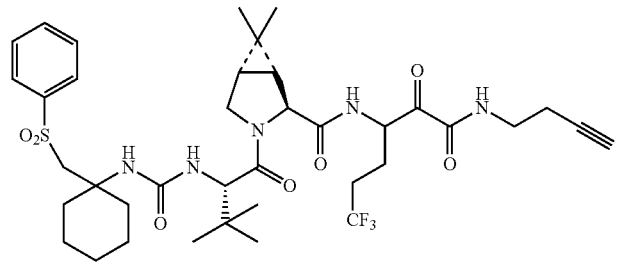
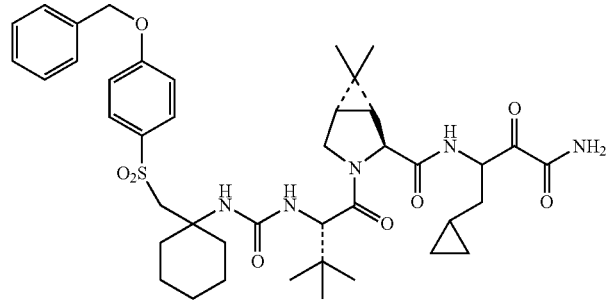
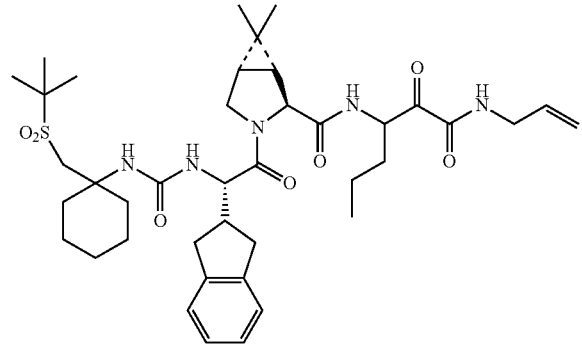
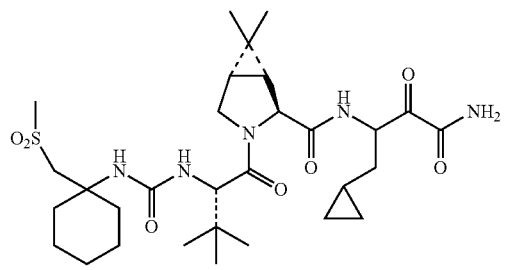

925 926
-continued
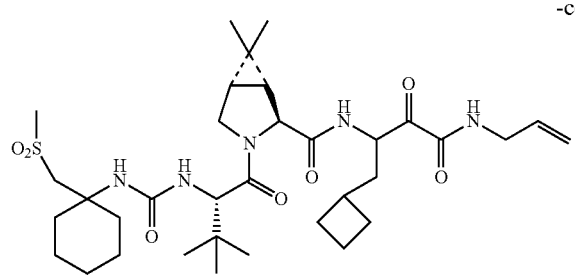
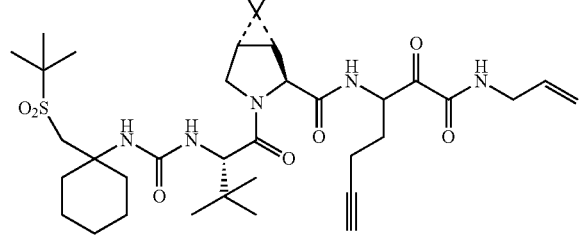
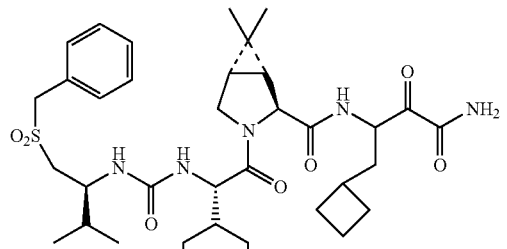
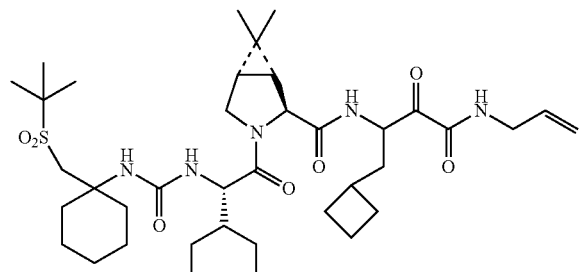
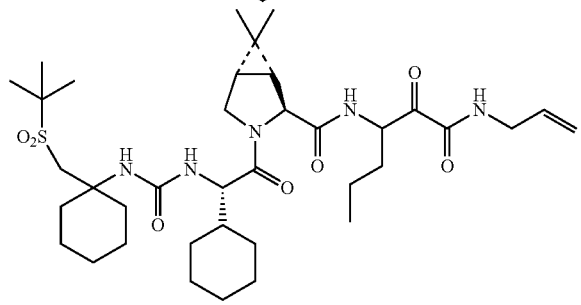
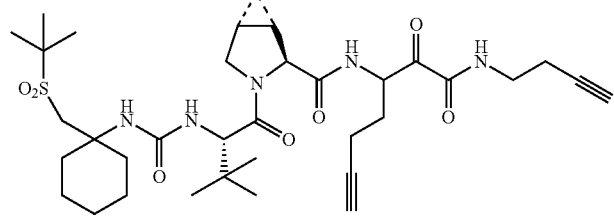
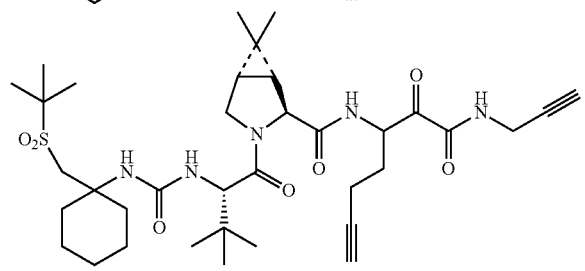
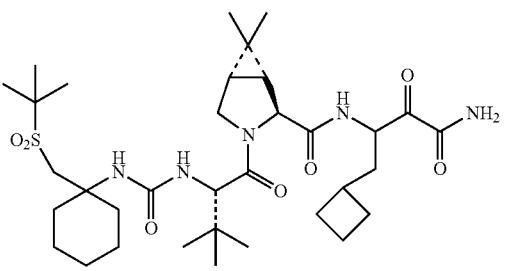
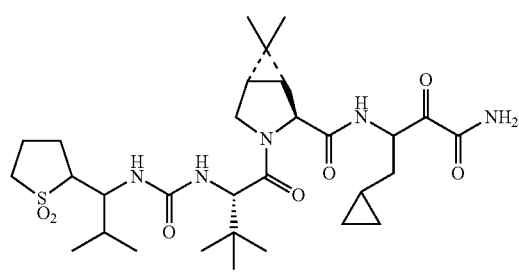
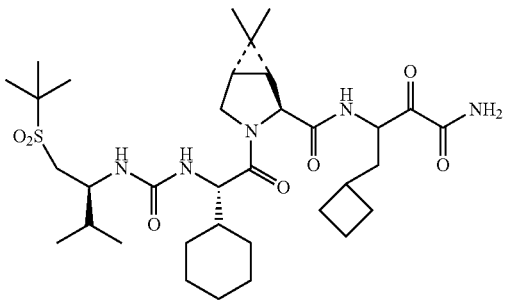

-continued
| 927 | 928 |
|---|---|
| 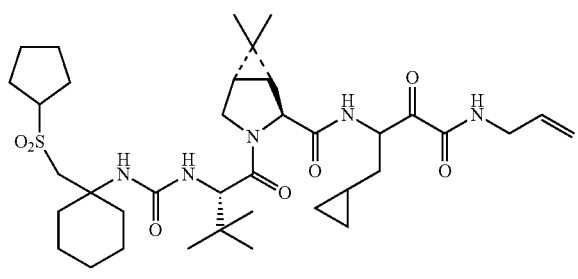 | 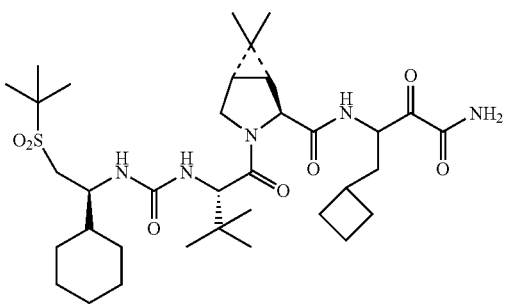 |
| 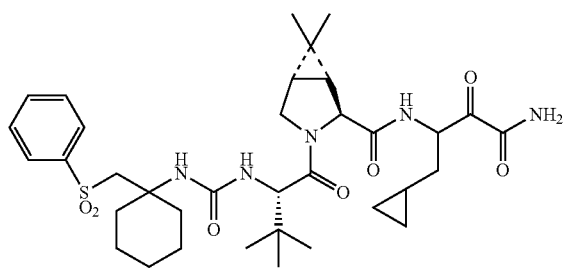 | 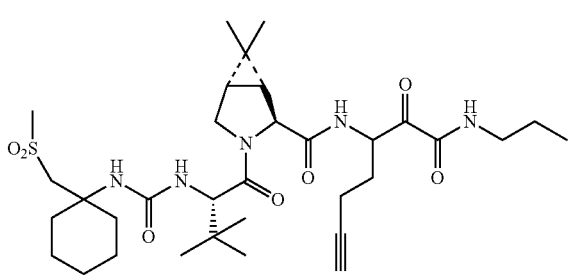 |
| 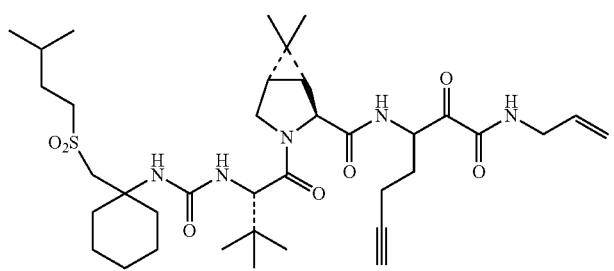 | 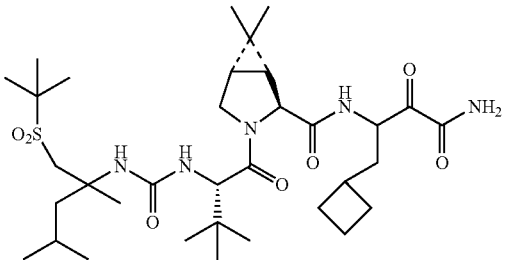 |
| 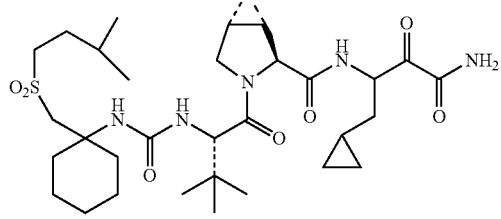 | |
| 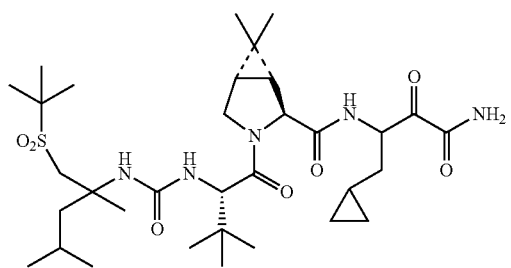 | 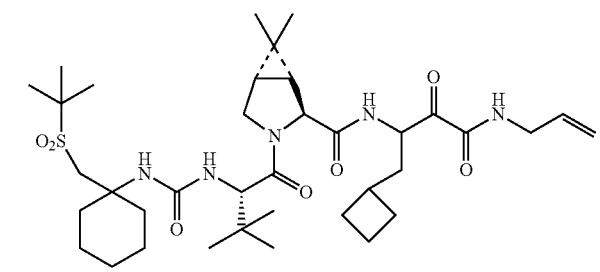 |
| 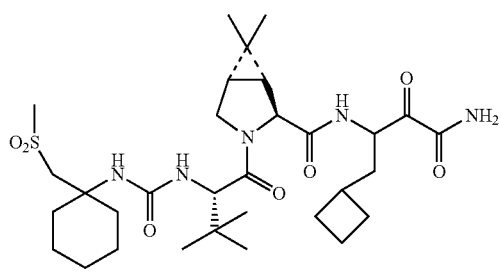 | 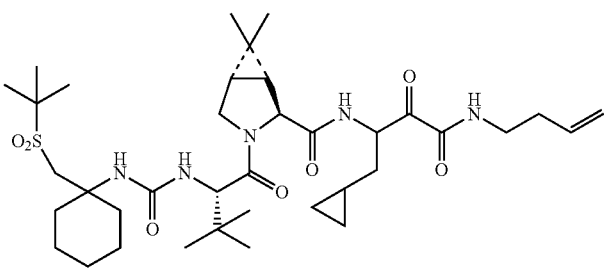 |

929 930
-continued
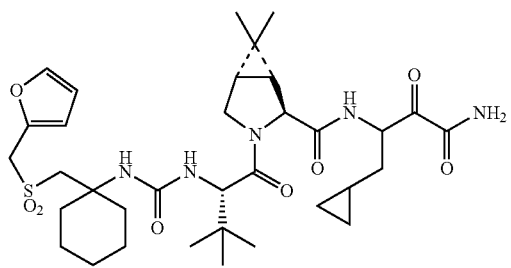
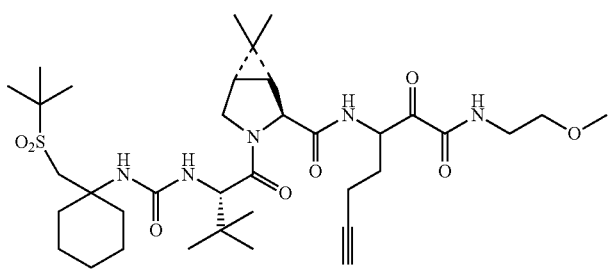
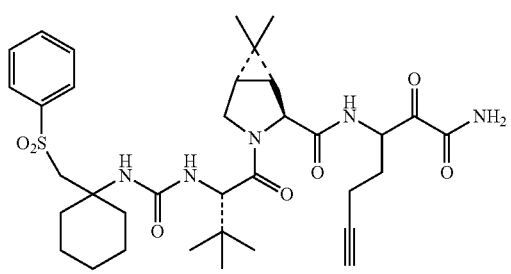
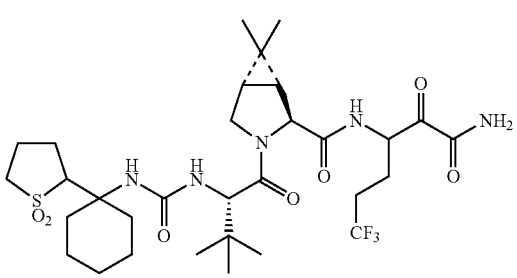
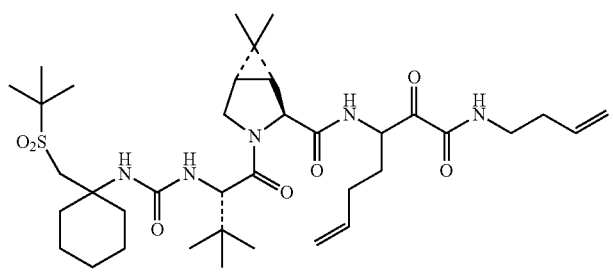
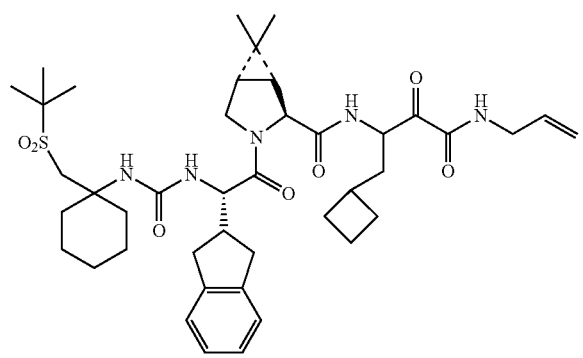
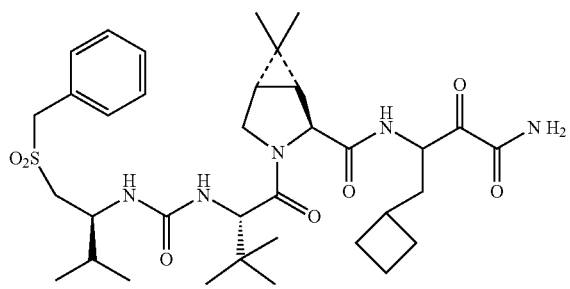
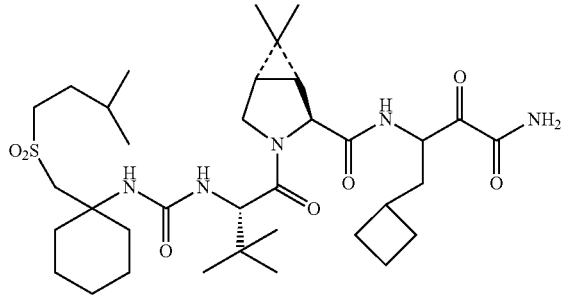
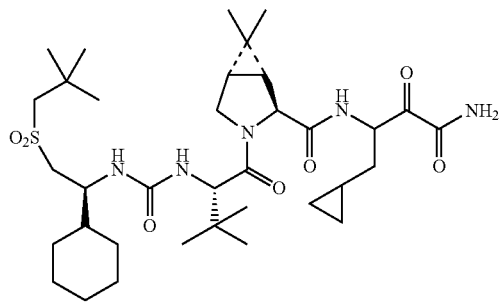
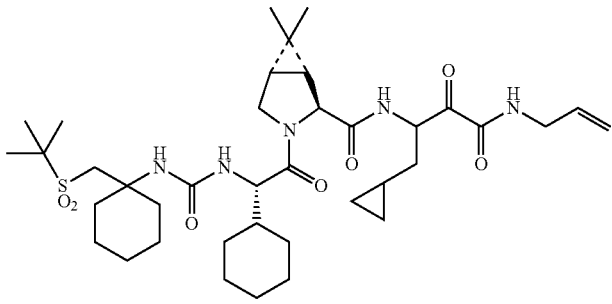

-continued
| 931 | 932 |
|---|---|
| 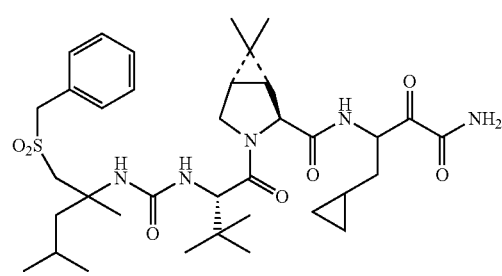 | 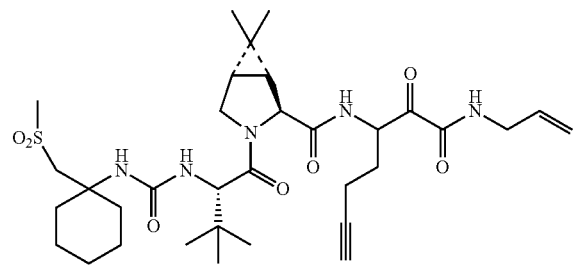 |
| 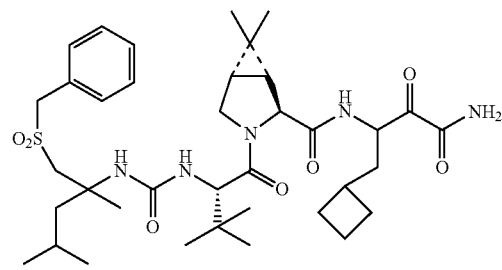 | |
| 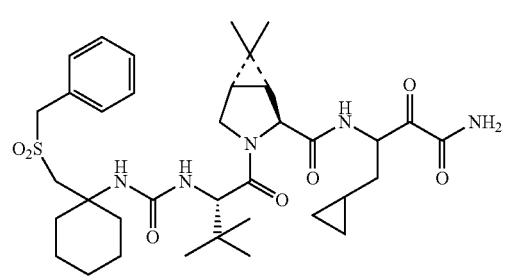 | 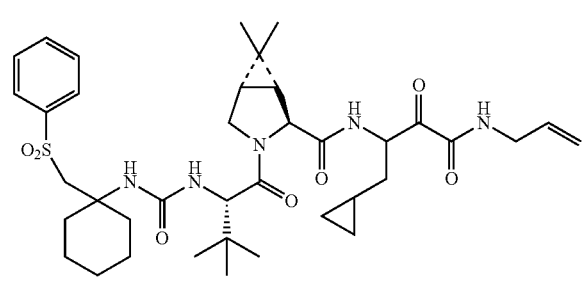 |
| 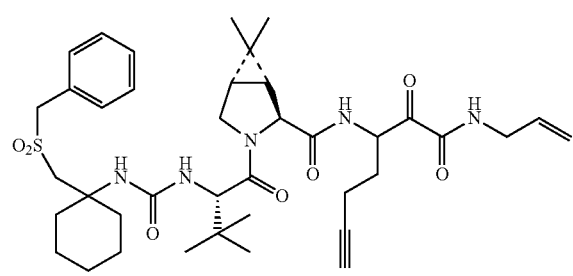 | 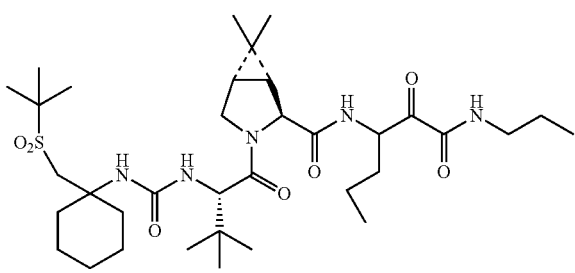 |
| 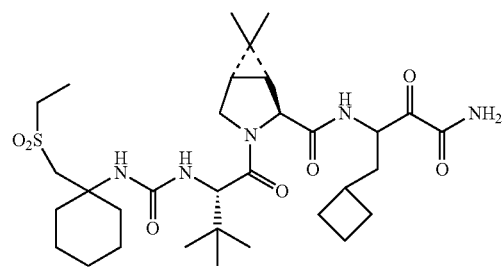 | 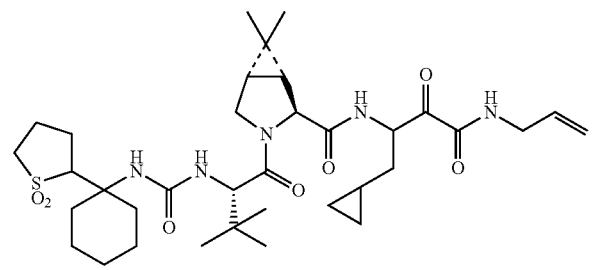 |
| | 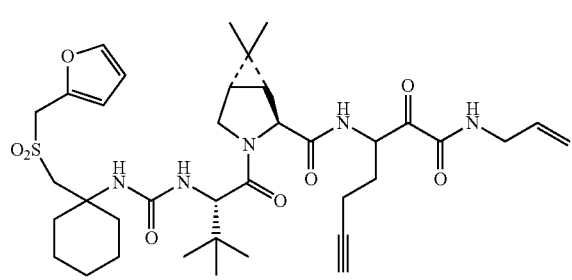 |

933
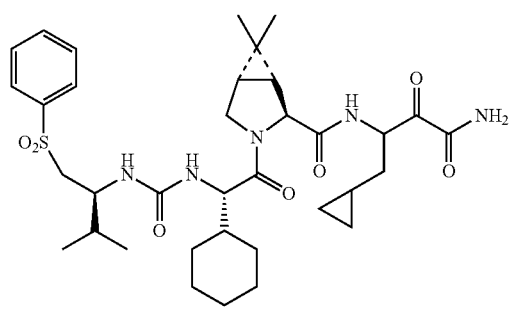
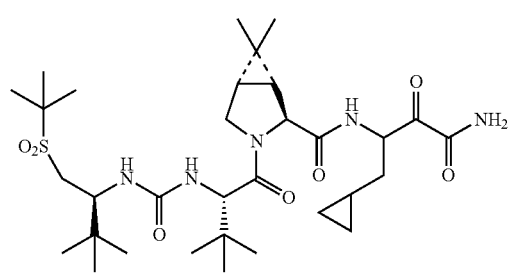
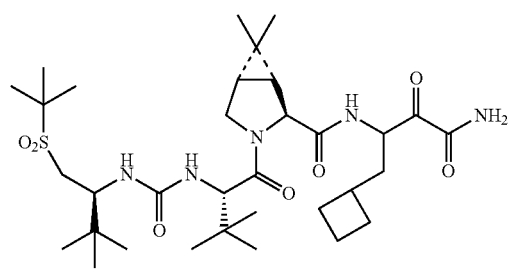
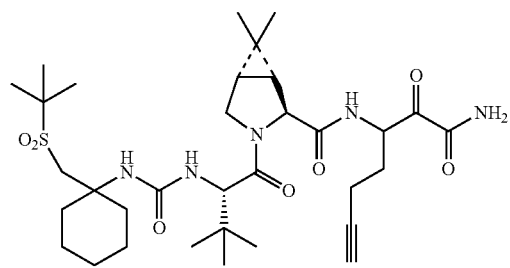
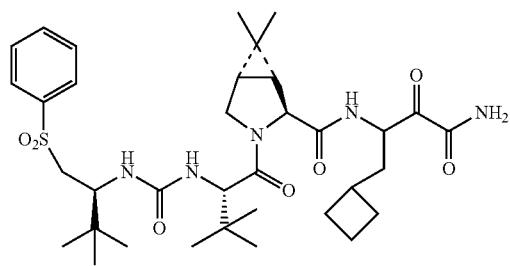
934
-continued
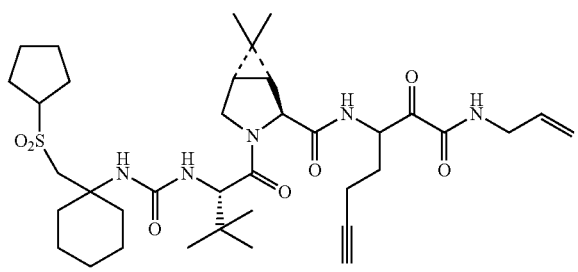
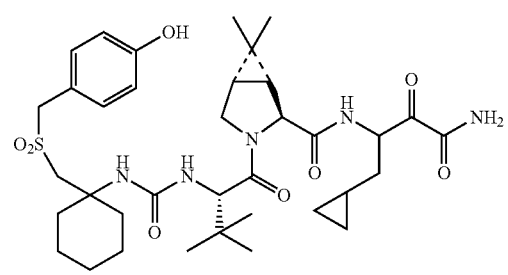
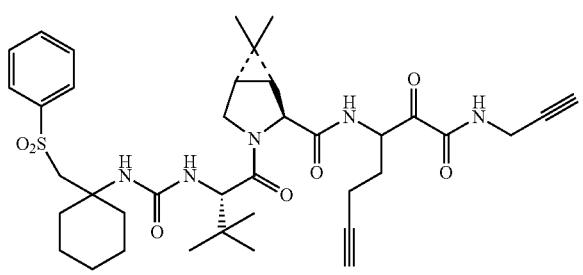
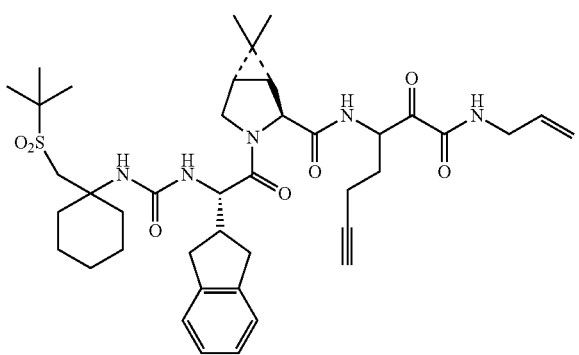
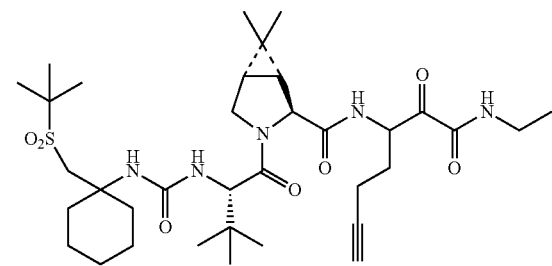

935 936
-continued
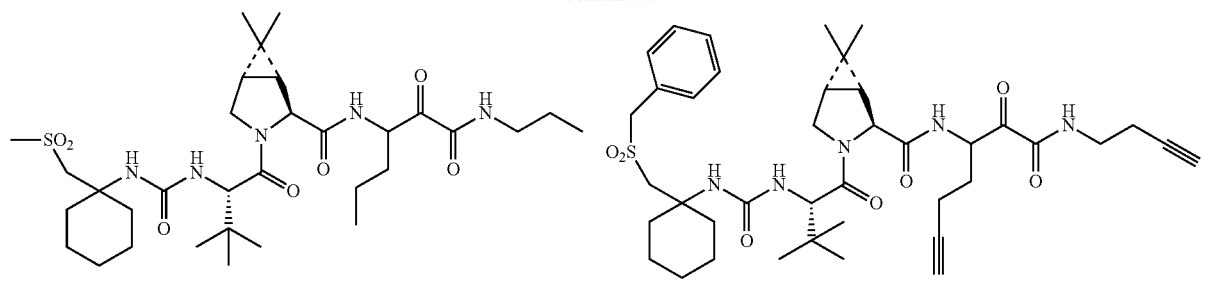
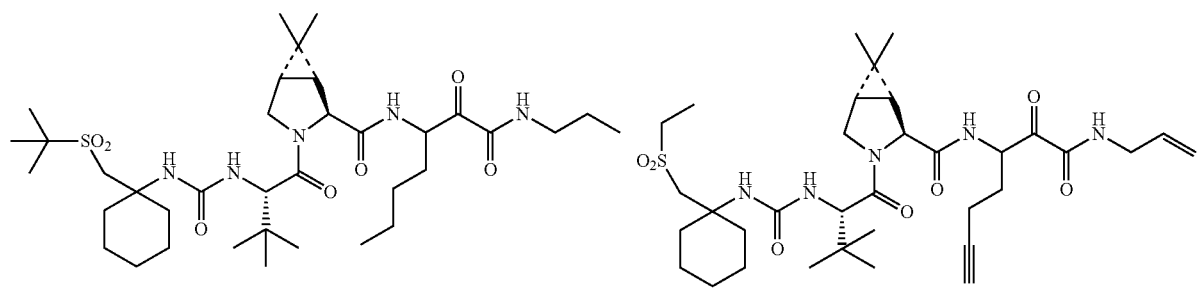
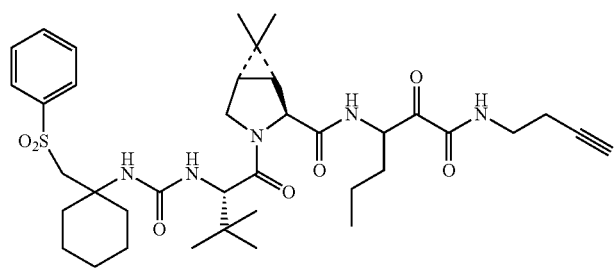
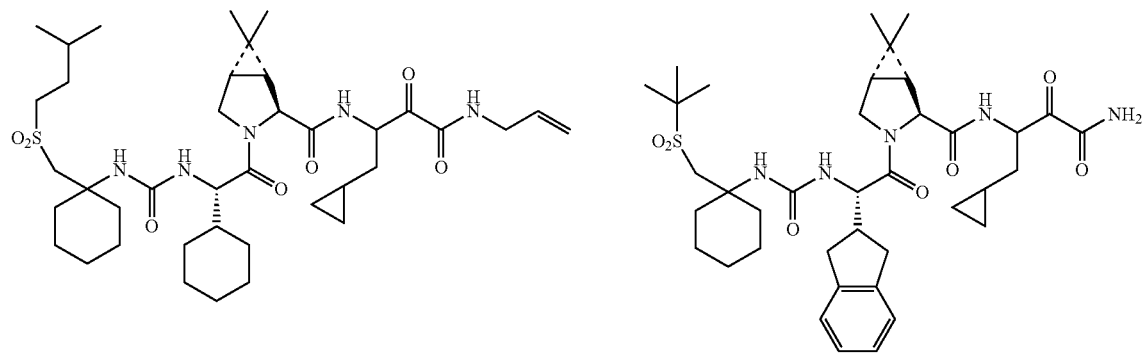
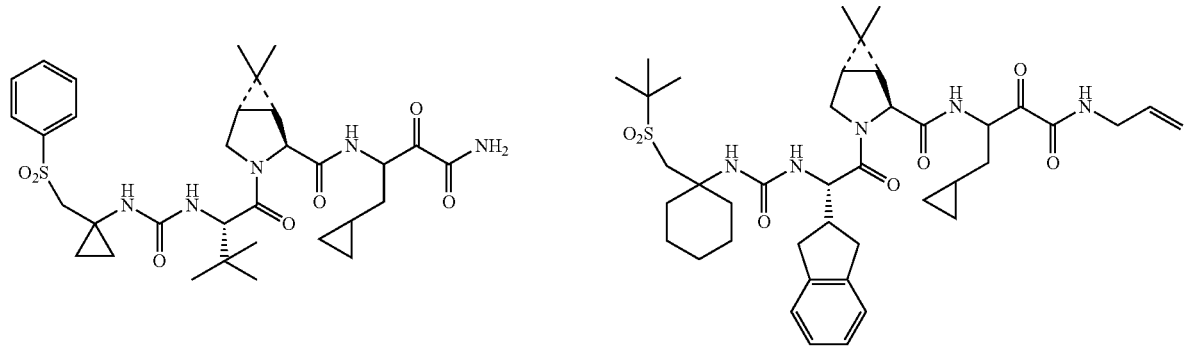

937 938
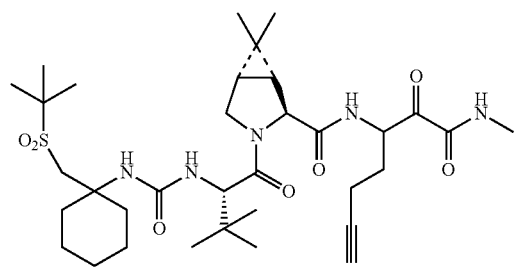
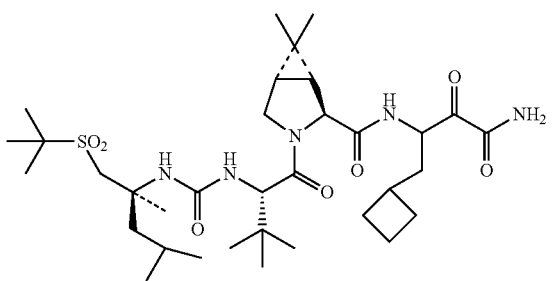
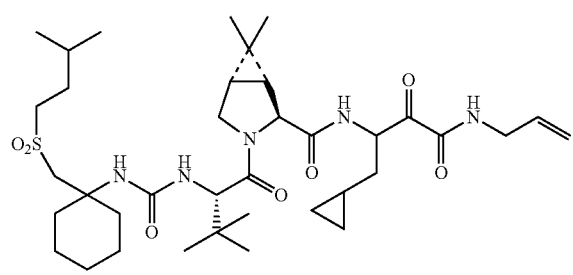
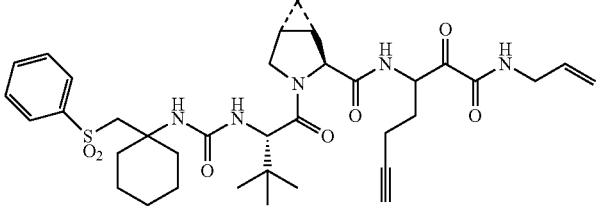
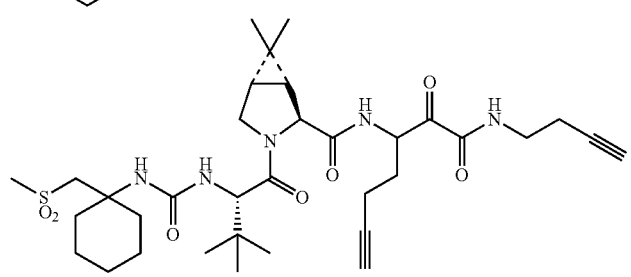
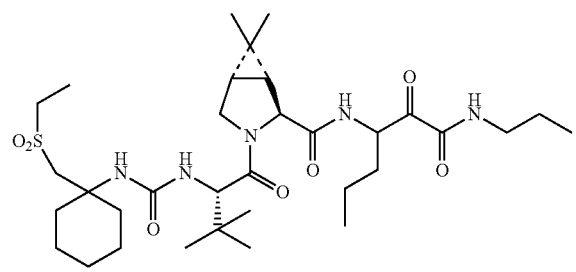
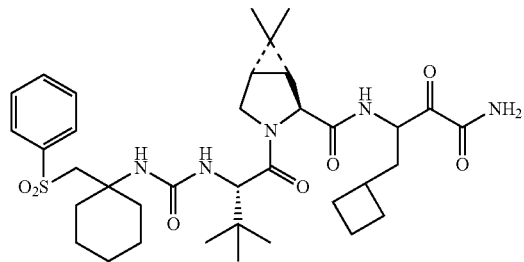
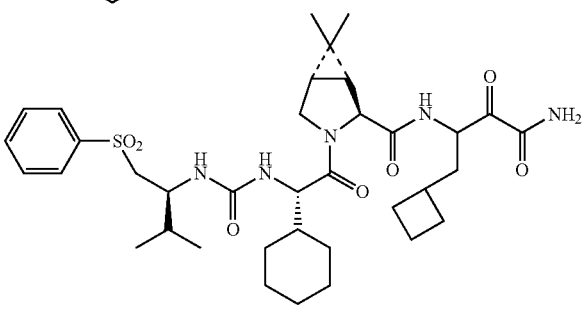
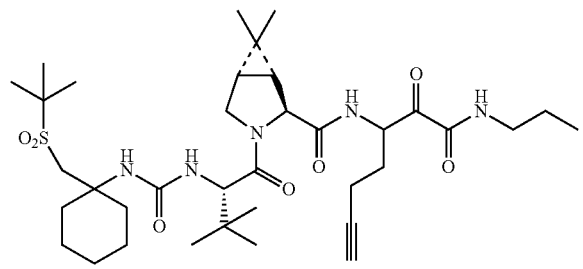
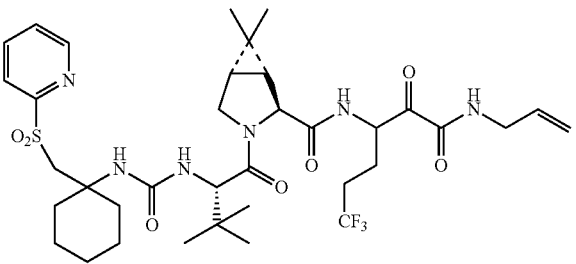

939 940
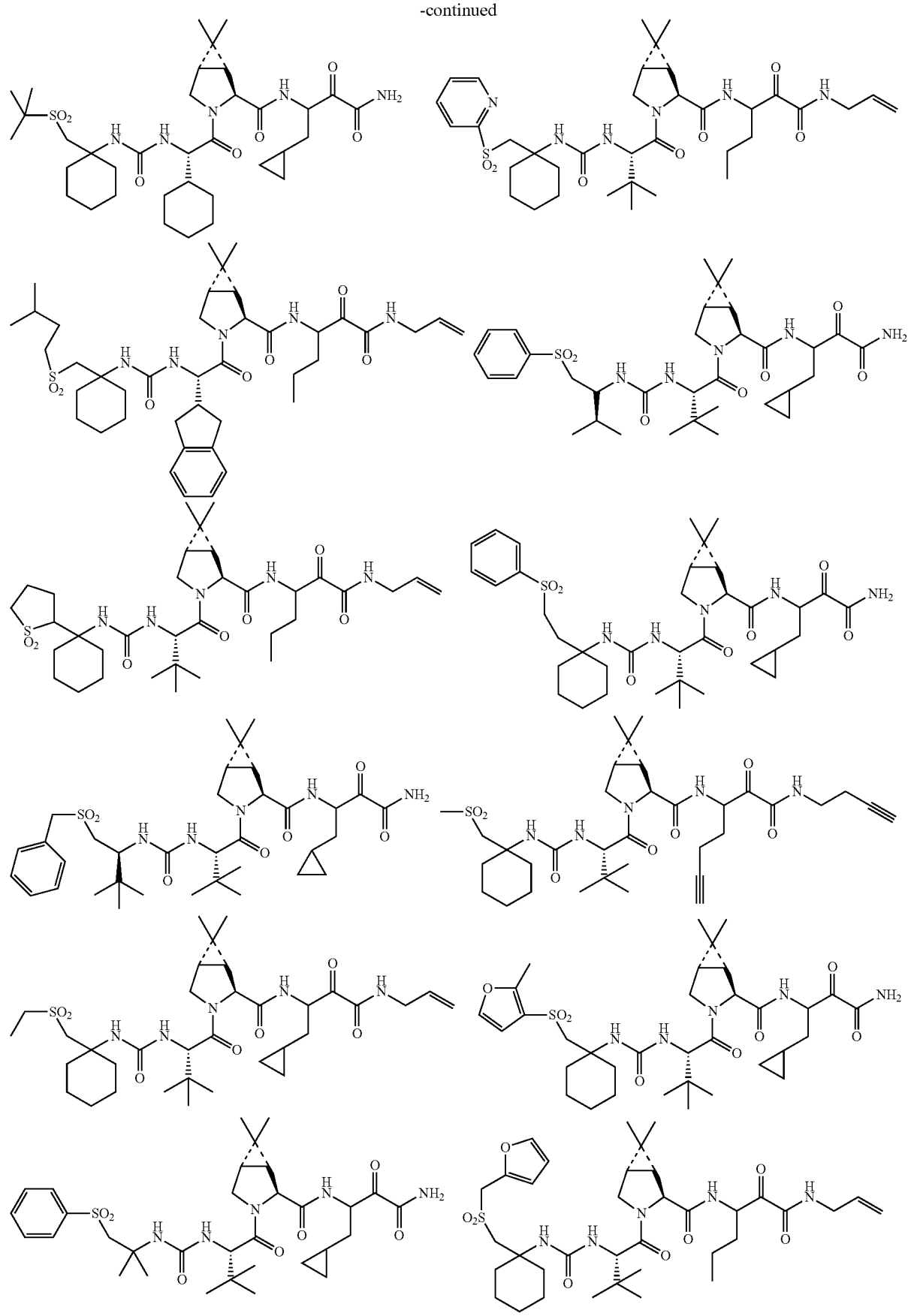

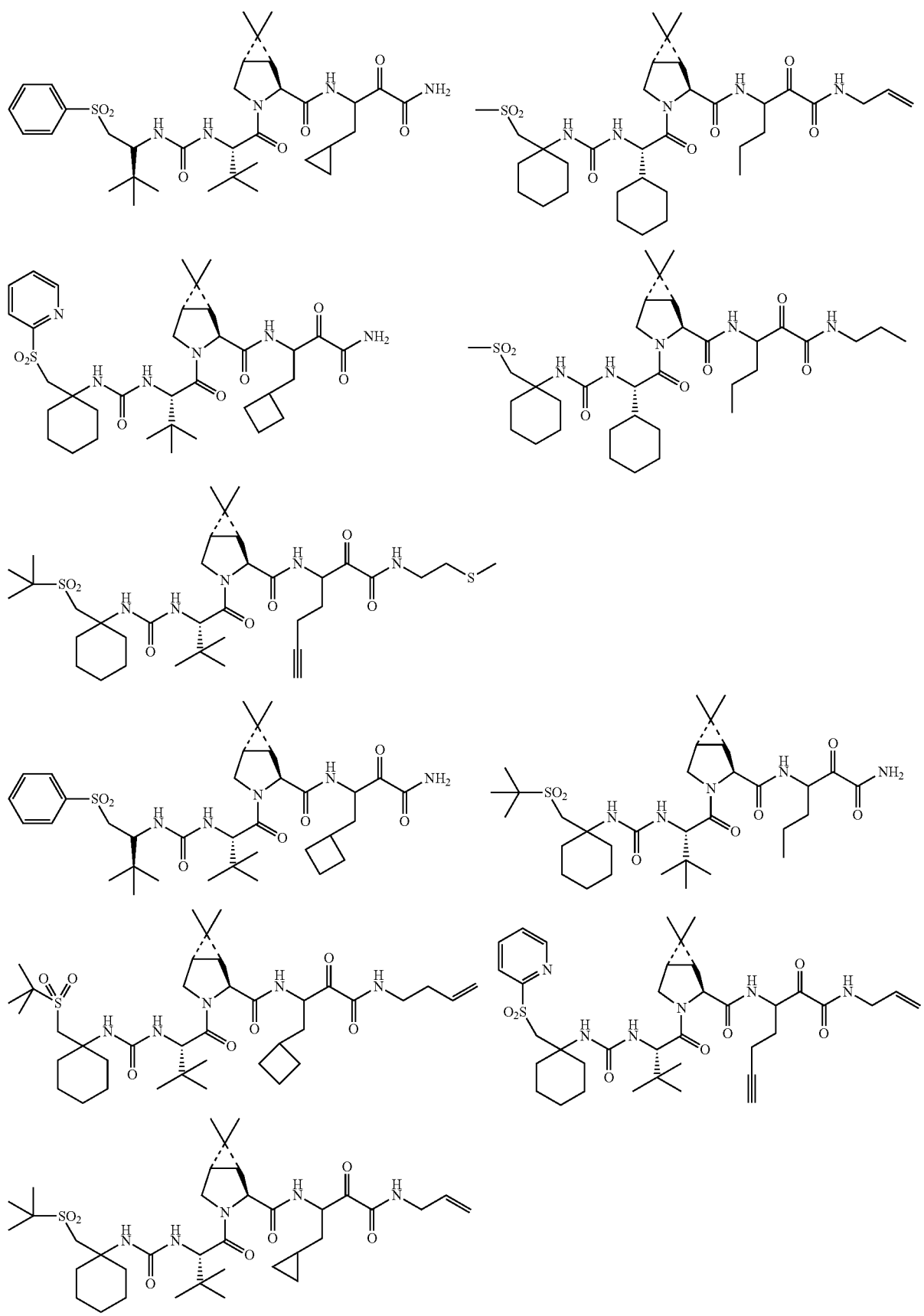

-continued
| 943 | 944 |
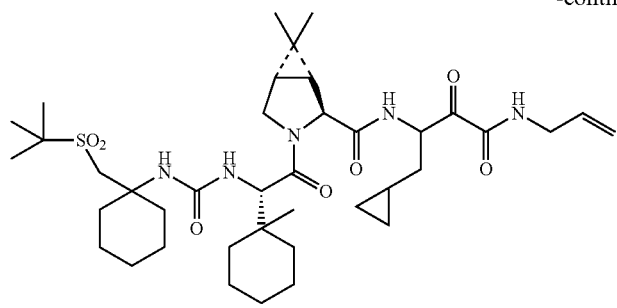
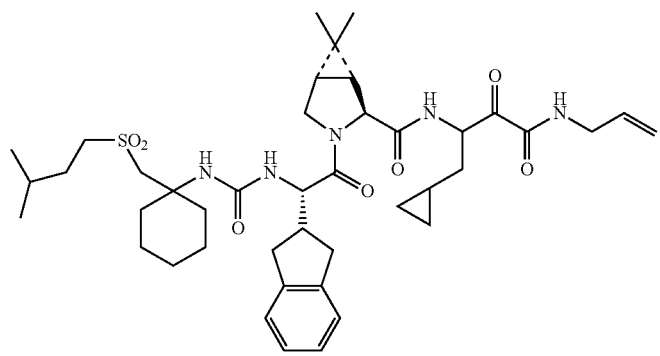
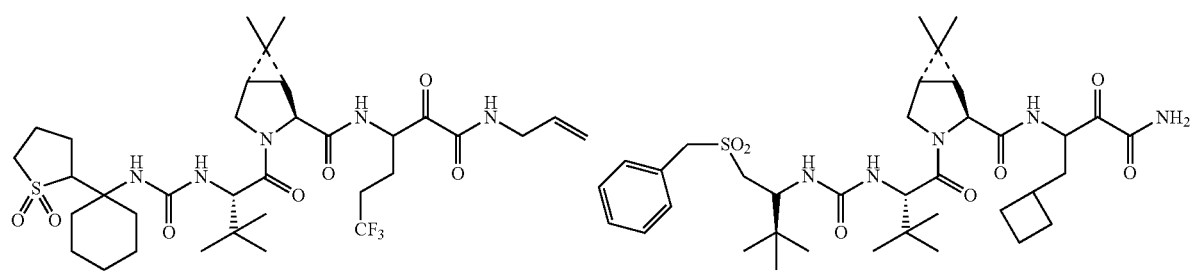
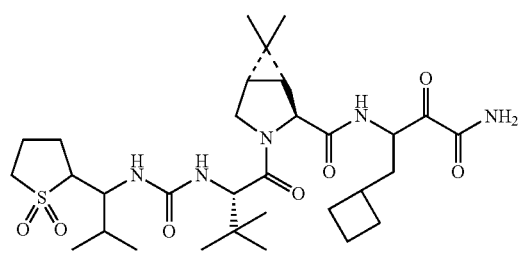 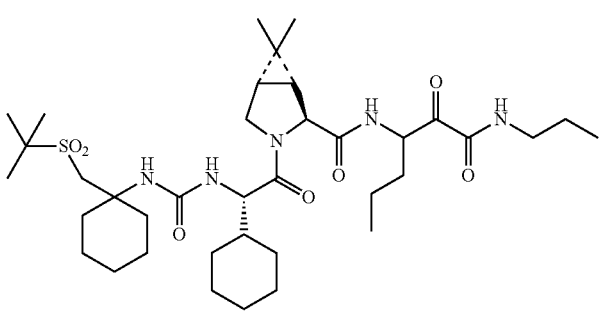
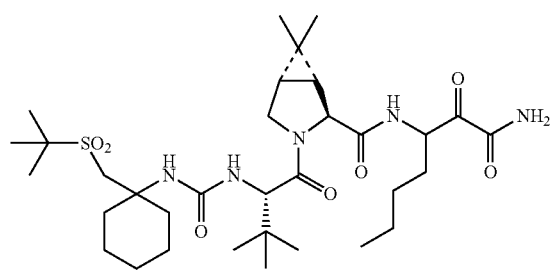

945 946
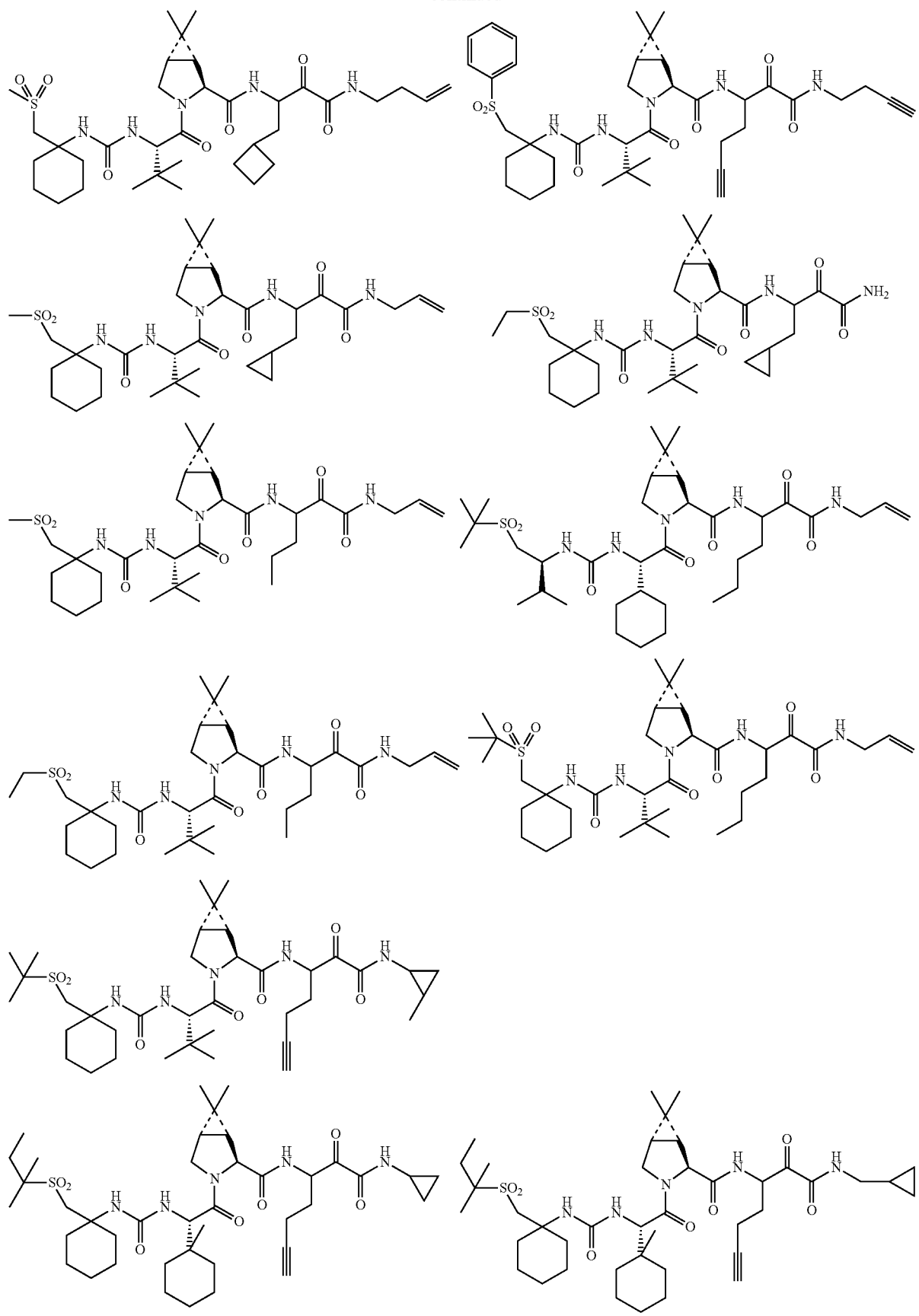

947 948
-continued
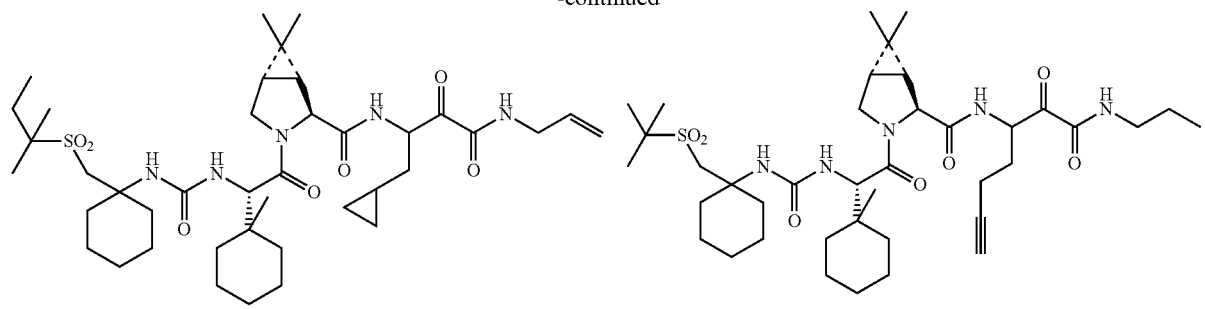
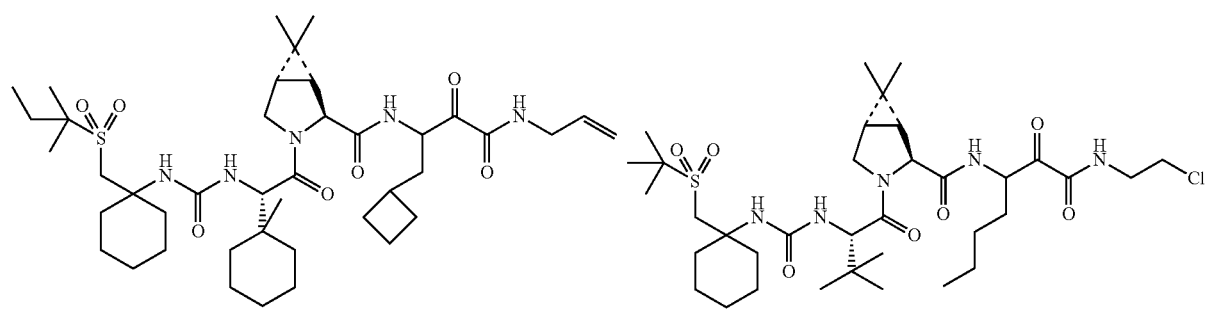
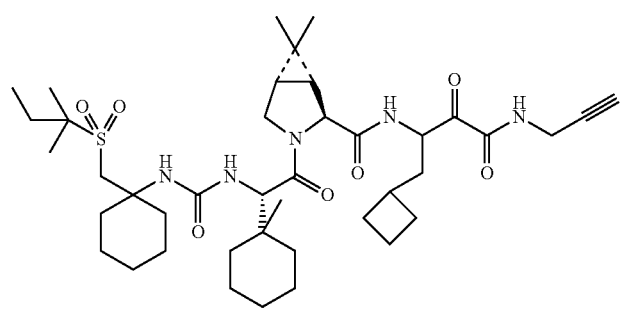
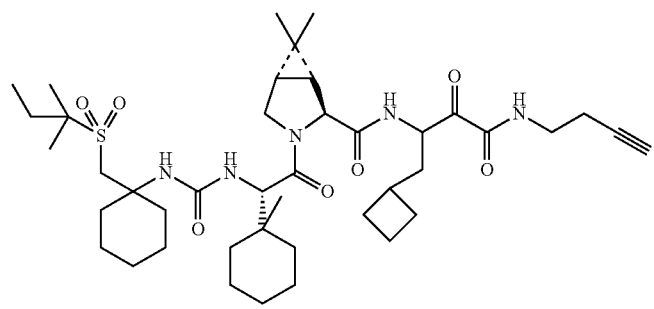
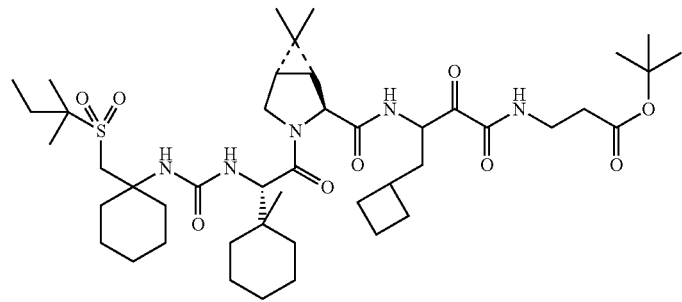

949 950
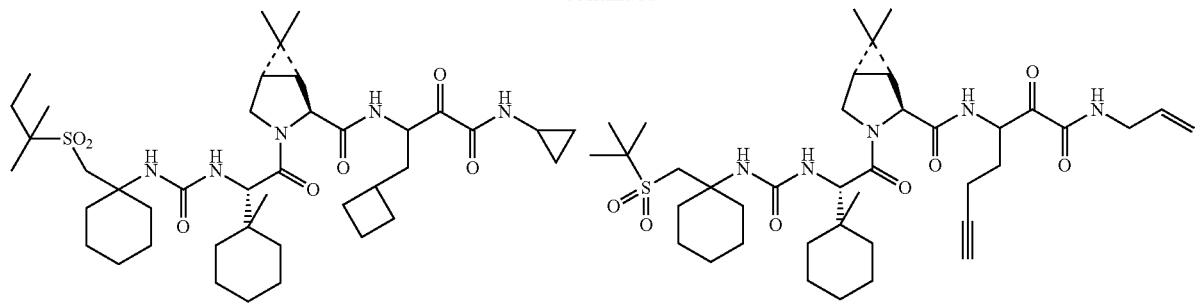
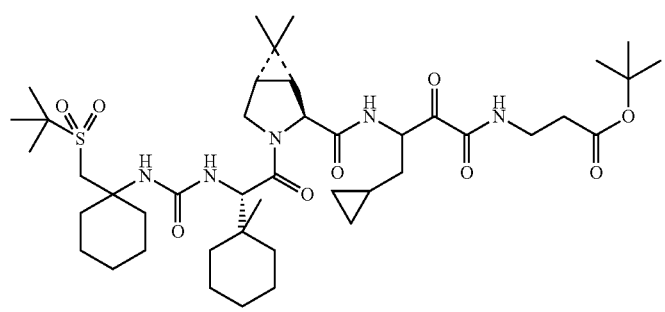
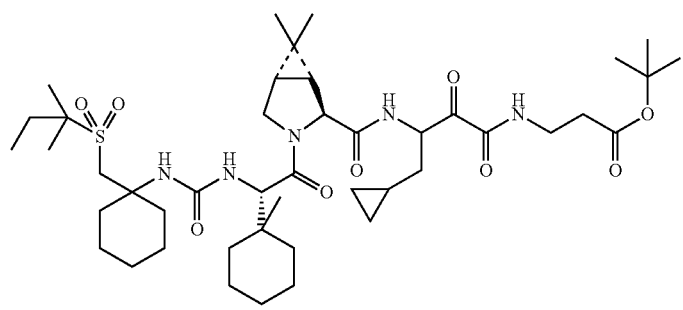
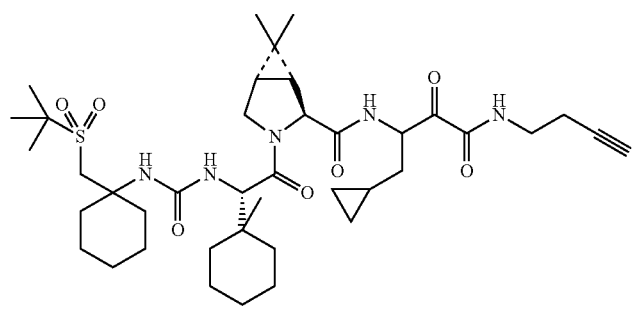
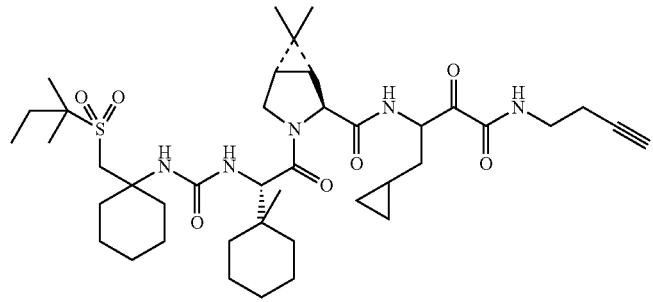

951 952
-continued
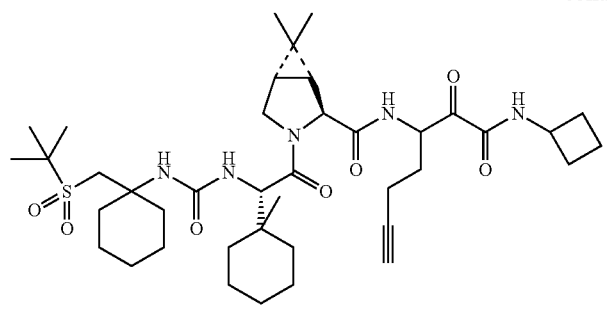
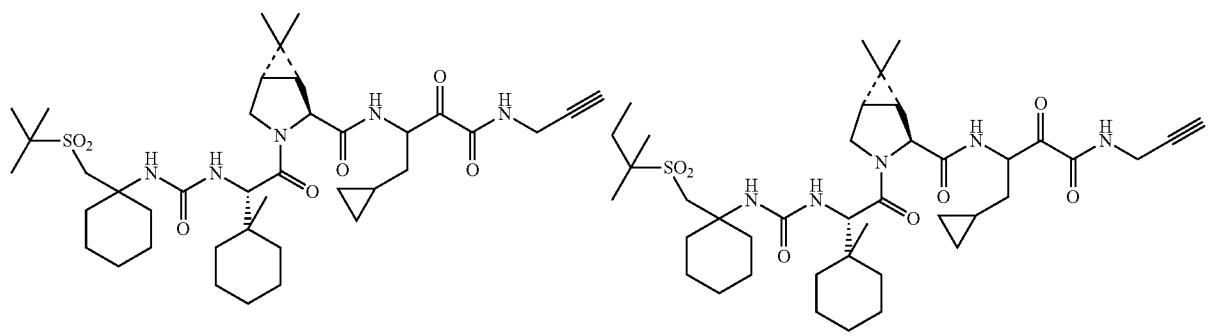
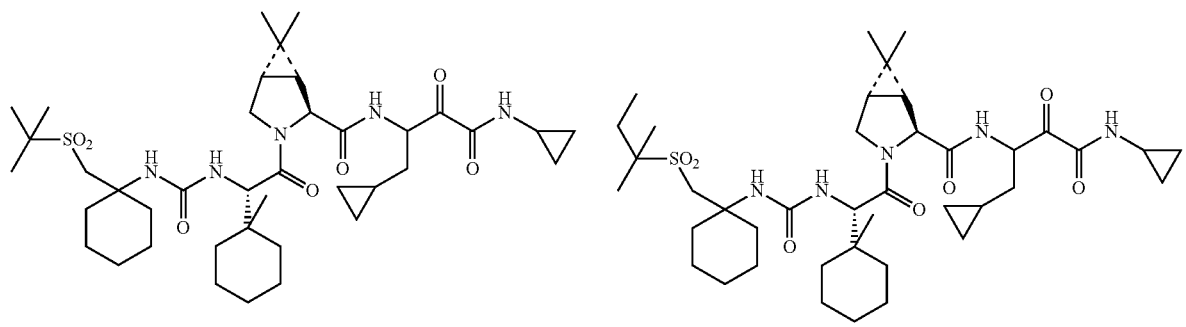
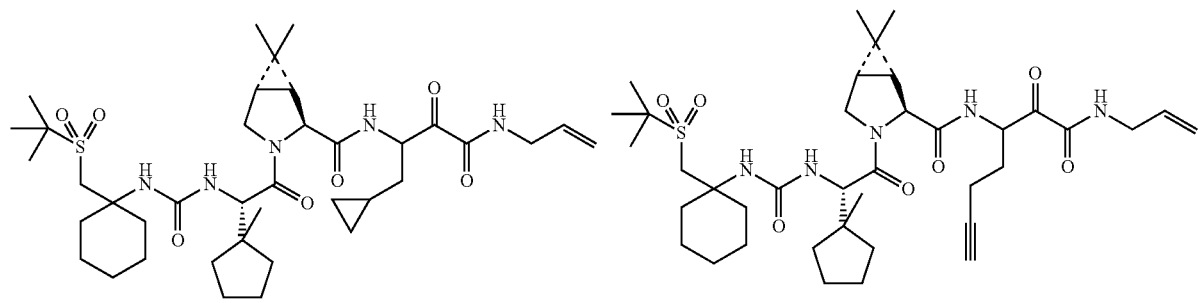
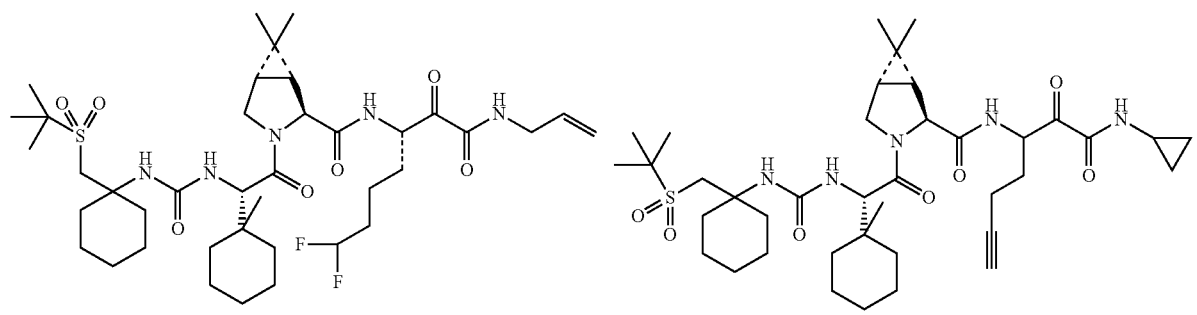

953 954
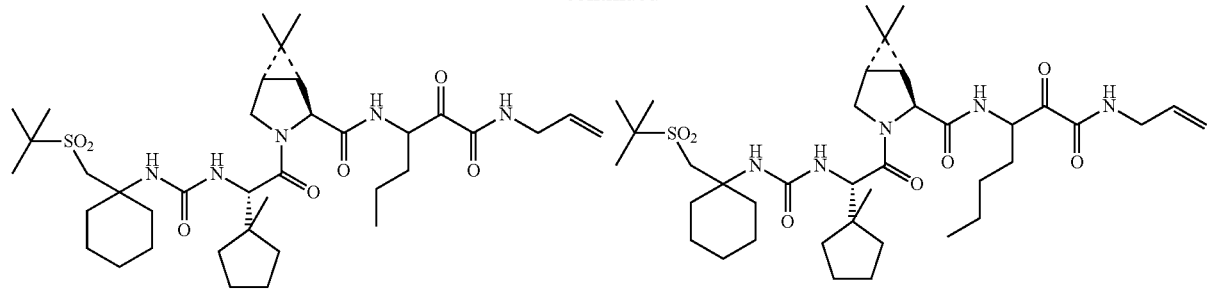
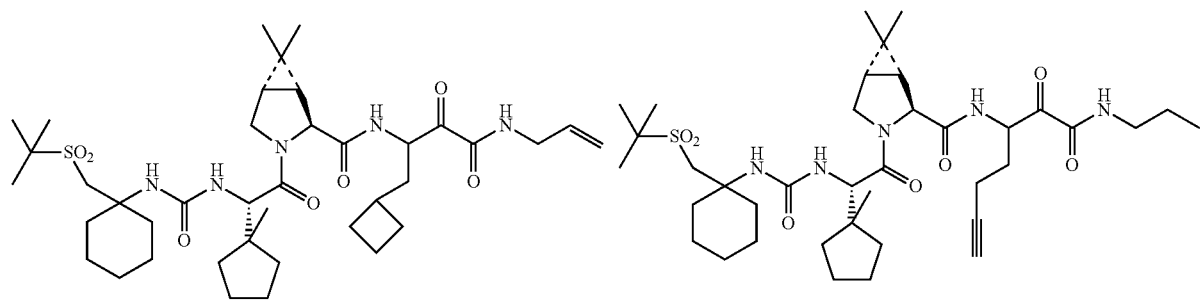
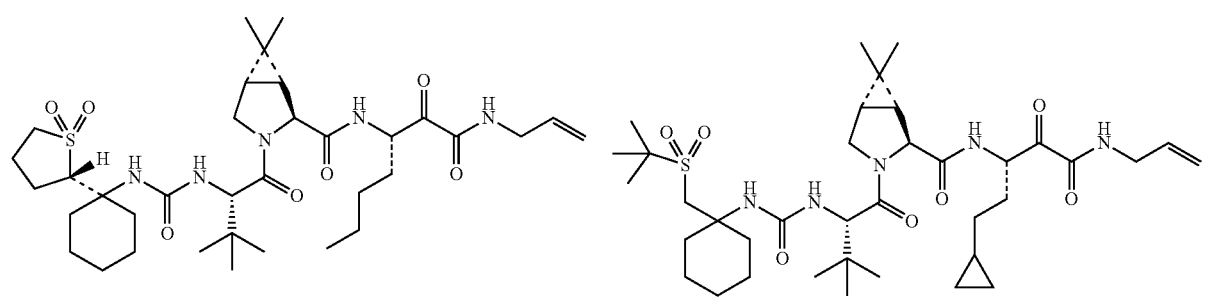
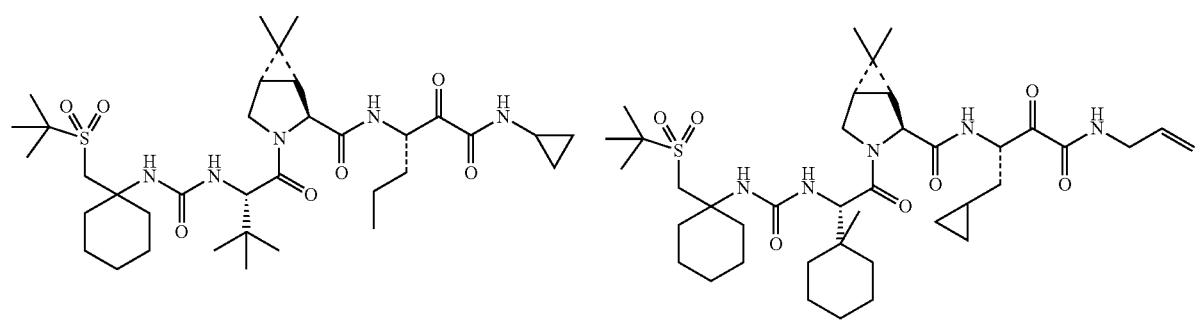
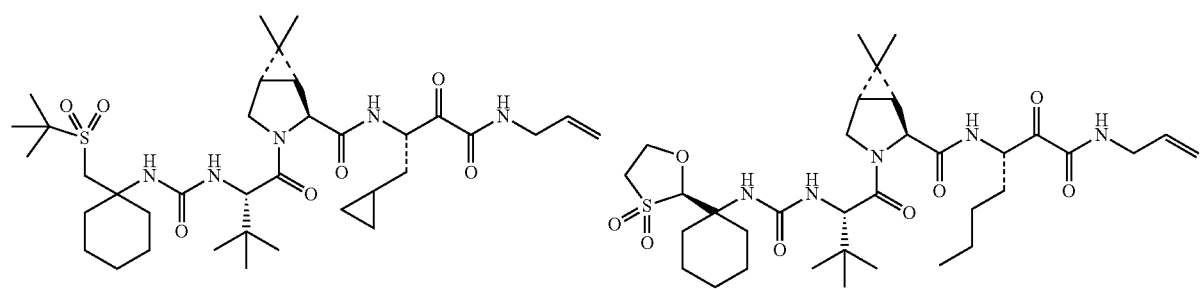

955 956
-continued
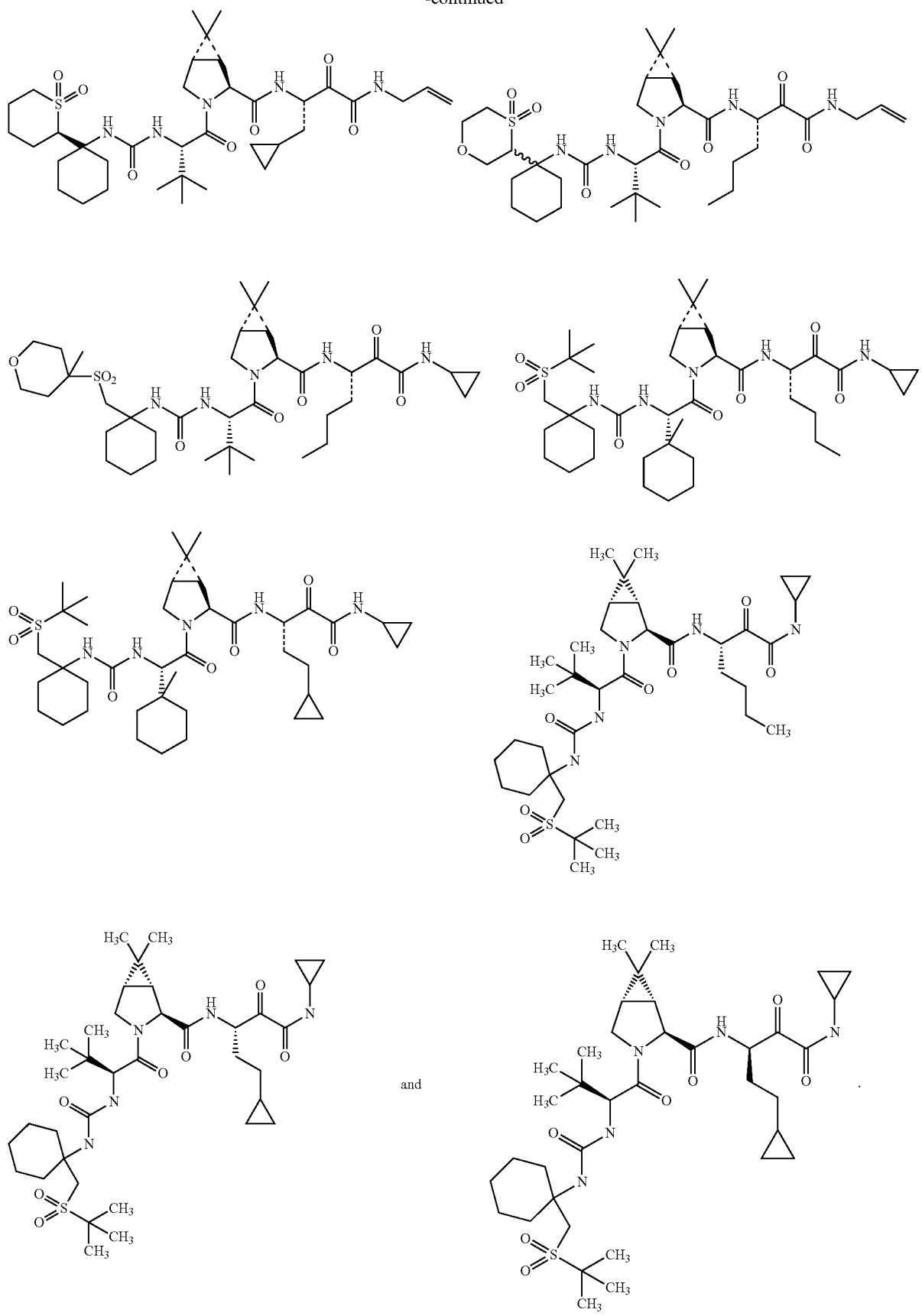
and

16. A pharmaceutical composition said composition comprising therapeutically effective amount of one or more compounds in claim 15 and a pharmaceutically acceptable carrier.

17. The pharmaceutical composition of claim 16, additionally containing at least one antiviral agent.

18. The pharmaceutical composition of claim 17, still additionally containing at least one interferon or PEG-interferon alpha conjugate.

19. The pharmaceutical composition of claim 18, wherein said at least one antiviral agent is ribavirin and said at least one interferon is α-interferon or pegylated interferon.

20. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having the structure:

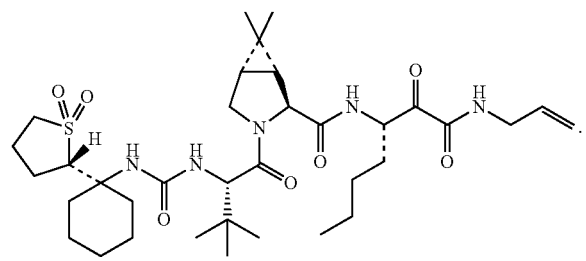

21. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having the structure:

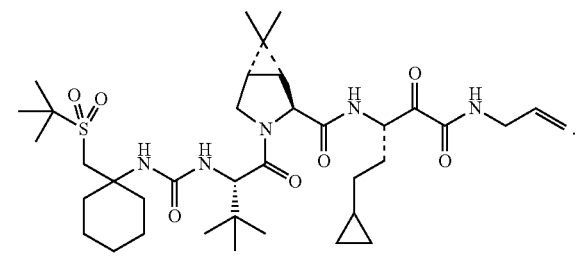

22. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having the structure:

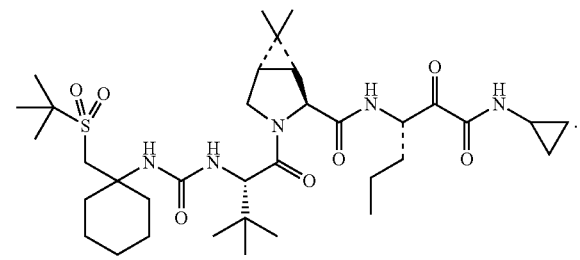

23. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having the structure:

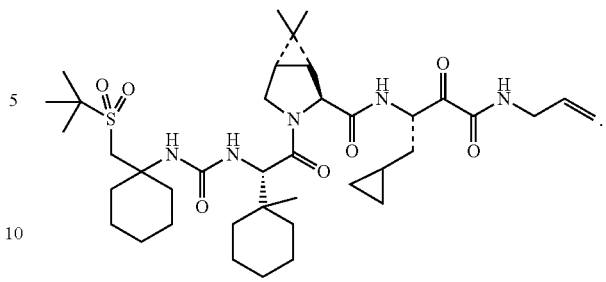

24. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having the structure:

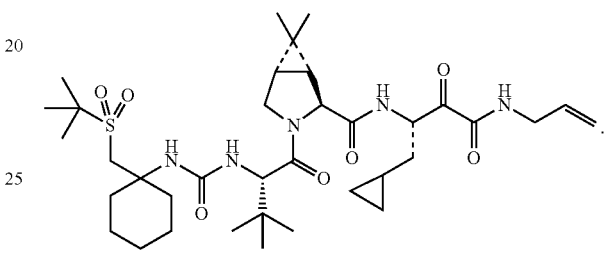

25. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having the structure:

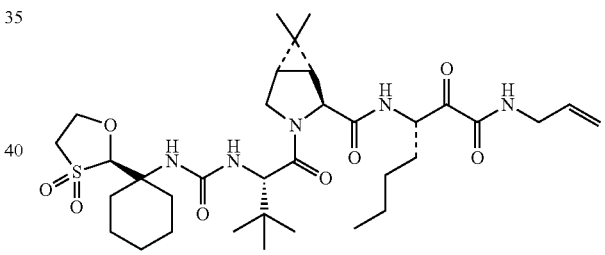

26. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having the structure:

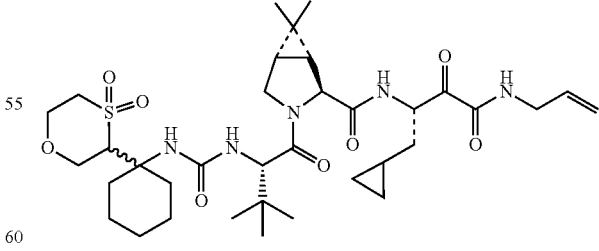

27. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having the structure:

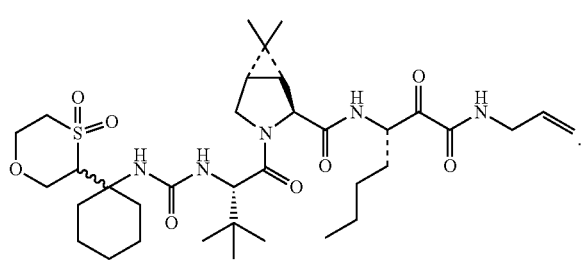

28. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having the structure:

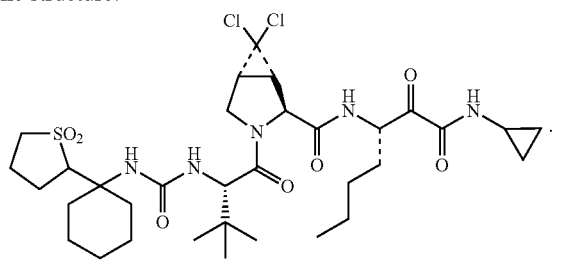

29. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having the structure:

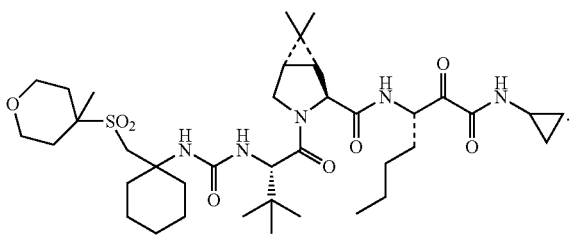

30. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having the structure:

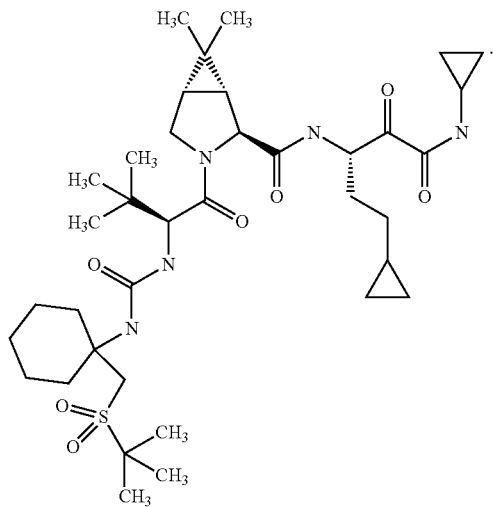

31. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having the structure:

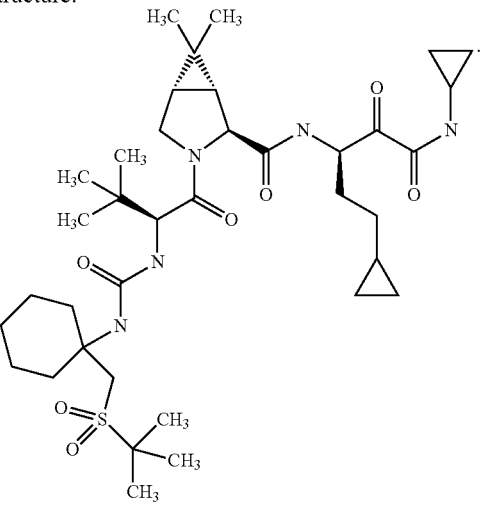

32. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having the structure:

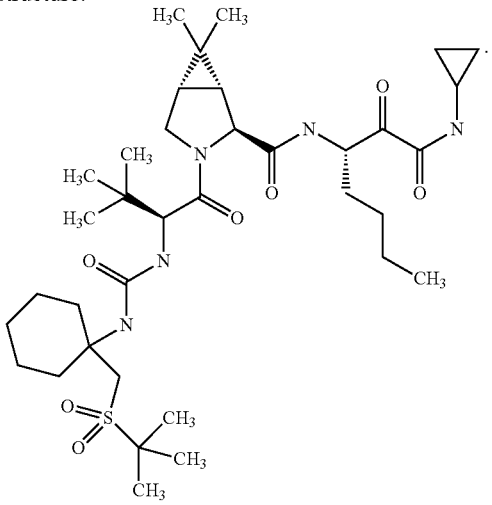

33. A compound or stereoisomer, rotamer, tautomer, or racemate of said compound, or a pharmaceutically acceptable salt of said compound or said stereoisomer, rotamer, tautomer, or racemate of said compound, or an ester of said compound or tautomer of said ester, said compound having a structure selected from the group consisting of:

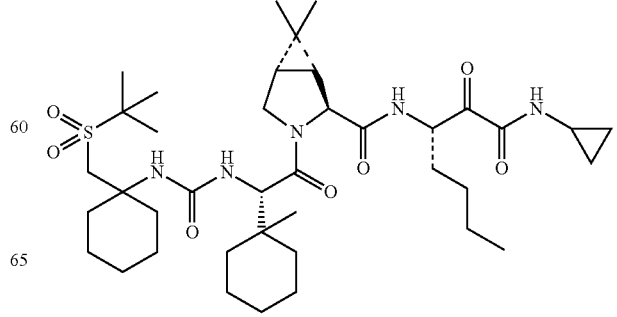

-continued
and

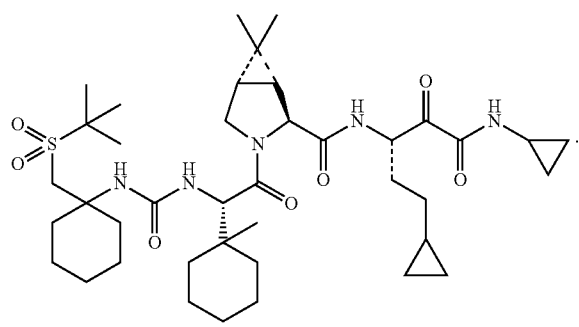

34. A compound of claim 1 in purified form.

35. A compound or stereoisomer, rotamer, tautomer, or racemate of said compound, or a pharmaceutically acceptable salt of said compound or said stereoisomer, rotamer, tautomer, or racemate of said compound, said compound having the structure:

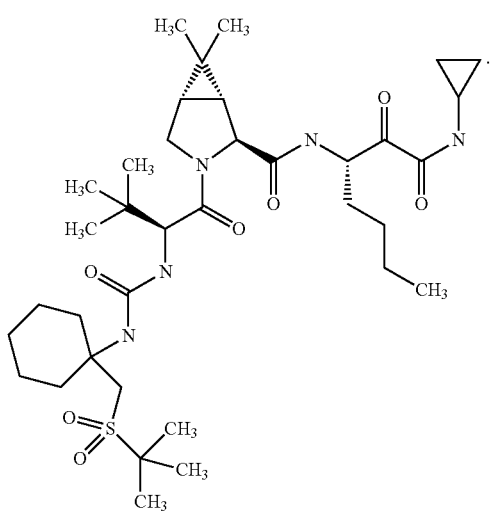

36. A pharmaceutical composition comprising the compound of claim 35 and at least one pharmaceutically acceptable carrier.

37. The pharmaceutical composition of claim 36, additionally containing at least one antiviral agent.

38. The pharmaceutical composition of claim 37, wherein said at least one antiviral agent is ribavirin.

39. A compound or a pharmaceutically acceptable salt of said compound, said compound having the structure:

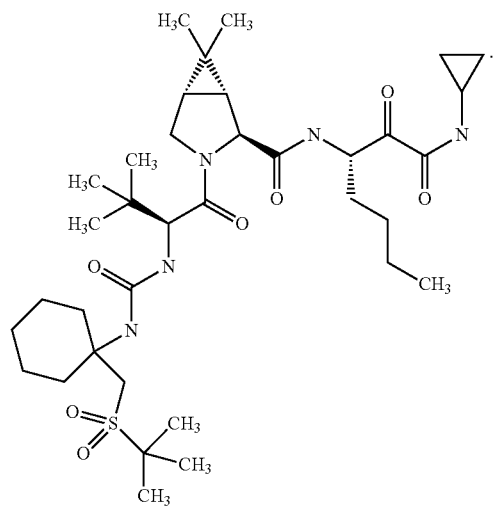

40. A pharmaceutical composition comprising the compound of claim 39 and at least one pharmaceutically acceptable carrier.

41. The pharmaceutical composition of claim 40, additionally containing at least one antiviral agent.

42. The pharmaceutical composition of claim 41, wherein said at least one antiviral agent is ribavirin.

43. A compound having the structure:

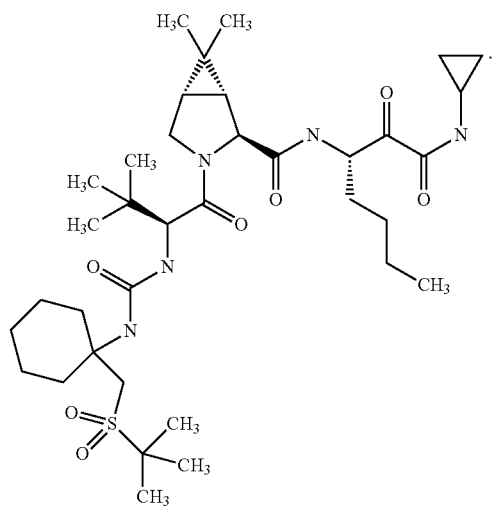

* * * * *